US008546118B2

(12) United States Patent
Weiner et al.

(10) Patent No.: US 8,546,118 B2
(45) Date of Patent: Oct. 1, 2013

(54) ALDOLASES, NUCLEIC ACIDS ENCODING THEM AND METHODS FOR MAKING AND USING THEM

(75) Inventors: David P. Weiner, Del Mar, CA (US); Lishan Zhao, Emeryville, CA (US); Peter Luginbuhl, San Diego, CA (US); Ellen Burke, San Diego, CA (US); Toby Richardson, San Diego, CA (US); Paula M. Hicks, Bend, OR (US)

(73) Assignee: Verenium Corporation, San Diego, CA (US)

( * ) Notice: Subject to any disclaimer, the term of this patent is extended or adjusted under 35 U.S.C. 154(b) by 708 days.

(21) Appl. No.: 12/281,052

(22) PCT Filed: Mar. 7, 2007

(86) PCT No.: PCT/US2007/063515
§ 371 (c)(1),
(2), (4) Date: Dec. 17, 2009

(87) PCT Pub. No.: WO2007/103989
PCT Pub. Date: Sep. 13, 2007

(65) Prior Publication Data
US 2010/0095390 A1  Apr. 15, 2010

Related U.S. Application Data

(60) Provisional application No. 60/780,515, filed on Mar. 7, 2006.

(51) Int. Cl.
| | |
|---|---|
| *C12N 9/10* | (2006.01) |
| *C12N 15/00* | (2006.01) |
| *C12N 1/20* | (2006.01) |
| *C12Q 1/68* | (2006.01) |
| *C12P 21/04* | (2006.01) |
| *C12P 21/06* | (2006.01) |
| *C07H 21/04* | (2006.01) |

(52) U.S. Cl.
USPC .......... 435/193; 435/6.1; 435/69.1; 435/71.1; 435/252.3; 435/320.1; 435/440; 536/23.2

(58) Field of Classification Search
None
See application file for complete search history.

(56) References Cited

U.S. PATENT DOCUMENTS

| 2004/0063175 A1 | 4/2004 | Abraham |
| 2005/0153405 A1* | 7/2005 | Sugiyama et al. ............ 435/121 |
| 2005/0282260 A1 | 12/2005 | Hicks |

FOREIGN PATENT DOCUMENTS

| JP | 5178841-07-20 | 7/1920 |
| JP | 2001-328984 | 11/2001 |
| WO | 9631615 | 10/1996 |
| WO | 00/53553 | 9/2000 |
| WO | 03/091396 A2 | 11/2003 |
| WO | WO 03/091396 | 11/2003 |
| WO | WO 2004/018672 | * 3/2004 |
| WO | 2005/042756 A2 | 5/2005 |
| WO | WO 2006/066072 | 6/2006 |

OTHER PUBLICATIONS

Branden et al. (Introduction to Protein Structure, Garland Publishing Inc., New York, p. 247, 1991.*
Hara et al. Characterization of the 4-carboxy-4-hydroxy-2-oxoadipate aldolase gene and operon structure of the protocatechuate 4,5-cleavage pathway genes in Sphingomonas paucimobilis SYK-6. J Bacteriol. Jan. 2003;185(1):41-50.*
Q8RQW0—TrEMBLrel Database—Jun. 2002.*
PCT/US2007/63515—International Preliminary Examination Report—Jul. 2, 2009 .
GIJSEN—J. Am. Chem. Soc. (1994)—116—8422-8423.
RADL—Tetrahedron Letters (2002)—43—2087-2090.
SIPO—May 5, 2010—Chinese Office Action and Translation—200780016408.6.
JPO—Dec. 7, 2009—Japanese Office Action and Translation—2004568922.
Maruyama, Database EMBL Accession No. AB050935 (2001).
Ochiai, UniProt Accession No. Q2NXC10 (2006).
EP Appl. No. 07758102, European Supplementary Search Report (May 7, 2009).
Dekker—Journal of Biological Chemistry (1992)—267—10507-10514.
Gijsen—Chem. Rev. (1996)—96—443-473.
Henderson—Journal of Organic Chem. (1997)—62—7910-7911.
Koshiba—J. Plant Research (1993)—106—25-29.
Nishihara—Biochim. Biophys. Acta (1969)—185—255-257.
Shannon—J. Biological Chem. (1962)—237—3342-3347.
Tack—J. Biological Chem. (1972)—247—6438-6443.
TAHA—Biochem. Biophys. Res. Comm. (1994)—1—459-466.
Wymer—Curr. Opin. Chem. Biol. (2000)—4—110-119.

(Continued)

*Primary Examiner* — Yong Pak
(74) *Attorney, Agent, or Firm* — Brian W. Siddons; Verenium Corporation

(57) ABSTRACT

This invention relates to polypeptides having aldolase activity, including pyruvate activity such as, without limitation, HMG and/or KHG aldolase activity, polynucleotides encoding these polypeptides, and methods of making and using these polynucleotides and polypeptides. In some embodiments, the invention is directed to polypeptides having aldolase activity, including pyruvate activity such as, without limitation, HMG and/or KHG aldolase activity, including thermostable and thermotolerant activity, and polynucleotides encoding these enzymes, and making and using these polynucleotides and polypeptides. The polypeptides in accordance with the invention can be used in a variety of pharmaceutical, agricultural and industrial contexts. In some embodiments, the invention provides polypeptides and biosynthetic pathways that are useful in the production of R-2-hydroxy 2-(indol-3ylmethyl)-4-keto glutaric acid (R-MP) and certain stereoisomers of monatin, such as R,R and S,R monatin, and salts thereof, as well as certain stereoisomers of monatin derivatives, such as the R,R and S,R configurations, and salts thereof.

12 Claims, 15 Drawing Sheets

(56) References Cited

OTHER PUBLICATIONS

EPO—Mar. 15, 2011—Office Action—EP03797874.9.
UNIPROT Accession No. O66540—Deckert (2002).
GENESEQ Accession No. ABB54781—Bolotine (2001).
UNIPROT Accession No. Q92A19—Glasser (2002).
UNIPROT Accession No. P39121—Yoshida (1995).
UNIPROT Accession No. Q9KD67—Takami (2001).
UNIPROT Accession No. Q8ZJV8—McClelland (2002).
UNIPROT Accession No. Q8Z0U3—Parkhill (2002).
UNIPROT Accession No. P39121—Kunst (1997).
UNIPROT Accession No. Q8UJ09—Goodner (2001).
Wong—J. Am. Chem. Soc. (1995)—117—3333-3339.
Greenberg—PNAS—(2004)—101—5788-5793.
CN200780016408.6—Office Action—May 3, 2011.
EPO—Oct. 12, 2011—Rule 62 Extended EP Search Report—EP11167410.7.
Maruyama—"Cloning, sequencing and expression of the gene encoding 4-Hydroxy-4methyl-2-oxoglutarate Aldolase from *Pseudomonas ochraceae* NGJ1" (2001)—65—2701-2709.
UNIPROT Accession No. Q92PI8—Capela (2001).
EP 11167408.1—Partial EP Search Report—Oct. 12, 2011.
UNIPROT Accession No. Q9AQ10—Maruyama (2001).
UNIPROT Accession No. Q8RQWO—Masai (2002).
Biosis Accession No. PREV199039041255—Biosciences Information Service, Philadelphia, PA (1990) Patil, R.V. "Cloning and expression of 2 keto-4-hydroxyglutarate (KHG) aldolase of *Escherichia-coli*" (abstract).
JPO—Apr. 10, 2012—Office Action+ English Translation—JP2008-558521.

\* cited by examiner

ALDOLASES, NUCLEIC ACIDS ENCODING THEM AND METHODS FOR MAKING AND USING THEM

CROSS-REFERENCE TO RELATED APPLICATION

This application is a national stage application filed in accordance with 35 U.S.C. §371 of International Application Number PCT/US2007/063515, filed Mar. 7, 2007 and claims the benefit of U.S. Provisional Patent Application No. 60/780,515, filed Mar. 7, 2006. The aforementioned applications are explicitly incorporated herein by reference in their entirety and for all purposes.

FIELD IN ACCORDANCE WITH THE INVENTION

This invention relates to molecular and cellular biology and biochemistry. More specifically, the invention relates to polypeptides having aldolase activity, polynucleotides encoding these polypeptides, and methods of making and using these polynucleotides and polypeptides.

BACKGROUND OF THE INVENTION

Monatin is a high-intensity sweetener having the chemical formula:

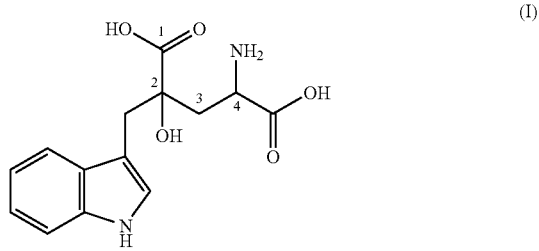 [SMILES: NC(CC(O)(Cc1c[nH]c2ccccc12)C(=O)O)C(=O)O]

(I)

Monatin includes two chiral centers leading to four potential stereoisomeric configurations. The R,R configuration (the "R,R stereoisomer" or "R,R monatin"); the S,S configuration (the "S,S stereoisomer" or "S,S monatin"); the R,S configuration (the "R,S stereoisomer" or "R,S monatin"); and the S,R configuration (the "S,R stereoisomer" or "S,R monatin"). As used herein, unless stated otherwise, the term "monatin" is used to refer to compositions including all four stereoisomers of monatin, compositions including any combination of monatin stereoisomers, (such as a composition including only the R,R and S,S, stereoisomers of monatin), as well as a single isomeric form.

For purposes of this disclosure, the monatin carbon backbone will be numbered as illustrated above, with the carbon directly covalently attached to the alcohol group being identified as the 2-position carbon and the carbon directly covalently attached to the amino group being identified as the 4-position carbon. Consequently, references herein to R,R monatin, S,S monatin, R,S monatin, and S,R monatin mean: 2R,4R monatin, 2S,4S monatin, 2R,4S monatin, and 2S,4R monatin, respectively, unless otherwise indicated.

It should be noted that in the literature, the monatin carbon backbone has also been numbered using an alternative convention, with the carbon attached to the alcohol group being the 4-position carbon, and the carbon attached to the amino group being the 2-position carbon. Accordingly, for example, references to 2S,4R monatin in this disclosure would be the same as references to 2R,4S monatin in literature using the alternative numbering convention.

Furthermore, because of various naming conventions, monatin is known by a number of alternative chemical names, including: 2-hydroxy-2-(indol-3-ylmethyl)-4-aminoglutaric acid; 4-amino-2-hydroxy-2-(1H-indol-3-ylmethyl)-pentanedioic acid; 4-hydroxy-4-(3-indolylmethyl)glutamic acid; and, 3-(1-amino-1,3-dicarboxy-3-hydroxy-but-4-yl)indole.

Certain isomeric forms of monatin can be found in the bark of roots of the *Schlerochiton ilicifolius* plant located in the Transvaal Region of South Africa. U.S. patent application Ser. Nos. 10/422,366 ("the '366 application") and 10/979,821 ("the '821 application"), which are hereby incorporated by reference, disclose, inter alia, polypeptides, pathways, and microorganisms for in vitro and in vivo production of monatin.

SUMMARY

The invention provides polypeptides having aldolase activity (hereinafter "aldolases"), including pyruvate aldolase activity such as, without limitation, HMG and KHG aldolase activity, polynucleotides encoding the polypeptides, and methods for making and using the polypeptides and polynucleotides. In some embodiments, the invention also provides compositions (such as pharmaceutical compositions, fuel and fuel additive compostions, foods and food additives, beverage and beverage additives, feeds and feed additives, drugs and drug additives, dietary supplements) comprising the polypeptides or polynucleotides in accordance with the invention. These compositions can be formulated in a variety of forms, such as tablets, gels, pills, implants, liquids, sprays, films, micelles, powders, food, feed pellets or as any type of encapsulated form.

In some embodiments, the aldolases and/or compositions thereof may be useful in pharmaceutical, industrial, and/or agricultural contexts.

In some embodiments, the aldolases and/or compositions thereof may be useful for forming or cleaving carbon-carbon bonds.

In some embodiments, aldolases are provided that catalyze carbon-carbon bond forming reactions between an alpha-keto acid acceptor and a pyruvate or a pyruvate derivative donor (see reaction scheme below). In some embodiments, the acceptor can also be a ketone or an aldehyde. In some embodiments, aldolases are provided that have 4-hydroxy-2-oxoglutarate aldolase (such as 2-keto-4-hydroxyglutarate aldolase, 2-oxo-4-hydroxyglutarate aldolase, KHG-aldolase, EC 4.1.3.16) activity and catalyze the following reaction: 4-hydroxy-2-oxoglutarate<=>pyruvate+glyoxylate. In some embodiments, aldolases are provided that have HMG-aldolase (such as 4-hydroxy-4-methyl-2-oxoglutarate aldolase, pyruvate aldolase, gamma-methyl-gamma-hydroxy-alpha-ketoglutaric aldolase, 4-hydroxy-4-methyl-2-ketoglutarate aldolase, EC 4.1.3.17) activity and catalyze the following reaction: 4-hydroxy-4-methyl-2-oxoglutarate<=>2 pyruvate. An HMG aldolase will also act on 4-hydroxy-4-methyl-2-oxoadipate and 4-carboxy-4-hydroxy-2-oxohexadioate.

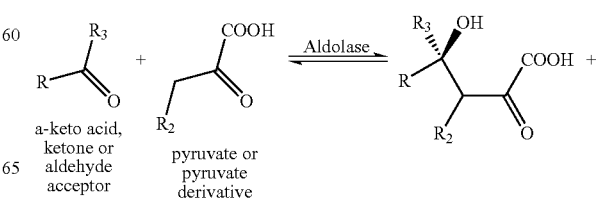

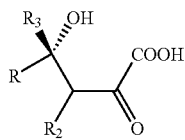

R=H, alkyl, substituted alkyl, aryl, substituted aryl, benzyl, substituted benzyl $R_2$=H, alkyl, substituted alkyl, aryl, substituted aryl, benzyl, substituted benzyl $R_3$=H, alkyl, substituted alkyl, aryl, substituted aryl, benzyl, substituted benzyl, carboxylic acid.

In some embodiments, aldolases, such as a pyruvate aldolase, such as, without limitation a HMG and/or a KHG aldolase, are provided that facilitate the production of a 3,4-substituted 2-keto-glutarate. In one embodiment, the invention provides a method of making a 3,4-substituted 2-keto-glutarate comprising: (a) providing a polypeptide having an aldolase activity, such as a pyruvate aldolase activity, such as, without limitation, a HMG aldolase and/or a KMG aldolase activity; (b) providing a donor and an acceptor compound; and (c) contacting the polypeptide of step (a) with the compounds of step (b) under conditions wherein the aldolase catalyzes the synthesis of a 3,4-substituted 2-keto-glutarate, wherein optionally the donor and the acceptor are a pyruvate or a pyruvate donor and an α-keto acid acceptor, a ketone and/or an aldehyde.

In some embodiments, aldolases are provided that facilitate the production of R-2-hydroxy 2-(indol-3ylmethyl)-4-keto glutaric acid (R-MP), a monatin precursor. In some embodiments, a pyruvate aldolase, such as a HMG and/or a KHG aldolase, can be used in conjunction with a D-aminotransferase to make a 4-substituted D-glutamic acid or a derivative thereof. A 4-substituted D-glutamic acid and/or a derivative thereof can be used as an antibiotic, as these compounds have been found to inhibit bacterial glutamate racemase (WO0214261A3). In one embodiment, the invention provides a method of making a 4-substituted D-glutamic acid comprising: (a) providing a polypeptide having an aldolase activity, such as a pyruvate aldolase activity, such as, without limitation, a HMG aldolase and/or a KMG aldolase activity; (b) providing an α-keto acid acceptor and a pyruvate or a pyruvate donor; and (c) contacting the polypeptide of step (a) with the compounds of step (b) under conditions wherein the aldolase catalyzes the synthesis of a 4-substituted D-glutamic acid, wherein optionally the polypeptide has pyruvate aldolase, HMG aldolase and/or KHG aldolase activity and wherein optionally the method further comprises use of a D-aminotransferase.

The invention provides isolated, synthetic or recombinant nucleic acids comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a nucleic acid in accordance with the invention, including SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:279, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305, SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, and SEQ ID NO:338, over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more residues. In some embodiments, one or more nucleic acids encode at least one polypeptide having an aldolase activity, including pyruvate activity such as, without limitation, HMG and/or KHG aldolase activity. In some embodiments, the sequence identities are determined by analysis with a sequence comparison algorithm or by a visual inspection.

In alternative embodiments, one or more nucleic acids encode at least one polypeptide capable of generating an antibody that can specifically bind to a polypeptide of the invention, or, these nucleic acids can be used as probes for identifying or isolating aldolase-encoding nucleic acids, or to inhibit the expression of aldolase-expressing nucleic acids.

Nucleic acids in accordance with the invention also include isolated, synthetic or recombinant nucleic acids encoding enzymes in accordance with the invention, such as enzymes including one or more polypeptides having a sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, SEQ ID NO:174, SEQ ID NO:176, SEQ ID NO:178, SEQ ID NO:180, SEQ ID NO:182, SEQ ID NO:184, SEQ ID NO:186, SEQ ID NO:188, SEQ ID NO:190, SEQ ID NO:192, SEQ ID NO:194, SEQ ID NO:196, SEQ ID NO:198, SEQ ID NO:200, SEQ ID NO:202, SEQ ID NO:204, SEQ ID NO:206, SEQ ID NO:208, SEQ ID NO:210, SEQ ID NO:212, SEQ ID NO:214, SEQ ID NO:216, SEQ ID NO:218, SEQ ID NO:220, SEQ ID NO:222, SEQ ID NO:224, SEQ ID NO:226, SEQ ID NO:228, SEQ ID NO:230, SEQ ID NO:232, SEQ ID NO:234, SEQ ID NO:236, SEQ ID NO:238, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:260, SEQ ID NO:262, SEQ ID NO:264, SEQ ID NO:266, SEQ ID NO:268, SEQ ID NO:270, SEQ ID NO:272, SEQ ID NO:274, SEQ ID NO:276, SEQ ID NO:278, SEQ ID NO:280, SEQ ID NO:282, SEQ ID NO:284, SEQ ID NO:286, SEQ ID NO:288, SEQ ID NO:290, SEQ ID NO:292, SEQ ID NO:294, SEQ ID NO:296, SEQ ID NO:298, SEQ ID NO:300, SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:320, SEQ ID NO:322, SEQ ID NO:324, SEQ ID NO:326, SEQ ID NO:328, SEQ ID NO:330, SEQ ID NO:332, and SEQ ID NO:334, and subsequences thereof, variants thereof and enzymatically active fragments thereof. In some embodiments, the polypeptide has an aldolase activity, including pyruvate activity such as, without limitation, HMG and/or KHG aldolase activity.

In some embodiments, the invention provides aldolase-encoding, such as pyruvate aldolase-, such as HMG and/or KHG aldolase-encoding nucleic acids preferably derived from mixed cultures. In some embodiments, the invention provides carbon-carbon bond forming or cleaving enzyme-encoding nucleic acids isolated from mixed cultures comprising polynucleotides in accordance with the invention, such as a sequence having at least about 10%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a nucleic acid in accordance with the invention, such as SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:279, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305, SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, and SEQ ID NO:338 over a region of at least about 50, 75, 100, 150, 200, 250, 300, 350, 400, 450, 500, 550, 600, 650, 700, 750, 800, 850, 900, 950, 1000, 1050, 1100, 1150, or more.

In some embodiments, the invention provides aldolase enzyme-, such as pyruvate aldolase enzyme-, HMG and/or KHG enzyme-encoding nucleic acids, including polynucleotide sequences in accordance with the invention and the polypeptides encoded by them, including enzymes in accordance with the invention, such as polypeptides in accordance with the invention, such as SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, SEQ ID NO:174, SEQ ID NO:176, SEQ ID NO:178, SEQ ID NO:180, SEQ ID NO:182, SEQ ID NO:184, SEQ ID NO:186, SEQ ID NO:188, SEQ ID NO:190, SEQ ID NO:192, SEQ ID NO:194, SEQ ID NO:196, SEQ ID NO:198, SEQ ID NO:200, SEQ ID NO:202, SEQ ID NO:204, SEQ ID NO:206, SEQ ID NO:208, SEQ ID NO:210, SEQ ID NO:212, SEQ ID NO:214, SEQ ID NO:216, SEQ ID NO:218, SEQ ID NO:220, SEQ ID NO:222, SEQ ID NO:224, SEQ ID NO:226, SEQ ID NO:228, SEQ ID NO:230, SEQ ID NO:232, SEQ ID NO:234, SEQ ID NO:236, SEQ ID NO:238, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:260, SEQ ID NO:262, SEQ ID NO:264, SEQ ID NO:266, SEQ ID NO:268, SEQ ID NO:270, SEQ ID NO:272, SEQ ID NO:274, SEQ ID NO:276, SEQ ID NO:278, SEQ ID NO:280, SEQ ID NO:282, SEQ ID NO:284, SEQ ID NO:286, SEQ ID NO:288, SEQ ID NO:290, SEQ ID NO:292, SEQ ID NO:294, SEQ ID NO:296, SEQ ID NO:298, SEQ ID NO:300, SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:320, SEQ ID NO:322, SEQ ID NO:324, SEQ ID NO:326, SEQ ID NO:328, SEQ ID NO:330, SEQ ID NO:332, or SEQ ID NO:334, and enzymatically-active fragments thereof, preferably derived from a common source, such as an environmental source. In some embodiments, the invention also provides aldolase enzyme-, such as pyruvate aldolase enzyme-, HMG and/or KHG enzyme-encoding nucleic acids preferably derived from environmental sources, such as mixed environmental sources.

In some embodiments, the sequence comparison algorithm is a BLAST version 2.2.2 algorithm where a filtering setting is set to blastall-p blastp-d "nr pataa"-F F, and all other options are set to default.

Other embodiments of the invention are isolated, synthetic or recombinant nucleic acids including at least 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more consecutive bases of a nucleic acid sequence in accordance with the invention, sequences substantially identical thereto, and the sequences complementary thereto.

In some embodiments, the isolated, synthetic or recombinant nucleic acids in accordance with the invention encodes a polypeptide having an aldolase activity, including pyruvate activity such as, without limitation, HMG and/or KHG aldolase activity, which is thermostable. The thermostable polypeptide according to the invention can retain an aldolase activity, such as a pyruvate aldolase activity, such as a HMG and/or a KHG aldolase activity, under conditions comprising a temperature range from about $-100°$ C. to about $-80°$ C., about $-80°$ C. to about $-40°$ C., about $-40°$ C. to about $-20°$ C., about $-20°$ C. to about $0°$ C., about $0°$ C. to about $37°$ C., about $0°$ C. to about $5°$ C., about $5°$ C. to about $15°$ C., about $15°$ C. to about $25°$ C., about $25°$ C. to about $37°$ C., about $37°$ C. to about $45°$ C., about $45°$ C. to about $55°$ C., about $55°$ C. to about $70°$ C., about $70°$ C. to about $75°$ C., about $75°$ C. to about $85°$ C., about $85°$ C. to about $90°$ C., about $90°$ C. to about $95°$ C., about $95°$ C. to about $100°$ C., about $100°$ C. to about $105°$ C., about $105°$ C. to about $110°$ C., about $110°$ C. to about $120°$ C., or $95°$ C., $96°$ C., $97°$ C., $98°$ C., $99°$ C., $100°$ C., $101°$ C., $102°$ C., $103°$ C., $104°$ C., $105°$ C., $106°$ C., $107°$ C., $108°$ C., $109°$ C., $110°$ C., $111°$ C., $112°$ C., $113°$ C., $114°$ C., $115°$ C. or more. The thermostable polypeptides according to the invention can retain an aldolase activity, such as a pyruvate aldolase activity, such as a HMG and/or a KHG aldolase activity, in temperatures in the range from about $-100°$ C. to about $-80°$ C., about $-80°$ C. to about $-40°$ C., about $-40°$ C. to about $-20°$ C., about $-20°$ C. to about $0°$ C., about $0°$ C. to about $5°$ C., about $5°$ C. to about $15°$ C., about $15°$ C. to about $25°$ C., about $25°$ C. to about $37°$ C., about $37°$ C. to about $45°$ C., about $45°$ C. to about $55°$ C., about $55°$ C. to about $70°$ C., about $70°$ C. to about $75°$ C., about $75°$ C. to about $85°$ C., about $85°$ C. to about $90°$ C., about $90°$ C. to about $95°$ C., about $95°$ C. to about $100°$ C., about $100°$ C. to about $105°$ C., about $105°$ C. to about $110°$ C., about $110°$ C. to about $120°$ C., or $95°$ C., $96°$ C., $97°$ C., $98°$ C., $99°$ C., $100°$ C., $101°$ C., $102°$ C., $103°$ C., $104°$ C., $105°$ C., $106°$ C., $107°$ C., $108°$ C., $109°$ C., $110°$ C., $111°$ C., $112°$ C., $113°$ C., $114°$ C., $115°$ C. or more. In some embodiments, the thermostable polypeptides according to the invention retains an aldolase activity at a temperature in the ranges described above, at about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more.

In other embodiments, the isolated, synthetic or recombinant nucleic acids encode a polypeptide having an aldolase activity, including pyruvate activity such as, without limitation, HMG and/or KHG aldolase activity, which is thermotolerant. The thermotolerant polypeptides according to the invention can retain an aldolase activity, such as a pyruvate aldolase activity, such as a HMG and/or a KHG aldolase activity, after exposure to conditions comprising a temperature in the range from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. The thermotolerant polypeptides according to the invention can retain an aldolase activity, such as a pyruvate aldolase activity, such as a HMG and/or a KHG aldolase activity, after exposure to a temperature in the range from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. In some embodiments, the thermotolerant polypeptides according to the invention retains an aldolase activity after exposure to a temperature in the ranges described above, at about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more.

The invention provides isolated, synthetic or recombinant nucleic acids comprising a sequence that hybridizes under stringent conditions to nucleic acids in accordance with the invention, including a sequence as set forth in SEQ ID NO:1, SEQ ID NO:3, SEQ ID NO:5, SEQ ID NO:7, SEQ ID NO:9, SEQ ID NO:1, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:279, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305, SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, or SEQ ID NO:338, or fragments or subsequences thereof. In some embodiments, the nucleic acids encode polypeptides having an aldolase activity, including pyruvate activity such as, without limitation, HMG and/or KHG aldolase activity. The nucleic acids can be at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200 or more residues in length or the full length of the gene or transcript. In some embodiments, the stringent conditions comprise a wash step comprising a wash in 0.2×SSC at a temperature of about 65° C. for about 15 minutes.

The invention provides nucleic acid probes for identifying or isolating nucleic acids encoding polypeptides having an aldolase activity, including pyruvate activity such as, without limitation, HMG and/or KHG aldolase activity, wherein the probes comprise about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000 or more, consecutive bases of a sequence in accordance with the invention, and wherein the probes identify the nucleic acid by binding or hybridization. The probes can comprise an oligonucleotide comprising between about 10-100 consecutive bases of a sequence in accordance with the invention, or fragments or subsequences thereof, for example, 10, 15, 20, 25, 30, 35, 40, 45, 50, 55, 60, 65, 70, 75, 80, 85, 90, 95 or 100 bases or more, or, any desired length in between.

The invention provides nucleic acid probes for identifying or isolating nucleic acids encoding polypeptides having an aldolase activity, including pyruvate activity such as, without limitation, HMG and/or KHG aldolase activity, wherein the probes comprise nucleic acids comprising a sequence at least about 10, 15, 20, 30, 40, 50, 60, 70, 80, 90, 100, 150, 200, 250, 300, 350, 400, 450, 500, 550, 600, 650, 700, 750, 800, 850, 900, 950, 1000 or more residues of a nucleic acid in accordance with the invention, such as a polynucleotide having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a nucleic acid of the invention. In some embodiments, the sequence identities are determined by analysis with a sequence comparison algorithm or by visual inspection. In other embodiments, the probes can comprise an oligonucleotide comprising between at least about 10-100 consecutive bases of a nucleic acid sequence in accordance with the invention, or a subsequence thereof, for example 10, 15, 20, 25, 30, 35, 40, 45, 50, 55, 60, 65, 70, 75, 80, 85, 90, 95, or 100 bases or more, or, any desired length in between.

The invention provides amplification primer pairs for amplifying (such as by PCR) a nucleic acids encoding polypeptides having aldolase activity, including pyruvate activity such as, without limitation, HMG and/or KHG aldolase activity, wherein each primer pair is capable of amplifying a nucleic acid comprising a sequence in accordance with the invention, or fragments or subsequences thereof (see the Sequence Listing). One or each member of the amplification primer sequence pair can comprise an oligonucleotide comprising at least about 10 to 50, or more, consecutive bases of the sequence, or about 10, 11, 12, 13, 14, 15, 16, 17, 18, 19, 20, 21, 22, 23, 24, 25, 26, 27, 28, 29, 30, 31, 32, 33, 34, 35, 36 or more consecutive bases of the sequence. In some embodiments, the invention provides amplification primer pairs, wherein each primer pair comprises a first member having a sequence as set forth by about the first (the 5') 12, 13, 14, 15, 16, 17, 18, 19, 20, 21, 22, 23, 24, 25, 26, 27, 28, 29, 30, 31, 32, 33, 34, 35, 36 or more residues of a nucleic acid in accordance with the invention, and a second member having a sequence as set forth by about the first (the 5') 12, 13, 14, 15, 16, 17, 18, 19, 20, 21, 22, 23, 24, 25, 26, 27, 28, 29, 30, 31, 32, 33, 34, 35, 36 or more residues of the complementary strand of the first member.

The invention provides aldolase-encoding, such as pyruvate aldolase-encoding, HMG and/or KHG aldolase-encoding nucleic acids generated by amplification, such as polymerase chain reaction (PCR), using an amplification primer pair in accordance with the invention. In some embodiments, the invention provides aldolase-encoding, such as pyruvate aldolase-encoding, HMG and/or KHG aldolase-encoding nucleic acids generated by amplification, such as polymerase chain reaction (PCR), using an amplification primer pair in accordance with the invention. In some embodiments, the invention provides methods of making an aldolase, such as pyruvate aldolase, HMG and/or KHG aldolase enzyme by amplification, such as polymerase chain reaction (PCR), using an amplification primer pair in accordance with the invention. In some embodiments, the amplification primer pair amplifies a nucleic acid from a library, such as a gene library, such as an environmental library.

The invention provides methods of amplifying a nucleic acid encoding a polypeptide having an aldolase activity, including pyruvate activity such as, without limitation, HMG and/or KHG aldolase activity comprising amplification of a template nucleic acid with an amplification primer sequence pair capable of amplifying a nucleic acid sequence in accordance with the invention, or fragments or subsequences thereof.

The invention provides expression cassettes comprising a nucleic acid in accordance with the invention or a subsequence thereof. In some embodiments, the expression cassette can comprise the nucleic acid that is operably linked to a promoter. The promoter can be a viral, bacterial, mammalian, fungal, yeast, or plant promoter. In some embodiments, the plant promoter can be a potato, rice, corn, wheat, tobacco or barley promoter. The promoter can be a constitutive promoter. The constitutive promoter can comprise CaMV35S. In other embodiments, the promoter can be an inducible promoter. In some embodiments, the promoter can be a tissue-specific promoter or an environmentally regulated or a developmentally regulated promoter. Thus, the promoter can be, such as a seed-specific, a leaf-specific, a root-specific, a stem-specific or an abscission-induced promoter. In some embodiments, the expression cassette can further comprise a plant or plant virus expression vector.

The invention provides cloning vehicles comprising an expression cassette (such as a vector) in accordance with the invention or a nucleic acid in accordance with the invention. The cloning vehicle can be a viral vector, a plasmid, a phage, a phagemid, a cosmid, a fosmid, a bacteriophage or an artificial chromosome. The viral vector can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC).

The invention provides transformed cells comprising nucleic acids in accordance with the invention or expression cassettes (such as vectors) in accordance with the invention, or cloning vehicles in accordance with the invention. In some embodiments, the transformed cell can be a bacterial cell, a mammalian cell, a fungal cell, a yeast cell, an insect cell or a plant cell. In some embodiments, the plant cell can be soybeans, rapeseed, oilseed, tomato, cane sugar, a cereal, a potato, wheat, rice, corn, tobacco or barley cell.

The invention provides transgenic non-human animals comprising a nucleic acid in accordance with the invention or an expression cassette (such as a vector) in accordance with the invention. In some embodiments, the animal is a mouse, a rat, a pig, a goat or a sheep.

The invention provides transgenic plants comprising a nucleic acid in accordance with the invention or an expression cassette (such as a vector) in accordance with the invention. The transgenic plant can be a cereal plant, a corn plant, a potato plant, a tomato plant, a wheat plant, an oilseed plant, a rapeseed plant, a soybean plant, a rice plant, a barley plant or a tobacco plant.

The invention provides transgenic seeds comprising a nucleic acid in accordance with the invention or an expression cassette (such as a vector) in accordance with the invention. The transgenic seed can be a cereal plant, a corn seed, a wheat kernel, an oilseed, a rapeseed, a soybean seed, a palm kernel, a sunflower seed, a sesame seed, a peanut or a tobacco plant seed.

The invention provides antisense oligonucleotides comprising nucleic acid sequences complementary to or capable of hybridizing under stringent conditions to nucleic acids in accordance with the invention. In some embodiments, the invention provides methods of inhibiting the translation of an aldolase, such as pyruvate aldolase, HMG and/or KHG aldolase enzyme message in a cell comprising administering to the cell or expressing in the cell an antisense oligonucleotide comprising a nucleic acid sequence complementary to or capable of hybridizing under stringent conditions to a nucleic acid in accordance with the invention. In some embodiments, the antisense oligonucleotide is about 10 to about 50, about 20 to about 60, about 30 to about 70, about 40 to about 80, or about 60 to about 100 bases in length, such as 10, 15, 20, 25, 30, 35, 40, 45, 50, 55, 60, 65, 70, 75, 80, 85, 90, 95, 100 or more bases in length.

The invention provides methods of inhibiting the translation of an aldolase enzyme, such as pyruvate aldolase, such as HMG and/or KHG aldolase enzyme message in a cell comprising administering to the cell or expressing in the cell an antisense oligonucleotide comprising a nucleic acid sequence complementary to or capable of hybridizing under stringent conditions to a nucleic acid in accordance with the invention.

The invention provides double-stranded inhibitory RNA (RNAi, or RNA interference) molecules (including small interfering RNA, or siRNAs, for inhibiting transcription, and microRNAs, or miRNAs, for inhibiting translation) comprising a subsequence of a sequence in accordance with the invention. In some embodiments, the siRNA is about 21 to about 24 residues, or, about at least 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 85, 90, 95, 100 or more duplex nucleotides in length. In some embodiments, the invention provides methods of inhibiting the expression of an aldolase enzyme, such as pyruvate aldolase, such as HMG and/or KHG aldolase enzyme in a cell comprising administering to the cell or expressing in the cell a double-stranded inhibitory RNA (siRNA or miRNA), wherein the RNA comprises a subsequence of a sequence in accordance with the invention.

The invention provides isolated, synthetic or recombinant polypeptides comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a polypeptide or peptide in accordance with the invention over a region of at least about 10, 15, 20, 25, 30, 35, 40, 45, 50, 55, 60, 65, 70, 75, 80, 85, 90, 95, 100, 125, 150, 175, 200, 225, 250, 275, 300, 325, 350 or more residues, or over the full length of the polypeptide. In some embodiments, the sequence identities are determined by analysis with a sequence comparison algorithm or by a visual inspection. Polypeptide or peptide sequences in accordance with the invention include SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, SEQ ID NO:174, SEQ ID NO:176, SEQ ID NO:178, SEQ ID NO:180, SEQ ID NO:182, SEQ ID NO:184, SEQ ID NO:186, SEQ ID NO:188, SEQ ID NO:190, SEQ ID NO:192, SEQ ID NO:194, SEQ ID NO:196, SEQ ID NO:198, SEQ ID NO:200, SEQ ID NO:202, SEQ ID NO:204, SEQ ID NO:206, SEQ ID NO:208, SEQ ID NO:210, SEQ ID NO:212, SEQ ID NO:214, SEQ ID NO:216, SEQ ID NO:218, SEQ ID NO:220, SEQ ID NO:222, SEQ ID NO:224, SEQ ID NO:226, SEQ ID NO:228, SEQ ID NO:230, SEQ ID NO:232, SEQ ID NO:234, SEQ ID NO:236, SEQ ID NO:238, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:260, SEQ ID NO:262, SEQ ID NO:264, SEQ ID NO:266, SEQ ID NO:268, SEQ ID NO:270, SEQ ID NO:272, SEQ ID NO:274, SEQ ID NO:276, SEQ ID NO:278, SEQ ID NO:280, SEQ ID NO:282, SEQ ID NO:284, SEQ ID NO:286, SEQ ID NO:288, SEQ ID NO:290, SEQ ID NO:292, SEQ ID NO:294, SEQ ID NO:296, SEQ ID NO:298, SEQ ID NO:300, SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:320, SEQ ID NO:322, SEQ ID NO:324, SEQ ID NO:326, SEQ ID NO:328, SEQ ID NO:330, SEQ ID NO:332, and SEQ ID NO:334, and subsequences thereof, variants thereof and enzymatically active fragments thereof. Polypeptides in accordance with the invention also include fragments of at least about 10, 15, 20, 25, 30, 35, 40, 45, 50, 75, 80, 85, 90, 95, 100, 150, 200, 250, 300, 350, 400, 450, 500, 550, 600 or more residues in length, or over the full length of an enzyme. Polypeptide or peptide sequences in accordance with the invention include sequence encoded by a nucleic acid in accordance with the invention. Polypeptide or peptide sequences in accordance with the invention include polypeptides or peptides specifically bound by an antibody in accordance with the invention (such as epitopes), or polypeptides or peptides that can generate an antibody in accordance with the invention (such as an immunogen).

In some embodiments, a polypeptide in accordance with the invention has at least one aldolase enzyme activity, such as pyruvate aldolase, such as HMG and/or KHG aldolase, enzyme activity. In other embodiments, a polynucleotide in accordance with the invention encodes a polypeptide that has at least one aldolase enzyme activity, such as pyruvate aldolase, such as HMG and/or KHG aldolase enzyme activity.

Another embodiment of the invention provides isolated, synthetic or recombinant polypeptides or peptides comprising at least 10, 15, 20, 25, 30, 35, 40, 45, 50, 55, 60, 65, 70, 75, 80, 85, 90, 95, 100, 125, 150 or more consecutive bases of polypeptide or peptide sequences in accordance with the invention, sequences substantially identical thereto, and the sequences complementary thereto. The peptide can be, such as an immunogenic fragment, a motif (such as a binding site), a signal sequence, a prepro sequence or an active site.

The invention provides isolated, synthetic or recombinant nucleic acids comprising a sequence encoding a polypeptide having an aldolase, such as pyruvate aldolase, such as HMG and/or KHG aldolase, enzyme activity and a signal sequence, wherein the nucleic acid comprises a sequence in accordance with the invention. A "signal sequence" means a secretion signal or other domain that facilitates secretion of the aldolase in accordance with the invention from the host cell. The signal sequence can be derived from another aldolase, such as pyruvate aldolase, such as HMG and/or KHG aldolase enzyme or a non-aldolase, such as non-pyruvate aldolase, such as non-HMG and/or non-KHG-aldolase enzyme (a heterologous) enzyme. In some embodiments, the invention provides isolated, synthetic or recombinant nucleic acids comprising a sequence encoding a polypeptide having an aldolase, such as pyruvate aldolase, such as HMG and/or KHG aldolase, enzyme activity, wherein the sequence does not contain a signal sequence and the nucleic acid comprises a sequence in accordance with the invention. In some embodiments, the invention provides isolated, synthetic or recombinant polypeptides comprising polypeptides in accordance with the invention lacking all or part of a signal sequence. In some embodiments, the isolated, synthetic or recombinant polypeptide can comprise the polypeptide in accordance with the invention comprising a heterologous signal sequence, such as a heterologous aldolase, such as pyruvate aldolase, such as HMG and/or KHG aldolase enzyme signal sequence or non-aldolase, such as non-pyruvate aldolase, such as non-HMG and/or non-KHG-aldolase enzyme signal sequence.

In some embodiments, the invention provides chimeric proteins comprising a first domain comprising a signal sequence in accordance with the invention and at least a second domain. The protein can be a fusion protein. The second domain can comprise an enzyme. The protein can be a non-enzyme.

The invention provides chimeric polypeptides comprising at least a first domain comprising signal peptide (SP), a prepro sequence and/or a catalytic domain (CD) in accordance with the invention and at least a second domain comprising a heterologous polypeptide or peptide, wherein the heterologous polypeptide or peptide is not naturally associated with the signal peptide (SP), prepro sequence and/or catalytic domain (CD). In some embodiments, the heterologous polypeptide or peptide is not an aldolase, such as pyruvate aldolase, HMG and/or KHG aldolase enzyme. The heterologous polypeptide or peptide can be amino terminal to, carboxy terminal to or on both ends of the signal peptide (SP), prepro sequence and/or catalytic domain (CD).

The invention provides isolated, synthetic or recombinant nucleic acids encoding a chimeric polypeptide, wherein the chimeric polypeptide comprises at least a first domain comprising signal peptide (SP), a prepro domain and/or a catalytic domain (CD) in accordance with the invention and at least a second domain comprising a heterologous polypeptide or peptide, wherein the heterologous polypeptide or peptide is not naturally associated with the signal peptide (SP), prepro domain and/or catalytic domain (CD).

The invention provides isolated, synthetic or recombinant signal sequences (such as signal peptides) consisting of or comprising a sequence as set forth in residues 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 40, 1 to 41, 1 to 42, 1 to 43, 1 to 44, 1 to 45, 1 to 46 or 1 to 47, of a polypeptide in accordance with the invention, such as SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, SEQ ID NO:174, SEQ ID NO:176, SEQ ID NO:178, SEQ ID NO:180, SEQ ID NO:182, SEQ ID NO:184, SEQ ID NO:186, SEQ ID NO:188, SEQ ID NO:190, SEQ ID NO:192, SEQ ID NO:194, SEQ ID NO:196, SEQ ID NO:198, SEQ ID NO:200, SEQ ID NO:202, SEQ ID NO:204, SEQ ID NO:206, SEQ ID NO:208, SEQ ID NO:210, SEQ ID NO:212, SEQ ID NO:214, SEQ ID NO:216, SEQ ID NO:218, SEQ ID NO:220, SEQ ID NO:222, SEQ ID NO:224, SEQ ID NO:226, SEQ ID NO:228, SEQ ID NO:230, SEQ ID NO:232, SEQ ID NO:234, SEQ ID NO:236, SEQ ID NO:238, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:260, SEQ ID NO:262, SEQ ID NO:264, SEQ ID NO:266, SEQ ID NO:268, SEQ ID NO:270, SEQ ID NO:272, SEQ ID NO:274, SEQ ID NO:276, SEQ ID NO:278, SEQ ID NO:280, SEQ ID NO:282, SEQ ID NO:284, SEQ ID NO:286, SEQ ID NO:288, SEQ ID NO:290, SEQ ID NO:292, SEQ ID NO:294, SEQ ID NO:296, SEQ ID NO:298, SEQ ID NO:300, SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:320, SEQ ID NO:322, SEQ ID NO:324, SEQ ID NO:326, SEQ ID NO:328, SEQ ID NO:330, SEQ ID NO:332, or SEQ ID NO:334. In some embodiments, the invention provides signal sequences comprising the first 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more amino terminal residues of a polypeptide in accordance with the invention.

In some embodiments, the aldolase, such as pyruvate aldolase, such as HMG and/or KHG aldolase enzyme, activity comprises a specific activity from about 10 to about 12,000 units per milligram of protein. In other embodiments, the aldolase, such as pyruvate aldolase, such as HMG and/or KHG aldolase, enzyme activity comprises a specific activity from about 1000 to about 10,000 units per milligram of protein, or, from about 5000 to about 7500 units per milligram of protein. Alternatively, the aldolase, such as pyruvate aldolase, such as HMG and/or KHG aldolase enzyme, activity comprises a specific activity in the range from about 10 to about 7500 units per milligram of protein, or, from about 5000 to about 12,000 units per milligram of protein. In some embodiments, the aldolase, such as pyruvate aldolase, such as HMG and/or KHG aldolase enzyme, activity comprises a specific activity in the range from about 10 to about 5000 units per milligram of protein, or, from about 7500 to about 10,000 units per milligram of protein. In order embodiments, the aldolase, such as pyruvate aldolase, such as HMG and/or KHG aldolase, enzyme activity comprises a specific activity in the range from about 10 to about 2500 units per milligram of protein. Alternatively, the aldolase, such as pyruvate aldolase, such as HMG and/or KHG aldolase enzyme, activity comprises a specific activity in the range from about 10 to about 1000 units per milligram of protein. An exemplary method to measure the activity of different aldolases, such as pyruvate aldolases, such as HMG and/or KHG aldolase enzymes, uses a general substrate, 4-carboxy-4-hydroxy-2-oxoadipate ("CHA"). A typical assay comprises 50 mM sodium phosphate pH 7.5, 1 mM MgCl2, 1 mM CHA, 10 µg/ml D-lactate dehydrogenase ("LDH") from *Lactobacillus leichmanii* (Sigma-Aldrich, St. Louis, Mo.), 0.5 mM NADH. The assay is started by adding the enzyme to be measured. Liberation of pyruvate, coupled to the formation of NAD+ is monitored continuously in a spectrophotometer at 340 nm. A unit of enzyme activity is defined as the amount that liberates sufficient pyruvate to lower the absorbance at 340 nm by 1 OD per minute.

In other embodiments, the thermotolerance of the aldolase, such as pyruvate aldolase, such as HMG and/or KHG aldolase enzyme, comprises retention of at least half of the specific activity of the aldolase, such as pyruvate aldolase, such as HMG and/or KHG aldolase enzyme after being heated to an elevated temperature, such as a temperature from about 0° C. to about 20° C., about 20° C. to about 37° C., about 37° C. to about 50° C., about 50° C. to about 70° C., about 70° C. to about 75° C., about 75° C. to about 80° C., about 80° C. to about 85° C., about 85° C. to about 90° C., about 90° C. to about 95° C., about 95° C. to about 100° C., about 100° C. to about 110° C., or higher. Alternatively, the thermotolerance can comprise retention of specific activity from about 10 to about 12,000 units per milligram of protein, or, from about 5000 to about 10,000 units per milligram of protein, after being heated to an elevated temperature, as described above. In other embodiments, the thermotolerance can comprise retention of specific activity in the range from about 10 to about 5000 units per milligram of protein after being heated to an elevated temperature, as described above.

The invention provides isolated, synthetic or recombinant polypeptides in accordance with the invention, wherein the polypeptides comprise at least one glycosylation site. In some embodiments, glycosylation can be an N-linked glycosylation. In some embodiments, the polypeptide can be glycosylated after being expressed in a *P. pastoris* or a *S. pombe* host or in a mammalian host cell.

In some embodiments, the polypeptide can retain aldolase, such as pyruvate aldolase, such as HMG and/or KHG aldolase enzyme, activity under conditions comprising about pH 6.5, pH 6, pH 5.5, pH 5, pH 4.5, pH 4.0, pH 3.5, pH 3.0 or less (more acidic) pH. In other embodiments, the polypeptide can retain an aldolase, such as pyruvate aldolase, such as HMG and/or KHG aldolase enzyme, activity under conditions comprising about pH 7, pH 7.5 pH 8.0, pH 8.5, pH 9, pH 9.5, pH 10, pH 10.5, pH 11.0, pH 11.5, pH 12, pH 12.5 or more (more basic) pH. In some embodiments, the polypeptide can retain an aldolase, such as pyruvate aldolase, such as HMG and/or KHG aldolase enzyme, activity after exposure to conditions comprising about pH 6.5, pH 6, pH 5.5, pH 5, pH 4.5, pH 4.0, pH 3.5, pH 3.0 or less (more acidic) pH. In other embodiments, the polypeptide can retain an aldolase, such as pyruvate aldolase, such as HMG and/or KHG aldolase enzyme, activity after exposure to conditions comprising about pH 7, pH 7.5 pH 8.0, pH 8.5, pH 9, pH 9.5, pH 10, pH 10.5, pH 11.0, pH 11.5, pH 12, pH 12.5 or more (more basic) pH.

In some embodiments, the aldolase, such as pyruvate aldolase, such as HMG and/or KHG aldolase enzyme in accordance with the invention has activity at under alkaline conditions, such as the alkaline conditions of the gut, such as the small intestine. In some embodiments, the polypeptide can retains activity after exposure to the acidic pH of the stomach.

The invention provides protein preparations comprising a polypeptide (including peptides) in accordance with the invention, wherein the protein preparation comprises a liquid, a solid or a gel. In some embodiments, the invention provides heterodimers comprising a polypeptide in accordance with the invention and a second member, such as a polypeptide or other (second) domain. The second member of the heterodimer can be a different aldolase, such as pyruvate aldolase, such as HMG and/or KHG aldolase enzyme, a different enzyme or another protein. In some embodiments, the second domain can be a polypeptide and the heterodimer can be a fusion protein. In some embodiments, the second domain can be an epitope or a tag. In some embodiments, the invention provides homomultimers, including, but not limited to, homodimers, homotrimers, homotetramers, homopentamers, and homohexamers, comprising a polypeptide in accordance with the invention.

The invention provides immobilized polypeptides (including peptides) having aldolase, such as pyruvate aldolase, such as HMG and/or KHG aldolase enzyme, activity, wherein the immobilized polypeptide comprises a polypeptide in accordance with the invention, a polypeptide encoded by a nucleic acid in accordance with the invention, or a polypeptide comprising a polypeptide in accordance with the invention and a second domain. In some embodiments, the polypeptide can be immobilized on a cell, a metal, a resin, a polymer, a ceramic, a glass, a microelectrode, a graphitic particle, a bead, a gel, a plate, an array or a capillary tube.

The invention also provides arrays comprising an immobilized nucleic acid in accordance with the invention, including, such as probes in accordance with the invention. In some embodiments, the invention also provides arrays comprising an antibody in accordance with the invention.

The invention provides isolated, synthetic or recombinant antibodies that specifically bind to a polypeptide in accordance with the invention or to a polypeptide encoded by a nucleic acid in accordance with the invention. These antibodies in accordance with the invention can be a monoclonal or a polyclonal antibody. In some embodiments, the invention provides hybridomas comprising an antibody in accordance with the invention, such as an antibody that specifically binds to a polypeptide in accordance with the invention or to a polypeptide encoded by a nucleic acid in accordance with the invention. In some embodiments, the invention provides nucleic acids encoding these antibodies.

The invention provides methods of isolating or identifying polypeptides having aldolase, such as pyruvate aldolase, such as HMG and/or KHG aldolase, enzyme activity comprising the steps of: (a) providing an antibody in accordance with the invention; (b) providing a sample comprising polypeptides; and (c) contacting the sample of step (b) with the antibody of step (a) under conditions wherein the antibody can specifically bind to the polypeptide, thereby isolating or identifying a polypeptide having an aldolase, such as pyruvate aldolase, such as HMG and/or KHG aldolase enzyme, activity.

The invention provides methods of making an anti-aldolase, such as anti-pyruvate aldolase, such as anti-HMG and/or anti-KHG aldolase enzyme antibody comprising administering to a non-human animal a nucleic acid in accordance with the invention or a polypeptide in accordance with the invention or subsequences thereof in an amount sufficient to generate a humoral immune response, thereby making an anti-aldolase, such as anti-pyruvate aldolase, such as anti-HMG and/or anti-KHG aldolase enzyme antibody. In some embodiments, the invention provides methods of making an anti-aldolase, such as anti-pyruvate aldolase, such as anti-HMG and/or anti-KHG aldolase immune response (cellular or humoral) comprising administering to a non-human animal a nucleic acid in accordance with the invention or a polypeptide in accordance with the invention or subsequences thereof in an amount sufficient to generate an immune response (cellular or humoral).

The invention provides methods of producing a recombinant polypeptide comprising the steps of: (a) providing a nucleic acid in accordance with the invention operably linked to a promoter; and (b) expressing the nucleic acid of step (a) under conditions that allow expression of the polypeptide, thereby producing a recombinant polypeptide. In some embodiments, the method can further comprise transforming a host cell with the nucleic acid of step (a) followed by expressing the nucleic acid of step (a), thereby producing a recombinant polypeptide in a transformed cell.

The invention provides methods for identifying a polypeptide having aldolase, such as pyruvate aldolase, such as HMG and/or KHG aldolase enzyme, activity comprising the following steps: (a) providing a polypeptide in accordance with the invention; or a polypeptide encoded by a nucleic acid in accordance with the invention; (b) providing aldolase, such as pyruvate aldolase, such as HMG and/or KHG aldolase enzyme substrate; and (c) contacting the polypeptide or a fragment or variant thereof of step (a) with the substrate of step (b) and detecting a decrease in the amount of substrate or an increase in the amount of a reaction product, wherein a decrease in the amount of the substrate or an increase in the amount of the reaction product detects a polypeptide having an aldolase, such as pyruvate aldolase, such as HMG and/or KHG aldolase enzyme, activity. In some embodiments, the substrate is a carbohydrate, a carbohydrate-comprising compound and/or a carbohydrate mimetic.

The invention provides methods for identifying aldolase, such as pyruvate aldolase, such as HMG and/or KHG aldolase enzyme substrate comprising the following steps: (a) providing a polypeptide in accordance with the invention; or a polypeptide encoded by a nucleic acid in accordance with the invention; (b) providing a test substrate; and (c) contacting the polypeptide of step (a) with the test substrate of step (b) and detecting a decrease in the amount of substrate or an increase in the amount of reaction product, wherein a decrease in the amount of the substrate or an increase in the amount of a reaction product identifies the test substrate as an aldolase, such as pyruvate aldolase, HMG and/or KHG aldolase enzyme substrate.

The invention provides methods of determining whether a test compound specifically binds to a polypeptide comprising the following steps: (a) expressing a nucleic acid or a vector comprising the nucleic acid under conditions permissive for translation of the nucleic acid to a polypeptide, wherein the nucleic acid comprises a nucleic acid in accordance with the invention, or, providing a polypeptide in accordance with the invention; (b) providing a test compound; (c) contacting the polypeptide with the test compound; and (d) determining whether the test compound of step (b) specifically binds to the polypeptide.

The invention provides methods for identifying a modulator of an aldolase, such as pyruvate aldolase, such as HMG and/or KHG aldolase enzyme, activity comprising the following steps: (a) providing a polypeptide in accordance with the invention or a polypeptide encoded by a nucleic acid in accordance with the invention; (b) providing a test compound; (c) contacting the polypeptide of step (a) with the test compound of step (b) and measuring an activity of the aldolase, such as pyruvate aldolase, such as HMG and/or KHG aldolase enzyme, wherein a change in the aldolase, such as pyruvate aldolase, such as HMG and/or KHG aldolase enzyme, activity measured in the presence of the test compound compared to the activity in the absence of the test compound provides a determination that the test compound modulates the aldolase, such as pyruvate aldolase, such as HMG and/or KHG aldolase enzyme, activity. In some embodiments, the aldolase, such as pyruvate aldolase, such as HMG and/or KHG aldolase enzyme, activity can be measured by providing an aldolase, such as pyruvate aldolase, HMG and/or KHG aldolase enzyme substrate and detecting a decrease in the amount of the substrate or an increase in the amount of a reaction product, or, an increase in the amount of the substrate or a decrease in the amount of a reaction product. A decrease in the amount of the substrate or an increase in the amount of the reaction product with the test compound as compared to the amount of substrate or reaction product without the test compound identifies the test compound as an activator of aldolase, such as pyruvate aldolase, such as HMG and/or KHG aldolase enzyme, activity. An increase in the amount of the substrate or a decrease in the amount of the reaction product with the test compound as compared to the amount of substrate or reaction product without the test compound identifies the test compound as an inhibitor of aldolase, such as pyruvate aldolase, such as HMG and/or KHG aldolase enzyme, activity.

The invention provides computer systems comprising a processor and a data storage device wherein said data storage device has stored thereon a polypeptide sequence or a nucleic acid sequence in accordance with the invention (such as a polypeptide or peptide encoded by a nucleic acid in accordance with the invention). In some embodiments, the computer system can further comprise a sequence comparison algorithm and a data storage device having at least one reference sequence stored thereon. In other embodiments, the sequence comparison algorithm comprises a computer program that indicates polymorphisms. In some embodiments, the computer system can further comprise an identifier that identifies one or more features in said sequence. In some embodiments, the invention provides computer readable media having stored thereon a polypeptide sequence or a nucleic acid sequence in accordance with the invention. In some embodiments, the invention provides methods for identifying a feature in a sequence comprising the steps of: (a) reading the sequence using a computer program which identifies one or more features in a sequence, wherein the sequence comprises a polypeptide sequence or a nucleic acid sequence in accordance with the invention; and (b) identifying one or more features in the sequence with the computer program. In some embodiments, the invention provides methods for comparing a first sequence to a second sequence comprising the steps of: (a) reading the first sequence and the second sequence through use of a computer program which compares sequences, wherein the first sequence comprises a polypeptide sequence or a nucleic acid sequence in accordance with the invention; and (b) determining differences between the first sequence and the second sequence with the computer program. The step of determining differences between the first sequence and the second sequence can further comprise the step of identifying polymorphisms. In some embodiments, the method can further comprise an identifier that identifies one or more features in a sequence. In other embodiments, the method can comprise reading the first sequence using a computer program and identifying one or more features in the sequence.

The invention provides methods for isolating or recovering a nucleic acid encoding a polypeptide having an aldolase, such as pyruvate aldolase, such as HMG and/or KHG aldolase enzyme, activity from a sample, such as an environmental sample, comprising the steps of: (a) providing an amplification primer sequence pair for amplifying a nucleic acid encoding a polypeptide having an aldolase, such as pyruvate aldolase, such as HMG and/or KHG aldolase enzyme, activity, wherein the primer pair is capable of amplifying a nucleic acid in accordance with the invention; (b) isolating a nucleic acid from the sample or treating the sample such that nucleic acid in the sample is accessible for hybridization to the amplification primer pair; and, (c) combining the nucleic acid of step (b) with the amplification primer pair of step (a) and amplifying nucleic acid from the sample, thereby isolating or recovering a nucleic acid encoding a polypeptide having an aldolase, such as pyruvate aldolase, such as HMG and/or KHG aldolase enzyme, activity from a sample. One or each member of the amplification primer sequence pair can comprise an oligonucleotide comprising an amplification primer sequence pair in accordance with the invention, such as having at least about 10 to 50 consecutive bases of a sequence in accordance with the invention. In one embodiment of the invention, the sample is an environmental sample.

The invention provides methods for isolating or recovering a nucleic acid encoding a polypeptide having an aldolase, such as pyruvate aldolase, such as HMG and/or KHG aldolase enzyme, activity from a sample, such as an environmental sample, comprising the steps of: (a) providing a polynucleotide probe comprising a nucleic acid in accordance with the invention or a subsequence thereof; (b) isolating a nucleic acid from the sample or treating the sample such that nucleic acid in the sample is accessible for hybridization to a polynucleotide probe of step (a); (c) combining the isolated nucleic acid or the treated sample of step (b) with the polynucleotide probe of step (a); and (d) isolating a nucleic acid that specifically hybridizes with the polynucleotide probe of step (a), thereby isolating or recovering a nucleic acid encoding a polypeptide having an aldolase, such as pyruvate aldolase, such as HMG and/or KHG aldolase enzyme, activity from a sample. The sample can comprise a water sample, a liquid sample, a soil sample, an air sample or a biological sample. In some embodiments, the biological sample can be derived from a bacterial cell, a protozoan cell, an insect cell, a yeast cell, a plant cell, a fungal cell or a mammalian cell. In one embodiment of the invention, the sample is an environmental sample.

The invention provides methods of generating a variant of a nucleic acid encoding a polypeptide having an aldolase, such as pyruvate aldolase, such as HMG and/or KHG aldolase enzyme, activity comprising the steps of: (a) providing a template nucleic acid comprising a nucleic acid in accordance with the invention; and (b) modifying, deleting or adding one or more nucleotides in the template sequence, or a combination thereof, to generate a variant of the template nucleic acid. In some embodiments, the method can further comprise expressing the variant nucleic acid to generate a variant aldolase, such as pyruvate aldolase, such as HMG and/or KHG aldolase enzyme polypeptide. The modifications, additions or deletions can be introduced by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis (GSSM), synthetic ligation reassembly (SLR), Chromosomal Saturation Mutagenesis (CSM) or a combination thereof. In other embodiments, the modifications, additions or deletions are introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

In some embodiments, the method can be iteratively repeated until an aldolase, such as pyruvate aldolase, HMG and/or KHG aldolase enzyme having an altered or different activity or an altered or different stability from that of a polypeptide encoded by the template nucleic acid is produced. In some embodiments, the variant aldolase, such as pyruvate aldolase, such as HMG and/or KHG aldolase enzyme polypeptide is thermotolerant, and retains some activity after being exposed to an elevated temperature. In other embodiments, the variant aldolase, such as pyruvate aldolase, such as HMG and/or KHG aldolase enzyme polypeptide has increased glycosylation as compared to the aldolase, such as pyruvate aldolase, such as HMG and/or KHG aldolase enzyme encoded by a template nucleic acid. Alternatively, the variant aldolase, such as pyruvate aldolase, such as HMG and/or KHG aldolase polypeptide has an aldolase, such as pyruvate aldolase, such as HMG and/or KHG aldolase enzyme, activity under a high temperature, wherein the aldolase, such as pyruvate aldolase, such as HMG and/or KHG aldolase enzyme encoded by the template nucleic acid is not active under the high temperature. In some embodiments, the method can be iteratively repeated until an aldolase, such as pyruvate aldolase, HMG and/or KHG aldolase enzyme coding sequence having an altered codon usage from that of the template nucleic acid is produced. In other embodiments, the method can be iteratively repeated until an aldolase, such as pyruvate aldolase, HMG and/or KHG aldolase enzyme gene having higher or lower level of message expression or stability from that of the template nucleic acid is produced.

The invention provides methods for modifying codons in a nucleic acid encoding a polypeptide having an aldolase, such as pyruvate aldolase, such as HMG and/or KHG aldolase enzyme, activity to increase its expression in a host cell, the method comprising the following steps: (a) providing a nucleic acid in accordance with the invention encoding a polypeptide having an aldolase, such as pyruvate aldolase, such as HMG and/or KHG aldolase enzyme, activity; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying codons in a nucleic acid encoding a polypeptide having an aldolase, such as pyruvate aldolase, such as HMG and/or KHG aldolase enzyme, activity; the method comprising the following steps: (a) providing a nucleic acid in accordance with the invention; and, (b) identifying a codon in the nucleic acid of step (a) and replacing it with a different codon encoding the same amino acid as the replaced codon, thereby modifying codons in a nucleic acid encoding an aldolase, such as pyruvate aldolase, HMG and/or KHG aldolase enzyme.

The invention provides methods for modifying codons in a nucleic acid encoding a polypeptide having an aldolase, such as pyruvate aldolase, such as HMG and/or KHG aldolase enzyme, activity to increase its expression in a host cell, the method comprising the following steps: (a) providing a nucleic acid in accordance with the invention encoding an aldolase, such as pyruvate aldolase, HMG and/or KHG aldolase enzyme polypeptide; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying a codon in a nucleic acid encoding a polypeptide having an aldolase, such as pyruvate aldolase, such as HMG and/or KHG aldolase enzyme, activity to decrease its expression in a host cell, the method comprising the following steps: (a) providing a nucleic acid in accordance with the invention; and (b) identifying at least one preferred codon in the nucleic acid of step (a) and replacing it with a non-preferred or less preferred codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to decrease its expression in a host cell. In some embodiments, the host cell can be a bacterial cell, a fungal cell, an insect cell, a yeast cell, a plant cell or a mammalian cell.

The invention provides methods for producing a library of nucleic acids encoding a plurality of modified aldolase, such as pyruvate aldolase, such as HMG and/or KHG aldolase enzyme active sites or substrate binding sites, wherein the modified active sites or substrate binding sites are derived from a first nucleic acid comprising a sequence encoding a first active site or a first substrate binding site the method comprising the following steps: (a) providing a first nucleic acid encoding a first active site or first substrate binding site, wherein the first nucleic acid sequence comprises a sequence that hybridizes under stringent conditions to a nucleic acid in accordance with the invention, and the nucleic acid encodes an aldolase, such as pyruvate aldolase, HMG and/or KHG aldolase enzyme active site or an aldolase, such as pyruvate aldolase, HMG and/or KHG aldolase enzyme substrate binding site; (b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified aldolase, such as pyruvate aldolase, such as HMG and/or KHG aldolase enzyme active sites or substrate binding sites. In some embodiments, the method comprises mutagenizing the first nucleic acid of step (a) by a method comprising an optimized directed evolution system, Gene Site Saturation Mutagenesis (GSSM), synthetic ligation reassembly (SLR), error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, and a combination thereof. In other embodiments, the method comprises mutagenizing the first nucleic acid of step (a) or variants by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

The invention provides methods for making a small molecule comprising the following steps: (a) providing a plurality of biosynthetic enzymes capable of synthesizing or modifying a small molecule, wherein one of the enzymes comprises an aldolase, such as pyruvate aldolase, HMG and/or KHG aldolase enzyme encoded by a nucleic acid in accordance with the invention; (b) providing a substrate for at least one of the enzymes of step (a); and (c) reacting the substrate of step (b) with the enzymes under conditions that facilitate a plurality of biocatalytic reactions to generate a small molecule by a series of biocatalytic reactions. In some embodiments, the invention provides methods for modifying a small molecule comprising the following steps: (a) providing an aldolase, such as pyruvate aldolase, HMG and/or KHG aldolase enzyme, wherein the enzyme comprises a polypeptide in accordance with the invention, or, a polypeptide encoded by a nucleic acid in accordance with the invention, or a subsequence thereof; (b) providing a small molecule; and (c) reacting the enzyme of step (a) with the small molecule of step (b) under conditions that facilitate an enzymatic reaction catalyzed by the aldolase, such as pyruvate aldolase, such as HMG and/or KHG aldolase enzyme, thereby modifying a small molecule by an aldolase, such as pyruvate aldolase, HMG and/or KHG aldolase enzymatic reaction. In some embodiments, the method can comprise a plurality of small molecule substrates for the enzyme of step (a), thereby generating a library of modified small molecules produced by at least one enzymatic reaction catalyzed by the aldolase, such as pyruvate aldolase, such as HMG and/or KHG aldolase enzyme. In some embodiments, the method can comprise a plurality of additional enzymes under conditions that facilitate a plurality of biocatalytic reactions by the enzymes to form a library of modified small molecules produced by the plurality of enzymatic reactions. In other embodiments, the method can further comprise the step of testing the library to determine if a particular modified small molecule that exhibits a desired activity is present within the library. The step of testing the library can further comprise the steps of systematically eliminating all but one of the biocatalytic reactions used to produce a portion of the plurality of the modified small molecules within the library by testing the portion of the modified small molecule for the presence or absence of the particular modified small molecule with a desired activity, and identifying at least one specific biocatalytic reaction that produces the particular modified small molecule of desired activity.

The invention provides methods for determining a functional fragment of an aldolase, such as pyruvate aldolase, HMG and/or KHG aldolase enzyme comprising the steps of: (a) providing an aldolase, such as pyruvate aldolase, HMG and/or KHG aldolase enzyme, wherein the enzyme comprises a polypeptide in accordance with the invention, or a polypeptide encoded by a nucleic acid in accordance with the invention, or a subsequence thereof; and (b) deleting a plurality of amino acid residues from the sequence of step (a) and testing the remaining subsequence for an aldolase, such as pyruvate aldolase, such as HMG and/or KHG aldolase enzyme, activity, thereby determining a functional fragment of an aldolase, such as pyruvate aldolase, HMG and/or KHG aldolase enzyme. In some embodiments, the aldolase, such as pyruvate aldolase, such as HMG and/or KHG aldolase enzyme, activity is measured by providing an aldolase, such as pyruvate aldolase, HMG and/or KHG aldolase enzyme substrate and detecting a decrease in the amount of the substrate or an increase in the amount of a reaction product.

The invention provides methods for whole cell engineering of new or modified phenotypes by using real-time metabolic flux analysis, the method comprising the following steps: (a) making a modified cell by modifying the genetic composition of a cell, wherein the genetic composition is modified by addition to the cell of a nucleic acid in accordance with the invention; (b) culturing the modified cell to generate a plurality of modified cells; (c) measuring at least one metabolic parameter of the cell by monitoring the cell culture of step (b) in real time; and, (d) analyzing the data of step (c) to determine if the measured parameter differs from a comparable measurement in an unmodified cell under similar conditions, thereby identifying an engineered phenotype in the cell using real-time metabolic flux analysis. In some embodiments, the genetic composition of the cell can be modified by a method comprising deletion of a sequence or modification of a sequence in the cell, or, knocking out the expression of a gene. In some embodiments, the method can further comprise selecting a cell comprising a newly engineered phenotype. In other embodiments, the method can comprise culturing the selected cell, thereby generating a new cell strain comprising a newly engineered phenotype.

The invention provides methods of increasing thermotolerance or thermostability of an aldolase, such as pyruvate aldolase, HMG and/or KHG aldolase enzyme polypeptide, the method comprising glycosylating an aldolase, such as pyruvate aldolase, HMG and/or KHG aldolase enzyme polypeptide, wherein the polypeptide comprises at least thirty contiguous amino acids of a polypeptide in accordance with the invention; or a polypeptide encoded by a nucleic acid sequence in accordance with the invention, thereby increasing the thermotolerance or thermostability of the aldolase, such as pyruvate aldolase, such as HMG and/or KHG aldolase polypeptide. In some embodiments, the aldolase, such as pyruvate aldolase, such as HMG and/or KHG aldolase enzyme specific activity can be thermostable or thermotolerant at a temperature in the range from greater than about 37° C. to about 95° C.

The invention provides methods for overexpressing a recombinant aldolase, such as pyruvate aldolase, such as HMG and/or KHG aldolase polypeptide in a cell comprising expressing a vector comprising a nucleic acid comprising a nucleic acid in accordance with the invention or a nucleic acid sequence in accordance with the invention, wherein the sequence identities are determined by analysis with a sequence comparison algorithm or by visual inspection, wherein overexpression is effected by use of a high activity promoter, a dicistronic vector or by gene amplification of the vector.

The invention provides methods of making a transgenic plant comprising the following steps: (a) introducing a heterologous nucleic acid sequence into the cell, wherein the heterologous nucleic sequence comprises a nucleic acid sequence in accordance with the invention, thereby producing a transformed plant cell; and (b) producing a transgenic plant from the transformed cell. In some embodiments, the step (a) can further comprise introducing the heterologous nucleic acid sequence by electroporation or microinjection of plant cell protoplasts. In other embodiments, the step (a) can further comprise introducing the heterologous nucleic acid sequence directly to plant tissue by DNA particle bombardment. Alternatively, the step (a) can further comprise introducing the heterologous nucleic acid sequence into the plant cell DNA using an *Agrobacterium tumefaciens* host. In some embodiments, the plant cell can be a cane sugar, beet, soybean, tomato, potato, corn, rice, wheat, tobacco or barley cell.

The invention provides methods of expressing a heterologous nucleic acid sequence in a plant cell comprising the following steps: (a) transforming the plant cell with a heterologous nucleic acid sequence operably linked to a promoter, wherein the heterologous nucleic sequence comprises a nucleic acid in accordance with the invention; (b) growing the plant under conditions wherein the heterologous nucleic acids sequence is expressed in the plant cell. In some embodiments, the invention provides methods of expressing a heterologous nucleic acid sequence in a plant cell comprising the following steps: (a) transforming the plant cell with a heterologous nucleic acid sequence operably linked to a promoter, wherein the heterologous nucleic sequence comprises a sequence in accordance with the invention; (b) growing the plant under conditions wherein the heterologous nucleic acids sequence is expressed in the plant cell.

The invention provides feeds or foods comprising a polypeptide in accordance with the invention, or a polypeptide encoded by a nucleic acid in accordance with the invention. In some embodiments, the invention provides foods, feeds, liquids, such as beverages (such as fruit juices or beer), breads or doughs or bread products, or beverage precursors (such as wort), comprising a polypeptide in accordance with the invention. In other embodiments, the invention provides foods, feeds, or beverage additives comprising a polypeptide in accordance with the invention. In some embodiments, the invention provides foods or nutritional supplements, such as for a human or an animal, comprising a polypeptide in accordance with the invention, such as a polypeptide encoded by the nucleic acid in accordance with the invention.

In some embodiments, the polypeptide in the food or nutritional supplement can be glycosylated. In some embodiments, the invention provides edible enzyme delivery matrices comprising a polypeptide in accordance with the invention, such as a polypeptide encoded by the nucleic acid in accordance with the invention. In some embodiments, the delivery matrix comprises a pellet. In some embodiments, the polypeptide can be glycosylated. In some embodiments, the aldolase, such as pyruvate aldolase, such as HMG and/or KHG aldolase enzyme, activity is thermotolerant. In other embodiments, the aldolase, such as pyruvate aldolase, such as HMG and/or KHG aldolase enzyme, activity is thermostable.

The invention provides foods, feeds or nutritional supplements comprising a polypeptide in accordance with the invention. In some embodiments, the invention provides methods for utilizing an aldolase, such as pyruvate aldolase, HMG and/or KHG aldolase enzyme as a nutritional supplement in an animal diet, the method comprising: preparing a nutritional supplement containing an aldolase, such as pyruvate aldolase, HMG and/or KHG aldolase enzyme comprising at least thirty contiguous amino acids of a polypeptide in accordance with the invention; and administering the nutritional supplement to an animal. The animal can be a human, a ruminant or a monogastric animal. The aldolase, such as pyruvate aldolase, such as HMG and/or KHG aldolase enzyme can be prepared by expression of a polynucleotide encoding the aldolase, such as pyruvate aldolase, such as HMG and/or KHG aldolase enzyme in an organism selected from the group consisting of a bacterium, a yeast, a plant, an insect, a fungus and an animal. The organism can be selected from the group consisting of an *S. pombe, S. cerevisiae,*

*Pichia pastoris*, *E. coli*, *Streptomyces* sp., *Bacillus* sp. *Pseudomonas* sp., *Aspergillus* sp. and *Lactobacillus* sp.

The invention provides edible enzyme delivery matrices comprising a thermostable recombinant aldolase, such as pyruvate aldolase, such as HMG and/or KHG aldolase enzyme, such as a polypeptide in accordance with the invention. In some embodiments, the invention provides methods for delivering an aldolase, such as pyruvate aldolase, HMG and/or KHG aldolase enzyme supplement to an animal, the method comprising: preparing an edible enzyme delivery matrix in the form of pellets comprising a granulate edible carrier and a thermostable recombinant aldolase, such as pyruvate aldolase, such as HMG and/or KHG aldolase enzyme, wherein the pellets readily disperse the aldolase, such as pyruvate aldolase, such as HMG and/or KHG aldolase enzyme contained therein into aqueous media, and administering the edible enzyme delivery matrix to the animal. The recombinant aldolase, such as pyruvate aldolase, such as HMG and/or KHG aldolase enzyme can comprise a polypeptide in accordance with the invention. The aldolase, such as pyruvate aldolase, such as HMG and/or KHG aldolase enzyme can be glycosylated to provide thermostability at pelletizing conditions. The delivery matrix can be formed by pelletizing a mixture comprising a grain germ and an aldolase, such as pyruvate aldolase, HMG and/or KHG aldolase enzyme. The pelletizing conditions can include application of steam. The pelletizing conditions can comprise application of a temperature in excess of about 80° C. for about 5 minutes and the enzyme retains a specific activity of at least 350 to about 900 units per milligram of enzyme.

In some embodiments, the invention provides pharmaceutical compositions comprising an aldolase, such as pyruvate aldolase, HMG and/or KHG aldolase enzyme in accordance with the invention, or a polypeptide encoded by a nucleic acid in accordance with the invention. In some embodiments, the pharmaceutical composition acts as a digestive aid.

In some embodiments, a carbon-carbon bond-containing compound is contacted a polypeptide in accordance with the invention having aldolase enzyme activity, such as pyruvate aldolase, such as HMG and/or KHG aldolase enzyme activity, at a pH ranging from about pH 3.0 to about 9.0, about 3.0 to about 10.0, about 3.0 to about 11.0 or more. In other embodiments, a carbon-carbon bond-containing compound is contacted with the aldolase, such as pyruvate aldolase, such as HMG and/or KHG aldolase enzyme, at a temperature of at least about 55° C., 60° C., 65° C., 70° C., 75° C., 80° C., 85° C., 90° C., or more.

This disclosure provides, among other things, polypeptides that are useful in facilitating a reaction in processes for producing monatin, monatin derivatives, and salts thereof, for example in the production of R-2-hydroxy 2-(indol-3-ylmethyl)-4-keto glutaric acid (also referred to as R-alpha keto acid monatin, R-monatin precursor, R-MP, and the alpha keto form of monatin), a precursor for certain stereoisomers of monatin, such as R,R and S,R monatin. The disclosure also provides methods of making monatin, monatin derivatives, and salts and internal condensation products thereof using one or more polypeptides of the invention. The methods of synthesizing R-MP, stereoisomers of monatin and/or stereoisomers of monatin derivatives include the use of one or more polypeptides with aldolase activity of any of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO: 110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, SEQ ID NO:174, SEQ ID NO:176, SEQ ID NO:178, SEQ ID NO:180, SEQ ID NO:182, SEQ ID NO:184, SEQ ID NO:186, SEQ ID NO:188, SEQ ID NO:190, SEQ ID NO:192, SEQ ID NO:194, SEQ ID NO:196, SEQ ID NO:198, SEQ ID NO:200, SEQ ID NO:202, SEQ ID NO:204, SEQ ID NO:206, SEQ ID NO:208, SEQ ID NO:210, SEQ ID NO:212, SEQ ID NO:214, SEQ ID NO:216, SEQ ID NO:218, SEQ ID NO:220, SEQ ID NO:222, SEQ ID NO:224, SEQ ID NO:226, SEQ ID NO:228, SEQ ID NO:230, SEQ ID NO:232, SEQ ID NO:234, SEQ ID NO:236, SEQ ID NO:238, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:260, SEQ ID NO:262, SEQ ID NO:264, SEQ ID NO:266, SEQ ID NO:268, SEQ ID NO:270, SEQ ID NO:272, SEQ ID NO:274, SEQ ID NO:276, SEQ ID NO:278, SEQ ID NO:280, SEQ ID NO:282, SEQ ID NO:284, SEQ ID NO:286, SEQ ID NO:288, SEQ ID NO:290, SEQ ID NO:292, SEQ ID NO:294, SEQ ID NO:296, SEQ ID NO:298, SEQ ID NO:300, SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:320, SEQ ID NO:322, SEQ ID NO:324, SEQ ID NO:326, SEQ ID NO:328, SEQ ID NO:330, SEQ ID NO:332, and SEQ ID NO:334, and enzymatically active fragments thereof.

Also, the methods of synthesizing R-MP, stereoisomers of monatin and/or stereoisomers of monatin derivatives may include the use of a polypeptide with aldolase activity encoded by a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to nucleic acid in accordance with the invention, including SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:279, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305, SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, and SEQ ID NO:338 over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more residues.

Furthermore, the methods of synthesizing R-MP, stereoisomers of monatin and/or stereoisomers of monatin derivatives may include the use of a polypeptide with aldolase activity encoded by a nucleic acid sequence that hybridizes under stringent condition to a nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:279, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305, SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, and SEQ ID NO:338.

The invention provides a method, comprising: producing a product chosen from monatin, monatin derivatives, salts thereof, and combinations thereof in a multi-step pathway, wherein a reaction in the pathway is facilitated by one or more polypeptides chosen from isolated or recombinant polypeptides comprising the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, SEQ ID NO:174, SEQ ID NO:176, SEQ ID NO:178, SEQ ID NO:180, SEQ ID NO:182, SEQ ID NO:184, SEQ ID NO:186, SEQ ID NO:188, SEQ ID NO:190, SEQ ID NO:192, SEQ ID NO:194, SEQ ID NO:196, SEQ ID NO:198, SEQ ID NO:200, SEQ ID NO:204, SEQ ID NO:206, SEQ ID NO:208, SEQ ID NO:210, SEQ ID NO:212, SEQ ID NO:214, SEQ ID NO:216, SEQ ID NO:218, SEQ ID NO:220, SEQ ID NO:222, SEQ ID NO:224, SEQ ID NO:226, SEQ ID NO:228, SEQ ID NO:230, SEQ ID NO:232, SEQ ID NO:234, SEQ ID NO:236, SEQ ID NO:238, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:260, SEQ ID NO:262, SEQ ID NO:264, SEQ ID NO:266, SEQ ID NO:268, SEQ ID NO:270, SEQ ID NO:272, SEQ ID NO:274, SEQ ID NO:276, SEQ ID NO:278, SEQ ID NO:282, SEQ ID NO:284, SEQ ID NO:286, SEQ ID NO:288, SEQ ID NO:290, SEQ ID NO:292, SEQ ID NO:294, SEQ ID NO:296, SEQ ID NO:298, SEQ ID NO:300, SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:320, SEQ ID NO:322, SEQ ID NO:324, SEQ ID NO:326, SEQ ID NO:328, SEQ ID NO:330, SEQ ID NO:332, or SEQ ID NO:334, or fragments or subsequences thereof having aldolase activity. In some embodiments, the fragments or subsequences thereof have an aldolase activity of at least 0.2 mg MP/mg protein/hr. In other embodiments, the fragments or subsequences thereof have an aldolase activity of at least 0.1 mg MP/mg protein/hr. In some embodiments, the reaction facilitated by one or more polypeptides in accordance with the invention is performed in about 1.0 to about 10.0 mM $MgCl_2$. In other embodiments, the reaction facilitated by one or more polypeptides in accordance with the invention is performed at about pH 7.0 to about pH 11.5. In still other embodiments, the reaction facilitated by one or more polypeptides in accordance with the invention is performed in about 0.005% to about 1% polysorbate detergent.

In some embodiments, the reaction is a reaction between indole-3-pyruvate and a C3 carbon source. In some embodiments, the reaction preferentially produces R-2-hydroxy-2-(indol-3-yl-methyl)-4-ketoglutaric acid over S-2-hydroxy-2-(indol-3-yl-methyl)-4-ketoglutaric acid.

In some embodiments, the product made by the multi-step pathway is monatin, salts thereof and combinations thereof.

In other embodiments, at least one of R,R-monatin, R—S monatin, or a combination thereof is produced in greater quantity than either S,S-monatin or S,R-monatin in the multi-step pathway. In some embodiments, R,R monatin is produced in greater quantity than R,S-monatin, S,S-monatin and S,R-monatin in the multi-step pathway.

The invention provides a method, comprising: producing a product chosen from monatin, monatin derivatives, salts thereof, and combinations thereof in a multi-step pathway, wherein a reaction in the pathway is facilitated by at least one polypeptide encoded by a nucleic acid sequence that comprises a sequence having a percent sequence identity of at least 50% to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305, SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, or SEQ ID NO:338. In some embodiments, the percent sequence identity is at least 95%. In other embodiments, the percent sequence identity is 100%.

The invention provides a method comprising a reaction that preferentially produces R-2-hydroxy-2-(indol-3-yl-methyl)-4-ketoglutaric acid over S-2-hydroxy-2-(indol-3-yl-methyl)-4-ketoglutaric acid wherein at least one polypeptide encoded by a nucleic acid sequence that comprises a sequence having at least 95% sequence identity to SEQ ID NO: 28, SEQ ID NO:116, SEQ ID NO:298, SEQ ID NO: 44, SEQ ID NO:54, SEQ ID NO:148, SEQ ID NO: 46, SEQ ID NO:134, SEQ ID NO:142, SEQ ID NO:122, SEQ ID NO:74, SEQ ID NO: 64, SEQ ID NO:108, SEQ ID NO:96, SEQ ID NO:126, SEQ ID NO:80, SEQ ID NO:36, SEQ ID NO:62, SEQ ID NO:112, SEQ ID NO:130, SEQ ID NO:94, SEQ ID NO:58, SEQ ID NO:50, SEQ ID NO:106, SEQ ID NO:42, SEQ ID NO:278, SEQ ID NO:162, SEQ ID NO:276, SEQ ID NO:178, SEQ ID NO:166, SEQ ID NO:218, SEQ ID NO:224, SEQ ID NO:226, SEQ ID NO:244, SEQ ID NO:250, SEQ ID NO:252, SEQ ID NO:264, SEQ ID NO:268, SEQ ID NO:272, SEQ ID NO:184, SEQ ID NO:282, SEQ ID NO:186, SEQ ID NO:192, SEQ ID NO:200, SEQ ID NO:284, SEQ ID NO:172, SEQ ID NO:180, SEQ ID NO:168, SEQ ID NO:228, SEQ ID NO:236, SEQ ID NO:238, SEQ ID NO:240, and SEQ ID NO:156 is utilized to facilitate one reaction in a multi-step pathway.

The invention provides a method comprising: producing a product chosen from monatin, monatin derivatives, salts thereof, and combinations thereof in a multi-step pathway, wherein a reaction in the pathway is facilitated by at least one polypeptide encoded by a nucleic acid sequence that comprises a sequence that hybridizes under stringent condition to a nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305, SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, or SEQ ID NO:338.

The invention also provides a method comprising: producing a product chosen from monatin precursor, salts thereof, and combinations thereof, in a multi-step pathway, wherein a reaction in the pathway is facilitated by one or more polypeptides chosen from isolated or recombinant polypeptides comprising the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, SEQ ID NO:174, SEQ ID NO:176, SEQ ID NO:178, SEQ ID NO:180, SEQ ID NO:182, SEQ ID NO:184, SEQ ID NO:186, SEQ ID NO:188, SEQ ID NO:190, SEQ ID NO:192, SEQ ID NO:194, SEQ ID NO:196, SEQ ID NO:198, SEQ ID NO:200, SEQ ID NO:204, SEQ ID NO:206, SEQ ID NO:208, SEQ ID NO:210, SEQ ID NO:212, SEQ ID NO:214, SEQ ID NO:216, SEQ ID NO:218, SEQ ID NO:220, SEQ ID NO:222, SEQ ID NO:224, SEQ ID NO:226, SEQ ID NO:228, SEQ ID NO:230, SEQ ID NO:232, SEQ ID NO:234, SEQ ID NO:236, SEQ ID NO:238, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:260, SEQ ID NO:262, SEQ ID NO:264, SEQ ID NO:266, SEQ ID NO:268, SEQ ID NO:270, SEQ ID NO:272, SEQ ID NO:274, SEQ ID NO:276, SEQ ID NO:278, SEQ ID NO:282, SEQ ID NO:284, SEQ ID NO:286, SEQ ID NO:288, SEQ ID NO:290, SEQ ID NO:292, SEQ ID NO:294, SEQ ID NO:296, SEQ ID NO:298, SEQ ID NO:300, SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:320, SEQ ID NO:322, SEQ ID NO:324, SEQ ID NO:326, SEQ ID NO:328, SEQ ID NO:330, SEQ ID NO:332, or SEQ ID NO:334, or fragments or subsequences thereof having aldolase activity, wherein said monatin precursor, salts thereof, and combinations thereof is sweet.

The invention additionally provides a method comprising: producing a product chosen from monatin precursor, salts thereof, and combinations thereof, in a multi-step pathway, wherein a reaction in the pathway is facilitated by at least one polypeptide encoded by a nucleic acid sequence that comprises a sequence having a percent sequence identity of at least 50% to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305, SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, or SEQ ID NO:338, wherein said monatin precursor, salts thereof, and combinations thereof is sweet.

The invention further provides a method, comprising: producing a product chosen from monatin precursor, salts thereof, and combinations thereof, in a multi-step pathway, wherein a reaction in the pathway is facilitated by at least one polypeptide encoded by a nucleic acid sequence that comprises a sequence that hybridizes under stringent condition to a nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305, SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, or SEQ ID NO:338, wherein said monatin precursor, salts thereof, and combinations thereof is sweet.

In an effort to be concise, where ever intermediates/products are identified in the specification and claims (such as monatin, monatin precursor, or monatin derivative(s)) as being formed, the term "and/or salts thereof" should be understood to be included where applicable. In other words, for example, the phrase "indole-3-pyruvate is converted to MP" should be understood to read "indole-3-pyruvic acid is converted to MP and/or salts thereof." A person of ordinary skill, in fact, would appreciate that under reaction conditions shown the salts of the intermediates/products are in fact present.

According to some embodiments, the method produces a monatin or monatin derivative composition wherein the monatin or monatin derivative component of the composition includes only the R,R and S,R forms of monatin or monatin derivative. The term "only" when used to indicate that only certain isomers are formed, means that the pathway would produce only the identified isomers if racemization did not occur. Consequently, the term "only" should not be taken to mean absence of other isomers, but rather a person of ordinary skill would understand that other isomeric forms may be present in a relatively small amount due to racemization which may occur. According to some embodiments, the method produces a composition wherein the monatin or monatin derivative component of the composition includes only the R,R form of monatin or monatin derivative (except to the extent racemization occurs resulting in other isomeric forms).

As used herein, the phrase "monatin composition" means compositions including one or more isomers of monatin; the term can also mean only a single isomeric form of monatin and nothing else.

As used herein, the phrase "monatin derivative composition" means compositions including one or more isomers of a monatin derivative; the term can also mean only a single isomeric form of the monatin derivative and nothing else.

As used herein, the phrase "monatin derivative" has the following structure:

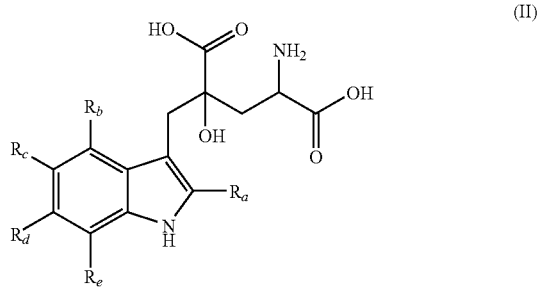

(II)

wherein, $R_a$, $R_b$, $R_c$, $R_d$, and $R_e$ each independently represent any substituent selected from a hydrogen atom, a hydroxyl group, a $C_1$-$C_3$ alkyl group, a $C_1$-$C_3$ alkoxy group, an amino group, or a halogen atom, such as an iodine atom, bromine atom, chlorine atom, or fluorine atom. However, $R_a$, $R_b$, $R_c$, $R_d$, and $R_e$ cannot simultaneously all be hydrogen. Alternatively, $R_b$ and $R_c$, and/or $R_d$ and $R_e$ may together form a $C_1$-$C_4$ alkylene group, respectively.

As used herein, "substituted indole-3-pyruvate" means one or more carbon atoms of the indole ring of the indole-3-pyruvate is independently substituted with one or more of the $R_a$, $R_b$, $R_c$, $R_d$, and $R_e$ substituent groups defined above. However, $R_a$, $R_b$, $R_c$, $R_d$, and $R_e$ cannot simultaneously all be hydrogen. Alternatively, $R_b$ and $R_c$, and/or $R_d$ and $R_e$ may together form a $C_1$-$C_4$ alkylene group, respectively.

As used herein, "substituted tryptophan" means one or more carbon atoms of the indole ring of the tryptophan is independently substituted with one or more of the $R_a$, $R_b$, $R_c$, $R_d$, and $R_e$ substituent groups defined above. However, $R_a$, $R_b$, $R_c$, $R_d$, and $R_e$ cannot simultaneously all be hydrogen. Alternatively, $R_b$ and $R_c$, and/or $R_d$ and $R_e$ may together form a $C_1$-$C_4$ alkylene group, respectively. In one embodiment, the substituted tryptophan contains the same substituent group(s) on the indole ring as the final monatin derivative.

Furthermore, the biosynthetic pathways for producing monatin described herein can utilize a substituted tryptophan to yield monatin derivatives that are likely to be sweet. In some embodiments, the substituted tryptophan to be used in the biosynthetic pathways described herein include chlorinated tryptophan and 5-hydroxytryptophan.

For example, chlorinated D-tryptophans, which have structural similarities to R,R monatin, have been identified as non-nutritive sweeteners (particularly 6-chloro-D-tryptophan). Similarly, halogenated and hydroxy-substituted forms of monatin have been found to be sweet. U.S. Published Patent Application No. 2005/0118317. Halogens and hydroxyl groups could be substitutable for hydrogen, particularly on positions 1-4 of the benzene ring in the indole of tryptophan, without interfering in subsequent conversions to D- or L-tryptophan, indole-3-pyruvate, MP, or monatin. Substituted indoles have been shown in the literature to be suitable substrates for PLP-enzymes and have yielded substituted tryptophans. Fukuda, D. S., et al., "Production of Substituted L-Tryptophans by Fermentation," *Appl. Environ. Microbiol.*, 21:841-43 (1971). The halogen does not appear to sterically hinder the tryptophan synthase beta subunits catalytic mechanism and the enantiospecificity was also intact.

In some embodiments of the present invention, a process for producing a monatin composition is provided, which includes producing indole-3-pyruvate from L-tryptophan, producing 2-hydroxy 2-(indol-3ylmethyl)-4-keto glutaric acid ("monatin precursor" or "MP") from indole-3-pyruvate, and producing monatin from MP. The reaction of L-tryptophan to produce indole-3-pyruvate is facilitated by an enzyme having greater specificity, greater activity, or both for L-tryptophan than for R-MP, R,R monatin, or both. According to certain embodiments, the reaction of indole-3-pyruvate is facilitated by an enzyme having R-specific aldolase activity and consequently produces R-MP. According to certain embodiments, a racemase enzyme is provided which can facilitate the epimerization of the amino acid byproduct of the tryptophan reaction from one isomeric form to another isomeric form.

In some embodiments according to the invention, a process for producing a monatin composition is provided, which includes producing indole-3-pyruvate from L-tryptophan, producing 2-hydroxy 2-(indol-3ylmethyl)-4-keto glutaric acid ("monatin precursor" or "MP") from indole-3-pyruvate, and producing monatin from MP. The reaction of L-tryptophan to produce indole-3-pyruvate is facilitated by an enzyme having greater specificity, greater activity, or both for L-tryptophan than for R-MP, R,R monatin, or both, and the reaction of MP to form monatin is facilitated by an enzyme, which is stereoselective for R-MP. The term "stereoselective" means that an enzyme has greater specificity, greater activity, or both for one isomer—in this case for R-MP versus S-MP— over another. In preferred embodiments, a stereoselective enzyme has limited activity for one isomer as compared to another. "Limited" activity means activity that is minimally or not perceptible, for example as determined according to experiments provided herein.

It should be noted that, where references are made to a series of reactions such as in the preceding paragraphs, the invention does not require each step to be explicitly performed; it is sufficient that the steps may be implicitly performed. In other words, for example, the process for producing a monatin composition, which includes producing indole-3-pyruvate from L-tryptophan, producing 2-hydroxy 2-(indol-3ylmethyl)-4-keto glutaric acid ("monatin precursor" or "MP") from indole-3-pyruvate, and producing monatin from MP, wherein each reaction is facilitated by an appropriate enzyme, can be performed by combining L-tryptophan with the enzymes and setting conditions so that the enumerated reactions could occur. In such an instance L-tryptophan could react to produce indole-3-pyruvate, the indole-3-pyruvate produced from the L-tryptophan reaction could react to form MP, and the MP produced from the indole-3-pyruvate reaction could react to form monatin. The process could also be performed, by way of example, by providing a compound that can produce L-tryptophan, under conditions suitable for L-tryptophan production to occur and combining that compound with enzymes capable of facilitating the series of reactions set forth under conditions which would be suitable for those reactions to occur. As yet another example, the process could be performed by providing a microorganism genetically engineered to produce monatin according to the described pathway, and providing appropriate conditions for the fermentation process to occur. For example, a microorganism, which naturally produces large amounts of L-tryptophan could be genetically engineered to produce or overproduce one or more of the enzymes used to facilitate reactions in the pathway to monatin, and appropriate conditions could be provided so that the microorganism would thereby produce monatin.

In other embodiments according to the invention, a process for producing monatin is provided, in which a substrate forms an L-amino acid when L-tryptophan is converted to indole-3-pyruvate, indole-3-pyruvate reacts to form MP (which can include both R-MP and S-MP though preferably includes only or predominately R-MP), and the L-amino acid reacts to regenerate (also referred to as "recycle") the substrate when R-MP is converted to R,R monatin. The reaction of R-MP to form R,R monatin is facilitated by a stereoinverting aminotransferase such as D-methionine aminotransferase (EC 2.6.1.41) or an enzyme having D-phenylglycine aminotransferase activity.

In other embodiments according to the invention, a process for producing a monatin composition is provided, which includes producing D-tryptophan from L-tryptophan, producing indole-3-pyruvate from D-tryptophan, producing R-MP from indole-3-pyruvate, and producing R,R monatin from R-MP. The production of the D-tryptophan from the L-tryptophan is facilitated by a tryptophan racemase and functional equivalents thereof. In certain further embodiments, the reactions of D-tryptophan to form indole-3-pyruvate and of MP to form monatin are facilitated by the same enzyme. In yet other further embodiments, the reaction of indole-3-pyruvate is facilitated by an enzyme having R-specific aldolase activity and consequently R-MP is formed, and the reactions of D-tryptophan to form indole-3-pyruvate and of R-MP to form R,R monatin are facilitated by the same enzyme.

In some embodiments according to the invention, a process for producing a monatin derivative is provided, which includes producing the monatin derivative from a substituted indole-3-pyruvate and pyruvate, using an enzyme having R-specific aldolase activity to catalyze the reaction.

The details of one or more embodiments of the invention are set forth in the accompanying drawings and the description below. Other features, objects, and advantages in accordance with the invention will be apparent from the description and drawings, and from the claims. As should be realized from the description herein, the invention is capable of modifications in various embodiments, all without departing from the spirit and scope of the present invention. Accordingly, the drawings and detailed description are to be regarded as illustrative in nature and not restrictive.

All publications, patents, patent applications, GenBank sequences and ATCC deposits, cited herein are hereby expressly incorporated by reference for all purposes.

BRIEF DESCRIPTION OF DRAWINGS

The following drawings are illustrative of embodiments of the invention and are not meant to limit the scope of the invention as encompassed by the claims.

Like reference symbols in the various drawings indicate like elements.

DETAILED DESCRIPTION

Figure 1:
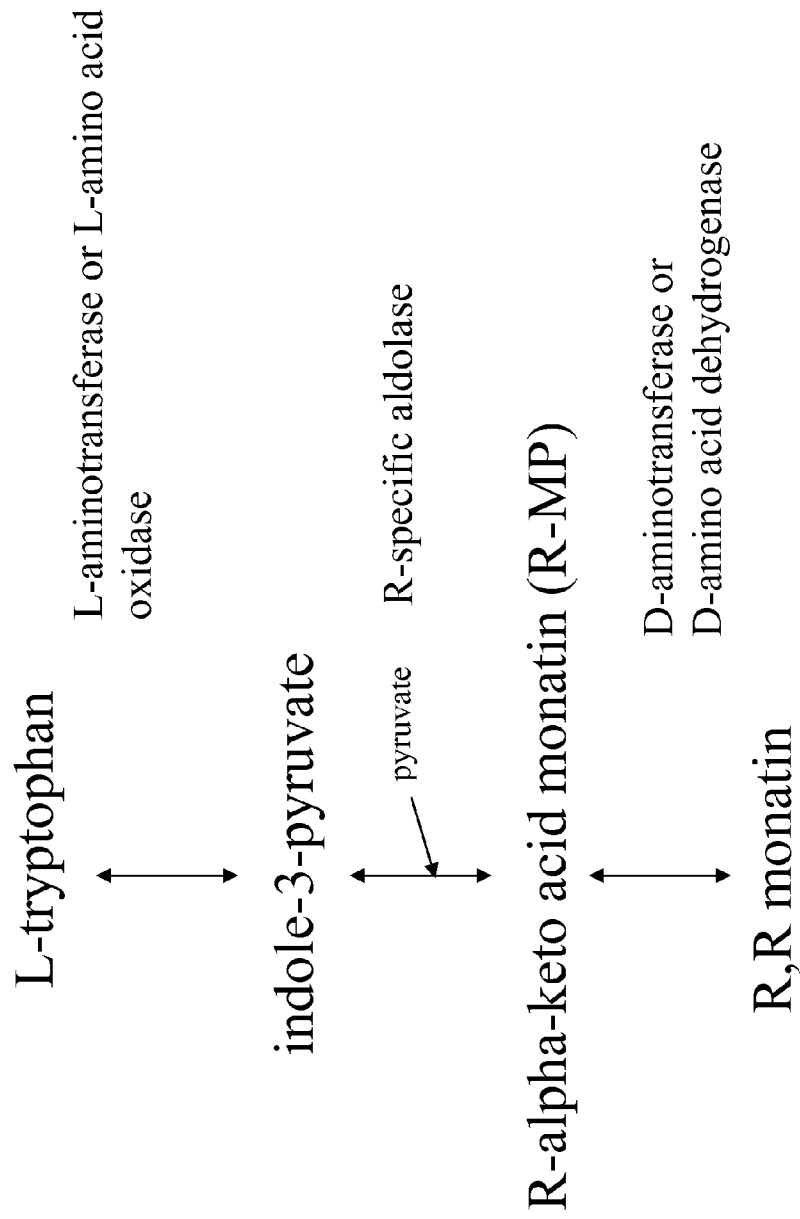
FIG. 1 is a flow chart that shows an example of an enzymatic process for producing R,R monatin from L-tryptophan in accordance with the invention. In this example, the process includes using an L-aminotransferase (examples of which include an L-tryptophan aminotransferase, an L-aromatic aminotransferase, an L-aspartate aminotransferase, and an L-alanine aminotransferase) in the reaction of L-tryptophan that has greater specificity and/or selectivity for L-tryptophan as a substrate than for R-MP and/or the process includes using an L-amino acid oxidase with limited activity and/or specificity for R,R monatin as a substrate. In the specific example diagrammed in FIG. 1, an L-aminotransferase or L-amino acid oxidase converts L-tryptophan to indole-3-pyruvate, indole-3-pyruvate is reacted with an R-specific aldolase and pyruvate to produce R-alpha-keto acid monatin (R-MP), and R-MP is converted to R,R monatin by a D-aminotransferase or a D-amino acid dehydrogenase. As shown on FIG. 1, the reactions are reversible, but for the purposes of the invention, it is not required that the reactions proceed in the reverse direction.

A number of embodiments have been described above and are described in more detail infra. Embodiments of the invention include one or more of the described aspects.

Abbreviations and Terms

The following explanations of terms and methods are provided to better describe the present disclosure and to guide those of ordinary skill in the art in the practice of the present disclosure. As used herein, "including" means "comprising." In addition, the singular forms "a" or "an" or "the" include plural references unless the context clearly dictates otherwise. For example, reference to "comprising a protein" includes one or a plurality of such proteins, and reference to "comprising the cell" includes reference to one or more cells and equivalents thereof known to those skilled in the art, and so forth. The term "about" encompasses the range of experimental error that occurs in any measurement. Unless otherwise stated, all measurement numbers are presumed to have the word "about" in front of them even if the word "about" is not expressly used.

Conservative substitution: a substitution of one amino acid for another amino acid in a polypeptide, which substitution has little to no impact on the activity of the polypeptide. The substitution is considered conservative independent of whether the exchanged amino acids appear structurally or functionally similar. For example, ideally, a tryptophan aminotransferase polypeptide including one or more conservative substitutions retains tryptophan aminotransferase activity. A polypeptide can be produced to contain one or more conservative substitutions by manipulating the nucleotide sequence that encodes that polypeptide using, for example, standard procedures such as site-directed mutagenesis or PCR or other methods known to those in the art.

Non-limiting examples of amino acids which may be substituted for an original amino acid in a protein and which may be regarded as conservative substitutions if there is little to no impact on the activity of the polypeptide include: Ala substituted with ser or thr; arg substituted with gln, his, or lys; asn substituted with glu, gln, lys, his, asp; asp substituted with asn, glu, or gln; cys substituted with ser or ala; gln substituted with asn, glu, lys, his, asp, or arg; glu substituted with asn, gln lys, or asp; gly substituted with pro; his substituted with asn, lys, gln, arg, tyr; ile substituted with leu, met, val, phe; leu substituted with ile, met, val, phe; lys substituted with asn, glu, gln, his, arg; met substituted with ile, leu, val, phe; phe substituted with trp, tyr, met, ile, or leu; ser substituted with thr, ala; thr substituted with ser or ala; trp substituted with phe, tyr; tyr substituted with his, phe, or trp; and val substituted with met, ile, leu.

Further information about conservative substitutions can be found in, among other locations, Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (Bio/Technology 6: 1321-5, 1988), WO 00/67796 (Curd et al.) and in standard textbooks of genetics and molecular biology.

Derived: For purposes of the specification and claims, a substance is "derived" from an organism or source if any one or more of the following are true: 1) the substance is present in the organism/source; 2) the substance is removed from the native host; or, 3) the substance is removed from the native host and is evolved, for example, by mutagenesis.

Isolated: The term "isolated" as used herein refers to any substance removed from its native host; the substance need not be purified. For example "isolated nucleic acid" refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (such as a cDNA or a genomic DNA fragment produced by PCR or restriction endonuclease treatment) independent of other sequences as well as recombinant DNA that is incorporated into a vector, an autonomously replicating plasmid, a virus (such as a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

As used herein, the term "isolated" means that the material (such as a protein or nucleic acid in accordance with the invention) is removed from its original environment (such as the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition and still be isolated in that such vector or composition is not part of its natural environment.

The term "isolated" as used herein with reference to nucleic acid also includes any non-naturally-occurring nucleic acid because non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (such as a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

Purified: The term "purified" as used herein does not require absolute purity, but rather is intended as a relative term. Thus, for example, a purified polypeptide or nucleic acid preparation can be one in which the subject polypeptide or nucleic acid is at a higher concentration than the polypeptide or nucleic acid would be in its natural environment within an organism or at a higher concentration than in the environment from which it was removed.

Individual nucleic acids obtained from a library have been conventionally purified to electrophoretic homogeneity. The sequences obtained from these clones could not be obtained directly either from the library or from total human DNA. The purified nucleic acids in accordance with the invention have been purified from the remainder of the genomic DNA in the organism by at least $10^4$-$10^6$ fold. In some embodiments, the term "purified" includes nucleic acids which have been purified from the remainder of the genomic DNA or from other sequences in a library or other environment by at least one order of magnitude, such as, in some embodiments, two or three orders, or, four or five orders of magnitude.

Amino acid: "Amino acid" or "amino acid sequence" as used herein refer to an oligopeptide, peptide, polypeptide, or protein sequence, or to a fragment, portion, or subunit of any of these and to naturally occurring or synthetic molecules. "Amino acid" or "amino acid sequence" include an oligopeptide, peptide, polypeptide, or protein sequence, or to a fragment, portion, or subunit of any of these, and to naturally occurring or synthetic molecules. The term "polypeptide" as used herein, refers to amino acids joined to each other by peptide bonds or modified peptide bonds, i.e., peptide isosteres and may contain modified amino acids other than the 20 gene-encoded amino acids. The polypeptides may be modified by either natural processes, such as post-translational processing, or by chemical modification techniques which are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also, a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, glucan hydrolase processing, phosphorylation, prenylation, racemization, selenoylation, sulfation and transfer-RNA mediated addition of amino acids to protein such as arginylation. (See Creighton, T. E., Proteins—Structure and Molecular Properties 2nd Ed., W.H. Freeman and Company, New York (1993); *Posttranslational Covalent Modification of Proteins*, B. C. Johnson, Ed., Academic Press, New York, pp. 1-12 (1983)). The peptides and polypeptides in accordance with the invention also include all "mimetic" and "peptidomimetic" forms, as described in further detail, below.

Polypeptide Having an Aldolase Activity: By a "polypeptide having an aldolase activity" is meant a polypeptide that either by itself, or in association with one or more additional polypeptides (having the same or a different sequence), is a protein with the enzymatic activity of an aldolase.

Recombinant: "Recombinant" polypeptides or proteins refer to polypeptides or proteins produced by recombinant DNA techniques; i.e., produced from cells transformed by an exogenous DNA construct encoding the desired polypeptide or protein. "Synthetic" polypeptides or protein are those prepared by chemical synthesis. Solid-phase chemical peptide synthesis methods can also be used to synthesize the polypeptide or fragments in accordance with the invention. Such method have been known in the art since the early 1960's (Merrifield, R. B., *J. Am. Chem. Soc.*, 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, *Proc. Natl. Acad. Sci., USA*, 81:3998 (1984) and provide for synthesizing peptides upon the tips of a multitude of "rods" or "pins" all of which are connected to a single plate.

Substantially identical: The phrase "substantially identical" in the context of two nucleic acids or polypeptides, refers to two or more sequences that have, such as at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more nucleotide or amino acid residue (sequence) identity, when compared and aligned for maximum correspondence, as measured using one of the known sequence comparison algorithms or by visual inspection. In other embodiments, the substantial identity exists over a region of at least about 100 or more residues and most commonly the sequences are substantially identical over at least about 150 to 200 or more residues. In some embodiments, the sequences are substantially identical over the entire length of the coding regions.

Additionally a "substantially identical" amino acid sequence is a sequence that differs from a reference sequence by one or more conservative or non-conservative amino acid substitutions, deletions, or insertions. In some embodiments, the substitution occurs at a site that is not the active site of the molecule, or, alternatively the substitution occurs at a site that is the active site of the molecule, provided that the polypeptide essentially retains its functional (enzymatic) properties. A conservative amino acid substitution, for example, substitutes one amino acid for another of the same class (such as substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from an aldolase, such as pyruvate aldolase, HMG and/or KHG aldolase polypeptide, resulting in modification of the structure of the polypeptide, without significantly altering its biological activity. For example, amino- or carboxyl-terminal amino acids that are not required for aldolase, such as pyruvate aldolase, such as HMG and/or KHG aldolase enzyme, biological activity can be removed. Modified polypeptide sequences in accordance with the invention can be assayed for aldolase, such as pyruvate aldolase, such as HMG and/or KHG aldolase enzyme, biological activity by any number of methods, including contacting the modified polypeptide sequence with a substrate and determining whether the modified polypeptide decreases the amount of specific substrate in the assay or increases the bioproducts of the enzymatic reaction of a functional aldolase, such as pyruvate aldolase, such as HMG and/or KHG aldolase polypeptide with the substrate.

Fragment: A "fragment" as used herein with regard to a protein or polypeptide or nucleic acid is a portion of the protein, polypeptide or nucleic acid, respectively. Fragments can have the same or substantially the same amino acid or nucleic acid sequence as the longer protein, polypeptide or nucleic acid sequence from which the fragment is derived. Fragments which have different three dimensional structures as compared to that of the longer protein, polypeptide or nucleic acid are also included. An example of this, is a "pro-form" molecule, such as a low activity proprotein that can be modified by cleavage to produce a mature enzyme with significantly higher activity. A fragment of a protein or polypeptide can be an enzymatically active portion of a protein or polypeptide.

Stereoinverting aminotransferase: A "stereoinverting aminotransferase" is a polypeptide capable of preferentially or selectively producing a chiral amino acid product (such as monatin) while using an opposite chirality substrate as the amino donor. For example, a stereoinverting aminotransferase may be a D-phenylglycine aminotransferase (also called D-4-hydroxyphenylglycine aminotransferase) that preferentially or selectively uses L-glutamate as a substrate to produce R,R monatin. Non-limiting examples of stereoinverting aminotransferases include D-methionine aminotransferase (EC 2.6.1.41) and enzymes having D-phenylglycine aminotransferase activity or D-4-hydroxyphenylglycine aminotransferase activity.

The invention provides polypeptides with aldolase, including pyruvate activity such as, without limitation, HMG and/or KHG aldolase activity, polynucleotides encoding them, and methods of making and using these polynucleotides and polypeptides. In some embodiments, the invention also provides aldolase enzymes, such as pyruvate aldolase, such as HMG and/or KHG aldolase enzymes, polynucleotides encoding these enzymes, the use of such polynucleotides and polypeptides.

In some embodiments, the invention provides modified or evolved aldolases, such as pyruvate aldolases, HMG and/or KHG aldolases, with an increased specific activity as compared to the unmodified or unevolved aldolases, respectively.

In some embodiments, aldolases, such as a pyruvate aldolase, such as, without limitation a HMG and/or a KHG aldolase, are provided that facilitate the production of a 3,4-substituted 2-keto-glutarate. In one embodiment, the invention provides a method of making a 3,4-substituted 2-keto-glutarate comprising: (a) providing a polypeptide having an aldolase activity, such as a pyruvate aldolase activity, such as, without limitation, a HMG aldolase and/or a KMG aldolase activity; (b) providing a donor and an acceptor compound; and (c) contacting the polypeptide of step (a) with the compounds of step (b) under conditions wherein the aldolase catalyzes the synthesis of a 3,4-substituted 2-keto-glutarate, wherein optionally the donor and the acceptor are a pyruvate or a pyruvate donor and an α-keto acid acceptor, a ketone and/or an aldehyde.

In another embodiment of the invention, a pyruvate aldolase, such as a HMG and/or a KHG aldolase, can be used in conjunction with a D-aminotransferase to make a 4-substituted D-glutamic acid or a derivative thereof. A 4-substituted D-glutamic acid and/or a derivative thereof can be used as an antibiotic, as these compounds have been found to inhibit bacterial glutamate racemase. In one embodiment, the invention provides a method of making a 4-substituted D-glutamic acid comprising: (a) providing a polypeptide having an aldolase activity, such as a pyruvate aldolase activity, such as, without limitation, a HMG aldolase and/or a KMG aldolase activity; (b) providing an α-keto acid acceptor and a pyruvate or a pyruvate donor; and (c) contacting the polypeptide of step (a) with the compounds of step (b) under conditions wherein the aldolase catalyzes the synthesis of a 4-substituted D-glutamic acid, wherein optionally the polypeptide has pyruvate aldolase, HMG aldolase and/or KHG aldolase activity and wherein optionally the method further comprises use of a D-aminotransferase.

In some embodiments the invention provides compositions (such as enzyme preparations, foods and food additives, feeds and feed additives, beverage and beverage additives, drugs and drug additives, and dietary supplements) comprising the enzymes, polypeptides or polynucleotides in accordance with the invention. These compositions can be formulated in a variety of forms, such as liquids, gels, pills, tablets, sprays, films, micelles, powders, food, feed pellets or encapsulated forms, including nanoencapsulated forms.

Assays for measuring aldolase activity, including pyruvate activity such as, without limitation, HMG and/or KHG aldolase activity, such as for determining if a polypeptide has aldolase activity, including pyruvate activity such as, without limitation, HMG and/or KHG aldolase activity, are well known in the art and are within the scope in accordance with the invention; see E. E. Dekker & R. P. Kitson, J. Biol. Chem. 267, 10507-10514, 1992; Taha T S, Deits T L, Purification and characterization of 2-keto-3-deoxy-6-phosphogluconate aldolase from *Azotobacter vinelandii*: evidence that the enzyme is bifunctional towards 2-keto-4-hydroxy glutarate cleavage, Biochem Biophys Res Commun. 1994 Apr. 15; 200(1):459-66; Dekker EE, Kobes R D, Grady S R, 2-keto-4-hydroxyglutarate aldolase from bovine liver, Methods Enzymol. 1975; 42:280-5; Dekker EE, Nishihara H, Grady S R, Methods Enzymol. 1975; 42:285-90, 2-keto-4-hydroxyglutarate aldolase from *Escherichia coli*; Nishihara H, Dekker EE, Biochim Biophys Acta. 1969 Jul. 8; 185(1):255-7, A stereospecific 2-keto-4-hydroxyglutarate aldolase from *Escherichia coli*. One example of a suitable assay for determining if a polypeptide has aldolase activity, such as pyruvate aldolase, such as HMG and/or KHG aldolase activity is described in Example 3.

In some embodiments, the aldolases of the invention can be used effectively at a variety of pH conditions, including for example, from a range of about 3.0 to about 12.0. In other embodiments, the aldolases of the invention can be used at about pH is 3.0, 4.0, 4.5, 5.0, 5.5, 6.0, 6.5, 7.0, 7.5, 8.0, 8.5, 9.0, 9.5, 10.0, 10.5, 11.0, 11.5, or about 12.0. Reaction conditions conducted under acidic or alkaline conditions also can be advantageous, such as in some industrial or pharmaceutical applications of enzymes in accordance with the invention.

The invention provides aldolase, such as pyruvate aldolase, such as HMG and/or KHG aldolase polypeptides in accordance with the invention in a variety of forms and formulations. In the methods in accordance with the invention, aldolase, such as pyruvate aldolase, such as HMG and/or KHG aldolase polypeptides in accordance with the invention are used in a variety of forms and formulations. For example, purified aldolase, such as pyruvate aldolase, such as HMG and/or KHG aldolase polypeptides can be used in enzyme preparations deployed in the production of R-2-hydroxy 2-(indol-3ylmethyl)-4-keto glutaric acid (R-MP) and certain stereoisomers of monatin, such as R,R and S,R monatin, and salts thereof, as well as certain stereoisomers of monatin derivatives, such as the R,R and S,R monatin derivative configurations, and salts thereof, or in pharmaceutical or dietary aid applications. Alternatively, the enzymes in accordance with the invention can be used directly in processes to produce R-2-hydroxy 2-(indol-3ylmethyl)-4-keto glutaric acid (R-MP) and certain stereoisomers of monatin, such as R,R and S,R monatin, and salts thereof, as well as certain stereoisomers of monatin derivatives, such as the R,R and S,R monatin derivative configurations, and salts thereof, to process foods, liquids or feeds, and the like.

In some embodiments, aldolase, such as pyruvate aldolase, such as HMG and/or KHG aldolase polypeptides in accordance with the invention can be expressed in a microorganism using procedures known in the art. In some embodiments, the aldolase, such as pyruvate aldolase, such as HMG and/or KHG aldolase polypeptides in accordance with the invention can be immobilized on a solid support prior to use in the methods in accordance with the invention. Methods for immobilizing enzymes on solid supports are commonly known in the art, for example J. Mol. Cat. B: Enzymatic 6 (1999) 29-39; Chivata et al. Biocatalysis: Immobilized cells and enzymes, J. Mol. Cat. 37 (1986) 1-24: Sharma et al., Immobilized Biomaterials Techniques and Applications, Angew. Chem. Int. Ed. Engl. 21 (1982) 837-54: Laskin (Ed.), Enzymes and Immobilized Cells in Biotechnology.

Nucleic Acids, Probes and Inhibitory Molecules

The invention provides isolated and recombinant nucleic acids, such as see Sequence Listing; nucleic acids encoding polypeptides, including the polynucleotide sequences in accordance with the invention, such as see Sequence Listing; including expression cassettes such as expression vectors and various cloning vehicles comprising nucleic acids in accordance with the invention. In some embodiments, the invention also includes methods for discovering, identifying or isolated new aldolase, such as pyruvate aldolase, HMG and/or KHG aldolase polypeptide sequences using the nucleic acids in accordance with the invention. In some embodiments, the invention also includes methods for inhibiting the expression of aldolase, such as pyruvate aldolase, such as HMG and/or KHG aldolase encoding genes and transcripts using the nucleic acids in accordance with the invention.

Also provided are methods for modifying the nucleic acids in accordance with the invention, including making variants of nucleic acids in accordance with the invention, by, such as synthetic ligation reassembly, optimized directed evolution system and/or saturation mutagenesis such as gene site saturation mutagenesis (GSSM). The term "saturation mutagenesis", Gene Site Saturation Mutagenesis, or "GSSM" includes a method that uses degenerate oligonucleotide primers to introduce point mutations into a polynucleotide, as described in detail, below. The term "optimized directed evolution system" or "optimized directed evolution" includes a method for reassembling fragments of related nucleic acid sequences, such as related genes, and explained in detail, below. The term "synthetic ligation reassembly" or "SLR" includes a method of ligating oligonucleotide fragments in a non-stochastic fashion, and explained in detail, below. The term "variant" refers to polynucleotides or polypeptides in accordance with the invention modified at one or more base pairs, codons, introns, exons, or amino acid residues (respectively) yet still retain the biological activity of an aldolase, such as pyruvate aldolase, HMG and/or KHG aldolase in accordance with the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM and any combination thereof.

The nucleic acids in accordance with the invention can be made, isolated and/or manipulated by, such as cloning and expression of cDNA libraries, amplification of message or genomic DNA by PCR, and the like. For example, sequences in accordance with the invention were initially derived from environmental sources. Thus, in some embodiments, the invention provides aldolase-, such as pyruvate aldolase-, such as HMG and/or KHG aldolase enzyme-encoding nucleic acids, and the polypeptides encoded by them, preferably derived from a common source, such as an environmental, mixed culture, or a bacterial source.

In practicing the methods in accordance with the invention, homologous genes can be modified by manipulating a template nucleic acid, as described herein. In some embodiments, the invention can be practiced in conjunction with any method or protocol or device known in the art, which are well described in the scientific and patent literature.

The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense (complementary) strand, to peptide nucleic acid (PNA), or to any DNA-like or RNA-like material, natural or synthetic in origin. The phrases "nucleic acid" or "nucleic acid sequence" includes oligonucleotide, nucleotide, polynucleotide, or to a fragment of any of these, to DNA or RNA (such as mRNA, rRNA, tRNA, iRNA) of genomic or synthetic origin which may be single-stranded or double-stranded and may represent a sense or antisense strand, to peptide nucleic acid (PNA), or to any DNA-like or RNA-like material, natural or synthetic in origin, including, such as iRNA, ribonucleoproteins (such as double stranded iRNAs, such as iRNPs). The term encompasses nucleic acids, i.e., oligonucleotides, containing known analogues of natural nucleotides. The term also encompasses nucleic-acid-like structures with synthetic backbones, see such as Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156. "Oligonucleotide" includes either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide can ligate to a fragment that has not been dephosphorylated.

A "coding sequence of" or a "nucleotide sequence encoding" a particular polypeptide or protein, is a nucleic acid sequence which can be transcribed and translated into a polypeptide or protein when placed under the control of appropriate regulatory sequences. The term "gene" means the segment of DNA involved in producing a polypeptide chain; it includes regions preceding and following the coding region (leader and trailer) as well as, where applicable, intervening sequences (introns) between individual coding segments (exons). A promoter sequence is "operably linked to" a coding sequence when RNA polymerase which initiates transcription at the promoter will transcribe the coding sequence into mRNA. "Operably linked" as used herein refers to a functional relationship between two or more nucleic acid (such as DNA) segments. It can refer to the functional relationship of transcriptional regulatory sequence to a transcribed sequence. For example, a promoter is operably linked to a coding sequence, such as a nucleic acid in accordance with the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" as used herein refers to a nucleotide sequence which is capable of affecting expression of a structural gene (i.e., a protein coding sequence, such as an aldolase, such as pyruvate aldolase, HMG and/or KHG aldolase enzyme in accordance with the invention) in a host compatible with such sequences. Expression cassettes include at least a promoter operably linked with the polypeptide coding sequence; and, optionally, with other sequences, such as transcription termination signals. Additional factors necessary or helpful in effecting expression may also be used, such as enhancers, alpha-factors. Thus, expression cassettes also include plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (such as a cell membrane, a viral lipid envelope, etc.). Vectors include, but are not limited to replicons (such as RNA replicons, bacteriophages) to which fragments of DNA may be attached and become replicated. Vectors thus include, but are not limited to RNA, autonomous self-replicating circular or linear DNA or RNA (such as plasmids, viruses, and the like, see U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

As used herein, the term "recombinant" encompasses nucleic acids adjacent to a "backbone" nucleic acid to which it is not adjacent in its natural environment. In some embodiments, to be "enriched" the nucleic acids will represent about 5% or more of the number of nucleic acid inserts in a population of nucleic acid backbone molecules. Backbone molecules according to the invention include nucleic acids such as expression vectors, self-replicating nucleic acids, viruses, integrating nucleic acids and other vectors or nucleic acids used to maintain or manipulate a nucleic acid insert of interest. In some embodiments, the enriched nucleic acids represent about 15% or more of the number of nucleic acid inserts in the population of recombinant backbone molecules. In some embodiments, the enriched nucleic acids represent about 50% or more of the number of nucleic acid inserts in the population of recombinant backbone molecules. In some embodiments, the enriched nucleic acids represent about 90% or more of the number of nucleic acid inserts in the population of recombinant backbone molecules.

One embodiment of the invention is an isolated, synthetic or recombinant nucleic acid comprising one of the sequences in accordance with the invention, or a fragment comprising at least 10, 15, 20, 25, 30, 35, 40, 50, 75, 100, 150, 200, 300, 400, or 500 or more consecutive bases of a nucleic acid in accordance with the invention. The isolated, synthetic or recombinant nucleic acids may comprise DNA, including cDNA, genomic DNA and synthetic DNA. The DNA may be double-stranded or single-stranded and if single stranded may be the coding strand or non-coding (anti-sense) strand. Alternatively, the isolated, synthetic or recombinant nucleic acids comprise RNA.

The isolated, synthetic or recombinant nucleic acids in accordance with the invention may be used to prepare one of the polypeptides in accordance with the invention, or fragments comprising at least 5, 10, 15, 20, 25, 30, 35, 40, 50, 75, 100, or 150 or more consecutive amino acids of one of the polypeptides in accordance with the invention. Accordingly, another embodiment of the invention is an isolated, synthetic or recombinant nucleic acid which encodes one of the polypeptides in accordance with the invention, or fragments comprising at least 5, 10, 15, 20, 25, 30, 35, 40, 50, 75, 100, or 150 or more consecutive amino acids of one of the polypeptides in accordance with the invention. The coding sequences of these nucleic acids may be identical to one of the coding sequences of one of the nucleic acids in accordance with the invention or may be different coding sequences which encode one of the in accordance with the invention having at least 5, 10, 15, 20, 25, 30, 35, 40, 50, 75, 100, or 150 or more consecutive amino acids of one of the polypeptides in accordance with the invention, as a result of the redundancy or degeneracy of the genetic code. The genetic code is well known to those of skill in the art and can be obtained, such as on page 214 of B. Lewin, Genes VI, Oxford University Press, 1997.

The isolated nucleic acid which encodes one of the polypeptides of the invention and sequences substantially identical thereto, may include, but is not limited to: the coding sequence of a nucleic acid in accordance with the invention and additional coding sequences, such as leader sequences or proprotein sequences and non-coding sequences, such as introns or non-coding sequences 5' and/or 3' of the coding sequence. Thus, as used herein, the term "polynucleotide encoding a polypeptide" encompasses a polynucleotide which includes the coding sequence for the polypeptide as well as a polynucleotide which includes additional coding and/or non-coding sequence.

Alternatively, the nucleic acid sequences of the invention and sequences substantially identical thereto, may be mutagenized using conventional techniques, such as site directed mutagenesis, or other techniques familiar to those skilled in the art, to introduce silent changes into the polynucleotides o in accordance with the invention. As used herein, "silent changes" include, for example, changes which do not alter the amino acid sequence encoded by the polynucleotide. Such changes may be desirable in order to increase the level of the polypeptide produced by host cells containing a vector encoding the polypeptide by introducing codons or codon pairs which occur frequently in the host organism.

The invention also relates to polynucleotides which have nucleotide changes which result in amino acid substitutions, additions, deletions, fusions and truncations in the polypeptides in accordance with the invention. Such nucleotide changes may be introduced using techniques such as site directed mutagenesis, random chemical mutagenesis, exonuclease III deletion and other recombinant DNA techniques. Alternatively, such nucleotide changes may be naturally occurring allelic variants which are isolated by identifying nucleic acids which specifically hybridize to probes comprising at least 10, 15, 20, 25, 30, 35, 40, 50, 75, 100, 150, 200, 300, 400, or 500 consecutive bases of one of the sequences in accordance with the invention (or the sequences complementary thereto) under conditions of high, moderate, or low stringency as provided herein.

General Techniques

The nucleic acids used to practice this invention, whether RNA, siRNA, miRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides (such as aldolase, such as pyruvate aldolase, such as HMG and/or KHG aldolase enzymes) generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, such as Adams (1983) J. Am. Chem. Soc. 105: 661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as subcloning, labeling probes (such as random-primer labeling using Klenow polymerase, nick translation, amplification), sequencing, hybridization and the like are well described in the scientific and patent literature, see Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods in accordance with the invention is to clone from genomic samples, and, if desired, screen and re-clone inserts isolated or amplified from, such as genomic clones or cDNA clones. Sources of nucleic acid used in the methods in accordance with the invention include genomic or cDNA libraries contained in, such as mammalian artificial chromosomes (MACs), see U.S. Pat. Nos. 5,721,118; 6,025,155; human artificial chromosomes, see Rosenfeld (1997) Nat. Genet. 15:333-335; yeast artificial chromosomes (YAC); bacterial artificial chromosomes (BAC); P1 artificial chromosomes, see Woon (1998) Genomics 50:306-316; P1-derived vectors (PACs), see Kern (1997) Biotechniques 23:120-124; cosmids, recombinant viruses, phages or plasmids.

In some embodiments, a nucleic acid encoding a polypeptide in accordance with the invention is assembled in appropriate phase with a leader sequence capable of directing secretion of the translated polypeptide or fragment thereof.

The invention provides fusion proteins and nucleic acids encoding them. A polypeptide in accordance with the invention can be fused to a heterologous peptide or polypeptide, such as N-terminal identification peptides which impart desired characteristics, such as increased stability or simplified purification. Peptides and polypeptides in accordance with the invention can also be synthesized and expressed as fusion proteins with one or more additional domains linked thereto for, such as producing a more immunogenic peptide, to more readily isolate a recombinantly synthesized peptide, to identify and isolate antibodies and antibody-expressing B cells, and the like. Detection and purification facilitating domains include, such as metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, Carlsbad, Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see such as Williams (1995) Biochemistry 34:1787-1797; Dobeli (1998) Protein Expr. Purif. 12:404-414). The histidine residues facilitate detection and purification while the enterokinase cleavage site provides means for purifying the epitope from the remainder of the fusion protein. Technology pertaining to vectors encoding fusion proteins and application of fusion proteins are well described in the scientific and patent literature, see such as Kroll (1993) DNA Cell. Biol., 12:441-53.

Transcriptional and Translational Control Sequences

The invention provides nucleic acid (such as DNA) sequences in accordance with the invention operatively linked to expression (such as transcriptional or translational) control sequence(s), such as promoters or enhancers, to direct or modulate RNA synthesis/expression. The expression control sequence can be in an expression vector. Exemplary bacterial promoters include lacI, lacZ, T3, T7, gpt, lambda PR, PL and trp. Exemplary eukaryotic promoters include CMV immediate early, HSV thymidine kinase, early and late SV40, LTRs from retrovirus, and mouse metallothionein 1.

As used herein, the term "promoter" includes all sequences capable of driving transcription of a coding sequence in a cell, such as a plant or animal cell. Thus, promoters used in the constructs in accordance with the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences can interact with proteins or other biomolecules to carry out (turn on/off, regulate, modulate, etc.) transcription. "Constitutive" promoters are those that drive expression continuously under most environmental conditions and states of development or cell differentiation. "Inducible" or "regulatable" promoters direct expression of the nucleic acid in accordance with the invention under the influence of environmental conditions or developmental conditions. Examples of environmental conditions that may affect transcription by inducible promoters include anaerobic conditions, elevated temperature, drought, or the presence of light.

"Tissue-specific" promoters are transcriptional control elements that are only active in particular cells or tissues or organs, such as in plants or animals. Tissue-specific regulation may be achieved by certain intrinsic factors which ensure that genes encoding proteins specific to a given tissue are expressed. Such factors are known to exist in mammals and plants so as to allow for specific tissues to develop.

Promoters suitable for expressing a polypeptide in bacteria include the E. coli lac or trp promoters, the lacI promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used. Promoters suitable for expressing the polypeptide or fragment thereof in bacteria include the E. coli lac or trp promoters, the lacI promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK) and the acid phosphatase promoter. Fungal promoters include the α-factor promoter. Eukaryotic promoters include the CMV immediate early promoter, the HSV thymidine kinase promoter, heat shock promoters, the early and late SV40 promoter, LTRs from retroviruses and the mouse metallothionein-I promoter. Other promoters known to control expression of genes in prokaryotic or eukaryotic cells or their viruses may also be used.

Tissue-Specific Plant Promoters

The invention provides expression cassettes that can be expressed in a tissue-specific manner, such as that can express an aldolase, such as pyruvate aldolase, HMG and/or KHG aldolase enzyme in accordance with the invention in a tissue-specific manner. In some embodiments, the invention also provides plants or seeds that express an aldolase, such as pyruvate aldolase, HMG and/or KHG aldolase enzyme in accordance with the invention in a tissue-specific manner. The tissue-specificity can be seed specific, stem specific, leaf specific, root specific, fruit specific and the like.

The term "plant" includes whole plants, plant parts (such as leaves, stems, flowers, roots, etc.), plant protoplasts, seeds and plant cells and progeny of same. The class of plants which can be used in the method in accordance with the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous states. As used herein, the term "transgenic plant" includes plants or plant cells into which a heterologous nucleic acid sequence has been inserted, such as the nucleic acids and various recombinant constructs (such as expression cassettes) in accordance with the invention.

In some embodiments, a constitutive promoter such as the CaMV 35S promoter can be used for expression in specific parts of the plant or seed or throughout the plant. For example, for overexpression, a plant promoter fragment can be employed which will direct expression of a nucleic acid in some or all tissues of a plant, such as a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Such genes include, such as ACT11 from *Arabidopsis* (Huang (1996) *Plant Mol. Biol.* 33:125-139); Cat3 from *Arabidopsis* (GenBank No. U43147, Zhong (1996) *Mol. Gen. Genet.* 251:196-203); the gene encoding stearoyl-acyl carrier protein desaturase from *Brassica napus* (Genbank No. X74782, Solocombe (1994) *Plant Physiol.* 104:1167-1176); GPc1 from maize (GenBank No. X15596; Martinez (1989) *J. Mol. Biol.* 208:551-565); the Gpc2 from maize (GenBank No. U45855, Manjunath (1997) *Plant Mol. Biol.* 33:97-112); plant promoters described in U.S. Pat. Nos. 4,962,028; 5,633,440.

The invention uses tissue-specific or constitutive promoters derived from viruses which can include, such as the tobamovirus subgenomic promoter (Kumagai (1995) Proc. Natl. Acad. Sci. USA 92:1679-1683; the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) Plant Mol. Biol. 31:1129-1139).

In some embodiments, the plant promoter directs expression of aldolase, such as pyruvate aldolase, such as HMG and/or KHG aldolase enzyme-expressing nucleic acid in a specific tissue, organ or cell type (i.e. tissue-specific promoters) or may be otherwise under more precise environmental or developmental control or under the control of an inducible promoter. Examples of environmental conditions that may affect transcription include anaerobic conditions, elevated temperature, the presence of light, or sprayed with chemicals/hormones. For example, the invention incorporates the drought-inducible promoter of maize (Busk (1997) supra); the cold, drought, and high salt inducible promoter from potato (Kirch (1997) Plant Mol. Biol. 33:897 909).

In some embodiments, tissue-specific promoters promote transcription only within a certain time frame of developmental stage within that tissue. See Blazquez (1998) Plant Cell 10:791-800, characterizing the *Arabidopsis* LEAFY gene promoter. See also Cardon (1997) *Plant J* 12:367-77, describing the transcription factor SPL3, which recognizes a conserved sequence motif in the promoter region of the *A. thaliana* floral meristem identity gene AP1; and Mandel (1995) Plant Molecular Biology, Vol. 29, pp 995-1004, describing the meristem promoter eIF4. Tissue specific promoters which are active throughout the life cycle of a particular tissue can be used. In some embodiments, the nucleic acids in accordance with the invention are operably linked to a promoter active primarily only in cotton fiber cells. In some embodiments, the nucleic acids in accordance with the invention are operably linked to a promoter active primarily during the stages of cotton fiber cell elongation, such as described by Rinehart (1996) supra. The nucleic acids can be operably linked to the Fb12A gene promoter to be preferentially expressed in cotton fiber cells (Ibid). See also, John (1997) Proc. Natl. Acad. Sci. USA 89:5769-5773; John, et al., U.S. Pat. Nos. 5,608,148 and 5,602,321, describing cotton fiber-specific promoters and methods for the construction of transgenic cotton plants. Root-specific promoters may also be used to express the nucleic acids in accordance with the invention. Examples of root-specific promoters include the promoter from the alcohol dehydrogenase gene (DeLisle (1990) Int. Rev. Cytol. 123:39-60). Other promoters that can be used to express the nucleic acids in accordance with the invention include, such as ovule-specific, embryo-specific, endosperm-specific, integument-specific, seed coat-specific promoters, or some combination thereof; a leaf-specific promoter (see Busk (1997) Plant J. 11:1285 1295, describing a leaf-specific promoter in maize); the ORF13 promoter from *Agrobacterium rhizogenes* (which exhibits high activity in roots, see Hansen (1997) supra); a maize pollen specific promoter (see Guerrero (1990) Mol. Gen. Genet. 224:161 168); a tomato promoter active during fruit ripening, senescence and abscission of leaves and, to a lesser extent, of flowers can be used (see Blume (1997) Plant J. 12:731 746); a pistil-specific promoter from the potato SK2 gene (see Ficker (1997) Plant Mol. Biol. 35:425 431); the Blec4 gene from pea, which is active in epidermal tissue of vegetative and floral shoot apices of transgenic alfalfa making it a useful tool to target the expression of foreign genes to the epidermal layer of actively growing shoots or fibers; the ovule-specific BEL1 gene (see Reiser (1995) Cell 83:735-742, GenBank No. U39944); and/or, the promoter in Klee, U.S. Pat. No. 5,589,583, describing a plant promoter region is capable of conferring high levels of transcription in meristematic tissue and/or rapidly dividing cells.

In some embodiments, plant promoters which are inducible upon exposure to plant hormones, such as auxins, are used to express the nucleic acids in accordance with the invention. For example, the invention can use the auxin-response elements E1 promoter fragment (AuxREs) in the soybean (*Glycine max* L.) (Liu (1997) Plant Physiol. 115: 397-407); the auxin-responsive *Arabidopsis* GST6 promoter (also responsive to salicylic acid and hydrogen peroxide) (Chen (1996) Plant J. 10: 955-966); the auxin-inducible parC promoter from tobacco (Sakai (1996) *Plant Cell Physiol.* 37:906-913); a plant biotin response element (Streit (1997) Mol. Plant. Microbe Interact. 10:933-937); and, the promoter responsive to the stress hormone abscisic acid (Sheen (1996) Science 274:1900-1902).

The nucleic acids in accordance with the invention can also be operably linked to plant promoters which are inducible upon exposure to chemicals reagents which can be applied to the plant, such as herbicides or antibiotics. For example, the maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. Coding sequence can be under the control of, such as a tetracycline-inducible promoter, such as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324). Using chemically- (such as hormone- or pesticide-) induced promoters, i.e., promoter responsive to a chemical which can be applied to the transgenic plant in the field, expression of a polypeptide in accordance with the invention can be induced at a particular stage of development of the plant. Thus, the invention also provides for transgenic plants containing an inducible gene encoding for polypeptides in accordance with the invention whose host range is limited to target plant species, such as corn, rice, barley, soybean, tomato, wheat, potato or other crops, inducible at any stage of development of the crop.

One of skill will recognize that a tissue-specific plant promoter may drive expression of operably linked sequences in tissues other than the target tissue. Thus, In some embodiments, a tissue-specific promoter is one that drives expression preferentially in the target tissue or cell type, but may also lead to some expression in other tissues as well.

The nucleic acids in accordance with the invention can also be operably linked to plant promoters which are inducible upon exposure to chemicals reagents. These reagents include, such as herbicides, synthetic auxins, or antibiotics which can be applied, such as sprayed, onto transgenic plants. Inducible expression of the aldolase, such as pyruvate aldolase, such as HMG and/or KHG aldolase enzyme-producing nucleic acids in accordance with the invention will allow the grower to select plants with the optimal aldolase, such as pyruvate aldolase, such as HMG and/or KHG aldolase enzyme expression and/or activity. The development of plant parts can thus controlled. In this way the invention provides the means to facilitate the harvesting of plants and plant parts. For example, in various embodiments, the maize In2-2 promoter, activated by benzenesulfonamide herbicide safeners, is used (De Veylder (1997) Plant Cell Physiol. 38:568-577); application of different herbicide safeners induces distinct gene expression patterns, including expression in the root, hydathodes, and the shoot apical meristem. Coding sequences in accordance with the invention are also under the control of a tetracycline-inducible promoter, such as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324).

In some embodiments, proper polypeptide expression may require polyadenylation region at the 3'-end of the coding region. The polyadenylation region can be derived from the natural gene, from a variety of other plant (or animal or other) genes, or from genes in the Agrobacterial T-DNA.

Expression Vectors and Cloning Vehicles

The invention provides expression vectors and cloning vehicles comprising nucleic acids in accordance with the invention, such as sequences encoding the aldolase, such as pyruvate aldolase, such as HMG and/or KHG aldolase enzymes in accordance with the invention. Expression vectors and cloning vehicles in accordance with the invention can comprise viral particles, baculovirus, phage, plasmids, phagemids, cosmids, fosmids, bacterial artificial chromosomes, viral DNA (such as vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors in accordance with the invention can include chromosomal, non-chromosomal and synthetic DNA sequences. Large numbers of suitable vectors are known to those of skill in the art, and are commercially available. Exemplary vectors include: bacterial: pQE™ vectors (Qiagen, Valencia, Calif.), pBLUESCRIPT™ plasmids, pNH vectors, lambda-ZAP vectors (Stratagene, La Jolla, Calif.); ptrc99a, pKK223-3, pDR540, pRIT2T (GE Healthcare, Piscataway, N.J.), pET vectors (Novagen, Madison, Wis.); Eukaryotic: pXT1, pSG5 (Stratagene, La Jolla, Calif.), pSVK3, pBPV, pMSG, pSV-LSV40 (Pharmacia). However, any other plasmid or other vector may be used so long as they are replicable and viable in the host. Low copy number or high copy number vectors may be employed with the present invention. "Plasmids" can be commercially available, publicly available on an unrestricted basis, or can be constructed from available plasmids in accord with published procedures. Equivalent plasmids to those described herein are known in the art and will be apparent to the ordinarily skilled artisan.

The expression vector can comprise a promoter, a ribosome binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some embodiments, DNA sequences derived from the SV40 splice and polyadenylation sites may be used to provide the required non-transcribed genetic elements.

In some embodiments, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene. Promoter regions can be selected from any desired gene using chloramphenicol transferase (CAT) vectors or other vectors with selectable markers.

In some embodiments, vectors for expressing the polypeptide or fragment thereof in eukaryotic cells contain enhancers to increase expression levels. Enhancers are cis-acting elements of DNA that can be from about 10 to about 300 bp in length. They can act on a promoter to increase its transcription. Exemplary enhancers include the SV40 enhancer on the late side of the replication origin bp 100 to 270, the cytomegalovirus early promoter enhancer, the polyoma enhancer on the late side of the replication origin, and the adenovirus enhancers.

A nucleic acid sequence can be inserted into a vector by a variety of procedures. In general, the sequence is ligated to the desired position in the vector following digestion of the insert and the vector with appropriate restriction endonucleases. Alternatively, blunt ends in both the insert and the vector may be ligated. A variety of cloning techniques are known in the art, such as described in Ausubel et al. Current Protocols in Molecular Biology, John Wiley & Sons, Inc. 1997 and Sambrook et al., Molecular Cloning: A Laboratory Manual 2nd Ed., Cold Spring Harbor Laboratory Press (1989). Such procedures and others are deemed to be within the scope of those skilled in the art.

The vector can be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, such as Sambrook.

Particular bacterial vectors which can be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen, Valencia, Calif.), pD10, psiX174 pBLUESCRIPT II KS, pNH8A, pNH16a, pNH18A, pNH46A (Stratagene, La Jolla, Calif.), ptrc99a, pKK223-3, pKK233-3, DR540, pRIT5 (Pharmacia), pKK232-8, pET (Novagen, Madison, Wis.), and pCM7. Particular eukaryotic vectors include pSV2CAT, pOG44, pXT1, pSG (Stratagene, La Jolla, Calif.) pSVK3, pBPV, pMSG, and pSVL (Pharmacia). However, any other vector may be used as long as it is replicable and viable in the host cell.

The nucleic acids in accordance with the invention can be expressed in expression cassettes, vectors or viruses and transiently or stably expressed in plant cells and seeds. One exemplary transient expression system uses episomal expression systems, such as cauliflower mosaic virus (CaMV) viral RNA generated in the nucleus by transcription of an episomal minichromosome containing supercoiled DNA, see Covey (1990) Proc. Natl. Acad. Sci. USA 87:1633-1637. Alternatively, coding sequences, i.e., all or sub-fragments of sequences in accordance with the invention can be inserted into a plant host cell genome becoming an integral part of the host chromosomal DNA. Sense or antisense transcripts can be expressed in this manner. A vector comprising the sequences (such as promoters or coding regions) from nucleic acids in accordance with the invention can comprise a marker gene that confers a selectable phenotype on a plant cell or a seed. For example, the marker may encode biocide resistance, such as antibiotic resistance, such as resistance to kanamycin, G418, bleomycin, hygromycin, or herbicide resistance, such as resistance to chlorosulfuron or Basta.

Expression vectors capable of expressing nucleic acids and proteins in plants are well known in the art, and can include, such as vectors from *Agrobacterium* spp., potato virus X (see Angell (1997) EMBO J. 16:3675-3684), tobacco mosaic virus (see Casper (1996) Gene 173:69-73), tomato bushy stunt virus (see Hillman (1989) Virology 169:42-50), tobacco etch virus (see Dolja (1997) Virology 234:243-252), bean golden mosaic virus (see Morinaga (1993) Microbiol Immunol. 37:471-476), cauliflower mosaic virus (see Cecchini (1997) Mol. Plant. Microbe Interact. 10:1094-1101), maize Ac/Ds transposable element (see Rubin (1997) Mol. Cell. Biol. 17:6294-6302; Kunze (1996) Curr. Top. Microbiol. Immunol. 204:161-194), and the maize suppressor-mutator (Spm) transposable element (see Schlappi (1996) Plant Mol. Biol. 32:717-725); and derivatives thereof.

In some embodiments, the expression vector can have two replication systems to allow it to be maintained in two organisms, for example in mammalian or insect cells for expression and in a prokaryotic host for cloning and amplification. Furthermore, for integrating expression vectors, the expression vector can contain at least one sequence homologous to the host cell genome. It can contain two homologous sequences which flank the expression construct. The integrating vector can be directed to a specific locus in the host cell by selecting the appropriate homologous sequence for inclusion in the vector. Constructs for integrating vectors are well known in the art.

Expression vectors in accordance with the invention may also include a selectable marker gene to allow for the selection of bacterial strains that have been transformed, such as genes which render the bacteria resistant to drugs such as ampicillin, chloramphenicol, erythromycin, kanamycin, neomycin and tetracycline. Selectable markers can also include biosynthetic genes, such as those in the histidine, tryptophan and leucine biosynthetic pathways.

The DNA sequence in the expression vector is operatively linked to an appropriate expression control sequence(s) (promoter) to direct RNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using chloramphenicol transferase (CAT) vectors or other vectors with selectable markers. In addition, the expression vectors in some embodiments contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Mammalian expression vectors may also comprise an origin of replication, any necessary ribosome binding sites, a polyadenylation site, splice donor and acceptor sites, transcriptional termination sequences and 5' flanking nontranscribed sequences. In some embodiments, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin and the adenovirus enhancers.

In addition, the expression vectors can contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli* and the *S. cerevisiae* TRP1 gene.

In some embodiments, the nucleic acid encoding one of the polypeptides in accordance with the invention, and sequences substantially identical thereto, or fragments comprising at least about 5, 10, 15, 20, 25, 30, 35, 40, 50, 75, 100, or 150 or more consecutive amino acids thereof is assembled in appropriate phase with a leader sequence capable of directing secretion of the translated polypeptide or fragment thereof. In some embodiments, the nucleic acid can encode a fusion polypeptide in which one of the polypeptides in accordance with the invention, or fragments comprising at least 5, 10, 15, 20, 25, 30, 35, 40, 50, 75, 100, or 150 or more consecutive amino acids thereof is fused to heterologous peptides or polypeptides, such as N-terminal identification peptides which impart desired characteristics, such as increased stability or simplified purification.

The appropriate DNA sequence may be inserted into the vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are disclosed in Ausubel et al. Current Protocols in Molecular Biology, John Wiley & Sons, Inc. 1997 and Sambrook et al., Molecular Cloning: A Laboratory Manual 2nd Ed., Cold Spring Harbor Laboratory Press (1989). Such procedures and others are deemed to be within the scope of those skilled in the art.

The vector may be, for example, in the form of a plasmid, a viral particle, or a phage. Other vectors include chromosomal, nonchromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus and pseudorabies. A variety of cloning and expression vectors for use with prokaryotic and eukaryotic hosts are described by Sambrook, et al., Molecular Cloning: A Laboratory Manual, 2nd Ed., Cold Spring Harbor, N.Y., (1989).

Host Cells and Transformed Cells

The invention also provides transformed cells comprising nucleic acid sequences in accordance with the invention, such as sequences encoding aldolases, such as pyruvate aldolases, HMG and/or KHG aldolase enzymes in accordance with the invention, or vectors in accordance with the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include any species of *Streptomyces, Staphylococcus, Pseudomonas* or *Bacillus*, including *E. coli, Bacillus subtilis, Pseudomonas fluorescens, Bacillus cereus*, or *Salmonella typhimurium*. Exemplary fungal cells include any species of *Aspergillus*. Exemplary yeast cells include any species of *Pichia, Saccharomyces, Schizosaccharomyces*, or *Schwanniomyces*, including *Pichia pastoris, Saccharomyces cerevisiae*, or *Schizosaccharomyces pombe*. Exemplary insect cells include any species of *Spodoptera* or *Drosophila*, including *Drosophila* S2 and *Spodoptera* Sf9. Exemplary animal cells include CHO, COS or Bowes melanoma or any mouse or human cell line. The selection of an appropriate host is within the abilities of those skilled in the art. Techniques for transforming a wide variety of higher plant species are well known and described in the technical and scientific literature. See Weising (1988) Ann. Rev. Genet. 22:421-477; U.S. Pat. No. 5,750,870.

The vector can be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

In some embodiments, the nucleic acids or vectors in accordance with the invention are introduced into the cells for screening, thus, the nucleic acids enter the cells in a manner suitable for subsequent expression of the nucleic acid. The method of introduction is largely dictated by the targeted cell type. Exemplary methods include $CaPO_4$ precipitation, liposome fusion, lipofection (such as LIPOFECTIN™), electroporation, viral infection, etc. The candidate nucleic acids may stably integrate into the genome of the host cell (for example, with retroviral introduction) or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets can be used.

Where appropriate, the engineered host cells can be cultured in conventional nutrient media modified as appropriate for activating promoters, selecting transformants or amplifying the genes in accordance with the invention. Following transformation of a suitable host strain and growth of the host strain to an appropriate cell density, the selected promoter may be induced by appropriate means (such as temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides in accordance with the invention may or may not also include an initial methionine amino acid residue.

Cell-free translation systems can also be employed to produce a polypeptide in accordance with the invention. Cell-free translation systems can use mRNAs transcribed from a DNA construct comprising a promoter operably linked to a nucleic acid encoding the polypeptide or fragment thereof. In some embodiments, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Host cells containing the polynucleotides of interest, such as nucleic acids in accordance with the invention, can be cultured in conventional nutrient media modified as appropriate for activating promoters, selecting transformants or amplifying genes. The culture conditions, such as temperature, pH and the like, are those previously used with the host cell selected for expression and will be apparent to the ordinarily skilled artisan. The clones which are identified as having the specified enzyme activity may then be sequenced to identify the polynucleotide sequence encoding an enzyme having the enhanced activity.

The invention provides methods for overexpressing recombinant aldolases, such as pyruvate aldolases, such as HMG and/or KHG aldolase enzymes in cells comprising expressing a vector comprising a nucleic acid in accordance with the invention, such as a nucleic acid comprising a nucleic acid sequence with at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to a sequence in accordance with the invention over a region of at least about 100 residues, wherein the sequence identities are determined by analysis with a sequence comparison algorithm or by visual inspection, or, a nucleic acid that hybridizes under stringent conditions to a nucleic acid sequence in accordance with the invention, or a subsequence thereof. The overexpression can be effected by any means, such as use of a high activity promoter, a dicistronic vector or by gene amplification of the vector.

The nucleic acids in accordance with the invention can be expressed, or overexpressed, in any in vitro or in vivo expression system. Any cell culture systems can be employed to express, or over-express, recombinant protein, including bacterial, insect, yeast, fungal or mammalian cultures. Overexpression can be effected by appropriate choice of promoters, enhancers, vectors (such as use of replicon vectors, dicistronic vectors (see Gurtu (1996) Biochem. Biophys. Res. Commun. 229:295-8), media, culture systems and the like. In some embodiments, gene amplification using selection markers, such as glutamine synthetase (see Sanders (1987) Dev. Biol. Stand. 66:55-63), in cell systems are used to overexpress the polypeptides in accordance with the invention.

Additional details regarding this approach are in the public literature and/or are known to the skilled artisan. In a particular non-limiting exemplification, such publicly available literature includes EP 0659215 (WO 9403612 A1) (Nevalainen et al.); Lapidot, A., Mechaly, A., Shoham, Y., "Overexpression and single-step purification of a thermostable xylanase from *Bacillus stearothermophilus* T-6," J. Biotechnol. November 51:259-64 (1996); Lüthi, E., Jasmat, N. B., Bergquist, P. L., "Xylanase from the extremely thermophilic bacterium Caldocellum saccharolyticum: overexpression of the gene in *Escherichia coli* and characterization of the gene product," Appl. Environ. Microbiol. September 56:2677-83 (1990); and Sung, W. L., Luk, C. K., Zahab, D. M., Wakarchuk, W., "Overexpression of the *Bacillus subtilis* and circulans xylanases in *Escherichia coli*," Protein Expr. Purif. June 4:200-6 (1993), although these references do not teach the inventive enzymes of the instant application.

The host cell may be any of the host cells familiar to those skilled in the art, including prokaryotic cells, eukaryotic cells, mammalian cells, insect cells, or plant cells. As representative examples of appropriate hosts, there may be mentioned: bacterial cells, such as *E. coli, Streptomyces, Bacillus subtilis, Bacillus cereus, Salmonella typhimurium* and various species within the genera *Pseudomonas, Streptomyces* and *Staphylococcus*, fungal cells, such as *Aspergillus*, yeast such as any species of *Pichia, Saccharomyces, Schizosaccharomyces, Schwanniomyces*, including *Pichia pastoris, Saccharomyces cerevisiae*, or *Schizosaccharomyces pombe*, insect cells such as *Drosophila* S2 and *Spodoptera* Sf9, animal cells such as CHO, COS or Bowes melanoma and adenoviruses. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes in accordance with the invention. Following transformation of a suitable host strain and growth of the host strain to an appropriate cell density, the selected promoter may be induced by appropriate means (such as temperature shift or chemical induction) and the cells may be cultured for an additional period to allow them to produce the desired polypeptide or fragment thereof.

Cells can be harvested by centrifugation, disrupted by physical or chemical means and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, Cell, 23:175, 1981) and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides in accordance with the invention may or may not also include an initial methionine amino acid residue.

Alternatively, the polypeptides in accordance with the invention, or fragments comprising at least 5, 10, 15, 20, 25, 30, 35, 40, 50, 75, 100, or 150 or more consecutive amino acids thereof can be synthetically produced by conventional peptide synthesizers, such as discussed below. In other embodiments, fragments or portions of the polypeptides may be employed for producing the corresponding full-length polypeptide by peptide synthesis; therefore, the fragments may be employed as intermediates for producing the full-length polypeptides.

Cell-free translation systems can also be employed to produce one of the polypeptides in accordance with the invention, or fragments comprising at least 5, 10, 15, 20, 25, 30, 35, 40, 50, 75, 100, or 150 or more consecutive amino acids thereof using mRNAs transcribed from a DNA construct comprising a promoter operably linked to a nucleic acid encoding the polypeptide or fragment thereof. In some embodiments, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

Amplification of Nucleic Acids

In practicing the invention, nucleic acids in accordance with the invention and nucleic acids encoding the aldolase, such as pyruvate aldolase, such as HMG and/or KHG aldolase enzymes in accordance with the invention, or modified nucleic acids in accordance with the invention, can be reproduced by amplification, such as PCR. Amplification can also be used to clone or modify the nucleic acids in accordance with the invention. Thus, the invention provides amplification primer sequence pairs for amplifying nucleic acids in accordance with the invention. One of skill in the art can design amplification primer sequence pairs for any part of or the full length of these sequences.

In some embodiments, the invention provides nucleic acids amplified by amplification primer pairs in accordance with the invention, such as primer pairs as set forth by about the first (the 5') 12, 13, 14, 15, 16, 17, 18, 19, 20, 21, 22, 23, 24, or 25 or more residues of nucleic acids in accordance with the invention, and about the first (the 5') 15, 16, 17, 18, 19, 20, 21, 22, 23, 24, or 25 or more residues of the complementary strands. In some embodiments, the invention provides amplification primer sequence pairs for amplifying a nucleic acid encoding a polypeptide having an aldolase, such as pyruvate aldolase, such as HMG and/or KHG aldolase enzyme, activity, wherein the primer pair is capable of amplifying a nucleic acid comprising a sequence in accordance with the invention, or fragments or subsequences thereof. One or each member of the amplification primer sequence pair can comprise an oligonucleotide comprising at least about 10 to 50 or more consecutive bases of the sequence, or about 12, 13, 14, 15, 16, 17, 18, 19, 20, 21, 22, 23, 24, or 25 or more consecutive bases of the sequence. In some embodiments, the invention provides amplification primer pairs, wherein the primer pair comprises a first member having a sequence as set forth by about the first (the 5') 12, 13, 14, 15, 16, 17, 18, 19, 20, 21, 22, 23, 24, or 25 or more residues of a nucleic acid in accordance with the invention, and a second member having a sequence as set forth by about the first (the 5') 12, 13, 14, 15, 16, 17, 18, 19, 20, 21, 22, 23, 24, or 25 or more residues of the complementary strand of the first member.

The invention provides aldolase, such as pyruvate aldolase, such as HMG and/or KHG aldolase enzymes generated by amplification, such as polymerase chain reaction (PCR), using an amplification primer pair in accordance with the invention. In some embodiments, the invention provides methods of making an aldolase, such as pyruvate aldolase, HMG and/or KHG aldolase enzyme by amplification, such as PCR, using an amplification primer pair in accordance with the invention. In some embodiments, the amplification primer pair amplifies a nucleic acid from a library, such as a gene library, such as an environmental library.

Amplification reactions can also be used to quantify the amount of nucleic acid in a sample (such as the amount of message in a cell sample), label the nucleic acid (such as to apply it to an array or a blot), detect the nucleic acid, or quantify the amount of a specific nucleic acid in a sample. In some embodiments of the invention, message isolated from a cell or a cDNA library are amplified.

The skilled artisan can select and design suitable oligonucleotide amplification primers. Amplification methods are also well known in the art, and include, such as polymerase chain reaction, PCR (see PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see Wu (1989) Genomics 4:560; Landegren (1988) Science 241: 1077; Barringer (1990) Gene 89:117); transcription amplification (see Kwoh (1989) Proc. Natl. Acad. Sci. USA 86:1173); and, self-sustained sequence replication (see Guatelli (1990) Proc. Natl. Acad. Sci. USA 87:1874); Q Beta replicase amplification (see Smith (1997) J. Clin. Microbiol. 35:1477-1491), automated Q-beta replicase amplification assay (see Burg (1996) Mol. Cell. Probes 10:257-271) and other RNA polymerase mediated techniques (such as NASBA, Cangene, Mississauga, Ontario); see also Berger (1987) Methods Enzymol. 152:307-316; Ausubel et al. Current Protocols in Molecular Biology, John Wiley & Sons, Inc. 1997 and Sambrook et al., Molecular Cloning: A Laboratory Manual 2nd Ed., Cold Spring Harbor Laboratory Press (1989). U.S. Pat. Nos. 4,683,195 and 4,683,202; Sooknanan (1995) Biotechnology 13:563-564.

Determining Sequence Identity in Nucleic Acids and Polypeptides

The invention provides nucleic acids comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity (homology) to a nucleic acid in accordance with the invention (see Sequence Listing) over a region of at least about 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues. In some embodiments, the invention provides polypeptides comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a polypeptide in accordance with the invention (see Sequence Listing). The extent of sequence identity (homology) may be determined using any computer program and associated parameters, including those described herein, such as BLAST 2.2.2. or FASTA version 3.0t78, with the default parameters.

Nucleic acid sequences in accordance with the invention can comprise at least 10, 15, 20, 25, 30, 35, 40, 50, 75, 100, 150, 200, 300, 400, or 500 or more consecutive nucleotides of a sequence in accordance with the invention and sequences substantially identical thereto. Homologous sequences and fragments of nucleic acid sequences in accordance with the invention can refer to a sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity (homology) to these sequences. Homology (sequence identity) may be determined using any of the computer programs and parameters described herein, including FASTA version 3.0t78 with the default parameters. Homologous sequences also include RNA sequences in which uridines replace the thymines in the nucleic acid sequences in accordance with the invention. The homologous sequences may be obtained using any of the procedures described herein or may result from the correction of a sequencing error. It will be appreciated that the nucleic acid sequences in accordance with the invention can be represented in the traditional single character format (See the inside back cover of Stryer, Lubert.

Biochemistry, 3rd Ed., W. H Freeman & Co., New York.) or in any other format which records the identity of the nucleotides in a sequence.

In some embodiments, sequence comparison programs identified herein are used in this aspect in accordance with the invention, i.e., to determine if a nucleic acid or polypeptide sequence is within the scope in accordance with the invention. However, protein and/or nucleic acid sequence identities (homologies) may be evaluated using any sequence comparison algorithm or program known in the art. Such algorithms and programs include, but are by no means limited to, TBLASTN, BLASTP, FASTA, TFASTA and CLUSTALW (see Pearson and Lipman, Proc. Natl. Acad. Sci. USA 85(8):2444-2448, 1988; Altschul et al., J. Mol. Biol. 215(3):403-410, 1990; Thompson Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

In some embodiments, homology or identity is measured using sequence analysis software (such as Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. In some embodiments, the terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. In some embodiments, for sequence comparison, one sequence acts as a reference sequence, to which test sequences are compared. When using a sequence comparison algorithm, test and reference sequences are entered into a computer, subsequence coordinates are designated, if necessary and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, such as by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BEST-FIT, FASTA and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (Gibbs, 1995). At least twenty-one other genomes have already been sequenced, including, for example, *M. genitalium* (Fraser et al., *Science* 270:397-403 (1995)), *M. jannaschii* (Bult et al., *Science* 23:1058-73 (1996)), *H. influenzae* (Fleischmann et al., *Science* 269:496-512 (1995)), *E. coli* (Blattner et al., *Science* 277:1453-74 (1997)) and yeast (*S. cerevisiae*) (Mewes et al., *Nature* 387:7-65 (1997)) and *D. melanogaster* (Adams et al., *Science* 287:2185-95 (2000)). Significant progress has also been made in sequencing the genomes of model organism, such as mouse, *C. elegans* and *Arabadopsis* sp. Several databases containing genomic information annotated with some functional information are maintained by different organizations and may be accessible via the internet.

In some embodiments, BLAST and BLAST 2.0 algorithms are used, which are described in Altschul et al., Nuc. Acids Res. 25:3389-3402, 1977 and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3 and expectations (E) of 10 and the BLOSUM62 scoring matrix (see Henikoff & Henikoff, Proc. Natl. Acad. Sci. USA 89:10915, 1989) alignments (B) of 50, expectation (E) of 10, M=5, N=−4 and a comparison of both strands.

The BLAST algorithm also performs a statistical analysis of the similarity between two sequences (see Karlin & Altschul, Proc. Natl. Acad. Sci. USA 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, n some embodiments less than about 0.01 and in other embodiments less than about 0.001.

In some embodiments, protein and nucleic acid sequence homologies are evaluated using the Basic Local Alignment Search Tool ("BLAST") In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is, in some embodiments, obtained from a protein or nucleic acid sequence database. High-scoring segment pairs are, in some embodiments, identified (i.e., aligned) by means of a scoring matrix, many of which are known in the art. In some embodiments, the scoring matrix used is the BLOSUM62 matrix (Gonnet (1992) Science 256:1443-1445; Henikoff and Henikoff (1993) Proteins 17:49-61). Less In some embodiments, the PAM or PAM250 matrices may also be used (see Schwartz and Dayhoff, eds., 1978, *Matrices for Detecting Distance Relationships: Atlas of Protein Sequence and Structure*, Washington: National Biomedical Research Foundation). BLAST programs are accessible through the U.S. National Library of Medicine.

The parameters used with the above algorithms may be adapted depending on the sequence length and degree of homology studied. In some embodiments, the parameters may be the default parameters used by the algorithms in the absence of instructions from the user.

Computer Systems and Computer Program Products

The invention provides computers, computer systems, computer readable mediums, computer programs products and the like recorded or stored thereon the nucleic acid and polypeptide sequences in accordance with the invention. Additionally, in practicing the methods in accordance with the invention, such as to determine and identify sequence identities (to determine whether a nucleic acid is within the scope in accordance with the invention), structural homologies, motifs and the like in silico, a nucleic acid or polypeptide sequence in accordance with the invention can be stored, recorded, and manipulated on any medium which can be read and accessed by a computer.

As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences in accordance with the invention. As used herein, the terms "computer," "computer program" and "processor" are used in their broadest general contexts and incorporate all such devices, as described in detail, below. A "coding sequence of" or a "sequence encodes" a particular polypeptide or protein, is a nucleic acid sequence which is transcribed and translated into a polypeptide or protein when placed under the control of appropriate regulatory sequences.

The polypeptides in accordance with the invention include sequences in accordance with the invention and sequences substantially identical thereto, and subsequences and enzymatically active fragments of any of the preceding sequences. In some embodiments, substantially identical, or homologous, polypeptide sequences refer to a polypeptide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity (homology) to sequence in accordance with the invention.

Homology (sequence identity) may be determined using any of the computer programs and parameters described herein. A nucleic acid or polypeptide sequence in accordance with the invention can be stored, recorded and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid sequences in accordance with the invention, one or more of the polypeptide sequences in accordance with the invention. Another embodiment of the invention is a computer readable medium having recorded thereon at least 2, 5, 10, 15, or 20 or more nucleic acid or polypeptide sequences in accordance with the invention.

Another embodiment of the invention is a computer readable medium having recorded thereon one or more of the nucleic acid sequences in accordance with the invention. Another embodiment of the invention is a computer readable medium having recorded thereon one or more of the polypeptide sequences in accordance with the invention. Another embodiment of the invention is a computer readable medium having recorded thereon at least 2, 5, 10, 15, or 20 or more of the nucleic acid or polypeptide sequences as set forth above.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Figure 9:
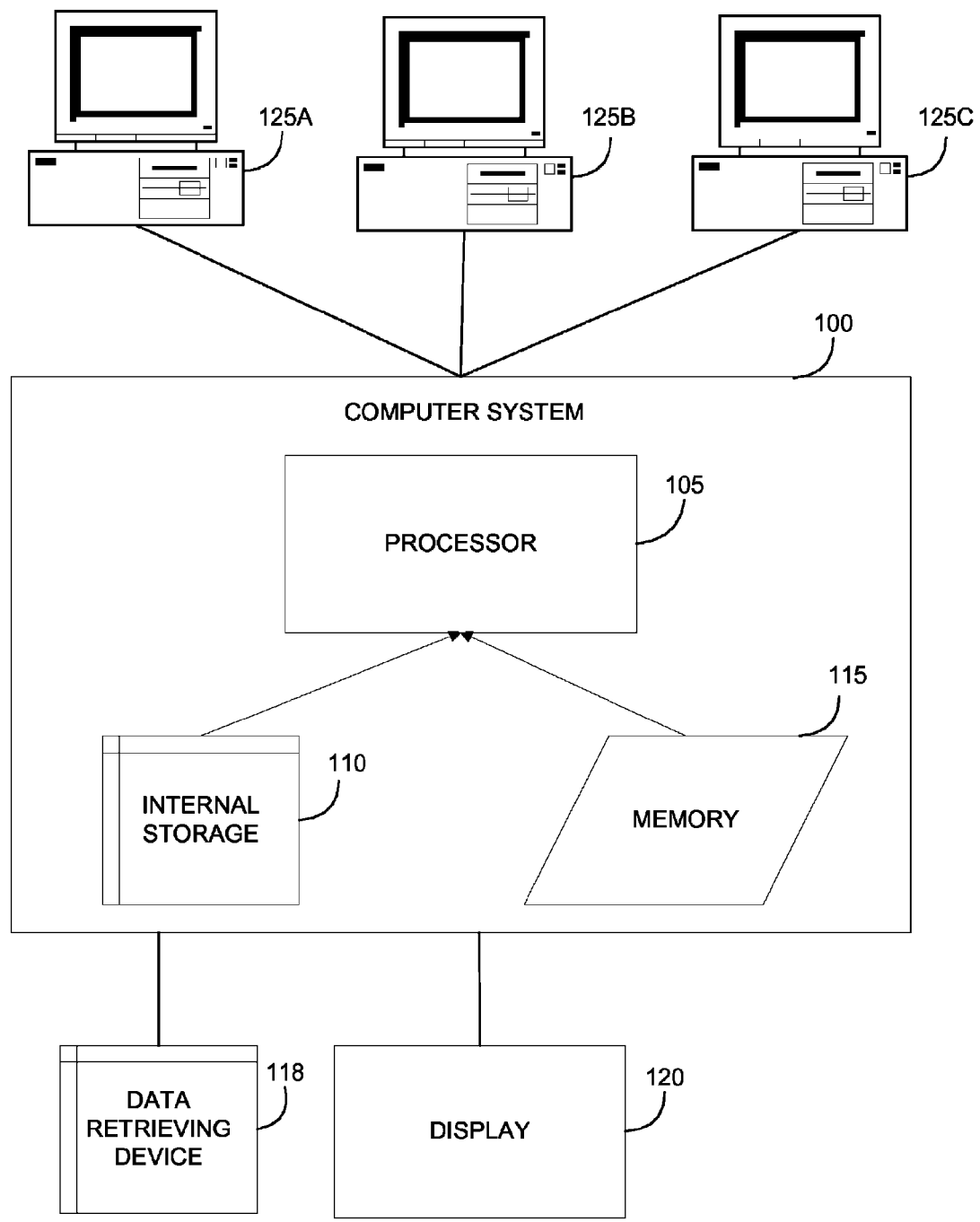
FIG. 9 is a block diagram of a computer system.

Some embodiments of the invention include systems (such as internet based systems), such as computer systems which store and manipulate the sequence information described herein. One example of a computer system 100 is illustrated in block diagram form in FIG. 9. As used herein, "a computer system" refers to the hardware components, software components and data storage components used to analyze a nucleotide sequence of a nucleic acid sequence in accordance with the invention, or a polypeptide sequence in accordance with the invention. In some embodiments, the computer system 100 includes a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines.

In some embodiments, the computer system 100 is a general purpose system that comprises the processor 105 and one or more internal data storage components 110 for storing data and one or more data retrieving devices for retrieving the data stored on the data storage components. A skilled artisan can readily appreciate that any one of the currently available computer systems are suitable.

In one embodiment, the computer system 100 includes a processor 105 connected to a bus which is connected to a main memory 115 (in one embodiment implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (such as via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125*a-c* in a network or wide area network to provide centralized access to the computer system 100.

Software for accessing and processing the nucleotide sequences of a nucleic acid sequence in accordance with the invention and sequences substantially identical thereto, or a polypeptide sequence in accordance with the invention and sequences substantially identical thereto, (such as search tools, compare tools and modeling tools etc.) may reside in main memory 115 during execution.

In some embodiments, the computer system 100 may further comprise a sequence comparison algorithm for comparing a nucleic acid sequence in accordance with the invention and sequences substantially identical thereto, or a polypeptide sequence in accordance with the invention and sequences substantially identical thereto, stored on a computer readable medium to a reference nucleotide or polypeptide sequence(s) stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of a nucleic acid sequence in accordance with the invention and sequences substantially identical thereto, or a polypeptide sequence in accordance with the invention and sequences substantially identical thereto, stored on a computer readable medium to reference sequences stored on a computer readable medium to identify homologies or structural motifs.

Figure 10:
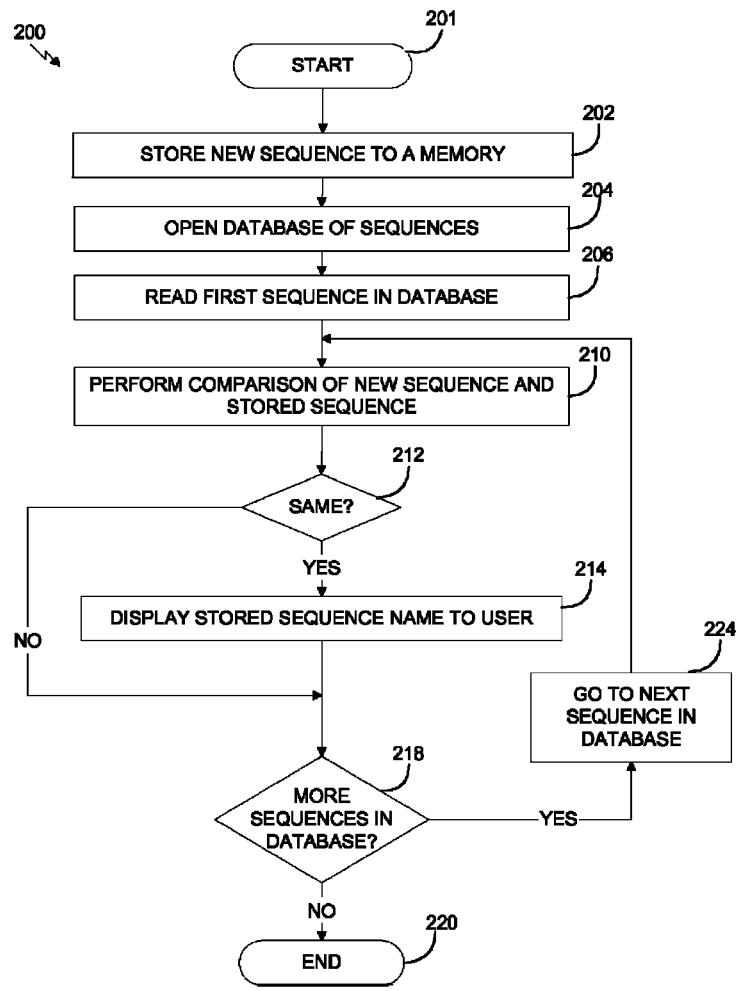
FIG. 10 is a flow diagram illustrating one embodiment of a process for comparing a new nucleotide or protein sequence with a database of sequences in order to determine the homology levels between the new sequence and the sequences in the database.

FIG. 10 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one embodiment of the invention is a computer system comprising a processor, a data storage device having stored thereon a nucleic acid sequence in accordance with the invention and sequences substantially identical thereto, or a polypeptide sequence in accordance with the invention and sequences substantially identical thereto, a data storage device having retrievably stored thereon reference nucleotide sequences or polypeptide sequences to be compared to a nucleic acid sequence in accordance with the invention and sequences substantially identical thereto, or a polypeptide sequence in accordance with the invention and sequences substantially identical thereto and a sequence comparer for conducting the comparison. The sequence comparer may indicate a homology level between the sequences compared or identify structural motifs in the above described nucleic acid code a nucleic acid sequence in accordance with the invention and sequences substantially identical thereto, or a polypeptide sequence in accordance with the invention and sequences substantially identical thereto, or it may identify structural motifs in sequences which are compared to these nucleic acid codes and polypeptide codes. In some embodiments, the data storage device may have stored thereon the sequences of at least 2, 5, 10, 15, 20, 25, 30 or 40 or more of the nucleic acid sequences in accordance with the invention and sequences substantially identical thereto, or the polypeptide sequences in accordance with the invention and sequences substantially identical thereto.

Another embodiment of the invention is a method for determining the level of homology between a nucleic acid sequence in accordance with the invention and sequences substantially identical thereto, or a polypeptide sequence in accordance with the invention and sequences substantially identical thereto and a reference nucleotide sequence. The method including reading the nucleic acid code or the polypeptide code and the reference nucleotide or polypeptide sequence through the use of a computer program which determines homology levels and determining homology between the nucleic acid code or polypeptide code and the reference nucleotide or polypeptide sequence with the computer program. The computer program may be any of a number of computer programs for determining homology levels, including those specifically enumerated herein, (such as BLAST2N with the default parameters or with any modified parameters). The method may be implemented using the computer systems described above. The method may also be performed by reading at least 2, 5, 10, 15, 20, 25, 30 or 40 or more of the above described nucleic acid sequences in accordance with the invention and sequences substantially identical thereto, or the polypeptide sequences in accordance with the invention and sequences substantially identical thereto through use of the computer program and determining homology between the nucleic acid codes or polypeptide codes and reference nucleotide sequences or polypeptide sequences.

Figure 11:
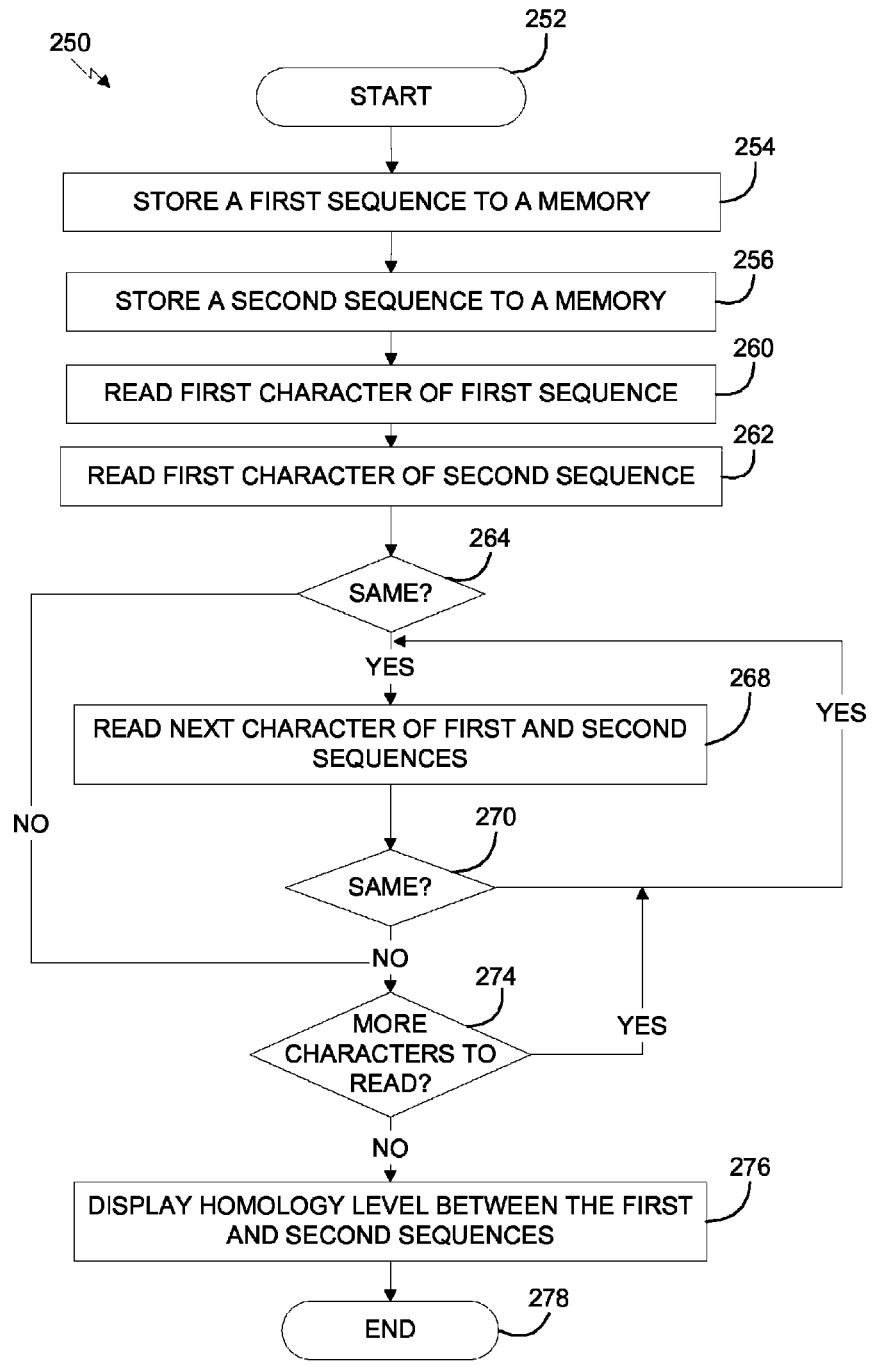
FIG. 11 is a flow diagram illustrating one embodiment of a process in a computer for determining whether two sequences are homologous.

FIG. 11 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it is, in some embodiments, in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of a nucleic acid sequence as set forth in the invention, to one or more reference nucleotide sequences in order to determine whether the nucleic acid code in accordance with the invention and sequences substantially identical thereto, differs from a reference nucleic acid sequence at one or more positions. Optionally such a program records the length and identity of inserted, deleted or substituted nucleotides with respect to the sequence of either the reference polynucleotide or a nucleic acid sequence in accordance with the invention and sequences substantially identical thereto. In some embodiments, the computer program may be a program which determines whether a nucleic acid sequence in accordance with the invention and sequences substantially identical thereto, contains a single nucleotide polymorphism (SNP) with respect to a reference nucleotide sequence.

Accordingly, another embodiment of the invention is a method for determining whether a nucleic acid sequence in accordance with the invention and sequences substantially identical thereto, differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms. The method may be implemented by the computer systems described above and the method illustrated in FIG. 11. The method may also be performed by reading at least 2, 5, 10, 15, 20, 25, 30, or 40 or more of the nucleic acid sequences in accordance with the invention and sequences substantially identical thereto and the reference nucleotide sequences through the use of the computer program and identifying differences between the nucleic acid codes and the reference nucleotide sequences with the computer program.

In other embodiments, the computer based system may further comprise an identifier for identifying features within a nucleic acid sequence in accordance with the invention or a polypeptide sequence in accordance with the invention and sequences substantially identical thereto. An "identifier" refers to one or more programs which identifies certain features within a nucleic acid sequence in accordance with the invention, or a polypeptide sequence in accordance with the invention. In some embodiments, the identifier may comprise a program which identifies an open reading frame in a nucleic acid sequence in accordance with the invention and sequences substantially identical thereto.

Figure 12:
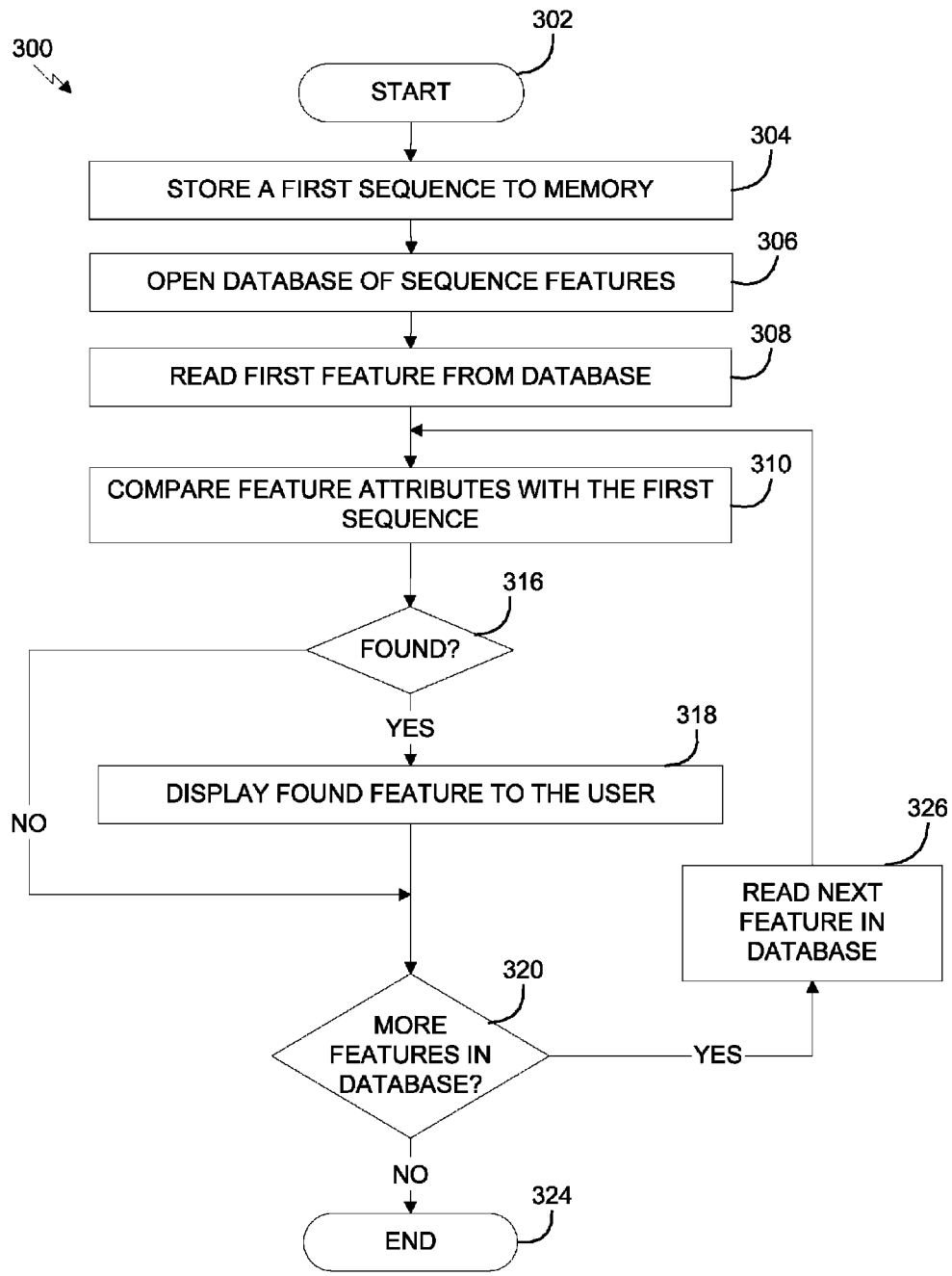
FIG. 12 is a flow diagram illustrating one embodiment of an identifier process 300 for detecting the presence of a feature in a sequence.

FIG. 12 is a flow diagram illustrating one embodiment of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic active sites, helix-turn-helix motifs or other motifs known to those skilled in the art.

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence. It should be noted, that if the feature attribute is not found in the first sequence at the decision state 316, the process 300 moves directly to the decision state 320 in order to determine if any more features exist in the database.

Accordingly, another embodiment of the invention is a method of identifying a feature within a nucleic acid sequence in accordance with the invention and sequences substantially identical thereto, or a polypeptide sequence in accordance with the invention and sequences substantially identical thereto, comprising reading the nucleic acid code(s) or polypeptide code(s) through the use of a computer program which identifies features therein and identifying features within the nucleic acid code(s) with the computer program. In some embodiments, the computer program comprises a computer program which identifies open reading frames. The method may be performed by reading a single sequence or at least 2, 5, 10, 15, 20, 25, 30, or 40 or more of the nucleic acid sequences in accordance with the invention and sequences substantially identical thereto, or the polypeptide sequences in accordance with the invention and sequences substantially identical thereto, through the use of the computer program and identifying features within the nucleic acid codes or polypeptide codes with the computer program.

A nucleic acid sequence in accordance with the invention and sequences substantially identical thereto, or a polypeptide sequence in accordance with the invention and sequences substantially identical thereto, may be stored and manipulated in a variety of data processor programs in a variety of formats. For example, a nucleic acid sequence in accordance with the invention and sequences substantially identical thereto, or a polypeptide sequence in accordance with the invention and sequences substantially identical thereto, may be stored as text in a word processing file, such as Microsoft WORD™ or WORDPERFECT™ or as an ASCII file in a variety of database programs familiar to those of skill in the art, such as DB2™, SYBASE™, or ORACLE™. In addition, many computer programs and databases may be used as sequence comparison algorithms, identifiers, or sources of reference nucleotide sequences or polypeptide sequences to be compared to a nucleic acid sequence in accordance with the invention and sequences substantially identical thereto, or a polypeptide sequence in accordance with the invention and sequences substantially identical thereto. The following list is intended not to limit the invention but to provide guidance to programs and databases which are useful with the nucleic acid sequences in accordance with the invention and sequences substantially identical thereto, or the polypeptide sequences in accordance with the invention and sequences substantially identical thereto.

The programs and databases which may be used include, but are not limited to: MACPATTERN™ (EMBL), DISCOVERYBASE™ (Molecular Applications Group), GENEMINE™ (Molecular Applications Group), LOOK™ (Molecular Applications Group), MACLOOK™ (Molecular Applications Group), BLAST and BLAST2 (NCBI), BLASTN and BLASTX (Altschul et al., J. Mol. Biol. 215: 403, 1990), FASTA (Pearson and Lipman, Proc. Natl. Acad. Sci. USA, 85: 2444, 1988), FASTDB (Brutlag et al. Comp. App. Biosci. 6:237-245, 1990), CATALYST™ (Molecular Simulations Inc.), Catalyst/SHAPE™ (Molecular Simulations Inc.), Cerius$^2$.DBAccess™ (Molecular Simulations Inc.), HYPOGEN™ (Molecular Simulations Inc.), INSIGHT II™, (Molecular Simulations Inc.), DISCOVER™ (Molecular Simulations Inc.), CHARMm™ (Molecular Simulations Inc.), FELIX™ (Molecular Simulations Inc.), DELPHI™, (Molecular Simulations Inc.), QuanteMM™, (Molecular Simulations Inc.), Homology (Molecular Simulations Inc.), MODELER™ (Molecular Simulations Inc.), ISIS™ (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwents's World Drug Index database, the BioByteMasterFile database, the Genbank database and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices and beta sheets, signal sequences encoding signal peptides which direct the secretion of the encoded proteins, sequences implicated in transcription regulation such as homeoboxes, acidic stretches, enzymatic active sites, substrate binding sites and enzymatic cleavage sites.

Hybridization of Nucleic Acids

The invention provides isolated, synthetic or recombinant nucleic acids that hybridize under stringent conditions to a sequence in accordance with the invention (such as SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:110, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:279, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305, SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, or SEQ ID NO:338. The stringent conditions can be highly stringent conditions, medium stringent conditions and/or low stringent conditions, including the high and reduced stringency conditions described herein. In some embodiments, it is the stringency of the wash conditions that set forth the conditions which determine whether a nucleic acid is within the scope in accordance with the invention, as discussed below.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature and are well known in the art. In other embodiments, stringency can be increased by reducing the concentration of salt, increasing the concentration of formamide, or raising the hybridization temperature. In other embodiments, nucleic acids in accordance with the invention are defined by their ability to hybridize under various stringency conditions (such as high, medium, and low), as set forth herein.

In some embodiments, hybridization under high stringency conditions comprise about 50% formamide at about 37° C. to 42° C. In some embodiments, hybridization conditions comprise reduced stringency conditions in about 35% to 25% formamide at about 30° C. to 35° C. In some embodiments, hybridization conditions comprise high stringency conditions, such as at 42° C. in 50% formamide, 5×SSPE, 0.3% SDS and 200 µg/ml sheared and denatured salmon sperm DNA. In some embodiments, hybridization conditions comprise these reduced stringency conditions, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

In other embodiments, nucleic acids in accordance with the invention as defined by their ability to hybridize under stringent conditions can be between about five residues and the full length of nucleic acid in accordance with the invention; such as they can be at least 5, 10, 15, 20, 25, 30, 35, 40, 50, 55, 60, 65, 70, 75, 80, 90, 100, 150, 200, 250, 300, 350, 400, 450, 500, 550, 600, 650, 700, 750, 800, 850, 900, 950, 1000, or more, residues in length. Nucleic acids shorter than full length are also included. These nucleic acids can be useful as, such as hybridization probes, labeling probes, PCR oligonucleotide probes, siRNA or miRNA (single or double stranded), antisense or sequences encoding antibody binding peptides (epitopes), motifs, active sites and the like.

In some embodiments, nucleic acids in accordance with the invention are defined by their ability to hybridize under high stringency comprises conditions of about 50% formamide at about 37° C. to 42° C. In some embodiments, nucleic acids in accordance with the invention are defined by their ability to hybridize under reduced stringency comprising conditions in about 35% to 25% formamide at about 30° C. to 35° C.

Alternatively, nucleic acids in accordance with the invention are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (such as 200 µg/ml sheared and denatured salmon sperm DNA). In some embodiments, nucleic acids in accordance with the invention are defined by their ability to hybridize under reduced stringency conditions comprising 35% or 40% formamide at a reduced temperature of 35° C. or 42° C.

In nucleic acid hybridization reactions, the conditions used to achieve a particular level of stringency will vary, depending on the nature of the nucleic acids being hybridized. For example, the length, degree of complementarity, nucleotide sequence composition (such as GC v. AT content) and nucleic acid type (such as RNA v. DNA) of the hybridizing regions of the nucleic acids can be considered in selecting hybridization conditions. An additional consideration is whether one of the nucleic acids is immobilized, for example, on a filter.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM NaH$_2$PO$_4$, pH 7.0, 5.0 mM Na$_2$EDTA, 0.5% SDS, 10× Denhardt's and 0.5 mg/ml polyriboadenylic acid. Approximately 2×10$^7$ cpm (specific activity 4-9×10$^8$ cpm/µg) of $^{32}$P end-labeled oligonucleotide probe are then added to the solution. After 12-16 hours of incubation, the membrane is washed for 30 minutes at room temperature in 1×SET (150 mM NaCl, 20 mM Tris hydrochloride, pH 7.8, 1 mM Na$_2$EDTA) containing 0.5% SDS, followed by a 30 minute wash in fresh 1×SET at $T_m$-10° C. for the oligonucleotide probe. The membrane is then exposed to auto-radiographic film for detection of hybridization signals. All of the foregoing hybridizations would be considered to be under conditions of high stringency.

Following hybridization, a filter can be washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (such as GC v. AT content) and the nucleic acid type (such as RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes. Some other examples are given below.

In some embodiments, hybridization conditions comprise a wash step comprising a wash for 30 minutes at room temperature in a solution comprising 1×150 mM NaCl, 20 mM Tris hydrochloride, pH 7.8, 1 mM $Na_2EDTA$, 0.5% SDS, followed by a 30 minute wash in fresh solution.

Nucleic acids which have hybridized to the probe are identified by autoradiography or other conventional techniques.

The above procedures may be modified to identify nucleic acids having decreasing levels of sequence identity (homology) to the probe sequence. For example, to obtain nucleic acids of decreasing sequence identity (homology) to the detectable probe, less stringent conditions may be used. For example, the hybridization temperature may be decreased in increments of 5° C. from 68° C. to 42° C. in a hybridization buffer having a $Na^+$ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

However, the selection of a hybridization format may not be critical—it is the stringency of the wash conditions that set forth the conditions which determine whether a nucleic acid is within the scope in accordance with the invention. Wash conditions used to identify nucleic acids within the scope in accordance with the invention include, such as: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook ed., MOLECULAR CLONING: A LABORATORY MANUAL (2nd ed.), vols. 1-3, Cold Spring Harbor Laboratory (1989), LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993) and Ausubel, ed. John Wiley & Sons, Inc., New York (1997) for a description of SSC buffer and equivalent conditions.

These methods may be used to isolate or identify nucleic acids in accordance with the invention and sequences substantially identical thereto. For example, the preceding methods may be used to isolate or identify nucleic acids having a sequence with at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity (homology) to a nucleic acid sequence selected from the group consisting of one of the sequences in accordance with the invention and sequences substantially identical thereto, or fragments comprising at least about 10, 15, 20, 25, 30, 35, 40, 50, 75, 100, 150, 200, 300, 400, or 500 consecutive bases thereof and the sequences complementary thereto. Sequence identity (homology) may be measured using the alignment algorithm. For example, the homologous polynucleotides may have a coding sequence which is a naturally occurring allelic variant of one of the coding sequences described herein. Such allelic variants may have a substitution, deletion or addition of one or more nucleotides when compared to the nucleic acids in accordance with the invention. Additionally, the above procedures may be used to isolate nucleic acids which encode polypeptides having at least about 99%, 95%, at least 90%, at least 85%, at least 80%, at least 75%, at least 70%, at least 65%, at least 60%, at least 55%, or at least 50% sequence identity (homology) to a polypeptide in accordance with the invention, or fragments comprising at least 5, 10, 15, 20, 25, 30, 35, 40, 50, 75, 100, or 150 consecutive amino acids thereof as determined using a sequence alignment algorithm (such as the FASTA version 3.0t78 algorithm with the default parameters).

Oligonucleotides Probes and Methods for Using Them

The invention also provides nucleic acid probes that can be used, such as for identifying, amplifying, or isolating nucleic acids encoding a polypeptide having an aldolase, such as pyruvate aldolase, such as HMG and/or KHG aldolase enzyme activity or fragments thereof or for identifying aldolase, such as pyruvate aldolase, such as HMG and/or KHG aldolase enzyme, genes. In some embodiments, the probe comprises at least about 10 consecutive bases of a nucleic acid in accordance with the invention. Alternatively, a probe in accordance with the invention can be at least about 5, 6, 7, 8, 9, 10, 11, 12, 13, 14, 15, 16, 17, 18, 19, 20, 21, 22, 23, 24, 25, 30, 35, 40, 45, 50, 60, 70, 80, 90, 100, 110, 120, 130, 150 or about 10 to 50, about 20 to 60 about 30 to 70, consecutive bases of a sequence as set forth in a nucleic acid in accordance with the invention. The probes identify a nucleic acid by binding and/or hybridization. The probes can be used in arrays in accordance with the invention, see discussion below, including, such as capillary arrays. The probes in accordance with the invention can also be used to isolate other nucleic acids or polypeptides.

The isolated, synthetic or recombinant nucleic acids in accordance with the invention, the sequences complementary thereto, or a fragment comprising at least about 10, 15, 20, 25, 30, 35, 40, 50, 75, 100, 150, 200, 300, 400, or 500 consecutive bases of one of the sequences in accordance with the invention, or the sequences complementary thereto may also be used as probes to determine whether a biological sample, such as a oil sample, contains an organism having a nucleic acid sequence in accordance with the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences from which are present therein.

Where necessary, conditions which permit the probe to specifically hybridize to complementary sequences may be determined by placing the probe in contact with complementary sequences from samples known to contain the complementary sequence as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids.

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product.

Many methods for using the labeled probes to detect the presence of complementary nucleic acids in a sample are familiar to those skilled in the art. These include Southern Blots, Northern Blots, colony hybridization procedures and dot blots. Protocols for each of these procedures are provided in Ausubel et al. Current Protocols in Molecular Biology, John Wiley & Sons, Inc. (1997) and Sambrook et al., Molecular Cloning: A Laboratory Manual 2nd Ed., Cold Spring Harbor Laboratory Press (1989).

Alternatively, more than one probe (at least one of which is capable of specifically hybridizing to any complementary sequences which are present in the nucleic acid sample), may be used in an amplification reaction to determine whether the sample contains an organism containing a nucleic acid sequence in accordance with the invention (such as an organism from which the nucleic acid was isolated). In some embodiments, the probes comprise oligonucleotides. In some embodiments, the amplification reaction may comprise a PCR reaction. PCR protocols are described in Ausubel and Sambrook, supra. Alternatively, the amplification may comprise a ligase chain reaction, 3SR, or strand displacement reaction. (See Barany, F., "The Ligase Chain Reaction in a PCR World", *PCR Methods and Applications* 1:5-16, 1991; E. Fahy et al., "Self-sustained Sequence Replication (3SR): An Isothermal Transcription-based Amplification System Alternative to PCR", *PCR Methods and Applications* 1:25-33, 1991; and Walker G. T. et al., "Strand Displacement Amplification—an Isothermal in vitro DNA Amplification Technique", *Nucleic Acid Research* 20:1691-1696, 1992). In such procedures, the nucleic acids in the sample are contacted with the probes, the amplification reaction is performed and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the ends of the sequences in accordance with the invention, may also be used in chromosome walking procedures to identify clones containing genomic sequences located adjacent to the sequences in accordance with the invention. Such methods allow the isolation of genes which encode additional proteins from the host organism.

In some embodiments, the isolated, synthetic or recombinant nucleic acids in accordance with the invention, the sequences complementary thereto, or a fragment comprising at least 10, 15, 20, 25, 30, 35, 40, 50, 75, 100, 150, 200, 300, 400, or 500 or more consecutive bases of one of the sequences in accordance with the invention, or the sequences complementary thereto are used as probes to identify and isolate related nucleic acids. In some embodiments, the related nucleic acids may be cDNAs or genomic DNAs from organisms other than the one from which the nucleic acid was isolated. For example, the other organisms may be related organisms. In such procedures, a nucleic acid sample is contacted with the probe under conditions which permit the probe to specifically hybridize to related sequences. Hybridization of the probe to nucleic acids from the related organism is then detected using any of the methods described above.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, $T_m$, is the temperature (under defined ionic strength and pH) at which 50% of the target sequence hybridizes to a perfectly complementary probe. Very stringent conditions are selected to be equal to or about 5° C. lower than the $T_m$ for a particular probe. The melting temperature of the probe may be calculated using the following formulas:

For probes between 14 and 70 nucleotides in length the melting temperature ($T_m$) is calculated using the formula: $T_m = 81.5 + 16.6(\log [\text{Na}+]) + 0.41(\text{fraction } G+C) - (600/N)$ where N is the length of the probe.

If the hybridization is carried out in a solution containing formamide, the melting temperature may be calculated using the equation: $T_m = 81.5 + 16.6(\log [\text{Na}+]) + 0.41(\text{fraction } G+C) - (0.63\% \text{ formamide}) - (600/N)$ where N is the length of the probe.

Prehybridization may be carried out in 6×SSC, 5× Denhardt's reagent, 0.5% SDS, 100 µg/ml denatured fragmented salmon sperm DNA or 6×SSC, 5× Denhardt's reagent, 0.5% SDS, 100 µg/ml denatured fragmented salmon sperm DNA, 50% formamide. The formulas for SSC and Denhardt's solutions are listed in Sambrook et al., supra.

In some embodiments, hybridization is conducted by adding the detectable probe to the prehybridization solutions listed above. Where the probe comprises double stranded DNA, it is denatured before addition to the hybridization solution. In some embodiments, the filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the $T_m$. For shorter probes, such as oligonucleotide probes, the hybridization may be conducted at 5-10° C. below the $T_m$. In some embodiments, for hybridizations in 6×SSC, the hybridization is conducted at approximately 68° C. Usually, for hybridizations in 50% formamide containing solutions, the hybridization is conducted at approximately 42° C.

Inhibiting Expression of Aldolase Enzymes

The invention provides nucleic acids complementary to (such as antisense sequences to) the nucleic acids in accordance with the invention, such as aldolase enzyme-encoding nucleic acids, such as nucleic acids comprising antisense, siRNA, miRNA, ribozymes. Nucleic acids in accordance with the invention comprising antisense sequences can be capable of inhibiting the transport, splicing or transcription of aldolase enzyme-encoding genes. The inhibition can be effected through the targeting of genomic DNA or messenger RNA. The transcription or function of targeted nucleic acid can be inhibited, for example, by hybridization and/or cleavage. One exemplary set of inhibitors provided by the present invention includes oligonucleotides which are able to either bind aldolase, such as pyruvate aldolase, such as HMG and/or KHG aldolase enzyme gene or message, in either case preventing or inhibiting the production or function of an aldolase, such as pyruvate aldolase, HMG and/or KHG aldolase enzyme. The association can be through sequence specific hybridization. Another useful class of inhibitors includes oligonucleotides which cause inactivation or cleavage of aldolase, such as pyruvate aldolase, such as HMG and/or KHG aldolase enzyme message. The oligonucleotide can have enzyme activity which causes such cleavage, such as ribozymes. The oligonucleotide can be chemically modified or conjugated to an enzyme or composition capable of cleaving the complementary nucleic acid. A pool of many different such oligonucleotides can be screened for those with the desired activity. Thus, the invention provides various compositions for the inhibition of aldolase, such as pyruvate aldolase, such as HMG and/or KHG aldolase enzyme expression on a nucleic acid and/or protein level, such as antisense, siRNA, miRNA and ribozymes comprising aldolase, such as pyruvate aldolase, such as HMG and/or KHG aldolase enzyme sequences in accordance with the invention and the anti-aldolase, such as anti-pyruvate aldolase, such as anti-HMG and/or anti-KHG aldolase antibodies in accordance with the invention.

Inhibition of aldolase, such as pyruvate aldolase, such as HMG and/or KHG aldolase enzyme expression can have a variety of industrial applications. For example, inhibition of aldolase, such as pyruvate aldolase, such as HMG and/or KHG aldolase enzyme expression can slow or prevent spoilage. In some embodiments, use of compositions in accordance with the invention that inhibit the expression and/or activity of aldolase, such as pyruvate aldolase, such as HMG and/or KHG aldolase enzymes, such as antibodies, antisense oligonucleotides, ribozymes, siRNA and miRNA are used to slow or prevent spoilage. Thus, in some embodiments, the invention provides methods and compositions comprising application onto a plant or plant product (such as a cereal, a grain, a fruit, seed, root, leaf, etc.) antibodies, antisense oligonucleotides, ribozymes, siRNA and miRNA in accordance with the invention to slow or prevent spoilage. These compositions also can be expressed by the plant (such as a transgenic plant) or another organism (such as a bacterium or other microorganism transformed with an aldolase, such as pyruvate aldolase, HMG and/or KHG aldolase enzyme gene in accordance with the invention).

The compositions in accordance with the invention for the inhibition of aldolase, such as pyruvate aldolase, such as HMG and/or KHG aldolase enzyme expression (such as antisense, iRNA, ribozymes, antibodies) can be used as pharmaceutical compositions, such as anti-pathogen agents or in other therapies, such as anti-microbials for, such as *Salmonella*.

Antisense Oligonucleotides

The invention provides antisense oligonucleotides capable of binding aldolase, such as pyruvate aldolase, such as HMG and/or KHG aldolase enzyme message which, In some embodiments, can inhibit aldolase, such as pyruvate aldolase, such as HMG and/or KHG aldolase enzyme, activity by targeting mRNA. Strategies for designing antisense oligonucleotides are well described in the scientific and patent literature, and the skilled artisan can design such aldolase, such as pyruvate aldolase, such as HMG and/or KHG aldolase enzyme oligonucleotides using the novel reagents in accordance with the invention. For example, gene walking/RNA mapping protocols to screen for effective antisense oligonucleotides are well known in the art, see Ho (2000) Methods Enzymol. 314:168-183, describing an RNA mapping assay, which is based on standard molecular techniques to provide an easy and reliable method for potent antisense sequence selection. See also Smith (2000) Eur. J. Pharm. Sci. 11:191-198.

Naturally occurring nucleic acids are used as antisense oligonucleotides. The antisense oligonucleotides can be of any length; for example, in other embodiments, the antisense oligonucleotides are about 5 to about 100, about 10 to about 80, about 15 to about 60, about 18 to about 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl)glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agrawal (Humana Press, Totowa, N.J., 1996). Antisense oligonucleotides having synthetic DNA backbone analogues provided by the invention can also include phosphorodithioate, methylphosphonate, phosphoramidate, alkyl phosphotriester, sulfamate, 3'-thioacetal, methylene(methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense aldolase, such as pyruvate aldolase, such as HMG and/or KHG aldolase enzyme sequences in accordance with the invention (see Gold (1995) J. of Biol. Chem. 270:13581-13584).

Inhibitory Ribozymes

The invention provides ribozymes capable of binding aldolase, such as pyruvate aldolase, such as HMG and/or KHG aldolase enzyme message. These ribozymes can inhibit aldolase, such as pyruvate aldolase, such as HMG and/or KHG aldolase enzyme activity by, such as targeting mRNA. Strategies for designing ribozymes and selecting the aldolase, such as pyruvate aldolase, such as HMG and/or KHG aldolase enzyme-specific antisense sequence for targeting are well described in the scientific and patent literature, and the skilled artisan can design such ribozymes using the novel reagents in accordance with the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In some embodiments, a ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The ribozyme in accordance with the invention, such as an enzymatic ribozyme RNA molecule, can be formed in a hammerhead motif, a hairpin motif, as a hepatitis delta virus motif, a group I intron motif and/or an RNaseP-like RNA in association with an RNA guide sequence. Examples of hammerhead motifs are described by, such as Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech U.S. Pat. No. 4,987,071. The recitation of these specific motifs is not intended to be limiting. Those skilled in the art will recognize that a ribozyme in accordance with the invention, such as an enzymatic RNA molecule of this invention, can have a specific substrate binding site complementary to one or more of the target gene RNA regions. A ribozyme in accordance with the invention can have a nucleotide sequence within or surrounding that substrate binding site which imparts an RNA cleaving activity to the molecule.

RNA Interference (RNAi)

In some embodiments, the invention provides RNA inhibitory molecules, so-called "RNAi" molecules, comprising aldolase, such as pyruvate aldolase, HMG and/or KHG aldolase enzyme sequences in accordance with the invention. The RNAi molecule can comprise a double-stranded RNA (dsRNA) molecule, such as siRNA, miRNA and/or short hairpin RNA (shRNA) molecules. The RNAi molecule, such as siRNA (small inhibitory RNA) and/or miRNA (micro RNA), can inhibit expression of an aldolase, such as pyruvate aldolase, HMG and/or KHG aldolase enzyme gene. In some embodiments, the RNAi molecule, such as siRNA and/or miRNA, is about 11, 12, 13, 14, 15, 16, 17, 18, 19, 20, 21, 22, 23, 24, 25, 26, 27, 28, 29 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi is the breaking of a double-stranded RNA (dsRNA) matching a specific gene sequence into short pieces called short interfering RNA, which trigger the degradation of mRNA that matches its sequence. In some embodiments, the RNAi's in accordance with the invention are used in gene-silencing therapeutics, see Shuey (2002) Drug Discov. Today 7:1040-1046. In some embodiments, the invention provides methods to selectively degrade RNA using the RNAi's molecules, such as siRNA and/or miRNA, in accordance with the invention. The process may be practiced in vitro, ex vivo or in vivo. In some embodiments, the RNAi molecules in accordance with the invention can be used to generate a loss-of-function mutation in a cell, an organ or an animal.

In one aspect, intracellular introduction of the RNAi is by internalization of a target cell specific ligand bonded to an RNA binding protein comprising an RNAi (such as microRNA) is adsorbed. The ligand is specific to a unique target cell surface antigen. The ligand can be spontaneously internalized after binding to the cell surface antigen. If the unique cell surface antigen is not naturally internalized after binding to its ligand, internalization can be promoted by the incorporation of an arginine-rich peptide, or other membrane permeable peptide, into the structure of the ligand or RNA binding protein or attachment of such a peptide to the ligand or RNA binding protein. See U.S. Patent App. Pub. Nos. 20060030003; 20060025361; 20060019286; 20060019258. In one aspect, the invention provides lipid-based formulations for delivering, such as introducing nucleic acids of the invention as nucleic acid-lipid particles comprising an RNAi molecule to a cell, see e.g., U.S. Patent App. Pub. No. 20060008910.

Modification of Nucleic Acids—Making Variant Enzymes of the Invention

The invention provides methods of generating variants of the nucleic acids in accordance with the invention, such as those encoding an aldolase, such as pyruvate aldolase, HMG and/or KHG aldolase enzyme. These methods can be repeated or used in various combinations to generate aldolase, such as pyruvate aldolase, such as HMG and/or KHG aldolase enzymes having an altered or different activity or an altered or different stability from that of an aldolase, such as pyruvate aldolase, HMG and/or KHG aldolase enzyme encoded by the template nucleic acid. These methods also can be repeated or used in various combinations, such as to generate variations in gene/message expression, message translation or message stability. In other embodiments, the genetic composition of a cell is altered by, such as modification of a homologous gene ex vivo, followed by its reinsertion into the cell.

A nucleic acid in accordance with the invention can be altered by any means. For example, random or stochastic methods, or, non-stochastic, or "directed evolution," methods, see U.S. Pat. No. 6,361,974. Methods for random mutation of genes are well known in the art, see U.S. Pat. No. 5,830,696. For example, mutagens can be used to randomly mutate a gene. Mutagens include, such as ultraviolet light or gamma irradiation, or a chemical mutagen, such as mitomycin, nitrous acid, photoactivated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, such as nitrosoguanidine, 5-bromouracil, 2-aminopurine, or acridine. These agents can be added to a PCR reaction in place of the nucleotide precursor thereby mutating the sequence. Intercalating agents such as proflavine, acriflavine, quinacrine and the like can also be used.

Any technique in molecular biology can be used, such as random PCR mutagenesis, see Rice (1992) Proc. Natl. Acad. Sci. USA 89:5467-5471; or, combinatorial multiple cassette mutagenesis, see Crameri (1995) Biotechniques 18:194-196. Alternatively, nucleic acids, such as genes, can be reassembled after random, or "stochastic," fragmentation, see U.S. Pat. Nos. 6,291,242; 6,287,862; 6,287,861; 5,955,358; 5,830,721; 5,824,514; 5,811,238; 5,605,793. In other embodiments, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly (such as GeneReassembly, see U.S. Pat. No. 6,537,776), Gene Site Saturation Mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, Chromosomal Saturation Mutagenesis (CSM) and/or a combination of these and other methods.

The following publications describe a variety of recursive recombination procedures and/or methods which can be incorporated into the methods in accordance with the invention: Stemmer (1999) "Molecular breeding of viruses for targeting and other clinical properties" Tumor Targeting 4:1-4; Ness (1999) Nature Biotechnology 17:893-896; Chang (1999) "Evolution of a cytokine using DNA family shuffling" Nature Biotechnology 17:793-797; Minshull (1999) "Protein evolution by molecular breeding" Current Opinion in Chemical Biology 3:284-290; Christians (1999) "Directed evolution of thymidine kinase for AZT phosphorylation using DNA family shuffling" Nature Biotechnology 17:259-264; Crameri (1998) "DNA shuffling of a family of genes from diverse species accelerates directed evolution" Nature 391: 288-291; Crameri (1997) "Molecular evolution of an arsenate detoxification pathway by DNA shuffling," Nature Biotechnology 15:436-438; Zhang (1997) "Directed evolution of an effective fucosidase from a galactosidase by DNA shuffling and screening" Proc. Natl. Acad. Sci. USA 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Gates et al. (1996) "Affinity selective isolation of ligands from peptide libraries through display on a lac repressor headpiece dimer" Journal of Molecular Biology 255:373-386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wildtype cassettes" BioTechniques 18:194-195; Stemmer et al. (1995) "Single-step assembly of a gene and entire plasmid form large numbers of oligodeoxyribonucleotides" Gene, 164:49-53; Stemmer (1995) "The Evolution of Molecular Computation" Science 270: 1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: In vitro recombination for molecular evolution." Proc. Natl. Acad. Sci. USA 91:10747-10751.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100:468-500; and Zoller (1987) Oligonucleotide-directed mutagenesis: a simple method using two oligonucleotide primers and a single-stranded DNA template" Methods in Enzymol. 154: 329-350); phosphorothioate-modified DNA mutagenesis (Taylor (1985) "The use of phosphorothioate-modified DNA in restriction enzyme reactions to prepare nicked DNA" Nucl. Acids Res. 13: 8749-8764; Taylor (1985) "The rapid generation of oligonucleotide-directed mutations at high frequency using phosphorothioate-modified DNA" Nucl. Acids Res. 13: 8765-8787 (1985); Nakamaye (1986) "Inhibition of restriction endonuclease Nci I cleavage by phosphorothioate groups and its application to oligonucleotide-directed mutagenesis" Nucl. Acids Res. 14: 9679-9698; Sayers (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154:350-367; Kramer (1988) "Improved enzymatic in vitro reactions in the gapped duplex DNA approach to oligonucleotide-directed construction of mutations" Nucl. Acids Res. 16: 7207; and Fritz (1988) "Oligonucleotide-directed construction of mutations: a gapped duplex DNA procedure without enzymatic reactions in vitro" Nucl. Acids Res. 16: 6987-6999).

Additional protocols that can be used to practice the invention include point mismatch repair (Kramer (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh (1986) "Use of oligonucleotides to generate large deletions" Nucl. Acids Res. 14: 5115), restriction-selection and restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shotgun' gene synthesis" Nucl. Acids Res. 13: 3305-3316), double-strand break repair (Mandecki (1986); Arnold (1993) "Protein engineering for unusual environments" Current Opinion in Biotechnology 4:450-455. "Oligonucleotide-directed double-strand break repair in plasmids of *Escherichia coli*: a method for site-specific mutagenesis" Proc. Natl. Acad. Sci. USA, 83:7177-7181). Additional details on many of the above methods can be found in Methods in Enzymology Volume 154, which also describes useful controls for trouble-shooting problems with various mutagenesis methods.

Protocols that can be used to practice the invention are described, such as in U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Protocols that can be used to practice the invention (providing details regarding various diversity generating methods) are described, such as in U.S. patent application Ser. No. 09/407,800, "SHUFFLING OF CODON ALTERED GENES" by Patten et al. filed Sep. 28, 1999; "EVOLUTION OF WHOLE CELLS AND ORGANISMS BY RECURSIVE SEQUENCE RECOMBINATION" by del Cardayre et al., U.S. Pat. No. 6,379,964; "OLIGONUCLEOTIDE MEDIATED NUCLEIC ACID RECOMBINATION" by Crameri et al., U.S. Pat. Nos. 6,319,714; 6,368,861; 6,376,246; 6,423,542; 6,426,224 and PCT/US00/01203; "USE OF CODON-VARIED OLIGONUCLEOTIDE SYNTHESIS FOR SYNTHETIC SHUFFLING" by Welch et al., U.S. Pat. No. 6,436,675; "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, such as "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549); and U.S. Pat. Nos. 6,177,263; 6,153,410.

Non-stochastic, or "directed evolution," methods include, such as saturation mutagenesis, such as Gene Site Saturation Mutagenesis (GSSM), synthetic ligation reassembly (SLR), or a combination thereof are used to modify the nucleic acids in accordance with the invention to generate aldolase, such as pyruvate aldolase, such as HMG and/or KEG aldolase enzymes with new or altered properties (such as activity under highly acidic or alkaline conditions, high or low temperatures, and the like). Polypeptides encoded by the modified nucleic acids can be screened for an activity before testing for carbon-carbon bond formation or cleavage or other activity. Any testing modality or protocol can be used, such as using a capillary array platform. See U.S. Pat. Nos. 6,361,974; 6,280,926; 5,939,250.

Gene Site Saturation Mutagenesis, or, GSSM

The invention also provides methods for making enzyme using Gene Site Saturation mutagenesis, or, GSSM, as described herein, and also in U.S. Pat. Nos. 6,171,820 and 6,579,258. In some embodiments, codon primers containing a degenerate N,N,G/T sequence are used to introduce point mutations into a polynucleotide, such as an aldolase, such as pyruvate aldolase, HMG and/or KHG aldolase enzyme or an antibody in accordance with the invention, so as to generate a set of progeny polypeptides in which a full range of single amino acid substitutions is represented at each amino acid position, such as an amino acid residue in an enzyme active site or ligand binding site targeted to be modified. These oligonucleotides can comprise a contiguous first homologous sequence, a degenerate N,N,G/T sequence, and, optionally, a second homologous sequence. The downstream progeny translational products from the use of such oligonucleotides include all possible amino acid changes at each amino acid site along the polypeptide, because the degeneracy of the N,N,G/T sequence includes codons for all 20 amino acids. In some embodiments, one such degenerate oligonucleotide (comprised of, such as one degenerate N,N,G/T cassette) is used for subjecting each original codon in a parental polynucleotide template to a full range of codon substitutions. In other embodiments, at least two degenerate cassettes are used—either in the same oligonucleotide or not, for subjecting at least two original codons in a parental polynucleotide template to a full range of codon substitutions. For example, more than one N,N,G/T sequence can be contained in one oligonucleotide to introduce amino acid mutations at more than one site. This plurality of N,N,G/T sequences can be directly contiguous, or separated by one or more additional nucleotide sequence(s). In other embodiments, oligonucleotides serviceable for introducing additions and deletions can be used either alone or in combination with the codons containing an N,N,G/T sequence, to introduce any combination or permutation of amino acid additions, deletions, and/or substitutions.

In some embodiments, simultaneous mutagenesis of two or more contiguous amino acid positions is done using an oligonucleotide that contains contiguous N,N,G/T triplets, i.e. a degenerate (N,N,G/T)n sequence. In other embodiments, degenerate cassettes having less degeneracy than the N,N,G/T sequence are used. For example, it may be desirable in some instances to use (such as in an oligonucleotide) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (such as in an oligo) a degenerate N,N,N triplet sequence.

In some embodiments, use of degenerate triplets (such as N,N,G/T triplets) allows for systematic and easy generation of a full range of possible natural amino acids (for a total of 20 amino acids) into each and every amino acid position in a polypeptide (in other embodiments, the methods also include generation of less than all possible substitutions per amino acid residue, or codon, position). For example, for a 100 amino acid polypeptide, 2000 distinct species (i.e. 20 possible amino acids per position X 100 amino acid positions) can be generated. Through the use of an oligonucleotide or set of oligonucleotides containing a degenerate N,N,G/T triplet, 32 individual sequences can code for all 20 possible natural amino acids. Thus, in a reaction vessel in which a parental polynucleotide sequence is subjected to saturation mutagenesis using at least one such oligonucleotide, there are generated 32 distinct progeny polynucleotides encoding 20 distinct polypeptides. In contrast, the use of a non-degenerate oligonucleotide in site-directed mutagenesis leads to only one progeny polypeptide product per reaction vessel. Nondegenerate oligonucleotides can optionally be used in combination with degenerate primers disclosed; for example, nondegenerate oligonucleotides can be used to generate specific point mutations in a working polynucleotide. This provides one means to generate specific silent point mutations, point mutations leading to corresponding amino acid changes, and point mutations that cause the generation of stop codons and the corresponding expression of polypeptide fragments.

In some embodiments, each saturation mutagenesis reaction vessel contains polynucleotides encoding at least 20 progeny polypeptide (such as aldolase, such as pyruvate aldolase, such as HMG and/or KHG aldolase enzymes) molecules such that all 20 natural amino acids are represented at the one specific amino acid position corresponding to the codon position mutagenized in the parental polynucleotide (other embodiments use less than all 20 natural combinations). The 32-fold degenerate progeny polypeptides generated from each saturation mutagenesis reaction vessel can be subjected to clonal amplification (such as cloned into a suitable host, such as E. coli host, using, such as an expression vector) and subjected to expression screening. When an individual progeny polypeptide is identified by screening to display a favorable change in property (when compared to the parental polypeptide, such as increased carbon-carbon formation or cleavage activity under alkaline or acidic conditions), it can be sequenced to identify the correspondingly favorable amino acid substitution contained therein.

In some embodiments, upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e. 2 at each of three positions) and no change at any position.

In yet another embodiment, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

The invention also provides for the use of proprietary codon primers (containing a degenerate N,N,N sequence) to introduce point mutations into a polynucleotide, so as to generate a set of progeny polypeptides in which a full range of single amino acid substitutions is represented at each amino acid position (Gene Site Saturation Mutagenesis (GSSM)). The oligos used are comprised contiguously of a first homologous sequence, a degenerate N,N,N sequence and, in some embodiments but not necessarily, a second homologous sequence. The downstream progeny translational products from the use of such oligos include all possible amino acid changes at each amino acid site along the polypeptide, because the degeneracy of the N,N,N sequence includes codons for all 20 amino acids.

In some embodiments, one such degenerate oligo (comprised of one degenerate N,N,N cassette) is used for subjecting each original codon in a parental polynucleotide template to a full range of codon substitutions. In other embodiments, at least two degenerate N,N,N cassettes are used—either in the same oligo or not, for subjecting at least two original codons in a parental polynucleotide template to a full range of codon substitutions. Thus, more than one N,N,N sequence can be contained in one oligo to introduce amino acid mutations at more than one site. This plurality of N,N,N sequences can be directly contiguous, or separated by one or more additional nucleotide sequence(s). In other embodiments, oligos serviceable for introducing additions and deletions can be used either alone or in combination with the codons containing an N,N,N sequence, to introduce any combination or permutation of amino acid additions, deletions and/or substitutions.

In some embodiments, it is possible to simultaneously mutagenize two or more contiguous amino acid positions using an oligo that contains contiguous N,N,N triplets, i.e. a degenerate $(N,N,N)_n$ sequence. In other embodiments, the present invention provides for the use of degenerate cassettes having less degeneracy than the N,N,N sequence. For example, it may be desirable in some instances to use (such as in an oligo) a degenerate triplet sequence comprised of only one N, where the N can be in the first second or third position of the triplet. Any other bases including any combinations and permutations thereof can be used in the remaining two positions of the triplet. Alternatively, it may be desirable in some instances to use (such as in an oligo) a degenerate N,N,N triplet sequence, N,N,G/T, or an N,N, G/C triplet sequence.

In some embodiments, use of a degenerate triplet (such as N,N,G/T or an N,N, G/C triplet sequence) is advantageous for several reasons. In some embodiments, this invention provides means to systematically and fairly easily generate the substitution of the full range of possible amino acids (for a total of 20 amino acids) into each and every amino acid position in a polypeptide. Thus, for a 100 amino acid polypeptide, the invention provides ways to systematically and fairly easily generate 2000 distinct species (i.e., 20 possible amino acids per position times 100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides means to generate specific silent point mutations, point mutations leading to corresponding amino acid changes and point mutations that cause the generation of stop codons and the corresponding expression of polypeptide fragments.

Thus, in some embodiments of this invention, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (such as cloned into a suitable E. coli host using an expression vector) and subjected to expression screening.

When an individual progeny polypeptide is identified by screening to display a favorable change in property (when compared to the parental polypeptide), it can be sequenced to identify the correspondingly favorable amino acid substitution contained therein.

In some embodiments, upon mutagenizing each and every amino acid position in a parental polypeptide using saturation mutagenesis as disclosed herein, a favorable amino acid changes is identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid and each of two favorable changes) and 3 positions. Thus, there are 3×3×3 or 27 total possibilities, including 7 that were previously examined—6 single point mutations (i.e., 2 at each of three positions) and no change at any position.

The invention provides for the use of saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, the instant invention provides that mutagenesis can be use to replace each of any number of bases in a polynucleotide sequence, wherein the number of bases to be mutagenized is, in some embodiments every integer from 15 to 100,000. Thus, instead of mutagenizing every position along a molecule, one can subject every or a discrete number of bases (in some embodiments a subset totaling from 15 to 100,000) to mutagenesis. In some embodiments, a separate nucleotide is used for mutagenizing each position or group of positions along a polynucleotide sequence. A group of 3 positions to be mutagenized may be a codon. The mutations can be introduced using a mutagenic primer, containing a heterologous cassette, also referred to as a mutagenic cassette. Exemplary cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo).

In some embodiments, saturation mutagenesis is comprised of mutagenizing a complete set of mutagenic cassettes (wherein each cassette is, in some embodiments, about 1-500 bases in length) in defined polynucleotide sequence to be mutagenized (wherein the sequence to be mutagenized is, in some embodiments, from about 15 to 100,000 bases in length). Thus, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons and groupings of particular nucleotide cassettes.

In some embodiments, defined sequences to be mutagenized include a whole gene, pathway, cDNA, an entire open reading frame (ORF) and entire promoter, enhancer, repressor/transactivator, origin of replication, intron, operator, or any polynucleotide functional group. Generally, a "defined sequences" for this purpose may be any polynucleotide that a 15 base-polynucleotide sequence and polynucleotide sequences of lengths between 15 bases and 15,000 bases (this invention specifically names every integer in between). Considerations in choosing groupings of codons include types of amino acids encoded by a degenerate mutagenic cassette.

In some embodiments, a grouping of mutations that can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19 and 20 amino acids at each position and a library of polypeptides encoded thereby.

Synthetic Ligation Reassembly (SLR)

The invention provides a non-stochastic gene modification system termed "synthetic ligation reassembly," or simply "SLR," a "directed evolution process," to generate polypeptides, such as aldolase, such as pyruvate aldolase, such as HMG and/or KHG aldolase enzymes or antibodies in accordance with the invention, with new or altered properties.

SLR is a method of ligating oligonucleotide fragments together non-stochastically. This method differs from stochastic oligonucleotide shuffling in that the nucleic acid building blocks are not shuffled, concatenated or chimerized randomly, but rather are assembled non-stochastically. See U.S. Pat. Nos. 6,773,900; 6,740,506; 6,713,282; 6,635,449; 6,605,449; 6,537,776. In some embodiments, SLR comprises the following steps: (a) providing a template polynucleotide, wherein the template polynucleotide comprises sequence encoding a homologous gene; (b) providing a plurality of building block polynucleotides, wherein the building block polynucleotides are designed to cross-over reassemble with the template polynucleotide at a predetermined sequence, and a building block polynucleotide comprises a sequence that is a variant of the homologous gene and a sequence homologous to the template polynucleotide flanking the variant sequence; (c) combining a building block polynucleotide with a template polynucleotide such that the building block polynucleotide cross-over reassembles with the template polynucleotide to generate polynucleotides comprising homologous gene sequence variations.

SLR does not depend on the presence of high levels of homology between polynucleotides to be rearranged. Thus, this method can be used to non-stochastically generate libraries (or sets) of progeny molecules comprised of over $10^{100}$ different chimeras. SLR can be used to generate libraries comprised of over $10^{1000}$ different progeny chimeras. Thus, embodiments of the present invention include non-stochastic methods of producing a set of finalized chimeric nucleic acid molecule shaving an overall assembly order that is chosen by design. This method includes the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, the overall assembly order in which the nucleic acid building blocks can be coupled is specified by the design of the ligatable ends. If more than one assembly step is to be used, then the overall assembly order in which the nucleic acid building blocks can be coupled is also specified by the sequential order of the assembly step(s). In some embodiments, the annealed building pieces are treated with an enzyme, such as a ligase (such as T4 DNA ligase), to achieve covalent bonding of the building pieces.

In some embodiments, the design of the oligonucleotide building blocks is obtained by analyzing a set of progenitor nucleic acid sequence templates that serve as a basis for producing a progeny set of finalized chimeric polynucleotides. These parental oligonucleotide templates thus serve as a source of sequence information that aids in the design of the nucleic acid building blocks that are to be mutagenized, such as chimerized or shuffled. In some embodiments of this method, the sequences of a plurality of parental nucleic acid templates are aligned in order to select one or more demarcation points. The demarcation points can be located at an area of homology, and are comprised of one or more nucleotides. These demarcation points are, in some embodiments, shared by at least two of the progenitor templates. The demarcation points can thereby be used to delineate the boundaries of oligonucleotide building blocks to be generated in order to rearrange the parental polynucleotides. The demarcation points identified and selected in the progenitor molecules serve as potential chimerization points in the assembly of the final chimeric progeny molecules. A demarcation point can be an area of homology (comprised of at least one homologous nucleotide base) shared by at least two parental polynucleotide sequences. Alternatively, a demarcation point can be an area of homology that is shared by at least half of the parental polynucleotide sequences, or, it can be an area of homology that is shared by at least two thirds of the parental polynucleotide sequences. Even more, in some embodiments, a serviceable demarcation points is an area of homology that is shared by at least three fourths of the parental polynucleotide sequences, or, it can be shared by at almost all of the parental polynucleotide sequences. In some embodiments, a demarcation point is an area of homology that is shared by all of the parental polynucleotide sequences.

In some embodiments, a ligation reassembly process is performed exhaustively in order to generate an exhaustive library of progeny chimeric polynucleotides. In other words, all possible ordered combinations of the nucleic acid building blocks are represented in the set of finalized chimeric nucleic acid molecules. At the same time, in other embodiments, the assembly order (i.e. the order of assembly of each building block in the 5' to 3 sequence of each finalized chimeric nucleic acid) in each combination is by design (or non-stochastic) as described above. Because of the non-stochastic nature of this invention, the possibility of unwanted side products is greatly reduced.

In other embodiments, the ligation reassembly method is performed systematically. For example, the method is performed in order to generate a systematically compartmentalized library of progeny molecules, with compartments that can be screened systematically, such as one by one. In other words this invention provides that, through the selective and judicious use of specific nucleic acid building blocks, coupled with the selective and judicious use of sequentially stepped assembly reactions, a design can be achieved where specific sets of progeny products are made in each of several reaction vessels. This allows a systematic examination and screening procedure to be performed. Thus, these methods allow a potentially very large number of progeny molecules to be examined systematically in smaller groups. Because of its ability to perform chimerizations in a manner that is highly flexible yet exhaustive and systematic as well, particularly when there is a low level of homology among the progenitor molecules, these methods provide for the generation of a library (or set) comprised of a large number of progeny molecules. Because of the non-stochastic nature of the instant ligation reassembly invention, the progeny molecules generated in some embodiments comprise a library of finalized chimeric nucleic acid molecules having an overall assembly order that is chosen by design. The saturation mutagenesis and optimized directed evolution methods also can be used to generate different progeny molecular species. It is appreciated that the invention provides freedom of choice and control regarding the selection of demarcation points, the size and number of the nucleic acid building blocks, and the size and design of the couplings. It is appreciated, furthermore, that the requirement for intermolecular homology is highly relaxed for the operability of this invention. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template. Alternatively, a codon can be altered such that the coding for an originally amino acid is altered. This invention provides that such substitutions can be introduced into the nucleic acid building block in order to increase the incidence of intermolecular homologous demarcation points and thus to allow an increased number of couplings to be achieved among the building blocks, which in turn allows a greater number of progeny chimeric molecules to be generated.

Synthetic Gene Reassembly

In some embodiments, the present invention provides a non-stochastic method termed synthetic gene reassembly, that is somewhat related to stochastic shuffling, save that the nucleic acid building blocks are not shuffled or concatenated or chimerized randomly, but rather are assembled non-stochastically. See U.S. Pat. No. 6,537,776.

The synthetic gene reassembly method does not depend on the presence of a high level of homology between polynucleotides to be shuffled. The invention can be used to non-stochastically generate libraries (or sets) of progeny molecules comprised of over $10^{100}$ different chimeras. Conceivably, synthetic gene reassembly can even be used to generate libraries comprised of over $10^{1000}$ different progeny chimeras.

Thus, in some embodiments, the invention provides a non-stochastic method of producing a set of finalized chimeric nucleic acid molecules having an overall assembly order that is chosen by design, which method is comprised of the steps of generating by design a plurality of specific nucleic acid building blocks having serviceable mutually compatible ligatable ends and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in some embodiments, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In a one embodiment, of the invention, the annealed building pieces are treated with an enzyme, such as a ligase (such as T4 DNA ligase) to achieve covalent bonding of the building pieces.

In a another embodiment, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, the invention provides for the chimerization of a family of related genes and their encoded family of related products. In a particular exemplification, the encoded products are enzymes. The aldolase, such as pyruvate aldolase, such as HMG and/or KHG aldolase enzymes of the present invention can be mutagenized in accordance with the methods described herein.

Thus according to one embodiment of the invention, the sequences of a plurality of progenitor nucleic acid templates (such as polynucleotides in accordance with the invention) are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

In some embodiments, a serviceable demarcation point is an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates and in some embodiments at almost all of the progenitor templates. Even more in some embodiments still a serviceable demarcation point is an area of homology that is shared by all of the progenitor templates.

In a one embodiment, the gene reassembly process is performed exhaustively in order to generate an exhaustive library. In other words, all possible ordered combinations of the nucleic acid building blocks are represented in the set of finalized chimeric nucleic acid molecules. At the same time, the assembly order (i.e. the order of assembly of each building block in the 5' to 3 sequence of each finalized chimeric nucleic acid) in each combination is by design (or non-stochastic). Because of the non-stochastic nature of the method, the possibility of unwanted side products is greatly reduced.

In other embodiments, the method provides that the gene reassembly process is performed systematically, for example to generate a systematically compartmentalized library, with compartments that can be screened systematically, such as one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant gene reassembly invention, the progeny molecules generated in some embodiments comprise a library of finalized chimeric nucleic acid molecules having an overall assembly order that is chosen by design. In some embodiments, such a generated library is comprised of greater than $10^3$ to greater than $10^{1000}$ different progeny molecular species.

In some embodiments, a set of finalized chimeric nucleic acid molecules, produced as described is comprised of a polynucleotide encoding a polypeptide. In one embodiment, this polynucleotide is a gene, which may be a man-made gene. In another embodiment, this polynucleotide is a gene pathway, which may be a man-made gene pathway. In some embodiments, the invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (such as one or more nucleotides, which may be, for example, codons or introns or regulatory sequences) that can later be optionally removed in an in vitro process (such as by mutagenesis) or in an in vivo process (such as by utilizing the gene splicing ability of a host organism). It is appreciated that in many instances the introduction of these nucleotides may also be desirable for many other reasons in addition to the potential benefit of creating a serviceable demarcation point.

Thus, in some embodiments, the invention provides that a nucleic acid building block can be used to introduce an intron. Thus, the invention provides that functional introns may be introduced into a man-made gene in accordance with the invention. In some embodiments, the invention also provides that functional introns may be introduced into a man-made gene pathway in accordance with the invention. Accordingly, the invention provides for the generation of a chimeric polynucleotide that is a man-made gene containing one (or more) artificially introduced intron(s).

The invention also provides for the generation of a chimeric polynucleotide that is a man-made gene pathway containing one (or more) artificially introduced intron(s). In some embodiments, the artificially introduced intron(s) are functional in one or more host cells for gene splicing much in the way that naturally-occurring introns serve functionally in gene splicing. In some embodiments, the invention provides processes of producing man-made intron-containing polynucleotides to be introduced into host organisms for recombination and/or splicing.

A man-made gene produced using the invention can also serve as a substrate for recombination with another nucleic acid. Likewise, a man-made gene pathway produced using the invention can also serve as a substrate for recombination with another nucleic acid. In some embodiments, the recombination is facilitated by, or occurs at, areas of homology between the man-made, intron-containing gene and a nucleic acid, which serves as a recombination partner. In some embodiments, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

In some embodiments, the synthetic gene reassembly method in accordance with the invention utilizes a plurality of nucleic acid building blocks, each of which, in some embodiments, has two ligatable ends. The two ligatable ends on each nucleic acid building block may be two blunt ends (i.e. each having an overhang of zero nucleotides), or in some embodiments one blunt end and one overhang, or more in some embodiments still two overhangs. In some embodiments, a useful overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

In some embodiments, a nucleic acid building block is generated by chemical synthesis of two single-stranded nucleic acids (also referred to as single-stranded oligos) and contacting them so as to allow them to anneal to form a double-stranded nucleic acid building block. A double-stranded nucleic acid building block can be of variable size. The sizes of these building blocks can be small or large. Exemplary sizes for building block range from 1 base pair (not including any overhangs) to 100,000 base pairs (not including any overhangs). Other exemplary size ranges are also provided, which have lower limits of from 1 bp to 10,000 bp (including every integer value in between) and upper limits of from 2 bp to 100,000 bp (including every integer value in between).

Many methods exist by which a double-stranded nucleic acid building block can be generated that is serviceable for the invention; and these are known in the art and can be readily performed by the skilled artisan. In some embodiments, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). In another embodiment, the two strands of a double-stranded nucleic acid building block are complementary at fewer than every nucleotide apart from any that form an overhang. Thus, according to this embodiment, a double-stranded nucleic acid building block can be used to introduce codon degeneracy. In some embodiments the codon degeneracy is introduced using the site-saturation mutagenesis described herein, using one or more N,N,G/T cassettes or alternatively using one or more N,N,N cassettes.

The in vivo recombination method in accordance with the invention can be performed blindly on a pool of unknown hybrids or alleles of a specific polynucleotide or sequence. However, it is not necessary to know the actual DNA or RNA sequence of the specific polynucleotide. The approach of using recombination within a mixed population of genes can be useful for the generation of any useful proteins, for example, an aldolase in accordance with the invention or a variant thereof. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to make ribozymes or aptamers in accordance with the invention.

In some embodiments the invention described herein is directed to the use of repeated cycles of reductive reassortment, recombination and selection which allow for the directed molecular evolution of highly complex linear sequences, such as DNA, RNA or proteins thorough recombination.

Optimized Directed Evolution System

The invention provides a non-stochastic gene modification system termed "optimized directed evolution system" to generate polypeptides, such as aldolase, such as pyruvate aldolase, such as HMG and/or KHG aldolase enzymes or antibodies in accordance with the invention, with new or altered properties. In some embodiments, optimized directed evolution is directed to the use of repeated cycles of reductive reassortment, recombination and selection that allow for the directed molecular evolution of nucleic acids through recombination.

Optimized directed evolution allows generation of a large population of evolved chimeric sequences, wherein the generated population is significantly enriched for sequences that have a predetermined number of crossover events. A crossover event is a point in a chimeric sequence where a shift in sequence occurs from one parental variant to another parental variant. Such a point is normally at the juncture of where oligonucleotides from two parents are ligated together to form a single sequence. This method allows calculation of the correct concentrations of oligonucleotide sequences so that the final chimeric population of sequences is enriched for the chosen number of crossover events. This provides more control over choosing chimeric variants having a predetermined number of crossover events.

In addition, this method provides convenient means for exploring a tremendous amount of the possible protein variant space in comparison to other systems. Previously, if one generated, for example, $10^{13}$ chimeric molecules during a reaction, it would be extremely difficult to test such a high number of chimeric variants for a particular activity. Moreover, a significant portion of the progeny population would have a very high number of crossover events which resulted in proteins that were less likely to have increased levels of a particular activity. By using these methods, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

One method for creating a chimeric progeny polynucleotide sequence is to create oligonucleotides corresponding to fragments or portions of each parental sequence. Each oligonucleotide in some embodiments includes a unique region of overlap so that mixing the oligonucleotides together results in a new variant that has each oligonucleotide fragment assembled in the correct order. Alternatively protocols for practicing these methods in accordance with the invention can be found in U.S. Pat. Nos. 6,773,900; 6,740,506; 6,713,282; 6,635,449; 6,605,449; 6,537,776; 6,361,974.

The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a ⅓ chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. By utilizing these methods, one can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events. These methods are directed to the use of repeated cycles of reductive reassortment, recombination and selection that allow for the directed molecular evolution of a nucleic acid encoding a polypeptide through recombination. This system allows generation of a large population of evolved chimeric sequences, wherein the generated population is significantly enriched for sequences that have a predetermined number of crossover events. A crossover event is a point in a chimeric sequence where a shift in sequence occurs from one parental variant to another parental variant. Such a point is normally at the juncture of where oligonucleotides from two parents are ligated together to form a single sequence. The method allows calculation of the correct concentrations of oligonucleotide sequences so that the final chimeric population of sequences is enriched for the chosen number of crossover events. This provides more control over choosing chimeric variants having a predetermined number of crossover events.

In addition, these methods provide a convenient means for exploring a tremendous amount of the possible protein variant space in comparison to other systems. By using the methods described herein, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

In some embodiments, the method creates a chimeric progeny polynucleotide sequence by creating oligonucleotides corresponding to fragments or portions of each parental sequence. Each oligonucleotide in some embodiments includes a unique region of overlap so that mixing the oligonucleotides together results in a new variant that has each oligonucleotide fragment assembled in the correct order. See also U.S. Pat. Nos. 6,773,900; 6,740,506; 6,713,282; 6,635, 449; 6,605,449; 6,537,776; 6,361,974.

Determining Crossover Events

Embodiments of the invention include a system and software that receive a desired crossover probability density function (PDF), the number of parent genes to be reassembled, and the number of fragments in the reassembly as inputs. The output of this program is a "fragment PDF" that can be used to determine a recipe for producing reassembled genes, and the estimated crossover PDF of those genes. The processing described herein is in some embodiments performed in MATLAB™ (The Mathworks, Natick, Mass.) a programming language and development environment for technical computing.

Iterative Processes

Any process in accordance with the invention can be iteratively repeated, such as a nucleic acid encoding an altered or new aldolase phenotype, such as pyruvate aldolase, such as HMG and/or KHG aldolase enzyme in accordance with the invention, can be identified, re-isolated, again modified, re-tested for activity. This process can be iteratively repeated until a desired phenotype is engineered. For example, an entire biochemical anabolic or catabolic pathway can be engineered into a cell, including, such as aldolase, such as pyruvate aldolase, such as HMG and/or KHG aldolase enzyme, activity.

Similarly, if it is determined that a particular oligonucleotide has no affect at all on the desired trait (such as a new aldolase, such as pyruvate aldolase, such as HMG and/or KHG aldolase enzyme phenotype), it can be removed as a variable by synthesizing larger parental oligonucleotides that include the sequence to be removed. Because incorporating the sequence within a larger sequence prevents any crossover events, there will no longer be any variation of this sequence in the progeny polynucleotides. This iterative practice of determining which oligonucleotides are most related to the desired trait, and which are unrelated, allows more efficient exploration all of the possible protein variants that might be provide a particular trait or activity.

In Vivo Shuffling

In various embodiments, in vivo shuffling of molecules is used in methods in accordance with the invention to provide variants of polypeptides in accordance with the invention, such as antibodies in accordance with the invention or aldolases in accordance with the invention, such as pyruvate aldolase, HMG and/or KHG aldolase enzymes, and the like. In vivo shuffling can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In other embodiments, the invention includes a method for producing a hybrid polynucleotide from at least a first polynucleotide and a second polynucleotide. In some embodiments, the invention can be used to produce a hybrid polynucleotide by introducing at least a first polynucleotide and a second polynucleotide (such as one, or both, being an aldolase, such as pyruvate aldolase, such as HMG and/or KHG aldolase enzyme-encoding sequence in accordance with the invention) which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

In some embodiments, vivo reassortment focuses on "inter-molecular" processes collectively referred to as "recombination"; which in bacteria, is generally viewed as a "RecA-dependent" phenomenon. In some embodiments, the invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process.

In other embodiments of the invention, novel polynucleotides can be generated by the process of reductive reassortment. The method involves the generation of constructs containing consecutive sequences (original encoding sequences), their insertion into an appropriate vector and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences and results in the production of novel molecular species. Various treatments may be applied to enhance the rate of reassortment. These could include treatment with ultra-violet light, or DNA damaging chemicals and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In some embodiments, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. In some embodiments, the constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:
a) Primers that include a poly-A head and poly-T tail which when made single-stranded would provide orientation can be utilized. This is accomplished by having the first few bases of the primers made from RNA and hence easily removed RNaseH.
b) Primers that include unique restriction cleavage sites can be utilized. Multiple sites, a battery of unique sequences and repeated synthesis and ligation steps would be required.
c) The inner few bases of the primer could be thiolated and an exonuclease used to produce properly tailed molecules.

In some embodiments, the recovery of the re-assorted sequences relies on the identification of cloning vectors with a reduced repetitive index (RI). The re-assorted encoding sequences can then be recovered by amplification. The products are re-cloned and expressed. The recovery of cloning vectors with reduced RI can be affected by:
1) The use of vectors only stably maintained when the construct is reduced in complexity.
2) The physical recovery of shortened vectors by physical procedures. In this case, the cloning vector would be recovered using standard plasmid isolation procedures and size fractionated on either an agarose gel, or column with a low molecular weight cut off utilizing standard procedures.
3) The recovery of vectors containing interrupted genes which can be selected when insert size decreases.
4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates an exemplary method in accordance with the invention. Encoding nucleic acid sequences (quasi-repeats) derived from three (3) unique species are described. Each sequence encodes a protein with a distinct set of properties. Each of the sequences differs by a single or a few base pairs at a unique position in the sequence. The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may, or may not be size fractionated on an agarose gel according to published protocols, inserted into a cloning vector and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations.

Optionally, the method comprises the additional step of screening the library members of the shuffled pool to identify individual shuffled library members having the ability to bind or otherwise interact, or catalyze a particular reaction (such as catalytic domain of an enzyme) with a predetermined macromolecule, such as for example a proteinaceous receptor, an oligosaccharide, virion, or other predetermined compound or structure.

The polypeptides that are identified from such libraries can be used for therapeutic, diagnostic, research and related purposes (such as catalysts, solutes for increasing osmolarity of an aqueous solution and the like) and/or can be subjected to one or more additional cycles of shuffling and/or selection.

In other embodiments, it is envisioned that prior to or during recombination or reassortment, polynucleotides generated by the method in accordance with the invention can be subjected to agents or processes which promote the introduction of mutations into the original polynucleotides. The introduction of Such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N3-Adenine (See Sun and Hurley, (1992); an N-acetylated or deacetylated 4'-fluoro-4-aminobiphenyl adduct capable of inhibiting DNA synthesis (See, for example, van de Poll et al. (1992)); or a N-acetylated or deacetylated 4-aminobiphenyl adduct capable of inhibiting DNA synthesis (See also, van de Poll et al. (1992), pp. 751-758); trivalent chromium, a trivalent chromium salt, a polycyclic aromatic hydrocarbon (PAH) DNA adduct capable of inhibiting DNA replication, such as 7-bromomethyl-benz[a]anthracene ("BMA"), tris(2,3-dibromopropyl)phosphate ("Tris-BP"), 1,2-dibromo-3-chloropropane ("DBCP"), 2-bromoacrolein (2BA), benzo[a]pyrene-7, 8-dihydrodiol-9-10-epoxide ("BPDE"), a platinum(II) halogen salt, N-hydroxy-2-amino-3-methylimidazo[4,5-f]-quinoline ("N-hydroxy-IQ") and N-hydroxy-2-amino-1-methyl-6-phenylimidazo[4,5-f]-pyridine ("N-hydroxy-PhIP"). Exemplary means for slowing or halting PCR amplification consist of UV light (+)-CC-1065 and (+)-CC-1065-(N-3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In other embodiments the invention is directed to a method of producing recombinant proteins having biological activity by treating a sample comprising double-stranded template polynucleotides encoding a wild-type protein under conditions according to the invention which provide for the production of hybrid or re-assorted polynucleotides.

Producing Sequence Variants

The invention also provides additional methods for making sequence variants of the nucleic acid (such as aldolase, such as pyruvate aldolase, such as HMG and/or KHG aldolase enzyme) sequences in accordance with the invention. In some embodiments, the invention also provides additional methods for isolating aldolase, such as pyruvate aldolase, such as HMG and/or KHG aldolase enzymes using the nucleic acids and polypeptides in accordance with the invention. In some embodiments, the invention provides for variants of an aldolase, such as pyruvate aldolase, HMG and/or KHG aldolase enzyme coding sequence (such as a gene, cDNA or message) in accordance with the invention, which can be altered by any means, including, such as random or stochastic methods, or, non-stochastic, or "directed evolution," methods, as described above.

The isolated variants may be naturally occurring. Variant can also be created in vitro. Variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures. Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. These nucleotide differences can result in amino acid changes with respect to the polypeptides encoded by the nucleic acids from the natural isolates.

For example, variants may be created using error prone PCR. In some embodiments of error prone PCR, the PCR is performed under conditions where the copying fidelity of the DNA polymerase is low, such that a high rate of point mutations is obtained along the entire length of the PCR product. Error prone PCR is described, such as in Leung, D. W. et al., (1989) Technique 1:11-15; and Caldwell, R. C. & Joyce, G. F., (1992) PCR Methods Applic. 2:28-33. Briefly, in such procedures, nucleic acids to be mutagenized are mixed with PCR primers, reaction buffer, $MgCl_2$, $MnCl_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM MgCl2, 0.5 mM $MnCl_2$, 5 units of Taq polymerase, 0.2 mM dGTP, 0.2 mM dATP, 1 mM dCTP, and 1 mM dTTP. PCR may be performed for 30 cycles of 94° C. for 1 minute, 45° C. for 1 minute, and 72° C. for 1 minute. However, it will be appreciated that these parameters may be varied as appropriate. The mutagenized nucleic acids are cloned into an appropriate vector and the activities of the polypeptides encoded by the mutagenized nucleic acids are evaluated.

In some embodiments, variants are created using oligonucleotide directed mutagenesis to generate site-specific mutations in any cloned DNA of interest. Oligonucleotide mutagenesis is described, such as in Reidhaar-Olson (1988) Science 241:53-57. Briefly, in such procedures a plurality of double stranded oligonucleotides bearing one or more mutations to be introduced into the cloned DNA are synthesized and inserted into the cloned DNA to be mutagenized. In some embodiments, clones containing the mutagenized DNA are recovered, expressed, and the activities of the polypeptide encoded therein assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in the art, such as in U.S. Pat. No. 5,965,408.

In some embodiments, sexual PCR mutagenesis is an exemplary method of generating variants in accordance with the invention. In some embodiments of sexual PCR mutagenesis forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described, such as in Stemmer (1994) Proc. Natl. Acad. Sci. USA 91:10747-10751. Briefly, in such procedures a plurality of nucleic acids to be recombined are digested with DNase to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/µl in a solution of 0.2 mM of each dNTP, 2.2 mM $MgCl_2$, 50 mM KCL, 10 mM Tris HCl, pH 9.0, and 0.1% Triton X-100. 2.5 units of Taq polymerase per 100 µl of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes. However, it will be appreciated that these parameters may be varied as appropriate. In some embodiments, oligonucleotides may be included in the PCR reactions. In other embodiments, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

In some embodiments, variants are created by in vivo mutagenesis. In some embodiments, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described in PCT Publication No. WO 91/16427, published Oct. 31, 1991, entitled "Methods for Phenotype Creation from Multiple Gene Populations".

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described, such as in Arkin (1992) Proc. Natl. Acad. Sci. USA 89:7811-7815.

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described, such as in Delegrave (1993) Biotechnology Res. 11:1548-1552. Random and site-directed mutagenesis are described, such as in Arnold (1993) Current Opinion in Biotechnology 4:450-455.

In some embodiments, the variants are created using shuffling procedures wherein portions of a plurality of nucleic acids which encode distinct polypeptides are fused together to create chimeric nucleic acid sequences which encode chimeric polypeptides as described in U.S. Pat. No. 5,965,408, filed Jul. 9, 1996, entitled, "Method of DNA Reassembly by Interrupting Synthesis" and U.S. Pat. No. 5,939,250, filed May 22, 1996, entitled, "Production of Enzymes Having Desired Activities by Mutagenesis.

The variants of the polypeptides in accordance with the invention may be variants in which one or more of the amino acid residues of the polypeptides of the sequences in accordance with the invention are substituted with a conserved or non-conserved amino acid residue (in some embodiments, a conserved amino acid residue) and such substituted amino acid residue may or may not be one encoded by the genetic code.

In some embodiments, conservative substitutions are those that substitute a given amino acid in a polypeptide by another amino acid of like characteristics. In some embodiments, conservative substitutions in accordance with the invention comprise the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue.

Other variants are those in which one or more of the amino acid residues of a polypeptide in accordance with the invention includes a substituent group. In some embodiments, other variants are those in which the polypeptide is associated with another compound, such as a compound to increase the half-life of the polypeptide (for example, polyethylene glycol). Additional variants are those in which additional amino acids are fused to the polypeptide, such as a leader sequence, a secretory sequence, a proprotein sequence or a sequence which facilitates purification, enrichment, or stabilization of the polypeptide.

In some embodiments, the fragments, derivatives and analogs retain the same biological function or activity as the polypeptides in accordance with the invention and sequences substantially identical thereto. In other embodiments, the fragment, derivative, or analog includes a proprotein, such that the fragment, derivative, or analog can be activated by cleavage of the proprotein portion to produce an active polypeptide.

Optimizing Codons to Achieve High Levels of Protein Expression in Host Cells

The invention provides methods for modifying aldolase, such as pyruvate aldolase, such as HMG and/or KHG aldolase, enzyme-encoding nucleic acids to modify (such as optimize) codon usage. In some embodiments, the invention provides methods for modifying codons in a nucleic acid encoding an aldolase, such as pyruvate aldolase, HMG and/or KHG aldolase enzyme to increase or decrease its expression in a host cell. In some embodiments, the invention also provides nucleic acids encoding an aldolase, such as pyruvate aldolase, HMG and/or KHG aldolase enzyme modified to increase its expression in a host cell, aldolase, such as pyruvate aldolase, such as HMG and/or KHG aldolase enzyme so modified, and methods of making the modified aldolase, such as pyruvate aldolase, such as HMG and/or KHG aldolase enzymes. The method comprises identifying a "non-preferred" or a "less preferred" codon in aldolase, such as pyruvate aldolase, such as HMG and/or KHG aldolase, enzyme-encoding nucleic acid and replacing one or more of these non-preferred or less preferred codons with a "preferred codon" encoding the same amino acid as the replaced codon and at least one non-preferred or less preferred codon in the nucleic acid has been replaced by a preferred codon encoding the same amino acid. A preferred codon is a codon over-represented in coding sequences in genes in the host cell and a non-preferred or less preferred codon is a codon under-represented in coding sequences in genes in the host cell.

Host cells for expressing the nucleic acids, expression cassettes and vectors in accordance with the invention include bacteria, yeast, fungi, plant cells, insect cells and mammalian cells (see discussion, above). Thus, the invention provides methods for optimizing codon usage in all of these cells, codon-altered nucleic acids and polypeptides made by the codon-altered nucleic acids. Exemplary host cells include gram negative bacteria, such as *Escherichia coli*; gram positive bacteria, such as *Streptomyces* sp., *Lactobacillus gasseri*, *Lactococcus lactis, Lactococcus cremoris, Bacillus subtilis, Bacillus cereus*. Exemplary host cells also include eukaryotic organisms, such as various yeast, such as *Saccharomyces* sp., including *Saccharomyces cerevisiae, Schizosaccharomyces pombe, Pichia pastoris*, and *Kluyveromyces lactis, Hansenula polymorpha, Aspergillus niger*, and mammalian cells and cell lines and insect cells and cell lines. Thus, the invention also includes nucleic acids and polypeptides optimized for expression in these organisms and species.

For example, the codons of a nucleic acid encoding an aldolase, such as pyruvate aldolase, HMG and/or KHG aldolase enzyme isolated from a bacterial cell are modified such that the nucleic acid is optimally expressed in a bacterial cell different from the bacteria from which the aldolase, such as pyruvate aldolase, such as HMG and/or KHG aldolase enzyme was derived, a yeast, a fungi, a plant cell, an insect cell or a mammalian cell. Methods for optimizing codons are well known in the art, see U.S. Pat. No. 5,795,737; Baca (2000) Int. J. Parasitol. 30:113-118; Hale (1998) Protein Expr. Purif 12:185-188; Narum (2001) Infect. Immun. 69:7250-7253. See also Narum (2001) Infect. Immun. 69:7250-7253, describing optimizing codons in mouse systems; Outchkourov (2002) Protein Expr. Purif. 24:18-24, describing optimizing codons in yeast; Feng (2000) Biochemistry 39:15399-15409, describing optimizing codons in *E. coli*; Humphreys (2000) Protein Expr. Purif. 20:252-264, describing optimizing codon usage that affects secretion in *E. coli*.

Transgenic Non-human Animals

The invention provides transgenic non-human animals comprising a nucleic acid, a polypeptide (such as an aldolase, such as pyruvate aldolase, HMG and/or KHG aldolase enzyme), an expression cassette or vector or a transfected or transformed cell in accordance with the invention. Tn some embodiments, the invention also provides methods of making and using these transgenic non-human animals.

The transgenic non-human animals can be, such as dogs, goats, rabbits, sheep, horses, fish, pigs (including all swine, hogs and related animals), cows, rats and mice, comprising the nucleic acids in accordance with the invention. These animals can be used, such as in vivo models to study aldolase, such as pyruvate aldolase, such as HMG and/or KHG aldolase enzyme, activity, or, as models to screen for agents that change the aldolase, such as pyruvate aldolase, such as HMG and/or KHG aldolase enzyme, activity in vivo. The coding sequences for the polypeptides to be expressed in the transgenic non-human animals can be designed to be constitutive, or, under the control of tissue-specific, developmental-specific or inducible transcriptional regulatory factors.

Transgenic non-human animals can be designed and generated using any method known in the art; see U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs, chickens, goats, fish and cows. See also, such as Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice. U.S. Pat. No. 6,187,992, describes making and using a transgenic mouse.

"Knockout animals" can also be used to practice the methods in accordance with the invention. For example, in some embodiments, the transgenic or modified animals in accordance with the invention comprise a "knockout animal," such as a "knockout mouse," engineered not to express an endogenous gene, which is replaced with a gene expressing an aldolase, such as pyruvate aldolase, HMG and/or KHG aldolase enzyme in accordance with the invention, or, a fusion protein comprising an aldolase, such as pyruvate aldolase, HMG and/or KHG aldolase enzyme in accordance with the invention.

Transgenic Plants and Seeds

The invention provides transgenic plants and seeds comprising a nucleic acid, a polypeptide (such as an aldolase, such as pyruvate aldolase, HMG and/or KHG aldolase enzyme), an expression cassette or vector or a transfected or transformed cell in accordance with the invention. The invention also provides plant products or byproducts, such as fruits, oils, seeds, leaves, extracts and the like, including any plant part, comprising a nucleic acid and/or a polypeptide (such as a xylanase) of the invention, such as wherein the nucleic acid or polypeptide of the invention is heterologous to the plant, plant part, seed etc. The transgenic plant (which includes plant parts, fruits, seeds etc.) can be dicotyledonous (a dicot) or monocotyledonous (a monocot). In some embodiments, the invention also provides methods of making and using these transgenic plants and seeds. The transgenic plant or plant cell expressing a polypeptide of the present invention may be constructed in accordance with any method known in the art. See, for example, U.S. Pat. No. 6,309,872.

Nucleic acids and expression constructs in accordance with the invention can be introduced into a plant cell by any means. For example, nucleic acids or expression constructs can be introduced into the genome of a desired plant host, or, the nucleic acids or expression constructs can be episomes. Introduction into the genome of a desired plant can be such that the host's aldolase, such as pyruvate aldolase, such as HMG and/or KHG aldolase enzyme production is regulated by endogenous transcriptional or translational control elements. In some embodiments, the invention also provides "knockout plants" where insertion of gene sequence by, such as homologous recombination, has disrupted the expression of the endogenous gene. Means to generate "knockout" plants are well-known in the art, see Strepp (1998) Proc Natl. Acad. Sci. USA 95:4368-4373; Miao (1995) Plant J 7:359-365. See discussion on transgenic plants, below.

The nucleic acids in accordance with the invention can be used to confer desired traits on essentially any plant, such as on starch-producing plants, such as potato, tomato, soybean, beets, corn, wheat, rice, barley, and the like. Nucleic acids in accordance with the invention can be used to manipulate metabolic pathways of a plant in order to optimize or alter host's expression of aldolase, such as pyruvate aldolase, such as HMG and/or KHG aldolase enzyme. The nucleic acids in accordance with the invention can change expression or activity levels or alter characteristics of compounds or enzymes naturally produced in a plant. Alternatively, an aldolase, such as pyruvate aldolase, HMG and/or KHG aldolase enzyme in accordance with the invention can be used in production of a transgenic plant to produce a compound not naturally produced by that plant. This can lower production costs or create a novel product.

In some embodiments, the first step in production of a transgenic plant involves making an expression construct for expression in a plant cell. These techniques are well known in the art. They can include selecting and cloning a promoter, a coding sequence for facilitating efficient binding of ribosomes to mRNA and selecting the appropriate gene terminator sequences. One exemplary constitutive promoter is CaMV35S, from the cauliflower mosaic virus, which generally results in a high degree of expression in plants. Other promoters are more specific and respond to cues in the plant's internal or external environment. An exemplary light-inducible promoter is the promoter from the cab gene, encoding the major chlorophyll a/b binding protein.

In some embodiments, the nucleic acid is modified to achieve greater expression in a plant cell. For example, a sequence in accordance with the invention is likely to have a higher percentage of A-T nucleotide pairs compared to that seen in a plant, some of which prefer G-C nucleotide pairs. Therefore, A-T nucleotides in the coding sequence can be substituted with G-C nucleotides without significantly changing the amino acid sequence to enhance production of the gene product in plant cells.

Selectable marker gene can be added to the gene construct in order to identify plant cells or tissues that have successfully integrated the transgene. This may be necessary because achieving incorporation and expression of genes in plant cells is a rare event, occurring in just a few percent of the targeted tissues or cells. Selectable marker genes encode proteins that provide resistance to agents that are normally toxic to plants, such as antibiotics or herbicides. Only plant cells that have integrated the selectable marker gene will survive when grown on a medium containing the appropriate antibiotic or herbicide. As for other inserted genes, marker genes also require promoter and termination sequences for proper function.

In some embodiments, making transgenic plants or seeds comprises incorporating sequences in accordance with the invention and, optionally, marker genes into a target expression construct (such as a plasmid), along with positioning of the promoter and the terminator sequences. This can involve transferring the modified gene into the plant through a suitable method. For example, a construct may be introduced directly into the genomic DNA of the plant cell using techniques such as electroporation and microinjection of plant cell protoplasts, or the constructs can be introduced directly to plant tissue using ballistic methods, such as DNA particle bombardment. For example, see Christou (1997) Plant Mol. Biol. 35:197-203; Pawlowski (1996) Mol. Biotechnol. 6:17-30; Klein (1987) Nature 327:70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available Bio-Rad (Biolistics) PDS-2000 particle acceleration instrument (Bio-Rad, Hercules, Calif.); see also, John, U.S. Pat. No. 5,608,148; and Ellis, U.S. Pat. No. 5,681,730, describing particle-mediated transformation of gymnosperms.

In some embodiments, protoplasts can be immobilized and injected with a nucleic acids, such as an expression construct. Although plant regeneration from protoplasts is not easy with cereals, plant regeneration is possible in legumes using somatic embryogenesis from protoplast derived callus. Organized tissues can be transformed with naked DNA using gene gun technique, where DNA is coated on tungsten microprojectiles, shot 1/100th the size of cells, which carry the DNA deep into cells and organelles. Transformed tissue is then induced to regenerate, usually by somatic embryogenesis. This technique has been successful in several cereal species including maize and rice.

Nucleic acids, such as expression constructs, can also be introduced into plant cells using recombinant viruses. Plant cells can be transformed using viral vectors, such as tobacco mosaic virus derived vectors (Rouwendal (1997) Plant Mol. Biol. 33:989-999), see Porta (1996) "Use of viral replicons for the expression of genes in plants," Mol. Biotechnol. 5:209-221.

Alternatively, nucleic acids, such as an expression construct, can be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See Horsch (1984) *Science* 233:496-498; Fraley (1983) *Proc. Natl. Acad. Sci. USA* 80:4803 (1983); *Gene Transfer to Plants*, Potrykus, ed. (Springer-Verlag, Berlin 1995). The DNA in an *A. tumefaciens* cell is contained in the bacterial chromosome as well as in another structure known as a Ti (tumor-inducing) plasmid. The Ti plasmid contains a stretch of DNA termed T-DNA (~20 kb long) that is transferred to the plant cell in the infection process and a series of vir (virulence) genes that direct the infection process. *A. tumefaciens* can only infect a plant through wounds: when a plant root or stem is wounded it gives off certain chemical signals, in response to which, the vir genes of *A. tumefaciens* become activated and direct a series of events necessary for the transfer of the T-DNA from the Ti plasmid to the plant's chromosome. The T-DNA then enters the plant cell through the wound. One speculation is that the T-DNA waits until the plant DNA is being replicated or transcribed, then inserts itself into the exposed plant DNA. In order to use *A. tumefaciens* as a transgene vector, the tumor-inducing section of T-DNA have to be removed, while retaining the T-DNA border regions and the vir genes. The transgene is then inserted between the T-DNA border regions, where it is transferred to the plant cell and becomes integrated into the plant's chromosomes.

The invention provides for the transformation of monocotyledonous plants using the nucleic acids in accordance with the invention, including important cereals, see Hiei (1997) Plant Mol. Biol. 35:205-218. See also, Horsch, Science (1984) 233:496; Fraley (1983) Proc. Natl. Acad. Sci. USA 80:4803; Thykjaer (1997) supra; Park (1996) Plant Mol. Biol. 32:1135-1148, discussing T-DNA integration into genomic DNA. See also D'Halluin, U.S. Pat. No. 5,712,135, describing a process for the stable integration of a DNA comprising a gene that is functional in a cell of a cereal, or other monocotyledonous plant.

In some embodiments, the third step involves selection and regeneration of whole plants capable of transmitting the incorporated target gene to the next generation. Such regeneration techniques may use manipulation of certain phytohormones in a tissue culture growth medium. In some embodiments, the method uses a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee (1987) Ann. Rev. of Plant Phys. 38:467-486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

In some embodiments, after the expression cassette is stably incorporated in transgenic plants, it can be introduced into other plants by sexual crossing. Any of a number of standard breeding techniques can be used, depending upon the species to be crossed. Because transgenic expression of the nucleic acids in accordance with the invention leads to phenotypic changes, plants comprising the recombinant nucleic acids in accordance with the invention can be sexually crossed with a second plant to obtain a final product. Thus, the seed in accordance with the invention can be derived from a cross between two transgenic plants in accordance with the invention, or a cross between a plant in accordance with the invention and another plant. The desired effects (such as expression of the polypeptides in accordance with the invention to produce a plant in which flowering behavior is altered) can be enhanced when both parental plants express the polypeptides (such as an aldolase, such as pyruvate aldolase, HMG and/or KHG aldolase enzyme) in accordance with the invention. The desired effects can be passed to future plant generations by standard propagation means.

In some embodiments, the nucleic acids and polypeptides in accordance with the invention are expressed in or inserted in any plant or seed. Transgenic plants in accordance with the invention can be dicotyledonous or monocotyledonous. Examples of monocot transgenic plants in accordance with the invention are grasses, such as meadow grass (blue grass, *Poa*), forage grass such as *festuca, lolium*, temperate grass, such as *Agrostis*, and cereals, such as wheat, oats, rye, barley, rice, sorghum, and maize (corn). Examples of dicot transgenic plants in accordance with the invention are tobacco, legumes, such as lupins, potato, sugar beet, pea, bean and soybean, and cruciferous plants (family Brassicaceae), such as cauliflower, rape seed, and the closely related model organism *Arabidopsis thaliana*. Thus, the transgenic plants and seeds in accordance with the invention include a broad range of plants, including, but not limited to, species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine,*

*Gossypium, Helianthus, Heterocallis, Hordeum, Hyoscyamus, Lactuca, Linum, Loluim, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanumm, Sorghum, Theobromus, Trigonella, Triticum, Vicia, Vitis, Vigna,* and *Zea.*

In alternative embodiments, the nucleic acids in accordance with the invention are expressed in plants which contain fiber cells, including, such as cotton, silk cotton tree (Kapok, Ceiba pentandra), desert willow, creosote bush, winterfat, balsa, ramie, kenaf, hemp, roselle, jute, sisal abaca and flax. In alternative embodiments, the transgenic plants in accordance with the invention can be members of the genus *Gossypium*, including members of any *Gossypium* species, such as *G. arboreum; G. herbaceum, G. barbadense,* and *G. hirsutum.*

The invention also provides for transgenic plants to be used for producing large amounts of the polypeptides (such as an aldolase, such as pyruvate aldolase, HMG and/or KHG aldolase enzyme or antibody) in accordance with the invention. For example, see Palmgren (1997) Trends Genet. 13:348; Chong (1997) Transgenic Res. 6:289-296 (producing human milk protein beta-casein in transgenic potato plants using an auxin-inducible, bidirectional mannopine synthase (mas1',2') promoter with *Agrobacterium tumefaciens*-mediated leaf disc transformation methods).

Using known procedures, one of skill can screen for plants in accordance with the invention by detecting the increase or decrease of transgene mRNA or protein in transgenic plants. Means for detecting and quantitation of mRNAs or proteins are well known in the art.

Polypeptides and Peptides

In some embodiments, the invention provides isolated, synthetic or recombinant polypeptides having a sequence identity (such as at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity, or homology) to a sequence in accordance with the invention, such as proteins having a sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, SEQ ID NO:174, SEQ ID NO:176, SEQ ID NO:178, SEQ ID NO:180, SEQ ID NO:182, SEQ ID NO:184, SEQ ID NO:186, SEQ ID NO:188, SEQ ID NO:190, SEQ ID NO:192, SEQ ID NO:194, SEQ ID NO:196, SEQ ID NO:198, SEQ ID NO:200, SEQ ID NO:202, SEQ ID NO:204, SEQ ID NO:206, SEQ ID NO:208, SEQ ID NO:210, SEQ ID NO:212, SEQ ID NO:214, SEQ ID NO:216, SEQ ID NO:218, SEQ ID NO:220, SEQ ID NO:222, SEQ ID NO:224, SEQ ID NO:226, SEQ ID NO:228, SEQ ID NO:230, SEQ ID NO:232, SEQ ID NO:234, SEQ ID NO:236, SEQ ID NO:238, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:260, SEQ ID NO:262, SEQ ID NO:264, SEQ ID NO:266, SEQ ID NO:268, SEQ ID NO:270, SEQ ID NO:272, SEQ ID NO:274, SEQ ID NO:276, SEQ ID NO:278, SEQ ID NO:280, SEQ ID NO:282, SEQ ID NO:284, SEQ ID NO:286, SEQ ID NO:288, SEQ ID NO:290, SEQ ID NO:292, SEQ ID NO:294, SEQ ID NO:296, SEQ ID NO:298, SEQ ID NO:300, SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:320, SEQ ID NO:322, SEQ ID NO:324, SEQ ID NO:326, SEQ ID NO:328, SEQ ID NO:330, SEQ ID NO:332, or SEQ ID NO:334 and enzymatically active fragments thereof. The percent sequence identity can be over the full length of the polypeptide, or, the identity can be over a region of at least about 50, 60, 70, 80, 90, 100, 150, 200, 250, 300, 350, 400, 450, 500, 550, 600, 650, 700 or more residues.

Polypeptides in accordance with some embodiments of the invention can also be shorter than the full length of the polypeptides. In other embodiments, the invention provides polypeptides (peptides, fragments) ranging in size between about 5 and the full length of a polypeptide, such as an enzyme, such as an aldolase, such as pyruvate aldolase, HMG and/or KHG aldolase enzyme; exemplary sizes being of about 5, 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, or more residues, such as contiguous residues of an aldolase, such as pyruvate aldolase, such as HMG and/or KHG aldolase enzyme in accordance with the invention. Peptides in accordance with the invention (such as a subsequence of a polypeptide in accordance with the invention) can be useful as, such as labeling probes, antigens (immunogens), toleragens, motifs, aldolase, such as pyruvate aldolase, such as HMG and/or KHG aldolase enzyme active sites (such as "catalytic domains"), signal sequences and/or prepro domains.

In other embodiments, polypeptides in accordance with the invention having aldolase activity, such as pyruvate aldolase, such as HMG and/or KHG aldolase activity are members of a genus of polypeptides sharing specific structural elements, such as amino acid residues, that correlate with aldolase activity, including pyruvate activity such as, without limitation, HMG and/or KHG aldolase activity. These shared structural elements can be used for the routine generation of aldolase, such as pyruvate aldolase, such as HMG and/or KHG aldolase variants. These shared structural elements of aldolase, such as pyruvate aldolase, such as HMG and/or KHG aldolase enzymes in accordance with the invention can be used as guidance for the routine generation of aldolase, such as pyruvate aldolase, such as HMG and/or KHG aldolase enzymes variants within the scope of the genus of polypeptides in accordance with the invention.

As used herein, the terms "aldolase, such as pyruvate aldolase, such as HMG and/or KHG aldolase" encompass any polypeptide or enzymes capable of catalyzing the aldol addition reaction or the retro-aldol reaction (such as polypeptides in accordance with the invention, see also Table 1 and Examples 4, 5 and 6, below), or any modification of a carbon-carbon bond containing material, such as in the production of R-2-hydroxy 2-(indol-3ylmethyl)-4-keto glutaric acid (R-MP) and certain stereoisomers of monatin, such as R,R and S,R monatin, and salts thereof.

Polypeptides in accordance with some embodiments of the invention catalyze the formation of carbon-carbon bonds in an aldol reaction and have the ability to utilize pyruvate or phosphoenolpyruvate as the nucleophilic component in the synthesis of a 4-hydroxy-2-ketobutyrate framework as shown in the general scheme below.

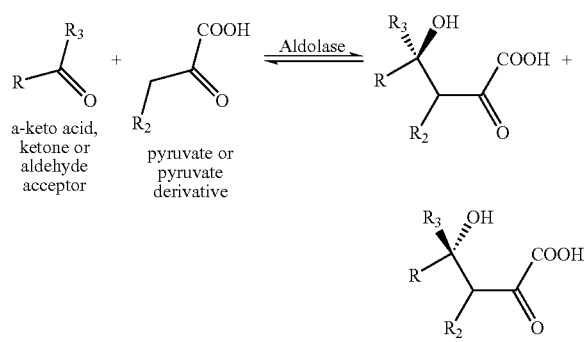

R=H, alkyl, substituted alkyl, aryl, substituted aryl, benzyl, substituted benzyl
$R_2$=H, alkyl, substituted alkyl, aryl, substituted aryl, benzyl, substituted benzyl
$R_3$=H, alkyl, substituted alkyl, aryl, substituted aryl, benzyl, substituted benzyl, carboxylic acid.

Without being bound by theory, it is believed that the conserved four-carbon fragment prepared in all pyruvate aldolase-catalyzed condensations is both densely and differentially functionalized. Moreover, in each adduct, four different oxidation states of carbon are contained in four contiguous carbons. The framework prepared by pyruvate aldolases thus allows the preparation of α-amino-γ-hydroxy-carboxylic acids, β-hydroxycarboxylic acids, α,γ-dihydroxy-carboxylic acids, and 2-deoxyaldose sugars as shown in the scheme below.

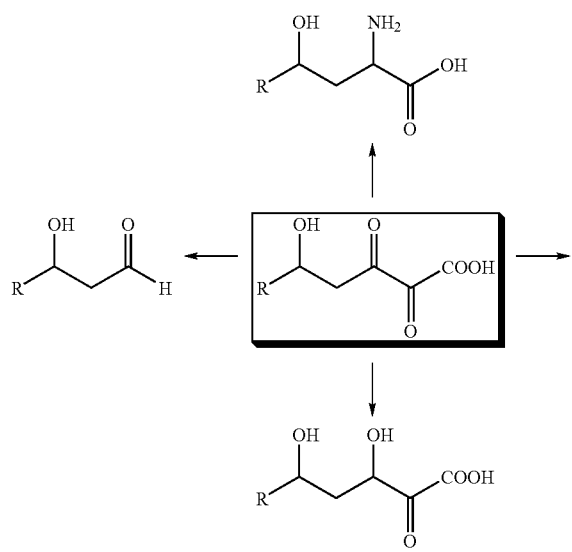

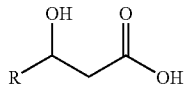

Therefore, pyruvate aldolases in accordance with some embodiments of the invention can be synthetically versatile and can be used in the preparation of a wide range of products for use in animal feeds, human foods, industrial processes, and pharmaceuticals (see, for example, Gijsen, H. J. M. et al., Recent Advances in the Chemoenzymatic Synthesis of Carbohydrates and Carbohydrate Mimetics, Chem. Rev. 1996, 96, 443-473; Henderson, D. P. et al. J. Org. Chem., Stereospecific Preparation of the N-Terminal Amino Acid Moiety of Nikkomycins KX and KZ via a Multiple Enzyme Synthesis, 1997, 62, 7910-7911; Wymer, N. & Toone, E. J. Enzyme-catalyzed Synthesis of Carbohydrates. Current Opin. Chemical Biology, 2000, 4, 110-119).

Polypeptides in accordance with some embodiments of the invention may have more than one type of enzymatic activity, specifically aldolase activity and an additional activity, for example, as set forth in Table 1, below. For example, a polypeptide in accordance with the invention can have aldolase activity, pyruvate aldolase, HMG and/or KHG aldolase activity. Additionally, the polypeptide may have, or may be thought to have, additional enzyme activity based on its EC classification. Table 1 includes the column "Predicted EC Number". An EC number is the number assigned to a type of enzyme according to a scheme of standardized enzyme nomenclature developed by the Enzyme Commission of the Nomenclature Committee of the International Union of Biochemistry and Molecular Biology (IUBMB). The results in the "Predicted EC Number" column are determined by a BLAST search against the Kegg (Kyoto Encyclopedia of Genes and Genomes) database. If the top BLAST match (also called a "hit") has an Evalue equal to or less than $e^{-6}$, the EC number assigned to the top match is entered into the table. The EC number of the top hit is used as a guide to what the EC number of the sequence of the invention might be. In instances where only a partial EC number is given, only a broad classification could be assigned based on the top hit. For instance, in the first row, for SEQ ID NO:2, encoded by SEQ ID NO:1, the Predicted EC Number is listed as "2 . . . ". Therefore, the classification assigned is broadly a transferase. For SEQ ID NO:26, encoded by SEQ ID NO:25, the most specific classification that could be assigned based on the top hit is as an aldehyde-lyase.

TABLE 1

| SEQ ID NO: | Activity | Aldolase subclass | Predicted EC Number | SignalP Signal (AA = Amino Acid) | Source |
|---|---|---|---|---|---|
| 1, 2 | Aldolase | HMG | 2 . . . | | Bacteria |
| 3, 4 | Aldolase | HMG | 2 . . . | | Unknown |
| 5, 6 | Aldolase | HMG | 2 . . . | | Unknown |
| 7, 8 | Aldolase | HMG | 2 . . . | | Unknown |
| 9, 10 | Aldolase | HMG | 2 . . . | | Unknown |
| 11, 12 | Aldolase | HMG | 2 . . . | | Unknown |
| 13, 14 | Aldolase | HMG | 2 . . . | | Unknown |
| 15, 16 | Aldolase | HMG | 2 . . . | | Unknown |
| 17, 18 | Aldolase | HMG | 2 . . . | | Unknown |
| 19, 20 | Aldolase | HMG | 2 . . . | | Unknown |
| 21, 22 | Aldolase | HMG | | | Unknown |
| 23, 24 | Aldolase | HMG | 2 . . . | | Unknown |
| 25, 26 | Aldolase | HMG | 4.1.2. | | Unknown |

TABLE 1-continued

| SEQ ID NO: | Activity | Aldolase subclass | Predicted EC Number | SignalP Signal (AA = Amino Acid) | Source |
|---|---|---|---|---|---|
| 27, 28 | Aldolase | HMG | 2... | | Unknown |
| 29, 30 | Aldolase | HMG | 2... | | Unknown |
| 31, 32 | Aldolase | HMG | 2... | | Unknown |
| 33, 34 | Aldolase | HMG | 2... | | Unknown |
| 35, 36 | Aldolase | HMG | 2... | | Unknown |
| 37, 38 | Aldolase | HMG | 2... | | Unknown |
| 39, 40 | Aldolase | HMG | 2... | | Unknown |
| 41, 42 | Aldolase | HMG | 2... | | Unknown |
| 43, 44 | Aldolase | HMG | 2... | | Unknown |
| 45, 46 | Aldolase | HMG | 2... | | Unknown |
| 47, 48 | Aldolase | HMG | 2... | | Unknown |
| 49, 50 | Aldolase | HMG | 2... | | Unknown |
| 51, 52 | Aldolase | HMG | 2... | | Unknown |
| 53, 54 | Aldolase | HMG | 2... | | Unknown |
| 55, 56 | Aldolase | HMG | 2... | | Unknown |
| 57, 58 | Aldolase | HMG | 2... | | Unknown |
| 59, 60 | Aldolase | HMG | 2... | | Unknown |
| 61, 62 | Aldolase | HMG | 2... | | Unknown |
| 63, 64 | Aldolase | HMG | 2... | | Unknown |
| 65, 66 | Aldolase | HMG | 2... | AA1-27 | Unknown |
| 67, 68 | Aldolase | HMG | 2... | | Unknown |
| 69, 70 | Aldolase | HMG | 2... | | Unknown |
| 71, 72 | Aldolase | HMG | 2... | | Unknown |
| 73, 74 | Aldolase | HMG | 2... | | Unknown |
| 75, 76 | Aldolase | HMG | 2... | | Unknown |
| 77, 78 | Aldolase | HMG | 2... | | Unknown |
| 79, 80 | Aldolase | HMG | 2... | | Unknown |
| 81, 82 | Aldolase | HMG | 2... | | Unknown |
| 83, 84 | Aldolase | HMG | 2... | | Unknown |
| 85, 86 | Aldolase | HMG | 2... | | Unknown |
| 87, 88 | Aldolase | HMG | 2... | | Unknown |
| 89, 90 | Aldolase | HMG | 2... | | Unknown |
| 91, 92 | Aldolase | HMG | 2... | | Unknown |
| 93, 94 | Aldolase | HMG | 2... | | Unknown |
| 95, 96 | Aldolase | HMG | 2... | | Unknown |
| 97, 98 | Aldolase | HMG | 2... | | Unknown |
| 99, 100 | Aldolase | HMG | 2... | | Unknown |
| 101, 102 | Aldolase | HMG | 2... | | Unknown |
| 103, 104 | Aldolase | HMG | 2... | | Unknown |
| 105, 106 | Aldolase | HMG | 2... | | Unknown |
| 107, 108 | Aldolase | HMG | 2... | | Unknown |
| 109, 110 | Aldolase | HMG | 2... | | Unknown |
| 111, 112 | Aldolase | HMG | 2... | | Unknown |
| 113, 114 | Aldolase | HMG | 2... | | Unknown |
| 115, 116 | Aldolase | HMG | 2... | | Unknown |
| 117, 118 | Aldolase | HMG | 2... | | Unknown |
| 119, 120 | Aldolase | HMG | 2... | | Unknown |
| 121, 122 | Aldolase | HMG | 2... | | Unknown |
| 123, 124 | Aldolase | HMG | 2... | | Unknown |
| 125, 126 | Aldolase | HMG | 2... | | Unknown |
| 127, 128 | Aldolase | HMG | 2... | | Unknown |
| 129, 130 | Aldolase | HMG | 2... | | Unknown |
| 131, 132 | Aldolase | HMG | 2... | | Unknown |
| 133, 134 | Aldolase | HMG | 2... | | Unknown |
| 135, 136 | Aldolase | HMG | 2... | | Unknown |
| 137, 138 | Aldolase | HMG | 2... | | Unknown |
| 139, 140 | Aldolase | HMG | 2... | | Unknown |
| 141, 142 | Aldolase | HMG | 2... | | Unknown |
| 143, 144 | Aldolase | HMG | 2... | | Unknown |
| 145, 146 | Aldolase | HMG | 2... | | Unknown |
| 147, 148 | Aldolase | HMG | 2... | | Unknown |
| 149, 150 | Aldolase | HMG | 2... | | Unknown |
| 151, 152 | Aldolase | HMG | 2... | | Unknown |
| 153, 154 | Aldolase | HMG | 2... | | Unknown |
| 155, 156 | Aldolase | HMG | 2... | | Unknown |
| 157, 158 | Aldolase | HMG | 2... | | Unknown |
| 159, 160 | Aldolase | HMG | 2... | | Unknown |
| 161, 162 | Aldolase | HMG | 2... | | Unknown |
| 163, 164 | Aldolase | HMG | 2... | | Unknown |
| 165, 166 | Aldolase | HMG | 2... | | Unknown |
| 167, 168 | Aldolase | HMG | 2... | | Unknown |
| 169, 170 | Aldolase | HMG | 2... | | Unknown |
| 171, 172 | Aldolase | HMG | 2... | | Unknown |
| 173, 174 | Aldolase | HMG | 2... | | Unknown |
| 175, 176 | Aldolase | HMG | 2... | | Unknown |
| 177, 178 | Aldolase | HMG | 2... | | Unknown |
| 179, 180 | Aldolase | HMG | 2... | | Unknown |
| 181, 182 | Aldolase | HMG | 2... | AA1-31 | Unknown |
| 183, 184 | Aldolase | HMG | 2... | | Unknown |
| 185, 186 | Aldolase | HMG | 2... | | Unknown |
| 187, 188 | Aldolase | HMG | 2... | | Unknown |
| 189, 190 | Aldolase | HMG | 2... | | Unknown |
| 191, 192 | Aldolase | HMG | 2... | | Unknown |
| 193, 194 | Aldolase | HMG | 2... | | Unknown |
| 195, 196 | Aldolase | HMG | 2... | | Unknown |
| 197, 198 | Aldolase | HMG | 2... | | Unknown |
| 199, 200 | Aldolase | HMG | 2... | | Unknown |
| 201, 202 | Aldolase | HMG | 2... | | Unknown |
| 203, 204 | Aldolase | HMG | 2... | | Unknown |
| 205, 206 | Aldolase | HMG | 2... | | Unknown |
| 207, 208 | Aldolase | HMG | 2... | | Unknown |
| 209, 210 | Aldolase | HMG | 2... | | Unknown |
| 211, 212 | Aldolase | HMG | 2... | | Unknown |
| 213, 214 | Aldolase | HMG | 2... | | Unknown |
| 215, 216 | Aldolase | HMG | 2... | | Unknown |
| 217, 218 | Aldolase | HMG | 2... | | Unknown |
| 219, 220 | Aldolase | HMG | 2... | | Unknown |
| 221, 222 | Aldolase | HMG | 2... | | Unknown |
| 223, 224 | Aldolase | HMG | 2... | | Unknown |
| 225, 226 | Aldolase | HMG | 2... | | Unknown |
| 227, 228 | Aldolase | HMG | 2... | | Unknown |
| 229, 230 | Aldolase | HMG | 2... | | Unknown |
| 231, 232 | Aldolase | HMG | 2... | | Unknown |
| 233, 234 | Aldolase | HMG | 2... | | Unknown |
| 235, 236 | Aldolase | HMG | 2... | | Unknown |
| 237, 238 | Aldolase | HMG | 2... | | Unknown |
| 239, 240 | Aldolase | HMG | 2... | | Unknown |
| 241, 242 | Aldolase | HMG | 2... | | Unknown |
| 243, 244 | Aldolase | HMG | 2... | | Unknown |
| 245, 246 | Aldolase | HMG | 2... | | Unknown |
| 247, 248 | Aldolase | HMG | 2... | | Unknown |
| 249, 250 | Aldolase | HMG | 2... | | Unknown |
| 251, 252 | Aldolase | HMG | 2... | | Unknown |
| 253, 254 | Aldolase | HMG | 2... | | Unknown |
| 255, 256 | Aldolase | HMG | 2... | | Unknown |
| 257, 258 | Aldolase | HMG | 2... | | Unknown |
| 259, 260 | Aldolase | HMG | 2... | AA1-18 | Unknown |
| 261, 262 | Aldolase | HMG | 2... | | Unknown |
| 263, 264 | Aldolase | HMG | 2... | | Unknown |
| 265, 266 | Aldolase | HMG | 2... | | Unknown |
| 267, 268 | Aldolase | HMG | 2... | | Unknown |
| 269, 270 | Aldolase | HMG | 2... | | Unknown |
| 271, 272 | Aldolase | HMG | 2... | | Unknown |
| 273, 274 | Aldolase | HMG | 2... | | Unknown |
| 275, 276 | Aldolase | HMG | 2... | | Unknown |
| 277, 278 | Aldolase | HMG | 2... | | Unknown |
| 279, 280 | Aldolase | HMG | 2... | | Unknown |
| 281, 282 | Aldolase | HMG | 2... | | Unknown |
| 283, 284 | Aldolase | HMG | 2... | | Unknown |
| 285, 286 | Aldolase | HMG | 2... | | Unknown |
| 287, 288 | Aldolase | HMG | 2... | | Unknown |
| 289, 290 | Aldolase | HMG | 2... | | Unknown |
| 291, 292 | Aldolase | HMG | 2... | | Unknown |
| 293, 294 | Aldolase | HMG | 2... | | Unknown |
| 295, 296 | Aldolase | HMG | 2... | | Unknown |
| 297, 298 | Aldolase | HMG | 2... | | Unknown |
| 299, 300 | Aldolase | HMG | 2.1... | | Unknown |
| 301, 302 | Aldolase | HMG | 2.1... | | Unknown |
| 303, 304 | Aldolase | HMG | 2.1... | | Unknown |
| 305, 306 | Aldolase | KHG | 4.1.2.14 | | Unknown |
| 307, 308 | Aldolase | KHG | 4.1.2.14 | | Unknown |
| 309, 310 | Aldolase | KHG | 4.1.2.14 | | Unknown |
| 311, 312 | Aldolase | KHG | 4.1.2.14 | | Unknown |
| 313, 314 | Aldolase | KHG | 4.1.2.14 | | Unknown |
| 315, 316 | Aldolase | KHG | 4.1.2.14 | | Unknown |
| 317, 318 | Aldolase | KHG | 4.1.2.14 | | Unknown |
| 319, 320 | Aldolase | KHG | 4.1.3.16 | | Unknown |
| 321, 322 | Aldolase | KHG | 4.1.2.14 | | Unknown |

TABLE 1-continued

| SEQ ID NO: | Activity | Aldolase subclass | Predicted EC Number | SignalP Signal (AA = Amino Acid) | Source |
|---|---|---|---|---|---|
| 323, 324 | Aldolase | KHG | 4.1.2.14 | | Unknown |
| 325, 326 | Aldolase | KHG | 4.1.2.14 | | Unknown |
| 327, 328 | Aldolase | KHG | 4.1.2.14 | | Unknown |
| 329, 330 | Aldolase | KHG | 4.1.3.16 | | Unknown |
| 331, 332 | Aldolase | KHG | 4.1.2.14 | | Unknown |
| 333, 334 | Aldolase | KHG | 4.1.2.14 | | Unknown |

Polypeptides and peptides in accordance with the invention can be isolated from natural sources, be synthetic, or be recombinantly generated polypeptides. Peptides and proteins can be recombinantly expressed in vitro or in vivo. The peptides and polypeptides in accordance with the invention can be made and isolated using any method known in the art. Polypeptide and peptides in accordance with the invention can also be synthesized, in whole or in part, using chemical methods well known in the art. See such as Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see such as Roberge (1995) Science 269:202; Merrifield (1997) Methods Enzymol. 289:3-13) and automated synthesis may be achieved, such as using the ABI 431A Peptide Synthesizer (Perkin Elmer) in accordance with the instructions provided by the manufacturer.

Peptides and polypeptides in accordance with the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

In some embodiments, when indicated, peptides and polypeptides in accordance with the invention can include all "mimetic" and "peptidomimetic" forms. The terms "mimetic" and "peptidomimetic" refer to a synthetic chemical compound which has substantially the same structural and/or functional characteristics of the polypeptides in accordance with the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides in accordance with the invention which are conservative variants or members of a genus of polypeptides in accordance with the invention (such as having about 50% or more sequence identity to a sequence in accordance with the invention), routine experimentation will determine whether a mimetic is within the scope in accordance with the invention, i.e., that its structure and/or function is not substantially altered. Thus, in some embodiments, a mimetic composition is within the scope in accordance with the invention if it has an aldolase, such as pyruvate aldolase, such as HMG and/or KHG aldolase enzyme, activity.

Polypeptide mimetic compositions in accordance with the invention can contain any combination of non-natural structural components. In an alternative embodiment, mimetic compositions in accordance with the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, such as a beta turn, gamma turn, beta sheet, alpha helix conformation, and the like. For example, a polypeptide in accordance with the invention can be characterized as a mimetic when all or some of its residues are joined by chemical means other than natural peptide bonds. Individual peptidomimetic residues can be joined by peptide bonds, other chemical bonds or coupling means, such as glutaraldehyde, N-hydroxysuccinimide esters, bifunctional maleimides, N,N'-dicyclohexylcarbodiimide (DCC) or N,N'-diisopropyl-carbodiimide (DIC). Linking groups that can be an alternative to the traditional amide bond ("peptide bond") linkages include, such as ketomethylene (such as —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see Spatola (1983) in Chemistry and Biochemistry of Amino Acids, Peptides and Proteins, Vol. 7, pp 267-357, "Peptide Backbone Modifications," Marcell Dekker, NY).

A polypeptide in accordance with the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, such as D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenylphenylalanine; D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, such as thiazolyl, thiophenyl, pyrazolyl, benzimidazolyl, naphthyl, furanyl, pyrrolyl, and pyridyl aromatic rings.

Mimetics of acidic amino acids can be generated by substitution by, such as non-carboxylate amino acids while maintaining a negative charge; (phosphono)alanine; sulfated threonine. Carboxyl side groups (such as aspartyl or glutamyl) can also be selectively modified by reaction with carbodiimides (R'—N=C=N—R') such as 1-cyclohexyl-3 (2-morpholinyl-(4-ethyl) carbodiimide or 1-ethyl-3(4-azo-nia-4,4-dimetholpentyl) carbodiimide. Aspartyl or glutamyl can also be converted to asparaginyl and glutaminyl residues by reaction with ammonium ions. Mimetics of basic amino acids can be generated by substitution with, such as (in addition to lysine and arginine) the amino acids ornithine, citrulline, or (guanidino)-acetic acid, or (guanidino)alkyl-acetic acid, where alkyl is defined above. Nitrile derivative (such as containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, such as one or more conventional reagents, including, such as phenylglyoxal, 2,3-butanedione, 1,2-cyclo-hexanedione, or ninhydrin, in some embodiments under alkaline conditions. Tyrosine residue mimetics can be generated by reacting tyrosyl with, such as aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, such as alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, such as bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, such as succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, such as methionine sulfoxide. Mimetics of proline include, such as pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, such as diethylprocarbonate or para-bromophenacyl bromide. Other mimetics include, such as those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methylamino acids; or amidation of C-terminal carboxyl groups.

In some embodiments, a residue, such as an amino acid, of a polypeptide in accordance with the invention can also be replaced by an amino acid (or peptidomimetic residue) of the opposite chirality. In some embodiments, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The invention also provides methods for modifying the polypeptides in accordance with the invention by either natural processes, such as post-translational processing (such as phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. In some embodiments, modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, Creighton, T.E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptide or fragments in accordance with the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain Solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides in accordance with the invention, either by direct synthesis or by synthesis of a series of fragments that can be coupled using other known techniques.

The polypeptides in accordance with the invention include aldolase, such as pyruvate aldolase, such as HMG and/or KHG aldolase enzymes in an active or inactive form. For example, the polypeptides in accordance with the invention include proproteins before "maturation" or processing of pre-pro sequences, such as by a proprotein-processing enzyme, such as a proprotein convertase to generate an "active" mature protein. The polypeptides in accordance with the invention include aldolase, such as pyruvate aldolase, such as HMG and/or KHG aldolase enzymes inactive for other reasons, such as before "activation" by a post-translational processing event, such as an endo- or exo-peptidase or proteinase action, a phosphorylation event, an amidation, a glycosylation or a sulfation, a dimerization event, and the like. The polypeptides in accordance with the invention include all active forms, including active subsequences, such as catalytic domains or active sites, of the enzyme.

The invention includes immobilized aldolase, such as pyruvate aldolase, such as HMG and/or KHG aldolase enzymes, anti-aldolase, such as anti-pyruvate aldolase, such as anti-HMG and/or anti-KHG aldolase antibodies and fragments thereof. In some embodiments, the invention provides methods for inhibiting aldolase, such as pyruvate aldolase, such as HMG and/or KHG aldolase enzyme, activity, such as using dominant negative mutants or anti-aldolase, such as anti-pyruvate aldolase, such as anti-HMG and/or anti-KHG aldolase antibodies in accordance with the invention. In some embodiments, the invention includes heterocomplexes, such as fusion proteins, heterodimers, etc., comprising the aldolase, such as pyruvate aldolase, such as HMG and/or KHG aldolase enzymes in accordance with the invention.

In some embodiments, polypeptides in accordance with the invention can have an aldolase, such as pyruvate aldolase, such as HMG and/or KHG aldolase enzyme, activity under various conditions, such as at extremes in pH and/or temperature or, in some embodiments, in the presence of oxidizing agents. In some embodiments, the invention provides methods leading to alternative aldolase, such as pyruvate aldolase, such as HMG and/or KHG aldolase enzyme preparations with different catalytic efficiencies and stabilities, such as towards temperature, oxidizing agents and changing wash conditions. In some embodiments, aldolase, such as pyruvate aldolase, such as HMG and/or KHG aldolase enzyme variants can be produced using techniques of site-directed mutagenesis and/or random mutagenesis. In some embodiments, directed evolution can be used to produce a great variety of aldolase, such as pyruvate aldolase, such as HMG and/or KHG aldolase enzyme variants with alternative specificities and stability.

The proteins in accordance with the invention are also useful as research reagents to identify aldolase, such as pyruvate aldolase, such as HMG and/or KHG aldolase enzyme modulators, such as activators or inhibitors of aldolase, such as pyruvate aldolase, such as HMG and/or KHG aldolase enzyme, activity. Briefly, test samples (compounds, broths, extracts, and the like) are added to aldolase, such as pyruvate aldolase, such as HMG and/or KHG aldolase enzyme assays to determine their ability to inhibit substrate cleavage. Inhibitors identified in this way can be used in industry and research to reduce or prevent undesired proteolysis. As with aldolase, such as pyruvate aldolase, such as HMG and/or KHG aldolase enzymes, inhibitors can be combined to increase the spectrum of activity.

The enzymes in accordance with the invention are also useful as research reagents to digest proteins or in protein sequencing. For example, the aldolase, such as pyruvate aldolase, such as HMG and/or KHG aldolase enzymes may be used to break polypeptides into smaller fragments for sequencing using, such as an automated sequencer.

The invention also provides methods of discovering new aldolase, such as pyruvate aldolase, such as HMG and/or KHG aldolase enzymes using the nucleic acids, polypeptides and antibodies in accordance with the invention. In some embodiments, phagemid libraries are screened for expression-based discovery of aldolase, such as pyruvate aldolase, such as HMG and/or KHG aldolase enzymes. In other embodiments, lambda phage libraries are screened for expression-based discovery of aldolase, such as pyruvate aldolase, such as HMG and/or KHG aldolase enzymes. Screening of the phage or phagemid libraries can allow the detection of toxic clones; improved access to substrate; reduced need for engineering a host, by-passing the potential for any bias resulting from mass excision of the library; and, faster growth at low clone densities. Screening of phage or phagemid libraries can be in liquid phase or in solid phase. In some embodiments, the invention provides screening in liquid phase. This gives a greater flexibility in assay conditions; additional substrate flexibility; higher sensitivity for weak clones; and ease of automation over solid phase screening.

The invention provides screening methods using the proteins and nucleic acids in accordance with the invention and robotic automation to enable the execution of many thousands of biocatalytic reactions and screening assays in a short period of time, such as per day, as well as ensuring a high level of accuracy and reproducibility (see discussion of arrays, below). As a result, a library of derivative compounds can be produced in a matter of weeks. For further teachings on modification of molecules, including small molecules, see PCT/US94/09174; U.S. Pat. No. 6,245,547.

In some embodiments, polypeptides or fragments in accordance with the invention are obtained through biochemical enrichment or purification procedures. The sequence of potentially homologous polypeptides or fragments may be determined by aldolase, such as pyruvate aldolase, such as HMG and/or KHG aldolase enzyme assays (see Examples 3, 4 and 5, below), gel electrophoresis and/or microsequencing. The sequence of the prospective polypeptide or fragment in accordance with the invention can be compared to a polypeptide in accordance with the invention, or a fragment, such as comprising at least about 5, 10, 15, 20, 25, 30, 35, 40, 50, 75, 100, or 150 or more consecutive amino acids thereof using any of the programs described above.

Another embodiment of the invention is an assay for identifying fragments or variants in accordance with the invention, which retain the enzymatic function of the polypeptides in accordance with the invention. For example the fragments or variants of said polypeptides, may be used to catalyze biochemical reactions, which indicate that the fragment or variant retains the enzymatic activity of a polypeptide in accordance with the invention. An exemplary assay for determining if fragments of variants retain the enzymatic activity of the polypeptides in accordance with the invention includes the steps of: contacting the polypeptide fragment or variant with a substrate molecule tinder conditions which allow the polypeptide fragment or variant to function and detecting either a decrease in the level of substrate or an increase in the level of the specific reaction product of the reaction between the polypeptide and substrate.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds, such as small molecules. Each biocatalyst is specific for one functional group, or several related functional groups and can react with many starting compounds containing this functional group.

In some embodiments, the biocatalytic reactions produce a population of derivatives from a single starting compound. These derivatives can be subjected to another round of biocatalytic reactions to produce a second population of derivative compounds. Thousands of variations of the original small molecule or compound can be produced with each iteration of biocatalytic derivatization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so-called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

In some embodiments, procedural steps are performed using robotic automation enabling the execution of many thousands of biocatalytic reactions and/or screening assays per day as well as ensuring a high level of accuracy and reproducibility. Robotic automation can also be used to screen for aldolase activity to determine if a polypeptide is within the scope in accordance with the invention. As a result, in some embodiments, a library of derivative compounds can be produced in a matter of weeks which would take years to produce using "traditional" chemical or enzymatic screening methods.

In one embodiment, the invention provides methods for modifying small molecules, comprising contacting a polypeptide encoded by a polynucleotide described herein or enzymatically active fragments thereof with a small molecule to produce a modified small molecule. A library of modified small molecules is tested to determine if a modified small molecule is present within the library, which exhibits a desired activity. A specific biocatalytic reaction which produces the modified small molecule of desired activity is identified by systematically eliminating each of the biocatalytic reactions used to produce a portion of the library and then testing the small molecules produced in the portion of the library for the presence or absence of the modified small molecule with the desired activity. The specific biocatalytic reactions which produce the modified small molecule of desired activity is optionally repeated. The biocatalytic reactions are conducted with a group of biocatalysts that react with distinct structural moieties found within the structure of a small molecule, each biocatalyst is specific for one structural moiety or a group of related structural moieties; and each biocatalyst reacts with many different small molecules which contain the distinct structural moiety.

Aldolase, Such as Pyruvate Aldolase, such as HMG and/or KHG Aldolase Enzyme Signal Sequences, Prepro and Catalytic Domains The invention provides aldolase, such as pyruvate aldolase, such as HMG and/or KHG aldolase enzyme signal sequences (such as signal peptides (SPs)), prepro domains and catalytic domains (CDs). The SPs, prepro domains and/or CDs in accordance with the invention can be isolated, synthetic or recombinant peptides or can be part of a fusion protein, such as a heterologous domain in a chimeric protein. In some embodiments, the invention provides nucleic acids encoding these catalytic domains (CDs), prepro domains and signal sequences (SPs, such as a peptide having a sequence comprising/consisting of amino terminal residues of a polypeptide in accordance with the invention).

The invention provides isolated, synthetic or recombinant signal sequences (such as signal peptides) consisting of or comprising a sequence as set forth in residues 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 40, 1 to 41, 1 to 42, 1 to 43, 1 to 44, 1 to 45, 1 to 46, or 1 to 47, or more, of a polypeptide in accordance with the invention, such as polypeptides in accordance with the invention, see also Table 1, Examples 4, 5 and 6, below, and Sequence Listing. For example, Table 1, above, sets forth exemplary signal (leader) sequences in accordance with the invention, such as in the polypeptide having a sequence as set forth in SEQ ID NO:66, encoded, such as by SEQ ID NO:65, has a signal sequence comprising (or consisting of) the amino terminal 27 residues, or, MSIVVTKIERAGAAAVAALRTS-GVATV (SEQ ID NO:407) which corresponds to the first 27 amino acids of SEQ ID NO:66.

In some embodiments, the invention provides signal sequences comprising the first 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more amino terminal residues of a polypeptide in accordance with the invention.

The invention includes polypeptides with or without a signal sequence and/or a prepro sequence. In some embodiments, the invention includes polypeptides with heterologous signal sequences and/or prepro sequences. The prepro sequence (including a sequence in accordance with the invention used as a heterologous prepro domain) can be located on the amino terminal or the carboxy terminal end of the protein. In some embodiments, the invention also includes isolated, synthetic or recombinant signal sequences, prepro sequences and catalytic domains (such as "active sites") comprising sequences in accordance with the invention. The polypeptide comprising a signal sequence in accordance with the invention can be an aldolase, such as pyruvate aldolase, HMG and/or KHG aldolase enzyme in accordance with the invention or another aldolase, such as pyruvate aldolase, such as HMG and/or KHG aldolase enzyme or another enzyme or other polypeptide. Methods for identifying "prepro" domain sequences and signal sequences are well known in the art, see Van de Ven (1993) Crit. Rev. Oncog. 4(2):115-136. For example, to identify a prepro sequence, the protein is purified from the extracellular space and the N-terminal protein sequence is determined and compared to the unprocessed form.

The aldolase, such as pyruvate aldolase, such as HMG and/or KHG aldolase enzyme signal sequences (SPs) and/or prepro sequences in accordance with the invention can be isolated, synthetic or recombinant peptides, or, sequences joined to another aldolase, such as pyruvate aldolase, such as HMG and/or KHG aldolase enzyme or a non-aldolase, such as non-pyruvate aldolase, e.g., non-HMG and/or non-KHG aldolase polypeptide, such as a fusion (chimeric) protein. In some embodiments, the invention provides polypeptides comprising aldolase, such as pyruvate aldolase, such as HMG and/or KHG aldolase enzyme signal sequences in accordance with the invention. In some embodiments, polypeptides comprising aldolase, such as pyruvate aldolase, such as HMG and/or KHG aldolase enzyme signal sequences SPs and/or prepro in accordance with the invention comprise sequences heterologous to an aldolase, such as pyruvate aldolase, HMG and/or KHG aldolase enzyme in accordance with the invention (such as a fusion protein comprising an SP and/or prepro in accordance with the invention and sequences from another aldolase, such as pyruvate aldolase, such as HMG and/or KHG aldolase enzyme or a non-aldolase, such as non-pyruvate aldolase, e.g., non-HMG and/or non-KHG aldolase protein). In some embodiments, the invention provides aldolase, such as pyruvate aldolase, such as HMG and/or KHG aldolase enzymes in accordance with the invention with heterologous SPs and/or prepro sequences, such as sequences with a yeast signal sequence. An aldolase, such as pyruvate aldolase, HMG and/or KHG aldolase enzyme in accordance with the invention can comprise a heterologous SP and/or prepro in a vector, such as a pPIC series vector (Invitrogen, Carlsbad, Calif.).

In some embodiments, SPs and/or prepro sequences in accordance with the invention are identified following identification of novel aldolase, such as pyruvate aldolase, such as HMG and/or KHG aldolase polypeptides. The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. The signal sequences can vary in length from about 10 to 65, or more, amino acid residues. Various methods of recognition of signal sequences are known to those of skill in the art. For example, in some embodiments, novel aldolase, such as pyruvate aldolase, such as HMG and/or KHG aldolase enzyme signal peptides are identified by a method referred to as SignalP. SignalP uses a combined neural network which recognizes both signal peptides and their cleavage sites. (Nielsen (1997) "Identification of prokaryotic and eukaryotic signal peptides and prediction of their cleavage sites." Protein Engineering 10:1-6.

In some embodiments, aldolase, such as pyruvate aldolase, such as HMG and/or KHG aldolase enzymes in accordance with the invention do not have SPs and/or prepro sequences or "domains." In some embodiments, the invention provides the aldolase, such as pyruvate aldolase, such as HMG and/or KHG aldolase enzymes in accordance with the invention lacking all or part of an SP and/or a prepro domain. In some embodiments, the invention provides nucleic acid sequences encoding a signal sequence (SP) and/or prepro from one aldolase, such as pyruvate aldolase, such as HMG and/or KHG aldolase enzyme operably linked to a nucleic acid sequence of a different aldolase, such as pyruvate aldolase, such as HMG and/or KHG aldolase enzyme or, optionally, a signal sequence (SPs) and/or prepro domain from a non-aldolase, such as non-pyruvate aldolase, e.g, non-HMG and/or non-KHG aldolase protein may be desired.

The invention also provides isolated, synthetic or recombinant polypeptides comprising signal sequences (SPs), prepro domain and/or catalytic domains (CDs) in accordance with the invention and heterologous sequences. The heterologous sequences are sequences not naturally associated (such as to a enzyme) with an SP, prepro domain and/or CD. The sequence to which the SP, prepro domain and/or CD are not naturally associated can be on the SP's, prepro domain and/or CD's amino terminal end, carboxy terminal end, and/or on both ends of the SP and/or CD. In some embodiments, the invention provides isolated, synthetic or recombinant polypeptides comprising (or consisting of) a polypeptide comprising a signal sequence (SP), prepro domain and/or catalytic domain (CD) in accordance with the invention with the proviso that it is not associated with any sequence to which it is naturally associated (such as an aldolase, such as pyruvate aldolase, HMG and/or KHG aldolase enzyme sequence). Similarly, in some embodiments, the invention provides isolated, synthetic or recombinant nucleic acids encoding these polypeptides. Thus, in some embodiments, the isolated, synthetic or recombinant nucleic acid in accordance with the invention comprises coding sequence for a signal sequence (SP), prepro domain and/or catalytic domain (CD) in accordance with the invention and a heterologous sequence (i.e., a sequence not naturally associated with the a signal sequence (SP), prepro domain and/or catalytic domain (CD) in accordance with the invention). The heterologous sequence can be on the 3' terminal end, 5' terminal end, and/or on both ends of the SP, prepro domain and/or CD coding sequence.

Hybrid (Chimeric) Aldolase, such as Pyruvate Aldolase, such as HMG and/or KHG Aldolase Enzymes and Peptide Libraries In some embodiments, the invention provides hybrid aldolase, such as pyruvate aldolase, such as HMG and/or KHG aldolase enzymes and fusion proteins, including peptide libraries, comprising sequences in accordance with the invention. The peptide libraries in accordance with the invention can be used to isolate peptide modulators (such as activators or inhibitors) of targets, such as aldolase, such as pyruvate aldolase, such as HMG and/or KHG aldolase enzyme substrates, receptors, enzymes. The peptide libraries in accordance with the invention can be used to identify formal binding partners of targets, such as ligands, such as cytokines, hormones and the like. In some embodiments, the invention provides chimeric proteins comprising a signal sequence (SP), prepro domain and/or catalytic domain (CD) in accordance with the invention or a combination thereof and a heterologous sequence (see above).

In some embodiments, the fusion proteins in accordance with the invention (such as the peptide moiety) are conformationally stabilized (relative to linear peptides) to allow a higher binding affinity for targets. In some embodiments, the invention provides fusions of aldolase, such as pyruvate aldolase, such as HMG and/or KHG aldolase enzymes in accordance with the invention and other peptides, including known and random peptides. They can be fused in such a manner that the structure of the aldolase, such as pyruvate aldolase, such as HMG and/or KHG aldolase enzymes is not significantly perturbed and the peptide is metabolically or structurally conformationally stabilized. This allows the creation of a peptide library that is easily monitored both for its presence within cells and its quantity.

Amino acid sequence variants in accordance with the invention can be characterized by a predetermined nature of the variation, a feature that sets them apart from a naturally occurring form, such as an allelic or interspecies variation of an aldolase, such as pyruvate aldolase, HMG and/or KHG aldolase enzyme sequence. In some embodiments, the variants in accordance with the invention exhibit the same qualitative biological activity as the naturally occurring analogue. Alternatively, the variants can be selected for having modified characteristics. In some embodiments, while the site or region for introducing an amino acid sequence variation is predetermined, the mutation per se need not be predetermined. For example, in order to optimize the performance of a mutation at a given site, random mutagenesis may be conducted at the target codon or region and the expressed aldolase, such as pyruvate aldolase, such as HMG and/or KHG aldolase enzyme variants screened for the optimal combination of desired activity. Techniques for making substitution mutations at predetermined sites in DNA having a known sequence are well known, as discussed herein for example, M13 primer mutagenesis and PCR mutagenesis. Screening of the mutants can be done using, such as assays of carbon-carbon bond formation or cleavage. In other embodiments, amino acid substitutions can be single residues; insertions can be on the order of from about 1 to 20 amino acids, although considerably larger insertions can be done. Deletions can range from about 1 to about 20, 30, 40, 50, 60, 70 residues or more. To obtain a final derivative with the optimal properties, substitutions, deletions, insertions or any combination thereof may be used. Generally, these changes are done on a few amino acids to minimize the alteration of the molecule. However, larger changes may be tolerated in certain circumstances.

The invention provides aldolase, such as pyruvate aldolase, such as HMG and/or KHG aldolase enzymes where the structure of the polypeptide backbone, the secondary or the tertiary structure, such as an alpha-helical or beta-sheet structure, has been modified. In some embodiments, the charge or hydrophobicity has been modified. In some embodiments, the bulk of a side chain has been modified. Substantial changes in function or immunological identity are made by selecting substitutions that are less conservative. For example, substitutions can be made which more significantly affect: the structure of the polypeptide backbone in the area of the alteration, for example a alpha-helical or a beta-sheet structure; a charge or a hydrophobic site of the molecule, which can be at an active site; or a side chain. In some embodiments, the invention provides substitutions in polypeptide in accordance with the invention where (a) a hydrophilic residues, such as seryl or threonyl, is substituted for (or by) a hydrophobic residue, such as leucyl, isoleucyl, phenylalanyl, valyl or alanyl; (b) a cysteine or proline is substituted for (or by) any other residue; (c) a residue having an electropositive side chain, such as lysyl, arginyl, or histidyl, is substituted for (or by) an electronegative residue, such as glutamyl or aspartyl; or (d) a residue having a bulky side chain, such as phenylalanine, is substituted for (or by) one not having a side chain, such as glycine. The variants can exhibit the same qualitative biological activity (i.e., an aldolase, such as pyruvate aldolase, such as HMG and/or KHG aldolase enzyme, activity) although variants can be selected to modify the characteristics of the aldolase, such as pyruvate aldolase, such as HMG and/or KHG aldolase enzymes as needed.

In some embodiments, aldolase, such as pyruvate aldolase, such as HMG and/or KHG aldolase enzymes in accordance with the invention comprise epitopes or purification tags, signal sequences or other fusion sequences, etc. In some embodiments, the aldolase, such as pyruvate aldolase, such as HMG and/or KHG aldolase enzymes in accordance with the invention can be fused to a random peptide to form a fusion polypeptide. By "fused" or "operably linked" herein is meant that the random peptide and the aldolase, such as pyruvate aldolase, such as HMG and/or KHG aldolase enzyme are linked together, in such a manner as to minimize the disruption to the stability of the aldolase, such as pyruvate aldolase, such as HMG and/or KHG aldolase enzyme structure, such as it retains aldolase, such as pyruvate aldolase, such as HMG and/or KHG aldolase enzyme, activity. The fusion polypeptide (or fusion polynucleotide encoding the fusion polypeptide) can comprise further components as well, including multiple peptides at multiple loops.

In some embodiments, the peptides and nucleic acids encoding them are randomized, either fully randomized or they are biased in their randomization, such as in nucleotide/residue frequency generally or per position. "Randomized" means that each nucleic acid and peptide consists of essentially random nucleotides and amino acids, respectively. In some embodiments, the nucleic acids which give rise to the peptides can be chemically synthesized, and thus may incorporate any nucleotide at any position. Thus, when the nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized nucleic acids. The library can provide a sufficiently structurally diverse population of randomized expression products to affect a probabilistically sufficient range of cellular responses to provide one or more cells exhibiting a desired response. Thus, the invention provides interaction libraries large enough so that at least one of its members will have a structure that gives it affinity for some molecule, protein, or other factor.

In some embodiments, an aldolase, such as pyruvate aldolase, HMG and/or KHG aldolase enzyme in accordance with the invention is a multidomain enzyme that comprises a signal peptide, a carbohydrate binding module, an aldolase, such as pyruvate aldolase, HMG and/or KHG aldolase enzyme catalytic domain, a linker and/or another catalytic domain.

The invention provides methods and sequences for generating chimeric polypeptides which may encode biologically active hybrid polypeptides (such as hybrid aldolase, such as pyruvate aldolase, such as HMG and/or KHG aldolase enzymes). In some embodiments, the original polynucleotides (such as a nucleic acid in accordance with the invention) encode biologically active polypeptides. In some embodiments, a method in accordance with the invention produces new hybrid polypeptides by utilizing cellular processes which integrate the sequence of the original polynucleotides such that the resulting hybrid polynucleotide encodes a polypeptide demonstrating activities derived, but different, from the original biologically active polypeptides (such as aldolase or antibody in accordance with the invention). For example, the original polynucleotides may encode a particular enzyme (such as aldolase) from or found in different microorganisms. An enzyme encoded by a first polynucleotide from one organism or variant may, for example, function effectively under a particular environmental condition, such as high salinity. An enzyme encoded by a second polynucleotide from a different organism or variant may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide in accordance with the invention may function effectively under environmental conditions shared by each of the enzymes encoded by the first and second polynucleotides, such as high salinity and extreme temperatures.

In some embodiments, a hybrid polypeptide generated by a method in accordance with the invention may exhibit specialized enzyme activity not displayed in the original enzymes. For example, following recombination and/or reductive reassortment of polynucleotides encoding aldolase, such as pyruvate aldolase, such as HMG and/or KHG aldolase enzymes, the resulting hybrid polypeptide encoded by a hybrid polynucleotide can be screened for specialized non-aldolase, such as non-pyruvate aldolase, such as non-HMG and/or non-KHG-aldolase enzyme activities, such as hydrolase, peptidase, phosphorylase, etc., activities, obtained from each of the original enzymes. In some embodiments, the hybrid polypeptide is screened to ascertain those chemical functionalities which distinguish the hybrid polypeptide from the original parent polypeptides, such as the temperature, pH or salt concentration at which the hybrid polypeptide functions.

In some embodiments, the invention relates to a method for producing a biologically active hybrid polypeptide and screening such a polypeptide for enhanced activity by:
1) introducing at least a first polynucleotide in operable linkage and a second polynucleotide in operable linkage, the at least first polynucleotide and second polynucleotide sharing at least one region of partial sequence homology, into a suitable host cell;

2) growing the host cell under conditions which promote sequence reorganization resulting in a hybrid polynucleotide in operable linkage;
3) expressing a hybrid polypeptide encoded by the hybrid polynucleotide;
4) screening the hybrid polypeptide under conditions which promote identification of enhanced biological activity; and
5) isolating the a polynucleotide encoding the hybrid polypeptide.

Isolating and Discovering Aldolase Enzymes

The invention provides methods for isolating and discovering aldolase, such as pyruvate aldolase, HMG and/or KHG aldolase enzymes and the nucleic acids that encode them. Polynucleotides or enzymes may be isolated from individual organisms ("isolates"), collections of organisms that have been grown in defined media ("enrichment cultures"), or, uncultivated organisms ("environmental samples"). The organisms can be isolated by, such as in vivo biopanning (see discussion, below). The use of a culture-independent approach to derive polynucleotides encoding novel bioactivities from environmental samples is most preferable because it allows one to access untapped resources of biodiversity. Polynucleotides or enzymes also can be isolated from any one of numerous organisms, such as bacteria. In addition to whole cells, polynucleotides or enzymes also can be isolated from crude enzyme preparations derived from cultures of these organisms, such as bacteria.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

In some embodiments, gene libraries generated from one or more uncultivated microorganisms are screened for an activity of interest. Potential pathways encoding bioactive molecules of interest are first captured in prokaryotic cells in the form of gene expression libraries. In some embodiments, polynucleotides encoding activities of interest are isolated from such libraries and introduced into a host cell. The host cell is grown under conditions which promote recombination and/or reductive reassortment creating potentially active biomolecules with novel or enhanced activities.

In vivo biopanning may be performed utilizing a FACS-based and non-optical (such as magnetic) based machines. In some embodiments, complex gene libraries are constructed with vectors which contain elements which stabilize transcribed RNA. For example, the inclusion of sequences which result in secondary structures such as hairpins which are designed to flank the transcribed regions of the RNA would serve to enhance their stability, thus increasing their half life within the cell. The probe molecules used in the biopanning process consist of oligonucleotides labeled with reporter molecules that only fluoresce upon binding of the probe to a target molecule. These probes are introduced into the recombinant cells from the library using one of several transformation methods. The probe molecules bind to the transcribed target mRNA resulting in DNA/RNA heteroduplex molecules. Binding of the probe to a target will yield a fluorescent signal which is detected and sorted by the FACS machine during the screening process.

In some embodiments, subcloning is performed to further isolate sequences of interest. In subcloning, a portion of DNA is amplified, digested, generally by restriction enzymes, to cut out the desired sequence, the desired sequence is ligated into a recipient vector and is amplified. At each step in subcloning, the portion is examined for the activity of interest, in order to ensure that DNA that encodes the structural protein has not been excluded. The insert may be purified at any step of the subcloning, for example, by gel electrophoresis prior to ligation into a vector or where cells containing the recipient vector and cells not containing the recipient vector are placed on selective media containing, for example, an antibiotic, which will kill the cells not containing the recipient vector. Specific methods of subcloning cDNA inserts into vectors are well-known in the art (Sambrook et al., Molecular Cloning: A Laboratory Manual, 2nd Ed., Cold Spring Harbor Laboratory Press (1989)). In other embodiments, the enzymes in accordance with the invention are subclones. Such subclones may differ from the parent clone by, for example, length, a mutation, a tag or a label.

The microorganisms from which the polynucleotide may be discovered, isolated or prepared include prokaryotic microorganisms, such as *Eubacteria* and *Archaebacteria* and lower eukaryotic microorganisms such as fungi, some algae and protozoa. Polynucleotides may be discovered, isolated or prepared from environmental samples in which case the nucleic acid may be recovered without culturing of an organism or recovered from one or more cultured organisms. In some embodiments, such microorganisms may be extremophiles, such as hyperthermophiles, psychrophiles, psychrotrophs, halophiles, barophiles and acidophiles. Polynucleotides encoding enzymes isolated from extremophilic microorganisms can be used. Enzymes of this invention can function at temperatures above 100° C., such as those found in terrestrial hot springs and deep sea thermal vents, or at temperatures below 0° C., such as those found in arctic waters, in a saturated salt environment, such as those found in the Dead Sea, at pH values around 0, such as those found in coal deposits and geothermal sulfur-rich springs, or at pH values greater than 11, such as those found in sewage sludge. In some embodiments, enzymes in accordance with the invention have high activity throughout a wide range of temperatures and pHs.

Polynucleotides selected and isolated as hereinabove described are introduced into a suitable host cell. A suitable host cell is any cell which is capable of promoting recombination and/or reductive reassortment. The selected polynucleotides are, in some embodiments, already in a vector which includes appropriate control sequences. The host cell can be a higher eukaryotic cell, such as a mammalian cell, or a lower eukaryotic cell, such as a yeast cell, or, in some embodiments, the host cell can be a prokaryotic cell, such as a bacterial cell. Introduction of the construct into the host cell can be effected by calcium phosphate transfection, DEAE-Dextran mediated transfection, or electroporation.

Exemplary hosts include bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; and plant cells; see discussion, above. The selection of an appropriate host is deemed to be within the scope of those skilled in the art from the teachings herein.

Various mammalian cell culture systems can be employed to express recombinant protein; examples of mammalian expression systems include the COS-7 lines of monkey kidney fibroblasts, described in "SV40-transformed simian cells support the replication of early SV40 mutants" (Gluzman, 1981) and other cell lines capable of expressing a compatible vector, for example, the C127, 3T3, CHO, HeLa and BHK cell lines. Mammalian expression vectors can comprise an origin of replication, a suitable promoter and enhancer and also any necessary ribosome binding sites, polyadenylation site, splice donor and acceptor sites, transcriptional termination sequences and 5' flanking nontranscribed sequences. DNA sequences derived from the SV40 splice and polyadenylation sites may be used to provide the required nontranscribed genetic elements.

In other embodiments, nucleic acids, polypeptides and methods in accordance with the invention are used in biochemical pathways, or to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function (an example of a biochemical pathway encoded by gene clusters are polyketides).

In some embodiments, gene cluster DNA is isolated from different organisms and ligated into vectors, such as vectors containing expression regulatory sequences which can control and regulate the production of a detectable protein or protein-related array activity from the ligated gene clusters. Use of vectors which have an exceptionally large capacity for exogenous DNA introduction can be appropriate for use with such gene clusters and are described by way of example herein to include the f-factor (or fertility factor) of *E. coli*. This f-factor of *E. coli* is a plasmid which affects high-frequency transfer of itself during conjugation and is ideal to achieve and stably propagate large DNA fragments, such as gene clusters from mixed microbial samples. In one embodiment, cloning vectors, referred to as "fosmids" or bacterial artificial chromosome (BAC) vectors are used. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library." Another type of vector for use in the present invention is a cosmid vector. Cosmid vectors were originally designed to clone and propagate large segments of genomic DNA. Cloning into cosmid vectors is described in detail in Sambrook et al., Molecular Cloning: A Laboratory Manual, 2nd Ed., Cold Spring Harbor Laboratory Press (1989). Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Methods for screening for various enzyme activities are known to those of skill in the art and are discussed throughout the present specification, see Examples 1, 2 and 3, below. Such methods may be employed when isolating the polypeptides and polynucleotides in accordance with the invention.

In some embodiments, the invention provides methods for discovering and isolating aldolases, such as pyruvate aldolase, such as HMG and/or KHG aldolase, or compounds to modify the activity of these enzymes, using a whole cell approach (see discussion, below). Putative clones encoding aldolase, such as pyruvate aldolase, such as HMG and/or KHG aldolase from genomic DNA library can be screened.

Screening Methodologies and "On-Line" Monitoring Devices

In practicing the methods in accordance with the invention, a variety of apparatus and methodologies can be used to in conjunction with the polypeptides and nucleic acids in accordance with the invention, such as to screen polypeptides for aldolase, such as pyruvate aldolase, such as HMG and/or KHG aldolase enzyme, activity, to screen compounds as potential modulators, such as activators or inhibitors, of an aldolase, such as pyruvate aldolase, such as HMG and/or KHG aldolase enzyme, activity, for antibodies that bind to a polypeptide in accordance with the invention, for nucleic acids that hybridize to a nucleic acid in accordance with the invention, to screen for cells expressing a polypeptide in accordance with the invention and the like. In addition to the array formats described in detail below for screening samples, alternative formats can also be used to practice the methods in accordance with the invention. Such formats include, for example, mass spectrometers, chromatographs, such as high-throughput HPLC and other forms of liquid chromatography, and smaller formats, such as 1536-well plates, 384-well plates and so on. High throughput screening apparatus can be adapted and used to practice the methods in accordance with the invention, see U.S. Patent Application Nos. 20020001809; 20050272044.

Capillary Arrays

Nucleic acids or polypeptides in accordance with the invention can be immobilized to or applied to an array. Arrays can be used to screen for or monitor libraries of compositions (such as small molecules, antibodies, nucleic acids, etc.) for their ability to bind to or modulate the activity of a nucleic acid or a polypeptide in accordance with the invention. Capillary arrays, such as the GIGAMATRIX™, Diversa Corporation, San Diego, Calif.; and arrays described in, such as U.S. Patent Application No. 20020080350 A1; WO 0231203 A; WO 0244336 A, provide an alternative apparatus for holding and screening samples. In some embodiments, the capillary array includes a plurality of capillaries formed into an array of adjacent capillaries, wherein each capillary comprises at least one wall defining a lumen for retaining a sample. The lumen may be cylindrical, square, hexagonal or any other geometric shape so long as the walls form a lumen for retention of a liquid or sample. The capillaries of the capillary array can be held together in close proximity to form a planar structure. The capillaries can be bound together, by being fused (Such as where the capillaries are made of glass), glued, bonded, or clamped side-by-side. Additionally, the capillary array can include interstitial material disposed between adjacent capillaries in the array, thereby forming a solid planar device containing a plurality of through-holes.

A capillary array can be formed of any number of individual capillaries, for example, a range from 100 to 4,000,000 capillaries. Further, a capillary array having about 100,000 or more individual capillaries can be formed into the standard size and shape of a Microtiter® plate for fitment into standard laboratory equipment. The lumens are filled manually or automatically using either capillary action or microinjection using a thin needle. Samples of interest may subsequently be removed from individual capillaries for further analysis or characterization. For example, a thin, needle-like probe is positioned in fluid communication with a selected capillary to either add or withdraw material from the lumen.

In a single-pot screening assay, the assay components are mixed yielding a solution of interest, prior to insertion into the capillary array. The lumen is filled by capillary action when at least a portion of the array is immersed into a solution of interest. Chemical or biological reactions and/or activity in each capillary are monitored for detectable events. A detectable event is often referred to as a "hit", which can usually be distinguished from "non-hit" producing capillaries by optical detection. Thus, capillary arrays allow for massively parallel detection of "hits".

In a multi-pot screening assay, a polypeptide or nucleic acid, such as a ligand, can be introduced into a first component, which is introduced into at least a portion of a capillary of a capillary array. An air bubble can then be introduced into the capillary behind the first component. A second component can then be introduced into the capillary, wherein the second component is separated from the first component by the air bubble. The first and second components can then be mixed by applying hydrostatic pressure to both sides of the capillary array to collapse the bubble. The capillary array is then monitored for a detectable event resulting from reaction or non-reaction of the two components.

In a binding screening assay, a sample of interest can be introduced as a first liquid labeled with a detectable particle into a capillary of a capillary array, wherein the lumen of the capillary is coated with a binding material for binding the detectable particle to the lumen. The first liquid may then be removed from the capillary tube, wherein the bound detectable particle is maintained within the capillary, and a second liquid may be introduced into the capillary tube. The capillary is then monitored for a detectable event resulting from reaction or non-reaction of the particle with the second liquid.

Arrays, or "Biochips"

Nucleic acids or polypeptides in accordance with the invention can be immobilized to or applied to an array. Arrays can be used to screen for or monitor libraries of compositions (such as small molecules, antibodies, nucleic acids, etc.) for their ability to bind to or modulate the activity of a nucleic acid or a polypeptide in accordance with the invention. For example, in some embodiments of the invention, a monitored parameter is transcript expression of an aldolase, such as pyruvate aldolase, HMG and/or KHG aldolase enzyme gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods in accordance with the invention. Polypeptide arrays" can also be used to simultaneously quantify a plurality of proteins. The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, such as oligonucleotides, immobilized onto a defined area of a substrate surface for specific binding to a sample molecule, such as mRNA transcripts.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface, as discussed in further detail, below.

In practicing the methods in accordance with the invention, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, such as WO 99/51773; WO 99/09217; WO 97/46313; WO 96/17958; see also, such as Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765.

Antibodies and Antibody-Based Screening Methods

The invention provides isolated, synthetic or recombinant antibodies that specifically bind to an aldolase, such as pyruvate aldolase, HMG and/or KHG aldolase enzyme in accordance with the invention. These antibodies can be used to isolate, identify or quantify the aldolase, such as pyruvate aldolase, such as HMG and/or KHG aldolase enzymes in accordance with the invention or related polypeptides. These antibodies can be used to isolate other polypeptides within the scope the invention or other related aldolase, such as pyruvate aldolase, such as HMG and/or KHG aldolase enzymes. The antibodies can be designed to bind to an active site of an aldolase, such as pyruvate aldolase, HMG and/or KHG aldolase enzyme. Thus, the invention provides methods of inhibiting aldolase, such as pyruvate aldolase, such as HMG and/or KHG aldolase enzymes using the antibodies in accordance with the invention (see discussion above regarding applications for anti-aldolase, such as anti-pyruvate aldolase, such as anti-HMG and/or anti-KHG aldolase enzyme compositions in accordance with the invention).

The term "antibody" includes a peptide or polypeptide derived from, modeled after or substantially encoded by an immunoglobulin gene or immunoglobulin genes, or fragments thereof, capable of specifically binding an antigen or epitope, see Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (such as fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The invention provides fragments of the enzymes in accordance with the invention (such as peptides) including immunogenic fragments (such as subsequences) of a polypeptide in accordance with the invention. In some embodiments, the invention provides compositions comprising a polypeptide or peptide in accordance with the invention and adjuvants or carriers and the like.

The antibodies can be used in immunoprecipitation, staining, immunoaffinity columns, and the like. If desired, nucleic acid sequences encoding for specific antigens can be generated by immunization followed by isolation of polypeptide or nucleic acid, amplification or cloning and immobilization of polypeptide onto an array in accordance with the invention. Alternatively, the methods in accordance with the invention can be used to modify the structure of an antibody produced by a cell to be modified, such as an antibody's affinity can be increased or decreased. Furthermore, the ability to make or modify antibodies can be a phenotype engineered into a cell by the methods in accordance with the invention.

Methods of immunization, producing and isolating antibodies (polyclonal and monoclonal) are known to those of skill in the art and described in the scientific and patent literature, see Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, such as using recombinant antibody binding site expressing phage display libraries, in addition to the traditional in vivo methods using animals. See, Hoogenboom (1997) Trends Biotechnol. 15:62-70; Katz (1997) Annu. Rev. Biophys. Biomol. Struct. 26:27-45.

The polypeptides in accordance with the invention or fragments comprising at least 5, 10, 15, 20, 25, 30, 35, 40, 50, 75, 100, or 150 consecutive amino acids thereof, may also be used to generate antibodies which bind specifically to the polypeptides or fragments. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides in accordance with the invention, or fragments comprising at least 5, 10, 15, 20, 25, 30, 35, 40, 50, 75, 100, or 150 consecutive amino acids thereof.

In immunoaffinity procedures, the antibody is attached to a solid support, such as a bead or other column matrix. The protein preparation is placed in contact with the antibody under conditions in which the antibody specifically binds to one of the polypeptides in accordance with the invention, or fragment thereof. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays and Western Blots.

Polyclonal antibodies generated against the polypeptides in accordance with the invention, or fragments comprising at least 5, 10, 15, 20, 25, 30, 35, 40, 50, 75, 100, or 150 consecutive amino acids thereof can be obtained by direct injection of the polypeptides into an animal or by administering the polypeptides to an animal, for example, a nonhuman. The antibody so obtained can bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique (Kohler and Milstein, Nature, 256:495-497, 1975), the trioma technique, the human B-cell hybridoma technique (Kozbor et al., Immunology Today 4:72, 1983) and the EBV-hybridoma technique (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to the polypeptides in accordance with the invention, or fragments comprising at least 5, 10, 15, 20, 25, 30, 35, 40, 50, 75, 100, or 150 consecutive amino acids thereof. Alternatively, transgenic mice may be used to express humanized antibodies to these polypeptides or fragments thereof.

Antibodies generated against the polypeptides in accordance with the invention, or fragments comprising at least 5, 10, 15, 20, 25, 30, 35, 40, 50, 75, 100, or 150 consecutive amino acids thereof may be used in screening for similar polypeptides from other organisms and samples. In such techniques, polypeptides from the organism are contacted with the antibody and those polypeptides which specifically bind the antibody are detected. Any of the procedures described above may be used to detect antibody binding. One such screening assay is described in Shulman H, Eberhard A, Eberhard C, Ulitzur S, Keinan E, Bioorg Med Chem. Lett. 2000 Oct. 16; 10(20):2353-6, Highly sensitive and rapid detection of antibody catalysis by luminescent bacteria.

Kits

The invention provides kits comprising the compositions, such as nucleic acids, expression cassettes, vectors, cells, transgenic seeds or plants or plant parts, polypeptides (such as an aldolase enzyme) and/or antibodies in accordance with the invention. The kits also can contain instructional material teaching the methodologies and industrial, medical and dietary uses in accordance with the invention, as described herein.

Whole Cell Engineering and Measuring Metabolic Parameters

The methods in accordance with the invention provide whole cell evolution, or whole cell engineering, of a cell to develop a new cell strain having a new phenotype, such as a new or modified aldolase, such as pyruvate aldolase, such as HMG and/or KHG aldolase enzyme, activity, by modifying the genetic composition of the cell. See U.S. patent application no. 20040033975.

The genetic composition can be modified by addition to the cell of a nucleic acid in accordance with the invention, such as a coding sequence for an enzyme in accordance with the invention. See WO0229032; WO0196551.

To detect the new phenotype, at least one metabolic parameter of a modified cell is monitored in the cell in a "real time" or "on-line" time frame. In some embodiments, a plurality of cells, such as a cell culture, is monitored in "real time" or "on-line." In some embodiments, a plurality of metabolic parameters is monitored in "real time" or "on-line." Metabolic parameters can be monitored using the aldolase, such as pyruvate aldolase, such as HMG and/or KHG aldolase enzymes in accordance with the invention.

Metabolic flux analysis (MFA) is based on a known biochemistry framework. A linearly independent metabolic matrix is constructed based on the law of mass conservation and on the pseudo-steady state hypothesis (PSSH) on the intracellular metabolites. In practicing the methods in accordance with the invention, metabolic networks are established, including the:

- identity of all pathway substrates, products and intermediary metabolites
- identity of all the chemical reactions interconverting the pathway metabolites, the stoichiometry of the pathway reactions,
- identity of all the enzymes catalyzing the reactions, the enzyme reaction kinetics,
- the regulatory interactions between pathway components, such as allosteric interactions, enzyme-enzyme interactions etc,
- intracellular compartmentalization of enzymes or any other supramolecular organization of the enzymes, and,
- the presence of any concentration gradients of metabolites, enzymes or effector molecules or diffusion barriers to their movement.

Once the metabolic network for a given strain is built, mathematic presentation by matrix notion can be introduced to estimate the intracellular metabolic fluxes if the on-line metabolome data is available. Metabolic phenotype relies on the changes of the whole metabolic network within a cell. Metabolic phenotype relies on the change of pathway utilization with respect to environmental conditions, genetic regulation, developmental state and the genotype, etc. In some embodiments of the methods in accordance with the invention, after the on-line MFA calculation, the dynamic behavior of the cells, their phenotype and other properties are analyzed by investigating the pathway utilization. For example, if the glucose supply is increased and the oxygen decreased during the yeast fermentation, the utilization of respiratory pathways will be reduced and/or stopped, and the utilization of the fermentative pathways will dominate. Control of physiological state of cell cultures will become possible after the pathway analysis. The methods in accordance with the invention can help determine how to manipulate the fermentation by determining how to change the substrate supply, temperature, use of inducers, etc. to control the physiological state of cells to move along desirable direction. In practicing the methods in accordance with the invention, the MFA results can also be compared with transcriptome and proteome data to design experiments and protocols for metabolic engineering or gene shuffling, etc.

In practicing the methods in accordance with the invention, any modified or new phenotype can be conferred and detected, including new or improved characteristics in the cell. Any aspect of metabolism or growth can be monitored.

Monitoring Expression of an mRNA Transcript

In some embodiments of the invention, the engineered phenotype comprises increasing or decreasing the expression of an mRNA transcript (such as an aldolase, such as pyruvate aldolase, HMG and/or KHG aldolase enzyme message) or generating new (such as aldolase, such as pyruvate aldolase, such as HMG and/or KHG aldolase enzyme) transcripts in a cell. This increased or decreased expression can be traced by testing for the presence of an aldolase, such as pyruvate aldolase, HMG and/or KHG aldolase enzyme in accordance with the invention or by aldolase, such as pyruvate aldolase, such as HMG and/or KHG aldolase enzyme activity assays. mRNA transcripts, or messages, also can be detected and quantified by any method known in the art, including, such as Northern blots, quantitative amplification reactions, hybridization to arrays, and the like. Quantitative amplification reactions include, such as quantitative PCR, including, such as quantitative reverse transcription polymerase chain reaction, or RT-PCR; quantitative real time RT-PCR, or "real-time kinetic RT-PCR" (see Kreuzer (2001) Br. J. Haematol. 114: 313-318; Xia (2001) Transplantation 72:907-914).

In some embodiments of the invention, the engineered phenotype is generated by knocking out expression of a homologous gene. The gene's coding sequence or one or more transcriptional control elements can be knocked out, such as promoters or enhancers. Thus, the expression of a transcript can be completely ablated or only decreased.

In some embodiments of the invention, the engineered phenotype comprises increasing the expression of a homologous gene. This can be effected by knocking out of a negative control element, including a transcriptional regulatory element acting in cis- or trans-, or, mutagenizing a positive control element. One or more, or, all the transcripts of a cell can be measured by hybridization of a sample comprising transcripts of the cell, or, nucleic acids representative of or complementary to transcripts of a cell, by hybridization to immobilized nucleic acids on an array.

Monitoring Expression of a Polypeptides, Peptides and Amino Acids

In some embodiments of the invention, the engineered phenotype comprises increasing or decreasing the expression of a polypeptide (such as an aldolase, such as pyruvate aldolase, HMG and/or KHG aldolase enzyme) or generating new polypeptides in a cell. This increased or decreased expression can be traced by determining the amount of aldolase, such as pyruvate aldolase, such as HMG and/or KHG aldolase enzyme present or by aldolase, such as pyruvate aldolase, such as HMG and/or KHG aldolase enzyme activity assays. Polypeptides, peptides and amino acids also can be detected and quantified by any method known in the art, including, such as nuclear magnetic resonance (NMR), spectrophotometry, radiography (protein radiolabeling), electrophoresis, capillary electrophoresis, high performance liquid chromatography (HPLC), thin layer chromatography (TLC), hyperdiffusion chromatography, various immunological methods, such as immunoprecipitation, immunodiffusion, immunoelectrophoresis, radioimmunoassays (RIAs), enzyme-linked immunosorbent assays (ELISAs), immuno-fluorescent assays, gel electrophoresis (such as SDS-PAGE), staining with antibodies, fluorescent activated cell sorter (FACS), pyrolysis mass spectrometry, Fourier-Transform Infrared Spectrometry, Raman spectrometry, GC-MS, and LC-Electrospray and cap-LC-tandem-electrospray mass spectrometries, and the like. Novel bioactivities can also be screened using methods, or variations thereof, described in U.S. Pat. No. 6,057,103. Furthermore, as discussed below in detail, one or more, or, all the polypeptides of a cell can be measured using a protein array.

Industrial, Pharmaceutical and other Applications

Polypeptides in accordance with the invention (such as having aldolase, such as pyruvate aldolase, such as HMG and/or KHG aldolase) can catalyze the formation or cleavage of carbon-carbon bonds. The enzymes in accordance with the invention can be highly selective catalysts. In some embodiments, the invention provides industrial processes using enzymes in accordance with the invention, such as in the pharmaceutical or nutrient (diet) supplement industry, in the food and feed industries, such as in methods for making food and feed products and food and feed additives. In some embodiments, the invention provides processes using enzymes in accordance with the invention in the medical industry, such as to make pharmaceuticals or dietary aids or supplements, or food supplements and additives.

Biomass Conversion and Production of Clean Bio Fuels

The invention provides enzymes, such aldolases, including pyruvate aldolases such as, without limitation, HMG and/or KHG aldolases (including mixtures, or "cocktails" of enzymes) and methods for the conversion of a biomass or any lignocellulosic material (e.g., any composition comprising cellulose, hemicellulose and lignin), to fuels (e.g., bioethanol, biobutanol, biopropanol, biomethanol, biodiesel), using the enzymes of the invention, in addition to feeds, foods and chemicals. Thus, the compositions and methods of the invention provide effective and sustainable alternatives or adjuncts to use of petroleum-based products, e.g., as a mixture of bioethanol and gasoline. The invention provides organisms expressing enzymes of the invention for participation in chemical cycles involving natural biomass conversion. In one embodiment, enzymes and methods for the conversion are used in enzyme ensembles for the efficient depolymerization of cellulosic and hemicellulosic polymers to metabolizeable carbon moieties. The invention provides methods for discovering and implementing the most effective of enzymes to enable these important new "biomass conversion" and alternative energy industrial processes.

The methods of the invention also include taking the converted lignocellulosic material (processed by enzymes of the invention) and making it into a fuel (e.g. bioethanol, biobutanol, biopropanol, biomethanol, biodiesel) by fermentation and/or by chemical synthesis. In one embodiment, the produced sugars are fermented and/or the non-fermentable products are gasified.

The enzymes of the invention (including, for example, organisms, such as microorganisms, e.g., fungi, yeast or bacteria, making and in some embodiments secreting recombinant enzymes of the invention) can be used in or included/integrated at any stage of any biomass conversion process, e.g., at any one step, several steps, or included in all of the steps, or all of the following methods of biomass conversion processes, or all of these biofuel alternatives:

Direct combustion: the burning of material by direct heat and is the simplest biomass technology; can be very economical if a biomass source is nearby.

Pyrolysis: is the thermal degradation of biomass by heat in the absence of oxygen. In one embodiment, biomass is heated to a temperature between about 800 and 1400 degrees Fahrenheit, but no oxygen is introduced to support combustion resulting in the creation of gas, fuel oil and charcoal.

Gasification: biomass can be used to produce methane through heating or anaerobic digestion. Syngas, a mixture of carbon monoxide and hydrogen, can be derived from biomass.

Landfill Gas: is generated by the decay (anaerobic digestion) of buried garbage in landfills. When the organic waste decomposes, it generates gas consisting of approximately 50% methane, the major component of natural gas.

Anaerobic digestion: converts organic matter to a mixture of methane, the major component of natural gas, and carbon dioxide. In one embodiment, biomass such as waterwaste (sewage), manure, or food processing waste, is mixed with water and fed into a digester tank without air.

Fermentation

Alcohol Fermentation: fuel alcohol is produced by converting starch to sugar, fermenting the sugar to alcohol, then separating the alcohol water mixture by distillation. Feedstocks such as wheat, barley, potatoes, and waste paper, sawdust, and straw containing sugar, starch, or cellulose can be converted to alcohol by fermentation with yeast.

Transesterification: An exemplary reaction for converting oil to biodiesel is called transesterification. The transesterification process reacts an alcohol (like methanol) with the triglyceride oils contained in vegetable oils, animal fats, or recycled greases, forming fatty acid alkyl esters (biodiesel) and glycerin. The reaction requires heat and a strong base catalyst, such as sodium hydroxide or potassium hydroxide.

Biodiesel: Biodiesel is a mixture of fatty acid alkyl esters made from vegetable oils, animal fats or recycled greases. Biodiesel can be used as a fuel for vehicles in its pure form, but it is usually used as a petroleum diesel additive to reduce levels of particulates, carbon monoxide, hydrocarbons and air toxics from diesel-powered vehicles.

Hydrolysis: includes hydrolysis of a compound, e.g., a biomass, such as a lignocellulosic material, catalyzed using an enzyme of the instant invention.

Congeneration: is the simultaneous production of more than one form of energy using a single fuel and facility. In one embodiment, biomass cogeneration has more potential growth than biomass generation alone because cogeneration produces both heat and electricity.

In one embodiment, the polypeptides of the invention have an aldolase activity, including pyruvate aldolase activity, such as, without limitation, HMG and/or KHG aldolase activity, or other enzymatic activity for generating biodiesel, bioethanol, biobutanol, biopropanol, or biomethanol, from an organic material, e.g., a biomass, such as compositions derived from plants and animals, including any agricultural crop or other renewable feedstock, an agricultural residue or an animal waste, or the organic components of municipal and industrial wastes, or microorganisms such as algae or yeast. In one embodiment, polypeptides of the invention are used in processes for converting lignocellulosic biomass to ethanol, butanol, propanol, methanol or otherwise are used in processes for hydrolyzing or digesting biomaterials such that they can be used as a biofuel (including bioethanol, biobutanol, biopropanol, biomethanol, or biodiesel), or for making it easier for the biomass to be processed into a fuel. In an alternative embodiment, polypeptides of the invention are used in processes for a transesterification process reacting an alcohol (like methanol) with a triglyceride oil contained in a vegetable oil, animal fat or recycled greases, forming fatty acid alkyl esters (biodiesel) and glycerin. In one embodiment, biodiesel is made from soybean oil or recycled cooking oils. Animal's fats, other vegetable oils, and other recycled oils can also be used to produce biodiesel, depending on their costs and availability. In another embodiment, blends of all kinds of fats and oils are used to produce a biodiesel fuel of the invention.

Enzymes of the invention can also be used in glycerin refining. The glycerin by-product contains unreacted catalyst and soaps that are neutralized with an acid. Water and alcohol are removed to produce 50% to 80% crude glycerin. The remaining contaminants include unreacted fats and oils, which can be processes using the polypeptides of the invention. In large biodiesel plants of the invention, the glycerin can be further purified, e.g., to 99% or higher purity, for the pharmaceutical and cosmetic industries.

Bioethanol, biobutanol, biopropanol, biomethanol, and/or biodiesel are made using the polypeptides of the invention can be used with fuel oxygenates to improve combustion characteristics. Adding oxygen results in more complete combustion, which reduces carbon monoxide emissions. This is another environmental benefit of replacing petroleum fuels with biofuels (e.g., a fuel of the invention). A bioethanol, biobutanol, biopropanol, biomethanol, and/or biodiesel made using the compositions and/or methods of this invention can be blended with gasoline to form an E10 blend (about 5% to 10% ethanol and about 90% to 95% gasoline), but it can be used in higher concentrations such as E85 or in its pure form. A bioethanol, biobutanol, biopropanol, biomethanol, and/or biodiesel made using the compositions and/or methods of this invention can be blended with petroleum diesel to form a B20 blend (20% biodiesel and 80% petroleum diesel), although other blend levels can be used up to B100 (pure biodiesel).

The invention also provides processes for making ethanol ("bioethanol"), butanol ("biobutanol"), propanol ("biopropanol"), methanol ("biomethanol"), and/or diesel ("biodiesel") from compositions comprising lignocellulosic biomass. The lignocellulose biomass material can be obtained from agricultural crops, as a byproduct of food or feed production, or as lignocellulosic waste products, such as plant residues and waste paper. Examples of suitable plant sources or plant residues for treatment with polypeptides of the invention include kelp, algae, grains, seeds, stems, leaves, hulls, husks, corn cobs, corn stover, straw, grasses (e.g., Indian grass, such as *Sorghastrum nutans*; or, switch grass, e.g., *Panicum* species, such as *Panicum virgatum*), and the like, as well as wood, wood chips, wood pulp, and sawdust. Examples of paper waste suitable for treatment with polypeptides of the invention include discard photocopy paper, computer printer paper, notebook paper, notepad paper, typewriter paper, and the like, as well as newspapers, magazines, cardboard, and paper-based packaging materials.

In one embodiment, the enzymes and methods of the invention can be used in conjunction with more "traditional" means of making ethanol, methanol, butanol, propanol and/or diesel from biomass, e.g., as methods comprising hydrolyzing lignocellulosic materials by subjecting dried lignocellulosic material in a reactor to a catalyst comprised of a dilute solution of a strong acid and a metal salt; this can lower the activation energy, or the temperature, of cellulose hydrolysis to obtain higher sugar yields; see, e.g., U.S. Pat. Nos. 6,660, 506; and 6,423,145.

Another embodiment that incorporates use of enzymes of the invention comprises hydrolyzing lignocellulosic material containing hemicellulose, cellulose and lignin by subjecting the material to a first stage hydrolysis step in an aqueous medium at a temperature and a pressure chosen to effect primarily depolymerization of hemicellulose without major depolymerization of cellulose to glucose. This step results in a slurry in which the liquid aqueous phase contains dissolved monosaccharides resulting from depolymerization of hemicellulose and a solid phase containing cellulose and lignin. A second stage hydrolysis step can comprise conditions such that at least a major portion of the cellulose is depolymerized, such step resulting in a liquid aqueous phase containing dissolved/soluble depolymerization products of cellulose. See, e.g., U.S. Pat. No. 5,536,325. Enzymes of the invention can be added at any stage of this exemplary process.

Another embodiment that incorporates use of enzymes of the invention comprises processing a lignocellulose-containing biomass material by one or more stages of dilute acid hydrolysis with about 0.4% to 2% strong acid; and treating an unreacted solid lignocellulosic component of the acid hydrolyzed biomass material by alkaline delignification to produce precursors for biodegradable thermoplastics and derivatives. See, e.g., U.S. Pat. No. 6,409,841. Enzymes of the invention can be added at any stage of this exemplary process.

Another embodiment that incorporates use of enzymes of the invention comprises prehydrolyzing lignocellulosic material in a prehydrolysis reactor; adding an acidic liquid to the solid lignocellulosic material to make a mixture; heating the mixture to reaction temperature; maintaining reaction temperature for time sufficient to fractionate the lignocellulosic material into a solubilized portion containing at least about 20% of the lignin from the lignocellulosic material and a solid fraction containing cellulose; removing a solubilized portion from the solid fraction while at or near reaction temperature wherein the cellulose in the solid fraction is rendered more amenable to enzymatic digestion; and recovering a solubilized portion. See, e.g., U.S. Pat. No. 5,705,369. Enzymes of the invention can be added at any stage of this exemplary process.

The invention provides methods for making motor fuel compositions (e.g., for spark ignition motors) based on liquid hydrocarbons blended with a fuel grade alcohol made by using an enzyme or a method of the invention. In one embodiment, the fuels made by use of an enzyme of the invention comprise, e.g., coal gas liquid- or natural gas liquid-ethanol, methanol, butanol, propanol and/or diesel blends. In one embodiment, a co-solvent is biomass-derived 2-methyltetrahydrofuran (MTHF). See, e.g., U.S. Pat. No. 6,712,866.

In one embodiment, methods of the invention for the enzymatic degradation of lignocellulose, e.g., for production of ethanol from lignocellulosic material, can also comprise use of ultrasonic treatment of the biomass material; see, e.g., U.S. Pat. No. 6,333,181.

In another embodiment, methods of the invention for producing bioethanol, biobutanol, biopropanol, biomethanol, and/or biodiesel from a cellulosic substrate comprise providing a reaction mixture in the form of a slurry comprising cellulosic substrate, an enzyme of this invention and a fermentation agent (e.g., within a reaction vessel, such as a semi-continuously solids-fed bioreactor), and the reaction mixture is reacted under conditions sufficient to initiate and maintain a fermentation reaction (as described, e.g., in U.S. Pat. App. No. 20060014260). In one embodiment, experiment or theoretical calculations can determine an optimum feeding frequency. In one embodiment, additional quantities of the cellulosic substrate and the enzyme are provided into the reaction vessel at an interval(s) according to the optimized feeding frequency.

One exemplary process for making biofuels (such as bioethanol, biobutanol, biopropanol, biomethanol, and/or biodiesel) of the invention is described in U.S. Pat. App. Pub. Nos. 20050069998; 20020164730; and in one embodiment comprises stages of grinding the lignocellulosic biomass (e.g., to a size of 15-30 mm), subjecting the product obtained to steam explosion pre-treatment (e.g., at a temperature of 190-230° C.) for between 1 and 10 minutes in a reactor; collecting the pre-treated material in a cyclone or related product of manufacture; and separating the liquid and solid fractions by filtration in a filter press, introducing the solid fraction in a fermentation deposit and adding one or more enzymes of the invention, e.g., a cellulase and/or beta-glucosidase enzyme (e.g., dissolved in citrate buffer pH 4.8).

Another exemplary process for making biofuels (such as bioethanol, biobutanol, biopropanol, biomethanol, and/or biodiesel) of the invention comprising using enzymes of the invention comprises pretreating a starting material comprising a lignocellulosic feedstock comprising at least hemicellulose and cellulose. In one embodiment, the starting material comprises potatoes, soybean (rapeseed), barley, rye, corn, oats, wheat, beets or sugar cane or a component or waste or food or feed production byproduct. The starting material ("feedstock") is reacted at conditions which disrupt the plant's fiber structure to effect at least a partial hydrolysis of the hemicellulose and cellulose. Disruptive conditions can comprise, e.g., subjecting the starting material to an average temperature of 180° C. to 270° C. at pH 0.5 to 2.5 for a period of about 5 seconds to 60 minutes; or, temperature of 220° C. to 270° C., at pH 0.5 to 2.5 for a period of 5 seconds to 120 seconds, or equivalent. This generates a feedstock with increased accessibility to being digested by an enzyme, e.g., a cellulase enzyme of the invention. U.S. Pat. No. 6,090,595.

Exemplary conditions for hydrolysis of lignocellulosic material include reactions at temperatures between about 30° C. and 48° C., and/or a pH between about 4.0 and 6.0. Other exemplary conditions include a temperature between about 30° C. and 60° C. and a pH between about 4.0 and 8.0.

The enzymes in accordance with the invention can catalyze reactions with exquisite stereo-, regio- and chemo-selectivities. The aldolase, such as pyruvate aldolase, such as HMG and/or KHG aldolase enzymes in accordance with the invention can be engineered to function in various solvents, operate at extreme pHs (for example, high pHs and low pHs) extreme temperatures (for example, high temperatures and low temperatures), extreme salinity levels (for example, high salinity and low salinity) and catalyze reactions with compounds that are structurally unrelated to their natural, physiological substrates.

Feeds and Food or Feed and Food Additives

In addition to providing dietary aids or supplements, or food supplements and additives, the invention also provides compositions and methods for treating human and animal feeds and foods and food or feed additives using a polypeptide in accordance with the invention, such as a protein having aldolase activity, such as pyruvate aldolase, such as HMG and/or KHG aldolase enzymes in accordance with the invention, and/or the antibodies in accordance with the invention. In some embodiments, the invention provides animal feeds, foods, and additives comprising aldolase, such as pyruvate aldolase, such as HMG and/or KHG aldolase enzymes in accordance with the invention and/or antibodies in accordance with the invention. The animal can be any farm animal or any animal.

The animal feed additive in accordance with the invention may be a granulated enzyme product that may readily be mixed with feed components. Alternatively, feed additives in accordance with the invention can form a component of a pre-mix. The granulated enzyme product in accordance with the invention may be coated or uncoated. The particle size of the enzyme granulates can be compatible with that of feed and pre-mix components. This provides a safe and convenient mean of incorporating enzymes into feeds. Alternatively, the animal feed additive in accordance with the invention may be a stabilized liquid composition. This may be an aqueous or oil-based slurry. See U.S. Pat. No. 6,245,546.

Aldolase, such as pyruvate aldolase, such as HMG and/or KHG aldolase enzymes of the present invention, in the modification of feed or a food, can process the food or feed either in vitro (by modifying components of the feed or food) or in vivo. Polypeptides in accordance with the invention can be added to feed or food compositions.

In some embodiments, an enzyme in accordance with the invention is added in combination with another enzyme, such as beta-galactosidases, catalases, laccases, cellulases, other aldolases, endoglycosidases, endo-beta-1,4-laccases, amyloglucosidases, glucosidases, glucose isomerases, glycosyltransferases, lipases, phospholipases, lipooxygenases, beta-laccases, endo-beta-1,3(4)-laccases, cutinases, peroxidases, amylases, phytases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, cellobiohydrolases and/or transglutaminases. These enzyme digestion products are more digestible by the animal. Thus, aldolase, such as pyruvate aldolase, such as HMG and/or KHG aldolase enzymes in accordance with the invention can contribute to the available energy of the feed or food, or to the digestibility of the food or feed by breaking down cellulose.

In other embodiments, aldolase, such as pyruvate aldolase, such as HMG and/or KHG aldolase enzyme in accordance with the invention can be supplied by expressing the enzymes directly in transgenic feed crops (as, such as transgenic plants, seeds and the like), such as grains, cereals, corn, soy bean, rape seed, lupin and the like. As discussed above, the invention provides transgenic plants, plant parts and plant cells comprising a nucleic acid sequence encoding a polypeptide in accordance with the invention. In some embodiments, the nucleic acid is expressed such that the aldolase, such as pyruvate aldolase, such as HMG and/or KHG aldolase enzyme in accordance with the invention is produced in recoverable quantities. The aldolase, such as pyruvate aldolase, such as HMG and/or KHG aldolase enzyme can be recovered from any plant or plant part. Alternatively, the plant or plant part containing the recombinant polypeptide can be used as such for improving the quality of a food or feed, such as improving nutritional value, palatability, etc.

In some embodiments, the enzyme delivery matrix in accordance with the invention is in the form of discrete plural particles, pellets or granules. By "granules" is meant particles that are compressed or compacted, such as by a pelletizing, extrusion, or similar compacting to remove water from the matrix. Such compression or compacting of the particles also promotes intraparticle cohesion of the particles. For example, the granules can be prepared by pelletizing the grain-based substrate in a pellet mill. The pellets prepared thereby are ground or crumbled to a granule size suitable for use as an adjuvant in animal feed. Because the matrix is itself approved for use in animal feed, it can be used as a diluent for delivery of enzymes in animal feed.

In some embodiments, the aldolase, such as pyruvate aldolase, such as HMG and/or KHG aldolase enzyme contained in the invention enzyme delivery matrix and methods is a thermostable aldolase, such as pyruvate aldolase, such as HMG and/or KHG aldolase enzyme, as described herein, so as to resist inactivation of the aldolase, such as pyruvate aldolase, such as HMG and/or KHG aldolase enzyme during manufacture where elevated temperatures and/or steam may be employed to prepare the palletized enzyme delivery matrix. During digestion of feed containing the invention enzyme delivery matrix, aqueous digestive fluids will cause release of the active enzyme. Other types of thermostable enzymes and nutritional supplements that are thermostable can also be incorporated in the delivery matrix for release under any type of aqueous conditions.

In some embodiments, a coating is applied to the enzyme matrix particles for many different purposes, such as to add a flavor or nutrition supplement to animal feed, to delay release of animal feed supplements and enzymes in gastric conditions, and the like. In some embodiments, the coating is applied to achieve a functional goal, for example, whenever it is desirable to slow release of the enzyme from the matrix particles or to control the conditions under which the enzyme will be released. The composition of the coating material can be such that it is selectively broken down by an agent to which it is susceptible (such as heat, acid or base, enzymes or other chemicals). Alternatively, two or more coatings susceptible to different such breakdown agents may be consecutively applied to the matrix particles.

The invention is also directed towards a process for preparing an enzyme-releasing matrix. In accordance with the invention, the process comprises providing discrete plural particles of a grain-based substrate in a particle size suitable for use as an enzyme-releasing matrix, wherein the particles comprise an aldolase, such as pyruvate aldolase, HMG and/or KHG aldolase enzyme encoded by an amino acid sequence in accordance with the invention. In some embodiments, the process includes compacting or compressing the particles of enzyme-releasing matrix into granules, which most In some embodiments is accomplished by pelletizing. The mold inhibitor and cohesiveness agent, when used, can be added at any suitable time, and, in some embodiments are mixed with the grain-based substrate in the desired proportions prior to pelletizing of the grain-based substrate. Moisture content in the pellet mill feed in some embodiments is in the ranges set forth above with respect to the moisture content in the finished product, and, in some embodiments, is about 14-15%. In some embodiments, moisture is added to the feedstock in the form of an aqueous preparation of the enzyme to bring the feedstock to this moisture content. The temperature in the pellet mill in some embodiments is brought to about 82° C. with steam. The pellet mill may be operated under any conditions that impart sufficient work to the feedstock to provide pellets. The pelleting process itself is a cost-effective process for removing water from the enzyme-containing composition.

The compositions and methods in accordance with the invention can be practiced in conjunction with administration of prebiotics, which are high molecular weight sugars, such as fructo-oligosaccharides (FOS); galacto-oligosaccharides (GOS), GRAS (Generally Recognized As Safe) material. These prebiotics can be metabolized by some probiotic lactic acid bacteria (LAB). They are non-digestible by the majority of intestinal microbes.

Treating Foods and Food Processing

The invention provides foods and feeds comprising enzymes in accordance with the invention, and methods for using enzymes in accordance with the invention in processing foods and feeds. Aldolase, such as pyruvate aldolase, HMG and/or KHG aldolase enzymes in accordance with the invention have numerous applications in food processing industry. In some embodiments, the invention provides methods for hydrolyzing cellulose-comprising compositions, including, such as a plant cell, a bacterial cell, a yeast cell, an insect cell, or an animal cell, or any plant or plant part, or any food or feed, a waste product and the like.

For example, the invention provides feeds or foods comprising an aldolase, such as pyruvate aldolase, HMG and/or KHG aldolase enzyme the invention, such as in a feed, a liquid, such as a beverage (such as a fruit juice or a beer), a bread or a dough or a bread product, or a drink (such as a beer) or a beverage precursor (such as a wort).

The food treatment processes in accordance with the invention can also include the use of any combination of other enzymes such as tryptophanases or tyrosine decarboxylases, laccases, catalases, laccases, other aldolases, cellulases, endoglycosidases, endo-beta-1,4-laccases, amyloglucosidases, glucosidases, glucose isomerases, glycosyltransferases, lipases, phospholipases, lipooxygenases, beta-laccases, endo-beta-1,3(4)-laccases, cutinases, peroxidases, amylases, phytases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, cellobiohydrolases and/or transglutaminases.

Pharmaceutical Compositions and Dietary Supplements

The invention also provides pharmaceutical compositions and dietary supplements (such as dietary aids) comprising an aldolase in accordance with the invention. The aldolase activity comprises pyruvate aldolase, HMG and/or KHG aldolase activity. In some embodiments, the pharmaceutical compositions and dietary supplements (such as dietary aids) are formulated for oral ingestion.

Periodontal treatment compounds can comprise an enzyme in accordance with the invention, such as described in U.S. Pat. No. 6,776,979. Compositions and methods for the treatment or prophylaxis of acidic gut syndrome can comprise an enzyme in accordance with the invention, such as described in U.S. Pat. No. 6,468,964.

In other embodiments, wound dressings, implants and the like comprise antimicrobial (such as antibiotic-acting) enzymes, including an enzyme in accordance with the invention (including, such as sequences in accordance with the invention). Enzymes in accordance with the invention can also be used in alginate dressings, antimicrobial barrier dressings, burn dressings, compression bandages, diagnostic tools, gel dressings, hydro-selective dressings, hydrocellular (foam) dressings, hydrocolloid dressings, I.V dressings, incise drapes, low adherent dressings, odor absorbing dressings, paste bandages, post operative dressings, scar management, skin care, transparent film dressings and/or wound closure. Enzymes in accordance with the invention can be used in wound cleansing, wound bed preparation, to treat pressure ulcers, leg ulcers, burns, diabetic foot ulcers, scars, IV fixation, surgical wounds and minor wounds. Enzymes in accordance with the invention can be used to in sterile enzymatic debriding compositions, such as ointments. In various embodiments, the aldolase is formulated as a tablet, gel, pill, implant, liquid, spray, film, micelle, powder, food, feed pellet or as an encapsulated formulation.

The pharmaceutical compositions and dietary supplements in accordance with the invention can also include the use of any combination of other enzymes such as beta-galactosidases, catalases, laccases, cellulases, other aldolases, endoglycosidases, endo-beta-1,4-laccases, amyloglucosidases, glucosidases, glucose isomerases, glycosyltransferases, lipases, phospholipases, lipooxygenases, beta-laccases, endo-beta-1,3(4)-laccases, cutinases, peroxidases, amylases, phytases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, cellobiohydrolases and/or transglutaminases.

Biosynthetic Pathways to Produce R,R and Other Stereoisomers of Monatin

As described, inter alia, in WO 03/091396 A2 (see FIGS. 1-3 and 11-13), monatin can be produced from tryptophan through a multi-step pathway involving biological conversions (i.e. facilitating the reaction of a substrate to a product with a polypeptide). A pathway described involves biologically converting tryptophan to indole-3-pyruvate, biologically converting indole-3-pyruvate to 2-hydroxy 2-(indol-3-ylmethyl)-4-keto glutaric acid ("MP"), and biologically converting MP to monatin. In some embodiments, polypeptides of the invention can be used to facilitate the reaction of indole-3-pyruvate to form MP. In some embodiments, polypeptides of the invention can be used to preferentially facilitate the production of R-MP.

In some embodiments, one or more polypeptides chosen from isolated or recombinant polypeptides of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ED NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, SEQ ID NO:174, SEQ ID NO:176, SEQ ID NO:178, SEQ ID NO:180, SEQ ID NO:182, SEQ ID NO:184, SEQ ID NO:186, SEQ ID NO:188, SEQ ID NO:190, SEQ ID NO:192, SEQ ID NO:194, SEQ ID NO:196, SEQ ID NO:198, SEQ ID NO:200, SEQ ID NO:202, SEQ ID NO:204, SEQ ID NO:206, SEQ ID NO:208, SEQ ID NO:210, SEQ ID NO:212, SEQ ID NO:214, SEQ ID NO:216, SEQ ID NO:218, SEQ ID NO:220, SEQ ID NO:222, SEQ ID NO:224, SEQ ID NO:226, SEQ ID NO:228, SEQ ID NO:230, SEQ ID NO:232, SEQ ID NO:234, SEQ ID NO:236, SEQ ID NO:238, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:260, SEQ ID NO:262, SEQ ID NO:264, SEQ ID NO:266, SEQ ID NO:268, SEQ ID NO:270, SEQ ID NO:272, SEQ ID NO:274, SEQ ID NO:276, SEQ ID NO:278, SEQ ID NO:280, SEQ ID NO:282, SEQ ID NO:284, SEQ ID NO:286, SEQ ID NO:288, SEQ ID NO:290, SEQ ID NO:292, SEQ ID NO:294, SEQ ID NO:296, SEQ ID NO:298, SEQ ID NO:300, SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:320, SEQ ID NO:322, SEQ ID NO:324, SEQ ID NO:326, SEQ ID NO:328, SEQ ID NO:330, SEQ ID NO:332, or SEQ ID NO:334, or fragments or subsequences thereof having aldolase activity may be useful in facilitating a reaction within a multi-step pathway to produce a product chosen from monatin, monatin derivatives, salts thereof and combinations thereof. In one embodiment, the polypeptides with aldolase activity may be useful in facilitating a reaction in which indole-3-pyruvate is converted to MP as one step within a multi-step pathway to produce a product chosen from monatin, monatin derivatives, salts thereof and combinations thereof.

In another embodiment, one or more polypeptides chosen from isolated or recombinant polypeptides with HMG aldolase activity of any of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, SEQ ID NO:174, SEQ ID NO:176, SEQ ID NO:178, SEQ ID NO:180, SEQ ID NO:182, SEQ ID NO:184, SEQ ID NO:186, SEQ ID NO:188, SEQ ID NO:190, SEQ ID NO:192, SEQ ID NO:194, SEQ ID NO:196, SEQ ID NO:198, SEQ ID NO:200, SEQ ID NO:202, SEQ ID NO:204, SEQ ID NO:206, SEQ ID NO:208, SEQ ID NO:210, SEQ ID NO:212, SEQ ID NO:214, SEQ ID NO:216, SEQ ID NO:218, SEQ ID NO:220, SEQ ID NO:222, SEQ ID NO:224, SEQ ID NO:226, SEQ ID NO:228, SEQ ID NO:230, SEQ ID NO:232, SEQ ID NO:234, SEQ ID NO:236, SEQ ID NO:238, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:260, SEQ ID NO:262, SEQ ID NO:264, SEQ ID NO:266, SEQ ID NO:268, SEQ ID NO:270, SEQ ID NO:272, SEQ ID NO:274, SEQ ID NO:276, SEQ ID NO:278, SEQ ID NO:280, SEQ ID NO:282, SEQ ID NO:284, SEQ ID NO:286, SEQ ID NO:288, SEQ ID NO:290, SEQ ID NO:292, SEQ ID NO:294, SEQ ID NO:296, SEQ ID NO:298, SEQ ID NO:300, SEQ ID NO:302, SEQ ID NO:304 or fragments or subsequences thereof having aldolase activity may be useful in facilitating a reaction between indole-3-pyruvate and a C3 carbon source as one step within a multi-step pathway to produce a product chosen from monatin, monatin derivatives, salts thereof and combinations thereof. In one embodiment, the polypeptides with HMG aldolase activity may be useful in facilitating a reaction in which indole-3-pyruvate is converted to MP as one step within a multi-step pathway to produce a product chosen from monatin, monatin derivatives, salts thereof and combinations thereof.

In yet another embodiment, one or more polypeptides chosen from isolated or recombinant polypeptides with KHG aldolase activity of any of SEQ ID NO:306, SEQ ID NO:308, SEQ ID NO:310, SEQ ID NO:312, SEQ ID NO:314, SEQ ID NO:316, SEQ ID NO:318, SEQ ID NO:320, SEQ ID NO:322, SEQ ID NO:324, SEQ ID NO:326, SEQ ID NO:328, SEQ ID NO:330, SEQ ID NO:332, or SEQ ID NO:334 or fragments or subsequences thereof having aldolase activity may be useful in facilitating a reaction between indole-3-pyruvate and a C3 carbon source as one step within a multi-step pathway to produce a product chosen from monatin, monatin derivatives, salts thereof and combinations thereof. In one embodiment, the polypeptides with KHG aldolase activity may be useful in facilitating a reaction in which indole-3-pyruvate is converted to MP as one step within a multi-step pathway to produce a product chosen from monatin, monatin derivatives, salts thereof and combinations thereof.

Additionally, one or more polypeptides encoded by one or more nucleic acids sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a nucleic acid in accordance with the invention, including SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:279, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305, SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, and SEQ ID NO:338 over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more residues may be useful in facilitating a reaction between indole-3-pyruvate and a C3 carbon source as one step within a multi-step pathway to produce a product chosen from monatin, monatin derivatives, salts thereof and combinations thereof. In one embodiment, the one or more polypeptides, or fragments or subsequences thereof with aldolase activity may be useful in facilitating a reaction in which indole-3-pyruvate is converted to MP as one step within a multi-step pathway to produce a product chosen from monatin, monatin derivatives, salts thereof and combinations thereof.

In another embodiment of the invention, one or more polypeptides with HMG aldolase activity encoded by a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a nucleic acid in accordance with the invention, including SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:279, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305 over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more residues may be useful in facilitating a reaction between indole-3-pyruvate and a C3 carbon source as one step within a multi-step pathway to produce a product chosen from monatin, monatin derivatives, salts thereof and combinations thereof. In one embodiment, the one or more polypeptides with HMG aldolase activity may be useful in facilitating a reaction in which indole-3-pyruvate is converted to MP as one step within a multi-step pathway to produce a product chosen from monatin, monatin derivatives, salts thereof and combinations thereof.

In yet another embodiment of the invention, one or more polypeptides with KHG aldolase activity encoded by a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a nucleic acid in accordance with the invention, including SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, and SEQ ID NO:338 over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more residues may be useful in facilitating a reaction between indole-3-pyruvate and a C3 carbon source as one step within a multi-step pathway to produce a product chosen from monatin, monatin derivatives, salts thereof and combinations thereof. In one embodiment, the one or more polypeptides with KHG aldolase activity may be useful in facilitating a reaction in which indole-3-pyruvate is converted to MP as one step within a multi-step pathway to produce a product chosen from monatin, monatin derivatives, salts thereof and combinations thereof.

Furthermore, one or more polypeptides with aldolase activity encoded by a nucleic acid sequence that hybridizes under stringent condition to a nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:279, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305, SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, and SEQ ID NO:338 may be useful in facilitating a reaction between indole-3-pyruvate and a C3 carbon source as one step within a multi-step pathway to produce a product chosen from monatin, monatin derivatives, salts thereof and combinations thereof. In one embodiment, the one or more polypeptides with aldolase activity may be useful in facilitating a reaction in which indole-3-pyruvate is converted to MP as one step within a multi-step pathway to produce a product chosen from monatin, monatin derivatives, salts thereof and combinations thereof.

In another embodiment of the invention, one or more polypeptides with HMG aldolase activity encoded by a nucleic acid sequence that hybridizes under stringent conditions to a nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:11, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:279, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305 may be useful in facilitating a reaction between indole-3-pyruvate and a C3 carbon source as one step within a multi-step pathway to produce a product chosen from monatin, monatin derivatives, salts thereof and combinations thereof. In one embodiment, the one or more polypeptides with HMG aldolase activity may be useful in facilitating a reaction in which indole-3-pyruvate is converted to MP as one step within a multi-step pathway to produce a product chosen from monatin, monatin derivatives, salts thereof and combinations thereof.

In yet another embodiment of the invention, one or more polypeptides with KHG aldolase activity encoded by a nucleic acid sequence that hybridizes under stringent conditions to a nucleic acid of SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, and SEQ ID NO:338 may be useful in facilitating a reaction between indole-3-pyruvate and a C3 carbon source as one step within a multi-step pathway to produce a product chosen from monatin, monatin derivatives, salts thereof and combinations thereof. In one embodiment, the one or more polypeptides with KHG aldolase activity may be useful in facilitating a reaction in which indole-3-pyruvate is converted to MP as one step within a multi-step pathway to produce a product chosen from monatin, monatin derivatives, salts thereof and combinations thereof.

The polypeptides with aldolase activity described herein may be useful in facilitating a reaction between indole-3-pyruvate and a C3 carbon source. The C3 carbon source may be, but is not limited to, oxaloacetate, pyruvate or a pyruvate derivative, such as phosphoenolpyruvate. In one embodiment, the C3 carbon source is pyruvate.

Figure 2:
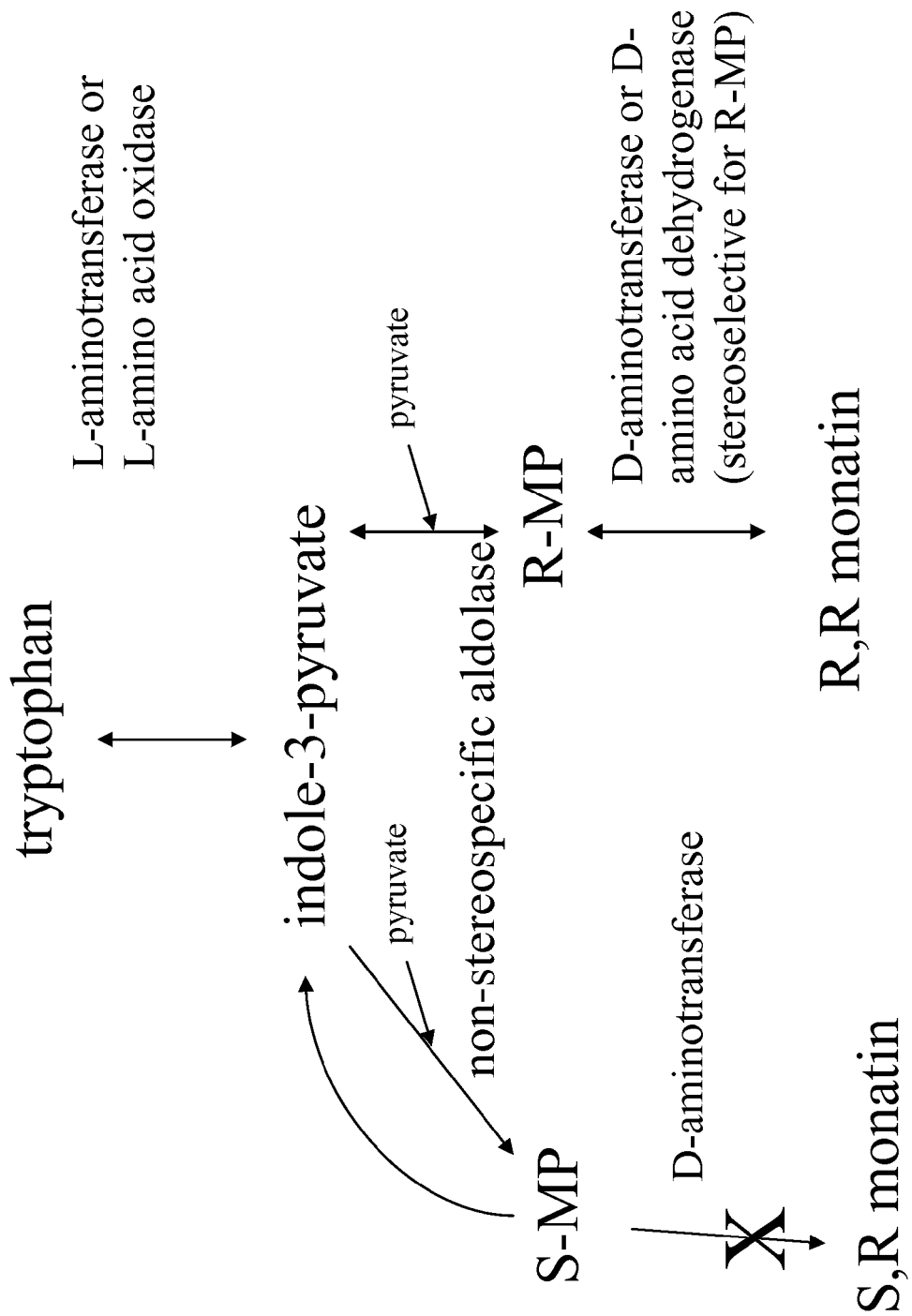
FIG. 2 is a flow chart that shows an example of another process for producing R,R monatin in accordance with the invention. In this example, the process includes using an enzyme to convert R-MP to monatin which is stereoselective for R-MP. In the specific example diagrammed in FIG. 2, tryptophan is shown to be converted to indole-3-pyruvate in a reversible reaction. The indole-3-pyruvate can be reacted with a non-stereospecific aldolase to reversibly form alpha-keto acid monatin (both R- and S-MP). The R-MP is reversibly converted to R,R monatin by a stereoselective D-aminotransferase or a stereoselective D-amino acid dehydrogenase. Any S-MP that is formed by the non-stereospecific aldolase can be converted back into indole-3-pyruvate if a stereoselective D-aminotransferase or D-amino acid dehydrogenase is utilized. For the purposes of the invention, it is not required that the reactions shown as being reversible proceed in the reverse direction.
Figure 13:
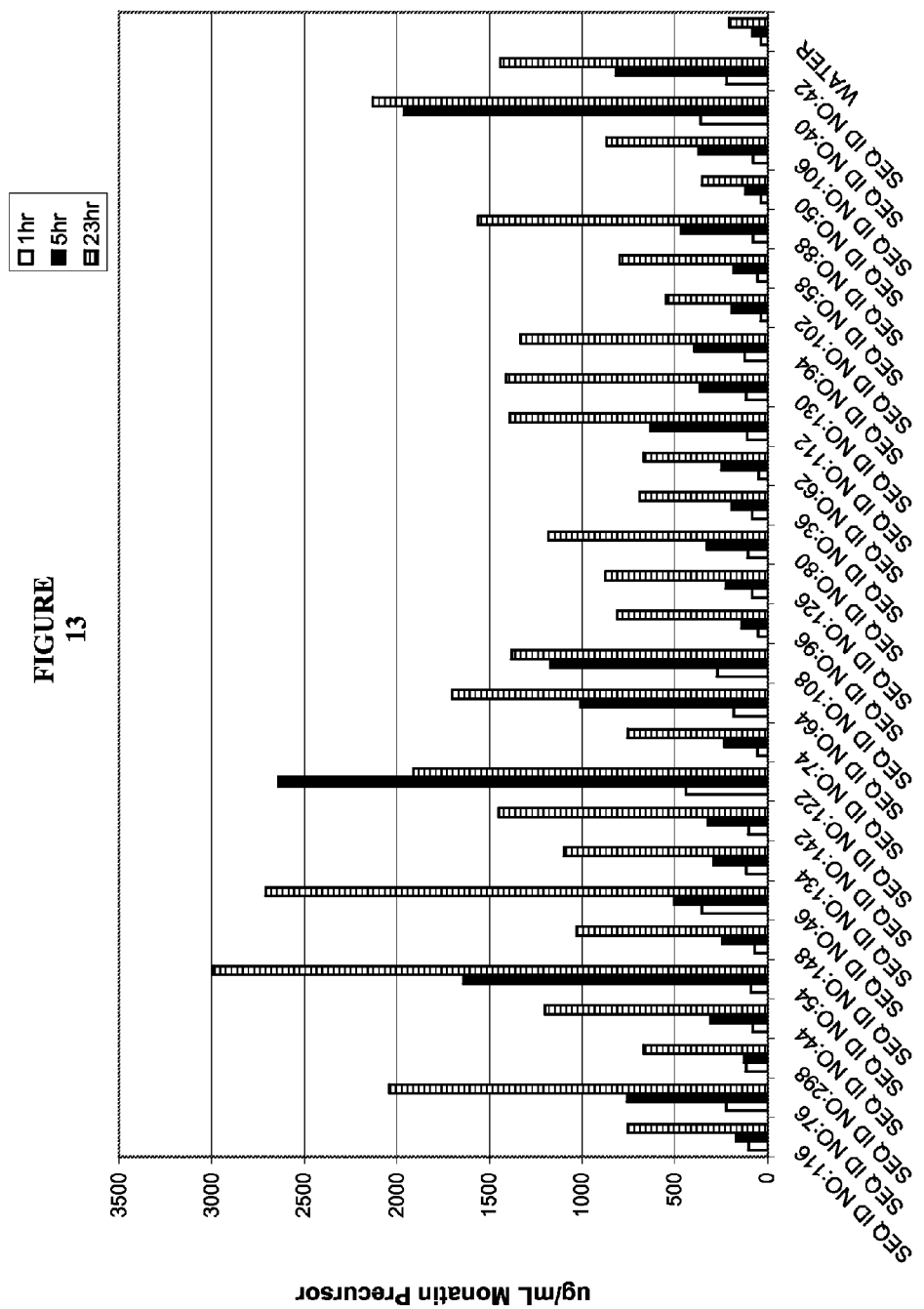
FIGS. 13 and 14 together illustrate the activities of 58 different aldolases (each identified by its specific SEQ ID number) in the formation of monatin precursor (MP) as measured by LC/MS/MS.

Exemplary enzymes useful for the conversion of the reaction product between indole-3-pyruvate and the C3 carbon source to monatin include members of the enzyme classes: tryptophan aminotransferases (2.6.1.27), tryptophan dehydrogenases (1.4.1.19), D-amino acid dehydrogenases (1.4.99.1), glutamate dehydrogenases (1.4.1.2-4), phenylalanine dehydrogenase (EC 1.4.1.20), tryptophan-phenylpyruvate transaminases (2.6.1.28), or more generally members of the aminotransferase family (2.6.1.-) such as aspartate aminotransferase (EC 2.6.1.1), tyrosine (aromatic) aminotransferase (2.6.1.5), D-tryptophan aminotransferase, or D-alanine (2.6.1.21) aminotransferase (see FIG. 2 of WO 03/091396 A2). This reaction can also be performed using chemical reactions. Amination of the keto acid (MP) is performed by reductive amination using ammonia and sodium cyanoborohydride. FIGS. 11-13 of WO 03/091396 A2 show additional polypeptides that can be used to convert MP to monatin, as well as providing increased yields of monatin from indole-3-pyruvate or tryptophan. In one embodiment, these enzymes are utilized to catalyze the conversion of MP, the reaction product between indole-3-pyruvate and pyruvate, to monatin.

The taste profile of a monatin composition can be altered by controlling the relative amount of the various stereoisomers of monatin in the composition. The present disclosure provides pathways and substances for producing monatin compositions with a desired percentage of R,R monatin and/or S,R monatin.

The chirality of the monatin compounds produced by the pathways disclosed can be affected both by pH and by the polypeptides used for the biological conversions. The polypeptides with aldolase activity described herein, may be utilized to control the chirality of the monatin carbon-2 (see Formula I, above) in the reaction in which indole-3-pyruvate is converted to MP.

Once the reaction product of the reaction between indole-3-pyruvate and the C3 carbon source is produced, the amino group can be added stereospecifically. Either the R or S configuration of carbon-4 (see Formula I above) can be generated depending on whether a D- or L-aromatic acid aminotransferase is used. Many aminotransferases are specific for the L-isomer, however, D-tryptophan aminotransferases exist in certain plants (Kohiba and Mito, Proceedings of the 8th International Symposium on Vitamin $B_6$ and Carbonyl Catalysis, Osaka, Japan 1990). Moreover, D-alanine aminotransferases (2.6.1.21), D-methionine-pyruvate aminotransferases (2.6.1.41) and both (R)-3-amino-2-methylpropanoate aminotransferase (2.6.1.61), (S)-3-amino-2-methylpropanoate aminotransferase (2.6.1.22), and D-phenylglycine aminotransferase have been identified. Certain aminotransferases may only accept the substrate for this reaction with a particular configuration at the C2 carbon. Therefore, even if the conversion to the reaction product between indole-3-pyruvate and the C3 carbon source is not stereospecific, the stereochemistry of the final product can be controlled through the appropriate selection of an aminotransferase. Because the reactions are reversible, the unreacted reaction product (undesired isomer) can be recycled back to its constituents and a racemic mixture of the reaction product can be reformed.

An example of a suitable amino donor for the addition of an amino group to the reaction product of the reaction between the indole-3-pyruvate and the C3 carbon source includes, but is not limited to an amino acid, such as alanine, aspartate, lysine, glutamate, glycine, and tryptophan.

Referring now to the figures, the following should be noted. The flow charts identify pathways for producing monatin, but are not limited to any particular method for practicing the pathways. For example, the pathways may be practiced in vivo, in vitro, or a combination thereof.

Furthermore, practice of the pathways does not require that each of the identified components (such as reactants and enzymes) is explicitly provided by the practitioner, so long as sufficient components, or sources of components, and reaction conditions are provided so that the pathway can potentially proceed. In other words, for example, if a figure depicts a process for producing a monatin composition, which includes producing indole-3-pyruvate from L-tryptophan, producing 2-hydroxy 2-(indol-3ylmethyl)-4-keto glutaric acid ("monatin precursor" or "MP") from indole-3-pyruvate, and producing monatin from MP, wherein each reaction is facilitated by an appropriate enzyme, it is contemplated that practice of that pathway includes combining L-tryptophan with α-ketoglutarate and enzymes contemplated for facilitating the identified reactions, and under conditions suitable for each of the reactions to occur without also explicitly providing indole-3-pyruvate or MP. In such an instance L-tryptophan could react with α-ketoglutarate to produce indole-3-pyruvate. Due to the set conditions and the provided enzyme, the indole-3-pyruvate produced from the L-tryptophan reaction could react to form MP, and then due to the set conditions and the provided enzyme, the MP produced from the indole-3-pyruvate reaction could react to form monatin.

It should also be noted that practice of the depicted pathways does not require the practitioner to explicitly provide the identified starting materials or enzymes. In other words, it is contemplated that practice of any pathways which identifies L-tryptophan as a starting material would include providing a compound that can produce L-tryptophan, under conditions suitable for L-tryptophan production to occur and combining that compound with enzymes capable of facilitating the series of reactions set forth under conditions which would be suitable for those reactions to occur. As another example, it is also contemplated that practicing the identified pathway would include providing a microorganism genetically engineered to produce monatin according to the described pathway, and providing appropriate conditions for the fermentation process to occur. For example, a microorganism, which naturally produces large amounts of L-tryptophan could be genetically engineered to produce or over-produce one or more of the enzymes used to facilitate reactions in the pathway to monatin, and appropriate conditions could be provided so that the microorganism would thereby produce monatin.

FIG. 1 identifies the particular embodiment wherein an R-specific aldolase facilitates the reaction of indole-3-pyruvate and pyruvate to form R-MP. The flow chart of FIG. 1 schematically depicts a process in accordance with the invention for making a monatin composition including R,R monatin. As shown in FIG. 1, the overall pathway involves a reaction of tryptophan to form indole-3-pyruvate, a reaction of indole-3-pyruvate to produce MP, and a reaction of MP to produce monatin, including R,R monatin.

FIG. 1 further illustrates specific permutations of this overall pathway, designed to increase the production of the R,R form of monatin at the expense of the S,S, R,S and S,R forms of monatin. In particular, FIG. 1 illustrates the embodiment wherein: the aminotransferase enzyme utilized in the L-tryptophan reaction has greater activity and/or specificity for that reaction versus the reactions of MP and 4S monatin or the oxidase has greater activity and/or specificity for L-tryptophan than for 4R monatin; the enzyme which facilitates the reaction of indole-3-pyruvate is a polypeptide with aldolase activity disclosed herein, and, the enzyme which facilitates the reaction of MP is a broad specificity D-enzyme, preferably evolved to work more efficiently with the R isomer of MP.

FIG. 1 also illustrates particular permutations designed to make the production of R,R monatin more economical. For example, in FIG. 1, L-tryptophan—as opposed to D-tryptophan or combinations of L- and D-tryptophan—is identified as the starting material. While the choice of the specific form of tryptophan does not impact the chirality of the ultimate monatin compounds in the monatin composition (because the tryptophan reaction forms indole-3-pyruvate, which has no chirality), some may prefer utilizing L-tryptophan as a starting material at least because L-tryptophan is currently less expensive and more easily obtainable than D-tryptophan Focusing now on the first reaction shown in FIG. 1, when tryptophan is converted to indole-3-pyruvate any one or more of alpha-ketoglutarate, oxaloacetate, and pyruvate reacts to form an amino acid (glutamate, aspartate, and alanine respectively). FIG. 1 depicts the embodiment wherein the tryptophan starting material is L-tryptophan, and the alpha-ketoglutarate, oxaloacetate, and/or pyruvate produce the L-isomer form of the amino acid (such as L-glutamate, L-aspartate, and/or L-alanine, respectively).

As shown in FIG. 1, an approach to enhancing the production of R,R monatin involves facilitating the reaction of L-tryptophan with an enzyme having greater specificity, greater activity, or both for tryptophan as opposed to MP or monatin, and facilitating the reaction of MP with a D-enzyme. As is disclosed in WO 03/091396 A2, certain enzymes can facilitate the reaction of tryptophan to produce indole-3-pyruvate, as well as the amination reaction of MP to produce monatin. Use of an L-aminotransferase in the amination step creates an S chiral center at the monatin C-4 position, whereas use of a D-enzyme creates a D chiral center at the monatin C-4 position. Thus, in the instance where an L-aminotransferase, which facilitates the tryptophan reaction, is also active in the MP reaction, R,S and S,S monatin can be formed, depending on the form of MP present. In addition, certain other enzymes—the L-amino acid oxidases—can not only facilitate the reaction of tryptophan to indole-3-pyruvate, but may have a side activity for the degradation of R,R monatin. According to some embodiments, this 4R side activity is minimized or eliminated. An oxidase side activity on 4S forms of monatin would decrease or minimize them from the final product and could be desirable depending on the final composition desired. Consequently, the greater the specificity and/or activity of the L-enzyme chosen for tryptophan versus the MP or monatin, the greater the amount of R,R and S,R produced versus S,S and R,S monatin.

Suitable enzymes for the tryptophan reaction, in accordance with the embodiment illustrated in FIG. 1, include: L-aminotransferases capable of facilitating a reaction of L-tryptophan to form indole-3-pyruvate, and which have greater specificity for that reaction over the reaction of R-MP to form 4S isomers of monatin; and, L-amino acid oxidases capable of facilitating a reaction of L-tryptophan to form indole-3-pyruvate, and which have greater specificity and/or activity for that reaction versus the reaction of 4R isomers of monatin to form MP, and functional equivalents of any of the foregoing. More specifically, non-limiting examples of suitable enzymes can be chosen from L-tryptophan aminotransferases (E.C. 2.6.1.27) and tyrosine (aromatic) aminotransferases (EC 2.6.1.5) and L-amino acid oxidases (EC 1.4.3.2), and mutants derived from enzymes having aspartate aminotransferase activity.

Example 16 identifies a specific enzyme, a mutant HEXaspC polypeptide which includes a Pro 9 to Tyr substitution and an Arg 122 to Gly substitution useful for facilitating the reactions of L-tryptophan and α-KG, oxaloacetate, pyruvate, or combinations thereof to form indole-3-pyruvate and L-glutamate, L-aspartate, and L-alanine, respectively. Another specific enzyme having "limited" activity is TatA, the L-tryptophan aminotransferase from *S. meliloti*. Other enzymes suitable for the tryptophan reaction in accordance with preferred embodiments of the pathway shown in FIG. 1 include those with the following characteristics: an enzyme that transaminates MP at 1/10 the rate or less than the rate of L-tryptophan as in Example 16 or an enzyme when used with a racemase, as in Example 18, that produces greater than 90% of the 4R isomers of monatin.

Examples of enzymes not having greater specificity for the L-tryptophan to indole-3-pyruvate conversion compared to the MP to monatin conversion include: HEXAspC (Example 16), *Leishmania major* broad specificity aminotransferase (WO 03/091396 A2), the Porcine aminotransferase (WO 03/091396 A2) and *Rhodobacter sphaeroides* TatA (Example 18). These enzymes may, however, be evolved, for example through mutagenesis to have limited activity for R-MP and/or R,R monatin versus tryptophan.

Focusing now on the second reaction identified in FIG. 1, the choice of enzyme for facilitating the reaction of indole-3-pyruvate to MP influences the relative amount of R,R monatin versus S,R monatin produced. In general, the greater the relative amount of R-MP versus S-MP produced, the greater the relative amount of R,R monatin versus S,R monatin produced (when a D-enzyme facilitates the reaction of MP to monatin). Where a monatin composition having the R,R form of monatin as its only monatin component is desired, an enzyme that selectively produces R-MP as opposed to S-MP (an "R-specific enzyme") should be used. The polypeptides with aldolase activity described herein are useful in selectively producing R-MP, as opposed to S-MP. Several examples of highly R-specific aldolase enzymes are demonstrated in Table 1, above, Examples 4, 5 and 6, below, and in the Sequence Listing.

Focusing now on the last step of the pathway identified in FIG. 1, the reaction of R-MP to form R,R monatin is shown to be facilitated by a broad specificity D-aminotransferase, for example D-alanine aminotransferase (E.C. 2.6.1.21, also known as D-amino acid aminotransferase or D-aspartate aminotransferase) or a D-amino acid dehydrogenase. As discussed above, the conversion of MP to monatin is an amination reaction, which creates a chiral center at the monatin C-4 carbon. Where the R-chiral form is desired at the C-4 position, enzymes should be used which produce "R" chiral centers in amino acids.

According to some embodiments, the D-aminotransferase has greater specificity, greater activity, or both for the R-MP than for indole-3-pyruvate. According to some embodiments, the D-aminotransferase has limited activity for the indole-3-pyruvate. Enzymes with such characteristics may be evolved or mutated from existing enzymes, for example as shown in Example 16.

Examples 9 to 12 illustrate the production of R,R-monatin from D-tryptophan.

FIG. 2 illustrates a method of producing R,R monatin and S,R monatin. Whereas in the embodiment of FIG. 1, the aldolase used in the reaction of indole-3-pyruvate to form R-MP influences the ratio of R,R:S,R formed, in the embodiment of FIG. 2, the D-enzyme that facilitates the conversion of MP to monatin influences the ratio of R,R:S,R formed. According to the pathway of FIG. 2, if a non-stereospecific enzyme is used to facilitate the conversion of indole-3-pyruvate to MP, then both S-MP and R-MP can be formed. If a non-stereoselective aldolase is utilized to convert indole-3-pyruvate to MP, then a stereoselective transaminase is required to convert the MP to either R,R monatin or S,R monatin. As shown on FIG. 2, use of a D-aminotransferase or D-amino acid dehydrogenase that is stereospecific for R-MP results in the production of R,R monatin.

Figure 3:
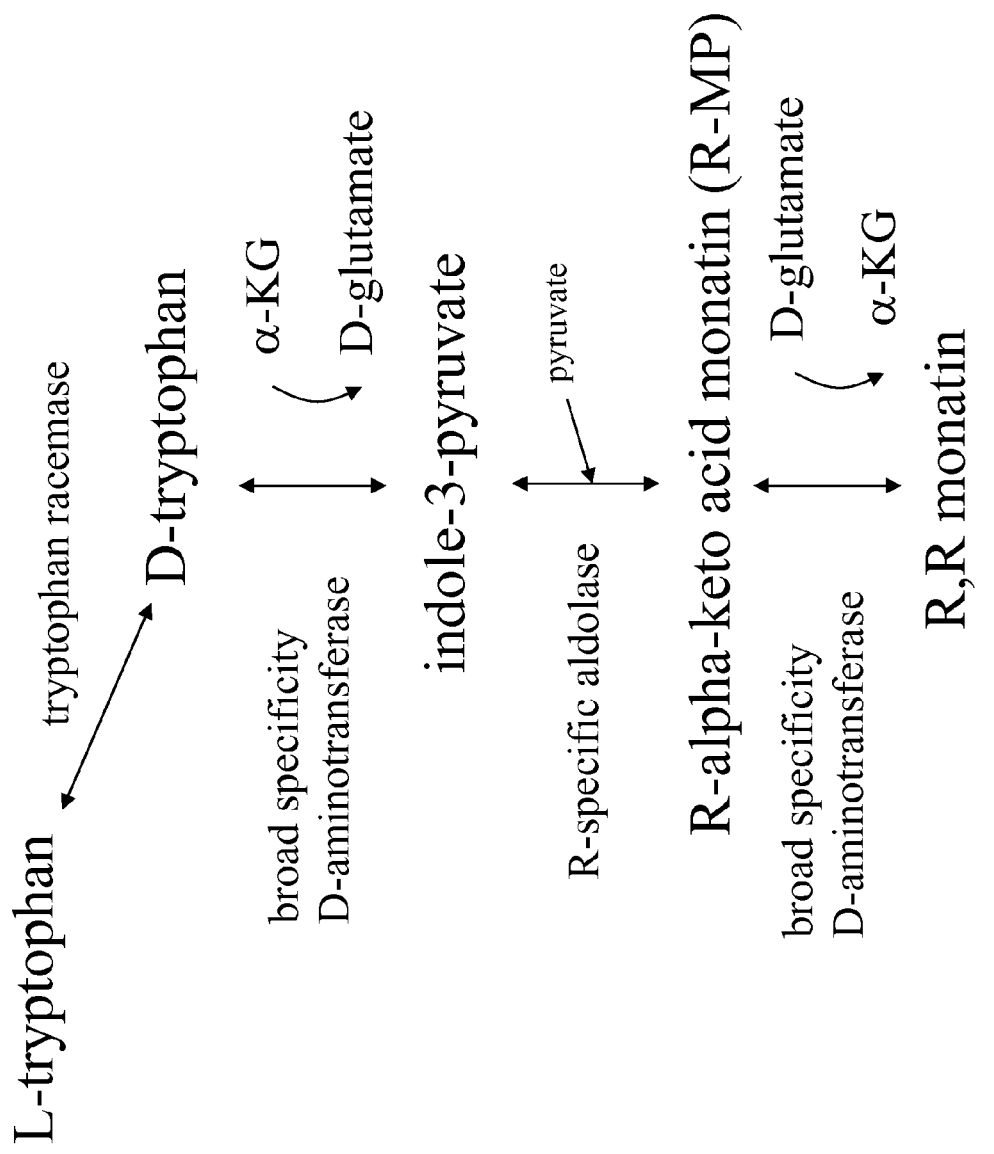
FIG. 3 is a flow chart that shows an example of yet another process for producing R,R monatin from L-tryptophan in accordance with the invention. In this example, the process includes converting L-tryptophan to D-tryptophan using a tryptophan racemase and using a D-amino acid product in the reaction coupled to the reaction forming indole-3-pyruvate as a substrate in the reaction coupled to the reaction forming R,R monatin. In the specific example diagrammed in FIG. 3, L-tryptophan is converted to D-tryptophan by a tryptophan racemase in a reversible reaction. The D-tryptophan is reacted with alpha-ketoglutarate ($\alpha$-KG) and a broad specificity D-aminotransferase to produce indole-3-pyruvate and D-glutamate. Indole-3-pyruvate is reacted with pyruvate and an R-specific aldolase and converted to R-alpha-keto acid monatin (R-MP), and R-MP is reacted with a broad specificity D-aminotransferase and D-glutamate to form R,R monatin and alpha-ketoglutarate ($\alpha$-KG). As shown on FIG. 3, each of the reactions are reversible, but for the purposes of the invention, it is not required that the reactions proceed in the reverse direction.

FIG. 3 illustrates another alternative pathway for targeting production of R,R monatin. The pathway of FIG. 3 is a modification of the pathway of FIG. 1, wherein indole-3-pyruvate is produced indirectly, rather than directly, from L-tryptophan. More specifically, L-tryptophan is converted to D-tryptophan, and D-tryptophan is then converted to indole-3-pyruvate.

The conversion of L-tryptophan to D-tryptophan can be facilitated by a tryptophan racemase or functional equivalent thereof. Example 15 provides potential sources of tryptophan racemases and screening methods for identifying such enzymes. It is also contemplated a tryptophan racemase may be evolved (such as via mutagenesis or recombinant engineering) for improved performance from an existing amino acid racemase.

Non-limiting examples of tryptophan racemases include homolog or mutants of amino acid racemases (EC 5.1.1.-), for example serine racemase, wherein the homologs or mutants are capable of converting L-tryptophan to D-tryptophan. Non-limiting examples of sources from which the amino acid racemase may be derived include: microorganisms such as *Salmonella typhimurium, Escherichia coli, Bacillus subtilis, Pseudomonas aeruginosa, Vibrio cholerae, Schizosaccaroyces pombe, Bacillus cereus, Enterococcus gallinarum, Pediococcus pentosaceus, Bacillus pumilus, Lactobacillus fermenti, Lactobacillus brevis, Aquifex pyrophilus, Lactobacilli, Streptococcus, Anabaena* sp., *Pseudomonas striata, Lentinus edodes, Scapharca brouhtonii Desulfurococcus* sp., *Thermococcus* sp., and *Pseudomonas striata*. Additional non-limiting examples of sources from which the amino acid racemase may be derived include silkworm, rat brain, or mouse brain.

Non-limiting examples of potential sources from which suitable tryptophan racemases may be derived include: microorganisms such as *Pseudomonas*, for example *Pseudomonas chlororaphis* (*Pseudomonas aurereofaciens*) (ATCC15926), and *Burkholderia pyrrocina* (ATCC15958). Additional non-limiting examples of potential sources from which suitable tryptophan racemases may be derived include plants, for example tobacco plants, such as *Nicotiana tabacum*, wheat plants, such as *Triticum aestivum*, beets, tomatoes, and *Sclerochiton ilicifolius*.

The pathway shown in FIG. 3 has certain benefits, including that even where R,R monatin is the desired product, the same enzyme may be used for the reaction producing indole-3-pyruvate as for the reaction producing monatin. That is, in the pathway illustrated in FIG. 1, an L-aminotransferase (or suitable L-enzyme) facilitates the reaction producing indole-3-pyruvate, but a D-aminotransferase facilitates the reaction producing monatin. By contrast in the pathway of FIG. 3, certain D-aminotransferase that facilitates the reaction producing indole-3-pyruvate, can also facilitate the reaction producing monatin. Consequently, in pathways according to FIG. 3 broad specificity D-aminotransferases may be preferred where there is a desire to use the same enzyme for the reaction forming indole-3-pyruvate as for the reaction forming monatin. By contrast, in pathways according to FIGS. 1, 2, 4, 6, 7, and 8 production of monatin may proceed forward more efficiently when a D-aminotransferase is chosen that has limited activity and/or specificity for indole-3-pyruvate as compared to R-MP.

Another benefit of the pathway schematically represented in FIG. 3 is that the amino acid product of the reaction coupled to the reaction producing indole-3-pyruvate can now be used as a starting material in the reaction coupled to the reaction producing monatin. That is, in the pathway illustrated in FIG. 1, L-tryptophan reacts to produce indole-3-pyruvate and at the same time oxaloacetate, alpha-ketoglutarate and/or pyruvate react to produce an L-amino acid. Because the reaction of R-MP to form monatin is coupled with a reaction utilizing a D-amino acid as a substrate, the L-amino acid of the reaction forming indole-3-pyruvate is not, under the conditions shown, recycled for use in the reaction coupled to the R-MP reaction. By contrast, in the pathway illustrated in FIG. 3, the reaction of D-tryptophan to form indole-3-pyruvate is coupled to a reaction forming a D-amino acid product, which D-amino acid can be recycled for use in the reaction coupled to the R-MP reaction. This allows one to use non-stoichiometric amounts of amino acceptor in step one. In some embodiments of the invention, the D-amino acid is D-alanine.

Figure 4:
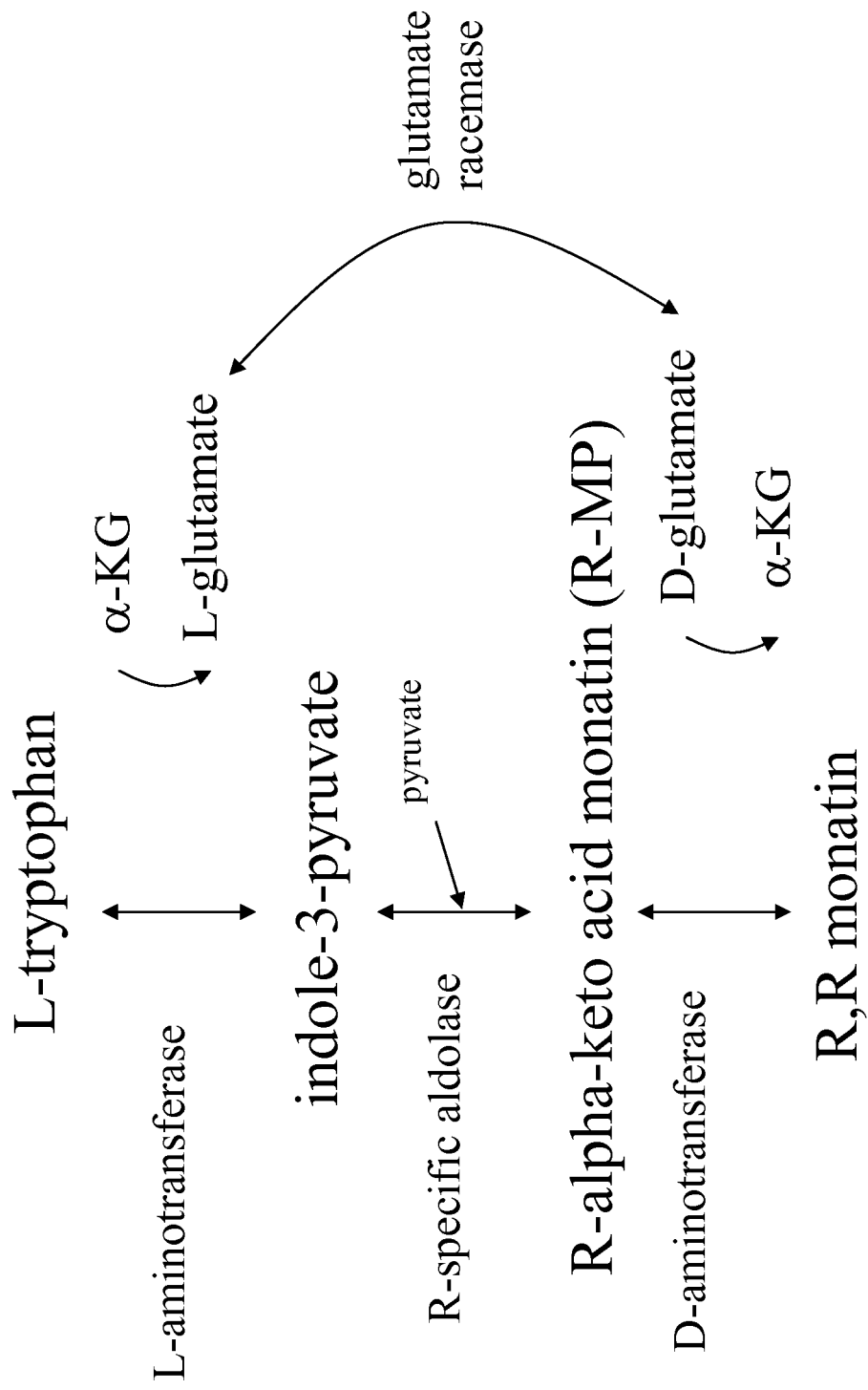
FIG. 4 is a flow chart that shows an example of yet another process for producing R,R monatin from L-tryptophan in accordance with the invention. In this example, the process includes converting the L-amino acid formed in the reaction coupled with the L-tryptophan reaction to a D-amino acid; this D-amino acid acts as an amino donor for the reaction in which R-MP is converted to R,R monatin. In the specific example diagrammed in FIG. 4, L-tryptophan is reacted with an L-aminotransferase and alpha-ketoglutarate to produce indole-3-pyruvate and L-glutamate. Indole-3-pyruvate is reacted with pyruvate and an R-specific aldolase and converted to R-alpha-keto acid monatin (R-MP), and R-MP is reacted with a broad specificity D-aminotransferase and D-glutamate to form R,R monatin and alpha-ketoglutarate. As shown on FIG. 4, the reactions are reversible, but for the purposes of the invention, it is not required that the reactions proceed in the reverse direction.
Figure 5:
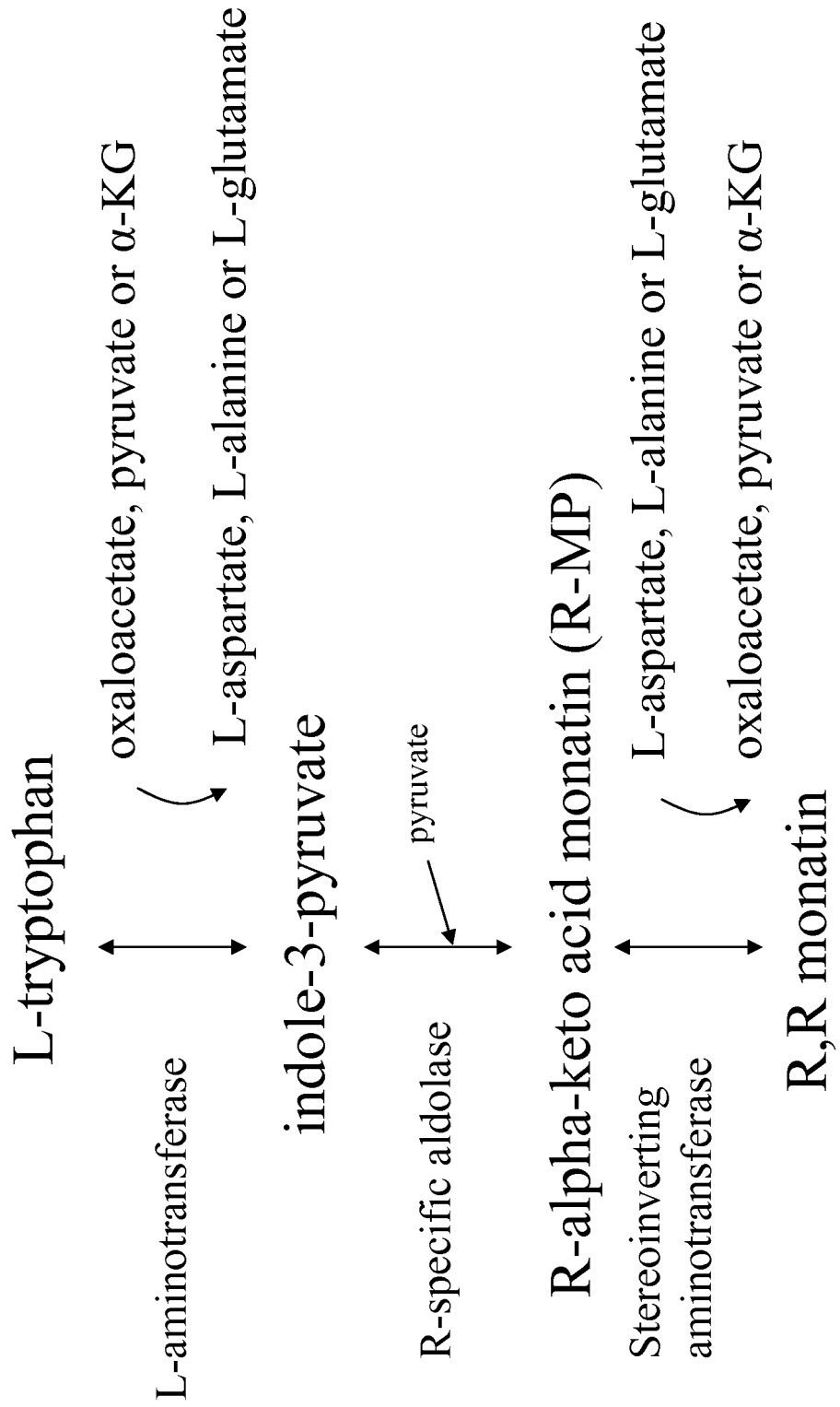
FIG. 5 is a flow chart that shows an example of yet another process for producing R,R monatin from L-tryptophan in accordance with the invention. In this example, the process includes enzymatically facilitating the conversion of R-MP to R,R monatin using a stereoinverting enzyme so that the L-amino acid formed by the reaction coupled to the L-tryptophan reaction can be used as a substrate for the reaction coupled to the R-MP to R,R monatin reaction. In the specific example diagrammed in FIG. 5, L-tryptophan is reacted with an L-aminotransferase and oxaloacetate, pyruvate or alpha-ketoglutarate ($\alpha$-KG) to produce indole-3-pyruvate, and L-aspartate (if oxaloacetate is used), L-alanine (if pyruvate is used) or L-glutamate (if $\alpha$-KG is used). Indole-3-pyruvate is reacted with pyruvate and an R-specific aldolase and converted to R-alpha-keto acid monatin (R-MP), and R-MP is reacted with a stereoinverting aminotransferase and L-aspartate, L-alanine or L-glutamate to form R,R monatin and oxaloacetate (if L-aspartate is used), pyruvate (if L-alanine is used) or alpha-ketoglutarate ($\alpha$-KG, if L-glutamate is used). As shown on FIG. 5, the reactions are reversible, but for the purposes of the invention, it is not required that the reactions proceed in the reverse direction.

FIGS. 4 and 5 illustrate additional modifications of the pathway shown in FIG. 1, which modifications are directed to recycling the amino acid product formed by the reaction coupled with the L-tryptophan reaction with the amino acid reactant of the reaction coupled to the MP to monatin reaction.

Turning to FIG. 4, the recycling is accomplished providing an enzyme that can facilitate the conversion of an L-amino acid to a D-amino acid and vice versa. More specifically, where as is shown in FIG. 4, α-KG reacts to form L-glutamate when L-tryptophan reacts to form indole-3-pyruvate, a glutamate racemase (EC 5.1.1.3) or functional equivalent can be provided that can facilitate the conversion of L-glutamate to D-glutamate and vice versa. In such an instance, the L-glutamate formed alongside the production of indole-3-pyruvate is removed by virtue of its conversion to D-glutamate, and the D-glutamate formed from the conversion of L-glutamate is then available as a substrate for the reaction coupled with the MP to monatin reaction. Similarly, the α-KG formed in the reaction of D-glutamate is available as a substrate for the reaction coupled to the L-tryptophan to indole-3-pyruvate reaction.

Non-limited examples of potential sources from which a glutamate racemase may be derived include *Pediococcus pentosaceus, Bacillus pumilus, Lactobacillus fermenti, Lactobacillus brevis, E. coli, Aquifex pyrophilus*, and *Bacillus subtilis*. More specifically (also non-limiting), the glutamate racemase may be expressed from a nucleic acid such as *pediococcus pentaosaceus* murI gene (Genbank Accession No. L22789), or *Lactobacillus brevis* glutamate racemase.

Where oxaloacetate reacts to form L-aspartate when L-tryptophan reacts to form indole-3-pyruvate, an aspartate racemase (EC 5.1.1.13) or functional equivalent can be provided to convert L-aspartate to D-aspartate. In such an instance, the L-aspartate alongside the production of indole-3-pyruvate is removed by virtue of its conversion to D-aspartate, and the D-aspartate formed from the conversion of L-aspartate is then available to as a substrate for the reaction coupled to the MP to monatin reaction. Similarly, the oxaloacetate formed in the reaction of D-aspartate is available to act as a substrate for the reaction coupled to the L-tryptophan to indole-3-pyruvate reaction.

Non-limiting examples of suitable enzymes having aspartate racemase activity include ASPR-101 (BioCatalytics, Inc., Pasadena, Calif.) and homologs or mutants of an amino acid racemase (EC 5.1.1.-) which are capable of facilitating the conversion of L-aspartate to D-aspartate.

Non-limiting examples of potential sources from which aspartate racemases may be derived include: *Desulfurococcus, Thermococcus*, bivalve mollusk *Scapharca brouhtonii, Acinetobacter, Agrobacterium, Archaeoglobus, Bacillus, Bordetella, Bradyrhizobium, Brevibacterium, Burkholderia, Campylobacter, Candida, Caulobacter, Clostridium, Desulfitobacterium, Desulfotalea, Enterococcus, Erwinia, Escherichia, Ferroplasma, Helicobacter, Klebsiella, Lactobacillus, Mannheimia, Medicago, Mesorhizobium, Methanococcus, Methanosarcina, Oceanobacillus, Oenococcus, Pediococcus, Polaribacter, Pseudomonas, Pyrococcus, Ralsonia, Shigella, Sinorhizobium, Salmonella, Sphingomonas, Streptococcus, Thermoanaerobacter, Vibrio, Wolinella, Xanthomonas, Xanthobacter, Yersinia* and *Zymomonas*.

Where pyruvate reacts to form L-alanine when L-tryptophan reacts to form indole-3-pyruvate, an alanine racemase or functional equivalent can be provided to convert L-alanine to D-alanine. In such an instance, the L-alanine formed alongside the production of indole-3-pyruvate is removed by virtue of its conversion to D-alanine, and the D-alanine formed from the conversion of L-alanine is then available to act as a substrate for the reaction coupled to the MP to monatin reaction. Similarly, the pyruvate formed in the reaction of D-alanine is available to act as a substrate for the reaction couple with the L-tryptophan to indole-3-pyruvate reaction.

Non-limiting examples of suitable alanine racemases include A8936 (Sigma-Aldrich, St. Louis, Mo.).

Non-limiting examples of potential sources from which the alanine racemase may be derived include: *Brucella abortus, Streptococcus faecalis Salmonella typhimurium, Escherichia coli, Bacillus subtilis, Bacillus stearothermophilus, Pseudomonas aeruginosa, Vibrio cholerae, Schizosaccaroyces pombe, Bacillus cereus* and *Lentinus edodes*.

Examples 18 and 21 illustrate the use of the above racemases, their impact on increasing the ratio of the desired monatin product, and provide potential sources for the racemase enzymes.

Turning to FIG. 5, a stereoinverting aminotransferase is used to facilitate the reaction of R-MP to monatin. Although typically the R-MP (or S-MP) reaction to form R,R monatin (or S,R monatin) is coupled with the reaction of a D-amino acid, a stereoinverting aminotransferase can facilitate the coupled reactions of R-MP (or S-MP) to form R,R monatin (or S,R monatin) using an L-amino acid. In this way, the L-amino acid product of the L-tryptophan aminotransferase reaction can be used as a substrate for the transamination of MP to monatin, and the product (i.e. oxaloacetate, pyruvate, and/or α-KG) of the reaction coupled to the MP to monatin reaction can be used as a starting material for the reaction coupled to the L-tryptophan to indole-3-pyruvate reaction.

Non-limiting examples of stereoinverting aminotransferases that may be used include D-phenylglycine aminotransferase (EC 2.6.1.72, also known as D-4-hydroxyphenylglycine aminotransferase) and D-methionine aminotransferase (EC 2.6.1.41, also known as D-met-aminotransferase and D-methionine-pyruvate aminotransferase). Non-limiting examples of potential sources from which the D-phenylglycine aminotransferase may be derived include *Pseudomonas*, such as *Pseudomonas putida* LW-4 and *Pseudomonas stutzeri* ST-201. Non-limiting examples of potential sources from which the D-methionine aminotransferase may be derived include cauliflower and peanut.

Examples 19 and 20 together provide potential sources of stereoinverting enzymes, and methods of making such enzymes. The examples also provide screening methods for identifying such enzymes. It is also contemplated that such enzymes may be evolved from stereoinverting enzymes known or found in nature. As a non-limiting example, the stereoinverting aminotransferase may be a homolog or mutant of a D-amino acid aminotransferase or a homolog or mutant of an amino acid racemase (EC 5.1.1.-).

Figure 6:
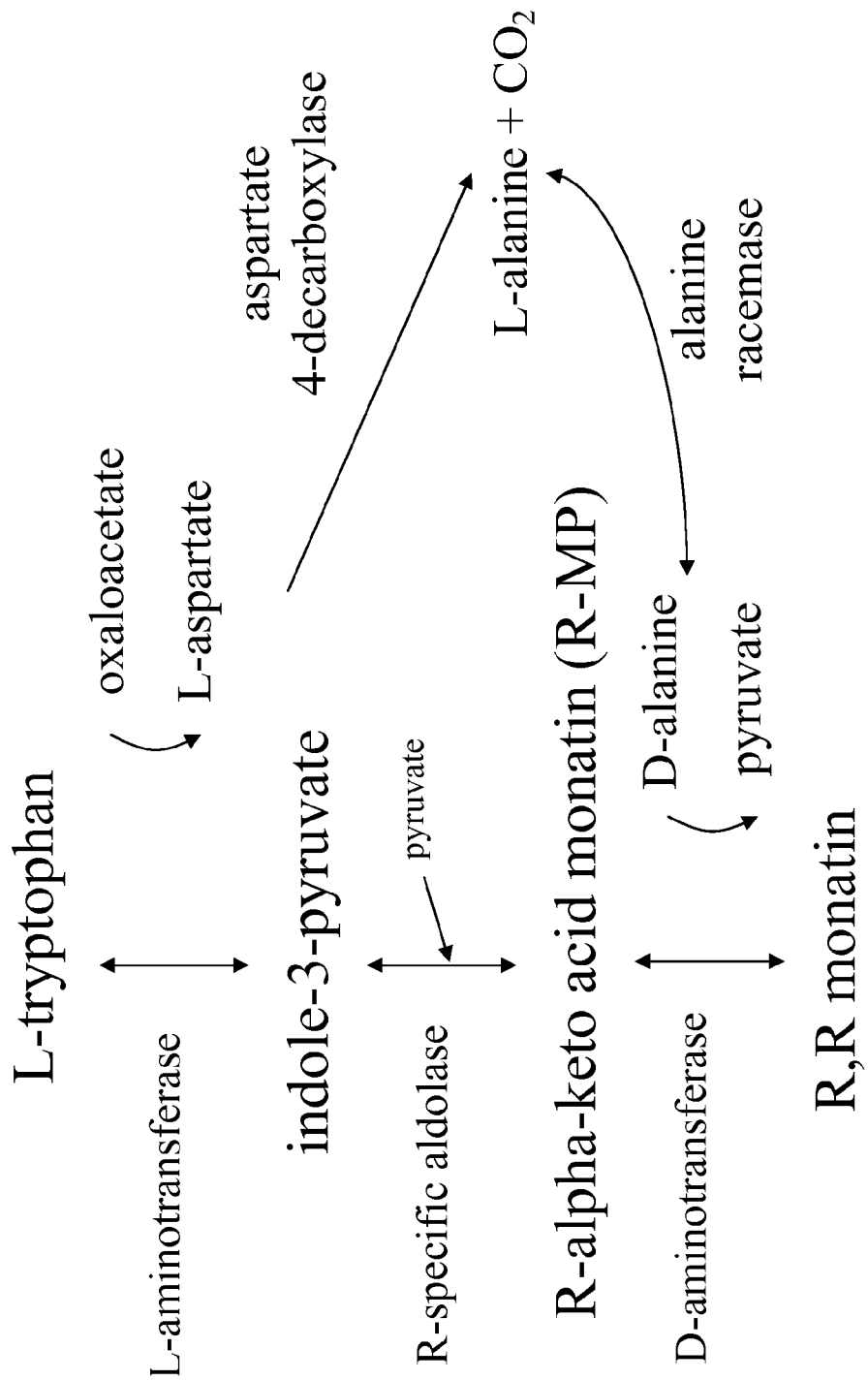
FIG. 6 is a flow chart that shows an example of yet another process for producing R,R monatin in accordance with the present invention. In this example, the process includes recycling the L-amino acid produced in the reaction forming indole-3-pyruvate with the D-amino acid used as a reactant with R-MP in the reaction forming R,R monatin through a series of conversion reactions. In the specific example diagrammed in FIG. 6, L-tryptophan is reversibly reacted with an L-aminotransferase and oxaloacetate to produce indole-3-pyruvate and L-aspartate. Indole-3-pyruvate is reacted in a reversible manner with pyruvate and an R-specific aldolase and converted to R-alpha-keto acid monatin (R-MP), and R-MP is reversibly reacted with a D-aminotransferase and D-alanine to form R,R monatin and pyruvate. The L-aspartate is converted to L-alanine and $CO_2$ using an aspartate 4-decarboxylase. The L-alanine is converted to D-alanine with an alanine racemase. For the purposes of the invention, it is not required that the reactions shown as being reversible proceed in the reverse direction.
Figure 7:
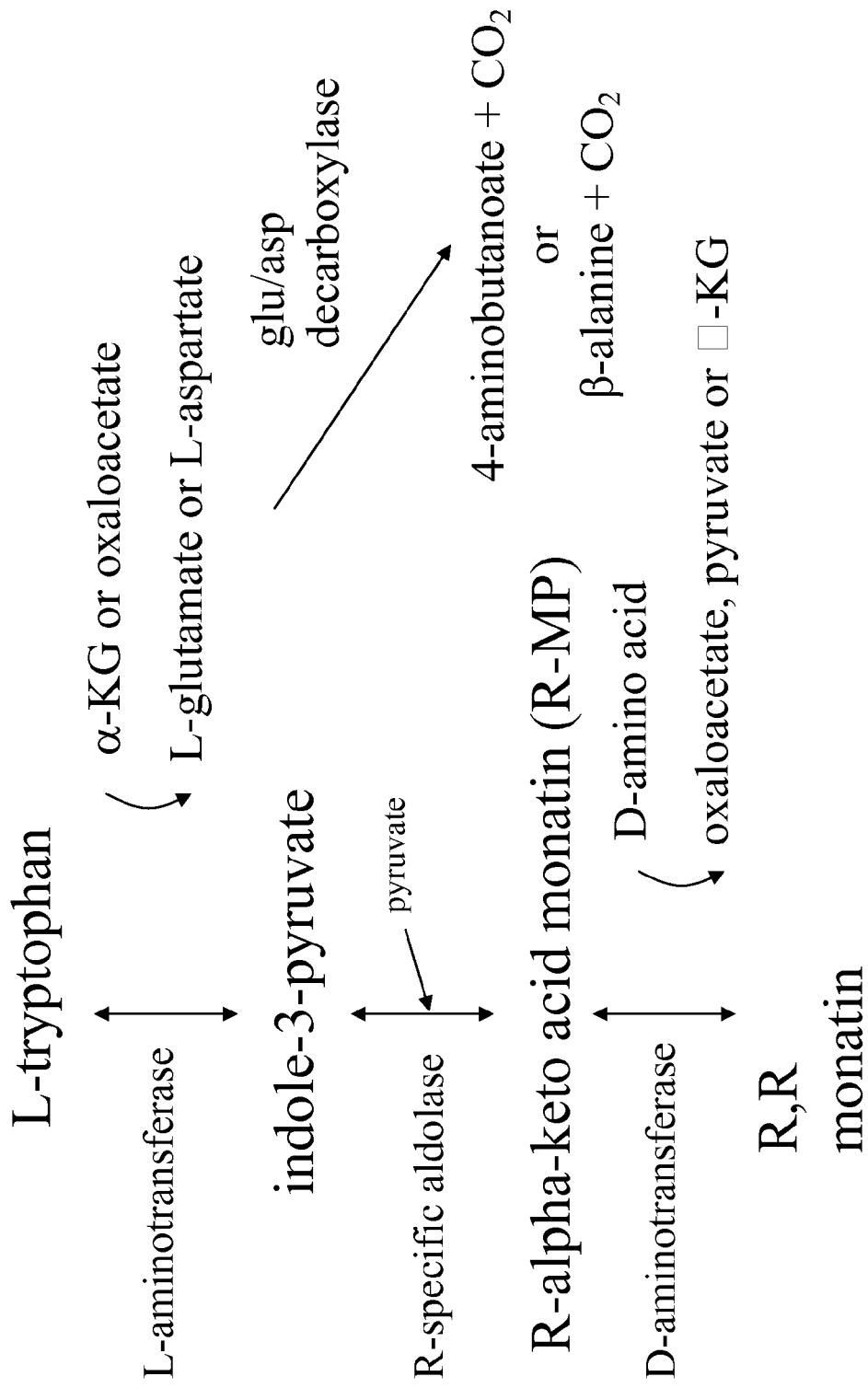
FIG. 7 is a flow chart that shows an example of yet another process for producing R,R monatin in accordance with the present invention. In this example, the process includes pushing the L-tryptophan reaction forward (i.e., driving the reaction toward the production of indole-3-pyruvate) by converting the L-amino acid byproduct of that reaction into another product. In this example, the L-amino acid L-aspartate byproduct is converted into L-alanine in an irreversible reaction using a decarboxylase. In the specific example diagrammed in FIG. 7, L-tryptophan is reversibly reacted with an L-aminotransferase and with alpha-ketoglutarate ($\alpha$-KG) or oxaloacetate to produce indole-3-pyruvate and L-glutamate (if $\alpha$-KG is used) or L-aspartate (if oxaloacetate is used). Indole-3-pyruvate is reversibly reacted with pyruvate and an R-specific aldolase and converted to R-alpha-keto acid monatin (R-MP). R-MP is reacted in a reversible manner with a D-aminotransferase and a D-amino acid to form R,R monatin and any of oxaloacetate, pyruvate or $\alpha$-KG. The L-glutamate or L-aspartate that was a product of the L-aminotransferase reaction is converted to either 4-aminobutanoate and $CO_2$ (if L-glutamate is the substrate) or to $\beta$-alanine and $CO_2$ (if L-aspartate is the substrate) using a glutamic acid or an aspartate decarboxylase. For the purposes of the invention, it is not required that the reactions shown as being reversible proceed in the reverse direction.
Figure 8:
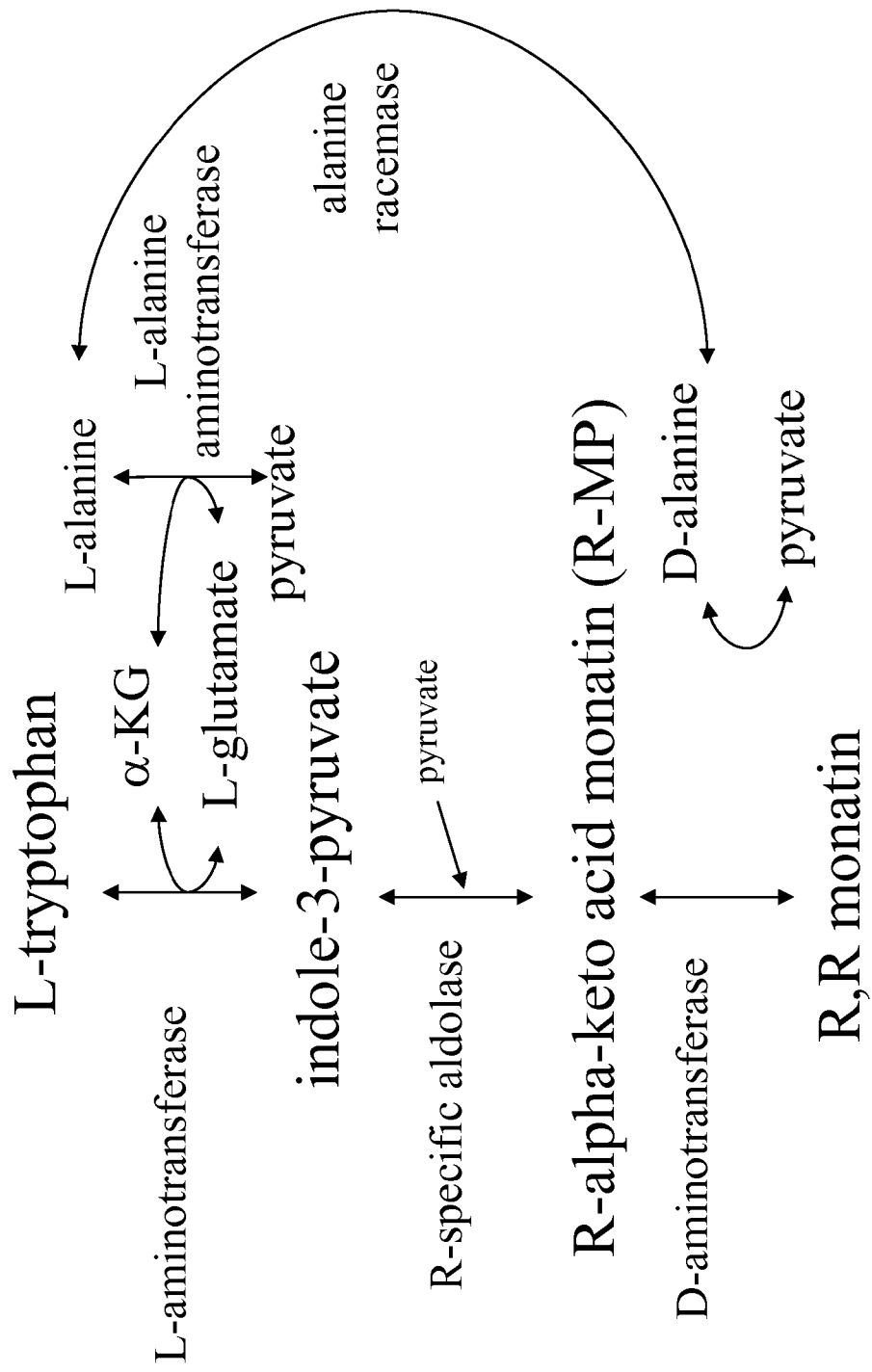
FIG. 8 is a flow chart that shows an example of yet another process for producing R,R monatin in accordance with the present invention. In this example, the process includes recycling the amino acid byproduct of the L-tryptophan reaction with the amino acid reactant of the R-MP reaction through a series of conversion reactions. In the specific example diagrammed in FIG. 8, L-tryptophan is reacted reversibly with an L-aminotransferase and with alpha-ketoglutarate ($\alpha$-KG) to produce indole-3-pyruvate and L-glutamate. Indole-3-pyruvate is reversibly reacted with pyruvate and an R-specific aldolase and converted to R-alpha-keto acid monatin (R-MP). R-MP is reacted in a reversible manner with a D-aminotransferase and D-alanine to form R,R monatin and pyruvate. An L-alanine aminotransferase and pyruvate are used to reversibly convert the L-glutamate that was a product of the L-aminotransferase reaction back to $\alpha$-KG, with L-alanine as a co-product. An alanine racemase reversibly converts the L-alanine to the D-alanine that is useful in the third reaction, (the D-aminotransferase reaction. For the purposes of the invention, it is not required that the reactions shown as being reversible proceed in the reverse direction.

FIGS. 6-8 also illustrate modifications to the pathway of FIG. 1. The pathways illustrated in FIGS. 6-8 provide methods to push equilibrium reactions forward by removing byproduct of the tryptophan reaction and in some cases providing substrate for the MP reaction.

Turning to FIG. 6, the pathway shown removes the L-amino acid product of the reaction coupled to the tryptophan reaction by converting it to a different L-amino acid, and then provides a substrate for reaction coupled to the MP reaction by converting the newly formed L-amino acid to a D-amino acid. Specifically, L-tryptophan is shown to react alongside oxaloacetate to form indole-3-pyruvate and L-aspartate. An aspartate 4-decarboxylase (EC 4.1.1.12) or functional equivalent is used to facilitate the conversion of L-aspartate to L-alanine and carbon dioxide, and an enzyme with alanine racemase activity is used to facilitate the conversion of L-alanine to D-alanine, which D-alanine can serve as an amino donor for the conversion of R-MP to monatin.

Turning to FIG. 7, the pathway shown illustrates additional methods for removing the L-amino acid product of the reaction coupled to the tryptophan reaction. Embodiments as presented in the figure produce a byproduct(s) that is unavailable to react in the reverse direction, for example due to volatility (such as carbon dioxide) or by spontaneous conversion to an unreactive endproduct. An example of such an approach includes where α-KG reacts alongside L-tryptophan to produce L-glutamate, a glutamate decarboxylase (EC 4.1.1.15) or functional equivalent can be provided which can facilitate the conversion of L-glutamate to 4-aminobutanoate (with carbon dioxide as a byproduct). Non-limiting examples of potential sources from which the L-glutamate decarboxylase may be derived include: *Clostridium perfringens, C. welchii*, or *E. coli*.

Another example of such an approach for moving the tryptophan reaction forward includes where oxaloacetate reacts alongside L-tryptophan, an aspartate decarboxylase (EC 4.1.1.1.1) or functional equivalent can be provided to facilitate the conversion of L-aspartate to β-alanine (with carbon dioxide as a byproduct).

Turning to FIG. 8, the pathway shown illustrates yet additional methods for removing the L-amino acid product of the reaction coupled to the tryptophan reaction and providing a substrate for the reaction coupled to the MP reaction. Specifically, where α-KG reacts alongside L-tryptophan to form L-glutamate, an enzyme with L-alanine aminotransferase activity and pyruvate can be provided, wherein the L-alanine aminotransferase enzyme facilitates the reaction of pyruvate and L-glutamate to form L-alanine. An alanine racemase or functional equivalent can also be provided in order to facilitate the conversion of the L-alanine to D-alanine, which D-alanine can be used as a substrate along with MP to form monatin and pyruvate. See Examples 18 and 21.

Biosynthetic Pathways to Produce R,R and Other Stereoisomers of Monatin Derivatives The methods of the described invention include using the polypeptides with aldolase activity described herein may be used to facilitate the reaction between a substituted indole-3-pyruvate and a C3 carbon source.

Enzymes useful for the facilitating a reaction between a substituted indole-3-pyruvate and a C3 carbon source include one or more polypeptides with aldolase activity of any of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, SEQ ID NO:174, SEQ ID NO:176, SEQ ID NO:178, SEQ ID NO:180, SEQ ID NO:182, SEQ ID NO:184, SEQ ID NO:186, SEQ ID NO:188, SEQ ID NO:190, SEQ ID NO:192, SEQ ID NO:194, SEQ ID NO:196, SEQ ID NO:198, SEQ ID NO:200, SEQ ID NO:202, SEQ ID NO:204, SEQ ID NO:206, SEQ ID NO:208, SEQ ID NO:210, SEQ ID NO:212, SEQ ID NO:214, SEQ ID NO:216, SEQ ID NO:218, SEQ ID NO:220, SEQ ID NO:222, SEQ ID NO:224, SEQ ID NO:226, SEQ ID NO:228, SEQ ID NO:230, SEQ ID NO:232, SEQ ID NO:234, SEQ ID NO:236, SEQ ID NO:238, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:260, SEQ ID NO:262, SEQ ID NO:264, SEQ ID NO:266, SEQ ID NO:268, SEQ ID NO:270, SEQ ID NO:272, SEQ ID NO:274, SEQ ID NO:276, SEQ ID NO:278, SEQ ID NO:280, SEQ ID NO:282, SEQ ID NO:284, SEQ ID NO:286, SEQ ID NO:288, SEQ ID NO:290, SEQ ID NO:292, SEQ ID NO:294, SEQ ID NO:296, SEQ ID NO:298, SEQ ID NO:300, SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:320, SEQ ID NO:322, SEQ ID NO:324, SEQ ID NO:326, SEQ ID NO:328, SEQ ID NO:330, SEQ ID NO:332, or SEQ ID NO:334, or fragments or subsequences thereof having aldolase activity.

In one embodiment, one or more polypeptides with HMG aldolase activity of any of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, SEQ ID NO:174, SEQ ID NO:176, SEQ ID NO:178, SEQ ID NO:180, SEQ ID NO:182, SEQ ID NO:184, SEQ ID NO:186, SEQ ID NO:188, SEQ ID NO:190, SEQ ID NO:192, SEQ ID NO:194, SEQ ID NO:196, SEQ ID NO:198, SEQ ID NO:200, SEQ ID NO:202, SEQ ID NO:204, SEQ ID NO:206, SEQ ID NO:208, SEQ ID NO:210, SEQ ID NO:212, SEQ ID NO:214, SEQ ID NO:216, SEQ ID NO:218, SEQ ID NO:220, SEQ ID NO:222, SEQ ID NO:224, SEQ ID NO:226, SEQ ID NO:228, SEQ ID NO:230, SEQ ID NO:232, SEQ ID NO:234, SEQ ID NO:236, SEQ ID NO:238, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:260, SEQ ID NO:262, SEQ ID NO:264, SEQ ID NO:266, SEQ ID NO:268, SEQ ID NO:270, SEQ ID NO:272, SEQ ID NO:274, SEQ ID NO:276, SEQ ID NO:278, SEQ ID NO:280, SEQ ID NO:282, SEQ ID NO:284, SEQ ID NO:286, SEQ ID NO:288, SEQ ID NO:290, SEQ ID NO:292, SEQ ID NO:294, SEQ ID NO:296, SEQ ID NO:298, SEQ ID NO:300, SEQ ID NO:302, SEQ ID NO:304 or fragments or subsequences thereof having aldolase activity may be useful in facilitating a reaction between a substituted indole-3-pyruvate and a C3 carbon source.

In another embodiment, one or more polypeptides with KHG aldolase activity of any of SEQ ID NO:306, SEQ ID NO:308, SEQ ID NO:310, SEQ ID NO:312, SEQ ID NO:314, SEQ ID NO:316, SEQ ID NO:318, SEQ ID NO:320, SEQ ID NO:322, SEQ ID NO:324, SEQ ID NO:326, SEQ ID NO:328, SEQ ID NO:330, SEQ ID NO:332, or SEQ ID NO:334 or fragments or subsequences thereof having aldolase activity may be useful in facilitating a reaction between a substituted indole-3-pyruvate and a C3 carbon source.

Alternatively, one or more polypeptides with aldolase activity encoded by a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a nucleic acid in accordance with the invention, including SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:279, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305, SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, and SEQ ID NO:338 over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more residues may be useful in facilitating a reaction between a substituted indole-3-pyruvate and a C3 carbon source.

In one embodiment of the invention, one or more polypeptides with HMG aldolase activity encoded by a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a nucleic acid in accordance with the invention, including SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO: 121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:279, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305 over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more residues may be useful in facilitating a reaction between a substituted indole-3-pyruvate and a C3 carbon source.

In another embodiment of the invention, one or more polypeptides with KHG aldolase activity encoded by a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a nucleic acid in accordance with the invention, including SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, and SEQ ID NO:338 over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more residues may be useful in facilitating a reaction between a substituted indole-3-pyruvate and a C3 carbon source.

One or more polypeptides with aldolase activity encoded by a nucleic acid sequence that hybridizes under stringent condition to a nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:279, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305, SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, and SEQ ID NO:338 may be useful in facilitating a reaction between a substituted indole-3-pyruvate and a C3 carbon source.

In one embodiment of the invention, one or more polypeptides with HMG aldolase activity encoded by a nucleic acid sequence that hybridizes under stringent condition to a nucleic acid of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, SEQ ID NO:273, SEQ ID NO:275, SEQ ID NO:277, SEQ ID NO:279, SEQ ID NO:281, SEQ ID NO:283, SEQ ID NO:285, SEQ ID NO:287, SEQ ID NO:289, SEQ ID NO:291, SEQ ID NO:293, SEQ ID NO:295, SEQ ID NO:297, SEQ ID NO:299, SEQ ID NO:301, SEQ ID NO:303, SEQ ID NO:305 may be useful in facilitating the reaction between the substituted indole-3-pyruvate and the C3 carbon source.

In another embodiment of the invention, one or more polypeptides with KHG aldolase activity encoded by a nucleic acid sequence that hybridizes under stringent condition to a nucleic acid of SEQ ID NO:307, SEQ ID NO:309, SEQ ID NO:311, SEQ ID NO:313, SEQ ID NO:315, SEQ ID NO:317, SEQ ID NO:319, SEQ ID NO:321, SEQ ID NO:323, SEQ ID NO:325, SEQ ID NO:327, SEQ ID NO:329, SEQ ID NO:331, SEQ ID NO:333, SEQ ID NO:335, SEQ ID NO:336, SEQ ID NO:337, and SEQ ID NO:338 may be useful in facilitating a reaction between a substituted indole-3-pyruvate and a C3 carbon source.

In one embodiment, the substituent group of the substituted indole-3-pyruvate is a halogen atom attached to any carbon atom of the indole ring. In another embodiment, the substituent group is a chlorine atom attached to any carbon of the indole ring. In yet another embodiment, the monatin derivative is 4-hydroxy-4-(6-methylindole-3-ylmethyl)glutamic acid.

Polypeptides having aldolase activity, and in accordance with some embodiments of the invention, may be used in a multi-step pathway in which one or more step is a chemical synthesis reaction. For example, in some embodiments, one or more polypeptides having aldolase activity can facilitate a reaction between pyruvate and indole-3-pyruvate to yield monatin precursor. The monatin precursor can then be purified. A reductive amination reaction of the monatin precursor can then be utilized to yield monatin.

Polypeptides having aldolase activity, and in accordance with some embodiments of the invention, as well as the other enzymes used in the process for producing monatin and monatin derivatives may be used in pure, crude, isolated, or ammonium sulfate suspension form.

Polypeptides having aldolase activity, and in accordance with some embodiments of the invention, may be optimized using stabilizing agents, including dithiothreitol ("DTT") and β-mercaptoethanol.

Monatin or monatin derivative that is produced utilizing one or more of the polypeptides disclosed herein, is generally at least about 50 to about 99% R,R-monatin or R,R-monatin derivative, by weight of the total monatin or monatin derivative produced. In other embodiments, the monatin or monatin derivative produced utilizing one or more of the polypeptides disclosed herein, is greater than 60% R,R-monatin or R,R-monatin derivative, by weight of the total monatin produced; for example, the R,R-monatin or R,R-monatin derivative is 70%, 75%, 80%, 85%, 90%, 91%, 92%, 93%, 94%, 95%, 96%, 97%, 98% or 99% of the total monatin or monatin derivative produced Alternatively, various amounts of two or more preparations of monatin or monatin derivative can be combined so as to result in a preparation that is a desired percentage of R,R-monatin or R,R-monatin derivative. For example, a monatin preparation that is 60% R,R-monatin can be combined with a monatin preparation that is 90% R,R-monatin; if equal amounts of 60% and 90% R,R-monatin preparations are combined, the resulting monatin preparation would be 75% R,R-monatin.

The monatin or monatin derivative, or an intermediate (including monatin precursor), produced utilizing one or more of the polypeptides disclosed herein, may be purified from the components of the reaction. In one embodiment, the monatin, monatin derivative or intermediate, such as monatin precursor, may be purified simply by removing the substance that is to be purified from the enzyme preparation in which it was synthesized.

In other embodiments, the intermediate, monatin precursor, monatin or monatin derivative is purified from a preparation in which it was synthesized so that the resulting "purified" composition or preparation is at least about 5-60% monatin by weight of total organic compounds. In another embodiment, the monatin, monatin derivative or intermediate, such as monatin precursor, may be purified to a degree of purity of at least about 70%, 80%, 90%, 95% or 99% by weight of total organic compounds. The monatin, monatin derivative or the intermediate (including monatin precursor), produced utilizing one or more of the polypeptides disclosed herein, may be purified from the components of the reaction by any method known to a person of ordinary skill in the art. Optimally, the purified monatin or intermediate may be repeatedly recrystallized until the desired degree of purity is achieved.

The following examples are offered to illustrate, but not to limit the claimed invention.

EXAMPLES

Example 1

Detection of Monatin, Monatin Precursor, Tryptophan, Alanine, Aspartate, and Glutamate This example describes methods used to detect the presence of monatin, monatin precursor ("MP"), tryptophan, aspartate, alanine, and glutamate. It also describes a method for the separation and detection of the four stereoisomers of monatin.

LC/MS/MS Multiple Reaction Monitoring ("MRM") Analysis of Monatin and Tryptophan Analyses of mixtures for monatin and tryptophan derived from in vitro or in vivo biochemical reactions were performed using a Waters/Micromass liquid chromatography-tandem mass spectrometry (LC/MS/MS) instrument including a Waters 2795 liquid chromatograph with a Waters 996 Photo-Diode Array (PDA) absorbance monitor placed in series between the chromatograph and a Micromass Quattro Ultima triple quadrupole mass spectrometer. LC separations were made using an Xterra MS $C_8$ reversed-phase chromatography column, 2.1 mm×250 mm at 40° C. The LC mobile phase consisted of A) water containing either (i) 0.05% (v/v) trifluoroacetic acid or (ii) 0.3% formic acid and 10 mM ammonium formate and B) methanol containing either (i) 0.05% (v/v) trifluoroacetic acid or (ii) 0.3% formic acid and 10 mM ammonium formate.

If the LC mobile phase consisted of A) water containing 0.05% (v/v) trifluoroacetic acid and B) methanol containing 0.05% (v/v) trifluoroacetic acid, gradient elution was linear from 5% B to 35% B, 0-4 minutes, linear from 35% B to 60% B, 4-6.5 minutes, linear from 60% B to 90% B, 6.5-7 minutes, isocratic at 90% B 7-11 minutes, linear from 90% B to 95% B, 11-12 minutes, linear from 95% B to 5% B, 12-13 minutes, with a 2 minute re-equilibration period between runs. The flow rate was 0.25 mL/min, and PDA absorbance was monitored from 200 nm to 400 nm. All parameters of the ESI-MS were optimized and selected based on generation of protonated molecular ions ([M+H]+) of the analytes of interest, and production of characteristic fragment ions. The following instrumental parameters were used for LC/MS/MS Multiple Reaction Monitoring (MRM) analysis of monatin and tryptophan: Capillary: 3.5 kV; Cone: 40 V; Hex 1: 20 V; Aperture: 0 V; Hex 2: 0 V; Source temperature: 100° C.; Desolvation temperature: 350° C.; Desolvation gas: 500 L/h; Cone gas: 50 L/h; Low mass resolution (Q1): 12.0; High mass resolution (Q1): 12.0; Ion energy: 0.2; Entrance: −5 V; Collision Energy: 8; Exit: 1V; Low mass resolution (Q2): 15; High mass resolution (Q2): 15; Ion energy (Q2): 3.5; Multiplier: 650. Five monatin-specific parent-to daughter MRM transitions are used to specifically detect monatin in in vitro and in vivo reactions. The transitions monitored are 293.1 to 158.3, 293.1 to 168.2, 293.1 to 211.2, 293.1 to 230.2, and 293.1 to 257.2. Tryptophan is monitored with the MRM transition 204.7 to 146.4. For internal standard quantification of monatin and tryptophan, four calibration standards containing four different ratios of each analyte to d5-tryptophan and d5-monatin, are analyzed. These data are subjected to a linear least squares analysis to form a calibration curve for monatin and tryptophan. To each sample is added a fixed amount of d5-tryptophan and d5-monatin (d5-monatin was synthesized from d5-tryptophan according to the methods from WO03/091396 A2), and the response ratios (monatin/d5-monatin; tryptophan/d5-tryptophan) used in conjunction with the calibration curves described above to calculate the amount of each analyte in the mixtures.

If the LC mobile phase was A) water containing 0.3% formic acid and 10 mM ammonium formate and B) methanol containing 0.3% formic acid and 10 mM ammonium formate, the gradient elution was linear from 5% B to 45% B, 0-8.5 minutes, linear from 45% B to 90% B, 8.5-9 minutes, isocratic from 90% B to 90% B, 9-12.5 minutes, linear from 95% B to 5% B, 12.5-13 minutes, with a 4 minute re-equilibration period between runs. The flow rate was 0.27 mL/min, and PDA absorbance was monitored from 210 nm to 400 nm. All parameters of the ESI-MS were optimized and selected based on generation of protonated molecular ions ([M+H]+) of the analytes of interest, and production of characteristic fragment ions. The instrumental parameters used for this secondary mobile phase are the same as above. Four monatin-specific parent-to daughter MRM transitions and one tryptophan specific parent to daughter transition are used to specifically detect monatin and tryptophan in in vitro and in vivo reactions. The transitions monitored are 293.1 to 158.0, 293.1 to 168.0, 293.1 to 211.5, and 293.1 to 257.0. Tryptophan is monitored with the MRM transition 205.2 to 146.1. For internal standard quantification of monatin and tryptophan, four calibration standards containing four different ratios of each analyte to d5-tryptophan and d5-monatin, are analyzed. These data are subjected to a linear least squares analysis to form a calibration curve for monatin and tryptophan. To each sample is added a fixed amount of d5-tryptophan and d5-monatin (d5-monatin was synthesized from d5-tryptophan according to the methods from WO03/091396 A2), and the response ratios (monatin/d5-monatin; tryptophan/d5-tryptophan) in conjunction with the calibration curves described above are used to calculate the amount of each analyte in the mixtures. Parent to daughter mass transitions monitored for d5-tryptophan and d5-monatin are 210.2 to 151.1, and 298.1 to 172.0 respectively.

Accurate Mass Measurement of Monatin

High resolution MS analysis was carried out using an Applied Biosystems-Perkin Elmer Q-Star hybrid quadrupole/time-of-flight mass spectrometer. The measured mass for protonated monatin used tryptophan as an internal mass calibration standard. The calculated mass of protonated monatin, based on the elemental composition C14H17N2O5 is 293.1137. Monatin produced using the biocatalytic process described in Examples 2 and 3 showed a measured mass of 293.1144. This is a mass measurement error of less than 2 parts per million ("ppm"), providing conclusive evidence of the elemental composition of monatin produced enzymatically.

Chiral LC/MS/MS ("MRM") Measurement of Monatin

Determination of the stereoisomer distribution of monatin in in vitro and in vivo reactions was accomplished by derivitization with 1-fluoro-2-4-dinitrophenyl-5-L-alanine amide ("FDAA"), followed by reversed-phase LC/MS/MS MRM measurement.

Derivatization of Monatin with FDAA

To 50 µL of sample or standard and 10 µL of internal standard was added either 100 µL or 200 µL of a 1% solution of FDAA in acetone. Twenty or forty µL, respectively, of 1.0 M sodium bicarbonate was added, and the mixture incubated for 1 h at 40° C. with occasional mixing. The sample was removed and cooled, and neutralized with 20 µL of 2.0 M HCl (more HCl may be required to effect neutralization of a buffered biological mixture). After degassing was complete, samples were ready for analysis by LC/MS/MS.

LC/MS/MS Multiple Reaction Monitoring for the Determination of the Stereoisomer Distribution of Monatin in in vitro and in vivo Reactions Analyses were performed using the LC/MS/MS instrumentation described above. LC separations capable of separating all four stereoisomers of monatin (specifically FDAA-monatin) were performed on a Phenomenex Luna 2.0×250 mm (3 µm) C18 (2) reversed phase chromatography column at 40° C. The LC mobile phase consisted of A) water containing 0.05% (mass/volume) ammonium acetate and B) acetonitrile. The elution was isocratic at 13% B, 0-2 minutes, linear from 13% B to 30% B, 2-15 minutes, linear from 30% B to 80% B, 15-16 minutes, isocratic at 80% B 16-21 minutes, and linear from 80% B to 13% B, 21-22 minutes, with an 8 minute re-equilibration period between runs. The flow rate was 0.23 mL/min, and PDA absorbance was monitored from 200 nm to 400 nm. All parameters of the ESI-MS were optimized and selected based on generation of deprotonated molecular ions ([M−H]−) of FDAA-monatin, and production of characteristic fragment ions.

The following instrumental parameters were used for LC/MS analysis of monatin in the negative ion ESI/MS mode: Capillary: 2.0 kV; Cone: 25 V; Hex 1: 10 V; Aperture: 0 V; Hex 2: 0 V; Source temperature: 100° C.; Desolvation temperature: 350° C.; Desolvation gas: 500 L/h; Cone gas: 50 L/h; Low mass resolution (Q1): 12.0; High mass resolution (Q1): 12.0; Ion energy: 0.2; Entrance: −5V; Collision Energy: 20; Exit: 1V; Low mass resolution (Q2): 12; High mass resolution (Q2): 12; Ion energy (Q2): 3.0; Multiplier: 650. Three FDAA-monatin-specific parent-to daughter transitions are used to specifically detect FDAA-monatin in in vitro and in vivo reactions. The transitions monitored for monatin are 543.2 to 268.1, 543.2 to 499.3, and 543.2 to 525.3. Monatin internal standard derivative mass transition monitored was 548.2 to 530.3. Identification of FDAA-monatin stereoisomers is based on chromatographic retention time as compared to purified synthetic monatin stereoisomers, and mass spectral data. An internal standard is used to monitor the progress of the reaction and for confirmation of retention time of the S,S stereoisomer.

Liquid Chromatography-Post Column Fluorescence Detection of Amino Acids Including Glutamate and Alanine Liquid chromatography with post-column fluorescence detection (LC/OPA) for the determination of glutamate and alanine in in vitro and in vivo reactions was performed on a Waters 2690 LC system or equivalent combined with a Waters 474 scanning fluorescence detector, and a Waters post-column reaction module. Semi-quantitative analyses of monatin and tryptophan were also performed using this method. LC separations were performed on an Interaction-Sodium loaded ion exchange column at 60° C. Mobile phase A was Pickering Na 328 buffer (Pickering Laboratories, Inc.; Mountain View, Calif.). Mobile phase B was Pickering Na 740 buffer. The gradient elution was from 0% B to 100% B, 0-20 minutes, isocratic at 100% B, 20-36 minutes, and linear from 100% B to 0% B, 36-37 minutes, with at least a 5 minute re-equilibration period between runs, depending on sample matrix. The flow rate for the mobile phase was 0.5 mL/min. The flow rate for the OPA post-column derivatization solution was 0.5 mL/min. The fluorescence detector settings were EX 338-340 nm and Em 420-425 nm. Norleucine was employed as an internal standard for the analysis. Identification of amino acids was based on chromatographic retention time data for purified standards.

Detection of L- and D-Amino Acids by LC/MS/MS

Samples containing a mixture of L- and D-amino acids such as lysine, alanine, methionine, tyrosine, leucine, phenylalanine, tryptophan, glutamate, and aspartate from biochemical reaction experiments were first treated with formic acid to denature protein. The sample was then centrifuged and filtered through a 0.45 µm nylon syringe filter prior to LC/MS/MS analysis. Identification of L- and D-amino acids was based on retention time and mass selective detection. LC separation was accomplished by using Waters 2690 liquid chromatography system and an ASTEC 2.1 mm×250 mm Chirobiotic TAG chromatography column with column temperature set at 45° C. LC mobile phase A and B were 0.25% acetic acid and 0.25% acetic acid in methanol, respectively. Isocratic elution was used for all methods to separate the L and D isomers. Lysine was eluted using 80% mobile phase A, and 20% B. Glutamate, alanine, and methionine were separated with elution of 60% mobile phase A and 40% B and a flow rate of 0.25 mL/min. Aspartate, tryptophan, tyrosine, leucine, and phenylalanine were separated isomerically with 30% mobile phase A and 70% B with a flow rate of 0.3 mL/min for all but phenylalanine, which was run at a flow rate of 0.25 mL/min.

The detection system for analysis of L- and D-amino acids included a Waters 996 Photo-Diode Array (PDA) detector and a Micromass Quattro Ultima triple quadrupole mass spectrometer. The PDA, scanning from 195 to 350 nm, was placed in series between the chromatography system and the mass spectrometer. Parameters for the Micromass Quattro Ultima triple quadrupole mass spectrometer operating in positive electrospray ionization mode (+ESI) were set as the following: Capillary: 3.0 kV; Cone: 20 V; Hex 1: 15 V; Aperture: 1 V; Hex 2: 0 V; Source temperature: 100° C.; Desolvation temperature: 350° C.; Desolvation gas: 530 L/h; Cone gas: 30 L/h; Low mass Q1 resolution: 12.5; High mass Q1 resolution: 12.5; Ion energy 1: 0.2; Entrance: −5; Collision: 8; Exit 1: 10; Low mass Q2 resolution: 12.5; High mass Q2 resolution: 12.5; Ion energy 2: 0.5; Multiplier: 650 V. MS/MS experiments with Multiple Reaction Monitoring (MRM) mode were set up to selectively monitor reaction transitions of 147.8 to 84.2 and 147.8 to 102.1 for glutamate, 134.00 to 74.30, and 134.00 to 88.2 for aspartate, 147.3 to 85.0 for lysine, 150.3 to 104.8 for methionine, 182.3 to 137.0 for tyrosine, 132.3 to 87.0 for leucine, and 166.3 to 121.0 for phenylalanine. In the case where two transitions are listed, the latter transitions were used for quantification. For tryptophan, MS/MS experiments with Multiple Reaction Monitoring (MRM) mode were set up to selectively monitor reaction transitions of 205.2 to 118.2, 205.2 to 146.1, and 205.2 to 188.2, and the transition from 212.1 to 151.1 for d8-DL tryptophan. Tryptophan quantification was achieved by determining the ratio of analyte response of transition 205.2 to 146.1 to that of the internal standard, d8-D,L tryptophan. Alternatively, quantification of tryptophan, glutamate, and aspartic acids were based off signal responses of m/z=146.5, m/z=102.1, and m/z=88.2, respectively.

Production of Monatin and Monatin Precursor ("MP") for Standards and for Assays

Production of Monatin

A racemic mixture of R,R and S,S monatin was synthetically produced as described in U.S. Pat. No. 5,128,482.

The R,R and S,S monatin were separated by a derivatization and hydrolysis step. Briefly, the monatin racemic mixture was esterified, the free amino group was blocked with Cbz, a lactone was formed, and the S,S lactone was selectively hydrolyzed using an immobilized protease enzyme. The monatin can also be separated as described in Bassoli, A. et al., Eur. J. Org. Chem., 8:1652-1658, (2005).

MP Production

R-MP was produced by the transamination of R,R monatin using AT-103 broad range D-aminotransferase (BioCatalytics, Pasadena, Calif.) in 0.1 M potassium phosphate buffer, using sodium pyruvate as the amino acceptor. S-MP was produced by the transamination of S,S monatin using AT-102 L-aminotransferase (BioCatalytics, Pasadena, Calif.) in 0.1 M potassium phosphate buffer, using sodium pyruvate as the amino acceptor. Both reactions were carried out at 30° C. and at a pH of approximately 8.0-8.3, for approximately 20 hours. Both compounds were purified using preparative scale HPLC with a Rohm and Haas (Philadelphia, Pa.) hydrophobic resin (XADTM1600), eluting in water. Samples containing greater than 90% purity monatin precursor were collected and freeze-dried.

Example 2

Detection of Monatin Precursor

This example describes methods used for the separation and detection of the two enantiomers of monatin precursor.

Non-chiral Method for Detection of Monatin Precursor

Reaction samples from 96-well plates were injected onto an Agilent Zorbax RX-C18, 3.5 um, 3.0×150 mm column using a CTCPal auto-sampler (LEAP Technologies, Carrboro, N.C.). Products were separated using a H2O/ACN (0.1% Formic acid) gradient:

| Time: 0.00 min | 5% B |
| Time: 4.00 min | 100% B |
| Time: 5.00 min | 100% B |
| Time: 5.10 min | 5% B |
| Time: 6.50 min | 5% B |

The gradient was provided by LC-10ADvp pumps (Shimadzu, Kyoto, Japan) at 0.8 mL/min. Products were detected using API4000 Turbolon-Spray triple-quad mass spectrometer (Applied Biosystems, Foster City, Calif.). Ion spray and Multiple-ion monitoring were performed for the analytes of interest in the negative ion mode, and each analysis lasted 6.5 minutes.

Pyruvate=87.1 [M−H+]−
Indole-3-pyruvate=202.1 [M−H+]−
Product=290.0 [M−H+]−

Chiral CE Analysis of R & S Monatin Precursors

A P/ACE™ MDQ capillary electrophoresis instrument (Beckman Coulter, Fullerton, Calif.) was used. The Chiral Development kit was used and includes small amounts of several chiral selectors, necessary buffers and 2 capillaries (Beckman Coulter, Fullerton, Calif.). Alternatively, for the MP assay only, the following reagents and other supplies can be obtained separately from Beckman Coulter (Fullerton, Calif.) or elsewhere:

Coated capillary N-CHO; 50 um ID, 65 cm total length or fused silica capillary.

25 mM phosphate buffer, pH 5

25 mg hydroxypropyl-β-cyclodextrin

Capillary conditioning solution, 10 mL (alternatively, can use 0.5% polyethylene oxide solution, $M_w$ 600,000 or 300,000 Daltons)

Capillary Electrophoresis ("CE") Analysis

A neutral coated capillary, 50 μm ID, 60 cm (50 cm to detection) or 30 (20) cm was used along with DAD detection (or simple UV) at 214 nm. The separation capillary was thermostated at 15° C., samples at 4° C. The separation buffer was 20 mM hydroxypropyl-β-cycylodextrin, 25 mM phosphate, pH 5. Sample injection was typically 0.5 psi, 5 s. Separation was at 500 V/cm, reversed polarity (15 kV for 30 cm capillary, 30 kV for 60 cm). Typical current used during separation was −28 μA. Typical migration times for MP peaks were around 3.5 minutes (20 cm effective length) or 8 minutes (50 cm)

An optional capillary cleaning/washing/conditioning step, prior to sample runs used $H_2O$ 4 minutes, 0.1 M HCl 1 minutes, $H_2O$ 1.5 minutes, capillary conditioning solution 4 minutes, $H_2O$, 1 minute, separation buffer 4 minutes.

A summary of the run method was: separation buffer rinse 1-2 minutes, sample injection 5 s at 0.5 psi, separation 5-10 minutes at reversed voltage polarity 15 or 30 kV, depending on capillary length.

Example 3

General Assay for Pyruvate Aldolases

An exemplary method to measure the activity of different pyruvate aldolases uses a general substrate, 4-Carboxy-4-hydroxy-2-oxoadipate (CHA). The CHA assay was adapted from literature assays (eg. See E. E. Dekker & R. P. Kitson, J. Biol. Chem. 267, 10507-10514, 1992). A typical assay comprised 50 mM sodium phosphate pH 7.5, 1 mM $MgCl_2$, 1 mM CHA, 10 μg/ml D-lactate dehydrogenase (LDH) from *Lactobacillus leichmanii* (Sigma-Aldrich, St. Louis, Mo.), 0.5 mM NADH. The assay was started by adding enzyme (typically between 1 to 5 μL). Liberation of pyruvate, coupled to the formation of $NAD^+$ was monitored continuously in a spectrophotometer at 340 nm.

The CHA was synthesized according to the procedure described in Tack, B.F. Chapman, P. J., and S. Dagley. *J. Biol. Chem.* 247 6438-6443 (1972).

A unit of enzyme activity, such as pyruvate aldolase, such as HMG and/or KHG aldolase enzyme, is defined as the amount that liberates sufficient pyruvate to lower the absorbance at 340 nm by 1 OD per minute.

Example 4

Discovery of Novel Keto-hydroxy-glutarate (KHG) and Hydroxy-methyl-keto-glutarate (HMG) Aldolases from Diversa Environmental Libraries Over 150 unique HMG aldolases and 15 KHG aldolases were discovered by screening Diversa DNA libraries. These aldolase genes were sequenced and subcloned into a suitable expression vector. This vector was then transformed into a suitable expression host for production of sufficient amounts of the aldolase for enzyme characterization. A selected set of aldolases were tested for the activity on CHA and also for the formation of monatin precursor (MP). All the enzymes discovered and described in this patent have potential for use in other carbon-carbon bond forming reactions between an alpha-keto acid acceptor and pyruvate or pyruvate derivative donor as exemplified in the general reaction scheme below.

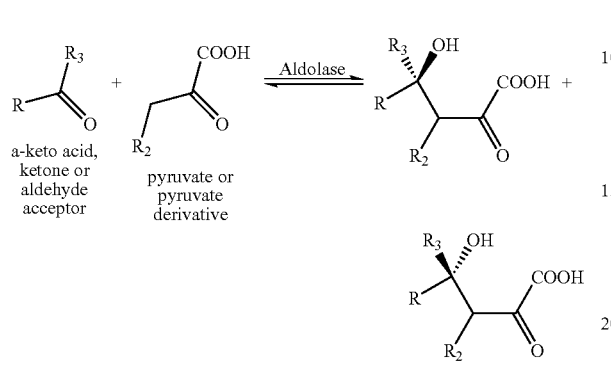

R=H, alkyl, substituted alkyl, aryl, substituted aryl, benzyl, substituted benzyl
$R_2$=H, alkyl, substituted alkyl, aryl, substituted aryl, benzyl, substituted benzyl
$R_3$=H, alkyl, substituted alkyl, aryl, substituted aryl, benzyl, substituted benzyl, carboxylic acid.

Example 5

Characterization of Selected Aldolases

Selected aldolases were characterized with respect to their ability to catalyze the conversion of indole-3-pyruvate and pyruvate to monatin precursor (MP) as shown in the following scheme:

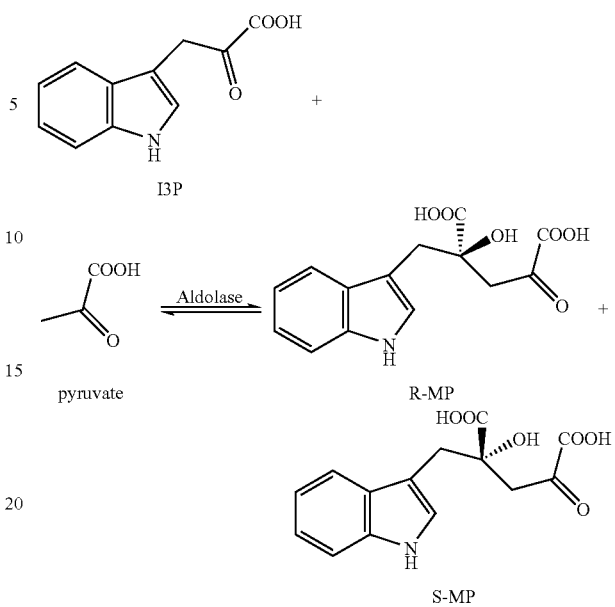

Figure 14:
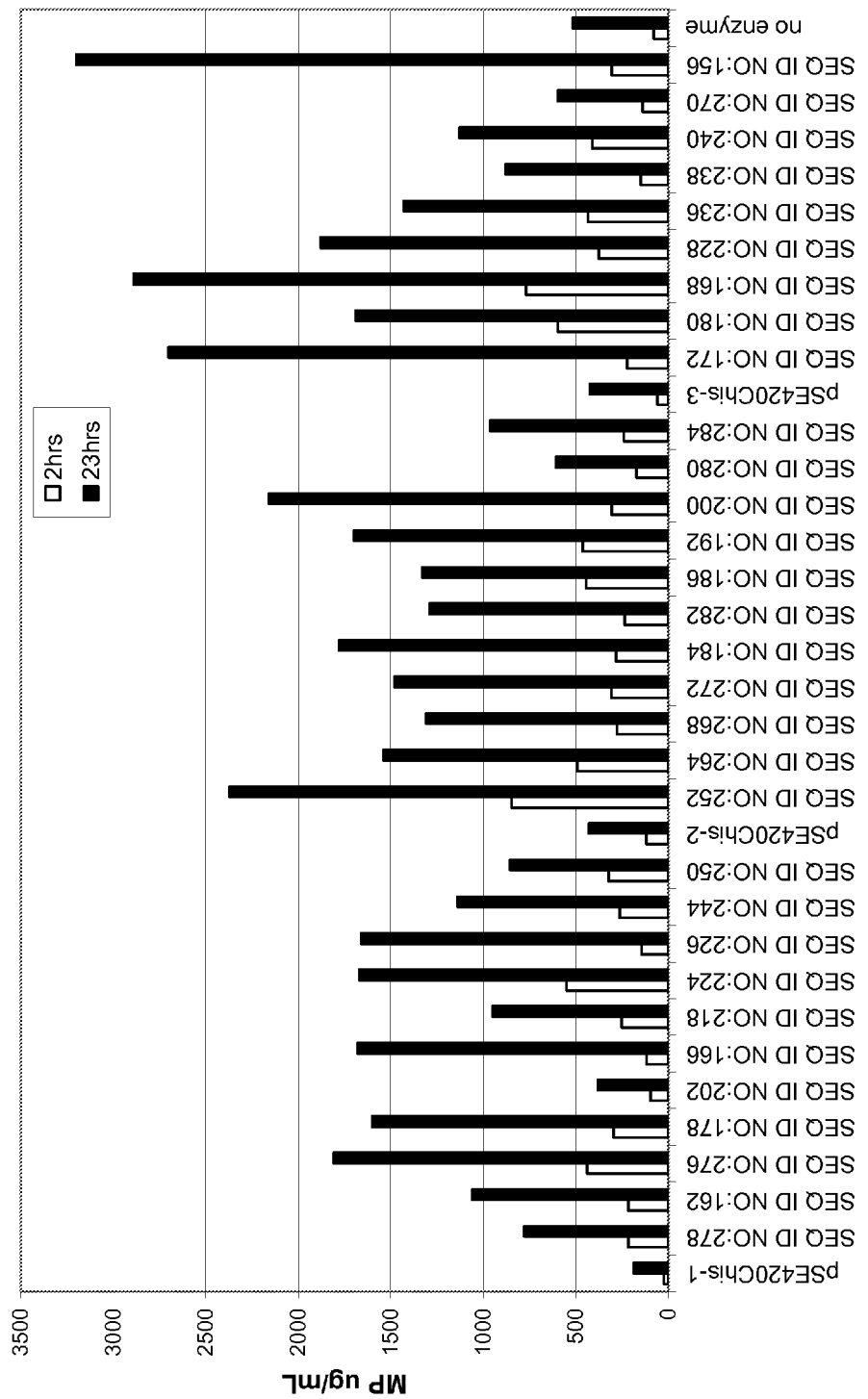

FIGS. 13 and 14 show the activities of 58 different aldolases in the formation of MP as measured by LC/MS/MS.

Aldol reactions were performed with 20 mM indole-3-pyruvate ("I3P"), 50 mM pyruvate, 100 mM sodium phosphate pH 7, 1 mM $MgCl_2$, 100 μg/mL aldolase. Reactions were incubated at room temperature in the dark. Aliquots (30 μL) were removed at various times and reactions were stopped by storing the samples on ice. A portion of each aliquot was submitted for CE analysis while the remaining portion was diluted 1:1000 in 50% acetonitrile and submitted for LC/MS analysis.

TABLE 2

Enantioselectivity of different aldolases for the formation of MP from I3P and pyruvate as determined by chiral CE

| Aldolase | % R-MP (23 hr time point) | CHA (U/mg) (based on total protein in lysate) | Relative Expression |
|---|---|---|---|
| SEQ ID NO: 28 (encoded by SEQ ID NO: 27) | 98+ | 31.8 | ### |
| SEQ ID NO: 116 (encoded by SEQ ID NO: 115) | 95 | 304 | ## |
| SEQ ID NO: 76 (encoded by SEQ ID NO: 75) | 50 | 424 | ### |
| SEQ ID NO: 298 (encoded by SEQ ID NO: 297) | 98+ | 388 | ## |
| SEQ ID NO: 44 (encoded by SEQ ID NO: 43) | 70 | 332 | ## |
| SEQ ID NO: 54 (encoded by SEQ ID NO: 53) | 98+ | 95 | # |
| SEQ ID NO: 148 (encoded by SEQ ID NO: 147) | 90 | 200 | ## |
| SEQ ID NO: 46 (encoded by SEQ ID NO: 45) | 70 | 174 | ## |
| SEQ ID NO: 134 (encoded by SEQ ID NO: 133) | 90 | 576 | ### |
| SEQ ID NO: 142 (encoded by SEQ ID NO: 141) | 98+ | 55 | # |
| SEQ ID NO: 122 (encoded by SEQ ID NO: 121) | 98+ | 38 | ## |
| SEQ ID NO: 74 (encoded by SEQ ID NO: 73) | 80 | 484 | ### |
| SEQ ID NO: 64 (encoded by SEQ ID NO: 63) | 95 | 38 | # |
| SEQ ID NO: 108 (encoded by SEQ ID NO: 107) | 98+ | 40 | # |
| SEQ ID NO: 96 (encoded by SEQ ID NO: 95) | 98+ | not detected | # |
| SEQ ID NO: 126 (encoded by SEQ ID NO: 125) | 95 | 124 | ## |
| SEQ ID NO: 80 (encoded by SEQ ID NO: 79) | 98+ | not detected | # |
| SEQ ID NO: 36 (encoded by SEQ ID NO: 35) | 98+ | 80 | ## |
| SEQ ID NO: 62 (encoded by SEQ ID NO: 61) | 98+ | not detected | # |
| SEQ ID NO: 112 (encoded by SEQ ID NO: 111) | 98+ | not detected | # |
| SEQ ID NO: 130 (encoded by SEQ ID NO: 129) | 98+ | 38 | ## |
| SEQ ID NO: 94 (encoded by SEQ ID NO: 93) | 98+ | 47 | ## |
| SEQ ID NO: 102 (encoded by SEQ ID NO: 101) | not detected | not detected | # |

TABLE 2-continued

Enantioselectivity of different aldolases for the formation of MP from I3P and pyruvate as determined by chiral CE

| Aldolase | % R-MP (23 hr time point) | CHA (U/mg) (based on total protein in lysate) | Relative Expression |
|---|---|---|---|
| SEQ ID NO: 58 (encoded by SEQ ID NO: 57) | 98+ | 59 | ## |
| SEQ ID NO: 88 (encoded by SEQ ID NO: 87) | 50 | 510 | ### |
| SEQ ID NO: 50 (encoded by SEQ ID NO: 49) | 98+ | 144 | ## |
| SEQ ID NO: 106 (encoded by SEQ ID NO: 105) | 98+ | not detected | ## |
| SEQ ID NO: 40 (encoded by SEQ ID NO: 39) | 40 | 406 | ### |
| SEQ ID NO: 42 (encoded by SEQ ID NO: 41) | 98+ | 92 | ## |
| SEQ ID NO: 278 (encoded by SEQ ID NO: 277) | 95 | 2.0 | # |
| SEQ ID NO: 162 (encoded by SEQ ID NO: 161) | 95 | 11.8 | # |
| SEQ ID NO: 276 (encoded by SEQ ID NO: 275) | 98+ | 100.4 | #### |
| SEQ ID NO: 178 (encoded by SEQ ID NO: 177) | 95 | 38.8 | # |
| SEQ ID NO: 202 (encoded by SEQ ID NO: 201) | not detected | not detected | # |
| SEQ ID NO: 166 (encoded by SEQ ID NO: 165) | 98+ | 85.5 | ## |
| SEQ ID NO: 218 (encoded by SEQ ID NO: 217) | 95 | 49.1 | ## |
| SEQ ID NO: 224 (encoded by SEQ ID NO: 223) | 98+ | 23.2 | # |
| SEQ ID NO: 226 (encoded by SEQ ID NO: 225) | 98+ | 128.3 | # |
| SEQ ID NO: 244 (encoded by SEQ ID NO: 243) | 98+ | 40.4 | # |
| SEQ ID NO: 250 (encoded by SEQ ID NO: 249) | 95 | 6.0 | # |
| SEQ ID NO: 252 (encoded by SEQ ID NO: 251) | 95 | 20.2 | ## |
| SEQ ID NO: 264 (encoded by SEQ ID NO: 263) | 95 | 9.9 | ## |
| SEQ ID NO: 268 (encoded by SEQ ID NO: 267) | 95 | 2.0 | # |
| SEQ ID NO: 272 (encoded by SEQ ID NO: 271) | 95 | 6.7 | # |
| SEQ ID NO: 184 (encoded by SEQ ID NO: 183) | 95 | not detected | # |
| SEQ ID NO: 282 (encoded by SEQ ID NO: 281) | 95 | 36.7 | ### |
| SEQ ID NO: 186 (encoded by SEQ ID NO: 185) | 95 | 4.2 | # |
| SEQ ID NO: 192 (encoded by SEQ ID NO: 191) | 95 | 11.9 | # |
| SEQ ID NO: 200 (encoded by SEQ ID NO: 199) | 95 | 17.9 | ## |
| SEQ ID NO: 280 (encoded by SEQ ID NO: 279) | 50 | not detected | # |
| SEQ ID NO: 284 (encoded by SEQ ID NO: 283) | 90 | 2.2 | # |
| SEQ ID NO: 172 (encoded by SEQ ID NO: 171) | 95 | 8.4 | # |
| SEQ ID NO: 180 (encoded by SEQ ID NO: 179) | 98+ | 61.0 | ### |
| SEQ ID NO: 168 (encoded by SEQ ID NO: 167) | 98+ | 9.3 | # |
| SEQ ID NO: 228 (encoded by SEQ ID NO: 227) | 98+ | 38.7 | ### |
| SEQ ID NO: 236 (encoded by SEQ ID NO: 235) | 95 | 13.1 | # |
| SEQ ID NO: 238 (encoded by SEQ ID NO: 237) | 98+ | 22.3 | ## |
| SEQ ID NO: 240 (encoded by SEQ ID NO: 239) | 95 | not detected | # |
| SEQ ID NO: 270 (encoded by SEQ ID NO: 269) | 40 | 4.6 | # |
| SEQ ID NO: 156 (encoded by SEQ ID NO: 155) | 98+ | 133.0 | ### |

Note that selectivities for R-MP of 98+% indicate that no S-MP was detected. Given the sensitivity of the CE assay, the results indicate that the at least 98% of MP formed is the R-enantiomer. Thus, enzymes that are listed as 98+% are at least 98% selective towards R-MP and may be up to 100% selective.

Table 2 also shows the activity of the enzymes on a general aldolase substrate, CHA, as well as the relative expression of each enzyme, as determined by SDS-PAGE. Note that several enzymes did not show detectable activity on CHA yet they did exhibit activity in making MP.

In summary, the aldolases show a wide range of activities, expression and selectivities. Moreover, there are numerous aldolases that show exquisitely high selectivities (98% or greater) for R-MP.

Example 6

Discovery of Plant Pyruvate Aldolases

Degenerate PCR primers (see below) were designed and used to extract aldolase genes from cDNA prepared from *Sclerochiton ilicifolius*. The 5' and 3' ends of the genes were recovered and the full length genes were then PCR amplified.

| SEQ ID NO: | primer name | Primer |
|---|---|---|
| 335 | F1 | AARGTBTWYGARGACAATG (SEQ ID NO: 335) |
| 336 | F2 | GCDCAGAWCAAYGGRTGG (SEQ ID NO: 336) |
| 337 | R1 | CCATCRSYATCDGCRTADAGCCA (SEQ ID NO: 337) |
| 338 | R2 | GCRTADAGCCAYTCNCCRTC (SEQ ID NO: 338) |

Example 7

Cloning of *Bacillus sphaericus* D-amino Acid Aminotransferase

The *B. sphaericus* D-amino acid aminotransferase (EC 2.6.1.21, also known as D-alanine aminotransferase or D-aspartate aminotransferase) was produced recombinantly for use in coupled assays with the various aldolases. This enzyme is homologous to D-aminotransferases described previously for production of monatin (U.S. Publication No. 20040063175 and U.S. Publication No. 20050282260).

Strains

*B. sphaericus* (ATCC number10208) was grown on Nutrient Agar at 30° C. overnight. Groups of colonies were placed in 100 μL of sterile water and heated for 5 minutes at 95° C., to disrupt the cells. Three μL was used in subsequent Polymerase Chain Reaction (PCR) amplifications.

Polymerase Chain Reaction Protocol

Primers were designed for cloning into pET 28b and pET 30a vectors (Novagen, Madison, Wis.), using the NcoI and BamHI sites. The pET 30 construct contains an N-terminal His-tag and S-tag, whereas the pET 28 construct is untagged. *Bacillus sphaericus* Dat Primers:

```
                                        (SEQ ID NO: 383)
N term: 5'-GATATACCATGGCATACTCATTATGGAATG-3'
and (SEQ ID NO: 384)
C term: 5'-GTTATCGGATCCTTAGGCATTAATTGAAATTG-3'.
```

The coding region was amplified using the following PCR protocol. In a 50 μL reaction 3 μL template, 1.6 μM of each primer, 0.25 mM each dNTP, 3.5 U Expand High Fidelity Polymerase (Roche, Indianapolis, Ind.), and 1× Expand™ buffer with Mg were used. The thermocycler program used included a hot start at 94° C. for 3 minutes, followed by 8 repetitions of the following steps: 94° C. for 30 seconds, 52° C. for 30 seconds, and 72° C. for 2 minutes. Twenty-two subsequent cycles were done with an annealing temperature of 58° C. After 30 cycles, the sample was maintained at 72° C. for 7 minutes and then stored at 4° C. Clean PCR products of the correct size were obtained (approximately 850 bp for the dat gene).

Cloning

The PCR products were purified using the Qiagen QIAquick PCR purification kit (Qiagen, Valencia, Calif.), and digested with BamHI and NcoI in BamHI buffer (New England Biolabs, Ipswich, Mass.).

Digested vector and inserts were purified using the Qiagen QIAquick Gel Extraction Kit (Qiagen, Valencia, Calif.). Ligations were done using the Roche Rapid DNA Ligation Kit (Roche, Indianapolis, Ind.) and purified using the QIAquick PCR purification kit (Qiagen, Valencia, Calif.). The ligations were transformed into *Escherichia coli* DH10B using a 0.2 cm cuvette and a Bio-Rad Gene Pulser II system as described in the Bio-Rad electroporation manual (Bio-Rad, Hercules, Calif.). The cells were allowed to recover in 900 μL SOC medium for 30 minutes at 37° C. at 225 rpm. Cells were plated on LB-agar plates containing kanamycin (25 μg/mL).

Plasmid DNA was purified using the Qiagen spin miniprep kit (Qiagen, Valencia, Calif.) and screened for the correct inserts by restriction digest with BamHI and NcoI. The sequences of plasmids that appeared to have the correct insert were verified by dideoxy chain termination DNA sequencing at Agencourt BioScience Corporation (Beverly, Mass.). Sequencing verified the coding sequence found in NCBI accession number AF081278 Region: 134.985 (gi: 3513754), which produces a protein with amino acid sequence as listed in accession number AAC33964 (gi: 3513755).

Gene Expression and Assays

Plasmid DNA was subcloned into *E. coli* expression host BL21(DE3) (Novagen, Madison, Wis.). The cultures were grown and the plasmids were isolated using Qiagen miniprep kit (Qiagen, Valencia, Calif.), and analyzed by restriction digest to confirm identity. Induction was typically performed in LB medium containing kanamycin (50 μg/mL). The cells were grown to an $OD_{600}$ of 0.4-0.8, induced with 0.1 mM IPTG (isopropyl thiogalacatoside) and sampled at 4 hours post induction. Cell extracts were prepared according to the protocol accompanying the Novagen BugBuster™ reagent (Novagen, Madison, Wis.) (with benzonase nuclease and Roche complete protease inhibitor cocktail added (Roche, Indianapolis, Ind.)). Very high levels of soluble protein were obtained at the predicted molecular weight, as judged by SDS-PAGE. For some reactions, the pET 30 gene product was purified using His-Bind cartridges following manufacturer's protocols (Novagen, Madison, Wis.). The eluent fractions were desalted on PD-10 (GE Healthcare, Piscataway, N.J.) columns and eluted in 25-100 mM potassium phosphate buffer, pH 7.5.

Cell extracts were analyzed for D-aminotransferase activity by following production of alanine from pyruvate and D-tryptophan using the following protocol. One mL reactions were typically carried out in 100 mM potassium phosphate buffer (pH 7.5), 50 μM pyridoxal phosphate, 25 mM sodium pyruvate, and 50 mM D-tryptophan. The reactions were initiated by the addition of cell free extracts or purified enzyme and were incubated 15 minutes-overnight at 30° C., with mild shaking. Formic acid was added to a final concentration of two percent to stop the reaction, and the precipitated protein was removed by centrifugation. Control reactions without added protein were also performed. Zero time points were also used as negative controls. Alanine was detected using OPA derivatization as described in Example 1.

Example 8

Comparison of Total Monatin Production and Isomeric Distribution for the Polypeptides with Aldolase Activity of SEQ ID NO:8, SEQ ID NO:4, SEQ ID NO:12, and SEQ ID NO:28, and *C. testosteroni* ProA AT-103 transaminase (a broad specificity D-aminotransferase) was purchased from BioCatalytics (Pasadena, Calif.) and either this enzyme or the recombinant enzyme produced in Example 7 was used in coupled reactions with HMG aldolases to produce monatin from D-tryptophan and pyruvate as described in U.S. Published Application No. 20050282260. The ProA aldolase from *C. testosteroni* was used as a benchmark aldolase for comparative purposes, and was prepared as described in U.S. Published Application No. 20040063175 and WO 03091396 A2. The aldolases tested were isolated and transformed as described above in Example 4.

To produce test quantities of each aldolase, 50 mL cultures were grown in LB medium containing ampicillin (100 μg/mL), to an $OD_{600}$ of approximately 0.5. The strains containing SEQ ID NO:7, SEQ ID NO:3, and SEQ ID NO:11 constructs were induced with 100 μM of IPTG. The strain containing the SEQ ID NO:27 construct was induced with 200 μg/L anhydrotetracycline. The cells were grown 5 hours post-induction, and cellular extracts were prepared according to manufacturer's protocols (Novagen, Madison, Wis., Bugbuster reagent). Benzonuclease and protease inhibitor were also added. The soluble proteins in the cellular extracts were separated on a Bio-Rad Laboratories Experion Automated Electrophoresis Station (Bio-Rad, Hercules, Calif.) and analyzed for concentration and percent expression using the Experion Software version 1.1.98.0.

The following were added per 1 mL of reaction mixture: approximately 50 μg aldolase (supplied in cellular extracts unless otherwise noted), 4 mM $MgCl_2$, 50 mM D-tryptophan, 0.5 mg purified *B. sphaericus* D-aminotransferase, 200 mM sodium pyruvate, 100 mM potassium phosphate buffer pH 7.5, and 0.05 mM PLP. Experiments were run in duplicate, with negative controls in which no aldolase was added.

Samples were incubated 1 hr, 2 hrs, and overnight (17-20 hours) at 30° C. with gentle shaking. Small amounts of monatin (<0.5 ppm) are produced without aldolase in overnight reactions, due to non-enzymatic reactions catalyzed by magnesium and phosphate. Those values were subtracted from the numbers shown below, and averaged results are shown. The only stereoisomers detected when producing monatin using these methods are R,R and S,R. The percent R,R is listed below, and was determined by reversed-phase LC peak area.

TABLE 3

Total monatin produced from D-tryptophan and % R,R

| Aldolase (time point) | Total monatin (ppm) | % R,R monatin |
|---|---|---|
| SEQ ID NO: 8 (1 hr) | 15.65 | 89.7 |
| SEQ ID NO: 8 (18 hr) | 129.22 | 79.0 |
| SEQ ID NO: 4 (1 hr) | 3.22 | 94.8 |
| SEQ ID NO: 4 (18 hr) | 12.14 | 93.8 |
| SEQ ID NO: 12 (1 hr) | 2.35 | 100 |
| SEQ ID NO: 12 (18 hr) | 11.89 | 98.65 |
| SEQ ID NO: 28 (1 hr) | 14.70 | 100 |
| SEQ ID NO: 28 (18 hr) | 95.14 | 97.35 |
| C. testosteroni ProA (1 hr) purified enzyme | 16.63 | 86.45 |
| C. testosteroni ProA (18 hr) purified enzyme | 86.86 | 63.1 |

The SEQ ID NO:28 18 hour sample was also analyzed for stereoisomeric distribution by the FDAA derivatization method listed in Example 1, which yielded a result of 94.9% R,R and 5.1% S,R monatin.

The same experiments were done, side by side, using L-tryptophan as the starting substrate and coupling the aldolases with HexAspC broad specificity L-aminotransferase produced as described in U.S. Published Application No. 20050282260 and purified. These reactions should yield primarily S,S monatin and R,S monatin. The reactions were also supplemented with 10 mM alpha-ketoglutarate as the amino acceptor for L-tryptophan transamination. Again, duplicate results are averaged below for total monatin (subtracting background levels without aldolase present), and percent S,S monatin is shown based on reversed phase LC peak area. In some cases, because the aldolases are quite R-specific and produce little total monatin, the reversed phase estimates of stereoisomeric distribution are less accurate due to some tailing of the tryptophan peak that can co-elute with the S,S/R,R monatin peak. The trends are still informative in comparing R-specificity of the aldolases. Results from further analysis using the FDAA derivatization method are shown in parentheses for several samples, and are more accurate. Total monatin numbers above approximately 400 ppm are higher than the linear range of the scale of the standards used to quantitate the results, so are qualitative results. The C. testosteroni ProA aldolase typically produces 95-100% S,S monatin, as shown in U.S. Published Application No. 20050282260.

TABLE 4

Total monatin produced from L-tryptophan and % S,S

| Aldolase (time point) | Total monatin (ppm) | % S,S monatin |
|---|---|---|
| SEQ ID NO: 8 (1 hr) | 138.65 | 78.9 |
| SEQ ID NO: 8 (18 hr) | 600.3 | 78.15 |
| SEQ ID NO: 4 (1 hr) | below negative control | 95.65 |

TABLE 4-continued

Total monatin produced from L-tryptophan and % S,S

| Aldolase (time point) | Total monatin (ppm) | % S,S monatin |
|---|---|---|
| SEQ ID NO: 4 (18 hr) | 28.5 | 87.6 |
| SEQ ID NO: 12 (1 hr) | below negative control | 93.55 |
| SEQ ID NO: 12 (18 hr) | 24.9 | 75 (59.35) |
| SEQ ID NO: 28 (1 hr) | 17.85 | 55.05 (18.9) |
| SEQ ID NO: 28 (18 hr) | 135.5 | 27.25 (19.1) |
| C. testosteroni ProA (1 hr) purified enzyme | 440.35 | 92.5 |
| C. testosteroni ProA (18 hr) purified enzyme | 958.3 | 92.15 |

One can see that the R-specificity of the polypeptide with aldolase activity of SEQ ID NO:28 is quite high compared to the benchmark ProA enzyme, this is also reflected in the low % S,S monatin produced, despite the high degree of specificity of the HexAspC aminotransferase for S-MP in these reactions. The total monatin numbers, when comparing S,S monatin production versus R,R monatin production, are not indicative of the aldolase activity. The D-aminotransferase is less active than HexAspC, particularly at the concentrations of MP that are present in these reactions.

For further comparison of the polypeptide with aldolase activity of SEQ ID NO:28 to the ProA enzyme from C. testosteroni, varying ratios of D-aminotransferase to aldolase were utilized in reactions starting with D-tryptophan (no duplicate samples for these experiments). Reactions were carried out as above. For reactions where aldolase concentration was kept constant, approximately 50 μg was used. For reactions where D-aminotransferase was kept constant, 0.5 mg was used. For the 2 and 10 mg/mL concentration of D-aminotransferase, lyophilized enzyme was used. For the 2 highest D-aminotransferase concentrations, duplicates were run.

TABLE 5

Effect of D-aminotransferase concentration on R,R monatin production

| Aldolase | Concentration of D-amino-transferase | Time | Total monatin (approximate ppm) | % R,R monatin |
|---|---|---|---|---|
| SEQ ID NO: 28 | 0.25 mg/ml | 1 hr | 2 | 100 |
| SEQ ID NO: 28 | 0.25 mg/ml | overnight | 141 | 97.1 |
| SEQ ID NO: 28 | 0.5 mg/ml | 1 hr | 8 | 100 |
| SEQ ID NO: 28 | 0.5 mg/ml | overnight | 273 | 96.5 |
| SEQ ID NO: 28 | 1 mg/ml | 1 hr | 34 | 100 |
| SEQ ID NO: 28 | 1 mg/ml | overnight | 638 | 96.5 |
| SEQ ID NO: 28 | 2 mg/ml | 1 hr | 979 | 100 |
| SEQ ID NO: 28 | 2 mg/ml | overnight | 1910 | 97.3 |
| SEQ ID NO: 28 | 10 mg/ml | 1 hr | 2930 | 99.1 |
| SEQ ID NO: 28 | 10 mg/ml | overnight | 2950 | 96.5 |
| C. testosteroni ProA (purified) | 0.25 mg/ml | 1 hr | 4 | 78.7 |
| C. testosteroni ProA (purified) | 0.25 mg/ml | overnight | 257 | 61.1 |
| C. testosteroni ProA (purified) | 0.5 mg/ml | 1 hr | 25 | 79.0 |
| C. testosteroni ProA (purified) | 0.5 mg/ml | overnight | 480 | 62.5 |
| C. testosteroni ProA (purified) | 1 mg/ml | 1 hr | 74 | 73.8 |
| C. testosteroni ProA (purified) | 1 mg/ml | overnight | 810 | 68.1 |
| C. testosteroni ProA (purified) | 2 mg/ml | 1 hr | 325 | 73.1 |
| C. testosteroni ProA (purified) | 2 mg/ml | overnight | 2220 | 71.9 |

TABLE 5-continued

Effect of D-aminotransferase concentration on R,R monatin production

| Aldolase | Concentration of D-amino-transferase | Time | Total monatin (approximate ppm) | % R,R monatin |
|---|---|---|---|---|
| C. testosteroni ProA (purified) | 10 mg/ml | 1 hr | 2910 | 59.7 |
| C. testosteroni ProA (purified) | 10 mg/ml | overnight | 2450 | 67.5 |
| SEQ ID NO: 8 | 0.25 mg/ml | 1 hr | 4 | 92.3 |
| SEQ ID NO: 8 | 0.25 mg/ml | overnight | 219 | 69.8 |
| SEQ ID NO: 8 | 0.5 mg/ml | 1 hr | 14 | 84.9 |
| SEQ ID NO: 8 | 0.5 mg/ml | overnight | 426 | 67.5 |
| SEQ ID NO: 8 | 1 mg/ml | 1 hr | 62 | 84.2 |
| SEQ ID NO: 8 | 1 mg/ml | overnight | 877 | 68.7 |

For monatin levels above 400 ppm, the results are not in the linear range of the standard curve and are approximate values only. The maximum amount of R,R monatin produced, when diluted appropriately, was 1100 ppm. FDAA stereoisomeric analysis was done for the polypeptide with aldolase activity of SEQ ID NO:28 with 10 mg/mL D-aminotransferase samples. At two hours, the sample contained 98.5% R,R monatin. At 17 hours, the sample contained 95.9% R,R monatin. The polypeptide with aldolase activity of SEQ ID NO:28 produced high percentages of R,R monatin, even after long incubation times and using large amounts of aminotransferase. If adequate D-aminotransferase is supplied, the polypeptide with aldolase activity of SEQ ID NO:28 produces as much total monatin as C. testosteroni ProA aldolase, indicating a similar specific activity.

TABLE 6

Effect of aldolase concentration on R,R monatin production

| Aldolase | Concentration of aldolase | Time | Total monatin (ppm) | % R,R monatin |
|---|---|---|---|---|
| SEQ ID NO: 28 | 25 µg/ml | 1 hr | 7.0 | 100 |
| SEQ ID NO: 28 | 25 µg/ml | overnight | 275 | 97.4 |
| SEQ ID NO28 | 50 µg/ml | 1 hr | 9.0 | 97.3 |
| SEQ ID NO: 28 | 50 µg/ml | overnight | 334 | 95.7 |
| SEQ ID NO: 28 | 100 µg/ml | overnight | 297 | 93.3 |
| C. testosteroni ProA (purified) | 25 µg/ml | 1 hr | 16 | 78.2 |
| C. testosteroni ProA (purified) | 25 µg/ml | overnight | 491 | 73.2 |
| C. testosteroni ProA (purified) | 50 µg/ml | 1 hr | 18 | 64.1 |
| C. testosteroni ProA (purified) | 50 µg/ml | overnight | 437 | 63.0 |
| C. testosteroni ProA (purified) | 100 µg/ml | 1 hr | 26 | 62.5 |
| C. testosteroni ProA (purified) | 100 µg/ml | overnight | 513 | 61.5 |
| SEQ ID NO: 8 | 25 µg/ml | 1 hr | 11.0 | 88.1 |
| SEQ ID NO: 8 | 25 µg/ml | overnight | 337.0 | 74.7 |
| SEQ ID NO: 8 | 50 µg/ml | 1 hr | 14.0 | 78.2 |
| SEQ ID NO: 8 | 50 µg/ml | overnight | 406.0 | 67.8 |
| SEQ ID NO: 8 | 100 µg/ml | 1 hr | 24.0 | 70.1 |
| SEQ ID NO: 8 | 100 µg/ml | overnight | 329.0 | 63.9 |

When the aldolase concentration is varied, there is not much of an increase in total monatin. The percent R,R decreases with time and also with aldolase concentration, particularly when the D-aminotransferase is limiting.

To further examine the R-specificity of the aldolases tested, experiments were done starting with L-tryptophan and Hex-AspC aminotransferase, which was produced and purified as described in U.S. Published Application No. 20050282260. The HexAspC shows a strong selectivity for transamination of S-MP versus R-MP, thus percentages above 50% R,S monatin indicate a highly stereospecific aldolase. Ten mM alpha-ketoglutarate was supplied as an amino acceptor; however, at high concentrations, pyruvate is also utilized by the L-aminotransferase. In these reactions, typically only S,S and R,S monatin are produced within the limits of detection of the FDAA derivatization protocol.

TABLE 7

Effect of L-aminotransferase concentration on S,S monatin production

| Aldolase | Concentration of D-amino-transferase | Time | Total monatin (approximate ppm) | % S,S monatin |
|---|---|---|---|---|
| SEQ ID NO: 28 | 0.25 mg/ml | 1 hr | 13 | 33.8 |
| SEQ ID NO: 28 | 0.25 mg/ml | overnight | 127 | 34.2 |
| SEQ ID NO: 28 | 0.5 mg/ml | 1 hr | 31 | 30.9 |
| SEQ ID NO: 28 | 0.5 mg/ml | overnight | 272 | 26.8 |
| SEQ ID NO: 28 | 1 mg/ml | 1 hr | 34 | 20.3 |
| SEQ ID NO: 28 | 1 mg/ml | overnight | 385 | 23.5 |
| C. testosteroni ProA (purified) | 0.25 mg/ml | 1 hr | 523 | 94.2 |
| C. testosteroni ProA (purified) | 0.25 mg/ml | overnight | 1817 | 93.7 |
| C. testosteroni ProA (purified) | 0.5 mg/ml | 1 hr | 602 | 91.8 |
| C. testosteroni ProA (purified) | 0.5 mg/ml | overnight | 2122 | 89.9 |
| C. testosteroni ProA (purified) | 1 mg/ml | 1 hr | 873 | 90.2 |
| C. testosteroni ProA (purified) | 1 mg/ml | overnight | 1237 | 82.6 |
| SEQ ID NO: 8 | 0.25 mg/ml | 1 hr | 339 | 86.3 |
| SEQ ID NO: 8 | 0.25 mg/ml | overnight | 1499 | 88.0 |
| SEQ ID NO: 8 | 0.5 mg/ml | 1 hr | 211 | 80.3 |
| SEQ ID NO: 8 | 0.5 mg/ml | overnight | 1328 | 83.1 |
| SEQ ID NO: 8 | 1 mg/ml | 1 hr | 400 | 74.6 |
| SEQ ID NO: 8 | 1 mg/ml | overnight | 1370 | 79.0 |

TABLE 8

Effect of aldolase concentration on S,S monatin production

| Aldolase | Concentration of aldolase | Time | Total monatin (ppm) | % S,S monatin |
|---|---|---|---|---|
| SEQ ID NO: 28 | 25 µg/ml | 1 hr | 11 | 25.1 |
| SEQ ID NO: 28 | 25 µg/ml | overnight | 112 | 20.0 |
| SEQ ID NO: 28 | 50 µg/ml | 1 hr | 18 | 31.8 |
| SEQ ID NO: 28 | 50 µg/ml | overnight | 160 | 27.0 |
| SEQ ID NO: 28 | 100 µg/ml | 1 hr | 33 | 33.2 |
| SEQ ID NO: 28 | 100 µg/ml | overnight | 238 | 41.4 |
| C. testosteroni ProA (purified) | 25 µg/ml | 1 hr | 305 | 86.4 |
| C. testosteroni ProA (purified) | 25 µg/ml | overnight | 1094 | 87.5 |
| C. testosteroni ProA (purified) | 50 µg/ml | 1 hr | 575 | 90.9 |
| C. testosteroni ProA (purified) | 50 µg/ml | overnight | 1449 | 89.5 |
| C. testosteroni ProA (purified) | 100 µg/ml | 1 hr | 817 | 93.6 |
| C. testosteroni ProA (purified) | 100 µg/ml | overnight | 1360 | 89.7 |
| SEQ ID NO: 8 | 25 µg/ml | 1 hr | 134 | 70.7 |
| SEQ ID NO: 8 | 25 µg/ml | overnight | 728 | 76.3 |
| SEQ ID NO: 8 | 50 µg/ml | 1 hr | 197 | 80.0 |
| SEQ ID NO: 8 | 50 µg/ml | overnight | 928 | 81.4 |
| SEQ ID NO: 8 | 100 µg/ml | 1 hr | 279 | 86.7 |
| SEQ ID NO: 8 | 100 µg/ml | overnight | 1383 | 86.8 |

For aldolases that are highly R-specific, such as the polypeptide with aldolase activity of SEQ ID NO:28, less total monatin is produced and increasing the amount of aldolase does increase total monatin (as well as % S,S). These aldolases produce less S-MP substrate, the preferred substrate for the L-aminotransferase used. For enzymes that are less R-specific, such as ProA, increasing aldolase does not significantly improve total monatin production or % S,S monatin. Increasing the amount of L-aminotransferase added decreases the percentage of S,S monatin produced. Based on the above analysis, the polypeptide with aldolase activity of SEQ ID NO:8 is between ProA and the polypeptide with aldolase activity of SEQ ID NO:28 in terms of R-specificity, which agrees with data above where % R-MP is measured for the aldol step alone.

Subcloning of SEQ ID NO:27

The following primers were used to PCR amplify the aldolase gene: 5'-gaggagctcgagtcagacgtatttcagtccttttc-3' (SEQ ID NO:385) and 5'-agaagacatatgatttatcagccggggac-3' (SEQ ID NO:386). The aldolase gene SEQ ID NO:27 encodes the polypeptide with aldolase activity of SEQ ID NO:28. The resulting PCR product was digested with XhoI and NdeI to cut at the sites that had been engineered into the primers. The fragment was gel purified (QIAquick Gel extraction Kit (Qiagen, Valencia, Calif.)) and ligated (using T4 DNA ligase) with pET28b that had been digested with XhoI and NdeI and gel purified. The ligation was transformed into TOP10F' chemically competent cells. Colonies growing on the plates were screened for inserts and several isolates with inserts were submitted for DNA sequence analysis (Agencourt, Beverly, Mass.).

Purification of the Polypeptide with Aldolase Activity of SEQ ID NO:28

Confirmed aldolase clones were transformed into either BL21 DE3 or BL21 DE3 pLysS. Overnight cultures grown with the appropriate antibiotic were diluted into fresh media (typically 1:100) and grown to an $OD_{600}$ ~0.6 with aeration at 37° C. Cultures were then induced with 1 mM IPTG and shifted to 30° C. (with aeration) and incubation was continued overnight. Cells were harvested by centrifugation. The cell pellet was typically subjected to one freeze thaw cycle to assist with cell lysis. The cell pellet was lysed in BugBuster and Benzonase (Novagen, Madison, Wis.) (according to the manufacturer's protocol). Cell debris was removed by centrifugation. The crude protein extract was applied to a His-Bind column (Novagen, Madison, Wis.) that had been prepared according to the manufacturer's protocol. The column was washed and protein was eluted according to the manufacturer's protocol. The purified protein was desalted with PD-10 columns (GE Healthcare, Piscataway, N.J.). The buffer used for the exchange was 50 mM potassium phosphate pH 7.5, 100 mM NaCl, 4 mM $MgCl_2$. Purified protein was concentrated with Amicon centrifugal concentrators (Millipore, Billerica, Mass.).

Example 9

Comparison of Total Monatin Production and Isomeric Distribution for Polypeptides with Aldolase Activity of SEQ ID NO:40, SEQ ID NO:298, SEQ ID NO:36, SEQ ID NO:62, SEQ ID NO:64, SEQ ID NO:96, SEQ ID NO:54, SEQ ID NO:122, SEQ ID NO:142, SEQ ID NO:42, SEQ ID NO:130, SEQ ID NO:112, SEQ ID NO:108, SEQ ID NO:94, SEQ ID NO:80, and SEQ ID NO:28

AT-103 transaminase (a broad specificity D-aminotransferase) was purchased from BioCatalytics (Pasadena, Calif.) and either this enzyme or the recombinant enzyme produced in Example 7 was used in coupled reactions with HMG aldolases to produce monatin from D-tryptophan and pyruvate as described in U.S. Published Application No. 20050282260. The polypeptide with aldolase activity of SEQ ID NO:28 (his-tagged) was used as a benchmark aldolase for comparative purposes, and was produced and purified as described at the end of Example 8. The other aldolases tested were isolated and transformed as described above in Example 4.

To produce test quantities of each aldolase, 25 mL cultures were grown in LB medium containing ampicillin (100 µg/mL), to an $OD_{600}$ of approximately 0.4. The strains were induced with 100 µM of IPTG. The cells were grown 4 hours post-induction, and cellular extracts were prepared according to manufacturer's protocols (Novagen, Madison, Wis., Bugbuster reagent) with benzonuclease. The soluble proteins in the cellular extracts were separated on a Bio-Rad Laboratories Experion Automated Electrophoresis Station (Bio-Rad, Hercules, Calif.) and analyzed for concentration and percent expression using the Experion Software version 1.1.98.0.

The following were added per 1 mL of reaction mixture: approximately 50 µg aldolase (supplied in cellular extracts unless otherwise noted), 4 mM $MgCl_2$, 50 mg/mL D-tryptophan, 2 mg AT-103 (BioCatalytics, Pasadena, Calif.), 200 mM sodium pyruvate, 100 mM potassium phosphate buffer pH 7.5, and 0.05 mM PLP. The D-tryptophan is not soluble at this higher concentration, but was used to ensure that the reactions were kept at saturating amounts of D-tryptophan. Experiments were run in duplicate, with negative controls in which no aldolase was added. Samples were incubated 2 hrs and overnight (17-20 hours) at 30° C. with gentle shaking. Small amounts of monatin are produced overnight without aldolase (~0.5 ppm), due to non-enzymatic reactions catalyzed by magnesium and phosphate. Typical values for % R,R monatin are 50% for these samples. The negative control values were subtracted from the numbers shown below, and averaged results are shown. The only stereoisomers detected when producing monatin using these methods are R,R and S,R. The percent R,R is listed below, and was determined by reversed-phase LC peak area. The same experiment was conducted after storage of the cell extracts and the purified polypeptide with aldolase activity of SEQ ID NO:28 for 2 months at −20° C., this time 50 mM D-tryptophan was used as in Example 8. Twice the amount of aldolase was added with the exception of the polypeptide with aldolase activity of SEQ ID NO:28, for which approximately 50 µg was utilized again. These results are shown to the right of Table 9. FDAA derivatization results for isomeric distribution are shown in parentheses.

TABLE 9

Total monatin produced from D-tryptophan and % R,R

| Aldolase (time point) | Total monatin (ppm) | % R,R monatin | Total monatin (ppm) | % R,R monatin |
|---|---|---|---|---|
| SEQ ID NO: 40 (2 hr) | 336 | 82.7 | 238 | 66.8 |
| SEQ ID NO: 40. (18 hr) | 707.55 | 76.2 | 748.5 | 62.4 |
| SEQ ID NO: 298 (2 hr) | 394.3 | 98.0 | 183 | 91.9 (91.6) |
| SEQ ID NO: 298 (18 hr) | 819.5 | 96.1 | 648.5 | 80.0 |
| SEQ ID NO: 36 (2 hr) | 56 | 98.2 | 52.5 | 94.0 |
| SEQ ID NO: 36 (18 hr) | 123.25 | 96.9 | 296 | 88.5 |
| SEQ ID NO: 62 (2 hr) | 1.15 | 78.4 | 0 | n/a |
| SEQ ID NO: 62 (18 hr) | 0.95 | 73.8 | 16 | 89.2 |
| SEQ ID NO: 64 (2 hr) | 16.7 | 98.8 | 24 | 96.9 |
| SEQ ID NO: 64 (18 hr) | 43.7 | 97.6 | 161 | 98.5 |
| SEQ ID NO: 96 (2 hr) | 30.4 | 99.2 | 29 | 96.0 |
| SEQ ID NO: 96 (18 hr) | 80.8 | 98.3 | 200 | 97.3 |
| SEQ ID NO: 54 (2 hr) | 183.1 | 99.4 | 135.5 | 98.2 (98.8) |
| SEQ ID NO: 54 (18 hr) | 457.7 | 98.9 | 488.5 | 96.9 |
| SEQ ID NO: 122 (2 hr) | 129.3 | 97.9 | 126 | 97.8 (99.1) |
| SEQ ID NO: 122 (18 hr) | 289.85 | 95.8 | 471.5 | 94.4 |
| SEQ ID NO: 142 (2 hr) | 40.4 | 98.3 | 58.5 | 95.9 |
| SEQ ID NO: 142 (18 hr) | 82.3 | 97.3 | 388 | 96.8 |
| SEQ ID NO: 42 (2 hr) | 335.9 | 98.2 | 206.5 | 93.3 |

TABLE 9-continued

Total monatin produced from D-tryptophan and % R,R

| Aldolase (time point) | Total monatin (ppm) | % R,R monatin | Total monatin (ppm) | % R,R monatin |
|---|---|---|---|---|
| SEQ ID NO: 42 (18 hr) | 612.45 | 96.6 | 630.5 | 82.9 |
| SEQ ID NO: 130 (2 hr) | 77.5 | 99.3 | 60.5 | 98.5 (99.6) |
| SEQ ID NO: 130 (18 hr) | 177.45 | 99.1 | 368.5 | 98.4 |
| SEQ ID NO: 112 (2 hr) | 20.4 | 99.0 | 27 | 98.6 |
| SEQ ID NO: 112 (18 hr) | 57.75 | 98.3 | 186.5 | 99.3 |
| SEQ ID NO: 108 (2 hr) | 44.4 | 98.7 | 41 | 97.0 |
| SEQ ID NO: 108 (18 hr) | 111.7 | 98.0 | 265.5 | 93.3 (96.4) |
| SEQ ID NO: 94 (2 hr) | 69.4 | 98.2 | 56 | 94.4 |
| SEQ ID NO: 94 (18 hr) | 181.95 | 96.9 | 341 | 84.8 |
| SEQ ID NO: 80 (2 hr) | 27.9 | 98.9 | 29.5 | 98.8 |
| SEQ ID NO: 80 (18 hr) | 74 | 97.9 | 219 | 96.6 |
| SEQ ID NO: 28 - purified (2 hr) | 131.3 | 99.5 | 53 | 96.7 (99.6) |
| SEQ ID NO: 28 - purified (18 hr) | 407.4 | 99.2 | 257 | 99.2 |

One can see that certain enzymes are more stable to storage than other aldolases, based on ratios of activity. A secondary product, most likely 4-hydroxy-4-methyl glutamate can also be formed during these reactions. The enzymes above were ranked for their specificity towards monatin production by comparing the peak areas of that versus the byproduct. The results were the polypeptide with aldolase activity of SEQ ID NO:122>SEQ ID NO:42>SEQ ID NO:80>SEQ ID NO:108>SEQ ID NO:96>SEQ ID NO:112>SEQ ID NO:130>SEQ ID NO:36>SEQ ID NO:94>SEQ ID NO:298>SEQ ID NO:40>SEQ ID NO:142>SEQ ID NO:54>SEQ ID NO:64>SEQ ID NO:28>SEQ ID NO:62.

Based on initial experiments, the polypeptides with aldolase activity of SEQ ID NO:298, SEQ ID NO:54, and SEQ ID NO:42 looked the most promising in terms of activity level and % R,R monatin produced. These enzymes were subcloned into pET expression vectors with and without his-tags. Cloning of SEQ ID NO:297, SEQ ID NO:53, and SEQ ID NO:41.

Primers Used for Cloning:

TABLE 10

| SEQ ID NO: | 5' primer | 3' primer |
|---|---|---|
| 297 | 5'-agaagacatatgggtgtcgtcgtccaaaac-3' (SEQ ID NO: 387) | 5'-ataataggatccttagacatatttgaggccc-3' (SEQ ID NO: 388) |
| 53 | 5'-ataatacatatgaagccggtggtggtgc-3' (SEQ ID NO: 389) | 5'-agaagaggatccttagacataggtgagcccc-3' (SEQ ID NO: 390) |
| 41 | 5'-ataataccatgggtgtcgtggtccag-3' (SEQ ID NO: 391) | 5'-agaagaggatccttagacatatttcaggcccc-3' (SEQ ID NO: 392) |

SEQ ID NO:297, SEQ ID NO:53, and SEQ ID NO:41 were amplified by PCR and digested with appropriate enzymes (NdeI and BamHI for the PCR products containing SEQ ID NO:297 and SEQ ID NO:53, NcoI and BamHI for the PCR products containing SEQ ID NO:41) and gel purified (QIAquick Gel extraction Kit (Qiagen, Valencia, Calif.)). SEQ ID NO:297 and SEQ ID NO:53 were individually ligated into pET28 that had been digested with NdeI and BamHI and gel purified. SEQ ID NO:41 was ligated to pET30 that had been digested with NcoI and BamHI and gel purified. The ligation was transformed into TOP10. Colonies were screened for inserts. Isolates with an insert were submitted for DNA sequence analysis (Agencourt, Beverly, Mass.).

Purification of Aldolases

Confirmed aldolase clones were transformed into either BL21 DE3 or BL21 DE3 pLysS. Overnight cultures grown with the appropriate antibiotic were diluted into fresh media (typically 1:100) and grown to an $OD_{600}$ ~0.6 with aeration at 37° C. Cultures were then induced with 1 mM IPTG and shifted to 30° C. (with aeration) and incubation was continued overnight. Cells were harvested by centrifugation. The cell pellet was typically subjected to one freeze thaw cycle to assist with cell lysis. The cell pellet was lysed in BugBuster and Benzonase (Novagen, Madison, Wis.) (according to the manufacturer's protocol). Cell debris was removed by centrifugation. The crude protein extract was applied to a His-Bind column (Novagen, Madison, Wis.) that had been prepared according to the manufacturer's protocol. The column was washed and protein was eluted according to the manufacturer's protocol. The purified protein was desalted with PD-10 columns (GE Healthcare, Piscataway, N.J.). The buffer used for the exchange was 50 mM potassium phosphate pH 7.5, 100 mM NaCl, 4 mM $MgCl_2$. Purified protein was concentrated with Amicon centrifugal concentrators (Millipore, Billerica, Mass.).

Testing of Purified Aldolases

Purified aldolases were tested for their ability to produce R,R monatin from D-tryptophan. The following were added per 1 mL of reaction mixture: approximately 50 µg purified aldolase, 4 mM $MgCl_2$, 50 mM D-tryptophan, 0.5 mg purified B. sphaericus D-aminotransferase, 200 mM sodium pyruvate, 100 mM potassium phosphate buffer pH 7.5, and 0.05 mM PLP. Samples were taken at 2 hours and overnight. Results are shown in Table 11 below.

TABLE 11

Total monatin produced from D-tryptophan and % R,R

| Aldolase (time point) | Total monatin (ppm) | % R,R monatin (Reversed Phase LC peak area) | % R,R monatin (FDAA derivatization) |
|---|---|---|---|
| SEQ ID NO: 298 (2 hr) | 16.95 | 88.5 | n/a |
| SEQ ID NO: 298 (overnight) | 212 | 77.6 | 71 |
| SEQ ID NO: 54 (2 hr) | 12.05 | 96.7 | n/a |
| SEQ ID NO: 54 (overnight) | 161.85 | 93.0 | 91.1 |
| SEQ ID NO: 42 (2 hr) | 20.95 | 80.3 | n/a |
| SEQ ID NO: 42 (overnight) | 223.2 | 69.1 | 62.1 |
| SEQ ID NO: 28 (2 hr) | 14.25 | 95.8 | n/a |
| SEQ ID NO: 28 (overnight) | 176.6 | 93.4 | 92.3 |

The same experiments were done using L-tryptophan as the starting substrate and coupling the aldolases with Hex-AspC broad specificity L-aminotransferase produced and purified as described in U.S. Published Application No. 20050282260 (0.5 mg of purified protein). Results are shown below in Table 12 for total monatin production (subtracting background levels without aldolase present), and percent S,S monatin is shown based on reversed phase LC peak area. Numbers above 400 ppm are outside the linear range of the standard curve, and are approximate.

TABLE 12

Total monatin produced from L-tryptophan and % S,S

| Aldolase (time point) | Total monatin (ppm) | % S,S monatin (Reversed Phase LC peak area) | % S,S monatin (FDAA derivatization) |
|---|---|---|---|
| SEQ ID NO: 298 (1 hr) | 186.6 | 64.0 | n/a |
| SEQ ID NO: 298 (overnight) | 197.5 | 64.3 | 67.6 |
| SEQ ID NO: 54 (1 hr) | 70.4 | 36.5 | n/a |
| SEQ ID NO: 54 (overnight) | 87.8 | 41.7 | 42.1 |
| SEQ ID NO: 42 (1 hr) | 401.1 | 80.9 | n/a |
| SEQ ID NO: 42 (overnight) | 507.5 | 82.9 | 85.8 |
| SEQ ID NO: 28 (1 hr) | 56.2 | 30.1 | n/a |
| SEQ ID NO: 28 (overnight) | 88.8 | 32.2 | 33.8 |

These data and the above R,R monatin data illustrate that for R-MP specificity, the polypeptides with aldolase activity have the following order: SEQ ID NO:28>SEQ ID NO:54>SEQ ID NO:298>SEQ ID NO:42.

Example 10

Comparison of Total Monatin Production and Isomeric Distribution for the Polypeptides with Aldolase Activity of SEQ ID NO:116, SEQ ID NO:76, SEQ ID NO:44, SEQ ID NO:148, SEQ ID NO:46, SEQ ID NO:134, SEQ ID NO:74, SEQ ID NO:126, SEQ ID NO:102, SEQ ID NO:58, SEQ ID NO:88, SEQ ID NO:50, SEQ ID NO:106, SEQ ID NO:304, SEQ ID NO:300, and SEQ ID NO:28

The recombinant enzyme produced in Example 7 was used in coupled reactions with HMG aldolases to produce monatin from D-tryptophan and pyruvate as described in U.S. Published Application No. 20050282260. The polypeptide with aldolase activity of SEQ ID NO:28 was used as a benchmark in these assays and had been purified as described in Example 8.

To produce test quantities of each aldolase, 25 mL cultures were grown in LB medium containing ampicillin (100 µg/mL), to an $OD_{600}$ of approximately 0.5. The cultures were induced with 1 mM of IPTG. The cells were shifted to 30° C. and were grown overnight. Cellular extracts were prepared according to manufacturer's protocols (Novagen, Madison, Wis., Bugbuster reagent). Benzonuclease was also added. The soluble proteins in the cellular extracts were separated on a Bio-Rad Laboratories Experion Automated Electrophoresis Station (Bio-Rad, Hercules, Calif.) and analyzed for concentration and percent expression using the Experion Software version 1.1.98.0.

The following were added per 1 mL of reaction mixture: approximately 50 µg aldolase (supplied in cellular extracts unless otherwise noted), 4 mM $MgCl_2$, 50 mM D-tryptophan, 0.5 mg purified *B. sphaericus* D-aminotransferase, 200 mM sodium pyruvate, 100 mM potassium phosphate buffer pH 7.5, and 0.05 mM PLP. Dithiothreitol ("DTT") was added (final concentration 2 mM) to the samples noted below. Experiments were run in duplicate. Samples were incubated 2 hrs, and overnight (20 hours) at 30° C. with gentle shaking. Averaged results are shown below. The only stereoisomers detected when producing monatin using these methods are R,R and S,R. The percent R,R is listed below, and was determined by reversed-phase LC peak area.

TABLE 13

Total monatin produced from D-tryptophan and % R,R

| Aldolase (time point) | Total monatin (ppm) | % R,R monatin |
|---|---|---|
| SEQ ID NO: 116 (2 hr) | 34.5 | 97 |
| SEQ ID NO: 116 (18 hr) | 99 | 95 |
| SEQ ID NO: 76 (2 hr) | 40 | 76 |
| SEQ ID NO: 76 (18 hr) | 112 | 67 |
| SEQ ID NO: 44 (2 hr) | 32.5 | 97 |
| SEQ ID NO: 44 (18 hr) | 93.5 | 94 |
| SEQ ID NO: 148 (2 hr) | 31.5 | 94 |
| SEQ ID NO: 148 (18 hr) | 98 | 89 |
| SEQ ID NO: 46 (2 hr) | 42.5 | 84 |
| SEQ ID NO: 46 (18 hr) | 169 | 72 |
| SEQ ID NO: 134 (2 hr) | 43.5 | 92 |
| SEQ ID NO: 134 (18 hr) | 113 | 86 |
| SEQ ID NO: 74 (2 hr) | 23.5 | 96 |
| SEQ ID NO: 74 (18 hr) | 78.5 | 92 |
| SEQ ID NO: 126 (2 hr) | 18 | 94 |
| SEQ ID NO: 126 (18 hr) | 72 | 92 |
| SEQ ID NO: 102 (2 hr) | 1 | 0 |
| SEQ ID NO: 102 (18 hr) | 4.5 | 91 |
| SEQ ID NO: 58 (2 hr) | 23 | 92 |
| SEQ ID NO: 58 (18 hr) | 122 | 88 |
| SEQ ID NO: 88 (2 hr) | 57.5 | 74 |
| SEQ ID NO: 88 (18 hr) | 200.5 | 64 |
| SEQ ID NO: 50 (2 hr) | 32.5 | 99 |
| SEQ ID NO: 50 (18 hr) | 131.5 | 97 |
| SEQ ID NO: 106 (2 hr) | 4.5 | 78 |
| SEQ ID NO: 106 (18 hr) | 20 | 95 |
| SEQ ID NO: 304 (2 hr) | 0 | 0 |
| SEQ ID NO: 304 (18 hr) | 0.45 | 55 |
| SEQ ID NO: 304 DTT (2 hr) | 0 | 0 |
| SEQ ID NO: 304 DTT (18 hr) | 0.55 | 53 |
| SEQ ID NO: 300 (2 hr) | 0.85 | 34 |
| SEQ ID NO: 300 (18 hr) | 5.5 | 36 |
| SEQ ID NO: 300 DTT (2 hr) | 1.5 | 55 |
| SEQ ID NO: 300 DTT (18 hr) | 9 | 40 |
| SEQ ID NO: 28 (2 hr) | 25 | 99 |
| SEQ ID NO: 28 (18 hr) | 69 | 97 |

Total monatin production numbers ranged from 1 ppm to over 200 ppm and % R,R ranged from 0% to 99%. Because the aminotransferase was the same for all of the aldolases, changing the aldolase can have a significant impact on both the amount of monatin produced and the stereoisomeric distribution of the monatin produced. DTT (as in the samples below) appeared to increase the amount of total monatin produced.

The same experiments as above were done using L-tryptophan as the starting substrate and coupling the aldolases (supplied as cellular extract) with HexAspC broad specificity L-aminotransferase partially purified (0.5 mg of HexAspC). Averaged results (of duplicates) are shown below in Table 14 for total monatin production (subtracting background levels without aldolase present), and percent S,S monatin is shown based on reversed phase LC peak area. Numbers above 400 ppm are outside the linear range of the standard curve, and are approximate. Purified polypeptide with aldolase activity of SEQ ID NO:28 was used as a benchmark. Polypeptides with aldolase activity of SEQ ID NO:304 and SEQ ID NO:300 (plant derived) were used with and without 2 mM DTT. Shannon and Marcus (The Journal of Biological Chemistry 237: 3342-3347, 1962) used mercaptoethanol as a reducing agent in the original purification of a peanut HMG aldolase.

TABLE 14

Total monatin produced from L-tryptophan and % S,S

| Aldolase (time point) | Total monatin (ppm) | % S,S monatin |
|---|---|---|
| SEQ ID NO: 116 (2 hr) | 129 | 47.9 |
| SEQ ID NO: 116 (21 hr) | 207 | 56.4 |
| SEQ ID NO: 76 (2 hr) | 949 | 90.6 |
| SEQ ID NO: 76 (21 hr) | 1181 | 89.0 |
| SEQ ID NO: 44 (2 hr) | 128 | 55.0 |
| SEQ ID NO: 44 (21 hr) | 237 | 61.7 |
| SEQ ID NO: 148 (2 hr) | 199 | 71.5 |
| SEQ ID NO: 148 (21 hr) | 358 | 74.4 |
| SEQ ID NO: 46 (2 hr) | 346 | 79.3 |
| SEQ ID NO: 46 (21 hr) | 757 | 83.3 |
| SEQ ID NO: 134 (2 hr) | 215 | 69.2 |
| SEQ ID NO: 134 (21 hr) | 370 | 74.1 |
| SEQ ID NO: 74 (2 hr) | 75 | 51.4 |
| SEQ ID NO: 74 (21 hr) | 137 | 58.8 |
| SEQ ID NO: 126 (2 hr) | 47 | 56.7 |
| SEQ ID NO: 126 (21 hr) | 113 | 56.7 |
| SEQ ID NO: 102 (2 hr) | same as control | n/a |
| SEQ ID NO: 102 (21 hr) | 11.5 | 61.1 |
| SEQ ID NO: 58 (2 hr) | 113 | 71.9 |
| SEQ ID NO: 58 (21 hr) | 351 | 75.5 |
| SEQ ID NO: 88 (2 hr) | 852 | 90.1 |
| SEQ ID NO: 88 (21 hr) | 1352 | 88.8 |
| SEQ ID NO: 50 (2 hr) | 62 | 30.8 |
| SEQ ID NO: 50 (21 hr) | 145 | 38.6 |
| SEQ ID NO: 106 (2 hr) | 3.5 | 31.0 |
| SEQ ID NO: 106 (21 hr) | 45 | 34.4 |
| SEQ ID NO: 304 (2 hr) | same as control | n/a |
| SEQ ID NO: 304 + DTT (2 hr) | 1 | n/a |
| SEQ ID NO: 304 (21 hr) | same as control | n/a |
| SEQ ID NO: 304 + DTT (21 hr) | 10 | n/a |
| SEQ ID NO: 300 (2 hr) | 73 | 75.2 |
| SEQ ID NO: 300 + DTT (2 hr) | 121 | 83 |
| SEQ ID NO: 300 (21 hr) | 91 | 63.6 |
| SEQ ID NO: 300 + DTT (21 hr) | 197 | 71.6 |
| SEQ ID NO: 28 (2 hr) | 55 | 35.1 |
| SEQ ID NO: 28 (21 hr) | 87 | 40.4 |

Example 11

Effect of Dithiothreitol (DTT) on Monatin Production

Several of the enzymes in Example 10 were chosen for further study. The plant derived aldolases showed improvement upon the addition of DTT as a reducing agent. It was noted that the microbially-derived aldolases from environmental samples also contain a high percentage of cysteine residues. Therefore, further experiments were conducted to see if DTT increased monatin production for non-plant aldolases as well.

The following were added per 1 mL of reaction mixture: approximately 50 μg aldolase (supplied in cellular extracts unless otherwise noted), 4 mM $MgCl_2$, 50 mM D-tryptophan, 2 mg AT-103, 200 mM sodium pyruvate, 100 mM potassium phosphate buffer pH 7.5, and 0.05 mM PLP. Dithiothreitol was added (final concentration 2 mM) to the samples noted below. Experiments were run in duplicate. Samples were incubated 2 hrs at 30° C. with gentle shaking. Averaged results are shown below for total monatin as determined by LC/MS/MS, with the background production of monatin (no aldolase control) subtracted.

TABLE 15

Total monatin produced from D-tryptophan

| Aldolase | Total monatin (ppm) |
|---|---|
| SEQ ID NO: 116 | 126 |
| SEQ ID NO: 116 + DTT | 102 |
| SEQ ID NO: 44 | 107 |
| SEQ ID NO: 44 + DTT | 103 |
| SEQ ID NO: 46 | 88 |
| SEQ ID NO: 46 + DTT | 161 |
| SEQ ID NO: 58 | 118 |
| SEQ ID NO: 58 + DTT | 141 |
| SEQ ID NO: 50 | 243 |
| SEQ ID NO: 50 + DTT | 170 |
| SEQ ID NO: 28 purified protein | 174 |
| SEQ ID NO: 28 + DTT purified protein | 196 |

The no aldolase control produced 10 ppm of total monatin with and without DTT, indicating that the DTT is not affecting the overall reaction by reduction of byproducts, and is not affecting the D-aminotransferase activity. The polypeptides with aldolase activity of SEQ ID NO:46, SEQ ID NO:58, and SEQ ID NO:28 all showed a benefit from the addition of DTT. The polypeptide with aldolase activity of SEQ ID NO:46 showed the highest benefit, approximately 1.8 fold higher activity with 2 mM DTT. Two polypeptides with aldolase activity appear to have been inhibited by DTT (SEQ ID NO:116 and SEQ ID NO:50) while no effect was noted, within experimental error, for the polypeptide with aldolase activity of SEQ ID NO:44. However, it is possible that for each aldolase utilized there is an optimal concentration of DTT in order to detect a benefit of providing the reducing agent.

Figure 15:
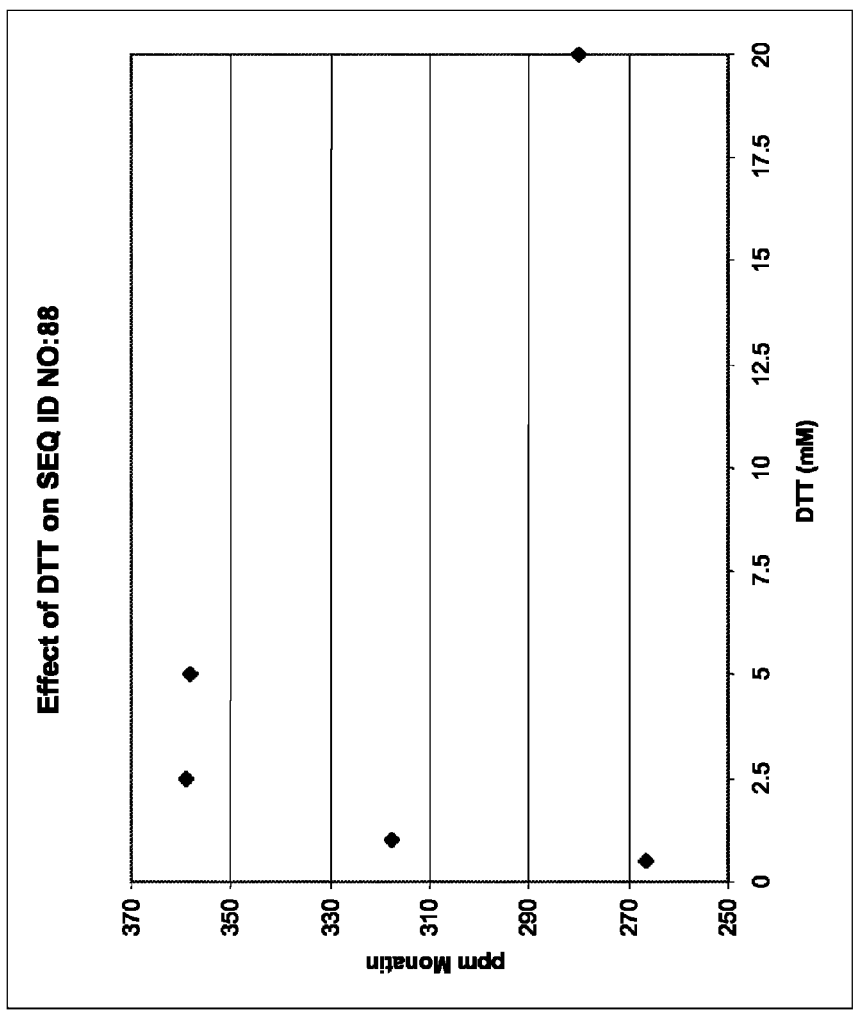
FIG. 15 illustrates the effect of dithiothreitol on the production of monatin by the polypeptide with aldolase activity of SEQ ID NO:88.

The polypeptide with aldolase activity of SEQ ID NO:88 was chosen to study the effect of DTT concentration on monatin production. Coupled reactions were carried out as above. Results are plotted in FIG. 15. The optimal concentration of DTT in this assay was between 2.5 and 5 mM, for the amount of aldolase added. Interestingly, if no DTT was added the amount of monatin produced was almost as high as the 2.5 mM DTT, but adding suboptimal amounts of DTT (0.5-1 mM) actually appears to be inhibitory, as well as addition of too much DTT (20 mM).

Example 12

Comparison of Total Monatin Production and Isomeric Distribution for the Polypeptides with Aldolase Activity of SEQ ID NO:278, SEQ ID NO:162, SEQ ID NO:276, SEQ ID NO:178, SEQ ID NO:202, SEQ ID NO:166, SEQ ID NO:218, SEQ ID NO:224, SEQ ID NO:226, SEQ ID NO:244, SEQ ID NO:250, SEQ ID NO:252, SEQ ID NO:264, SEQ ID NO:268, SEQ ID NO:272, SEQ ID NO:184, SEQ ID NO:282, SEQ ID NO:186, SEQ ID NO:192, SEQ ID NO:200, SEQ ID NO:280, SEQ ID NO:284, SEQ ID NO:172, SEQ ID NO:180, SEQ ID NO:168, SEQ ID NO:228, SEQ ID NO:236, SEQ ID NO:238, SEQ ID NO:240, SEQ ID NO:270, SEQ ID NO:156, and SEQ ID NO:28

The recombinant enzyme produced in Example 7 was used in coupled reactions with HMG aldolases to produce monatin from D-tryptophan and pyruvate as described in U.S. Published Application No. 20050282260. The polypeptide with aldolase activity of SEQ ID NO:28 was used as a benchmark in these assays and had been purified as described in Example 8.

To produce test quantities of each aldolase, 25 mL cultures were grown in LB medium containing ampicillin (100 µg/mL), to an OD$_{600}$ of approximately 0.5. The cultures were induced with 1 mM of IPTG. The cells were shifted to 30° C. and were grown overnight. Cellular extracts were prepared using Bugbuster reagent according to manufacturer's protocols (Novagen, Madison, Wis.). Benzonuclease was also added. The soluble proteins in the cellular extracts were separated on a Bio-Rad Laboratories Experion Automated Electrophoresis Station (Bio-Rad, Hercules, Calif.) and analyzed for concentration and percent expression using the Experion Software version 1.1.98.0.

The following were added per 1 mL of reaction mixture: approximately 200 µg of the polypeptides with aldolase activity of SEQ ID NO:278, SEQ ID NO:162, SEQ ID NO:276, SEQ ID NO:178, SEQ ID NO:202, SEQ ID NO:166, SEQ ID NO:218, SEQ ID NO:224, SEQ ID NO:226, SEQ ID NO:244, SEQ ID NO:250, SEQ ID NO:252, SEQ ID NO:264, SEQ ID NO:268, SEQ ID NO:272, SEQ ID NO:184, SEQ ID NO:282, SEQ ID NO:186, SEQ ID NO:192, and SEQ ID NO:200 or 50 µg of the polypeptide with aldolase activity of SEQ ID NO:280, SEQ ID NO:284, SEQ ID NO:172, SEQ ID NO:180, SEQ ID NO:168, SEQ ID NO:228, SEQ ID NO:236, SEQ ID NO:238, SEQ ID NO:240, SEQ ID NO:270, and SEQ ID NO:156 (supplied in cellular extracts unless otherwise noted), 4 mM MgCl$_2$, 50 mM D-tryptophan, 0.5 mg purified *B. sphaericus* D-aminotransferase, 200 mM sodium pyruvate, 100 mM potassium phosphate buffer pH 7.5, and 0.05 mM PLP. Experiments were run in duplicate. Samples were incubated 2 hrs, and overnight (20 hours) at 30° C. with gentle shaking. Averaged results are shown below. The only stereoisomers detected when producing monatin using these methods are R,R and S,R. The percent R,R is listed below, and was determined by reversed-phase LC peak area.

TABLE 16

Total monatin produced from D-tryptophan and % R,R

| Aldolase (time point) | Total monatin (ppm) | % R,R monatin |
|---|---|---|
| SEQ ID NO: 278 (1 hr) | 11.35 | 100 |
| SEQ ID NO: 278 (18 hr) | 282.15 | 96 |
| SEQ ID NO: 162 (1 hr) | 19.35 | 100 |
| SEQ ID NO: 162 (18 hr) | 277.9 | 98 |
| SEQ ID NO: 276 (1 hr) | 27.2 | 100 |
| SEQ ID NO: 276 (18 hr) | 421 | 98 |
| SEQ ID NO: 178 (1 hr) | 24.8 | 98 |
| SEQ ID NO: 178 (18 hr) | 394.25 | 94 |
| SEQ ID NO: 202 (1 hr) | 0 | 0 |
| SEQ ID NO: 202 (18 hr) | 19.2 | 91 |
| SEQ ID NO: 166 (1 hr) | 42.8 | 89 |
| SEQ ID NO: 166 (18 hr) | 601.25 | 71 |
| SEQ ID NO: 218 (1 hr) | 15.6 | 99 |
| SEQ ID NO: 218 (18 hr) | 456.05 | 96 |
| SEQ ID NO: 224 (1 hr) | 19.7 | 98 |
| SEQ ID NO: 224 (18 hr) | 406.55 | 93 |
| SEQ ID NO: 226 (1 hr) | 41.3 | 95 |
| SEQ ID NO: 226 (18 hr) | 460.15 | 84 |
| SEQ ID NO: 244 (1 hr) | 11.6 | 99 |
| SEQ ID NO: 244 (18 hr) | 168.3 | 98 |
| SEQ ID NO: 250 (1 hr) | 20.25 | 95 |
| SEQ ID NO: 250 (18 hr) | 289.25 | 89 |
| SEQ ID NO: 252 (1 hr) | 48.4 | 81 |
| SEQ ID NO: 252 (18 hr) | 335.8 | 73 |
| SEQ ID NO: 264 (1 hr) | 31.65 | 82 |
| SEQ ID NO: 264 (18 hr) | 252.35 | 77 |
| SEQ ID NO: 268 (1 hr) | 12.95 | 98 |
| SEQ ID NO: 268 (18 hr) | 252.55 | 95 |
| SEQ ID NO: 272 (1 hr) | 13.8 | 98 |
| SEQ ID NO: 272 (18 hr) | 165.8 | 98 |
| SEQ ID NO: 184 (1 hr) | 19.55 | 96 |

TABLE 16-continued

Total monatin produced from D-tryptophan and % R,R

| Aldolase (time point) | Total monatin (ppm) | % R,R monatin |
|---|---|---|
| SEQ ID NO: 184 (18 hr) | 221.85 | 94 |
| SEQ ID NO: 282 (1 hr) | 29.75 | 95 |
| SEQ ID NO: 282 (18 hr) | 399.05 | 91 |
| SEQ ID NO: 186 (1 hr) | 14.4 | 94 |
| SEQ ID NO: 186 (18 hr) | 116.15 | 93 |
| SEQ ID NO: 192 (1 hr) | 17.1 | 97 |
| SEQ ID NO: 192 (18 hr) | 131.25 | 97 |
| SEQ ID NO: 200 (1 hr) | 32.1 | 97 |
| SEQ ID NO: 200 (18 hr) | 331.05 | 94 |
| SEQ ID NO: 28 (1 hr) (200 µg) | 32.1 | 100 |
| SEQ ID NO: 28 (18 hr) (200 µg) | 111.45 | 99 |
| SEQ ID NO: 280 (1 hr) | 0 | n/a |
| SEQ ID NO: 280 (18 hr) | 3.25 | 61 |
| SEQ ID NO: 284 (1 hr) | 2.3 | 100 |
| SEQ ID NO: 284 (18 hr) | 55.35 | 98 |
| SEQ ID NO: 172 (1 hr) | 12.75 | 99 |
| SEQ ID NO: 172 (18 hr) | 205.9 | 96 |
| SEQ ID NO: 180 (1 hr) | 38.7 | 93 |
| SEQ ID NO: 180 (18 hr) | 310.9 | 75 |
| SEQ ID NO: 168 (1 hr) | 28 | 98 |
| SEQ ID NO: 168 (18 hr) | 301.1 | 90 |
| SEQ ID NO: 228 (1 hr) | 39.2 | 99 |
| SEQ ID NO: 228 (18 hr) | 367 | 95 |
| SEQ ID NO: 236 (1 hr) | 14.85 | 96 |
| SEQ ID NO: 236 (18 hr) | 250.05 | 90 |
| SEQ ID NO: 238 (1 hr) | 30.05 | 97 |
| SEQ ID NO: 238 (18 hr) | 466.15 | 90 |
| SEQ ID NO: 240 (1 hr) | 2.65 | 100 |
| SEQ ID NO: 240 (18 hr) | 51.55 | 96 |
| SEQ ID NO: 270 (1 hr) | 12.2 | 91 |
| SEQ ID NO: 270 (18 hr) | 214.3 | 83 |
| SEQ ID NO: 156 (1 hr) | 62.5 | 88 |
| SEQ ID NO: 156 (18 hr) | 623.9 | 71 |
| SEQ ID NO: 28 (1 hr) (50 µg) | 31.3 | 98 |
| SEQ ID NO: 28 (18 hr) (50 µg) | 444.25 | 97 |

Total monatin production numbers ranged from undetectable to over 600 ppm and % R,R ranged from 61% to 100%. Because the aminotransferase was the same for all of the aldolases, changing the aldolase can have a significant impact on both the amount of monatin produced and the stereoisomeric distribution of the monatin produced.

The same experiments as above were done using L-tryptophan as the starting substrate and coupling the aldolases (supplied as cellular extract) with HexAspC broad specificity L-aminotransferase produced and purified as described in U.S. Published Application No. 20050282260 (0.5 mg of purified protein). Results are shown below in Table 17 for total monatin production (subtracting background levels without aldolase present), and percent S,S monatin is shown based on reversed phase LC peak area. Numbers above 400 ppm are outside the linear range of the standard curve, and are approximate. Table 12 shows results for the benchmark R-specific enzyme, the polypeptide with aldolase activity of SEQ ID NO:28, which was assayed at the same time.

TABLE 17

Total monatin produced from L-tryptophan and % S,S

| Aldolase (time point) | Total monatin (ppm) | % S,S monatin (Reversed Phase LC peak area) | % S,S monatin (FDAA derivatization) |
|---|---|---|---|
| SEQ ID NO: 278 (1 hr) | 14.6 | 21.0 | n/a |
| SEQ ID NO: 278 (overnight) | 7905 | 24.6 | n/a |
| SEQ ID NO: 162 (1 hr) | 14 | 15.4 | n/a |
| SEQ ID NO: 162 (overnight) | 105.6 | 17.3 | n/a |
| SEQ ID NO: 276 (1 hr) | 35.8 | 10.2 | n/a |

TABLE 17-continued

Total monatin produced from L-tryptophan and % S,S

| Aldolase (time point) | Total monatin (ppm) | % S,S monatin (Reversed Phase LC peak area) | % S,S monatin (FDAA derivatization) |
|---|---|---|---|
| SEQ ID NO: 276 (overnight) | 67.8 | 9 | 15.1 |
| SEQ ID NO: 218 (1 hr) | 11.7 | 20.3 | n/a |
| SEQ ID NO: 218 (overnight) | 49.9 | 17.7 | 22.0 |
| SEQ ID NO: 244 (1 hr) | 6.2 | 18.0 | n/a |
| SEQ ID NO: 244 (overnight) | 24.4 | 14.7 | 19.6 |
| SEQ ID NO: 268 (1 hr) | 6.3 | 24.1 | n/a |
| SEQ ID NO: 268 (overnight) | 61.2 | 23.3 | 29.2 |
| SEQ ID NO: 272 (1 hr) | 5.7 | 20.5 | n/a |
| SEQ ID NO: 272 (overnight) | 43.6 | 19.9 | 22.9 |
| SEQ ID NO: 192 (1 hr) | 6.8 | 19.0 | n/a |
| SEQ ID NO: 192 (overnight) | 56.4 | 20.0 | 24.4 |
| SEQ ID NO: 172 (1 hr) | 29.9 | 35.6 | n/a |
| SEQ ID NO: 172 (overnight) | 184.2 | 42.4 | 45.6 |
| SEQ ID NO: 228 (1 hr) | 59.6 | 23.9 | n/a |
| SEQ ID NO: 228 (overnight) | 182 | 35.6 | 38.0 |

Example 13

Production of Monatin from indole-3-pyruvate Using a D-aminotransferase

AT-103 transaminase was part of a transaminase library purchased from BioCatalytics (Pasadena, Calif.) and the enzyme was tested for production of monatin in coupled reactions using the ProA aldolase from *C. testosteroni*. The aldolase was prepared as described in WO 03/091396 A2. AT-103 is a broad specificity D-transaminase (E.C. 2.6.1.21) from a *Bacillus* species that requires a D-amino acid (such as D-glutamate, D-aspartate, or D-alanine) as the amino acid donor. Enzymes and additional components/substrates were added directly to the reaction buffer provided in the kit, which contained 100 mM potassium phosphate buffer pH 7.5, 100 mM amino donor, and 0.1 mM PLP. To one mL of reaction buffer were added: 4 mg indole-3-pyruvate, 20 mg pyruvate, approximately 50 μg ProA provided in a cellular extract, 1 μL 2 M MgCl$_2$, and 2 mg of aminotransferase enzyme. Reactions were performed in duplicate. The reactions were incubated overnight at 30° C. with gentle shaking (100 rpm). The samples were filtered and submitted for reversed-phase LC/MS/MS analysis as described in Example 1. The results indicated that approximately 370 μg/mL monatin were produced using AT-103 enzyme. The results were further analyzed to determine ratios of S,R/R,S versus R,R/S,S monatin, on the basis of the peak areas of the two stereoisomer pools that resolve during the chromatographic separation. Of the total monatin produced by AT-103, 69% was R,R/S,S monatin in comparison to the mixed isomers. This enzyme is homologous to the *Bacillus subtilis* DAT enzyme described in WO 03/091396 A2, which is known to have a broad specificity for D-amino acids. Chiral analysis was performed using the FDAA methodology described in Example 1, which verified that the D-aminotransferase was making predominantly R,R monatin, and some S,R monatin as expected. Further transamination experiments with S,S monatin or R,R monatin and α-ketoglutarate as substrates verified that the BioCatalytics enzyme was highly selective for the D-configuration at carbon 4, as expected. In these experiments, no glutamate was detected in the reaction with S,S monatin and α-ketoglutarate as substrates.

To decrease the amount of S,S monatin or R,S monatin produced as byproducts in coupled reactions with AT-103 (the broad range D-transaminase) and the ProA aldolase, the aldolase was purified using His-Bind cartridges, following manufacturer's protocols (Novagen, Madison, Wis.). The purified enzyme preferably should not contain wildtype L-aminotransferase activities that can be present in cellular extracts (such as the native *E. coli* AspC or TyrB activities). The His-Bind eluent was desalted to remove imidazole using PD-10 columns (G25 Sephadex, GE Healthcare, Piscataway, N.J.) and was eluted in 50 mM Tris-Cl, pH 7. Experiments were carried out in duplicate in a volume of 1 mL and contained 100 mM Tris-Cl buffer, pH 7.8, 50 μg ProA aldolase, 4 mg indole-3-pyruvate, 1 or 2 mg D-aminotransferase, 200 mM sodium pyruvate, 2 mM MgCl$_2$, 3 mM potassium phosphate, 0.1 mM PLP, and 14.7 mg of D-glutamate. The tubes were incubated at 30° C. with gentle shaking. Two-hour time points were taken and frozen immediately at −20° C. The pH was adjusted at two hours from 5 to between 7-8 using NaOH, and the assays were incubated overnight. Samples were filtered and analyzed for monatin as described in Example 1. The two-hour samples did not have detectable amounts of monatin, probably due to the low pH. The overnight samples contained approximately 190 ng/mL monatin when 1 mg of D-aminotransferase was used, and approximately 84% was R,R monatin and 16% was S,R monatin. When 2 mg of D-aminotransferase were used, 540 ng/mL monatin was produced, approximately 71% was R,R monatin.

Similar experiments were conducted using BioCatalytics Aminotransferase buffer (BioCatalytics, Pasadena, Calif.), which contained 100 mM potassium phosphate pH 7.5, 0.1 mM PLP, and 100 mM D-glutamate. Solid indole-3-pyruvate and D-aminotransferase were added as above. ProA aldolase (50 μg), MgCl$_2$, and 50 mM pyruvate were added from stock solutions. The assays were treated as above, although no pH adjustment was required in this case. A negative control was done with just the BioCatalytics supplied enzyme and buffer, which did not contain monatin. The experimental results are shown in Table 18.

TABLE 18

Production of Monatin from Indole-3-Pyruvate in Phosphate Buffer

| Mg D-aminotransferase | Time (hrs) | Total Monatin (ng/mL) | % R,R |
|---|---|---|---|
| 0 | 2 | 0 | n/a |
| 1 | 2 | 6780 | not determined |
| 2 | 2 | 13170 | 55% |
| 0 | 16 | 0 | n/a |
| 1 | 16 | 15000 | not determined |
| 2 | 16 | 28930 | 51% |

The production of monatin in phosphate buffer is clearly higher than that in Tris buffered systems.

To compare activities of the cloned *B. subtilis* DAT from WO 03/091396 A2 with the BioCatalytics enzyme (AT-103) (BioCatalytics, Pasadena, Calif.), additional assays were done. The *B. subtilis* dat gene was also subcloned into pET30a to remove the His-6 tag. Untagged and tagged enzyme were produced in BL21(DE3), as described in WO 03/091396 A2. Cellular extracts were made and total protein assays were done to estimate protein concentration as described previously. Duplicate one mL reactions were done which contained: 500 μg D-aminotransferase, 50 μg ProA aldolase, 100 mM potassium phosphate pH 7.5, 3 mM MgCl$_2$, 4 mg indole-3-pyruvate, 200 mM sodium pyruvate, 7.35 mg (50 mM) D-glutamate, and 0.1 mM PLP. Samples were incubated at 30° C. for 1 hr, 2 hr, and overnight, and were filtered for LC/MS/MS analysis. The samples contained only the S,R and R,R stereoisomers of monatin, as determined by the FDAA derivitization protocol described in Example 1. The results are summarized in Table 19 below. The % RR was determined by peak areas that were separated by reversed phase chromatography.

TABLE 19

Comparison of D-aminotransferase enzymes

| Enzyme | Time (hr) | Monatin (ppb) | % RR monatin |
|---|---|---|---|
| B. sub DAT-HIS | 1 | 512 | not determined |
| B. sub DAT untagged | 1 | 1056 | not determined |
| BioCatalytics AT-103 | 1 | 2353 | not determined |
| B. sub DAT-HIS | 2 | 894 | ~80-90% |
| B. sub DAT untagged | 2 | 1913 | ~80% |
| BioCatalytics AT-103 | 2 | 6887 | 92.5% |
| B. sub DAT-HIS | 16 | 3014 | 31 |
| B. sub DAT untagged | 16 | 5612 | 33 |
| BioCatalytics AT-103 | 16 | 16131 | 66 |

The removal of the HIS-6 tag appears to have improved the activity of the *B. subtilis* D-aminotransferase; however, the BioCatalytics D-aminotransferase homolog clearly had the highest activity. The BioCatalytics D-aminotransferase homolog also showed greater substrate specificity for the R-monatin precursor. Increased incubation times appear to reduce the enantiomeric excess of R,R monatin that is produced.

Because the *Bacillus* D-aminotransferase enzymes have a preference for pyruvate as an amino acceptor and D-alanine as an amino donor. It was expected that D-alanine could be utilized as the amino donor for conversion of MP to monatin with similar or better results. Duplicate one mL reactions were done which contained: 500 µg D-aminotransferase, 50 µg purified ProA aldolase, 100 mM potassium phosphate pH 7.5, 3 mM MgCl$_2$, 4 mg indole-3-pyruvate, 100 mM sodium pyruvate, 25 mM D-glutamate or D-alanine, and 0.1 mM PLP. Samples were incubated for 2 hours, and treated as above prior to analysis. When D-alanine was used as the amino donor, slightly higher levels of monatin were produced (23 versus 21 ppm) as expected. Additionally, it is expected that high concentrations of pyruvate may inhibit the transamination step, thus dosing in smaller amounts of pyruvate over time may improve the overall rate of monatin production. One can see from the above data that even though one-half of the pyruvate was used in this case compared to the above table, significantly more monatin was produced. AT-103 is an example of an enzyme with limited activity for S-MP. Even though the ProA aldolase used in this study makes greater than 90-95% S-MP, AT-103 makes up to 92% R,R monatin.

Example 14

Production of R,R Monatin from D-tryptophan

The following were added per 1 mL of reaction mixture: approximately 60 µg *C. testosteroni* ProA aldolase (supplied in cellular extracts, as described in WO 03/091396 A2), 4 mM MgCl$_2$, 50 mM D-tryptophan, 0.5 mg BioCatalytics D-aminotransferase (AT-103) (BioCatalytics, Pasadena, Calif.), 100 mM sodium pyruvate, 100 mM potassium phosphate buffer pH 7.5 or 100 mM sodium acetate buffer pH 8, 0.05 mM PLP, 3 mM potassium phosphate (only to the acetate reactions), and 10 mM α-ketoglutarate. Experiments were run in duplicate, with negative controls in which no aldolase was added. Samples were incubated overnight (20 hours) at 30° C. with gentle shaking. The actual pH of the sodium acetate samples was approximately 5, while the final pH for the phosphate buffered samples was approximately 7. None of the aldolases appeared to have significant activity at pH 5, the sample containing ProA aldolase was slightly above the negative control but probably not above experimental error. In potassium phosphate, the ProA aldolase produced 73.4 ppm monatin with a ratio of R,R:S,R of 1.7:1 (~63% R,R from D-tryptophan).

Because the *Bacillus* D-aminotransferase enzymes have a preference for pyruvate as an amino acceptor and D-alanine as an amino donor, it was expected that the addition of alpha-ketoglutarate is unnecessary when producing R,R or S,R monatin from D-tryptophan. The above experiment was repeated (in 100 mM potassium phosphate buffer) using purified ProA aldolase (50-60 µg), and an incubation time of 2.5 hours. Duplicate experiments were run, with and without alpha-ketoglutarate. With 10 mM alpha-ketoglutarate added, 56.1 ppm monatin was formed from D-tryptophan (79.5% R,R, 20.5% S,R). Without alpha-ketoglutarate, 102.5 ppm monatin was formed (79% R,R, 21% S,R).

Example 15

Tryptophan Racemase

R,R-monatin has been produced using D-aminotransferase and an aldolase when D-tryptophan was used as the starting material (Example 14). That notwithstanding, L-tryptophan may be a preferred starting material for several reasons. For example, L-tryptophan may be less expensive and more readily available than D-tryptophan. This disclosure describes several methods for obtaining an active tryptophan racemase. Yields of R,R monatin are improved by using an R-specific aldolase, i.e., an aldolase that preferentially or selectively produces R-MP. FIG. 3 illustrates a method for producing stereoisomerically-enriched R,R monatin from L-tryptophan using a tryptophan racemase, a D-aminotransferase and an R-specific aldolase.

A selection for a tryptophan racemase is created by constructing a strain that would require an active racemase for growth. A tryptophan auxotroph needs a source of L-tryptophan when grown on minimal medium. Supplementing the medium with D-tryptophan is one way to select for a racemase that converts D-tryptophan to L-tryptophan. The tryptophan auxotrophs were tested for growth on minimal medium supplemented with D-tryptophan. The strains, CAG18455 and CAG18579 from the Coli Genetic Stock Center and NRRL12264 (Also lipA⁻, λDE3lysogenized, and cured of its plasmid), did not grow when supplemented with D-tryptophan but grew when supplemented with L-tryptophan. *E. coli* may be used as a host organism but other host organisms also may used, such as yeast, other bacteria, or other eukaryotic organisms. A tryptophan auxotroph (specifically NRRL12264 (also lipA⁻, λDE3 lysogenized and cured of its plasmid)) will grow on D-tryptophan when it has been transformed with a D-aminotransferase. This confirms the ability of *E. coli* to transport D-tryptophan into the cell.

Saicher and Lingens described the presence of a tryptophan racemase in *Pseudomonas aurereofaciens* (ATCC15926). Tryptophan racemase has also been described in several plants including tobacco, beets, tomato, and wheat and the enzyme appears to be induced by conditions of osmotic stress or drought. Tryptophan racemase may play a role in *Sclerochiton ilicifolius* in the native monatin production pathway. To isolate this racemase activity, an expression library is constructed from ATCC15926 (or another organism with tryptophan racemase activity) and the library is transformed into the tryptophan auxotroph. A strain is selected that will grow using D-tryptophan as the tryptophan source. A similar method is also used to screen many strains with known racemases to look for a racemase with activity on D-tryptophan. Examples include: alanine, serine, and glutamate racemases (T. Yoshimura and N. Esaki, "Amino Acid Racemases: Functions and Mechanisms." Journal of Bioscience and Bioengineering, Vol. 96, No. 2, 103-109, 2003). Alanine racemase is PLP dependent and has been cloned from *Salmonella typhimurium* (dadB gene). Other sources are *Escherichia coli, Bacillus subtilis, Pseudomonas aeruginosa, Vibrio cholerae, Schizosaccaroyces pombe*, and *Bacillus cereus*. A basidiomycetous mushroom, *Lentinus edodes*, also contains a broad activity alanine racemase. Serine racemase is also PLP dependent and is found in Eukaryotes (such as silkworm, rat brain, mouse brain cDNA) as well as bacteria (*Enterococcus gallinarum*). Glutamate racemase is PLP-independent and has been cloned from *Pediococcus pentosaceus, Bacillus pumilus, Lactobacillus fermenti, Lactobacillus brevis, E. coli, Aquifex pyrophilus*, and *Bacillus subtilis*. The glutamate racemase is very specific and, consequently, even structurally similar amino acids aspartate, asparagine, and glutamine are not substrates for the enzyme. Aspartate racemases also exist and are PLP independent. These enzymes are found in *Lactobacilli, Streptococcus* strains, and some archaea such as *Desulfurococcus* and *Thermococcus* strains. The bivalve mollusk *Scapharca brouhtonii* also contains an aspartate racemase. Other racemases found in the literature include amino acid racemase (EC 5.1.1.10) from *Anabaena* sp. and *Pseudomonas striata*, proline racemase, multifunctional phenylalanine racemase. Related epimerases or racemases are also being tested. Potential racemases are tested to make sure they are not D-tryptophan aminotransferases. This screening is done by sequence analysis and/or an enzyme assay.

Enzymes that pass the test as a racemase are screened for activity on monatin as described in Example 17. Ideally, one obtains an enzyme that is very specific for tryptophan and has little or no racemase activity on monatin.

A tryptophan racemase also may be evolved and/or improved (via mutagenesis or recombinant engineering) from an existing racemase, transaminase, or epimerase. Additionally, because crystal structures for alanine aminotransferases are known, these may be used as a basis for rational, structure based mutagenesis. The process described above is used as an initial selection for tryptophan racemase activity and as a screen for improved activity.

Tryptophan Racemase Libraries

Construction of Libraries:

*Burkholderia pyrrocina* (ATCC15958) and *Pseudomonas chlororaphis* (ATCC15926) were obtained from the American Type Culture Collection. They were grown as recommended by ATCC and genomic DNA was prepared according to the method of Mekalanos J J. (Duplication and amplification of toxin genes in *Vibrio cholerae*. Cell. 1983. 35:253-63). The genomic DNA was partially digested with the Sau3AI restriction enzyme. 1-3 Kbp fragments were gel purified using a Qiagen QIAquick Gel Extraction Kit (Qiagen, Valencia, Calif.). The purified DNA was ligated into pTrc99a (Amersham, Piscataway, N.J.) that had been digested with BamHI and purified as above. The ligation was done at room temperature with overnight incubation using a 3:1 molar ratio of insert to vector. The ligated library was transformed into TOP10F' chemically competent cells (Invitrogen, Carlsbad, Calif.) and plated on LB medium with 100 µg/ml ampicillin. After overnight incubation of the transformation plates, colonies were scraped off of the plates washed with liquid LB medium and an appropriate size cell pellet was mini-prepped using a Qiagen QIAquick mini-prep kit (Qiagen, Valencia, Calif.). Approximately 30,000 colonies were pooled and mini-prepped.

The pooled plasmid was transformed into CAG18455 (trpC83::Tn10, rph-1) or CAG18579 (trpC::Tn10kan, rph-1). Both strains are tryptophan auxotrophs so they will not grow on M9 minimal medium (Difco) unless the medium is supplemented with tryptophan. The transformants were plated on M9 minimal medium supplemented with D-tryptophan. This selects for a strain that can convert D-tryptophan to L-tryptophan.

Prior to transformation of the library, the strains were tested for growth on minimal medium with L- or D-tryptophan. The strains were tested for growth on minimal medium supplemented with D-tryptophan and no growth was observed. Both strains grew on identical medium supplemented with L-tryptophan instead of D-tryptophan. Additionally, a derivative of NRRL12264 (the strain used had been cured of the tryptophan operon plasmid, lysogenized with λDE3, and deleted for lipA, in addition to the other chromosomally encoded mutations (serB, ΔtrpED, tnaA2, aroP) (this strain could not grow on minimal medium supplemented with D-tryptophan but grew on identical medium supplemented with L-tryptophan instead of D-tryptophan) was transformed with a D specific aminotransferase from *Bacillus subtilis* (WO 03/091396). Expression of the D-aminotransferase was driven by the T7 promoter. The transformed strain was able to grow on M9 minimal medium supplemented with D-tryptophan.

The colonies that grow on the D-tryptophan medium are screened. The plasmid is isolated and retransformed into the parent strain (CAG18455 or CAG18579) to confirm that growth on D-tryptophan medium is dependent on the plasmid and not on a host mutation. The nucleotide sequences of the plasmids that complement the tryptophan auxotrophy are analyzed. Clones that are determined to contain a tryptophan racemase gene are further analyzed.

The tryptophan racemase from other tissue sources is isolated in a similar fashion. There are literature reports of tryptophan racemase activity in both tobacco tissue culture cells (*Nicotiana tabacum* L. var. Wisconsin 38) (Miura, G. A. and Mills, S. E. The conversion of D-tryptophan to L-tryptophan in cell cultures of tobacco. Plant Physiol. 1971. 47:483-487) and in crude protein extracts of wheat (*Triticum aestivum*) (Rekoslavskaya, N. I., Yur'eve, O. V., Shibanova, L. A., and Salyaev, R. K. Synthesis and physiological function of D-tryptophan during wheat germination. Russian J. Plant Physiol. 1997. 44:196-203). A cDNA expression library is made from tissue, as described in the literature, and the expression library is used to transform a tryptophan auxotroph as described above.

Tryptophan Racemase Assay

Clones that are identified as potentially having a tryptophan racemase are transformed into a strain of *E. coli* commonly used for expression of recombinant proteins, such as BL21. The cells are grown in LB broth to an optical density at 600 nm of 0.4-0.6. The promoter driving expression of the racemase is induced with IPTG (0.1 mM final concentration). After induction, the cells are allowed to express the protein for 1-3 hours at 37° C. (with aeration). The cells are harvested and lysed by French press, sonication, or by chemical means (such as BugBuster (Novagen, Madison, Wis.)). The lysed cells are centrifuged to remove the cell debris. The clarified extract is used directly in assays.

Varying amounts of extract is added to a solution such that the final concentration is 50 mM potassium phosphate (pH 7.0) and 2 mM L-tryptophan. Pyridoxal-5'-phosphate is added at a final concentration of 10 µM. The samples are incubated and then analyzed by LC/MS. The presence of a D-tryptophan peak when only L-tryptophan is used as a substrate indicates a positive result. D-tryptophan concentration should increase with increasing time until equilibrium is reached, and the rate should also increase with protein concentration until the concentration of enzyme is high enough that it is no longer saturated with substrate. D-tryptophan may also be converted to L-tryptophan as above.

A complementing gene may code for a D-aminotransferase. (A "complementing gene" is a gene that, when expressed, nullifies a mutation in an organism. For example, if an organism has a null mutation in one of the genes required for synthesis of tryptophan by the cell, a complementing gene could be one that, when expressed, allows the strain to grow on minimal medium (i.e., without tryptophan). This reaction requires an alpha-keto acid such as α-ketoglutarate, oxaloacetate, or pyruvate as an amino acceptor. These compounds will likely be present in a cell extract (in small amounts). These compounds may be removed using a PD-10 desalting column (GE Healthcare, Piscataway, N.J.) and the assay may still be performed in crude extract. The tryptophan racemase activity is purified using conventional column chromatography. Finally, the open reading frame identified as a potential tryptophan racemase is cloned into an expression vector with an affinity tag. The potential tryptophan racemase is then purified by affinity chromatography. In either case the purified protein is used in enzyme assays essentially as described above.

Reverse Genetic Engineering of Tryptophan Racemase

The tryptophan racemase may be purified from either plant or microbial sources by conventional protein purification techniques including ammonium sulfate fractionation, and conventional column chromatography. Once the protein has been purified such that a spot can be isolated on a 2-D gel, peptide microsequencing techniques or conventional Edman type amino acid sequencing are utilized (see golgi.harvard.edu/microchem/ for descriptions of the protocols and equipment used for this type of work). In some cases, however, the genome sequence of the organism cannot be used as a source of the protein for the protein purification because such sequence has not been determined yet. In that situation, the first set of degenerate primers may be designed based on sequence available from the closest known relative of the protein source. Degenerate PCR and genome walking is then be performed according to established protocols to isolate the tryptophan racemase coding sequence.

Tryptophan Racemase Monatin Production

The following is added per 1 mL of reaction mixture: approximately 60 µg *C. testosteroni* ProA aldolase (supplied in cellular extracts, as described in WO 03/091396 A2), 100 µL/mL of tryptophan racemase cellular extract or 1 mg/mL purified tryptophan racemase, 4 mM $MgCl_2$, 50 mM L-tryptophan, 0.5 mg BioCatalytics D-aminotransferase (AT-103) (BioCatalytics, Pasadena, Calif.), 100 mM sodium pyruvate, 100 mM potassium phosphate buffer pH 7.5, 0.05 mM PLP, and 10 mM α-ketoglutarate. Because pyruvate is an acceptable amino acceptor for the broad specificity D-aminotransferase, α-ketoglutarate is optional. Experiments are run in duplicate, with negative controls in which no aldolase was added or no tryptophan racemase was added. Samples are incubated ~1 hour or overnight (20 hours) at 30° C. with gentle shaking.

The tryptophan racemase is tested for activity on monatin. An assay similar to that in Example 17 is used with monatin as a substrate, and compared to the activity of the enzyme on tryptophan. The ideal enzyme has activity on tryptophan but little or no activity on other amino acids particularly glutamate and monatin. If the enzyme has significant activity on monatin, the enzyme may be mutagenized to decrease the activity on monatin and or glutamate while keeping the tryptophan activity unchanged or at a level high enough for the enzyme to be useful in monatin production. Techniques that may be used for mutagenesis include, but are not limited to, error prone PCR, site-directed mutagenesis, modeling to identify site-directed mutagenesis targets (sites that may be involved in substrate binding), passage through mutagenic strains, and DNA shuffling.

Mutagenized racemases may be screened for tryptophan activity using a plate assay as described above. Clones that retain tryptophan activity are then screened for a loss of activity on monatin.

Example 16

Site Directed Mutagenesis of HEXAspC

Experimental Overview

A hexamutant of *E. coli* AspC (HEXaspC) was found to have better activity as compared to AspC for the production of S,S monatin as described in Example 6 of WO 03/091396 A2. HEX (accession number:/AHFA gi:127190) contains the following mutations from AspC (*E. coli* numbering): V35L, K37Y, T43I, N64L, T104S, and N285S. Based on structural analysis and literature reports (S. Rothman and J. Kirsch, J. Mol. Biol. (2003), 327, 593-608; S. Rothman et al., Protein Science (2004), 13: 763-772), 5 more mutants were created that were expected to increase the kinetic activity toward substrates utilized in the monatin production pathway: L-tryptophan, S-MP, or both. Two of the mutants increased transamination rates for both tryptophan and S,S monatin. Two of the mutants showed an increased stereoselectivity for the formation of S,S monatin while one was less stereoselective. Based on this, it is expected that the broad specificity D-aminotransferase from *Bacillus* sp. having similar mutations is useful as the D-aminotransferase in the R,R monatin pathways shown in FIG. 3, and described in Example 15. One of the mutants (HEXaspCP9T/R122G) had increased activity for L-tryptophan transamination, but activity in S,S monatin production or S,S monatin transamination was decreased significantly. Thus, it is expected that this enzyme is useful in the first step of the R,R monatin production pathways shown in FIGS. 1, 2, 4, 5, 6, 7, and 8 and described in Examples 18 and 19. In general, an aminotransferase that has activity similar to that of AspC on L-tryptophan and limited activity on R-MP and S-MP would be useful for the processes depicted in FIGS. 1, 2, 4, 5, 6, 7, and 8.

Methods and Materials

The HEX gene cloned in pUC19 was provided by Professor J. F. Kirsch (Department of Molecular and Cell Biology, University of California, Berkeley, Berkeley, Calif. 94720-3206) and used as the template for the cloning of the gene into pET23a. See James J. Onuffer and Jack F. Kirsch, Redesign of the substrate specificity of *Escherichia coli* aspartate aminotransferase to that of *Escherichia coli* tyrosine aminotransferase by homology modeling and site-directed mutagenesis, Protein Science, 4: 1750-1757 (1995). See also NCBI accession number 1AHF_A GI:1127190 (HEX amino acid sequence). The following primers were designed for cloning the HEX gene into the pET23a vector (Novagen, Madison, Wis.):

```
HEXaspC primers:
                                      (SEQ ID NO: 393)
N term: 5'-GCGGAACATATGTTTGAGAACATTACCGCC-3';

(SEQ ID NO: 394)
C term: 5'-ATAACCGGATCCTTACAGCACTGCCACAATCG-3'
```

The following PCR protocol was used for gene amplification: In a 100 µL reaction, 50 ng DNA template, 1.0 µM of each primer, 0.2 mM each dNTP, 1 U Pfu Turbo Polymerase (Stratagene, La Jolla, Calif.), and 1× Cloned Pfu buffer were added. The thermocycler program utilized a hot start of 94° C. for 5 minutes; followed by 25 cycles of a denaturing step at 94° C. (30 sec), an annealing step at 55° C. (1 min), and an extension step at 72° C. (2 min) and finally a finishing step at 72° C. (7 min). Standard molecular biology techniques were utilized to clone the PCR product into pET23a using NdeI and BamHI restriction sites.

The tryptophan residue at position 130 is thought to be important for stacking interactions with the pyridoxyl ring, but also appears to be a source of steric hindrance with the S-monatin precursor (MP) substrate, based on protein modeling observations. Therefore, an amino acid with a smaller hydrophobic side chain (phenylalanine) was used to replace the tryptophan. The rest of the mutations were based on kinetics data in literature, although new combinations of desirable mutations were created. All mutations to HEXaspC, with the exception of W130F, were made using the Stratagene Multi-Change kit (Stratagene, La Jolla, Calif.) by following the manufacturer's instructions. The W130F mutation was made using the Stratagene QuikChange kit (Stratagene, La Jolla, Calif.) according to the manufacturer's instructions with the only exception being that the extension temperature for the PCR reaction was decreased to 66° C. The primers for the multi-change kit were designed using the QuikChange multi-kit primer design tool on <www.stratagene.com>, except for the W130F single mutation primers.

The primer sequences are listed below in Table 20.

TABLE 20

| Primer | Sequence (5' to 3') |
|---|---|
| aspCW130F_backward | CGCTCTTATGGTTCGGTTTGCTTGGGTTGCT CACCC (SEQ ID NO: 395) |
| aspCW130F_forward | GGGTGAGCAACCCAAGCTTTCCGAACCATAA GAGCG (SEQ ID NO: 396) |
| R122G-1[a] | CAAAAAATACCAGCGTTAAGGGAGTGTGGGT GAGCAACC (SEQ ID NO: 397) |
| P9T_4[a] | CATTACCGCCGCTACTGCCGACCCGATTC (SEQ ID NO: 398) |
| I68V-1[a] | CACCAAAAATTACCTCGGCGTAGACGGCATC CCTGAATT (SEQ ID NO: 399) |
| T156A[a] | TGATGCGGAAAATCACGCTCTTGACTTCGAT GCAC (SEQ ID NO: 400) |

[a]Denotes a primer that was modified by 5' phosphorylation

Expression of HEXaspC Mutant Genes and Analysis of Enzyme Activity

Liquid cultures (5 mL) of Novagen Overnight Express™ Autoinduction System 2 (Catalog #71366-3; solutions 1-6) (Novagen, Madison, Wis.) were inoculated from fresh plates or frozen glycerol stocks of the following strains:

E. coli BL21(DE3)::HEXaspCpET23a
E. coli BL21(DE3)::HEXaspCW130FpET23a
E. coli BL21(DE3)::HEXaspCT156ApET23a
E. coli BL21(DE3)::HEXaspCP9T/T156ApET23a
E. coli BL21 (DE3)::HEXaspCP9T/R122GpET23a
E. coli BL21 (DE3)::HEXaspCR122G/T156ApET23a.

The cultures were incubated at 37° C. at 230 rpm for 6-8 h. The $OD_{600}$ of each culture was determined and the volume of culture necessary to obtain an $OD_{600}$ of 0.03-0.05 in 25 mL was calculated. The calculated volumes of each liquid culture were transferred to flasks containing 25 mL of the same medium. The Overnight Express™ Autoinduction System 2 is a complete, chemically defined medium for high-level expression with IPTG-inducible expression systems that uses lactose as the inducing agent and does not require monitoring of cell growth. The Overnight Express cultures were incubated at 30° C. with shaking at 230 rpm for 18 h. The cells were harvested by centrifugation and washed once with cold 50 mM MOPS, pH 7.0. The cells were then lysed using Bugbuster™ (primary amine free) Extraction Reagent (Novagen Catalog #70923-3) (Novagen, Madison, Wis.) containing 1 µL/mL benzonase nuclease (Novagen Catalog #70746-3) (Novagen, Madison, Wis.), 5 µL/mL Protease Inhibitor Cocktail Set II (Novagen Catalog #539132) (Novagen, Madison, Wis.) and 0.33 µL/10 mL r-Lysozyme (Novagen Catalog #71110-3) (Novagen, Madison, Wis.) following the Novagen recommended protocol. After incubation at 25° C. for 15 minutes with gentle shaking, the cell debris from each suspension was pelleted by centrifugation at 21,000 g for 15 minutes at 4° C. The supernatant was carefully decanted and analyzed as the cell free extract. Inclusion body fractions were isolated by suspending the cell debris fractions in 30% Bugbuster™ (primary amine free) Extraction Reagent, centrifuging at 21,000×g for 10 min; suspending the centrifuged pellets in 10% Bugbuster™ (primary amine free) Extraction Reagent, centrifuging again to isolate the washed pellets. The cell free extracts and inclusion body fractions were analyzed for protein expression by SDS-PAGE on 4-15% gradient gels (BioRad # 161-1104, Hercules, Calif.). For the cell extract samples, twenty micrograms of soluble protein were loaded in each gel lane (premixed with 1× protein loading buffer and heated at 95 C for 5 min). The inclusion body fractions were dissolved in 1× protein loading buffer (0.2 mL), heated for 10 minutes at 95 C and 5 µL of each solution was loaded per gel lane. The amount of each HEX mutant in comparison to the total soluble protein loaded into each lane was calculated by band intensity analysis using Labworks BioImaging 1D-gel tool (UVP, Inc. Upland, Calif.), and is reported below:

TABLE 21

| Sample | HEXaspC protein/total soluble protein |
|---|---|
| E. coli BL21(DE3)::HEXaspCP9T/T156ApET23a CFE | 0.310 |
| E. coli BL21(DE3)::HEXaspCP9T/R122ApET23a CFE | 0.145 |
| E. coli BL21(DE3)::HEXaspCpET23a CFE | 0.172 |
| E. coli BL21(DE3)::HEXaspCR122A/T156ApET23a CFE | 0.174 |
| E. coli BL21(DE3)::HEXaspCW130FpET23a CFE | 0.114 |
| E. coli BL21(DE3)::HEXaspCT156ApET23a CFE | 0.120 |

Analysis of the gels showed that the HEXaspCR122A/T156A mutant was the only protein that was found in substantial quantities as inclusion bodies. The HEXaspCP9T/T156A protein gave the highest level of expression, approximately 90% better than HEXaspC protein. In contrast, the W130F, T156A and P9T/R122G proteins were expressed in lower concentrations than HEXaspC.

The activity of the HEXaspC mutant proteins for the production of S,S-monatin was measured using the following reaction conditions: Each 1 mL reaction contained 50 mM TAPS, pH 8.2, 4 mM MgCl$_2$, 3 mM sodium phosphate, pH 8.0, 200 mM sodium pyruvate (pH adjusted to 8), 5 mM α-ketoglutarate (pH adjusted to 8), 50 mM tryptophan, 0.05 mM pyridoxal 3-phosphate, 50 µg/mL ProA aldolase (added as a cell free extract) and varying concentrations (approximately 50 and 500 µg/mL) of aminotransferase (added as a cell free extract). Deaerated water was used to prepare the stock solutions and to adjust the volume of the reaction mixtures to 1.0 mL. The pyridoxal phosphate was added just prior to the addition of the enzymes. The reaction tubes were incubated at 30° C. with gentle shaking for 4 h. Samples (0.01 mL) were withdrawn at 1, 2, and 4 h after the addition of the enzymes, filtered, and analyzed by LC/MS/MS, as described in Example 1. Monatin production was normalized based on the amount of aminotransferase present in the reactions. Under the conditions of these assays, the HEXaspC and the HEXaspCT156A produced the most total monatin per mg of aminotransferase while the P9T/R122G protein produced the least, followed by HEXaspCW130F. The HEXaspCW130F and P9T/R122G enzymes showed the greatest stereoselectivity for S-MP (greater than 98% S,S-monatin), even when high enzyme concentrations were used (greater than 300 µg/mL). The percentage of S,S-monatin product decreased to less than 90% in the enzymatic reactions containing the P9T/T156A enzyme at high concentration. The other mutants showed a product stereoselectivity very similar to the original HEXaspC mutant (approximately 95% S,S-monatin). Analysis of the product of the reaction containing the HEXaspC enzyme using the FDAA derivitazation reagent described in Example 1 showed that the second stereoisomer formed is R,S-monatin.

Assaying of Tryptophan and Monatin Aminotransferase Activity

The mutants were tested for transamination activity using S,S monatin and L-tryptophan as substrates. The aminotransferase activity was measured by following the formation of the co-product of the reaction, glutamate, by HPLC with OPA-post-column derivitization as described in Example 1. The reaction mixture contained, in 1.0 mL, 100 mM HEPPS buffer, pH 8.0, 20 mM alpha-ketoglutarate, 0.08 mM pyridoxal phosphate, 25 mM tryptophan or S,S monatin, and enzyme (supplied as 2.5 mg of in cellular extracts protein). All components except the enzyme were mixed together, the enzyme was added to start the reaction and the reaction solution was incubated at 30° C. (gentle shaking) for 90 minutes. Reactions were done in duplicate, with negative controls in which no enzyme was added. The reaction was stopped by the addition of 10% formic acid (final concentration), the mixture was centrifuged at 21,000 rpm, and the supernatant was carefully removed and filtered. The data were corrected for background levels of glutamate and for the dilution from the addition of acid to precipitate the proteins, then normalized by amount of mutant aminotransferase added. When tryptophan was utilized as a substrate, HEXaspC produced 13.0 mM glutamate per mg of aminotransferase per hour. The relative activity, expressed as a percentage, of the mutants is as follows: HEXaspCW130F (156%), HEXaspCT156A (151%), HEXaspCP9T/T156A (63.7%), HEXaspCP9T/R122G (116%), and HEXaspCR122G/T156A (107%). When S,S monatin was utilized as a substrate, HEXaspC produced 7.43 mM glutamate per mg of aminotransferase per hour. The relative activity, expressed as a percentage, of the mutants is as follows: HEXaspCW130F (113%), HEXaspCT156A (87.7%), HEXaspCP9T/T156A (67.3%), HEXaspCP9T/R122G (11.2%), and HEXaspCR122G/T156A (114%).

The HEXaspCP9T/R122G mutant had increased activity for tryptophan to indole-3-pyruvate conversion, but decreased activity for S,S monatin transamination. The ratio of tryptophan to monatin activity was 18.2 in comparison to 1.75 for HEXaspC, making it a desirable candidate for production of R,R monatin using pathways that require an L-aminotransferase such as those described in Examples 18 and 19. As such, the HEXaspCP9T/R122G is an example of an aminotransferase with limited activity on S,S monatin (and MP).

Most of the mutations improved L-tryptophan activity, but only two mutants increase activity toward both L-tryptophan and S,S monatin (HEXaspCW130F and HEXaspCR122G/T156A). Because 25 mM of substrate was used in these assays, the enzymes were most likely saturated and the activity is a reflection of the $k_{cat}$ of the enzymes. However, under the conditions in which the assays for S,S monatin production were performed (above) it is unlikely that the concentration of S-MP is sufficient to saturate the enzyme, thus the increase in $k_{cat}$ is not reflected. It has been reported, for similar substrates, that some of the mutations made increase the $k_{cat}$ but also increase the apparent $K_m$ for the amino acid substrate. If increasing concentrations of substrates were used, it is expected that these two mutants would provide a benefit in production rates of S,S monatin in comparison to HEXaspC. The HEXaspCT156A mutation appears to have increased tryptophan transamination rates without having a significant effect on MP transamination rate under the conditions above for S,S monatin production.

By comparison of the structures of HEXaspC and one of the *Bacillus* sp. D-aminotransferase enzymes (see, for example, S. Sugio, G. A. Petsko, J. M. Manning, K. Soda, and D. Ringe, *Biochemistry* 34 (1995) pp. 9661-9669), the W130F, R122G, T156A, and HEX mutations of AspC could be mapped to corresponding residues in the D-aminotransferase structure. It is expected that similar mutations in the broad specificity D-aminotransferase would improve the overall production of R,R monatin as described in Example 14. For example, the functionality provided by tryptophan 130 in AspC is replaced in *Bacillus* D-aminotransferases by hydrogen bonding between the side chains of serines 179-181 and glutamate 166 (YM-1 numbering scheme). To lessen steric hindrance, the glutamate could be mutated to an aspartate residue. Some D-aminotransferases have a threonine residue at position 179, which would increase steric hindrance and should be avoided. The *B. sphearicus* enzyme has an alanine in place of serine at position 181, which may also reduce steric hindrance.

Additional information from studies of aspartate aminotransferase can be applied to the D-aminotransferase as well. While the AspC enzyme has an arginine in the active site that interacts with the side chain of dicarboxylate substrates, the D-aminotransferase has a loop from Ser240 to Ser243. The side chains of Ser240, Thr242, and Ser243 face the same direction and form a pocket with the hydroxyl group of Ser180 which provides a surface for both nonpolar and polar substrates can interact. Ser180 is involved in PLP binding; however, to improve the activity of a D-aminotransferase with R-MP, one can modify the Ser240, Thr242, or Ser243 residues to accept larger substrates or to favor negatively charged substrates. For instance, Thr242 can be mutated to Ser to reduce the side chain length. One of the residues can be mutated to lysine or arginine, such as Ser243. The residues (YM-1 numbering) Val30-Val36 are located in a beta strand across the active site of the D-aminotransferase, and are also important for activity. Tyr31, Val33, Glu32, and Lys35 are thought to face the active site. Tyr31, Glu32, and Val33 are invariant in all the *Bacillus* homologs. Ro et al. (FEBS Lett 398 (1996) pp. 141-145) mutagenized Val33 to Ala and found a slightly increased catalytic efficiency for alpha-ketoglutarate transamination and a significantly improved catalytic efficiency for bulkier substrates (less steric hindrance). In some homologs Lys35 is replaced with Arg, but if steric hindrance is a concern the Lys residue is preferable. Valines 34 and 36 are also preferable over conservative substitutions such as isoleucine, again due to less steric hindrance for large molecules such as MP.

Example 17

Cloning, Expression, and Testing of Glutamate and Aspartate Racemases

This example describes methods used to clone and test amino acid racemase enzymes, which can be used to interconvert between L-glutamate and D-glutamate (or L- and D-aspartate or L- and D-alanine). Glutamate, aspartate, or alanine racemases are useful in a biosynthetic pathway to produce R,R monatin when a step in that pathway produces an L-amino acid (such as L-glutamate, L-aspartate, or L-alanine) and another step in the pathway consumes a D-amino acid (such as D-glutamate, D-aspartate, or D-alanine). FIG. 4 illustrates a biosynthetic pathway for producing R,R monatin from L-tryptophan using an L-tryptophan-specific aminotransferase, an R-specific aldolase, a D-aminotransferase and a glutamate (or aspartate or alanine) racemase.

Genes were cloned into the pET28 and pET30 vectors to generate both non-tagged proteins and fusion proteins with cleavable N-terminal HIS$_6$-Tag/T7-Tags. The resulting proteins were purified using immobilized metal affinity chromatography.

Experimental Overview

Genes encoding glutamate racemases (EC 5.1.1.3) from *Lactobacillus brevis* (Genbank Accession No. D29627, nucleic acid sequence), and *Pediococcus pentosaceus* (murI gene) (Genbank Accession No. L22789) were cloned and expressed in *E. coli*. The extracts were tested for activity in conversion of L-glutamate to D-glutamate and D-glutamate to L-glutamate. BioCatalytics aspartate racemase enzyme (EC 5.1.1.13) (BioCatalytics, Pasadena, Calif.) was also tested for interconversion between L- and D-aspartate.

Isolation of Genomic DNA for Cloning

*L. brevis* genomic DNA (ATCC 8287D) was obtained from the American Type Culture Collection. *P. pentosaceus* (ATCC 25745) was grown at 37° C. in *lactobacilli* MRS broth and 2 ml was used for genomic DNA isolation using the method of Mekalanos J J. Duplication and amplification of toxin genes in *Vibrio cholerae*. Cell. 1983. 35:253-63.

Polymerase Chain Reaction Protocol

Primers were designed with 5' restriction sites and overhangs for cloning into the pET 28 and pET30 vectors (Novagen, Madison, Wis.).

*L. brevis* glutamate racemase primers:
(SEQ ID NO: 401)
N term: 5'-GCGGCGCCATGGAAAATGATCCGATTGGTCTAATG-3', and (SEQ ID NO: 402)
C term: 5'-GCGGCGGTCGACGCAATTACAATTGTGTTTGTC-3'.

*P. pentosaceus* glutamate racemase primers:
(SEQ ID NO: 403)
N term: '-GCGGCGCCATGGATGTATGTATAATTTTATTTAG-3', and (SEQ ID NO: 404)
C term:
5'-GCGGCGGTCGACAAATTTCATTATTCATTCTAATTT-3'.

The gene derived from *L. brevis* was amplified using the following PCR protocol. In a 50 μL reaction 0.150 μg template, 1.6 μM of each primer, 0.4 mM each dNTP, 2.8 U Expand High Fidelity™ Polymerase (Roche, Indianapolis, Ind.), 0.5 U Pfu polymerase (Stratagene, La Jolla, Calif.) and 1× Expand™ buffer with Mg were used. The thermocycler program used included a hot start at 96° C. for 3 minutes, 8 repetitions of the following steps: 94° C. for 30 seconds, 52° C. for 45 seconds, and 72° C. for 2 minutes, followed by 22 repetitions of the following steps: 94° C. for 30 seconds, 60° C. for 45 seconds, and 72° C. for 2 minutes. After the 22 repetitions the sample was maintained at 72° C. for 7 minutes and then stored at 4° C. This PCR protocol produced a product of ~830 bp, as judged by comparison to DNA size markers.

The gene derived from *P. pentosaceus* was amplified using the following PCR protocol. In a 50 μL reaction, 0.15 μg template, 1.6 μM of each primer, 0.4 mM each dNTP, 2.8 U Expand High Fidelity™ Polymerase, 0.5 U Pfu polymerase and 1× Expand™ buffer with Mg were added. The thermocycler program used included a hot start at 96° C. for 3 minutes, followed by 8 repetitions of the following steps: 94° C. for 30 seconds, 37° C. for 45 seconds, and 72° C. for 2 minutes, followed by 8 repetitions of the following steps: 94° C. for 30 seconds, 45° C. for 45 seconds, and 72° C. for 2 minutes, followed by 14 repetitions of the following steps: 94° C. for 30 seconds, 55° C. for 45 seconds, and 72° C. for 2 minutes. After the 14 repetitions the sample was maintained at 72° C. for 7 minutes and then stored at 4° C. This PCR protocol produced a product of ~840 bp, as judged by comparison to DNA size markers.

Cloning

The PCR products were gel purified from 0.8% TAE-agarose gels using the Qiagen gel extraction kit (Qiagen, Valencia, Calif.). The PCR products were quantified using a SmartSpec 3000™ spectrophotometer. The products were digested with restriction enzymes NcoI and SalI following the manufacturer's recommended protocols (New England Biolabs, Beverly, Mass.) and gel purified from 0.8% TAE-agarose gels using the Qiagen gel extraction kit (Qiagen, Valencia, Calif.). Vectors pET28 and pET30 were prepared by digestion with restriction enzymes NcoI and SalI followed by treatment with shrimp alkaline phosphatase and purification from 0.8% TAE-agarose gels using the Qiagen gel extraction kit (Qiagen, Valencia, Calif.).

The digested vectors and inserts were ligated using the Rapid™ DNA Ligation Kit (Roche, Indianapolis, Ind.). Approximately 50 ng of treated insert, 100 ng of treated vector (3 to 1 molar ratio of insert to vector), 5 U of T4 DNA ligase, and 1× ligation buffer were incubated for 5 minutes at room temperature. The ligation reactions were purified using the High Pure PCR Product Purification Kit (Roche, Indianapolis, Ind.) and used to transform *E. coli* DH10B electrocompetent cells (Invitrogen, Carlsbad, Calif.). Ten μl of each ligation reaction was added to 40 μl of DH10B cells and were transformed by electroporation using the Bio-Rad Gene Pulser II (Bio-Rad, Hercules, Calif.) under the following conditions: 2.5 kV, 25 μF, 200 ohm in a 0.2 cm cuvette. The cells were allowed to recover in 1 mL of room temperature SOC for 1 hour at 37° C. with shaking at 225 rpm. Cells were plated on LB plates containing kanamycin (50 µg/mL).

Plasmid DNA was purified from the resulting transformants using the Qiagen spin miniprep kit (Qiagen, Valencia, Calif.) and screened for the correct inserts by restriction digest with NcoI and SalI. The sequences of plasmids appearing to have the correct insert were verified by dideoxy chain termination DNA sequencing.

Gene Expression and Assays

Plasmid DNA, verified by sequence analysis, was subcloned into E. Coli expression host BL21(DE3) (Novagen, Madison, Wis.). The cultures were grown. The plasmids were isolated using a Qiagen miniprep kit (Qiagen, Valencia, Calif.) and analyzed by restriction digest to confirm identity.

Induction in BL21(DE3) was initially performed with L. brevis and P. pentosaceus glutamate racemases in both pET28 (untagged) and pET 30 (histidine-tagged) vectors. A time course study was performed with cultures grown in 250 mL LB containing kanamycin (50 mg/L) to an $OD_{600}$ of 0.5-0.6, induced with 100 mM IPTG (isopropyl thiogalacatoside) and sampled at 0 and 3 hours post induction. Cells from 600 µL (0 hour) and 275 µL (3 hour) were resuspended in 40 µL sodium dodecyl sulfate buffer containing 2-mercaptoethanol, heated at 95° C. for 10 minutes, and cooled. Aliquots of these total cellular protein samples were analyzed by SDS-PAGE using a 4-15% gradient gel.

Cell extracts were also prepared from the 3 hour cultures by suspending cell pellets from 5 mL of culture in 0.625 mL Novagen BugBuster™ reagent (Novagen, Madison, Wis.) containing 0.625 µL benzonase nuclease and 3 µL protease inhibitor cocktail set #3 (Calbiochem-Novabiochem Corp., San Diego, Calif.) at room temperature for 20 minutes with gentle shaking, and centrifuging at 16,000×g to remove cell debris. The supernatants (cell extracts) were loaded onto 4-15% gradient gels for analysis of the cellular soluble proteins.

The 3-hour samples from cloned L. brevis glutamate racemase and P. pentosaceus glutamate racemase showed both total and soluble protein that corresponded to the correct size (approximately 31 kDa). The L. brevis pET30 (histidine-tagged) gene product was over-expressed at a higher level than, and was also more soluble (>20% of soluble protein) than the L. brevis pET 28 (untagged) gene product, as well as the P. pentosaceus gene products in both vectors. The P. pentosaceus gene product showed equal overexpression and solubility in the pET28 and pET30 vectors, which was significantly less than that observed for the L. brevis pET30 gene product.

Cells from the induced cultures (250 mL) were centrifuged and washed once with 0.85% NaCl. Cell pellets were resuspended in 5 mL/g wet cell weight of BugBuster™ (Novagen, Madison, Wis.) reagent containing 5 µL/mL protease inhibitor cocktail set #3 (Calbiochem-Novabiochem Corp., San Diego, Calif.) and 1 µL/mL benzonase nuclease. Samples were incubated at room temperature for 20 minutes on an orbital shaker. Insoluble cell debris was removed by centrifugation at 16,000×g for 20 minutes at 4° C.

Cell extracts were assayed for glutamate racemase activity using the following protocol. 400-µL reactions were carried out in 10 mM potassium phosphate (pH 8.0), 0.2 mM DTT, and 10 mM L-glutamate or D-glutamate. The reactions were initiated by the addition of 20-100 µL of cell free extracts and were incubated at room temperature. Sample aliquots were taken over a time course of 1 minute, 5 minutes, 10 minutes, 20 minutes and 1 hour (zero minute samples served as control reactions). 2 M formic acid (25 µL) was added to each 40-µL sample aliquot to stop the reaction and the precipitated protein was removed by centrifugation. Supernatants were removed and frozen at −80° C. until they were analyzed by LC/MS/MS.

Assay results from cell extracts from pET30 induction with 100 mM IPTG (3 hours) demonstrate that L. brevis (Genbank Accession No. BAA06106.1 GI:468450) and P. pentosaceus (Genbank Accession No. AAA16761.1 GI:349029) enzymes have significant levels of racemase activity on both glutamate isomers. The P. pentosaceus racemase (20 µL of cellular extracts) reached equilibrium between L- and D-glutamate in 10-20 minutes starting with either substrate. The L. brevis enzyme (20 µL of cellular extracts) also reached equilibrium in approximately 20 minutes.

A partially purified aspartate racemase enzyme (catalog #ASPR-101) purchased from BioCatalytics, Inc. (Pasadena, Calif.) was assayed for activity on L-aspartate and D-aspartate using a protocol similar to the one above. The commercial enzyme showed racemase activity on both isomers. Using 0.5-1 mg of enzyme, equilibrium was achieved in 20-60 minutes.

All three racemases (L. brevis glutamate racemase, P. pentosaceus glutamate racemase and BioCatalytics aspartate racemase) were also assayed for activity on S,S monatin using the following protocol. 400-µL reactions were carried out in 10 mM potassium phosphate (pH 8.0), 0.2 mM DTT, and 10 mM S,S monatin. The reactions were initiated by the addition of cell free extracts (L. brevis and P. pentosaceus) or purified enzyme (BioCatalytics aspartate racemase) and were incubated at room temperature. Sample aliquots were taken over a time course of 1 minute, 5 minutes, 10 minutes, 20 minutes and 1 hour (zero minute samples served as control reactions as well as samples without enzyme). 2 M formic acid (25 µL) was added to each 40-µL sample aliquot to stop the reaction and the precipitated protein was removed by centrifugation. Supernatants were removed and frozen at −80° C. until they were analyzed by LC/MS/MS (Example 1). No decrease in S,S monatin concentration was noted over time, nor was there any increase in S,R monatin (present initially as <5% contaminating byproduct, even in the no enzyme control). Therefore, none of the racemases assayed showed activity towards monatin.

Example 18

Production of R,R Monatin from L-tryptophan Using Glutamate or Aspartate Racemases This example describes methods of producing stereoisomerically-enriched R,R monatin from L-tryptophan using an L-tryptophan (L-tyrosine, or aromatic) aminotransferase, ProA aldolase, glutamate or aspartate racemase, and a broad specificity D-amino acid aminotransferase. FIG. 5 is a diagram that illustrates the pathway. This approach to production of stereoisomerically enriched R,R monatin requires an enzyme for step 1 that has low activity in the production of monatin from monatin precursor (MP). Based upon earlier results, we used the Sinorhizobium meliloti and Rhodobacter sphaeroides tatA gene products described in Example 1 from WO 03/091396 A2.

Materials and Methods

Glutamate racemases from L. brevis and P. pentosaceus were produced in E. coli as described in Example 17. In some cases the $His_6$-tagged version of these enzymes were purified using His-Bind 900 cartridges according to manufacturer's protocols (Novagen, Madison, Wis.) and were desalted to remove imidazole using PD-10 columns (G25 Sephadex, GE Healthcare, Piscataway, N.J.). The enzymes were eluted in 25 mM potassium phosphate pH 8.0. Aspartate racemase (ASPR-101) and D-aminotransferase (AT-103) were purchased from BioCatalytics, Inc. (Pasadena, Calif.). *S. meliloti* and *R. sphaeroides* tyrosine (aromatic) aminotransferases were prepared as described in Example 1 from WO 03/091396 A2. *Comamonas testosteroni* ProA aldolase was prepared as described in Example 4 from WO 03/091396 A2. Total protein assays were done utilizing the Bio-Rad Protein Assay according to manufacturer's protocols (Hercules, Calif.).

Reduction in Amount of S,S Monatin Produced Using Racemases

Reaction mixtures (1 mL volume, run in duplicate) contained 100 mM potassium phosphate buffer (pH 8), 2 mM $MgCl_2$, 0.05 mM pyridoxal 5'-phosphate (PLP), 200 mM sodium pyruvate, 5 mM sodium α-ketoglutarate or oxaloacetate, approximately 280 μg/mL *S. meliloti* TatA supplied in a cellular extract, 1 mg/mL BioCatalytics D-aminotransferase (AT-103) (BioCatalytics, Pasadena, Calif.), 100 μL/mL of glutamate racemase cellular extract or 1 mg/mL aspartate racemase, and approximately 100 μg/mL of ProA aldolase provided as a cellular extract. Solid tryptophan was added at a concentration of 10.2 mg/ml. Negative controls did not contain racemase. Samples were incubated at 30° C. (shaking at 250 rpm) for 1 hour, 2 hours, or overnight. Samples were centrifuged to remove precipitate, syringe filtered, and stored at −80° C. prior to analysis for monatin using the LC/MS/MS method described in Example 1. Most of the samples contained >95% S,S monatin, due to the amounts of native L-aminotransferase present in the cellular extracts. However, the samples that contained racemase had a reduced amount of total monatin as a result of the racemase enzymes making L-glutamate less available for transamination of MP. Without racemase, 1545-2355 ppm monatin (predominantly S,S) was produced during the timecourse. With the racemases present, only 340-879 ppm (*L. brevis* enzyme), 444-531 ppm (*P. pentosaceus* enzyme), and 506-1460 ppm monatin (aspartate racemase) were produced. These data indicate that the racemases are active in the reaction conditions required to produce monatin. To minimize formation of S,S monatin from cellular extract enzymes such as aspartate aminotransferases, further experiments were done with purified enzymes and a higher ratio of D-aminotransferase to L-aminotransferase enzymes.

Conversion of L-Tryptophan to 4-R Containing Isomers of Monatin

The above experiments were repeated using approximately 54 μg of purified L-aminotransferase (either *S. meliloti* or *R. sphaeroides* TatA), 1 mg aspartate aminotransferase (BioCatalytics, Pasadena, Calif.), 1 mg D-aminotransferase, oxaloacetate as the amino acceptor, and 75 μg purified aldolase. Reactions were run in duplicate with a 2-hour sampling time and an overnight incubation time. Negative controls were done with *S. meliloti* L-aminotransferase but no racemase. In addition to quantification of R,R/S,S and S,R/R,S monatin peak quantification based on reversed phase chromatography, the percentage of each stereoisomer was determined using the FDAA derivitization technique described in Example 1. The results are as follows:

TABLE 22

| L-Aminotransferase | Incubation Time | Total Monatin (ppm) | % S, S | % R, R | % R, S | % S, R |
|---|---|---|---|---|---|---|
| S. meliloti TatA | 2 hr | 17.1 | 10.2 | 58.1 | 0.8 | 31.0 |
| S. meliloti TatA | 2 hr | 15.8 | 13.3 | 55.3 | 1.0 | 30.4 |
| S. meliloti TatA | overnight | 77.7 | 25.8 | 40.0 | 1.3 | 32.9 |
| S. meliloti TatA | overnight | 67.9 | 29.4 | 37.3 | 1.5 | 31.8 |

TABLE 22-continued

| L-Aminotransferase | Incubation Time | Total Monatin (ppm) | % S, S | % R, R | % R, S | % S, R |
|---|---|---|---|---|---|---|
| R. sphaeroides TatA | 2 hr | 241.2 | 96.3 | 2.3 | 0.8 | 0.6 |
| R. sphaeroides TatA | 2 hr | 223.2 | 95.7 | 2.7 | 1.0 | 0.6 |
| R. sphaeroides TatA | overnight | 600.4 | 96.6 | 1.8 | 0.5 | 1.1 |
| R. sphaeroides TatA | overnight | 618.5 | 96.1 | 2.1 | 0.5 | 1.3 |
| no racemase control | 2 hr | 7.1 | 92.0 | 1.4 | 6.6 | 0.0 |
| no racemase control | 2 hr | 5.7 | 94.0 | 1.2 | 4.8 | 0.0 |
| no racemase control | overnight | 44.6 | 93.5 | 1.3 | 4.7 | 0.5 |
| no racemase control | overnight | 37.5 | 95.4 | 0.9 | 3.7 | 0.0 |

Clearly the presence of the racemase increased the total amount of monatin produced when *S. meliloti* TatA was used as the enzyme for L-tryptophan transamination. Monatin levels increased from an average of 6.4 to 16.5 ppm in the two-hour assay, and from 41-73 ppm in the overnight assay. Additionally, the percent of R,R formed increased from about 1% up to as much as 58% by utilizing the racemase enzyme. The S,R stereoisomer of monatin, another potent sweetener, was the other major component, increasing from nearly 0 in the negative controls to 31%. The *R. sphaeroides* TatA clearly had more activity on S-MP then the *S. meliloti* L-transaminase, demonstrating the importance of having an enzyme that has a high substrate specificity for L-tryptophan as compared to MP when 4-R isomers of monatin are the desired products. With about 10% of the total monatin being 4S at the two-hour time point, the *S. meliloti* TatA could be considered as having limited activity on MP.

The experiments were repeated with the purified *S. meliloti* TatA (54 μg) and the *L. brevis* glutamate racemase. When purified glutamate racemase was used, approximately 64 μg was used per 1 mL reaction. Cellular extracts containing the glutamate racemase were also tested, and 1.4 mg of soluble protein was used. A no racemase negative control was utilized again, and all samples were run in duplicate. The results are as follows:

TABLE 23

| Glutamate racemase | Incubation Time | Total Monatin (ppm) | % S, S | % R, R | % R, S | % S, R |
|---|---|---|---|---|---|---|
| L. brevis (purified) | 2 hr | 3.3 | 49.1 | 34.2 | 3.7 | 13.0 |
| L. brevis (purified) | 2 hr | 3.6 | 47.9 | 35.2 | 3.5 | 13.4 |
| L. brevis (purified) | overnight | 29.3 | 58.9 | 24.7 | 3.2 | 13.2 |
| L. brevis (purified) | overnight | 40.2 | 55.1 | 25.0 | 4.7 | 15.3 |
| L. brevis (cell extract) | 2 hr | 10.5 | 45.8 | 35.9 | 1.1 | 17.2 |
| L. brevis (cell extract) | 2 hr | 10.5 | 47.4 | 33.9 | 1.1 | 17.6 |
| L. brevis (cell extract) | overnight | 79.4 | 70.3 | 17.9 | 1.3 | 10.5 |
| L. brevis (cell extract) | overnight | 80.1 | 69.1 | 19.1 | 1.1 | 10.7 |
| none | 2 hr | 2.7 | 84.1 | 7.1 | 6.3 | 2.4 |
| none | 2 hr | 3.2 | 84.9 | 6.0 | 6.8 | 2.2 |
| none | overnight | 36.5 | 92.3 | 2.3 | 4.2 | 1.2 |
| none | overnight | 30.5 | 92.7 | 2.0 | 4.1 | 1.3 |

Again, it is clear that the addition of the racemase increases the total monatin produced from L-tryptophan, as well as increasing the relative amounts of 4R-containing isomers of monatin as compared to S,S monatin. The use of purified aldolase, racemase, and L-aminotransferase greatly improves the ability to control the desired stereoisomer formation. The ratio of L to D aminotransferase is also a way to manipulate stereochemistry of the final product.

When comparing results shown in Tables 18 and 19 in Example 13 to results with reaction conditions similar to the conditions above, one can see that approximately 7-29 ppm of monatin were formed from indole-3-pyruvate and the percentages of R,R monatin formed were approximately 51-90%. Using the aspartate racemase increased the total amount of monatin produced to 16-78 ppm monatin with % R,R of approximately 40-58%. Additionally, a more stable and less expensive raw material, L-tryptophan, was utilized. In Example 14, approximately 73 ppm monatin was produced from D-tryptophan at a ratio of R,R:S,R of approximately 1.7:1. The total amount of 4R isomers was >80% of the total monatin. Because both R,R-monatin and S,R-monatin are potent sweeteners (>1000 times sweeter than sucrose) the ability to enrich for these isomers without the need for expensive D-amino acid substrates is critical.

As described in Examples 13 and 14, D-alanine can serve as the amino donor for transamination of MP to monatin. Many L-aminotransferases have the ability to utilize pyruvate as an amino acceptor to some extent, and produce L-alanine. Because the above-mentioned reactions use high concentrations of pyruvate, it is likely that some of the pyruvate is converted to L-alanine. For example, during transamination of L-tryptophan, the HexAspC enzyme described in Example 16 has been found to convert 10-18% of pyruvate (50-200 mM initial concentrations) to L-alanine in 2 hours if alpha-ketoglutarate is absent. The enzyme showed a 10-fold preference for alpha-ketoglutarate when both amino acceptors were present at high (>50 mM) concentrations. AspC (described in WO 03/091396 A2) also produced some L-alanine from pyruvate. Therefore, it is expected that one can omit the addition of alpha-ketoglutarate or oxaloacetate in the above reactions, and utilize an alanine racemase (EC 5.1.1.1) in place of glutamate or aspartate racemase. Alanine racemase enzymes were first identified in *Brucella abortus* and *Streptococcus faecalis* (Marr, A. G. and Wilson, P. W. Arch. Biochem. Biophys., 49 (1954) 424-433 and Wood, W. A. and Gunsalus, I. C. J. Biol. Chem., 190 (1951) 403-416). The dadB gene in *Salmonella typhimurium* was identified as the source of alanine racemase activity, and several hundred homologs can be found in genomics databases. Other known sources of alanine racemase activity are *Escherichia coli, Bacillus subtilis, Pseudomonas aeruginosa, Vibrio cholerae, Schizosaccaroyces pombe*, and *Bacillus cereus*. A basidiomycetous mushroom, *Lentinus edodes*, also contains a broad activity alanine racemase. A thermostable homolog from *Bacillus stearothermophilus* is available for purchase from Sigma-Aldrich (catalog #A8936) (Sigma-Aldrich, St. Louis, Mo.) and has been immobilized for commercial applications (Inagaki, K., Biochemistry, 25: 3268 1986). An alanine racemase is converted to a glutamate or aspartate racemase by random methods such as mutagenic PCR, passage through mutagenic strains, or other methods to those known in the art. A more focused evolution of the alanine racemase is focused on active site residues, including Lys129, Met134, and the residues including and between Gly283 and Trp288 (numbering from *Bacillus stearothermophilus*).

Example 19

D-phenylglycine aminotransferase
(D-4-hydroxyphenylglycine aminotransferase)

As shown in FIG. 3, D-phenylglycine aminotransferase is useful in a biosynthetic pathway for the production of monatin. For example, D-phenylglycine aminotransferase produces R,R monatin from R-MP with L-glutamate as the amino donor.

PCR synthesis of *P. stutzeri* 4 D-hydroxyphenylglycine Aminotransferase from Oligonucleotide Primers This example describes methods that were used to synthesize 4 D-hydroxyphenylglycine aminotransferase, a stereoinverting enzyme that can be used to convert R monatin precursor to R,R monatin using L-glutamate as the amino donor.

Primer Design

The published sequence (Genbank Accession No. AY319935, nucleic acid sequence; Genbank Accession No. AAQ8290, protein sequence) for Pseudomonas stutzeri 4 D-hydroxyphenylglycine aminotransferase (4 D-HPG AT) was used as a template for PCR primer design. Alternatively, the 4-D-hydroxyphenylglycine aminotransferase from *Pseudomonas putida*, (CAD42450 (protein), AX467211 (nucleotide)) is used as a sequence template. A total of 34 forward primers and 35 reverse primers were designed; forward and reverse primers were 40-mers sharing 20 overlapping base pairs. In addition, 2 outer primers were designed with 5' restriction sites and overhangs for cloning into the pET 28 and pET30 vectors (Novagen, Madison, Wis.).

```
P. stutzeri 4 D-HPG AT outer primers: N term
(with NdeI Site):
                                      (SEQ ID NO: 405)
5'-GGCCGGCATATGTCGATCCTTAACGACTACAAACGT-3',
and C term (with XhoI site):
                                      (SEQ ID NO: 406)
5'-GGAAGGCTCGAGTCATGATTGGTTTCCAGACAAATT-3'.
```

Polymerase Chain Reaction Protocol

The gene sequence from *P. stutzeri* was amplified using the following protocols. The primary 100 μL PCR reaction included 0.05 μM of each of the internal 69 primers, 0.4 mM each dNTP, 10 U rTth Polymerase XL (Roche, Indianapolis, Ind.), 0.625 U Pfu polymerase (Stratagene, La Jolla, Calif.), 1×XL buffer and 1 mM Mg(OAc)$_2$. The thermocycler program used included a hot start at 94° C. for 3 minutes, 15 repetitions of the following steps: 94° C. for 30 seconds, 42° C. for 30 seconds, and 68° C. for 15 seconds, followed by 10 repetitions of the following steps: 94° C. for 30 seconds, 52° C. for 30 seconds, and 68° C. for 30 seconds, followed by 10 repetitions of the following steps: 94° C. for 30 seconds, 60° C. for 30 seconds, and 68° C. for 1 minute and 15 seconds. After the final 10 cycles the sample was maintained at 68° C. for 7 minutes and then stored at 4° C. This PCR protocol produced a smear of product at ~0.5 kb on a 0.8% TAE-agarose gel.

The secondary PCR reaction was set up using the primary PCR reaction as template. The secondary 100 μL PCR reaction included 2.5 μL of the primary PCR reaction, 0.5 μM of each of the 2 outer primers (with NdeI and XhoI restriction sites), 0.4 mM each dNTP, 10 U rTth Polymerase XL, 0.625 U Pfu polymerase, 1×XL buffer and 1 mM Mg(OAc)$_2$. The thermocycler program used included a hot start at 94° C. for 3 minutes, 10 repetitions of the following steps: 94° C. for 30 seconds, 52° C. for 30 seconds, and 68° C. for 1 minute 30 seconds, followed by 15 repetitions of the following steps: 94° C. for 30 seconds, 60° C. for 30 seconds, and 68° C. for 1 minute 30 seconds. After the repetitions, the sample was maintained at 68° C. for 7 minutes and then stored at 4° C. This PCR protocol produced a distinctive product band at ~1.4 kb on a 0.8% TAE-agarose gel.

The PCR product was gel purified from 0.8% TAE-agarose gel using the Qiagen gel extraction kit (Qiagen, Valencia, Calif.). The product was TOPO cloned and transformed into TOP 10 cells according to manufacturer's protocol (Invitrogen, Carlsbad, Calif.). Plasmid DNA was purified from the resulting transformants using the Qiagen spin miniprep kit (Qiagen, Valencia, Calif.) and screened for the correct inserts by restriction digest with NdeI and XhoI. The sequences of plasmids appearing to have the correct insert were verified by dideoxy chain termination DNA sequencing with universal M13 forward and M13 Reverse primers. Of the 10 clones sequenced, all had at least one mutation from the desired sequence. The best clone had a single base-pair mutation that resulted in an amino acid change. The sequence of this clone was corrected using the QuickChange Mutagenesis protocol according to manufacturer recommendations (Stratagene, La Jolla, Calif.).

The corrected TOPO clone was digested with restriction enzymes NdeI and XhoI following the manufacturer's recommended protocols (New England Biolabs, Beverly, Mass.) and gel purified from 0.8% TAE-agarose gels using the Qiagen gel extraction kit (Qiagen, Valencia, Calif.). Vectors pET 28 and pET 30 were prepared by digestion with restriction enzymes NdeI and XhoI followed by treatment with shrimp alkaline phosphatase and purification from 0.8% TAE-agarose gels using the Qiagen gel extraction kit (Qiagen, Valencia, Calif.).

The digested vectors and insert were ligated using the NEB Quick Ligation Kit (Beverly, Mass.). Approximately 50 ng of treated insert, 100 ng of treated vector (3 to 1 molar ratio of insert to vector), 5 U of T4 DNA ligase, and 1× ligation buffer were incubated for 5 minutes at room temperature. The ligation mixture was transformed in to TOP10F' chemically competent cells (Invitrogen, Carlsbad, Calif.). The cells were allowed to recover in 0.25 mL of room temperature SOC for 1 hour at 37° C. with shaking at 225 rpm. Cells were plated on LB plates containing kanamycin (50 μg/mL). Plasmid DNA is purified from the resulting transformants using the Qiagen spin miniprep kit (Qiagen, Valencia, Calif.) and screened for the correct inserts by restriction digest with NdeI and XhoI.

Gene Expression and Assays

Plasmid DNA was transformed into *E. coli* expression host BL21(DE3) (Novagen, Madison, Wis.). The cultures were grown and the plasmids were isolated using Qiagen miniprep kit (Qiagen, Valencia, Calif.), and analyzed by restriction digest to confirm identity.

Induction in BL21(DE3) is initially performed with *P. stutzeri* 4 D-HPG in both pET 28 (histidine-tagged) and pET 30 (untagged) vectors. A time course study is performed with cultures grown in 250 mL LB containing kanamycin (50 mg/L) to an $OD_{600}$ of 0.5-0.6, induced with 100 mM IPTG (isopropyl thiogalacatoside) and sampled at 0 and 3 hours post induction. An appropriate volume of cells from 0 hours and 3 hours is resuspended in 40 μL sodium dodecyl sulfate buffer containing 2-mercaptoethanol and heated at 95° C. for 10 minutes, and cooled. Aliquots of these total cellular protein samples is analyzed by SDS-PAGE using a 4-15% gradient gel.

Cell extracts are also prepared from the 3 hour cultures by suspending cell pellets from 5 mL of culture in 0.625 mL Novagen BugBuster™ reagent (Novagen, Madison, Wis.) containing 0.625 μL benzonase nuclease and 3 μL protease inhibitor cocktail set #3 (Calbiochem-Novabiochem Corp., San Diego, Calif.) at room temperature for 20 minutes with gentle shaking, and centrifuging at 16,000×g to remove cell debris. The supernatants (cell extracts) are loaded onto 4-15% gradient gels for analysis of the cellular soluble proteins. When required, protein is purified using His-Bind 900 cartridges according to manufacturer's protocols (Novagen, Madison, Wis.) and is desalted to remove imidazole using PD-10 columns (G25 Sephadex, GE Healthcare, Piscataway, N.J.).

Organisms with D-phenylglycine Aminotransferase (DP-GAT)

Organisms of the genus *Pseudomonas* and like genera, with a stereoinverting D-phenylglycine aminotransferase (also called D-4-hydroxyphenylglycine aminotransferase) are isolated in the following manner. Soil samples are incubated on petri plates with the following medium: (per liter) 15 g Agar, 3.4 g $KH_2PO_4$, 3.55 g $Na_2HPO_4$, 0.2 g $MgSO_4.7H_2O$, 8 mg $CaCl_2.2H_2O$, 10 mg yeast extract, 1 ml 1000× trace elements solution, 1 g D-phenylglycine (D-4-hydroxyphenylglycine).

Isolates are tested by PCR for the presence of a stereoinverting aminotransferase (primers designed from known D-phenylglycine aminotransferases) or are further enriched for the presence of a stereoinverting aminotransferase as follows: isolated from the plates could be grown in liquid medium as above minus the agar at 30° C. with shaking to an $OD_{600}$ of about 1.0. Cells are harvested by centrifugation and washed twice with 0.85% NaCl. A 10 mg (wet weight) sample is suspended in 1 ml potassium phosphate buffer (pH 7.0) and 5 mM D-phenylglycine (or D-4-hydroxyphenylglycine). Neutralized 15 mM (aminooxy)acetic acid is added to duplicate samples prepared as described above. Consumption of D-phenylglycine (or D-4-hydroxyglycine) is measured by HPLC. Isolates capable of degrading D-phenylyglycine (or D-4-hydroxyphenylglycine), but do so at a slower rate in the presence of (aminooxy)acetic acid are selected for further analysis. Isolates are tested, by PCR, for the presence of a stereoinverting aminotransferase (primers designed from known D-phenylglycine aminotransferases).

The presence of the stereoinverting aminotransferase is confirmed by growing a culture in liquid medium as described above, harvesting the cells and making a cell free crude extract (CFE) and testing for D-phenylglycine aminotransferase (or D-4-hydroxyphenylglycine aminotransferase) enzyme activity. CFE is added to a reaction mixture with the following final concentrations: 0.1 M CAPS (pH 9.5), 60 mM L-glutamate (sodium salt), 5 mM benzoylformate (or 4-hydroxybenzoate) and 50 μM PLP. The reverse reaction is measured by adding CFE to a reaction mixture with the following concentrations: 50 mM potassium phosphate (pH 7.0), 60 mM D-phenylglycine (or D-4-hydroxyphenylglycine), 5 mM α-ketoglutarate, 50 μM PLP. The assays are incubated at 35° C. and aliquots are taken at time points and stopped by boiling for 2 minutes. Product will be quantitated by the HLPC method of Gil-Av, E., Tishbee, A., Hare, P. E., Resolution of underivatized amino acids by reversed phase chromatography. J. Am. Chem. Soc., 102: 5115-5117 (1980) or by methods described in Example 1 (measurement of glutamate formation).

As an alternative to PCR based methods, the stereoinverting D-phenylglycine aminotransferase is purified from the isolated bacteria by conventional protein purification techniques including ammonium sulfate fractionation, and conventional column chromatography. Once the protein has been purified to a reasonable degree peptide microsequencing techniques or conventional Edman type amino acid sequencing are utilized (see golgi.harvard.edu/microchem/ for descriptions of the protocols and equipment used for this type of work). Degenerate primers are designed based on sequence available from the closest known relative of the protein source. Degenerate PCR and genome walking is then performed according to established protocols to isolate the stereoinverting D-phenylglycine aminotransferase coding sequence.

DPGAT Monatin Production

D-hydroxyphenylglycine aminotransferases, as described in (1) and (2) above, are used in crude cell free protein extracts or purified as described in (1) above. *S. meliloti* and *R. sphaeroides* tyrosine (aromatic) aminotransferases are prepared as described in Example 1 from WO 03/091396 A2.

*Comamonas testosteroni* ProA aldolase is prepared as described in Example 4 from WO 03/091396 A2. Total protein assays are done utilizing the Bio-Rad Protein Assay according to manufacturer's protocols (Hercules, Calif.).

Reaction mixtures (1 mL volume, run in duplicate) contain 100 mM potassium phosphate buffer (pH 8), 2 mM $MgCl_2$, 0.05 mM pyridoxal 5'-phosphate (PLP), 200 mM sodium pyruvate, 5 mM sodium α-ketoglutarate, approximately 280 μg/mL *S. meliloti* TatA supplied in a cellular extract, 100 μL/mL of D-hydroxyphenylglycine aminotransferase cellular extract or 1 mg/mL purified D-hydroxyphenylglycine aminotransferase, and approximately 100 μg/mL of ProA aldolase provided as a cellular extract. Solid tryptophan is added at a concentration of 10.2 mg/ml. Negative controls are set up without D-hydroxyphenylglycine aminotransferase. Samples are incubated at 30° C. with gentle shaking for ~1 hour or overnight. Samples are centrifuged to remove precipitate, syringe filtered, and stored at −80° C. prior to analysis for monatin using the LC/MS/MS method described in Example 1.

D-hydroxyphenylglycine aminotransferases with improved activity for monatin production are made my mutagenesis techniques known to those in the art, including: mutagenic PCR, passage through mutagenic strains, or site-directed mutagenesis. The improved D-hydroxyphenylglycine aminotransferases are selected by growth on minimal medium with R,R-monatin as the source of nitrogen. Initially the selection is based on growth but as improved aminotransferases are selected the screen is growth rate based. That is, cells with mutated versions of the gene are grown and the gene is expressed in minimal medium with R,R-monatin as the nitrogen source. The growth rates of the cells with the mutated versions of the gene are compared to the unmutated version. Those cells with a faster growth rate are selected and the aminotransferase is analyzed further. The D-hydroxyphenylglycine aminotransferase is mutagenized by available techniques such as error-prone PCR and passage through mutagenic strains or by methods for which a license has been obtained such as DNA shuffling and other directed evolution technologies.

DPGAT Assay

Cells with the recombinant D-hydroxyphenylglycine aminotransferase were grown, the protein expressed, and the cells lysed as described in Example 17 or by standard protocols. The protein is expressed in its native host using described methods (Wiyakrutta, W., Meevootisom, V. A stereoinverting D-phenylglycine aminotransferase from *Pseudomonas stutzeri* ST-201: purification, characterization, and application for D-phenylglycine synthesis. J. Biotechnol., 55: 193-203 (1997)).

Cell free extract was added to a reaction mixture with the following final concentrations: 100 mM potassium phosphate (pH 7.0-8.5), 60 mM D-phenylglycine (or D-4-hydroxyphenylglycine), 5 mM α-ketoglutarate, 50 μM PLP. The assays were incubated at room temperature and aliquots were taken at time points and stopped by adding an equal volume of formic acid. Product (L-glutamate) is quantitated by methods described in Example 1.

Example 20

Discovery of a D-methionine Aminotransferase Gene

Background

D-methionine-pyruvate aminotransferase (EC 2.6.1.41) is thought to be another example, although rare, of a stereoinverting transaminase. This enzyme catalyzes the reversible conversion of D-methionine and pyruvate to L-alanine and 4-methylthio-2-oxobutanoate. Oxaloacetate, phenylpyruvate, 2-oxobutyrate, 2-oxovalerate, 2-oxoheptanoate, glyoxylate, and oxoglutarate can also serve as amino acceptors.

Transamination of D or L methionine is thought to be part of a pathway to ethylene production in higher plants (cauliflower, tomato, apple, pea stem, banana, peanut) as well as in soil microorganisms (*Escherichia coli, Pseudomonas pisi, Pseudomonas aeruginosa, Bacillus mycoides, Acinetobacter calcoaceticus, Aeromonas hydrophila* B12E, *Rhizobium trifolii* N2P7, *Penicillium digitatum, Saccharomyces cerevisiae, Corynebacterium* D7F). D.C. Billington, B. T. Golding, and S. B. Primrose *Biochem J*. (1979) 182, 827-836. In bacteria, L-methionine is typically used as the substrate in the ethylene production studies and broad specificity enzymes such as TyrB or AspC from *E. coli* are thought to be responsible for the transamination. However, S. B. Primrose *J. Gen. Microbiol*. (1976), 95(1), 159-65 and S. B. Primrose *J. Gen. Microbiol*. (1977), 98, 519-528. showed that *E. coli* strain SPA O (University of Warwick culture collection) produced nearly as much ethylene from D-methionine as from L-methionine in batch cultures. Because no broad specificity D-aminotransferase has been identified in *E. coli*, one possible explanation could be that the *E. coli* D-amino acid dehydrogenase (encoded by the dadA gene) converts the D-methionine to 4-methylthio-2-oxobutanoate. It is also possible that there is a methionine racemase in *E. coli*; however, no such enzyme has been described in the literature.

In contrast to *E. coli*, in cauliflower florets (mitochondrial extract preparations) and germinating peanut seeds production of ethylene was higher when D-methionine and pyruvate were supplied to the enzyme extract as compared to L-methionine and pyruvate (L. W. Mapson, J. F. March, and D. A. Wardale *Biochem J* (1969) 115, 653-661; J. I. Durham, P. W. Morgan, J. M. Prescott and C. M. Lyman *Phytochemistry* (1973) 12, 2123-2126). Therefore the possibility of a combination of methionine racemase and an L-aminotransferase is not supported by the data. Dehydrogenase activity was ruled out by dialysis of cellular extracts of cauliflower, no NAD was present in the assay mixtures. Oxidase activity was ruled out as no consumption of oxygen was noted and there was no requirement for FAD. The D-methionine aminotransferase from peanut tissues was purified, shown to be dependent on PLP, and shown to be independent of L-methionine aminotransferase activity. There is a possibility that these D-methionine—pyruvate aminotransferases actually produce D-alanine as a byproduct (similar to the *Bacillus* enzymes described in Examples 13 and 14), and that the cells contain alanine racemase to recycle the D-alanine back to L-alanine (or an analogous amino donor). In either case, discovery of the broad specificity D-aminotransferase from higher plants is advantageous for development of processes that produce R, R monatin or S,R monatin.

Experimental Overview

D-methionine aminotransferase is partially purified from cauliflower florets and germinating peanut embryos using standard chromatography protocols and a Pharmacia AKTA Explorer system. The protein sequences of homologous proteins are determined by LC/MS/MS fingerprinting techniques and database searching performed by Harvard Microchemistry facility. The coding regions of the plant genes are cloned from a cDNA library using standard PCR protocols or by synthesis of the gene as described in Example 19.

Alternatively, cDNA expression libraries are constructed (Stratagene, La Jolla, Calif.) from cauliflower tissue or peanut seeds grown in the presence of D-methionine (and producing ethylene). The libraries are transformed into *E. coli* methionine auxotrophs from the *E. coli* Genetic Stock Center (Yale) such as strains RC519 or AB1931. Plasmids of strains capable of growth on minimal media containing D-methionine contain the coding region of interest (see Example 15, an analogous screening technique).

Once the coding regions of interest are obtained and are expressed in a standard *E. coli* laboratory strain, the resulting gene products can be used in assays to produce R,R monatin as described in Example 19 in place of the D-hydroxyphenylglycine aminotransferase, with the exception of the pH being 7.5 (the optimal pH for the aminotransferase). If the D-methionine aminotransferase has a strict requirement for D-amino acid donor substrates, the enzyme can be used to make R,R monatin as described in Examples 13 and 14. The gene can be mutagenized and screened for increased activity as described in Example 19.

Methods

Isolation from Cauliflower

Four hundred grams of freshly picked cauliflower florets are extracted with 400 mL of a 4° C. sucrose/buffer solution (0.4 M sucrose and 0.1 M sodium phosphate buffer pH 7.4) by alternating soaking and mixing using a blender. Cell debris is removed by filtration with cheesecloth and the resulting solution is centrifuged at 40,000×g for 30 minutes at 4° C. The solid material (containing mitochondrial organelles) is resuspended in 20 mL 10 mM sodium phosphate buffer pH 7.4, and enzymes are extracted with 200 mL cold (−30° C.) acetone. The suspension is recentrifuged and the precipitate is dried using a Savant Speed Vac. The solid material is dissolved in 10 mM sodium phosphate buffer pH 7.4, and residual acetone is removed using a PD-10 column (GE Healthcare, Piscataway, N.J.).

Aminotransferase activity is assayed by incubation of the enzyme preparation with 5 mM D-methionine, 1 mM pyruvate, 0.05 mM PLP and 2 mM EDTA in 0.1 M sodium phosphate buffer pH 7.4. Assays are performed at 25° C. for 16 hours. The 4-Methylthio-2-oxobutanoate is measured by formation of the 2,4-dinitrophenylhydrazone derivative, using LC/MS (m/z of 328) and similar methodology described in Example 1. A 0.4% (w/v) solution of 2,4-dinitrophenylhydrazine in 2M sulfuric acid is prepared, and a half volume is added to the assay mixture after incubation. The mixture is mixed with gentle shaking at 30° C. for 30 minutes and the precipitate is collected by centrifugation and analyzed by LC/MS. Protein fractions separated by standard chromatographic techniques are assayed for activity in a similar manner, but the co-product alanine is measured by the OPA post-column derivitization technique described in Example 1.

Isolation from Peanut (*Arachia hypogea* L. cv. Starr)

The D-methionine aminotransferase enzyme from germinating peanut embryo homogenate (minus the cotyledons) is purified according to the method of J. I. Durham, P. W. Morgan, J. M. Prescott and C. M. Lyman *Phytochemistry* (1973) 12, 2123-2126. Reducing agents are used during the preparation of crude extracts to stabilize the enzymes, and the cell debris is removed by centrifugation at 33,000×g. A 35-50% ammonium sulfate fraction is further purified by incubation at low temperature, and by removal of the proteins in the precipitate. The supernatant is further fractionated using acetone. The active pools are then further purified by gel filtration chromatography (Sephadex 200, GE Healthcare, Piscataway, N.J.).

As protein fractions become enriched with the transaminase protein, 2D-gel electrophoresis is utilized to separate the enzyme of interest for microsequencing. After elucidation of homologous coding regions in plant sequences deposited at NCBI, the D-aminotransferase protein is produced recombinantly in *Escherichia coli* using standard molecular biology techniques. It is expected that the cellular extracts from cauliflower florets or peanut seeds or recombinantly produced homologous enzymes can be used in production of R,R monatin as described in Example 19 (if a stereoinverting transaminase) or Examples 13 and 14 (if a broad specificity D-aminotransferase).

Example 21

L-alanine Aminotransferase/Alanine Racemase/D-Alanine Aminotransferase

FIGS. 4, 6, and 8 illustrate biosynthetic pathways for producing stereoisomerically-enriched R,R monatin from L-tryptophan using a L-amino acid aminotransferase (such as L-alanine-aminotransferase and/or L-tryptophan-aminotransferase), an R-specific aldolase, an alanine racemase and a D-alanine aminotransferase.

A tryptophan-specific aminotransferase is described in Example 16. Alternatively, *S. meliloti* and *R. sphaeroides* tyrosine (aromatic) aminotransferases are prepared as described in Example 1 from WO 03/091396 A2. *Comamonas testosteroni* ProA aldolase is prepared as described in Example 4 from WO 03/091396 A2. Total protein assays are done utilizing the Bio-Rad Protein Assay according to manufacturer's protocols (Bio-Rad, Hercules, Calif.). Alanine racemase is purchased from Sigma-Aldrich (St. Louis, Mo.) (catalog number A8936). D-alanine aminotransferase is purchased from BioCatalytics (catalog number AT-103) (Bio-Catalytics, Pasadena, Calif.).

L-alanine aminotransferases are widely distributed in eukaryotes, bacteria, and archaea. The following organisms have been identified (based on sequence homology) as containing an L-alanine aminotransferase (E.C. 2.6.1.2): *Arabidopsis thaliana, Ashbya gossypii, Azotobacter vinelandii, Bifidobacterium longum, Caenorhabditis elegans, Candida albicans, Candida glabrata, Chlamydomonas reinhardtii, Cryptococcus neoformans, Debaryomyces hansenii, Homo sapiens, Hordeum vulgare, Kluyveromyces lactis, Magnaporthe grisea, Medicago truncatula, Mus musculus, Neurospora crassa, Oryza sativa, Phanerochaete chrysosporium, Pinus taeda, Pseudomonas putida, Pyrococcus abyssi, Pyrococcus furiosus, Pyrococcus horikoshii, Rattus norvegicus, Saccharomyces cerevisiae, Schizosaccharomyces pombe, Takifugu rubripes, Trypanosoma cruzi, Vibrio cholerae, Vibrio parahaemolyticus, Vibrio vulnificus, Yarrowia lipolytica,* and *Zea mays.* Additionally many aminotransferases have low-level alanine aminotransferase activity and given high levels of L-glutamate and pyruvate can convert it to L-alanine and α-ketoglutarate. An enzyme with low activity is improved with standard mutagenesis techniques such as error-prone PCR and passage through mutagenic strains or by directed evolution techniques. The gene for an L-alanine aminotransferase is cloned using publicly available to design primers and using standard techniques to amplify, clone, express and purify the gene/enzyme.

Reaction mixtures (1 mL volume, run in duplicate) contain 100 mM potassium phosphate buffer (pH 8), 2 mM $MgCl_2$, 0.05 mM pyridoxal 5'-phosphate (PLP), 200 mM sodium pyruvate, 5 mM sodium α-ketoglutarate, approximately 280 μg/mL *S. meliloti* TatA supplied in a cellular extract (or other L-tryptophan specific aminotransferase), 100 μL/mL of alanine racemase cellular extract or 1 mg/mL purified alanine racemase, approximately 280 μg/mL D-alanine aminotransferase supplied in a cellular extract and approximately 100 μg/mL of ProA aldolase provided as a cellular extract. Solid tryptophan is added at a concentration of 10.2 mg/ml. Negative controls are set up without alanine racemase. Samples are incubated at 30° C. with gentle shaking for ~1 hour or overnight. Samples are centrifuged to remove precipitate, syringe filtered, and stored at −80° C. prior to analysis for monatin using the LC/MS/MS method described in Example 1. In these reaction mixtures, if the L-tryptophan aminotransferase can use α-ketoglutarate, but not pyruvate, as an amino acceptor, one can add an L-alanine aminotransferase, which converts L-glutamate and pyruvate and to L-alanine and α-ketoglutarate, as shown in FIG. 6.

Example 22

Subcloning of Genes Encoding the Aldolases of SEQ ID NO: 276, 244, 218, 228, 162, 50, 74, 44, and 116

The genes encoding aldolases having the amino acid sequences of SEQ ID NO: 276, 244, 218, 228, 162, 50, 74, 44, and 116 were subcloned into the pET28b expression vector (Novagen, Madison, Wis.) with N-terminal His-tags to allow for purification. SEQ ID NO:275 is the sequence of the gene that encodes the aldolase having the amino acid sequence of SEQ ID NO:276. SEQ ID NO:243 is the sequence of the gene that encodes the aldolase having the amino acid sequence of SEQ ID NO:244. SEQ ID NO:217 is the sequence of the gene that encodes the aldolase having the amino acid sequence of SEQ ID NO:218. SEQ ID NO:227 is the sequence of the gene that encodes the aldolase having the amino acid sequence of SEQ ID NO:228. SEQ ID NO:161 is the sequence of the gene that encodes the aldolase having the amino acid sequence of SEQ ID NO:162. SEQ ID NO:49 is the sequence of the gene that encodes the aldolase having the amino acid sequence of SEQ ID NO:50. SEQ ID NO:73 is the sequence of the gene that encodes the aldolase having the amino acid sequence of SEQ ID NO:74. SEQ ID NO:43 is the sequence of the gene that encodes the aldolase having the amino acid sequence of SEQ ID NO:44. SEQ ID NO:115 is the sequence of the gene that encodes the aldolase having the amino acid sequence of SEQ ID NO:116.

The primers used for cloning are shown in Table 24.

The genes encoding the above aldolases were amplified by PCR and digested with appropriate enzymes (Nde I and BamH I) and gel purified (QiAquick® Gel extraction Kit (Qiagen, Valencia, Calif.)). The digests were individually ligated into pET28 that had been digested with Nde I and BamH I and gel purified. The ligation was transformed into TOP10 cells (Invitrogen, Carlsbad, Calif.). Miniprep DNA from individual colonies was analyzed for the presence of inserts by size analysis using agarose gel electrophoresis. Isolates with an insert were submitted for DNA sequence analysis (Agencourt, Beverly, Mass.).

Purification of Aldolases

Confirmed aldolase clones were transformed into either BL21(DE3) or BL21(DE3) pLysS. Induction was carried out overnight in Terrific Broth at 30° C. Overnight cultures grown with the appropriate antibiotic were diluted into fresh medium (typically 1:100) and grown to an $OD_{600}$ ~0.6 with aeration at 37° C. Cultures were then induced with 1 mM IPTG and shifted to 30° C. (with aeration) and incubation was continued overnight. Cells were harvested by centrifugation. The cell pellet was typically subjected to one freeze thaw cycle to assist with cell lysis. The cell pellet was lysed in BugBuster and Benzonase Nuclease (Novagen, Madison, Wis.) (according to the manufacturer's protocol). Cell debris was removed by centrifugation. The crude protein extract was applied to a 10 mg capacity HIS-Bind column (Novagen, Madison, Wis.) that had been prepared according to the manufacturer's protocol. The column was washed and the protein was eluted according to the manufacturer's protocol. The purified protein was desalted with PD-10 columns (GE Healthcare, Piscataway, N.J.) and eluted in 50 mM potassium

TABLE 24

| Aldolase DNA SEQ ID NO: | 5' primer | 3' primer |
|---|---|---|
| 275 | 5'-ATAAGACATATGCCTATCGTTGTTACGAAG-3' (SEQ ID NO: 339) | 5'-ATAAGAGGATCCTTATTCCTCGGGCAGCCGCTC-3' (SEQ ID NO: 340) |
| 243 | 5'-ATAAGACATATGAACAGACCTGTGGTTGTC-3' (SEQ ID NO: 341) | 5'-ATAAGAGGATCCTTACAGGTACTTGAGACCGAG-3' (SEQ ID NO: 342) |
| 217 | 5'-ATAAGACATATGAGCGTGGTCATCCGAAAC-3' (SEQ ID NO: 343) | 5'-ATAAGAGGATCCTTACTTCGCTTTGTTATAGGC-3' (SEQ ID NO: 344) |
| 227 | 5'-ATAAGACATATGAACAAGCCCGTGGTTGTG-3' (SEQ ID NO: 345) | 5'-ATAAGAGGATCCTTACAAGTACTTGAGACCGAGG-3' (SEQ ID NO: 346) |
| 161 | 5'-ATAAGACATATGAGCGTGGTCGTCACCGG-3' (SEQ ID NO: 347) | 5'-ATAAGAGGATCCTTAGCCGTTTTTCCCGTCGGTG-3' (SEQ ID NO: 348) |
| 49 | 5'-AGAAGACATATGATGAGCATCGTCGTCCAGAAC-3' (SEQ ID NO: 349) | 5'-AGAAGAGGATCCTCAGACATATTTCAGGCCCTTG-3' (SEQ ID NO: 350) |
| 73 | 5'-AGAAGACATATGATGAGCGTGGTCATCACC-3' (SEQ ID NO: 351) | 5'-ACAACAGGATCCCTATTTCTTCTCCGGCGTTTC-3' (SEQ ID NO: 352) |
| 43 | 5'-ATAATACATATGAGCGTCGTCGTTCAGAAC-3' (SEQ ID NO: 353) | 5'-ATAATAGGATCCTTAGACATATTTGAGCCCCTTC-3' (SEQ ID NO: 354) |
| 115 | 5'-AGAAGACATATGATGTCGGTTGTCGTTCAGAAC-3' (SEQ ID NO: 355) | 5'-AGAAGAGGATCCTCAGATATACTTCAGGCCC-3' (SEQ ID NO: 356) | phosphate buffer, pH 7.5, containing 4 mM $MgCl_2$, 200 mM NaCl. Purified protein was concentrated with Amicon centrifugal concentrators (5000 MW cutoff) (Millipore, Billerica, Mass.). After concentration, it was noted that the aldolases of SEQ ID NO: 44, SEQ ID NO: 28, and SEQ ID NO: 276 showed some level of precipitation, although the activity was still quite high. Proteins were stored at −80° C. until assayed.

Protein assays were done using the Pierce BCA kit (Pierce, Rockford, Ill.) and the microtiter plate protocol with Bovine Serum Albumin ("BSA") as the protein standard. The Experion Pro260 electrophoresis system (Bio-Rad, Hercules, Calif.) or SDS-PAGE was used to estimate the percentage of aldolase in the purified sample, and to evaluate expression levels in the soluble cell extract and in total protein.

Testing of Purified Aldolases

Purified aldolases were tested for their ability to produce R,R monatin from D-tryptophan, and were compared to the aldolases of SEQ ID NO:28 and SEQ ID NO:54 prepared in the same manner. Assays were run in microcentrifuge tubes (in duplicate) with purified protein, using the same concentration of enzyme per assay (50 μg/mL) with the exception of SEQ ID NO:244, for which 25 μg/mL was used. SEQ ID NO:243 did not express well and yielded smaller amounts of purified protein. Two mg/mL of BioCatalytics AT-103 (BioCatalytics, Pasadena, Calif.) was used as the D-aminotransferase. The following were added per 1 mL of reaction mixture: aldolase, 4 mM $MgCl_2$, 50 mM D-tryptophan, D-aminotransferase, 200 mM sodium pyruvate, 100 mM potassium phosphate buffer pH 7.5, and 0.05 mM PLP. Samples were incubated at 30° C. Thirty minute, 1 hour, 3 hour, and overnight (19 hour) samples were taken. Table 25 shows the averaged results of total monatin produced at each time point and the % R,R monatin produced, as determined by reversed phase peak areas. In column 3 of Table 25, additional FDAA-derivatization LC/MS/MS analysis as described in Example 1 was done for some of the reactions and those results are shown in the parentheses.

TABLE 25

Total monatin produced from D-tryptophan and % R,R

| Aldolase (hr) | Total monatin (ppm) | % R,R monatin |
|---|---|---|
| SEQ ID NO: 28 (0.5) | 16 | 99.1 |
| SEQ ID NO: 28 (1) | 53.2 | 99.2 (99.0) |
| SEQ ID NO: 28 (3) | 207.8 | 98.6 (98.1) |
| SEQ ID NO: 28 (19) | 544.9 | 95.3 (93.2) |
| SEQ ID NO: 44 (0.5) | 46.2 | 88.0 |
| SEQ ID NO: 44 (1) | 92.5 | 86.8 |
| SEQ ID NO: 44 (3) | 319.7 | 76.4 |
| SEQ ID NO: 44 (19) | 762.9 | 67.1 |
| SEQ ID NO: 54 (0.5) | 35.3 | 96.2 |
| SEQ ID NO: 54 (1) | 82.7 | 96.1 |
| SEQ ID NO: 54 (3) | 280.1 | 92.9 |
| SEQ ID NO: 54 (19) | 715.3 | 77.1 |
| SEQ ID NO: 74 (0.5) | 51.1 | 92.6 |
| SEQ ID NO: 74 (1) | 89.3 | 94.3 |
| SEQ ID NO: 74 (3) | 269.5 | 89.9 |
| SEQ ID NO: 74(19) | 701.9 | 76.2 |
| SEQ ID NO: 50 (0.5) | 55.9 | 96.7 |
| SEQ ID NO: 50 (1) | 96.5 | 96.2 |
| SEQ ID NO: 50 (3) | 272.2 | 95.6 |
| SEQ ID NO: 50 (19) | 645.8 | 88.5 |
| SEQ ID NO: 162 (0.5) | 37.3 | 95.7 |
| SEQ ID NO: 162 (1) | 75.0 | 97.1 |
| SEQ ID NO: 162 (3) | 261.0 | 95.9 |
| SEQ ID NO: 162 (19) | 633.1 | 87.0 |
| SEQ ID NO: 276 (0.5) | 37.8 | 98.8 |
| SEQ ID NO: 276 (1) | 71.2 | 99.3 (99.5) |
| SEQ ID NO: 276 (3) | 245.2 | 99.0 (99.0) |

TABLE 25-continued

Total monatin produced from D-tryptophan and % R,R

| Aldolase (hr) | Total monatin (ppm) | % R,R monatin |
|---|---|---|
| SEQ ID NO: 276 (19) | 585.4 | 96.7 (96.1) |
| SEQ ID NO: 244 (0.5) | 30.2 | 97.7 |
| SEQ ID NO: 244 (1) | 46.4 | 98.3 (99.2) |
| SEQ ID NO: 244 (3) | 165 | 98.4 (98.7) |
| SEQ ID NO: 244 (19) | 572.5 | 95.6 (93.7) |
| SEQ ID NO: 228 (0.5) | 52 | 95.0 |
| SEQ ID NO: 228 (1) | 81.7 | 96.5 |
| SEQ ID NO: 228 (3) | 251 | 95.9 |
| SEQ ID NO: 228 (19) | 723 | 87.1 |
| no aldolase (0.5) | 0 | |
| no aldolase (1) | 0 | |
| no aldolase (3) | 0.6 | 58.3 |
| no aldolase (19) | 6.5 | 61.5 |

The SEQ ID NO:276 aldolase maintained a high level of activity, as well as the highest stereospecificity for production of R,R monatin. Storage of this enzyme in a buffer omitting the sodium chloride appears to reduce the level of precipitation noted earlier. Magnesium concentration in the storage buffer does not appear to have an impact on the level of precipitation.

The aldolases of SEQ ID NO:276, SEQ ID NO: 28, and SEQ ID NO: 244 all demonstrated high activity and high stereoselectivity for production of R,R monatin. These three enzymes were prepared as described in Example 23 and assayed anaerobically, as described in Example 24, using 10 mL serum vials. Seven mL assays were done using 0.05 mg/mL of each aldolase (purified) and 2 mg/mL of purified *B. sphaericus* D-aminotransferase prepared as described in Example 24. The activity of each aldolase in production of monatin from D-tryptophan was compared to the *S. meliloti* HMG aldolase prepared as described in Example 27. Total monatin was estimated using the LC-OPA method described in Example 1. The percentage of R,R monatin formed was determined using the FDAA derivatization method described in Example 1. The results are shown below in Table 26.

TABLE 26

| Aldolase | Time (hr) | Monatin (g/L) | % R,R formed |
|---|---|---|---|
| *S. meliloti* | 23 | 3.9 | 82.0 |
| SEQ ID NO: 28 | 23 | 4.0 | 84.6 |
| SEQ ID NO: 276 | 23 | 4.0 | 95.7 |
| SEQ ID NO: 244 | 23 | 3.7 | 88.8 |
| *S. meliloti* | 47 | 4.5 | 76.2 |
| SEQ ID NO: 28 | 47 | 4.3 | 84.6 |
| SEQ ID NO: 276 | 47 | 4.3 | 93.2 |
| SEQ ID NO: 244 | 47 | 4.5 | 85.2 |

These results demonstrate that the aldolase of SEQ ID NO: 276 produces high levels of R,R monatin in larger volume anaerobic reactions as well.

Example 23

Expression and Purification of the SEQ ID NO:276 Aldolase

The cloning of the *E. coli* BL21 (DE3)pLysS host carrying the aldolase gene listed as SEQ ID NO:275 on the pET28b plasmid is described above in Example 22.

The SEQ ID NO:276 aldolase with an amino-terminal $HIS_6$-purification tag was produced using the EMD Biosciences Overnight Express System II (Novagen, Madison, Wis.) (solutions 1-6) containing 50 μg/mL kanamycin in shake flasks. This expression system induces the expression of IPTG-inducible systems without the need to monitor cell growth. After inoculation of 200-mL aliquots of the medium (in 1 L flasks) from either liquid cultures or plates of the aldolase construct, the cultures were incubated at 30° C. overnight with shaking at 225 rpm. When the $OD_{600\ nm}$ had reached a minimum of 6, the cells were harvested by centrifugation and washed once with buffer.

To prepare cell free extract containing the aldolase, the cells were suspended in 3-4 volumes of 100 mM potassium phosphate, pH 7.8 and then disrupted using a Microfluidics homogenizer (Microfluidics, Newton, Mass.) (3 passes at 18,000 psi), maintaining the temperature of the suspension at less than 15° C. Alternatively, cell free extract was prepared using EMD Biosciences BugBuster® (primary amine-free) Extraction Reagent (Novagen, Madison, Wis.) containing 1 μL/mL Benzonase® Nuclease, 5 μL/mL Protease Inhibitor Cocktail Set II, and 0.033 μL/mL rLysozyme™ following the manufacturer's protocol. All subsequent purification steps were carried out at 4° C. The cell suspension was centrifuged for 20-30 minutes at 15,000-20,000×g to remove the cell debris. A 20-25 mL aliquot of the cell free extract was applied to a 45 mL column of GE Healthcare Chelating Sepharose™ Fast Flow resin (nickel (II) form) (GE Healthcare, Piscataway, N.J.) that had been previously equilibrated with 100 mM potassium phosphate containing 200 mM sodium chloride. To generate the nickel form of the resin, the resin was washed with 150 mL of 200 mM nickel (II) sulfate hexahydrate and then with 150 mL of distilled water. After loading the sample, the column was washed/eluted with 150 mL of the equilibration buffer containing 25 mM imidazole, 150 mL of the equilibration buffer containing 50 mM imidazole and 150 mL of the equilibration buffer containing 500 mM imidazole. The $HIS_6$-tagged protein eluted in the last wash. The 500 mM imidazole wash was concentrated with Millipore/Amicon Centricon Plus-70 centrifugal filter devices (MWCO 10 kDa) (Millipore, Billerica, Mass.) to 15-20 mL according to the manufacturer's instructions. The imidazole and sodium chloride were removed by passage through disposable GE Healthcare PD10 columns (GE Healthcare, Piscataway, N.J.) (2.5 mL sample per column) previously equilibrated with 100 mM potassium phosphate, pH 7.8. The purified aldolase was eluted with 3.5 mL per column of the same buffer.

The protein concentration of each fraction was determined using the Pierce BCA assay kit (Pierce, Rockford, Ill.) using BSA as the protein standard. The purity of each fraction and the level of expression in the cell free extract were determined using a Bio-Rad Experion microcapillary chip system (Bio-Rad, Hercules, Calif.) or using Bio-Rad 4-15% SDS-polyacrylamide gradient gels run in a Mini PROTEAN® 3 cell apparatus (Bio-Rad, Hercules, Calif.). The protein was visualized in the polyacrylamide gels using Bio-Rad Bio-Safe G-250 Coomassie stain (Bio-Rad, Hercules, Calif.) and destained with water. Typically this procedure produces ~50 mg of enzyme from 400 mL of overnight culture that is 85-95% pure as judged by the Experion software. Aliquots (1-5 mL) of the purified enzyme were stored at −80° C. until use. Preparation of the enzyme in this manner reduced the level of precipitation of the enzyme previously noted. The presence of magnesium in the storage buffer had no effect on the level of precipitation.

Example 24

Production of R,R-Monatin Using the SEQ ID NO:276 Aldolase: Optimization of Reaction Conditions The *Bacillus sphaericus* (ATCC strain 10208) D-alanine aminotransferase cloned in Example 7 was purified as the $HIS_6$-tagged protein as described below using EMD Biosciences Overnight Express System II (Novagen, Madison, Wis.) for growth and induction. The EMD Biosciences Overnight Express System II (solutions 1-6) (Novagen, Madison, Wis.) contained 50 μg/mL kanamycin in shake flasks. This expression system induces the expression of IPTG-inducible systems without the need to monitor cell growth. After inoculation of 200-mL aliquots of the medium (in 1 L flasks) from either liquid cultures or plates of the aminotransferase construct, the cultures were incubated at 30° C. overnight with shaking at 225 rpm. When the $OD_{600\ nm}$ had reached a minimum of 6, the cells were harvested by centrifugation and washed once with buffer.

To prepare cell free extract containing the D-alanine aminotransferase, the cells were suspended in 3-4 volumes of 100 mM potassium phosphate, pH 7.8, containing 50 μM pyridoxal phosphate (PLP) and then disrupted using a Microfluidics homogenizer (Microfluidics, Newton, Mass.) (3 passes at 18,000 psi), maintaining the temperature of the suspension at less than 15° C. Alternatively, cell free extract was prepared using EMD Biosciences BugBuster® (primary amine-free) Extraction Reagent (Novagen, Madison, Wis.) containing 1 μL/mL Benzonase® Nuclease, 5 μL/mL Protease Inhibitor Cocktail Set II, and 0.033 μL/mL rLysozyme™ following the manufacturer's protocol. All subsequent purification steps were carried out at 4° C. The cell extract was centrifuged for 20-30 minutes at 15,000×g to remove the cell debris. A 20-25 mL aliquot of the cell free extract was applied to a 45 mL column of GE Healthcare Chelating Sepharose™ Fast Flow resin (nickel (II) form) (GE Healthcare, Piscataway, N.J.) that had been previously equilibrated with 100 mM potassium phosphate containing 200 mM sodium chloride and 50 μM PLP. To generate the nickel form of the resin, the resin was washed with 150 mL of 200 mM nickel (II) sulfate hexahydrate and then with 150 mL of distilled water. After loading the sample, the column was washed/eluted with 150 mL of the equilibration buffer containing 25 mM imidazole, 150 mL of the equilibration buffer containing 50 mM imidazole and 150 mL of the equilibration buffer containing 500 mM imidazole. The $HIS_6$-tagged protein eluted in the last wash. The 500 mM imidazole wash was concentrated with Millipore/Amicon Centricon Plus-70 centrifugal filter devices (MWCO 10 kDa) (Millipore, Billerica, Mass.) to 15-20 mL according to the manufacturer's instructions. The imidazole and sodium chloride were removed by passage through disposable GE Healthcare PD10 columns (GE Healthcare, Piscataway, N.J.) (2.5 mL sample per column) previously equilibrated with 100 mM potassium phosphate, pH 7.8 containing 0.5 μM PLP. The purified aminotransferase was eluted with 3.5 mL per column of the same buffer.

The protein concentration of each fraction was determined using the Pierce BCA assay kit (Pierce, Rockford, Ill.) with BSA as the protein standard. The purity of each fraction and the level of expression in the cell free extract fraction were determined using a Bio-Rad Experion microcapillary chip system (Bio-Rad, Hercules, Calif.) or using Bio-Rad 4-15% SDS-polyacrylamide gradient gels (Bio-Rad, Hercules, Calif.) run in a Mini PROTEAN® 3 cell apparatus. The protein was visualized in the polyacrylamide gels using Bio-Rad Bio-Safe G-250 Coomassie stain (Bio-Rad, Hercules, Calif.) and destained with water. Typically this procedure produces ~50 mg of enzyme from 200 mL of overnight culture that is 85-90% pure as judged by the Experion software or from analysis of the SDS-PAGE gels. Aliquots (1-5 mL) of the purified enzyme were stored at −80° C. until use.

The SEQ ID NO:276 aldolase (cloned in Example 22) was purified as the $HIS_6$-tagged protein as described in Example 23.

The preferred metal cofactor for the SEQ ID NO:276 aldolase was determined by screening a variety of divalent metals. The reactions were set up anaerobically in 10 mL serum bottles with 7 mL final volumes. A bulk solution consisting of 100 mM potassium phosphate (pH 7.8), 200 mM sodium pyruvate, 0.05 mM PLP and 0.01% (v/v) Tween 80 was prepared to a final volume of 48.8 mL and sparged with nitrogen for 30 minutes. D-Tryptophan (143 mg; final concentration of 100 mM) was dispensed into seven 10 mL serum vials. To each of the vials was added 0.014 mL of a 2 M stock solution of a divalent metal cation, prepared from the chloride salt (final concentration of 4 mM). For the negative control, 0.014 mL of $dH_2O$ was added. The serum vials were capped with rubber septa and sparged with nitrogen via 16-18 gauge needles. Under anaerobic conditions, 5.625 mL of the anaerobic bulk solution was added to each anaerobic serum bottle. Subsequently, the *B. sphaericus* D-alanine aminotransferase and the SEQ ID NO:276 aldolase were added anaerobically to each serum bottle to a final concentration of 2 mg/mL and 0.05 mg/mL, respectively. The solutions were incubated at room temperature with gentle mixing for 18 hours. Final monatin was analyzed according to the methods described in Example 1 using the Liquid Chromatography-Post Column Fluorescence Detection of Amino Acids method. (Table 27).

TABLE 27

| Metal Cofactor | Final Monatin (mM) at 18 h |
| --- | --- |
| None (negative control) | 1.7 |
| Magnesium | 10.6 |
| Manganese | 10.0 |
| Cobalt | 6.7 |
| Zinc | 4.9 |
| Nickel | 1.5 |
| Calcium | 0.7 |

The reaction conditions for the SEQ ID NO:276 aldolase were further investigated with a two-level fractional factorial experiment designed using the statistical software Design Expert 7.0.0 (Stat-Ease, Inc.; Minneapolis, Minn.). The screening design consisted of a single block of five factors at two levels with four centerpoints (20 runs total). The five factors to be optimized were the metal cofactor concentration, reaction pH, Tween® 80 concentration, pyruvate to tryptophan ratio, and the aldolase concentration (Table 28).

Conical polypropylene tubes (14 mL) containing 143 mg of D-tryptophan were de-oxygenated in an anaerobic glove box (Coy Laboratory Products, Inc; Grass Lake, Mich.) overnight. Stock solutions of 2 M $MgCl_2$; 1 M potassium phosphate at pH 7.0, 7.75, and 8.5; 10% (v/v) Tween® 80; 2 M sodium pyruvate, and 10 mM PLP (pyridoxal 5'-phosphate) were prepared in degassed water and equilibrated in the anaerobic glove box overnight. Stock solutions of purified *B. sphaericus* D-alanine aminotransferase and the SEQ ID NO:276 aldolase were thawed on ice and used in the anaerobic glove box immediately. Stock solutions were added to the 14 mL conical tubes containing the D-tryptophan to obtain the concentrations determined by the statistical design (Table 28). Degassed water was added to each tube to bring the final volume, along with the enzyme additions, to 7.0 mL. The tubes were incubated at room temperature in the anaerobic glove box with gentle mixing for up to 24 hours. Monatin concentration and isomeric purity were analyzed according to the methods described in Example 1 using the Liquid Chromatography-Post Column Fluorescence Detection of Amino Acids method and the LC/MS/MS Multiple Reaction Monitoring for the Determination of the Stereoisomer Distribution of Monatin in in vitro and in vivo Reactions method (FDAA derivatization method).

TABLE 28

| Run # | std # | Block | Mg (mM) | pH | Tween ® (%) | Pyr:Trp | Aldolase of SEQ ID NO: 276 (mg/mL) |
| --- | --- | --- | --- | --- | --- | --- | --- |
| 20 | 1 | Block 1 | 5.00 | 7.75 | 0.01 | 2.00 | 0.05 |
| 8 | 2 | Block 1 | 9.00 | 8.50 | 0.02 | 1.00 | 0.01 |
| 3 | 3 | Block 1 | 1.00 | 8.50 | 0.00 | 1.00 | 0.01 |
| 16 | 4 | Block 1 | 9.00 | 8.50 | 0.02 | 3.00 | 0.09 |
| 7 | 5 | Block 1 | 1.00 | 8.50 | 0.02 | 1.00 | 0.09 |
| 12 | 6 | Block 1 | 9.00 | 8.50 | 0.00 | 3.00 | 0.01 |
| 6 | 7 | Block 1 | 9.00 | 7.00 | 0.02 | 1.00 | 0.09 |
| 2 | 8 | Block 1 | 9.00 | 7.00 | 0.00 | 1.00 | 0.01 |
| 15 | 9 | Block 1 | 1.00 | 8.50 | 0.02 | 3.00 | 0.01 |
| 4 | 10 | Block 1 | 9.00 | 8.50 | 0.00 | 1.00 | 0.09 |
| 5 | 11 | Block 1 | 1.00 | 7.00 | 0.02 | 1.00 | 0.01 |
| 1 | 12 | Block 1 | 1.00 | 7.00 | 0.00 | 1.00 | 0.09 |
| 13 | 13 | Block 1 | 1.00 | 7.00 | 0.02 | 3.00 | 0.09 |
| 14 | 14 | Block 1 | 9.00 | 7.00 | 0.02 | 3.00 | 0.01 |
| 17 | 15 | Block 1 | 5.00 | 7.75 | 0.01 | 2.00 | 0.05 |
| 11 | 16 | Block 1 | 1.00 | 8.50 | 0.00 | 3.00 | 0.09 |
| 18 | 17 | Block 1 | 5.00 | 7.75 | 0.01 | 2.00 | 0.05 |
| 9 | 18 | Block 1 | 1.00 | 7.00 | 0.00 | 3.00 | 0.01 |
| 19 | 19 | Block 1 | 5.00 | 7.75 | 0.01 | 2.00 | 0.05 |
| 10 | 20 | Block 1 | 9.00 | 7.00 | 0.00 | 3.00 | 0.09 |

Statistical analysis of the data indicated that reaction pH, pyruvate:tryptophan ratio and aldolase concentration were the significant factors affecting monatin titer, isomeric purity and carbon yield. A desirability graph was generated using the Design Expert software in which the factors were varied in order to maximize the goals of highest monatin titer and highest isomeric purity under conditions of excess pyruvate. The reactions conditions indicated as optimum were 1 mM $MgCl_2$, pH>8.0, 0.01% (v/v) Tween® 80, and 0.01 mg/mL SEQ ID NO:276 aldolase. This is a 5 fold reduction in the typical amount of aldolase utilized, as well as a 4-fold reduction in the amount of divalent metal typically used.

Additional experiments were performed to determine the optimum pH range for the reaction process. Stock solutions of 1 M EPPS buffer were prepared at increments of 0.2 pH units between pH 7.0 and 9.0. These solutions were degassed and equilibrated in the anaerobic glove box overnight. Polypropylene tubes (14 mL) containing 143 mg of D-tryptophan were de-oxygenated in an anaerobic glove box overnight. Stock solutions of 2 M $MgCl_2$, 10% (v/v) Tween® 80, 2 M sodium pyruvate and 10 mM PLP were prepared in degassed water and equilibrated in the anaerobic glove box. Preparations of purified *B. sphaericus* D-alanine aminotransferase and SEQ ID NO:276 aldolase were thawed on ice and used immediately in the anaerobic glove box. The stock solutions were added to the 14 mL conical tubes to give a final concentration of 100 mM EPPS, 200 mM pyruvate, 100 mM tryptophan, 1 mM $MgCl_2$, 0.01% (v/v) Tween® 80, 0.05 mM PLP, 2 mg/mL *B. sphaericus* D-alanine aminotransferase, and 0.01 mg/mL SEQ ID NO:276 aldolase in a total volume of 7 mL per tube. The reactions were incubated at room temperature in the anaerobic glove box with gentle agitation for 22 hours. Samples were removed and analyzed for monatin as described in Example 1 using the LC/MS/MS multiple reaction monitoring method (Table 29).

TABLE 29

| Reaction pH | Monatin (mM) at 22 h |
| --- | --- |
| 7.0 | 5.8 |
| 7.2 | 9.9 |
| 7.4 | 7.8 |
| 7.6 | 10.6 |
| 7.8 | 14.0 |
| 8.0 | 14.2 |
| 8.2 | 14.3 |
| 8.4 | 12.6 |
| 8.6 | 12.3 |
| 8.8 | 10.8 |
| 9.0 | 11.1 |

The results indicated that monatin formation increased with increasing pH between 7.0-8.0. Monatin formation reached a maximum in the range of pH 8.0-8.2, and decreased above pH 8.4. Additionally, the isomeric purity of monatin decreased above pH 8.4.

Further reaction optimization was done using the aldolase of SEQ ID NO: 276 (0.01 mg/mL), 2 mg/mL of the T243N 4978 DAT (untagged, from Example 26), 1 mM MgCl$_2$, 200 mM sodium pyruvate, 0.05 mM PLP, 0.01% Tween-80, and 100 mM D-tryptophan at pH 8.5. The cells used to produce the aldolase and the D-aminotransferase were broken open in 50 mM EPPS, pH 8.4 using a Microfluidics homogenizer (Microfluidics, Newton, Mass.) (3 passes at 20,000 psi). The cell debris was removed by centrifugation (20,000×g for 30 minutes) and the clarified cell extracts were used in the enzymatic reactions. No additional buffer was utilized, but the reaction mixtures were adjusted to pH 8.5 using sodium hydroxide and flushed with nitrogen prior to addition of enzyme. Two-hundred fifty mL reactions were carried out in 0.7 L Six for agitated fermenters (Infors AG, Bottmingen, Switzerland) at 30° C. using nitrogen in the headspace. Potassium phosphate was added to a final concentration of 0, 5, 10, 20, and 50 mM. The addition of 5-10 mM phosphate was found to be optimal, producing 3.5 g/L monatin (quantitated by LC/MS/MS as described in Example 1).

Example 25

Cloning of a Novel *Bacillus* D-Amino Acid Aminotransferase

A *Bacillus* D-amino acid aminotransferase ("DAAT" or "DAT") (EC 2.6.1.21, also known as D-alanine aminotransferase or D-aspartate aminotransferase) was produced recombinantly. This aminotransferase was used in coupled assays with aldolases for production of R,R monatin. This aminotransferase enzyme is homologous to D-aminotransferases described previously for production of monatin (U.S. Published Application No. 20040063175 and U.S. Published Application No. 20050282260). The organism ATCC 4978—*Bacillus sphaericus* originally deposited as *Bacillus rotans*—was ordered from the ATCC and used to prepare genomic DNA. Degenerate primers were designed in the regions of protein sequence conservation of known *Bacillus* D-aminotransferases and used for polymerase chain reaction ("PCR") amplification of internal DAAT gene sequence from the ATCC strain mentioned above. Genome walking was performed using the BD GenomeWalker™ Universal Kit (Clontech, Mountain View, Calif.). Sequence analyses (Agencourt BioScience Corporation, Beverly, Mass.) verified a full-length coding sequence for the DAAT gene from ATCC 4978. The DNA sequence of the DAAT gene from ATCC 4978 is SEQ ID NO:357 and is shown below. The gene of SEQ ID NO:357 may be amplified by standard PCR protocols and cloned using standard recombinant DNA techniques. The gene of SEQ ID NO:357 may also be reconstructed by any method known to a person of ordinary skill in the art, such as assembly PCR methods known to one skilled in the art.

The ATCC 4978 DAAT DNA sequence is:

(SEQ ID NO: 357)
```
atgagttata gcttatggaa tgaccaaatt gtgaatgatg aagaagtagt agttgataag gaggaccgtg gctatcaatt tggcgatggt gtttatgaag ttgtaaaagt atataacggt gaattattta cagcggagga gcatgtcgat cgtttttacg cgagtgctga aaaaattcgc gttacgatcc cttatacaaa agacaaattg catcaattat tgcatcagtt agttgaaatg aataaagttc aaacaggaca tatttatttc caaattacgc gtggtgcagg ccctcgtaat catatttttcc ctggtgatga agtgaagcca gtattaacag gtaataccaa ggaaaatcca cgtcccgtag caaactttga aaaaggtgtg aaagcaacat ttgtagaaga cattcgttgg ttacgctgtg acattaaatc attaaattta cttggtgcgg tacttgctaa acaagaagca catgaaaaag gatgctatga agcggtttta catcgtgatg aaatcgtaac agaaggctct tcttcaaata tttatggaat taaagatggc gtattataca cacatccagc gaataacttc atcttaaatg gtattacacg tcaagtaatc attaaatgtg ctgctgaaat tggcttacca gtgaaggaag aagcaatgac aaaaactcag cttcttgcaa tggatgaagt gattgtttca tcaacgactt cagaagtaac gccaattatc gacatagatg aacagtaat tggtgcgggt aaaccgggtg actggacacg taaattacaa gcacaatttg atacgaaaat cccaaaaggt attcgcgcat aa
```

The amino acid sequence of the DAAT gene from ATCC 4978 as encoded by the above DNA sequence is SEQ ID NO:358 and is shown below:

(SEQ ID NO: 358)

```
Met Ser Tyr Ser Leu Trp Asn Asp Gln Ile Val Asn Asp Glu Glu Val Val

Val Asp Lys Glu Asp Arg Gly Tyr Gln Phe Gly Asp Gly Val Tyr Glu Val

Val Lys Val Tyr Asn Gly Glu Leu Phe Thr Ala Glu Glu His Val Asp Arg

Phe Tyr Ala Ser Ala Glu Lys Ile Arg Val Thr Ile Pro Tyr Thr Lys Asp Lys

Leu His Gln Leu Leu His Gln Leu Val Glu Met Asn Lys Val Gln Thr Gly

His Ile Tyr Phe Gln Ile Thr Arg Gly Ala Gly Pro Arg Asn His Ile Phe Pro

Gly Asp Glu Val Lys Pro Val Leu Thr Gly Asn Thr Lys Glu Asn Pro Arg

Pro Val Ala Asn Phe Glu Lys Gly Val Lys Ala Thr Phe Val Glu Asp Ile

Arg Trp Leu Arg Cys Asp Ile Lys Ser Leu Asn Leu Leu Gly Ala Val Leu

Ala Lys Gln Glu Ala His Glu Lys Gly Cys Tyr Glu Ala Val Leu His Arg

Asp Glu Ile Val Thr Glu Gly Ser Ser Ser Asn Ile Tyr Gly Ile Lys Asp Gly

Val Leu Tyr Thr His Pro Ala Asn Asn Phe Ile Leu Asn Gly Ile Thr Arg

Gln Val Ile Ile Lys Cys Ala Ala Glu Ile Gly Leu Pro Val Lys Glu Glu Ala

Met Thr Lys Thr Gln Leu Leu Ala Met Asp Glu Val Ile Val Ser Ser Thr

Thr Ser Glu Val Thr Pro Ile Ile Asp Ile Asp Gly Thr Val Ile Gly Ala Gly

Lys Pro Gly Asp Trp Thr Arg Lys Leu Gln Ala Gln Phe Asp Thr Lys Ile

Pro Lys Gly Ile Arg Ala
```

The novel D-aminotransferase obtained from strain ATCC 4978 has a protein sequence that has distinct amino acid residue changes when compared to the *B. sphaericus* ATCC 10208 published D-aminotransferase sequence. The DAAT from ATCC 4978 has only 72% identity with the DAAT from *B. sphaericus* (ATCC 10208). While this strain is currently listed as *B. sphaericus* in the ATCC, it was deposited as *B. rotans*. Based on the sequence alignments and the highlighted differences between this novel DAAT and the DAAT from *B. sphaericus*, a number of candidate residues are identified that can be evaluated for their role (individually or in combination) in increasing DAAT activity for R,R monatin biosynthesis, in these, as well as other DAAT sequences.

Example 26

Characterization of Mutants of D-Aminotransferase from ATCC 4978

Experimental Overview

The novel D-aminotransferase gene (described in Example 25) from *Bacillus* strain ATCC 4978 was mutagenized using site-directed methods. The mutant genes were expressed and assayed for activities of interest for monatin production pathways, especially when coupled with one or more aldolases.

In addition to the ideas listed in Example 16 for site directed mutagenesis targets, other ideas were developed by the actual docking of R-MP into the active site of the YM-1 crystal structure primary amino acid sequence alignments were used to determine if the 4978 aminotransferase protein was likely to have similar structural characteristics in that region. It was expected that the following additional mutations would be beneficial (using the 4978 aminotransferase's amino acid numbering). It was thought that mutagenesis of alanine 153 to arginine would stabilize the second carboxyl group of the substrate (R-MP). This change is likely to increase steric hindrance, so to compensate, the serine residues at positions 181 and 182 were changed to alanine or glycine. It was also hypothesized that one could introduce an arginine at position 180, 181, or 182 and convert one or more of the other serine residues to alanine or glycine to make room for the bulkier side chain of arginine. The phenylalanine at amino acid 200 is spatially close to where R-MP is predicted to dock into the active site and there is a large amount of variability in this residue amongst the D-aminotransferases that catalyze monatin transamination fairly well. It was thought that amino acid modifications at this position could be useful. Mutation of leucine 151 to phenylalanine was predicted to potentially improve interactions with the indole ring of the substrate.

Based upon literature, it was hypothesized that mutation of threonine 243 to asparagine may improve R-MP selectivity for transamination reactions. Likewise, it was thought that mutagenesis of asparagine 100 to alanine may improve the specific activity of the enzyme for monatin transamination reactions (Ro, et al., *FEBS Lett* 398:141-145, (1996); Sugio, S, et al., *Biochemistry* 34:9661-9669, (1995); EP1580268).

Lee et al. characterized mutants of the 141-144 region (loop) and found that D-aminotransferases with the EYcY rather than the LRcD (which is native to our protein) tend to have a lower Km for dicarboxylic acid substrates. (Lee S G, Hong S P, Song J J, Kim S J, Kwak M S, Sung M H. Functional and structural characterization of thermostable D-amino acid aminotransferases from *Geobacillus* spp. Appl Environ Microbiol. 2006 February; 72(2):1588-94). Because MP is a dicarboxylic acid substrate, similar to alpha-keto glutarate, and the concentrations of MP are fairly low in a typical monatin production reaction mixture, a decreased $K_m$ could potentially help the activity of a mutant DAT for monatin production.

Below, methods are described for creating the 4978 D-aminotransferase mutants, as well as assay results using these mutants.

Mutagenesis

The primers for mutagenesis were designed following the suggestions listed in the Stratagene Multi-Change kit (Stratagene, La Jolla, Calif.). The primers were 5'-phosphorylated. Mutagenesis was done using the Stratagene Multi-Change kit (Stratagene, La Jolla, Calif.) following the manufacturer's instructions. The templates used for mutagenesis were either the pET30 (untagged) or pET28 (tagged) 4978 DAT constructs described in Example 25. The primers are listed below in Table 30:

TABLE 30

| Mutant Name | Amino acid change | Primer |
|---|---|---|
| 4978-22 | T243N | GTGATTGTTTCATCAACGAATTCAGAAGTA ACGCC (SEQ ID NO: 359) |
| 10 | T243R | GTGATTGTTTCATCAACGCGTTCAGAAGTA ACGCC (SEQ ID NO: 360) |
| 7 | T243S | GTGATTGTTTCATCAACGAGTTCAGAAGTA ACGCC (SEQ ID NO: 361) |
| 19 | T243A | GTGATTGTTTCATCAACGGCTTCAGAAGTA ACGCC (SEQ ID NO: 362) |
| 15 | N100A | GTGCAGGCCCTCGTGCTCATATTTTCCCTGG (SEQ ID NO: 363) |
| B | T243Q | GAAGTGATTGTTTCATCAACGCAGTCAGAAG TAACGCCAATTATC (SEQ ID NO: 364) |
| 2 | T243N/N100 | above primers used together |

E. coli XL10-Gold cells (Stratagene, La Jolla, Calif.) were transformed, and resultant purified plasmid preparations were sequenced to verify that the correct mutations were incorporated.

Expression and Assay

Plasmid DNA preparations containing the correct mutants or the wildtype 4978 DAT were transformed into the E. coli expression host BL21(DE3) (Novagen, Madison, Wis.). The cultures were grown using the protocols described above, the plasmids were isolated using Qiagen miniprep kit (Qiagen, Valencia, Calif.) and analyzed by restriction digestion, as described above, to confirm the presence of an insert.

Induction of the DAAT gene was typically performed in LB medium containing kanamycin (50 μg/mL). The cells were grown to an $OD_{600\,nm}$ of 0.4-0.8 at 37° C., induced with 0.1 mM IPTG (isopropyl thiogalacatoside) and sampled at 3-4 hours post induction.

Cellular extracts were prepared with BugBuster Reagent and Benzonase Nuclease (Novagen, Madison, Wis.). One ml assays were performed at 30° C. with gentle shaking and contained 10.2 mg D-tryptophan, 0.05 mM PLP, 4 mM $MgCl_2$, 100 mM potassium phosphate buffer pH 7.5, approximately 50 μg of aldolase, 200 mM pyruvate, and 0.150-0.5 mg/mL D-aminotransferase supplied as cellular extracts. Total protein assays were done using the Bio-Rad total protein kit (Coomassie) (Bio-Rad, Hercules, Calif.) or the Pierce BCA kit (Pierce, Rockford, Ill.), and percent expression of the D-aminotransferase was estimated by SDS-PAGE or the Bio-Rad Experion Automated Electrophoresis System (Bio-Rad, Hercules, Calif.). Samples were taken at 3 hours and overnight.

The R-specific aldolase of SEQ ID NO: 28 was used in assays with approximately 0.150 mg/mL D-aminotransferase.

The first assays showed that the following mutants (untagged) had transamination activity (in order of highest to lowest): T243N, T243S, T243N/N100A, N100A. It was also noted that the T243N appeared to raise the stereo-purity of the R,R monatin produced. Assays were repeated using purified Comamonas testosteroni ProA aldolase (100 μg/ml) and 0.50 mg/ml of D-aminotransferase mutants (untagged, supplied as cellular extract). Samples were taken at 2 hours and overnight. The results for the active proteins are shown below, duplicate results were averaged. The % R,R monatin was determined by peak area on reversed phase HPLC, and then measured using the FDAA derivatization method described in Example 1. In column 3 of Table 31, additional FDAA-derivatization LC/MS/MS analysis as described in Example 1 was done for some of the reactions and those results are shown in the parentheses. Only R,R and S,R monatin are produced from D-tryptophan. The T243R mutant did not appear to produce monatin under the conditions tested, and the T243A mutant produced very low levels of monatin.

TABLE 31

| Enzyme untagged (time - hr or overnight) | Total monatin (ppm) | % R,R |
|---|---|---|
| 4978 wildtype (2 hours) | 4.7 | 41.6 |
| 4978 wildtype (overnight) | 43.2 | 35.1 (30.9) |
| T243S (2 hours) | 55.0 | 37.4 (21.7) |
| T243S (overnight) | 97.7 | 35.5 (29.8) |
| T243N (2 hours) | 73.2 | 86.7 (88.3) |
| T243N overnight | 120.9 | 86.3 (86.1) |
| N100A (2 hours) | 12.0 | 40.8 |
| N100A (overnight) | 22.3 | 41 |
| T243A (2 hours) | 0.8 | ~100 |
| T243A (overnight) | 1.3 | ~100 |

Although the assays were performed estimating percent D-aminotransferase using Bio-Rad Experion software, it is clear that the T243S and T243N mutants had increased activity compared to the wildtype enzyme. The T243N mutant also provided an additional benefit of increasing dramatically the % R,R monatin formed. This enzyme has an increased preference for R-MP as compared to S-MP in transamination reactions. The N100A mutant did not increase activity alone or in combination with T243N contrary to what was suggested in the literature. A V34A site directed mutant of the untagged 4978 DAT was also created using similar methods, as described above. The V34A sited directed mutant was found to have significantly less activity than the wild-type enzyme under the conditions tested.

Another point of interest in the initial assays was that the wildtype enzyme appeared to have more activity when it was produced with an N-terminal His-tag. Subsequent mutagenesis was done on the tagged version of the gene. Additionally, the most promising mutants above were subcloned into pET28b that has an N-terminal His-tag. These were purified using Novagen HIS-bind columns and the manufacturer's protocol with the recommended buffers (Novagen, Madison, Wis.). The buffer of the eluent fractions was exchanged, using GE Healthcare PD10 columns (GE Healthcare, Piscataway, N.J.), to the buffer used in the assays One ml assays with purified D-aminotransferase (0.5 mg/ml) and purified R-specific aldolase SEQ ID NO:276 (50 μg/ml) were conducted at 30° C. with gentle shaking and contained 10.2 mg D-tryptophan, 0.05 mM PLP, 200 mM pyruvate, 4 mM $MgCl_2$, and 100 mM potassium phosphate buffer pH 7.5. Duplicate samples were incubated for 2 hours and overnight. As a positive control, the Bacillus sphaericus DAT (cloned in Example 7) was used in the same assays. The results are presented in Table 32:

TABLE 32

| Enzyme - tagged (time: hours or overnight) | Total monatin (ppm) | % R,R |
|---|---|---|
| 4978 wildtype (2 hours) | 43 | 98.4 |
| 4978 wildtype (overnight) | 96.7 | 98.3 (95.9) |
| T243N (2 hours) | 197.5 | 100 |
| T243N overnight | 301.2 | 99.9 (99.6) |
| B. sphaericus DAT (2 hours) | 58.2 | 99.7 |
| B. sphaericus DAT (overnight) | 221.7 | 98.7 (96.6) |
| T243Q (2 hours) | 7.1 | 100 |
| T243Q (overnight) | 12.4 | 98.8 |

The data above show that the T243N mutant clearly produces the highest amount of monatin at 2 hours. As time increases, the ratio of T243N mutant to B. sphaericus DAT positive control is reduced. This result suggests that the T243N mutant is not as stable during the monatin reaction as the B. sphaericus DAT. When assayed under similar conditions, the T243S (purified tagged) enzyme had similar levels of activity to the T243N mutant; however, the percent R,R monatin produced was lower (97.2% at both 2 h and overnight). The T243N/N100A mutant had less activity than the T243N mutant. However, both T243S and T243N/N100A had higher activity than the wildtype 4978 DAT.

Transamination assays were performed to determine which reaction rates were improved when using the T243N mutant in place of the B. sphaericus DAT. One-half mL assays were performed at 30° C. taking time points at 1 hour, 2 hours, and 5 hours. The assays contained 25 mM monatin or D-tryptophan, 25 mM pyruvate, 100 mM potassium phosphate pH 7.5, 50 µM PLP, and 0.1 mg D-aminotransferase (tagged, purified). In the case where less than 100 µg DAT was used, the amount of alanine was normalized to 100 µg of D-aminotransferase. Samples were treated with formic acid and analyzed by LC-OPA for the presence of the coproduct, alanine. The results are shown in Tables 33 and 34.

TABLE 33

Transamination activity with R,R monatin as substrate

| Enzyme | D-alanine (mM) |
|---|---|
| wildtype 4978 DAT (2 hr) | 0.54 |
| wildtype 4978 DAT (5 hr) | 1.11 |
| T243N/N100A (2 hr) | 1.32 |
| T243N/N100A (5 hr) | 2.78 |
| T243S (2 hr) | 1.5 |
| T243S (5 hr) | 2.61 |
| T243N (2 hr) | 1.26 |
| T243N (5 hr) | 2.65 |
| B. sphaericus DAT (2 hr) | 0.97 |
| B. sphaericus DAT (5 hr) | 2.2 |

TABLE 34

Transamination activity with D-tryptophan as substrate

| Enzyme | D-alanine (mM) |
|---|---|
| wildtype 4978 DAT (1 hr) | 4.55 |
| wildtype 4978 DAT (2 hr) | 8.47 |
| T243N/N100A (1 hr) | 8.52 |
| T243N/N100A (2 hr) | 12.67 |
| T243S (1 hr) | 4.89 |
| T243S (2 hr) | 8.1 |
| T243N (1 hr) | 7.19 |

TABLE 34-continued

Transamination activity with D-tryptophan as substrate

| Enzyme | D-alanine (mM) |
|---|---|
| T243N (2 hr) | 10.83 |
| B. sphaericus DAT (1 hr) | 8.7 |
| B. sphaericus DAT (2 hr) | 12.54 |

For the D-tryptophan reactions, the results show that some of the enzymes had reached equilibrium at 2 hours. The R,R monatin reactions are clearly rate-limiting and improvements to this activity have more of an impact on monatin production rates from D-tryptophan.

Further assays were done to examine the stability of the T243N 4978 DAT mutant. The wildtype enzyme also loses activity over time. Example 27 describes methods to improve the stability of the T243N D-aminotransferase mutant. When freshly prepared untagged and tagged versions of the T243N mutant are prepared and compared for activity, it was found that the untagged version had a better temporal stability, making it overall a better version of the enzyme to use in monatin production reactions.

Additional mutants of 4978 DAT were made by methods commonly known to those skilled in the art. However, these mutations all resulted in protein that was insoluble under the conditions that they were prepared, and thus could not be assayed for activity. The mutations that resulted in insoluble protein were:
S180A/S181A/S182R;
L151F;
V34G
S181R
A153R/S181A/S182A;
A153R/S182A;
A153R/S182G;
S180R/S181A/S182G;
S180R/S181A/S182A;
S180R/S181G/S182G;
S180G/S181R/S182G; and
S180A/S181R/S182A.

Additional Mutagenesis

To create the F200M 4978 DAT mutant, the wildtype 4978 DAT open reading frame from Example 25 (tagged) was amplified with primers 73 and 80 (below) and PfuTurbo DNA Polymerase (Stratagene, La Jolla, Calif.) and cloned into pCRII-Blunt (Invitrogen, Carlsbad, Calif.). Its sequence was verified (Agencourt, Beverly, Mass.). The 5' and 3' regions were amplified using primers 80 and 96 and 99 and 103, respectively. The amplified DNA was then gel purified using Qiagen QIAquick Gel Extraction Kit (Qiagen, Valencia, Calif.). They amplified DNA was subjected again to PCR using primers 80 and 99. The amplified DNA was gel purified as described above and cloned into pCRII Blunt and its sequence verified. The DAT open reading frame was subcloned as an NdeI/XhoI restriction digest fragment into pET28b.

TABLE 35

| Primer Number | Sequence |
|---|---|
| 73 | CATATGAGTTATAGCTTATGGAATGACCAAATTGTGAATG (SEQ ID NO: 365) |
| 80 | CTCGAGTGCGGCCGCAAGCTTGTCGACGGAGCTC (SEQ ID NO: 366) |

TABLE 35-continued

| Primer Number | Sequence |
|---|---|
| 96 | AATATTTATGGAATTAAAGATGGCGTATTATACACACATCCAG CGAATAACATGATCTTAAATGGTATTACACGTCAAGTAATCAT TAAATGTGC (SEQ ID NO: 367) |
| 99 | GGCCAGTGAATTGTAATACGACTCACTATAGGGC (SEQ ID NO: 368) |
| 103 | CGCCATCTTTAATTCCATAAATATTTGAAGAAGAGCCTTCTG (SEQ ID NO: 369) |

The following primers were designed for additional site-directed mutagenesis using the QuikChange® Multi Site-Directed Mutagenesis Kit (Stratagene, La Jolla, Calif.). Mutagenesis was done using the Stratagene Multi-Change kit (Stratagene, La Jolla, Calif.) following the manufacturer's instructions. The template used for mutagenesis was the pET28 (tagged) 4978 DAT construct described in Example 25. A double mutant was also created using the F200Y mutant as template and doing an additional round of mutagenesis with the T243N (listed above) primer.

TABLE 36

| Mutant | Oligo |
|---|---|
| 141-LRcD-144 -> EYcY | GCAACATTTGTAGAAGACATTCGTTGGGAATAC TGTTACATTAAATCATTAAATTTACTTGGTGCG (SEQ ID NO: 370) |
| F200Y | GTATTATACACACATCCAGCGAATAACTACATC TTAAATGGTATTACACGTCAAG (SEQ ID NO: 371) |
| S244K | GCAATGGATGAAGTGATTGTTTCATCAACGACT AAAGAAGTAACGCCAATTATCGACATAGATG (SEQ ID NO: 372) |
| 243-TS-244 -> NK | GCAATGGATGAAGTGATTGTTTCATCAACGAAT AAAGAAGTAACGCCAATTATCGACATAGATG (SEQ ID NO: 373) |
| 243-TS-244 -> NR | GCAATGGATGAAGTGATTGTTTCATCAACGAAT CGTGAAGTAACGCCAATTATCGACATAGATG (SEQ ID NO: 374) |

The mutant coding regions were verified by DNA sequencing (Agencourt). The sequence-verified plasmids were transformed into BL21(DE3) cells (Novagen, Madison, Wis.).

Expression and Assay

Cultures containing 100 ml LB with 50 µg/ml kanamycin in a 500 ml baffled flask were inoculated with one ml of an overnight culture and grown at 37° C. to an optical density (at 600 nm) of approximately 0.6. Production of the protein was induced by IPTG at a final concentration of 1 mM. Cells were incubated at 30° C. for 4.5 hours after the addition of the IPTG. Cells were centrifuged and frozen at −80° C. Cells were disrupted (prepared using Novagen BugBuster reagent (Novagen, Madison, Wis.) containing 1 µL/mL benzonase nuclease, 5 µL/mL protease inhibitor cocktail II, and 0.033 µL/mL rLysozyme following Novagen's recommended protocol) and analyzed by SDS-PAGE. Mutants (141-LRcD-144->EYcY) and (243-TS-244->NR) resulted in insoluble proteins under the conditions in which they were prepared. Mutant 243-TS-244->NK did not have quantifiable activity under the conditions tested, and is probably a weak activity enzyme in comparison to wildtype as is the S244K mutant.

His-tagged proteins were purified as follows. HIS-bind columns (Novagen, Madison, Wis.) were equilibrated with 10 mL of 100 mM potassium phosphate, pH 7.8, containing 200 mM NaCl and 50 µM PLP. Cell-free extracts were loaded on the column. The columns were washed with 10 mL of equilibration buffer, 10 mL equilibration buffer containing 25 mM imidazole, and 10 mL equilibration buffer containing 50 mM imidazole. Proteins were eluted with 5 ml equilibration buffer containing 500 mM imidazole. Proteins were desalted using PD10 columns which were equilibrated in 100 mM potassium phosphate, pH 7.8 containing 50 µM PLP. The purified proteins were concentrated and quantified using the Bradford Assay (Bio-Rad, Hercules, Calif.).

The D-aminotransferase mutants were assayed using 500 µg/ml of the D-aminotransferase, 50 µg/ml of the aldolase of SEQ ID NO:276, 4 mM MgCl$_2$, 50 mM potassium phosphate pH 8, 200 mM sodium pyruvate, 0.05 mM PLP and 20.4 mg/ml D-tryptophan for assay conditions. The final volume was 1.25 ml. Samples (200 µl) were taken after 0.5, 1, 2 and 14 hours and frozen until the experiment was complete. Samples were filtered, diluted 1 to 10, and analyzed by LC/MS/MS as described in Example 1.

The wildtype 4978 D-aminotransferase from Example 25 was used as a reference for percent relative activity. Table 37 shows relative activity of each mutant at each time point.

TABLE 37

| D-aminotransferase | time (hr) | % activity |
|---|---|---|
| 4978 wildtype | 0.5 | 100 |
| T243N | 0.5 | 270 |
| F200M | 0.5 | 50 |
| F200Y | 0.5 | 70 |
| F200M/T243N | 0.5 | 183 |
| S244K | 0.5 | 4 |
| 4978 wildtype | 1 | 100 |
| T243N | 1 | 289 |
| F200M | 1 | 55 |
| F200Y | 1 | 81 |
| F200M/T243N | 1 | 203 |
| S244K | 1 | 6 |
| 4978 wildtype | 2 | 100 |
| T243N | 2 | 266 |
| F200M | 2 | 51 |
| F200Y | 2 | 79 |
| F200M/T243N | 2 | 185 |
| S244K | 2 | 6 |
| 4978 wildtype | 14 | 100 |
| T243N | 14 | 254 |
| F200M | 14 | 56 |
| F200Y | 14 | 80 |
| F200M/T243N | 14 | 168 |
| S244K | 14 | 8 |

The T243N was the best mutant of all tested for activity in the production of R,R monatin.

Example 27

Stabilization of the T243N Mutant of the D-aminotransferase from Strain ATCC 4978

As shown in Example 25, the initial activity of the T243N mutant DAT is significantly higher than the *B. sphaericus* DAT, but activity decreases more rapidly. Additional experiments, using the anaerobic protocol described below, indicated that the initial activity of the T243N mutant DAT was up to 8-fold higher than the *B. sphaericus* DAT, however the activity decreased rapidly even under the anaerobic conditions. The following studies were done to try to maintain the higher activity for an extended period of time.

The T243N mutant of the D-aminotransferase from strain 4978 (described in Example 25) and the *S. meliloti* HMG aldolase were purified as the HIS$_6$-tagged proteins as described below. The SEQ ID NO:276 aldolase was purified as described in Example 23.

Purification of the DAT from ATCC 4978 (T243N Mutant)

The T243N mutant of the D-aminotransferase from ATCC strain 4978 with an amino-terminal $HIS_6$-purification tag (described in Example 26) was produced using the EMD Biosciences Overnight Express System II (solutions 1-6) (Novagen, Madison, Wis.) containing 50 µg/mL kanamycin in shake flasks. This expression system induces the expression of IPTG-inducible systems without the need to monitor cell growth. After inoculation of 200-mL aliquots of the medium (in 1 L flasks) from either liquid cultures or plates of the E. coli BL21(DE3) host carrying the gene for the T243N mutant D-aminotransferase from ATCC strain 4978 on the plasmid pET28b, the cultures were incubated at 30° C. overnight with shaking at 225 rpm. When the OD600 had reached a minimum of 6, the cells were harvested by centrifugation and washed once with buffer.

Cell free extract was prepared using EMD Biosciences BugBuster® (primary amine-free) Extraction Reagent (Novagen, Madison, Wis.) containing 1 µL/mL Benzonase® Nuclease (Novagen, Madison, Wis.), 5 µL/mL Protease Inhibitor Cocktail Set II (Calbiochem—Novabiochem Corp., San Diego, Calif.), and 0.033 µL/mL rLysozyme™ (Novagen, Madison, Wis.) following the manufacturer's protocol. All subsequent purification steps were carried out at 4° C. The cell extract was centrifuged for 20-30 minutes at 15,000×g to remove the cell debris. A 20-25 mL aliquot of the cell free extract was applied to a 45 mL column of GE Healthcare Chelating Sepharose™ Fast Flow resin (nickel (II) form) (GE Healthcare, Piscataway, N.J.) that had been previously equilibrated with 100 mM potassium phosphate containing 200 mM sodium chloride and 50 µM PLP. To generate the nickel form of the resin, the resin was washed with 150 mL of 200 mM nickel (II) sulfate hexahydrate and then with 150 mL of distilled water. After loading the sample, the column was washed/eluted with 150 mL of the equilibration buffer containing 25 mM imidazole, 150 mL of the equilibration buffer containing 50 mM imidazole and 150 mL of the equilibration buffer containing 500 mM imidazole. The $HIS_6$-tagged protein eluted in the last wash. The 500 mM imidazole wash was concentrated with Millipore/Amicon Centricon Plus-70 centrifugal filter devices (MWCO 10 kDa) (Millipore, Billerica, Mass.) to 15-20 mL according to the manufacturer's instructions. The imidazole and sodium chloride were removed by passage through disposable GE Healthcare PD10 columns (GE Healthcare, Piscataway, N.J.) (2.5 mL sample per column) previously equilibrated with 100 mM potassium phosphate, pH 7.8 containing 0.5 µM PLP. The purified aminotransferase was eluted with 3.5 mL per column of the same buffer. The protein concentration of each fraction was determined using the Pierce BCA assay kit (Pierce, Rockford, Ill.) with BSA as the protein standard.

The purity of each fraction and the level of expression in the cell free extract fraction were determined using a Bio-Rad Experion microcapillary chip system (Bio-Rad, Hercules, Calif.) or using Bio-Rad 4-15% SDS-polyacrylamide gradient gels (Bio-Rad, Hercules, Calif.) run in a Mini PROTEAN® 3 cell apparatus. The protein was visualized in the polyacrylamide gels using Bio-Rad Bio-Safe G-250 Coomassie stain (Bio-Rad, Hercules, Calif.) and destained with water. Typically this procedure produces ~20 mg of enzyme from 200 mL of overnight culture that is 85-90% pure as judged by the Experion software or from analysis of the SDS-PAGE gels. Aliquots (1-5 mL) of the purified enzyme were stored at −80° C. until use.

The purification of the SEQ ID NO:276 aldolase is as described in Example 23.

Purification of the S. meliloti HMG Aldolase

The S. meliloti HMG aldolase with an amino-terminal $HIS_6$-purification tag (cloning described in U.S. Published Application No. 20040063175 and WO 03091396 A2) was produced by induction of cultures grown in Luria-Bertani broth containing 50 mg/L kanamycin with 0.2 mM IPTG. After inoculation of 800-mL aliquots of the medium from either liquid cultures or plates of the E. coli BL21(DE3) host carrying the gene for the S. meliloti HMG aldolase in pET30 (Xa/LIC), the cultures were incubated at 37° C. with shaking at 225 rpm. When the optical density reached an $OD_{600\ nm}$ of 0.5-0.75, the IPTG was added and the cultures were incubated 30° C. with shaking at 225 rpm for 4 hours. The cells were harvested by centrifugation and washed once with buffer.

To prepare cell free extract containing the S. meliloti aldolase, the cells were suspended in 3-4 volumes of 50 mM EPPS(N-(2-hydroxyethyl)piperazine-N'-(3-propanesulfonic acid), pH 8.2 containing 100 mM NaCl and then disrupted using a Microfluidics homogenizer (Microfluidics, Newton, Mass.) (3 passes at 18,000 psi), maintaining the temperature of the suspension at less than 15° C. The cell suspension was centrifuged for 20-30 minutes at 15,000-20,000×g to remove the cell debris. The $HIS_6$-tagged protein was purified using EMD Biosciences HIS-Bind® columns (Novagen, Madison, Wis.) following the manufacturer's recommended protocol with one exception: the columns were washed with a 1:1 solution of Binding buffer:Wash buffer instead of the Wash buffer alone. The elution fraction was concentrated with Millipore/Amicon 15 mL centrifugal filter devices (MWCO 5 kDa) (Millipore, Billerica, Mass.) to 7-10 mL according to the manufacturer's instructions. The imidazole and sodium chloride were removed by passage through disposable GE Healthcare PD10 columns (GE Healthcare, Piscataway, N.J.) (2.5 mL sample per column) previously equilibrated with 50 mM EPPS, pH 8.2 containing 100 mM NaCl. The purified aldolase was eluted with 3.5 mL per column of the same buffer. The protein concentration of each fraction was determined using the Pierce BCA assay kit (Pierce, Rockford, Ill.) using BSA as the protein standard.

The purity of each fraction and the level of expression in the cell free extract fraction were determined using Bio-Rad 4-15% SDS-polyacrylamide gradient gels (Bio-Rad, Hercules, Calif.) run in a Mini PROTEAN® 3 cell apparatus. The protein was visualized in the polyacrylamide gels using Bio-Rad Bio-Safe G-250 Coomassie stain (Bio-Rad, Hercules, Calif.) and destained with water. Typically, this procedure produces ~15-20 mg of enzyme from 800 mL of culture and is 85-95% pure. Aliquots (1-5 mL) of the purified enzyme were stored at −80° C. until use.

Monatin Production Assays

Conical polypropylene tubes (14 mL) containing 143 mg of D-tryptophan were de-oxygenated in an anaerobic glove box overnight. Stock solutions of 1 M EPPS buffer (pH 8.2), 2 M $MgCl_2$, 2 M sodium pyruvate and 10 mM PLP were prepared in degassed water and equilibrated in an anaerobic glove box overnight. Stock solutions of 10% (v/v) Tween 80, 1% (v/v) Tween 20, 1% (v/v) Triton X-100, 100% acetone, 100% ethanol and 50% (w/v) glycerol were equilibrated in the anaerobic glove box along with 0.7 g each of trehalose, inositol, sorbitol and erythritol in 2 mL microcentrifuge tubes. Preparations of the purified enzymes were thawed on ice and used immediately in the anaerobic glove box. The stock solutions were added to the 14 mL conical tubes to give a final concentration of 100 mM EPPS, 200 mM pyruvate, 100 mM tryptophan, 1 mM $MgCl_2$, 0.05 mM PLP, 0.5 mg/mL D-aminotransferase, and 0.01 mg/mL of SEQ ID NO:276 aldolase or 0.05 mg/mL of S. meliloti HMG aldolase. The proposed enzyme stabilizing components were added at various final concentrations (Tables 38 and 39) to bring the final reaction volume to 7 mL per tube. The reactions were incubated at room temperature in the anaerobic glove box with gentle agitation for up to 24 hours. Samples were removed periodically and analyzed for monatin as described in Example 1 using the LC/MS/MS multiple reaction monitoring method. The initial rates were calculated from the samples withdrawn between 0 and 3 h after the addition of the enzyme.

TABLE 38

| Additive | Fold Improvement in Initial Rate of Monatin Formation | Fold Improvement in Final Monatin Titer (20 h) |
|---|---|---|
| None | 1.0 | 1.0 |
| 0.01% (v/v) Tween 80 | 1.3 | 1.4 |
| 0.1% (v/v) Tween 80 | 1.3 | 1.5 |
| 0.01% (v/v) Tween 20 | 1.1 | 1.5 |
| 0.01% (v/v) Triton X-100 | 1.1 | 1.2 |
| 5% (v/v) Acetone | 0.4 | 0.3 |
| 5% (v/v) Ethanol | 0.7 | 0.5 |
| 1% (w/v) Glycerol | 1.9 | 1.1 |
| 5% (w/v) Glycerol | 1.4 | 1.4 |
| 10% (w/v) Glycerol | 1.1 | 1.7 |
| 10% (w/v) Trehalose | 1.0 | 1.3 |
| 10% (w/v) Inositol | 1.3 | 1.5 |
| 10% (w/v) Sorbitol | 1.1 | 1.3 |
| 10% (w/v) Erythritol | 0.8 | 1.0 |

TABLE 39

(SEQ ID NO: 276 aldolase)

| Additive | Fold Improvement in Initial Rate of Monatin Formation | Fold Improvement in Final Monatin Titer at 22 h |
|---|---|---|
| 0.01% (v/v) Tween 80 | 1.0 | 1.0 |
| 1% (w/v) Glycerol | 1.2 | 0.9 |
| 5% (w/v) Glycerol | 1.5 | 1.5 |
| 10% (w/v) Glycerol | 1.7 | 2.1 |

The addition of 0.01%-0.1% (v/v) detergent, such as Triton X-100, Tween 20 or Tween 80, or 1%-10% (w/v) polyol, such as glycerol, trehalose, inositol or sorbitol, improved the stability of the T243N D-aminotransferase over the lifetime of the experiment.

Example 28

A: Cloning of *Pseudomonas putida* KT2440 Broad-Specificity Amino acid Racemase (BAR)

A BAR was identified in *P. putida* KT2440 using information from literature (Roise, D., Soda, K., Yagi, T., Walsch, C. T., Biochemistry 23, 5195-5201, (1984)). The active site of a BAR enzyme from *P. striata* was sequenced and reported—LTAVLKADAYGXGIGL (SEQ ID NO:375). This sequence was used to BLAST the *P. putida* KT2440 genome sequence available in NCBI. A protein with a nearly identical consensus sequence was identified. Primers were designed to clone the gene from genomic DNA obtained from the American Type Culture Collection (ATCC, Manassas, Va.)

```
(5'-AGAAGACATATGCCCTTTCGCCGTAGGG-3' (SEQ ID NO:

376 and 5'-AGAAGAGGATCCTCAGTCGACGAGTATCTTCG-3')

(SEQ ID NO: 377)).
```

PCR was conducted under standard conditions and the PCR product was purified (QIAquick PCR purification kit, Qiagen, Valencia, Calif.). The purified PCR product was digested with Nde I and BamH I. The digested PCR product was gel purified (QIAquick Gel Extraction Kit, Qiagen, Valencia, Calif.) and ligated to pET30 and pET28 that had been digested and gel purified in a similar manner. Clones with inserts were sequenced (Agencourt, Beverly, Mass.) and isolates with the correct sequence were identified (pET30 KT2440 BAR and pET28 KT2440BAR) and used in later studies.

The KT2440 BAR DNA sequence is:

```
(SEQ ID NO: 378)
atgcccttcgccgtacccttctggctgcatccctggcacttctgatcac cggacaggccccctgtatgcggcaccaccgttgtcgatggacaacggca ccaacaccctgaccgtgcaaaacagcaatgcctgggtcgaagtcagcgcc agcgccctgcagcacaacatccgcacgctgcaggccgagctggccggcaa gtccaagctgtgcgccgtgctcaaggccgatgcctatggccacggtatcg gcctggtaatgccatcgatcatcgcccaaggcgtgccctgcgtggcggtg gccagcaacgaggagggcccgcgtggtccgcgccagtggcttcaccgggca actggtgcgggtacgcctggccagcctcagcgagctggaagatggcttgc agtacgacatggaagagctggtgggcagcgcggaatttgcccgccaggcc gatgccatcgccgcgccatggcaagaccttgcgcattcacatggcgct caactccagcggcatgagccgcaacggggtggagatggccacctggtccg gccgtggcgaagcgctgcagatcaccgaccagaagcacctcaagctggtc gcgctgatgacccacttcgccgtggaagacaaggacgatgtacgcaaggg cctggcggcattcaacgagcagaccgactggttgatcaagcacgccaggc tggaccgcagcaagctcaccctgcacgccgccaactcgttcgctacgctg gaagtgccggaagcgcgcctggacatggtacgaacgggtggcgcgctgtt cggcgacaccgtgccggcgcgcaccgagtacaaacgtgcgatgcagttca aatcgcacgtggcggcggtgcacagctatccggccggcaacaccgtgggc tatgaccgcaccttcaccctggcccgtgattcgcggctggccaacattac ggtcgggtactccgatggctaccgccgggtattcaccaacaagggccatg tgctgatcaacggccaccgtgtgccggtcgtgggcaaggtgtcgatgaac acgctgatggtcgatgtcaccgacttccctgatgtgaaggggggtaacga agtggtgctgttcggcaagcaggccggggggcgaaatcacccaggccgaga tggaagaaatcaacggcgcgttgctcgccgatttgtacaccgtatggggc aattccaacccgaagatactcgtcgactga.
```

The KT2440 BAR amino acid sequence is:

```
(SEQ ID NO: 379)
Mpfrrtllaaslallitgqaplyaapplsmdngtntltvqnsnawvevsa salqhnirtlqaelagksklcavlkadayghgiglvmpsiiaqgvpcvav asneearvvrasgftgqlvrvrlaslseledglqydmeelvgsaefarqa daiaarhgktlrihmalnssgmsrngvematwsgrgealqitdqkhlklv almthfavedkddvrkglaafneqtdwlikharldrskltlhaansfatl evpearldmvrtggalfgdtvparteykramqfkshvaavhsypagntvg ydrtftlardsrlanitvgysdgyrrvftnkghvlinghrvpvvgkvsmn tlmvdvtdfpdvkggnevvlfgkqaggeitqaemeeingalladlytvwg nsnpkilvd
```

B) Purification of *P. putida* KT2440 BAR.

The pET30 KT2440 BAR plasmid described above was transformed into BL21 DE3 pLysS (Invitrogen, Carlsbad, Calif.). The resulting strain was grown in LB or Terrific Broth at 37° C. with aeration to an $OD_{600\,nm}$ of 0.4-0.6 and induced with 1 mM IPTG. Incubation was continued 3-4 hours at 37° C. with aeration. The cells were harvested by centrifugation and the cell pellet was stored at −80° C. until use. The cell pellet was thawed on ice. The cells were lysed with Bug-Buster (Novagen, Madison, Wis.) and Benzonase (Novagen, Madison, Wis.). Cell debris was removed by centrifugation and the cell free extract was either used immediately or stored at −80° C. The KT2440 BAR gene was also cloned into the NdeI-BamHI sites of pET28 and transformed into BL21 DE3 pLysS. This construct did not appear to express soluble protein very efficiently so the untagged version (pET30 KT2440 BAR) was used in future studies.

The extract was applied to an UnoQ column (Bio-Rad, Hercules, Calif.) that had been equilibrated with at least 5 column volumes buffer A (25 mM potassium phosphate pH 8.0, 10 μM pyridoxal-5'-phosphate (PLP)). The column was washed with 2 column volumes of buffer A. The protein was eluted with a linear gradient of buffer B (buffer A+1 M NaCl) from 0-100% buffer B over 20 column volumes and 5 ml fractions were collected from the time the gradient started. Fractions were assayed using the Amplex Red method described in Example 4-part 7. Briefly, 100 μg D-amino acid oxidase (Sigma-Aldrich, St. Louis, Mo.), 0.05 mM FAD, 25 mM L-trp, and a small volume of the fraction to be assayed were combined in 50 μL $H_2O$ and added to 50 μL Amplex Red reaction buffer prepared as directed in the manufacturer's protocol. Fractions with activity were desalted with a PD-10 column (GE Healthcare, Piscataway, N.J.) and concentrated with Amicon centrifugal concentrators (Millipore, Billercia, Mass.). Purified protein was stored at −80° C.

C) Production and Assay of an Alanine Racemase Mutant Y354A of *Geobacillus stearothermophilus* with Tryptophan Racemase Activity The wild-type *Geobacillus stearothermophilus* alanine racemase (SEQ ID NO:380, shown below was cloned into pET30 was used as a template for site-directed mutagenesis to make the Y354A change. The gene of SEQ ID NO:380 can be amplified by standard PCR protocols and cloned using standard recombinant DNA techniques. The gene of SEQ ID NO:380 can also be reconstructed by any method known to a person of ordinary skill in the art, such as assembly PCR methods known to one skilled in the art.

The wild-type *Geobacillus stearothermophilus* alanine racemase DNA and amino acid sequences is shown below as SEQ ID NO:380:

```
                                                       (SEQ ID NO: 380)
          atggacgagt ttcaccgcga tacgtgggcg gaagtggatt tggacgccat ttacgacaat gtggagaatt tgcgccgttt gctgccggac gacacgcaca ttatggcggt cgtgaaggcg aacgcctatg gacatgggga tgtgcaggtg gcaaggacag cgctcgaagc gggggcctcc cgcctggcgg ttgccttttt ggatgaggcg ctcgctttaa gggaaaaagg aatcgaagcg ccgattctag ttctcggggc ttcccgtcca gctgatgcgg cgctggccgc ccagcagcgc attgccctga ccgtgttccg ctccgactgg ttggaagaag cgtccgccct ttacagcggc ccttttccta ttcatttcca tttgaaaatg gacaccggca tgggacggct tggagtgaaa gacgaggaag agacgaaacg aatcgtagcg ctgattgagc gccatccgca ttttgtgctt gaagggtgt acacgcattt tgcgactgcg gatgaggtga acaccgatta tttttcctat cagtataccc gttttttgca catgctcgaa tggctgccgt cgcgcccgcc gctcgtccat tgcgccaaca gcgcagcgtc gctccgtttc cctgaccgga cgttcaatat ggtccgcttc ggcattgcca tgtatgggct tgccccgtcg cccggcatca agccgctgct gccgtatcca ttaaaagaag cattttcgct ccatagccgc ctcgtacacg tcaaaaaact gcaaccaggc gaaaaggtga gctatggtgc gacgtacact gcgcagacgg aggagtggat cgggacgatt ccgatcggct atgcggacgg ctggctccgc cgcctgcagc actttcatgt ccttgttgac ggacaaaagg cgccgattgt cggccgcatt tgcatggacc agtgcatgat ccgcctgcct ggtccgctgc cggtcggcac gaaggtgaca ctgattggtc gccaagggga cgaggtaatt tccattgatg atgtcgctcg ccatttggaa acgatcaact acgaagtgcc ttgcacgatc agttatcgag tgccccgtat ttttttccgc cataagcgta taatggaagt gagaaacgcc gttggccgcg ga.
```

The encoded amino acid sequence of the Alanine Racemase (*Geobacillus stearothermophilus*) is shown below as SEQ ID NO:381:

```
                                                       (SEQ ID NO: 381)
          Met Asp Glu Phe His Arg Asp Thr Trp Ala Glu Val Asp Leu Asp Ala Ile Tyr Asp

Asn Val Glu Asn Leu Arg Arg Leu Leu Pro Asp Asp Thr His Ile Met Ala Val Val
```

-continued

Lys Ala Asn Ala Tyr Gly His Gly Asp Val Gln Val Ala Arg Thr Ala Leu Glu Ala

Gly Ala Ser Arg Leu Ala Val Ala Phe Leu Asp Glu Ala Leu Ala Leu Arg Glu Lys

Gly Ile Glu Ala Pro Ile Leu Val Leu Gly Ala Ser Arg Pro Ala Asp Ala Ala Leu

Ala Ala Gln Gln Arg Ile Ala Leu Thr Val Phe Arg Ser Asp Trp Leu Glu Glu Ala

Ser Ala Leu Tyr Ser Gly Pro Phe Pro Ile His Phe His Leu Lys Met Asp Thr Gly

Met Gly Arg Leu Gly Val Lys Asp Glu Glu Thr Lys Arg Ile Val Ala Leu Ile

Glu Arg His Pro His Phe Val Leu Glu Gly Val Tyr Thr His Phe Ala Thr Ala Asp

Glu Val Asn Thr Asp Tyr Phe Ser Tyr Gln Tyr Thr Arg Phe Leu His Met Leu Glu

Trp Leu Pro Ser Arg Pro Pro Leu Val His Cys Ala Asn Ser Ala Ala Ser Leu Arg

Phe Pro Asp Arg Thr Phe Asn Met Val Arg Phe Gly Ile Ala Met Tyr Gly Leu Ala

Pro Ser Pro Gly Ile Lys Pro Leu Leu Pro Tyr Pro Leu Lys Glu Ala Phe Ser Leu

His Ser Arg Leu Val His Val Lys Lys Leu Gln Pro Gly Glu Lys Val Ser Tyr Gly

Ala Thr Tyr Thr Ala Gln Thr Glu Glu Trp Ile Gly Thr Ile Pro Ile Gly Tyr Ala Asp

Gly Trp Leu Arg Arg Leu Gln His Phe His Val Leu Val Asp Gly Gln Lys Ala Pro

Ile Val Gly Arg Ile Cys Met Asp Gln Cys Met Ile Arg Leu Pro Gly Pro Leu Pro

Val Gly Thr Lys Val Thr Leu Ile Gly Arg Gln Gly Asp Glu Val Ile Ser Ile Asp

Asp Val Ala Arg His Leu Glu Thr Ile Asn Tyr Glu Val Pro Cys Thr Ile Ser Tyr

Arg Val Pro Arg Ile Phe Phe Arg His Lys Arg Ile Met Glu Val Arg Asn Ala Val

Gly Arg Gly

The mutagenesis was performed using the QuickChange-Multi site-directed mutagenesis kit (Stratagene, La Jolla, Calif.). The following mutagenic primer was used to make the Y354A change, 5'-gccatttggaaacgatcaacgcggaagt-gccttgcacgatcag-3' (SEQ ID NO:382). The site-directed mutagenesis was done as described in the manufacturer's protocol. Several isolates were sequenced (Agencourt, Beverly, Mass.) and an isolate with the correct sequence was selected and used for further analysis.

The pET30Y354A single mutant was transformed into *E. coli* BL21(DE3)pLysS. Purified protein was prepared in the following manner. The strain was grown in LB or Terrific Broth (at 37° C. with aeration) to an OD$_{600\,nm}$ of 0.4-0.6 and induced with 1 mM IPTG. Incubation was continued at 37° C. with aeration for ~3 hours. The cells were harvested by centrifugation and the cell pellet was stored at −80° C.

The cell pellet was thawed on ice and then re-suspended in an appropriate volume of BugBuster (Novagen, Madison, Wis.) plus Benzonase nuclease (Novagen, Madison, Wis.). Cell debris was removed by centrifugation, and the cell-free extract was applied to a HIS-Bind column (Novagen, Madison, Wis.) that had been equilibrated with Binding buffer. The column was washed with Binding buffer and Wash buffer and the protein was eluted with Elution buffer (as directed in the manufacturer's protocol). The purified protein was desalted using a PD-10 column (GE Healthcare, Piscataway, N.J.). The protein was desalted into 50 mM potassium phosphate pH 8.0 and 10 μM pyridoxal-5'-phosphate according to the manufacturer's protocol. The protein was concentrated using an Amicon centrifugal concentrator (Millipore, Billercia, Mass.). The purified and concentrated protein was divided into small aliquots and stored at −80° C. until use.

The purified Y354A was compared to wild-type alanine racemase (prepared in the manner described above) in both alanine and tryptophan assays. Assays were performed at 37° C. in 50 mM potassium phosphate buffer, pH 8, and 10 μM PLP using 400 μL of concentrated purified protein (>1 mg/ml) and 50 mM substrate. Detection of D-alanine and D-tryptophan was performed using the chiral amino acid methodology described in Example 1.

TABLE 40

| Enzyme | Substrate | Time | D isomer produced (ppm) |
|---|---|---|---|
| Wild-type | L-tryptophan | 0 | nd* |
|  |  | 10 | nd |
|  |  | 30 | nd |
|  |  | 60 | nd |
|  |  | 1080 | nd |
| Y354A |  | 0 | nd |
|  |  | 10 | 198 |
|  |  | 30 | 568 |
|  |  | 60 | 1386 |
|  |  | 1080 | 10080 |
| Wild-type | L-alanine | 0 | 5140 |
|  |  | 10 | 5960 |
|  |  | 30 | 6280 |
|  |  | 60 | 6500 |
|  |  | 1080 | 5040 |
| Y354A |  | 0 | 4760 |
|  |  | 10 | 4980 |
|  |  | 30 | 4980 |
|  |  | 60 | 4200 |
|  |  | 1080 | 5000 |

*nd = none detected

These data were analyzed without the use of an internal standard; thus, these data are semi-quantitative and should be used for comparative purposes. Nonetheless, these results show that the Y354A single mutation is sufficient to broaden the specificity of the alanine racemase so that it can catalyze amino acid racemization using alternative substrates.

D) Assay of the BAR Enzyme.

The Bar enzyme was assayed as follows. Amplex Red assays were set up as described in this example. *P. putida* KT2440 BAR was used at 200 µg (purified as described in this example). Wildtype *G. stearothermophilus* alanine racemase and the Y354A were purified as described in this example and used at either 200 µg/mL or 1000 µg/mL. CE is cell-free extract that was prepared as described in this example. The results for the 60 minute time point are shown in the Table 41 below.

TABLE 41

| Enzyme | Fluorometer reading (at 60 minutes) |
|---|---|
| BAR (200) | 56943 |
| Y354A (200) | 7860 |
| Y354A (1000) | 13587 |
| WT alanine racemase (200) | 3646 |
| WT alanine racemase (1000) | 3639 |
| BAR CE (5 µl) | 16228 |
| BAR CE (10 µl) | 26662 |
| BAR CE (50 µl) | >58000 |
| No Enzyme | 1510 |

The purified protein was also assayed for tryptophan racemase activity in 50 mM potassium phosphate pH 8, 10 µM PLP, and 30 mM L-tryptophan as described above. Either 200 µg/mL or 1000 µg/mL of purified enzyme was used in the assays (indicated in parentheses). D-tryptophan was analyzed using the chiral amino acid method described in Example 1 for detection.

TABLE 42

| Enzyme | Time | D-tryptophan (ppm) |
|---|---|---|
| BAR (200) | 0 | 0 |
|  | 5 | 172 |
|  | 10 | 410 |
|  | 20 | 844 |
|  | 30 | 1318 |
|  | 60 | 2362 |
|  | 120 | 2594 |
|  | 240 | 2762 |
|  | 1080 | 2294 |
| Y354A (200) | 0 | 0 |
|  | 5 | 0 |
|  | 10 | 0 |
|  | 20 | 0 |
|  | 30 | 12 |
|  | 60 | 22 |
|  | 120 | 44 |
|  | 240 | 56 |
|  | 1080 | 368 |
| Y354A (1000) | 0 | 0 |
|  | 5 | 0 |
|  | 10 | 12 |
|  | 20 | 18 |
|  | 30 | 40 |
|  | 60 | 80 |
|  | 120 | 146 |
|  | 240 | 218 |
|  | 1080 | 1164 |

The assay indicate that the *P. putida* KT2440 BAR enzyme is much more active on tryptophan than the *G. stearothermophilus* derived enzyme and the Y354A mutant thereof.

E) Monatin Production with *P. putida* KT2440 BAR.

A monatin production assay was done with the purified *P. putida* KT2440 BAR (as purified above) (100 µg) or purified Y354A (as purified above) (500 µg), D-aminotransferase (BioCatalytics AT-103 (Pasadena, Calif.)) (500 µg), and the aldolase of SEQ ID NO:276) (as purified in Example 23) (50 µg). The monatin production experiment starting with L-tryptophan was done as follows. In addition to the enzymes above, the following were added per 1 mL of reaction mixture: 4 mM $MgCl_2$, 50 mM L-tryptophan, 100 mM sodium pyruvate, 100 mM potassium phosphate buffer pH 7.5, and 0.05 mM PLP.

As a control, the experiment was done as described above without racemase and starting with D-tryptophan instead of L-tryptophan. A summary of the results is presented in Table 43 below.

TABLE 43

| Substrate | Racemase | Time | Total Monatin | % R, R | % S, S | % R, S | % S, R |
|---|---|---|---|---|---|---|---|
| L-Trp | Y354A | 2 hours | None detected |  |  |  |  |
|  |  | 18 hours | None detected |  |  |  |  |
| L-trp | BAR | 2 hours | None detected |  |  |  |  |
|  |  | 18 hours | 38.6 ppm | 92.1 | 5 |  | 2.9 |
| L-trp | None | 2 hours | None detected |  |  |  |  |
|  |  | 18 hours | None detected |  |  |  |  |
| D-trp | None | 2 hours | 19.9 ppm | Not tested | Not Tested | Not tested | Not tested |
|  |  | 18 hours | 221.25 ppm | 97.8 | 0.2 |  | 2 |

No monatin was detected using Y354A in this experiment. This racemase has been used in the past (data not shown) to produce monatin, but a much higher level of enzyme was used (at least 2 mg and up to 10 mg to see higher levels of monatin). The *P. putida* KT2440 BAR was used to produce monatin from L-tryptophan. The 100 µg used in this experiment was not enough to see monatin production after two hours but was enough to see monatin production after 18 hours. The stereoisomer distribution indicated that most of the monatin produced is the R,R isomer. There was no R,S isomer produced. This result indicates that KT2440 BAR is not able to detectably racemize the R,R isomer of monatin (racemization of the R,R isomer would produce the R,S isomer). There was a significant amount of the S,S isomer produced in this experiment. This is probably due to the fact that the AT-103 used in this experiment is not highly purified and may contain L-aminotransferases from the cellular extract, and that there is a large amount of L-tryptophan present to serve as an amino donor for transamination of S-MP.

Example 29

Cloning and Expression of *Pseudomonas taetrolens* Arginine Racemase

Experimental Overview

*Pseudomonas taetrolens* (also known as *P. graveolens*) arginine racemase (Genbank Accession No. AB096176, nucleic acid sequence) and an I384M mutant thereof, was cloned, expressed, and tested for activity in conversion of L-tryptophan to D-tryptophan. This gene is 72% identical to the *P. putida* BAR gene from KT2440 and 73% identical to the *P. putida* BAR gene from NBRC 12996 described above. The amino acid sequence is 72% identical to both *P. putida* BAR proteins.

Polymerase Chain Reaction Protocol

*Pseudomonas taetrolens* (ATCC 4683) was grown in nutrient broth at 28° C. with shaking at 225 rpm. Polymerase chain reaction was performed on whole cells using primers designed with 5' restriction sites and overhangs for cloning into the pET 28 and pET30 vectors (Novagen, Madison, Wis.).

The primer sequences were:

```
                                         (SEQ ID NO: 408)
N term: 5'-ATAATACATATGCCCTTCTCCCGTACCC-3'
and (SEQ ID NO: 409)
C term: 5'-GCGGCGGGATCCTTACTGATCTTTCAGGATT-3'.
```

The gene derived from *P. taetrolens* was amplified using the following PCR protocol. Twenty-five µL of grown cells were lysed at 96° C. for 10 minutes. Cell debris was removed by centrifugation and the supernatant was used as template for PCR. A 100 µL reaction contained 5 µL template (lysed cell supernatant), 1.6 µM of each primer, 0.3 mM each dNTP, 10 U rT$^{th}$ Polymerase XL (Applied Biosystems, Foster City, Calif.), 1×XL buffer and 1 mM Mg(OAc)$_2$. The thermocycler program used included a hot start at 94° C. for 3 minutes, 8 repetitions of the following steps: 94° C. for 30 seconds, 52° C. for 30 seconds, and 68° C. for 2 minutes, followed by 22 repetitions of the following steps: 94° C. for 30 seconds, 58° C. for 30 seconds, and 68° C. for 2 minutes. After the 22 repetitions, the sample was maintained at 68° C. for 7 minutes and then stored at 4° C. This PCR protocol produced a product of 1230 bp.

Cloning

The PCR product was gel purified from 0.8% TAE-agarose gel using the Qiagen gel extraction kit (Qiagen, Valencia, Calif.). The product was TOPO cloned and transformed into TOP 10 cells according to manufacturer's protocol (Invitrogen, Carlsbad, Calif.). Plasmid DNA was purified from the resulting transformants using the Qiagen spin miniprep kit (Qiagen, Valencia, Calif.) and screened for the correct inserts by restriction digest with Nde I and BamH I. The sequences of plasmids appearing to have the correct insert were verified by dideoxy chain termination DNA sequencing with universal M13 forward and M13 Reverse primers.

The correct TOPO clone was digested with restriction enzymes Nde I and BamH I following the manufacturer's recommended protocols (New England Biolabs, Beverly, Mass.) and gel purified from 0.8% TAE-agarose gels using the Qiagen gel extraction kit (Qiagen, Valencia, Calif.). Vectors pET 28 and pET 30 were prepared by digestion with restriction enzymes Nde I and BamH I followed by treatment with shrimp alkaline phosphatase (Roche, Indianapolis, Ind.) and purification from 0.8% TAE-agarose gels using the Qiagen gel extraction kit (Qiagen, Valencia, Calif.). The digested vectors and insert were ligated using the Rapid™ DNA Ligation Kit (Roche, Indianapolis, Ind.). Approximately 50 ng of treated insert, 100 ng of treated vector (3 to 1 molar ratio of insert to vector), 5 U of T4 DNA ligase, and 1× ligation buffer were incubated for 5 minutes at room temperature. The ligation reaction was desalted using the High Pure PCR Product Purification Kit (Roche, Indianapolis, Ind.) and used to transform *E. coli* DH10B electrocompetent cells (Invitrogen, Carlsbad, Calif.). Ten µL of each ligation reaction was added to 40 µL of DH10B cells, which were transformed by electroporation using the BioRad Gene Pulsar II under the following conditions: 2.5 kV, 25 µF, 200 ohm in a 0.2 cm cuvette. The cells were allowed to recover in 1 mL of room temperature SOC for 1 hour at 37° C. with shaking at 225 rpm. Cells were plated on LB plates containing kanamycin (50 µg/mL). Plasmid DNA was purified from the resulting transformants using the Qiagen spin miniprep kit (Qiagen, Valencia, Calif.) and screened for the correct inserts by restriction digest with Nde I and BamH I.

Gene Expression and Assays

Plasmid DNA was transformed into *E. coli* expression host BL21(DE3) pLysS (Novagen, Madison, Wis.). The cultures were grown and the plasmids were isolated using the Qiagen miniprep kit (Qiagen, Valencia, Calif.) and analyzed by restriction digest to confirm identity.

Induction in BL21DE3 pLysS was initially performed in both pET 28 (histidine-tagged) and pET 30 (untagged) vectors. A time course study was performed with cultures grown at 37° C. in 100 mL LB containing kanamycin (50 mg/L) to an OD$_{600}$ of 0.5 and induced with 100 µM IPTG (isopropyl thiogalacatoside) and sampled at 0 and 3 hours post induction. Cells from 0 hour and 3 hour time points were resuspended in 1× sodium dodecyl sulfate buffer containing 2-mercaptoethanol and heated at 95° C. for 10 minutes, and cooled. Aliquots of these total cellular protein samples were analyzed by SDS-PAGE using a 4-15% gradient gel.

Cell extracts were also prepared from the 3 hour cultures by suspending cell pellets from 5 mL of culture in Novagen BugBuster™ reagent containing benzonase nuclease and protease inhibitor cocktail set #3 (Calbiochem-Novabiochem Corp., San Diego, Calif.) at room temperature for 20 minutes with gentle shaking and centrifuging at 16,000×g to remove cell debris. The supernatants (cell extracts) were loaded onto 4-15% gradient gels for analysis of the cellular soluble proteins.

The 3 hour sample from cloned *P. taetrolens* arginine racemase showed a total protein band that corresponded to the correct size (approximately 45 kDa) in the pET 30 (untagged) vector. The *P. taetrolens* pET 30 gene product was overexpressed at a higher level than the *P. taetrolens* pET 28 (histidine-tagged) gene product, but neither of the vectors gave a visible soluble protein band.

Cells from the induced cultures (100 mL) were centrifuged and washed once with 0.85% NaCl. Cell pellets were resuspended in 5 mL/g wet cell weight of BugBuster™ Novagen, Madison, Wis.) reagent containing 5 µL/mL protease inhibitor cocktail set #3 Calbiochem-Novabiochem Corp., San Diego, Calif.) and 1 µL/mL benzonase nuclease. Samples were incubated at room temperature for 20 minutes on an orbital shaker. Insoluble cell debris was removed by centrifugation at 16,000×g for 20 minutes at 4° C.

Cell extracts were assayed for tryptophan racemase activity using the following protocol. One mL reactions were carried out in 50 mM potassium phosphate (pH 8.0), 0.05 mM PLP and 30 mM L tryptophan. The reactions were initiated by the addition of cell free extracts and were incubated at 30° C. overnight. Sample aliquots were taken after overnight incubation (zero minute samples served as control reaction). Concentrated formic acid (5 µL) was added to each 250 µL sample aliquot to stop the reaction and the precipitated protein was removed by centrifugation. Supernatants were removed and frozen at −80° C. until they were analyzed for D-tryptophan by the chiral amino acid method described in Example 1.

Assay results from cell extracts from pET28 and pET30 induction with 100 µM IPTG (3 hours) demonstrate that *P. taetrolens* clones show racemase activity on L-tryptophan. Again, the tagged version of the BAR appears to be less active and may precipitate or be less soluble than the untagged (pET28). Table 44, below, shows the initial results, although not quantitative as very poor soluble protein was obtained.

TABLE 44

| Treatment | Time Point | Substrate | Racemase extract (200 µg) | D-trp conc (µg/mL) |
|---|---|---|---|---|
| pET28/*P. taetrolens* | 0 | L-trp | 500 µL | nd |
| pET30/*P. taetrolens* | 0 | L-trp | 500 µL | nd |
| pET28/*P. taetrolens* | overnight | L-trp | 500 µL | 140 |
| pET30/*P. taetrolens* | overnight | L-trp | 500 µL | 226 |

Induction of the pET30 (untagged) construct was repeated using same conditions as mentioned above and a visible soluble protein band was observed in SDS-PAGE. The assay was repeated using same the conditions described above and the results, as shown in Table 45 below, were obtained.

TABLE 45

| Treatment | Time Point | Substrate | Racemase extract (µL) | D-trp conc (µg/mL) |
|---|---|---|---|---|
| *P. taetrolens*-pET30 | 0 | L-trp | 300 | Nd |
| *P. taetrolens*-pET30 | 0 | L-trp | 150 | Nd |
| *P. taetrolens*-pET30 | 2 hr | L-trp | 300 | 319 |
| *P. taetrolens*-pET30 | 2 hr | L-trp | 150 | 308 |
| *P. taetrolens*-pET30 | Overnight | L-trp | 300 | 1586 |
| *P. taetrolens*-pET30 | Overnight | L-trp | 150 | 1658 |

Again, it was noted that doubling of the volumes did not scale to more activity. For future work, it was determined to remove the protein from Bugbuster as quickly as possible after preparation of cell extracts and to store the protein in 50 mM phosphate buffer pH 8 containing 0.01 mM PLP. The detergent in Bugbuster may inhibit the reaction or may cause a loss of activity upon storage.

Induction of the pET30 construct was carried out again and the cell extract was processed with anion exchange chromatography (as in Example 28) to give a more pure extract. The assay was repeated with this partially purified prep. The numbers in parenthesis in the Racemase extract column of Table 46 below indicate the approximate amount of partially purified racemase enzyme used in the assay. The results of the assay are shown in Table 46 below.

TABLE 46

| Enzyme Source | Time Point | Substrate | Racemase extract | D-trp conc (µg/mL) |
|---|---|---|---|---|
| KT2440 | 0 | L-trp | 75 µL (90 µg) | nd |
| NBRC 12996 | 0 | L-trp | 42 µL (200 µg) | nd |
| NBRC 12996 | 0 | L-trp | 21 µL (100 µg) | nd |
| *P. taetrolens* | 0 | L-trp | 108 µL (200 µg) | nd |
| *P. taetrolens* | 0 | L-trp | 54 µL (100 µg) | nd |
| KT2440 | 2 hr | L-trp | 75 µL (90 µg) | 661 |
| NBRC 12996 | 2 hr | L-trp | 42 µL (200 µg) | 408 |
| NBRC 12996 | 2 hr | L-trp | 21 µL (100 µg) | 208 |
| *P. taetrolens* | 2 hr | L-trp | 108 µL (200 µg) | 862 |
| *P. taetrolens* | 2 hr | L-trp | 54 µL (100 µg) | 547 |
| KT2440 | overnight | L-trp | 75 µL (90 µg) | 2386 |
| NBRC 12996 | overnight | L-trp | 42 µL (200 µg) | 2382 |
| NBRC 12996 | overnight | L-trp | 21 µL (100 µg) | 1706 |
| *P. taetrolens* | overnight | L-trp | 108 µL (200 µg) | 2029 |
| *P. taetrolens* | overnight | L-trp | 54 µL (100 µg) | 2099 |

The non-linearity of the overnight sample in this case is probably due to the fact that the reactions are reaching equilibrium. Clearly, the *P. taetrolens* BAR has significant activity for racemization of tryptophan, as do the 12996 BAR and KT2440 BAR. It appears that the KT2440 BAR and the *P. taetrolens* BAR have similar activity, which is slightly higher than the 12996 BAR.

The DNA Sequence of the *P. taetrolens* arginine racemase is shown below as SEQ ID NO:410. The PCR sequence gave two changes as compared with the published NCBI sequence. Specifically, the PCR sequence contained an adenosine rather than a guanine at position 902 and a cytosine rather than a guanine at position 921. These DNA changes resulted in one silent mutation as well as one change from glycine to aspartate at amino acid position 301.

```
                                       (SEQ ID NO: 410)
ATGCCCTTCTCCCGTACCCTGCTCGCCCTTTCCCTTGGCAT

GGCATTGCTGCAAAACCCGGCCTTTGCTGCGCCACCCCTG

TCGATGACCGACGGCGTAGCTCAAGTGAATACCCAGGAC

AGCAATGCCTGGGTCGAAATCAATAAAGCCGCGTTCGAG

CACAACATACGGACTCTGCAAACCGCCCTCGCCGGCAAG

TCGCAGATCTGCGCCGTACTCAAGGCGGATGCCTATGGC

CACGGTATCGGCTTGTTGATGCCCTCGGTGATCGCCATGG

GTGTTCCCTGTGTCGGTGTCGCCAGCAACGAAGAAGCCC

GCGTCGTGCGCGAGAGCGGTTTCAAGGGTCAACTGATAC

GCGTGCGCACCGCTGCCCTGAGCGAACTGGAAGCTGCAC

TGCCGTACAACATGGAAGAGCTGGTGGGCAACCTGGACT

TCGCGGTCAAGGCCAGCCTGATTGCCGAGGATCACGGTC
```

-continued
```
GCCCGCTGGTGGTGCACCTGGGTCTGAATTCCAGCGGCA

TGAGCCGTAACGGAGTGGACATGACCACCGCTCAGGGCC

GTCGTGATGCGGTAGCTATCACCAAGGTGCCAAACCTGG

AAGTGCGGGCGATCATGACCCACTTCGCGGTCGAAGATG

CTGCCGACGTGCGTGCCGGGCTCAAGGCCTTCAATCAGC

AAGCCCAATGGCTGATGAACGTGGCCCAGCTTGATCGCA

GCAAGATCACCCTGCACGCGGCCAACTCGTTCGCCACAC

TGGAGGTGCCCGAATCGCATCTGGACATGGTCCGCCCCG

GCGGCGCGCTGTTCGGCGACACCGTACCGTCCCACACCG

AGTACAAGCGGGTCATGCAGTTCAAGTCCCACGTGGCGT

CGGTCAACAGCTACCCCAAGGGCAACACCGTCGGTTATG

ACCGCACGTACACCCTGGGCCGCGACTCGCGGCTGGCCA

ACATCACCGTCGGCTACTCTGACGGCTACCGCCGCGCGTT

TACCAATAAAGGGATTGTGCTGATCAACGGCCATCGCGT

GCCAGTGGTGGGCAAAGTCTCGATGAACACCCTGATGGT

GGACGTCACTGACGCGCCGGATGTGAAAAGCGGCGATGA

AGTGGTGCTGTTCGGGCACCAGGGCAAGGCCGAGATTAC

CCAGGCTGAGATCGAAGACATCAACGGTGCACTGCTTGC

GGATCTGTATACCGTGTGGGGCAATTCCAACCCTAAAAT

CCTGAAAGATCAGTAA.
```

The protein encoded by the gene of SEQ ID NO:410 was analyzed by the signal peptide prediction program Signal P 3.0 (www.cbs.dtu.dk/services/SignalP/) and a leader sequence of 23 amino acids was predicted.

I384M Mutagenesis of *P. taetrolens* BAR

Mutagenesis was done using the QuickChange-Multi site-directed mutagenesis kit (Stratagene, La Jolla, Calif.), using the *P. taetrolens* BAR gene in pET30 which results in an untagged protein. The following mutagenic primer was used to make the I384M change: 5'-TACCCAGGCTGAGATGGAAGACATCAACG-3' (SEQ ID NO:411).

The site-directed mutagenesis was done as described in the manufacturer's protocol. Several isolates were sequenced (Agencourt, Beverly, Mass.) and an isolate with the correct sequence was selected and used for further analysis.

The plasmid was transformed into BL21 (DE3) cells (Novagen, Madison, Wis.). Recombinant protein was produced in Overnight Express II medium (Novagen, Madison, Wis.) containing 50 µg/mL kanamycin according to manufacturer's protocols. Cell-free extracts were prepared using BugBuster (Novagen, Madison, Wis.) according to manufacturer's protocols, desalted, and analyzed for percent expression of the target protein using the Experion method described above.

Total protein assays were done using a Pierce BCA kit (Pierce, Rockford, Ill.). Tryptophan racemase assays with the mutant enzyme were performed using the wild-type enzyme prepared in the same manner as a positive control. Assays contained per mL: 30 mM L-tryptophan, 50 mM potassium phosphate pH 8, 10 µM PLP, and approximately 100 µg of racemase protein in a cell free extract. In the case where 100 µg was not used (based on Experion % expression and Pierce total protein numbers), the results were normalized. Zero, 30 minute, 2 hour, and overnight samples were collected, treated with 2% formic acid, filtered, and diluted 1:10 for analysis using the chiral amino acid method described in Example 1.

The wild-type enzyme appeared to produce 49.1 ppm D-tryptophan in 30 minutes, whereas the I384M mutant produced 108 ppm. The 2 hour time point was similar—229.4 ppm D-tryptophan was produced by the wild-type enzyme versus 541.7 for the I384M mutant. The I384M mutation appears to have approximately doubled the activity of the *P. taetrolens* BAR. The overnight time point for the mutant is also higher, but as the reactions approach equilibrium the difference between activities is reduced. When assays were done for monatin production as in Example 28, the I384M did not appear to provide any benefit over the wild-type *P. taetrolens* enzyme.

Example 30

*A. caviae* Extract Assay

*Aeromonas caviae* ATCC 14486 was grown in nutrient broth at 37° C. Cells from the culture (200 mL) were centrifuged and washed once with 0.85% NaCl. Cell pellets were resuspended in 5 mL/g wet cell weight of BugBuster™ (Novagen, Madison, Wis.) reagent containing 5 µL/mL protease inhibitor cocktail set #3 (Calbiochem-Novabiochem Corp., San Diego, Calif.) and 1 µL/mL benzonase nuclease. Samples were incubated at room temperature for 20 minutes on an orbital shaker. Insoluble cell debris was removed by centrifugation at 16,000×g for 20 minutes at 4° C. Cell-free extract was desalted on a PD-10 column (GE Healthcare, Piscataway, N.J.).

Cell-free extract was assayed for tryptophan racemase activity using the following protocol. One mL reactions were carried out in 50 mM potassium phosphate (pH 8.0), 0.05 mM PLP and 30 mM L tryptophan. The reactions were initiated by the addition of cell free extract (either 100 µL or 500 µL) and were incubated at 30° C. overnight. Sample aliquots were taken at 2 hours and after overnight incubation (zero minute samples served as control reactions). Concentrated formic acid (5 µL) was added to each 250 µL sample aliquot to stop the reaction and the precipitated protein was removed by centrifugation. Supernatants were removed and frozen at −80° C. until they were analyzed for D-tryptophan by the chiral amino acid method described in Example 1.

The assay results from cell extracts of *A. caviae* demonstrated racemase activity on L-tryptophan, as shown in Table 47.

TABLE 47

| Treatment | Time Point | substrate | Racemase extract | D-trp conc (µg/mL) |
|---|---|---|---|---|
| A. caviae | 0 | L-trp | 100 µL | nd |
| A. caviae | 0 | L-trp | 500 µL | nd |
| A. caviae | 2 hr | L-trp | 100 µL | 2 |
| A. caviae | 2 hr | L-trp | 500 µL | 19 |
| A. caviae | overnight | L-trp | 100 µL | 45 |
| A. caviae | overnight | L-trp | 500 µL | 130 |

After finding activity in the *A. caviae* cell extracts, degenerate primers were designed (based on conserved regions of known BAR homologs) to obtain the BAR gene from this species. Degenerate primer sequences are shown below:

```
                                           (SEQ ID NO: 412)
Aer deg F2: 5'-GCCAGCAACGARGARGCMCGCGT-3';
and (SEQ ID NO: 413)
Aer deg R1: 5'-TGGCCSTKGATCAGCACA-3'
``` wherein K indicates G or T, R indicates A or G, S indicates C or G, and M indicates A or C.

The above primers were used to PCR amplify a 715 bp DNA fragment from *A. caviae* (ATCC 14486) genomic DNA. The following PCR protocol was used: A 50 μL reaction contained 0.5 μL template (~100 ng of *A. caviae* genomic DNA), 1.6 μM of each primer, 0.3 mM each dNTP, 10 U rT$^{th}$ Polymerase XL (Applied Biosystems, Foster City, Calif.), 1× XL buffer, 1 mM Mg(OAc)$_2$ and 2.5 μL dimethyl sulfoxide. The thermocycler program used included a hot start at 94° C. for 3 minutes and 30 repetitions of the following steps: 94° C. for 30 seconds, 53° C. for 30 seconds, and 68° C. for 2 minutes. After the 30 repetitions, the sample was maintained at 68° C. for 7 minutes and then stored at 4° C. This PCR protocol produced a product of 715 bp.

Cloning

The PCR product was gel purified from 0.8% TAE-agarose gel using the Qiagen gel extraction kit (Qiagen, Valencia, Calif.). The product was TOPO cloned and transformed into TOP 10 cells according to manufacturer's protocol (Invitrogen, Carlsbad, Calif.). The plasmid DNA was purified from the resulting transformants using the Qiagen spin miniprep kit (Qiagen, Valencia, Calif.) and screened for the correct inserts by restriction digest with EcoR 1. The sequences of plasmids appearing to have the correct insert were verified by dideoxy chain termination DNA sequencing with universal M13 forward primers.

The DNA sequence of the *A. caviae* PCR product is shown below as SEQ ID NO:414), with degenerate primer sequence regions underlined:

```
                                          (SEQ ID NO: 414)
GCCAGCAACGARGARGCMCGCGTTGCCCGCGAGAAGGGCTTCG

AAGGTCGCCTGATGCGGGTACGTGCCGCCACCCCGGATGAAGT

GGAGCAGGCCCTGCCCTACAAGCTGGAGGAGCTCATCGGCAGC

CTGGAGAGCGCCAAGGGGATCGCCGACATCGCCCAGCGCCATC

ACACCAACATCCCGGTGCACATCGGCCTGAACTCCGCCGGCAT

GAGCCGCAACGGCATCGATCTGCGCCAGGACGATGCCAAGGCC

GATGCCCTGGCCATGCTCAAGCTCAAGGGGATCACCCCGGTCG

GCATCATGACCCACTTCCCGGTGGAGGAGAAAGAGGACGTCAA

GCTGGGGCTGGCCCAGTTCAAGCTGGACTACCAGTGGCTCATC

GACGCCGGCAAGCTGGATCGCAGCAAGCTCACCATCCACGCCG

CCAACTCCTTCGCCACCCTGGAAGTACCGGAAGCCTACTTTGAC

ATGGTGCGCCCGGGCGGCATCATCTATGGCGACACCATTCCCTC

CTACACCGAGTACAAGAAGGTGATGGCGTTCAAGACCCAGGTC

GCCTCCGTCAACCACTACCCGGCGGGCAACACCGTCGGCTATG

ACCGCACCTTCACCCTCAAGCGCGACTCCCTGCTGGCCAACCTG

CCGATGGGCTACTCCGACGGCTACCGCCGCGCCATGAGCAACA

AGGCCTATGTGCTGATCMASGGCCA,
``` wherein R indicates A or G, S indicates C or G, and M indicates A or C.

The amino acid sequence of the partial *A. caviae* BAR enzyme is shown as SEQ ID NO:415 below.

```
                                          (SEQ ID NO: 415)
ASNEEARVAREKGFEGRLMRVRAATPDEVEQALPYKLEELIGSLESAKGI

ADIAQRHHTNIPVHIGLNSAGMSRNGIDLRQDDAKADALAMLKLKGITPV

GIMTHFPVEEKEDVKLGLAQFKLDYQWLIDAGKLDRSKLTIHAANSFATL

EVPEAYFDMVRPGGIIYGDTIPSYTEYKKVMAFKTQVASVNHYPAGNTVG

YDRTFTLKRDSLLANLPMGYSDGYRRAMSNKAYVLIXG.
``` wherein X is H, Q, N, or K.

The consensus protein sequence fragment of SEQ ID NO:415 above is 89% homologous at the amino acid level to the published TIGR sequence for *A. hydrophila*. It was expected that because the highly related *Aeromonas hydrophila* protein exhibited broad specificity racemase activity, as well as the *A. caviae* cellular extracts, the full length coding region for *A. caviae*, once obtained, would produce a racemase that also would have a broad specificity with activity on tryptophan. Genome Walker methods were utilized to obtain the full-length gene sequence of the *A. caviae* BAR gene shown below as SEQ ID NO:416.

```
                                                            (SEQ ID NO: 416)
atgcacaaga aaacactgct cgcgaccctg atctttggcc tgctggccgg ccaggcagtc gccgccccct atctgccgct cgccgacgac caccgcaacg gtcaggaaca gaccgccgcc aacgcctggc tggaagtgga tctcggcgcc ttcgagcaca acatccagac cctgaagaat cgcctcggtg acaagggccc gcagatctgc gccatcatga aggcggacgc ctacggtcac ggcatcgacc tgctggtccc ttccgtggtc aaggcaggca tccccctgcat cggcatcgcc agcaacgaag aagcacgtgt tgcccgcgag aagggcttcg aaggtcgcct gatgcgggta cgtgccgcca ccccggatga agtggagcag gccctgccct acaagctgga ggagctcatc ggcagcctgg agagcgccaa ggggatcgcc gacatcgccc agcgccatca ccaacatc ccggtgcaca tcggcctgaa ctccgccggc atgagccgca acggcatcga tctgcgccag gacgatgcca aggccgatgc cctggccatg ctcaagctca aggggatcac cccggtcggc atcatgaccc acttcccggt ggaggagaaa gaggacgtca agctggggct ggcccagttc aagctggact accagtggct catcgacgcc ggcaagctgg atcgcagcaa gctcaccatc
```

```
                                     -continued
cacgccgcca actccttcgc cacccrggaa gtaccggaag cctactttga catggtgcgc ccgggcggca tcatctatgg cgacaccatt ccctcctaca ccgagtacaa gaaggtgatg gcgttcaaga cccaggtcgc ctccgtcaac cactacccgg cgggcaacac cgtcggctat gaccgcacct tcaccctcaa gcgcgactcc ctgctggcca acctgccgat gggctactcc gacggctacc gccgcgccat gagcaacaag gcctatgtgc tgatccatgg ccagaaggcc cccgtcgtgg gcaagacttc catgaacacc accatggtgg acgtcaccga catcaagggg atcaaacccg gtgacgaggt ggtcctgttc ggacgccagg gtgatgccga ggtgaaacaa tctgatctgg aggagtacaa cggtgccctc ttggcggaca tgtacaccgt ctggggctat accaacccca agaagatcaa gcgctaa.
```

The corresponding amino acid sequence for the *A. caviae* native BAR is shown below as SEQ ID NO:417:

```
                                                 (SEQ ID NO: 417)
  1 mhkktllatl ifgllagqav aapylpladd hrngqeqtaa 41 nawlevdlga fehniqtlkn rlgdkgpqic aimkadaygh 81 gidllvpsvv kagipcigia sneearvare kgfegrlmrv 121 raatpdeveq alpykleeli gslesakgia diaqrhhtni 161 pvhiglnsag msrngidlrq ddakadalam lklkgitpvg 201 imthfpveek edvklglaqf kldyqwlida gkldrsklti 241 haansfatle vpeayfdmvr pggiiygdti psyteykkvm 281 afktqvasvn hypagntvgy drtftlkrds llanlpmgys 321 dgyrramsnk ayvlihgqka pvvgktsmnt tmvdvtdikg 361 ikpgdevvlf grqgdaevkq sdleeyngal ladmytvwgy 401 tnpkkikr.
```

The first 21 N-terminal amino acid residues of SEQ ID NO:417 are predicted to be a signal peptide using the program Signal P 3.0 (www.cbs.dtu.dk/services/SignalP/). Experimental evidence confirmed that the expression product was secreted into the periplasm of *E. coli*, and the signal peptide was cleaved as predicted. The full length gene, when cloned and expressed using methods described above, was found to have activity comparable to, but greater than, the *P. taetrolens* BAR.

Example 31

Production of the Aldolase of SEQ ID NO: 276 in an Alternative Expression Host

The gene of SEQ ID NO: 275 was subcloned using standard molecular biology procedures into a derivative of the pET23d vector (Novagen, Madison, Wis.) containing the *E. coli* metE gene and promoter inserted at the NgoMIV restriction site and a second psiI restriction site that was added for facile removal of the beta lactamase gene (baa). The construction of this vector containing an insert for a myo-inositol oxygenase gene is described in PCT WO2006066072 in Examples 2 and 20. The aldolase insert was confirmed by DNA sequencing (Agencourt Bioscience Corporation; Beverly, Mass.) and the plasmid with the correct insert sequence was transformed into the *E. coli* expression host BW30384 (DE3)ΔompTΔmetE. The construction of this expression host and the transformation protocol are also described in PCT WO2006066072 (Examples 21 and 22). The aldolase gene was expressed using the Novagen Overnight Express™ Autoinduction System II (Novagen, Madison, Wis.) containing 100 mg/L ampicillin. This system was described in Example 24 for the expression of *Bacillus sphaericus* (ATCC strain 10208) D-alanine aminotransferase. Cell free extracts containing the aldolase were produced using Novagen Bug-Buster™ Extraction Reagent (primary amine free) (Novagen, Madison, Wis.) containing 1 µL/mL benzonase nuclease, 0.033 µL/mL r-Lysozyme, and 5 µL/mL Protease Inhibitor Cocktail Set II following the manufacturer's recommended protocol for cell lysis. The soluble proteins in the cell free extracts were separated on a Bio-Rad Laboratories Experion™ Automated Electrophoresis Station (Bio-Rad, Hercules, Calif.) and analyzed for percent soluble protein expression using the Experion Software version 1.1.98.0 as described in Example 12.

To attempt to improve the aldolase expression in *E. coli*, codons two through seven of the DNA coding sequence were mutated to changes suggested from the analysis of the wild type sequence using the Roche ProteoExpert RTS *E. coli* HY algorithm. The changes were made using a QuikChange® Multi Site-Directed Mutagenesis Kit or QuikChange® II XL Site-Directed Mutagenesis Kit (Stratagene, La Jolla, Calif.) following the manufacturer's suggested protocol with 0.75 µL of Quik Solution per 25 µL reaction mixture and transformation into XL10-Gold® ultracompetent cells. The mutations were generated using primers (each 45 nucleotides in length) designed with Stratagene's web-based QuikChange® Primer Design Program available on-line at www.stratagene.com.qcprimerdesign.

TABLE 48

|  | Codon 1 | Codon 2 | Codon 3 | Codon 4 | Codon 5 | Codon 6 | Codon 7 |
|---|---|---|---|---|---|---|---|
| Wild type | ATG | CCT | ATC | GTT | GTT | ACG | AAG |
| ProteoExpert #1 | ATG | CCA | ATT | GTT | GTA | ACT | AAA |
| ProteoExpert #2 | ATG | CCA | ATT | GTT | GTT | ACT | AAA |
| ProteoExpert #6 | ATG | CCA | ATT | GTT | GTA | ACC | AAA |
| ProteoExpert #10 | ATG | CCA | ATT | GTT | GTT | ACC | AAA |

The aldolase gene sequences with the above codon changes were transformed into the E. coli expression host BW30384 (DE3)ΔompTΔmetE and then expressed using Novagen Overnight Express™ Autoinduction System II (Novagen, Madison, Wis.). None of these mutations resulted in higher levels of gene expression when compared to the wild type sequence. Typical results from cell free extracts analyzed by the Bio-Rad Experion Pro260 software 1.1.98.0 are shown in Table 49 below, in which the column entitled Protein Expression shows values for % total soluble protein.

The cell free extracts (0.025 mg/mL soluble protein per assay) were assayed for their ability to produce R,R-monatin from 200 mM sodium pyruvate and 100 mM D-tryptophan using the protocol described in Example 7. The reactions (7 mL total volume) were carried out in 14 mL polypropylene tubes in an anaerobic glove box using purified B. sphaericus (ATCC 10208) D-aminotransferase at 2 mg/mL final concentration. The concentrations of monatin produced at 1, 4 and 20 h after the addition of the enzymes are shown in Table 49 below. Table 49 shows that the cell free extract generated from the construct containing the wild type aldolase sequence produced a slightly higher concentration of monatin at 20 hours than the cell free extracts from the constructs carrying the ProteoExpert mutations. The monatin concentrations were determined by the LC/MS/MS method described in Example 1.

TABLE 49

| | Protein Expression (%) | [Monatin] mM-1 hr | [Monatin] mM-4 hr | [Monatin] mM-20 hr |
|---|---|---|---|---|
| Wild type | 22 | 2.1 | 4.2 | 13.4 |
| ProteoExpert #1 | 18 | 1.3 | 3.1 | 12.4 |
| ProteoExpert #2 | 18 | 2.1 | 4.7 | 11.6 |
| ProteoExpert #6 | 18 | 1.4 | 1.9 | 12.4 |
| ProteoExpert #10 | 20 | 1.8 | 1.8 | 11.7 |

These data demonstrate that the aldolase of SEQ ID NO: 276 can be produced in an alternative expression host without IPTG induction.

The bla gene was removed from the vector and subsequent fermentations to produce aldolase were done without the use of antibiotic as described in PCT WO2006066072 for another enzyme. Expression levels in fed-batch fermentations at 30° C. reached a maximum at 6-8 hours post-induction, producing the aldolase of SEQ ID NO: 276 at 25-30% of the soluble protein, according to Experion data. Stability studies showed no apparent loss of aldolase activity when the fermentation product was left for 6 hours at 15 or 30° C. (under both oxygen limiting conditions as well as aerated conditions) prior to cell concentration and disruption. The aldolase was found to be equally stable stored as either a cell free extract or as a cell pellet when stored for 5 days at −80° C. Washing the cell pellet in buffer prior to storage at −80° C. was not required and actually caused a slight decrease in activity. Cells resuspended in distilled water, fermentation supernatant, or 100 mM potassium phosphate buffer (pH 7.8) were found to have no loss in activity or protein concentration (judged by SDS-PAGE) when stored for 11 days at room temperature or 4° C. Cell-free extract produced in potassium phosphate buffer showed no loss of aldolase activity when stored at 4° C. or room temperature for 5 days. Cells can be broken open in phosphate buffer, up to 25% culture supernatant or water with comparable recovery of aldolase activity; however, addition of 1 mM $MgCl_2$ to water was found to slightly improve the aldolase activity. These data show that the aldolase protein is sufficiently stable to be commercially useful.

A number of embodiments of the invention have been described. The embodiments of the invention include one or more of the above described aspects. It will be understood that various modifications may be made without departing from the spirit and scope in accordance with the invention. Accordingly, other embodiments are within the scope of the following claims.

What is claimed is:

1. An isolated, synthetic, or recombinant polypeptide or peptide having an aldolase activity comprising
   (a) an amino acid sequence having at least 90%, 91%, 92%, 93%, 94%, 95%, 96%, 97%, 98%, 99%, or more, or 100% sequence identity to the full length of SEQ ID NO:276; or,
   (b) an amino acid sequence encoded by a nucleic acid sequence having the full length of SEQ ID NO:275.

2. The isolated, synthetic, or recombinant polypeptide of claim 1 wherein the polypeptide comprises at least one glycosylation site or further comprises a polysaccharide.

3. A protein preparation comprising the polypeptide of claim 1, wherein the protein preparation comprises a liquid, a solid, or a gel.

4. A heterodimer or a homodimer comprising the polypeptide of claim 1.

5. A method for utilizing an aldolase of claim 1 as a supplement in an animal diet, the method comprising: preparing a supplement containing an aldoase enzyme comprising the polypeptide of claim 1; and administering the supplement to an animal.

6. A composition comprising the polypeptide of claim 1.

7. The polypeptide of claim 1, but lacking a signal sequence.

8. The potypeptide of claim 1, further comprising a heterologous sequence; wherein the heterologous sequence comprises one or more of: a tag an epitope, a targeting peptide, a cleavable sequence, a detectable moiety, or a polypeptide that does not have aldolase activity.

9. The polypeptide of claim 1, wherein, the aldolase activity comprises a pyruvate, HMG, or KHG aldolase activity.

10. The polypeptide of claim 1, wherein the amino acid sequence is a fragment of the full length of SEQ ID NO:276 and the fragment has aldolase activity.

11. An isolated, synthetic, or recombinant polypeptide or peptide having an aldolase activity comprising an amino acid sequence that is at least 95% identical to the full length of SEQ ID NO:276.

12. An isolated, synthetic, or recombinant polypeptide comprising an amino acid sequence that is SEQ ID NO:276.

* * * * *

UNITED STATES PATENT AND TRADEMARK OFFICE
CERTIFICATE OF CORRECTION

PATENT NO.       : 8,546,118 B2
APPLICATION NO.  : 12/281052
DATED            : October 1, 2013
INVENTOR(S)      : David P. Weiner et al.

It is certified that error appears in the above-identified patent and that said Letters Patent is hereby corrected as shown below:

On the title page, item (75), lines 5 and 6, delete "Paula M. Hicks, Bend, OR (US)" and insert --Paula M. Hicks, Eden Prairie, MN--, therefor.

On the title page, item (56), under Foreign Patent Documents, line 1, delete "JP 5178841-07-20 7/1920" and insert --JP 5178841-07-20 7/1993--, therefor.

On the title page, item (56), under Other Publications, lines 12 and 13, delete "SIPO-May 5, 2010-Chinese Office Action and Translation-200780016408.6" and insert --SIPO-May 20, 2010-Chinese Office Action and Translation-200780016408.6--, therefor.

In the Claims:

In column 687, line 28, in claim 5, delete "aldoase" and insert --aldolase--, therefor.

In column 688, line 13, in claim 8, delete "potypeptide" and insert --polypeptide--, therefor.

In column 688, line 15, in claim 8, delete "tag" and insert --tag,--, therefor.

In column 688, line 18, in claim 9, delete "wherein," and insert --wherein--, therefor.

Signed and Sealed this
Eleventh Day of March, 2014

Michelle K. Lee
*Deputy Director of the United States Patent and Trademark Office*

SEQUENCE LISTING

<160> NUMBER OF SEQ ID NOS: 417

<210> SEQ ID NO 1
<211> LENGTH: 699
<212> TYPE: DNA
<213> ORGANISM: Unknown
<220> FEATURE:
<223> OTHER INFORMATION: Bacterial DNA

<400> SEQUENCE: 1

```
atgcagccgc tgaaggaatt cgccgagctc tccacccgc tgatcgccga cgcctgcgtg      60
cggctcgggg aaccctgcg cgtcgcgccc gccggcatcc tgcccgtcgt cgcgggccgg     120
cgcgtcgccg gcgggcct gcccgtacgg cactacggca gcgtcgacgt cttcctggag     180
gcgttcggcg aggccgagcc cggtgacgtc ctcgtcatcg acaacgcggg ccgcgtcgac    240
gaggcctgca tcggcgacct cgccgtcctg gaggcggcgg cggccggcat cgccggggtc    300
gtcgtgtggg gcctgcaccg ggacaccccc gacctcgtcg agatcgggct gcccgtcttc    360
tcctacggac gccacgcgcc cggcccgtg cgcgtcgacc cccgggaccc ggacgcgctg    420
acgaccgcgc ggttcggcga gcacgaggtg accgccgccg acgtcgtgtt cggcgacgac    480
gacggcgtgg tcttcgtcgc cgccgcccgg gccgcgccg tcctggaggc ggcccggcc     540 ctgttccgta cggagcgcga gcaggcgcgg cggatcaggg cggggagac gctgcgcgcc    600
```

```
cagacccggt tcgacgcgta cctggcgggc cgggccgagg accccctcgta caccttccgg    660 cagcacctgc gccggatcgg cggcgcgatc gaggagtga                            699
```

<210> SEQ ID NO 2
<211> LENGTH: 232
<212> TYPE: PRT
<213> ORGANISM: Unknown
<220> FEATURE:
<223> OTHER INFORMATION: Bacterial protein
<220> FEATURE:
<221> NAME/KEY: DOMAIN
<222> LOCATION: (8)...(165)
<223> OTHER INFORMATION: Demethylmenaquinone methyltransferase

<400> SEQUENCE: 2

```
Met Gln Pro Leu Lys Glu Phe Ala Glu Leu Ser Thr Pro Leu Ile Ala
1               5                   10                  15

Asp Ala Cys Val Arg Leu Gly Glu Pro Leu Arg Val Ala Pro Ala Gly
            20                  25                  30

Ile Leu Pro Val Val Ala Gly Arg Val Ala Gly Arg Ala Leu Pro
        35                  40                  45

Val Arg His Tyr Gly Ser Val Asp Val Phe Leu Glu Ala Phe Gly Glu
    50                  55                  60

Ala Glu Pro Gly Asp Val Leu Val Ile Asp Asn Ala Gly Arg Val Asp
65                  70                  75                  80

Glu Ala Cys Ile Gly Asp Leu Ala Val Leu Glu Ala Ala Ala Gly
                85                  90                  95

Ile Ala Gly Val Val Val Trp Gly Leu His Arg Asp Thr Pro Asp Leu
            100                 105                 110

Val Glu Ile Gly Leu Pro Val Phe Ser Tyr Gly Arg His Ala Pro Gly
        115                 120                 125

Pro Val Arg Val Asp Pro Arg Asp Pro Asp Ala Leu Thr Thr Ala Arg
    130                 135                 140

Phe Gly Glu His Glu Val Thr Ala Ala Asp Val Val Phe Gly Asp Asp
145                 150                 155                 160

Asp Gly Val Val Phe Val Ala Ala Ala Arg Ala Gly Ala Val Leu Glu
                165                 170                 175

Ala Ala Arg Ala Leu Phe Arg Thr Glu Arg Glu Gln Ala Arg Arg Ile
            180                 185                 190

Arg Ala Gly Glu Thr Leu Arg Ala Gln Thr Arg Phe Asp Ala Tyr Leu
        195                 200                 205

Ala Gly Arg Ala Glu Asp Pro Ser Tyr Thr Phe Arg Gln His Leu Arg
    210                 215                 220

Arg Ile Gly Gly Ala Ile Glu Glu
225                 230
```

<210> SEQ ID NO 3
<211> LENGTH: 693
<212> TYPE: DNA
<213> ORGANISM: Unknown
<220> FEATURE:
<223> OTHER INFORMATION: DNA obtained from environmental sample

<400> SEQUENCE: 3

```
gtgaccggcc acgtcatcgt ccgcgagatc gaccgcgccg acgcgaacgc cctcgacggc    60
ctcgccgcgc tcggcgtctc gacggtgcac gaggccgacg gccgccgcgg cgcgctcgcc    120
accgccattc gaccgatcca cagtggattc acgatcgccg gttcggcggt gacggtctcc    180
tcccagccgg gcgacaacgt catgatccac gccgccattg aggtgtgccg gcccggcgac    240
```

-continued

```
atcctcgtgg tcaccaccac ctcgccgtcc accgacggga tgatcggcga actgctggcg    300
acgtcgctgc gcgcgcacgg ggtgcggggt gtcgtcaccg atgccggcgt acgcgacgtc    360
gcccagctcc gggcgatgaa cttcccggtg tggacgcgcg ccatcagtcc acaggggacg    420
gtcaaggcga gcccgggctc ggtgaacata ccggtcgtct gcgccggcca ggtcgtccac    480
cccggcgatg ccatcgtcgc cgacgacgac ggcgttgtcg tcgtcccgcg cgaccgggtg    540
ccggcggtgc tggcggccgg ccgggcgcgg gccgagagcg aggacgacaa acgcgtccgg    600
ctcgccggtg gcgaactctc ggtcgacatg tacgggctgc gcgagctgct cacccgactc    660
ggagtggagt acgtcgaccg gcggccggcg tga                                 693
```

<210> SEQ ID NO 4
<211> LENGTH: 230
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (28)...(174)
<223> OTHER INFORMATION: Demethylmenaquinone methyltransferase

<400> SEQUENCE: 4

```
Met Thr Gly His Val Ile Val Arg Glu Ile Asp Arg Ala Asp Ala Asn
1               5                   10                  15

Ala Leu Asp Gly Leu Ala Ala Leu Gly Val Ser Thr Val His Glu Ala
                20                  25                  30

Asp Gly Arg Arg Gly Ala Leu Ala Thr Ala Ile Arg Pro Ile His Ser
            35                  40                  45

Gly Phe Thr Ile Ala Gly Ser Ala Val Thr Val Ser Ser Gln Pro Gly
        50                  55                  60

Asp Asn Val Met Ile His Ala Ala Ile Glu Val Cys Arg Pro Gly Asp
65                  70                  75                  80

Ile Leu Val Val Thr Thr Thr Ser Pro Ser Thr Asp Gly Met Ile Gly
                85                  90                  95

Glu Leu Leu Ala Thr Ser Leu Arg Ala His Gly Val Arg Gly Val Val
                100                 105                 110

Thr Asp Ala Gly Val Arg Asp Val Ala Gln Leu Arg Ala Met Asn Phe
            115                 120                 125

Pro Val Trp Thr Arg Ala Ile Ser Pro Gln Gly Thr Val Lys Ala Ser
130                 135                 140

Pro Gly Ser Val Asn Ile Pro Val Val Cys Ala Gly Gln Val Val His
145                 150                 155                 160

Pro Gly Asp Ala Ile Val Ala Asp Asp Gly Val Val Val Val Pro
                165                 170                 175

Arg Asp Arg Val Pro Ala Val Leu Ala Ala Gly Arg Ala Arg Ala Glu
            180                 185                 190

Ser Glu Asp Asp Lys Arg Val Arg Leu Ala Gly Gly Glu Leu Ser Val
        195                 200                 205

Asp Met Tyr Gly Leu Arg Glu Leu Leu Thr Arg Leu Gly Val Glu Tyr
    210                 215                 220

Val Asp Arg Arg Pro Ala
225                 230
```

<210> SEQ ID NO 5
<211> LENGTH: 762
<212> TYPE: DNA
<213> ORGANISM: Unknown

```
<220> FEATURE:
<223> OTHER INFORMATION: DNA obtained from environmental sample

<400> SEQUENCE: 5
atggcgttga ataccggttc cgacattatt cgcccgtcca aggagctcgt tgccgggctc      60
aaagctcttg gcagtgcgac catcgcgggc acgctcggcc acatggggtt caagaacccg     120
cacatgacgg gcatcctgcc acagacggcg ggcaaggtca tggccggccc ggcgctgacg     180
ctgcagtgca tgccgcagcg accggacctg ttcagcgaag gcgaatacgc cgatcctgaa     240
acgcagctcc accgccatgt gctctatcac gtgcaggagg gcgacgtggt cgtcgtcgat     300
gcgcgcggcg atatgaagtc gggcatcttc ggcgacatga tgtcgaccta cttcaagggc     360
cgcggcggcg ccggcatcgt catcgacggc tgcatgcgcg atcgtcccaa tgtcgaaaag     420
ctcgacctgt cgctctggct caagggctgg acgccgaact accacgtcca gaccgacatc     480
tttccctacg cggtgaacgt tccagtcgca tgtggcggcg ttcttgtgct ccccggcgac     540
atcatcgttg ccgatgacga cggcgctgtc gtcgtgccgg tgaagatggc gcagcacatc     600
gtcgaggacg gcaagaagca cgccgagtgg gaagtgttct cgcgcgagaa gctgatggcc     660
ggcgagtcgc tccgccgtta ctacccgctg caccccgatg ccgaggacga ataccaggcc     720
tggcggaagg cgaaggggct gccgccgtcg ccctcgcgct aa                         762

<210> SEQ ID NO 6
<211> LENGTH: 253
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (21)...(191)
<223> OTHER INFORMATION: Demethylmenaquinone methyltransferase

<400> SEQUENCE: 6

Met Ala Leu Asn Thr Gly Ser Asp Ile Ile Arg Pro Ser Lys Glu Leu
1               5                   10                  15

Val Ala Gly Leu Lys Ala Leu Gly Ser Ala Thr Ile Ala Gly Thr Leu
            20                  25                  30

Gly His Met Gly Phe Lys Asn Pro His Met Thr Gly Ile Leu Pro Gln
        35                  40                  45

Thr Ala Gly Lys Val Met Ala Gly Pro Ala Leu Thr Leu Gln Cys Met
    50                  55                  60

Pro Gln Arg Pro Asp Leu Phe Ser Glu Gly Tyr Ala Asp Pro Glu
65                  70                  75                  80

Thr Gln Leu His Arg His Val Leu Tyr His Val Gln Glu Gly Asp Val
                85                  90                  95

Val Val Val Asp Ala Arg Gly Asp Met Lys Ser Gly Ile Phe Gly Asp
            100                 105                 110

Met Met Ser Thr Tyr Phe Lys Gly Arg Gly Gly Ala Gly Ile Val Ile
        115                 120                 125

Asp Gly Cys Met Arg Asp Arg Pro Asn Val Glu Lys Leu Asp Leu Ser
    130                 135                 140

Leu Trp Leu Lys Gly Trp Thr Pro Asn Tyr His Val Gln Thr Asp Ile
145                 150                 155                 160

Phe Pro Tyr Ala Val Asn Val Pro Val Ala Cys Gly Gly Val Leu Val
                165                 170                 175

Leu Pro Gly Asp Ile Ile Val Ala Asp Asp Gly Ala Val Val Val
            180                 185                 190
```

-continued

```
Pro Val Lys Met Ala Gln His Ile Val Glu Asp Gly Lys His Ala
            195                 200                 205

Glu Trp Glu Val Phe Ser Arg Glu Lys Leu Met Ala Gly Glu Ser Leu
    210                 215                 220

Arg Arg Tyr Tyr Pro Leu His Pro Asp Ala Glu Asp Glu Tyr Gln Ala
225                 230                 235                 240

Trp Arg Lys Ala Lys Gly Leu Pro Pro Ser Pro Ser Arg
                245                 250
```

<210> SEQ ID NO 7
<211> LENGTH: 672
<212> TYPE: DNA
<213> ORGANISM: Unknown
<220> FEATURE:
<223> OTHER INFORMATION: DNA obtained from environmental sample

<400> SEQUENCE: 7

```
atgagtgtag tggtgcaaaa tatcgagcgg gcagatcagg caattatcaa ggcgcttgct      60
gaatgcggtg tagcaactgt gcatgaggcc caaggccgca cggggttgct ggcttcttat     120
atgcggccaa tttatagcgg tgcttgcatt ggtgcatcag cggtaaccat tctggctccg     180
ccttgcgata actggatggt ccatgtggcc attgagcaga taaagccggg tgatgctctg     240
gttatggcaa caacatcgtc atctgatgcc ggatattttg gtgacctgct ggcgacctcg     300
atgcaggcgc gtggcggggt tggcatgatt atcgatgccg gggtgcgcga tattaaagac     360
ctgaccgaga tgaaatgtcc tgtctggtca aaagcgatct cgctgaagg acggtgaaa      420
gaaacacttg gctctgtaaa tattccggtg gtttgcgccg ccagttggt caaccccggc     480
gatattgtca tcgctgatga tgatgggtc tgtgtcgttg agcgcaaag ggctggcgaa      540
gttctggaaa agcgcaagc ccgcatggct ttggaagaag acaaacgtaa acgtttggcc     600
tccggtgaac ttgggctgga tatgtataat atgcgcgagc gtctggctga aaaaggtctc     660
aaatatgttt aa                                                         672
```

<210> SEQ ID NO 8
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 8

```
Met Ser Val Val Val Gln Asn Ile Glu Arg Ala Asp Gln Ala Ile Ile
1               5                   10                  15

Lys Ala Leu Ala Glu Cys Gly Val Ala Thr Val His Glu Ala Gln Gly
            20                  25                  30

Arg Thr Gly Leu Leu Ala Ser Tyr Met Arg Pro Ile Tyr Ser Gly Ala
        35                  40                  45

Cys Ile Gly Ala Ser Ala Val Thr Ile Leu Ala Pro Pro Cys Asp Asn
    50                  55                  60

Trp Met Val His Val Ala Ile Glu Gln Ile Lys Pro Gly Asp Ala Leu
65                  70                  75                  80

Val Met Ala Thr Thr Ser Ser Asp Ala Gly Tyr Phe Gly Asp Leu
                85                  90                  95

Leu Ala Thr Ser Met Gln Ala Arg Gly Gly Val Gly Met Ile Ile Asp
```

```
                        100                 105                 110
Ala Gly Val Arg Asp Ile Lys Asp Leu Thr Glu Met Lys Cys Pro Val
            115                 120                 125

Trp Ser Lys Ala Ile Cys Ala Glu Gly Thr Val Lys Glu Thr Leu Gly
        130                 135                 140

Ser Val Asn Ile Pro Val Cys Ala Gly Gln Leu Val Asn Pro Gly
145                 150                 155                 160

Asp Ile Val Ile Ala Asp Asp Gly Val Cys Val Val Glu Arg Glu
                165                 170                 175

Arg Ala Gly Glu Val Leu Glu Lys Ala Gln Ala Arg Met Ala Leu Glu
            180                 185                 190

Glu Asp Lys Arg Lys Arg Leu Ala Ser Gly Leu Gly Leu Asp Met
        195                 200                 205

Tyr Asn Met Arg Glu Arg Leu Ala Glu Lys Gly Leu Lys Tyr Val
        210                 215                 220
```

<210> SEQ ID NO 9
<211> LENGTH: 552
<212> TYPE: DNA
<213> ORGANISM: Unknown
<220> FEATURE:
<223> OTHER INFORMATION: DNA obtained from environmental sample

<400> SEQUENCE: 9

```
atgaacggga ccgtcgtgcg caacatccat cgcgccgagg cggggccat cgcggcgctc      60
gggcgcatcg gcgtctcgac cgtccacgag gcgcagggc gcaccgggct catgcaggcc     120
tacatgcggc ccgtatggcg gggcgcgcgc atcgccggca gcgccgtgac cgtcctgtgc    180
catcccaacg acaactggat gatccacgtc gcgatggagg tggcaaggcc cggcgacgtg    240
ctcgtggtgg cttgctcgag cgagaacacg aacggcgcga tcggcgacct gatcgccacc    300
tcgctcatgg cgcgcggcgt gaaaggcgcg atcctcgaca tgggctgccg cgacgtgctg    360
gagctcgagc agatgaggtt tccgctctgg tcgcgggcca tctcggcgca gggaaccatc    420
aagggcacgc tcggctcggt caacttcccg gtcacctgcg ccggcgccca cgtcaggccg    480
ggcgacatcg tggtcgcgga cgacgacggc gtggtggtcg tgccccgcca ggacgcggcg    540
aaagtgatcc aa                                                        552
```

<210> SEQ ID NO 10
<211> LENGTH: 184
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (21)...(173)
<223> OTHER INFORMATION: Demethylmenaquinone methyltransferase
<220> FEATURE:
<221> NAME/KEY: SITE
<222> LOCATION: (2)...(5)
<223> OTHER INFORMATION: N-glycosylation site. Prosite id = PS00001

<400> SEQUENCE: 10

```
Met Asn Gly Thr Val Val Arg Asn Ile His Arg Ala Glu Ala Gly Ala
1               5                   10                  15

Ile Ala Ala Leu Gly Arg Ile Gly Val Ser Thr Val His Glu Ala Gln
            20                  25                  30

Gly Arg Thr Gly Leu Met Gln Ala Tyr Met Arg Pro Val Trp Arg Gly
        35                  40                  45
```

```
Ala Arg Ile Ala Gly Ser Ala Val Thr Val Leu Cys His Pro Asn Asp
         50                  55                  60

Asn Trp Met Ile His Val Ala Met Glu Val Ala Arg Pro Gly Asp Val
 65                  70                  75                  80

Leu Val Val Ala Cys Ser Ser Glu Asn Thr Asn Gly Ala Ile Gly Asp
                 85                  90                  95

Leu Ile Ala Thr Ser Leu Met Ala Arg Gly Val Lys Gly Ala Ile Leu
                100                 105                 110

Asp Met Gly Cys Arg Asp Val Leu Glu Leu Glu Gln Met Arg Phe Pro
            115                 120                 125

Leu Trp Ser Arg Ala Ile Ser Ala Gln Gly Thr Ile Lys Gly Thr Leu
        130                 135                 140

Gly Ser Val Asn Phe Pro Val Thr Cys Ala Gly Ala His Val Arg Pro
145                 150                 155                 160

Gly Asp Ile Val Val Ala Asp Asp Gly Val Val Val Pro Arg
                165                 170                 175

Gln Asp Ala Ala Lys Val Ile Gln
            180
```

<210> SEQ ID NO 11
<211> LENGTH: 645
<212> TYPE: DNA
<213> ORGANISM: Unknown
<220> FEATURE:
<223> OTHER INFORMATION: DNA obtained from environmental sample

<400> SEQUENCE: 11

```
atggatccag gggtcatcag gcgtctgggg gagctgggcg ttgcgaccgt tcacgaggcg    60
ctcggccgcc agggccttct cgatcccgtc gtgcgcccga tctacccggg cgcgcgggcg   120
gccggaaccg ccgtaacggt gtgctgtccg gccggggaca acctgatgat ccatgcggcg   180
ctccaggtcg tggcgcgcgg cgacgtgctc gtcgtcacga ccgagccgcc gtcgacgtac   240
ggcatgttcg gcgacgtgct ggggacgtcg tgccaggcgc tcggggtcgc ggggctcgtc   300
atcgacgccg gcatccgtga cacggaggag ctcgagcgga tggcgttccc gcctgggcg   360
cgcgcgacgt cggcgcaggg cacggtgaaa gtggctccgg gcatcgtcaa cgcgccgatt   420
gtgtgcgcgg gcgcggacgt cgtccgggc gacgttgtcg tggcggatcg cgacggcgtc   480
gtcatcgtcc cgcgcgagcg ggctgccgaa gcggcggagc ttggtgagca gcggcgcgat   540
cgcgagatcg aataccgccg gcggctggca ggtggagagc tgaccctgga cgtgctcgac   600
ctccggcgca ccctgcggga gatcgggatg gacaggctgg actga                  645
```

<210> SEQ ID NO 12
<211> LENGTH: 214
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (10)...(162)
<223> OTHER INFORMATION: Demethylmenaquinone methyltransferase

<400> SEQUENCE: 12

```
Met Asp Pro Gly Val Ile Arg Arg Leu Gly Glu Leu Gly Val Ala Thr
 1               5                  10                  15

Val His Glu Ala Leu Gly Arg Gln Gly Leu Leu Asp Pro Val Val Arg
                20                  25                  30

Pro Ile Tyr Pro Gly Ala Arg Ala Ala Gly Thr Ala Val Thr Val Cys
```

```
                35                  40                  45
Cys Pro Ala Gly Asp Asn Leu Met Ile His Ala Ala Leu Gln Val Val
 50                  55                  60
Ala Arg Gly Asp Val Leu Val Val Thr Thr Glu Pro Pro Ser Thr Tyr
 65                  70                  75                  80
Gly Met Phe Gly Asp Val Leu Gly Thr Ser Cys Gln Ala Leu Gly Val
                 85                  90                  95
Ala Gly Leu Val Ile Asp Ala Gly Ile Arg Asp Thr Glu Glu Leu Glu
            100                 105                 110
Arg Met Ala Phe Pro Ala Trp Ala Arg Ala Thr Ser Ala Gln Gly Thr
            115                 120                 125
Val Lys Val Ala Pro Gly Ile Val Asn Ala Pro Ile Val Cys Ala Gly
            130                 135                 140
Ala Asp Val Arg Pro Gly Asp Val Val Val Ala Arg Asp Gly Val
145                 150                 155                 160
Val Ile Val Pro Arg Glu Arg Ala Ala Glu Ala Glu Leu Gly Glu
                165                 170                 175
Gln Arg Arg Asp Arg Glu Ile Glu Tyr Arg Arg Arg Leu Ala Gly Gly
            180                 185                 190
Glu Leu Thr Leu Asp Val Leu Asp Leu Arg Arg Thr Leu Arg Glu Ile
            195                 200                 205
Gly Met Asp Arg Leu Asp
        210

<210> SEQ ID NO 13
<211> LENGTH: 498
<212> TYPE: DNA
<213> ORGANISM: Unknown
<220> FEATURE:
<223> OTHER INFORMATION: DNA obtained from environmental sample

<400> SEQUENCE: 13
atggcgaccg gggagtacga cgcatgggcc ggctcctggt actcgaagct ctcgccggag    60
ccgttcatgg atctcattcg tcccggcact gccctggtga tcgacgatgc cccgcagcg   120
gatgtcggct ccatcgggtc gaacaacatc ctccaatgga agacgcgtgg atggtggcg   180
gtcgtgacga acgcgacggc gcgggacacc gacgaaatcg ttgtcgagcg cgtgccgctc   240
tatttccggc agcctggccg cggcatccgt ccgggccgca atgagatcga atcggtcaac   300
cgtcccgtgg tcgtgggcgg ggtgctcgtg atgcccggcg acgtcatcgt cggagacggc   360
gacggcgtgg ttgtcgtccc acgcgcgcag gccgaggccg tggcgcgata tgctcacacg   420
atcctcgaga aggacacgga aggacgtcgg cggctctacc agcagctgaa gcttccaacc   480
gattcgacgg tccggtag                                                  498

<210> SEQ ID NO 14
<211> LENGTH: 165
<212> TYPE: PRT
<213> ORGANISM: Unknown
<220> FEATURE:
<223> OTHER INFORMATION: Protein obtained from environmental sample

<400> SEQUENCE: 14

Met Ala Thr Gly Glu Tyr Asp Ala Trp Ala Gly Ser Trp Tyr Ser Lys
  1               5                  10                  15
Leu Ser Pro Glu Pro Phe Met Asp Leu Ile Arg Pro Gly Thr Ala Leu
                 20                  25                  30
Val Ile Asp Asp Ala Pro Ala Ala Asp Val Gly Ser Ile Gly Ser Asn
```

```
                    35                  40                  45
Asn Ile Leu Gln Trp Lys Thr Arg Gly Met Val Ala Val Val Thr Asn
 50                  55                  60
Ala Thr Ala Arg Asp Thr Asp Glu Ile Val Val Glu Arg Val Pro Leu
 65                  70                  75                  80
Tyr Phe Arg Gln Pro Gly Arg Gly Ile Arg Pro Gly Arg Asn Glu Ile
                 85                  90                  95
Glu Ser Val Asn Arg Pro Val Val Gly Gly Val Leu Val Met Pro
                100                 105                 110
Gly Asp Val Ile Val Gly Asp Gly Asp Gly Val Val Val Pro Arg
                115                 120                 125
Ala Gln Ala Glu Ala Val Ala Arg Tyr Ala His Thr Ile Leu Glu Lys
                130                 135                 140
Asp Thr Glu Gly Arg Arg Arg Leu Tyr Gln Gln Leu Lys Leu Pro Thr
145                 150                 155                 160
Asp Ser Thr Val Arg
                165

<210> SEQ ID NO 15
<211> LENGTH: 723
<212> TYPE: DNA
<213> ORGANISM: Unknown
<220> FEATURE:
<223> OTHER INFORMATION: DNA obtained from environmental sample

<400> SEQUENCE: 15
atgacaacaa gcactaaaaa tatgcaggta agtcagaaag ttattgacga tcttcgtcgc      60
gtgtcaacag caactctgca cactgcgctg ttcaaaagag gtttacgcaa cacctacatc     120
cagggtgtca gcctcatcaa caaccaaaaa ctgaagatgt cggccaggc gttcaccctg      180 cgctacatcc cggctcgtga agacgttgac accgttgcgg cattcaaaag ccctgagcac     240
cctcagcgcc tggccgttga atccgtcccg gaaggcatgg tgctggtttc agactgtcgt    300
caggacgcaa cagctgcttc tgccgggagc atccttctta ctcgattgga agttcgcaag     360
tgtgcgggtt ttgtttccga tgcgggcatc agagatttca acgatgcatc tgaaatgaac    420
atgccgattt tttgcgccaa gccaagcgct ccaaccaacc tgaccaagca ccacgccgta    480
gacatacaag taccgatcgg ctgccggcggt gtgatggtta tccaggcga tgtgttagtc     540 ggcgatggtg acggcatcat cgttatccct gtggaaattg cacaggaggt ttcagaagaa    600
gcacttgcaa tggaactctt cgaagatttt gtgctggata agttcgggc gggaagcaaa     660 gtcattgggc tgtaccctcc taacgcagaa actctggagg agtacaacaa ccaaaaggca    720
tag                                                                  723

<210> SEQ ID NO 16
<211> LENGTH: 240
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (19)...(188)
<223> OTHER INFORMATION: Demethylmenaquinone methyltransferase
<220> FEATURE:
<221> NAME/KEY: SITE
<222> LOCATION: (155)...(158)
<223> OTHER INFORMATION: N-glycosylation site. Prosite id = PS00001

<400> SEQUENCE: 16
```

| Met | Thr | Thr | Ser | Thr | Lys | Asn | Met | Gln | Val | Ser | Gln | Lys | Val | Ile | Asp |
| --- | --- | --- | --- | --- | --- | --- | --- | --- | --- | --- | --- | --- | --- | --- | --- |
| 1 | | | | 5 | | | | | 10 | | | | | 15 | |

| Asp | Leu | Arg | Arg | Val | Ser | Thr | Ala | Thr | Leu | His | Thr | Ala | Leu | Phe | Lys |
| --- | --- | --- | --- | --- | --- | --- | --- | --- | --- | --- | --- | --- | --- | --- | --- |
| | | | 20 | | | | | 25 | | | | | 30 | | |

| Arg | Gly | Leu | Arg | Asn | Thr | Tyr | Ile | Gln | Gly | Val | Ser | Leu | Ile | Asn | Asn |
| --- | --- | --- | --- | --- | --- | --- | --- | --- | --- | --- | --- | --- | --- | --- | --- |
| | | | | 35 | | | | | 40 | | | | 45 | | |

| Gln | Lys | Leu | Lys | Met | Val | Gly | Gln | Ala | Phe | Thr | Leu | Arg | Tyr | Ile | Pro |
| --- | --- | --- | --- | --- | --- | --- | --- | --- | --- | --- | --- | --- | --- | --- | --- |
| | 50 | | | | | 55 | | | | | 60 | | | | |

| Ala | Arg | Glu | Asp | Val | Asp | Thr | Val | Ala | Ala | Phe | Lys | Ser | Pro | Glu | His |
| --- | --- | --- | --- | --- | --- | --- | --- | --- | --- | --- | --- | --- | --- | --- | --- |
| 65 | | | | | 70 | | | | | 75 | | | | | 80 |

| Pro | Gln | Arg | Leu | Ala | Val | Glu | Ser | Val | Pro | Glu | Gly | Met | Val | Leu | Val |
| --- | --- | --- | --- | --- | --- | --- | --- | --- | --- | --- | --- | --- | --- | --- | --- |
| | | | | 85 | | | | | 90 | | | | | 95 | |

| Ser | Asp | Cys | Arg | Gln | Asp | Ala | Thr | Ala | Ala | Ser | Ala | Gly | Ser | Ile | Leu |
| --- | --- | --- | --- | --- | --- | --- | --- | --- | --- | --- | --- | --- | --- | --- | --- |
| | | | 100 | | | | | 105 | | | | | 110 | | |

| Leu | Thr | Arg | Leu | Glu | Val | Arg | Lys | Cys | Ala | Gly | Phe | Val | Ser | Asp | Ala |
| --- | --- | --- | --- | --- | --- | --- | --- | --- | --- | --- | --- | --- | --- | --- | --- |
| | | | 115 | | | | | 120 | | | | | 125 | | |

| Gly | Ile | Arg | Asp | Phe | Asn | Asp | Ala | Ser | Glu | Met | Asn | Met | Pro | Ile | Phe |
| --- | --- | --- | --- | --- | --- | --- | --- | --- | --- | --- | --- | --- | --- | --- | --- |
| | | 130 | | | | | 135 | | | | | 140 | | | |

| Cys | Ala | Lys | Pro | Ser | Ala | Pro | Thr | Asn | Leu | Thr | Lys | His | His | Ala | Val |
| --- | --- | --- | --- | --- | --- | --- | --- | --- | --- | --- | --- | --- | --- | --- | --- |
| 145 | | | | | 150 | | | | | 155 | | | | | 160 |

| Asp | Ile | Gln | Val | Pro | Ile | Gly | Cys | Gly | Gly | Val | Met | Val | Asn | Pro | Gly |
| --- | --- | --- | --- | --- | --- | --- | --- | --- | --- | --- | --- | --- | --- | --- | --- |
| | | | | 165 | | | | | 170 | | | | | 175 | |

| Asp | Val | Leu | Val | Gly | Asp | Gly | Asp | Gly | Ile | Ile | Val | Ile | Pro | Val | Glu |
| --- | --- | --- | --- | --- | --- | --- | --- | --- | --- | --- | --- | --- | --- | --- | --- |
| | | | 180 | | | | | 185 | | | | | 190 | | |

| Ile | Ala | Gln | Glu | Val | Ser | Glu | Glu | Ala | Leu | Ala | Met | Glu | Leu | Phe | Glu |
| --- | --- | --- | --- | --- | --- | --- | --- | --- | --- | --- | --- | --- | --- | --- | --- |
| | | | 195 | | | | | 200 | | | | | 205 | | |

| Asp | Phe | Val | Leu | Asp | Lys | Val | Arg | Ala | Gly | Ser | Lys | Val | Ile | Gly | Leu |
| --- | --- | --- | --- | --- | --- | --- | --- | --- | --- | --- | --- | --- | --- | --- | --- |
| | 210 | | | | | 215 | | | | | 220 | | | | |

| Tyr | Pro | Pro | Asn | Ala | Glu | Thr | Leu | Glu | Glu | Tyr | Asn | Asn | Gln | Lys | Ala |
| --- | --- | --- | --- | --- | --- | --- | --- | --- | --- | --- | --- | --- | --- | --- | --- |
| 225 | | | | | 230 | | | | | 235 | | | | | 240 |

```
<210> SEQ ID NO 17
<211> LENGTH: 792
<212> TYPE: DNA
<213> ORGANISM: Unknown
<220> FEATURE:
<223> OTHER INFORMATION: DNA obtained from environmental sample

<400> SEQUENCE: 17
atgattcggt tgaccaacct gaacccctttt gagcggtttg acgatggccg ccccaaggtg    60
cccgatgacc tgctggagcg gatgaagctg gtcaccaccg aggaggcctg gggcacgctc   120
tatcacgccg gctacctgcg ccagttcgaa ggcaagtggc acgagaccca cccgggcgtc   180
atcactgtcg gccgcgccgt caccgcccag ttcctgcccc atcgcccga ctaccacgcc    240 gtggtgcaag aaaccggcgt cggcgaaggc cgcggcagcg ccggtggtca gaactcgtgg   300
atcatcgaga gcctgcagcg caacgacgtc atggtggtcg acatcttcgg caaggtcaaa   360
gacggcacgg tcgtcggcga caacctgggc accgccgtgc gcacccgcac cgcgccggg    420 gccgtcatcg acggcggcgt gcgcgactac cagggcctga cccagctcac cgacgtcaac   480
ttctacatcc gcggtatgga cccgaccggc atcgccgacg tcaccctggc cggcctgaac   540
atccccatcc gcatcggtgg ctgcacagtc ctgcccggcg acgtggtcct cggcacgccc   600
agcggcgtcc tgttcatccc gccgcacctg gtgtcgaagg tggtcgagga gagcgaggac   660
gtccgcgtcc gcgacgagtt tggcaagagc cgcctggccg aaggcatttg acctccggc    720 cagatcgact cggcctggag cgacgagatc aaggccgact tcgagaactg gaaggccaac   780
```

```
<210> SEQ ID NO 18
<211> LENGTH: 263
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (39)...(205)
<223> OTHER INFORMATION: Demethylmenaquinone methyltransferase

<400> SEQUENCE: 18
```

| | | | | | | | | | | | | | | | |
|---|---|---|---|---|---|---|---|---|---|---|---|---|---|---|---|
| Met | Ile | Arg | Leu | Thr | Asn | Leu | Asn | Pro | Phe | Glu | Arg | Phe | Asp | Asp | Gly |
| 1 | | | | 5 | | | | | 10 | | | | | 15 | |
| Arg | Pro | Lys | Val | Pro | Asp | Asp | Leu | Leu | Glu | Arg | Met | Lys | Leu | Val | Thr |
| | | | 20 | | | | | 25 | | | | | 30 | | |
| Thr | Glu | Glu | Ala | Trp | Gly | Thr | Leu | Tyr | His | Ala | Gly | Tyr | Leu | Arg | Gln |
| | | | | 35 | | | | | 40 | | | | | 45 | |
| Phe | Glu | Gly | Lys | Trp | His | Glu | Thr | His | Pro | Gly | Val | Ile | Thr | Val | Gly |
| 50 | | | | | 55 | | | | | 60 | | | | | |
| Arg | Ala | Val | Thr | Ala | Gln | Phe | Leu | Pro | His | Arg | Pro | Asp | Tyr | His | Ala |
| 65 | | | | | 70 | | | | | 75 | | | | | 80 |
| Val | Val | Gln | Glu | Thr | Gly | Val | Gly | Glu | Gly | Arg | Gly | Ser | Ala | Gly | Gly |
| | | | | 85 | | | | | 90 | | | | | 95 | |
| Gln | Asn | Ser | Trp | Ile | Ile | Glu | Ser | Leu | Gln | Arg | Asn | Asp | Val | Met | Val |
| | | | 100 | | | | | 105 | | | | | 110 | | |
| Val | Asp | Ile | Phe | Gly | Lys | Val | Lys | Asp | Gly | Thr | Val | Val | Gly | Asp | Asn |
| | | | | 115 | | | | | 120 | | | | | 125 | |
| Leu | Gly | Thr | Ala | Val | Arg | Thr | Arg | Thr | Arg | Ala | Gly | Ala | Val | Ile | Asp |
| 130 | | | | | 135 | | | | | 140 | | | | | |
| Gly | Gly | Val | Arg | Asp | Tyr | Gln | Gly | Leu | Thr | Gln | Leu | Thr | Asp | Val | Asn |
| 145 | | | | | 150 | | | | | 155 | | | | | 160 |
| Phe | Tyr | Ile | Arg | Gly | Met | Asp | Pro | Thr | Gly | Ile | Ala | Asp | Val | Thr | Leu |
| | | | | 165 | | | | | 170 | | | | | 175 | |
| Ala | Gly | Leu | Asn | Ile | Pro | Ile | Arg | Ile | Gly | Gly | Cys | Thr | Val | Leu | Pro |
| | | | 180 | | | | | 185 | | | | | 190 | | |
| Gly | Asp | Val | Val | Leu | Gly | Thr | Pro | Ser | Gly | Val | Leu | Phe | Ile | Pro | Pro |
| | | | | 195 | | | | | 200 | | | | | 205 | |
| His | Leu | Val | Ser | Lys | Val | Val | Glu | Glu | Ser | Gly | Asp | Val | Arg | Val | Arg |
| 210 | | | | | 215 | | | | | 220 | | | | | |
| Asp | Glu | Phe | Gly | Lys | Ser | Arg | Leu | Ala | Glu | Gly | Ile | Trp | Thr | Ser | Gly |
| 225 | | | | | 230 | | | | | 235 | | | | | 240 |
| Gln | Ile | Asp | Ser | Ala | Trp | Ser | Asp | Glu | Ile | Lys | Ala | Asp | Phe | Glu | Asn |
| | | | | 245 | | | | | 250 | | | | | 255 | |
| Trp | Lys | Ala | Asn | Arg | Pro | Lys | | | | | | | | | |
| | | | 260 | | | | | | | | | | | | |

```
<210> SEQ ID NO 19
<211> LENGTH: 723
<212> TYPE: DNA
<213> ORGANISM: Unknown
<220> FEATURE:
<223> OTHER INFORMATION: DNA obtained from environmental sample

<400> SEQUENCE: 19
atgagcgatt ataccaacga gattaccggc gaaccgccag ctgctgaacc tttgccggac      60
```

-continued

```
gagcaggaaa tcttggattt tgtacggcag aagctgcatg tcgccgcggt ttgcgatatt        120
ttggatgatt tgggctaccg caatcaagcc atgcaccagc gattgcgccc gctcctaccc        180
gatattcgga actgtggttt tgtcgggcga gcgcgtacgt tgcgctggat ggagaccgat        240
tatattgtcg aggaagatcc ctatgggctg agatcgact ttatggatag tctgggcgcg         300
ggtgatgtca ttgttcattc caccgaccct ggcggcacca atgccccgtg gggcgaactc        360
atgaccacca tcgccaagtt gcgcggcgca gttggctgcg tctgcgacag ccagatacgc        420
gacacggtgc agatcatcga catgggcttc cccgtctact acacgggaat tcgtccgttg        480
gattccaaag gcggggcgcg cgtgatgggt ttggatctgc ccgtacgctg tggtgatgtg        540
ttggtgcatc ctggcgatct catcttcgcc gaccatgacg gcatcgtggt cattccgcaa        600
gcgcaggtgc agcaggtact caagctggcc caagaaaaga tggagaagga gaaccacacg        660
cgcaatgacc tgctcgcggg caagacactg cgcgaggtct atgatacgta tggggtgttg        720
tag                                                                      723
```

<210> SEQ ID NO 20
<211> LENGTH: 240
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (30)...(197)
<223> OTHER INFORMATION: Demethylmenaquinone methyltransferase
<220> FEATURE:
<221> NAME/KEY: SITE
<222> LOCATION: (221)...(224)
<223> OTHER INFORMATION: N-glycosylation site. Prosite id = PS00001

<400> SEQUENCE: 20

```
Met Ser Asp Tyr Thr Asn Glu Ile Thr Gly Glu Pro Pro Ala Ala Glu
1               5                  10                  15

Pro Leu Pro Asp Glu Gln Glu Ile Leu Asp Phe Val Arg Gln Lys Leu
            20                  25                  30

His Val Ala Ala Val Cys Asp Ile Leu Asp Leu Gly Tyr Arg Asn
        35                  40                  45

Gln Ala Met His Gln Arg Leu Arg Pro Leu Leu Pro Asp Ile Arg Asn
    50                  55                  60

Cys Gly Phe Val Gly Arg Ala Arg Thr Leu Arg Trp Met Glu Thr Asp
65                  70                  75                  80

Tyr Ile Val Glu Glu Asp Pro Tyr Gly Leu Glu Ile Asp Phe Met Asp
                85                  90                  95

Ser Leu Gly Ala Gly Asp Val Ile Val His Ser Thr Asp Pro Gly Gly
            100                 105                 110

Thr Asn Ala Pro Trp Gly Glu Leu Met Thr Thr Ile Ala Lys Leu Arg
        115                 120                 125

Gly Ala Val Gly Cys Val Cys Asp Ser Gln Ile Arg Asp Thr Val Gln
    130                 135                 140

Ile Ile Asp Met Gly Phe Pro Val Tyr Tyr Thr Gly Ile Arg Pro Leu
145                 150                 155                 160

Asp Ser Lys Gly Arg Ala Arg Val Met Gly Leu Asp Leu Pro Val Arg
                165                 170                 175

Cys Gly Asp Val Leu Val His Pro Gly Asp Leu Ile Phe Ala Asp His
            180                 185                 190

Asp Gly Ile Val Val Ile Pro Gln Ala Gln Val Gln Gln Val Leu Lys
        195                 200                 205
```

```
Leu Ala Gln Glu Lys Met Glu Lys Glu Asn His Thr Arg Asn Asp Leu
    210                 215                 220

Leu Ala Gly Lys Thr Leu Arg Glu Val Tyr Asp Thr Tyr Gly Val Leu
225                 230                 235                 240

<210> SEQ ID NO 21
<211> LENGTH: 444
<212> TYPE: DNA
<213> ORGANISM: Unknown
<220> FEATURE:
<223> OTHER INFORMATION: DNA obtained from environmental sample

<400> SEQUENCE: 21
atgaccaagc cgctgagtga agccgcgcgc gccaagctcg ccaccgtcag taccgccacg      60
ctgacgacgc aactgttcaa gcgcgggctg cgcaacacct tcatccaggg cgcacgcccc     120
ctcaatcccg acgcgccgcc gatggtcggc ccggcctaca cgctgcgcta tcccggca      180 cgcgaggaca tcgacacgct cgatgtgttc aatgaccgca cccacccgca acgcaaggcc     240
gtggaggaca tcccgccggg cagcgtgctg gtgatggact gccgcggcga cgcgagcgtc     300
gcgtcggccg gcagcatcct ggtgaccccg atgatgatgc gcggcgcagc cggcgtggtc     360
agcgacggcg gcctgcgcga ttcccccgag atcgcgaagc tcccctcccc cacctactgc     420
cagggcgggt cggcgcccac caac                                             444

<210> SEQ ID NO 22
<211> LENGTH: 148
<212> TYPE: PRT
<213> ORGANISM: Unknown
<220> FEATURE:
<223> OTHER INFORMATION: Protein obtained from environmental sample

<400> SEQUENCE: 22

Met Thr Lys Pro Leu Ser Glu Ala Ala Arg Ala Lys Leu Ala Thr Val
1               5                   10                  15

Ser Thr Ala Thr Leu Thr Thr Gln Leu Phe Lys Arg Gly Leu Arg Asn
            20                  25                  30

Thr Phe Ile Gln Gly Ala Arg Pro Leu Asn Pro Asp Ala Pro Pro Met
        35                  40                  45

Val Gly Pro Ala Tyr Thr Leu Arg Tyr Ile Pro Ala Arg Glu Asp Ile
    50                  55                  60

Asp Thr Leu Asp Val Phe Asn Asp Arg Thr His Pro Gln Arg Lys Ala
65                  70                  75                  80

Val Glu Asp Ile Pro Pro Gly Ser Val Leu Val Met Asp Cys Arg Gly
                85                  90                  95

Asp Ala Ser Val Ala Ser Ala Gly Ser Ile Leu Val Thr Arg Met Met
            100                 105                 110

Met Arg Gly Ala Ala Gly Val Val Ser Asp Gly Gly Leu Arg Asp Ser
        115                 120                 125

Pro Glu Ile Ala Lys Leu Pro Phe Pro Thr Tyr Cys Gln Gly Gly Ser
    130                 135                 140

Ala Pro Thr Asn
145

<210> SEQ ID NO 23
<211> LENGTH: 801
<212> TYPE: DNA
<213> ORGANISM: Unknown
<220> FEATURE:
<223> OTHER INFORMATION: DNA obtained from environmental sample
```

<400> SEQUENCE: 23

```
atgatcaatt gcctcgcggc taaaccacag cggccttccc aattatccaa tccctatcag      60
gagcctgcca tgccagccat ctccctcgaa gtgcttgaga aactgcgcgc atacgatacg     120
cccaccattt gcaacgtgat cgagctgttc gacgtgcggc cgcgcaccag cggctacatg     180
gatgcccgca tccgcgcctg cttccccgag atgccgccgg tggtgggctt tgcctccacc     240
gccaccttcc gcgcttctga agcgccgctc tccggcccgg atatctacgg ctcgctgaac     300
ctgcaagtgg agagctttgg cacgctctcc ggcccggcca tcgtggtctt tcaagacctg     360
gacgacccgg cggtggcggc aacctttggc gaggtgatgt gcaccaccta ccagacgtac     420
ggatcggtcg gctgatcac ctctggcgcg gggcgcgacc tggaccaggt acgcaagatt      480
ggttactcgg tcttcaccaa cggcgcgatt tgctcgcacg gctactgcca cattccggat     540
gtcaacgtgc cggtgcgggt gggcggctta atcgtgcgcc cggatgatct gctgcacatg     600
gacgtgaacg gcgtgaccaa catccccaag gagatcgcgg cggaggtggc ggaggcctgc     660
gaggcctacg tggcggcgga gatggcgacg ctgaacgggc tgcatgcgta taggcaagat     720
ggggatgccg ggaagctgca agaggcgaag aaggagagta aaggctgat gcaggcgctg      780
aaggaacggg tgaggaggta a                                               801
```

<210> SEQ ID NO 24
<211> LENGTH: 266
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (36)...(207)
<223> OTHER INFORMATION: Demethylmenaquinone methyltransferase

<400> SEQUENCE: 24

```
Met Ile Asn Cys Leu Ala Ala Lys Pro Gln Arg Pro Ser Gln Leu Ser
1               5                   10                  15
Asn Pro Tyr Gln Glu Pro Ala Met Pro Ala Ile Ser Leu Glu Val Leu
            20                  25                  30
Glu Lys Leu Arg Ala Tyr Asp Thr Pro Thr Ile Cys Asn Val Ile Glu
        35                  40                  45
Leu Phe Asp Val Arg Pro Arg Thr Ser Gly Tyr Met Asp Ala Arg Ile
    50                  55                  60
Arg Ala Cys Phe Pro Glu Met Pro Pro Val Val Gly Phe Ala Ser Thr
65                  70                  75                  80
Ala Thr Phe Arg Ala Ser Glu Ala Pro Leu Ser Gly Pro Asp Ile Tyr
                85                  90                  95
Gly Ser Leu Asn Leu Gln Val Glu Ser Phe Gly Thr Leu Ser Gly Pro
            100                 105                 110
Ala Ile Val Val Phe Gln Asp Leu Asp Asp Pro Ala Val Ala Ala Thr
        115                 120                 125
Phe Gly Glu Val Met Cys Thr Thr Tyr Gln Thr Tyr Gly Ser Val Gly
    130                 135                 140
Leu Ile Thr Ser Gly Ala Gly Arg Asp Leu Asp Gln Val Arg Lys Ile
145                 150                 155                 160
Gly Tyr Ser Val Phe Thr Asn Gly Ala Ile Cys Ser His Gly Tyr Cys
                165                 170                 175
His Ile Pro Asp Val Asn Val Pro Val Arg Val Gly Gly Leu Ile Val
            180                 185                 190
```

```
Arg Pro Asp Asp Leu Leu His Met Asp Val Asn Gly Val Thr Asn Ile
            195                 200                 205

Pro Lys Glu Ile Ala Ala Glu Val Ala Glu Ala Cys Glu Ala Tyr Val
        210                 215                 220

Ala Ala Glu Met Ala Thr Leu Asn Gly Leu His Ala Tyr Arg Gln Asp
225                 230                 235                 240

Gly Asp Ala Gly Lys Leu Gln Glu Ala Lys Lys Glu Ser Lys Arg Leu
                245                 250                 255

Met Gln Ala Leu Lys Glu Arg Val Arg Arg
            260                 265

<210> SEQ ID NO 25
<211> LENGTH: 741
<212> TYPE: DNA
<213> ORGANISM: Unknown
<220> FEATURE:
<223> OTHER INFORMATION: DNA obtained from environmental sample

<400> SEQUENCE: 25
atggctgaga agaaactgac cgggcggatt gcgcgggaga aaatcaggtt gatggaggtg      60
ccgcggccgc cgcaaggcgt cgtcgagcgg ttcaagtcgc tcggcgattg caccggcatc     120
atttccgaca ccatggatga actgggcatc ccgaacggcg tgatcggcgc gtcagtgctg     180
cgaccaacca tccccggcac cgtcatcgcc gggccggcgt tgacgctgcg caacattctc     240
cagcgcatcg atccactcgc cggcgcgcgc gagcacgtca acaagatggc cgagttcgaa     300
tgtcacaacc tcgcgacccc gggcgacgtg ctggtgatcc aggggggtgcc gaacgtctcc    360 agtatgggag gcatctcggc gctgaccggc aagcgcgccg gtgaagtcgg cgccatcgtc     420
gaaggcggca tccgcgacat tgcacattcg cgtgaggttg gctttccact gtggtcgagc     480
cagatcacgc cggtcaccgg caagtggcgg ctggaggcgg ccgagatcaa cggcaccatc     540
gaaatcggcg gcgtgcaggt gcaccccggc gatctggtgg tggccgacga caccggcgtc     600
tgcttcatcc cgcgcgacaa cattctggaa gtgctcgccg agtgcgagaa gaaagcgaag     660
gccgaggacc tgcgctgcaa ggcgatcgat ggcggcgtcc cggtgccgga tatctcgaaa     720
tcgacgtatg gagagacgtg a                                              741

<210> SEQ ID NO 26
<211> LENGTH: 246
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (38)...(202)
<223> OTHER INFORMATION: Demethylmenaquinone methyltransferase
<220> FEATURE:
<221> NAME/KEY: SITE
<222> LOCATION: (119)...(122)
<223> OTHER INFORMATION: N-glycosylation site. Prosite id = PS00001
<220> FEATURE:
<221> NAME/KEY: SITE
<222> LOCATION: (179)...(182)
<223> OTHER INFORMATION: N-glycosylation site. Prosite id = PS00001

<400> SEQUENCE: 26

Met Ala Glu Lys Lys Leu Thr Gly Arg Ile Ala Arg Glu Lys Ile Arg
1               5                   10                  15

Leu Met Glu Val Pro Arg Pro Pro Gln Gly Val Val Arg Phe Lys
            20                  25                  30
```

Ser Leu Gly Asp Cys Thr Gly Ile Ile Ser Asp Thr Met Asp Glu Leu
            35                   40                  45

Gly Ile Pro Asn Gly Val Ile Gly Ala Ser Val Leu Arg Pro Thr Ile
        50                  55                  60

Pro Gly Thr Val Ile Ala Gly Pro Ala Leu Thr Leu Arg Asn Ile Leu
65                  70                  75                  80

Gln Arg Ile Asp Pro Leu Ala Gly Ala Arg Glu His Val Asn Lys Met
                85                  90                  95

Ala Glu Phe Glu Cys His Asn Leu Ala Thr Pro Gly Asp Val Leu Val
            100                 105                 110

Ile Gln Gly Val Pro Asn Val Ser Ser Met Gly Gly Ile Ser Ala Leu
        115                 120                 125

Thr Gly Lys Arg Ala Gly Glu Val Gly Ala Ile Val Glu Gly Gly Ile
    130                 135                 140

Arg Asp Ile Ala His Ser Arg Glu Val Gly Phe Pro Leu Trp Ser Ser
145                 150                 155                 160

Gln Ile Thr Pro Val Thr Gly Lys Trp Arg Leu Glu Ala Ala Glu Ile
                165                 170                 175

Asn Gly Thr Ile Glu Ile Gly Gly Val Gln Val His Pro Gly Asp Leu
            180                 185                 190

Val Val Ala Asp Asp Thr Gly Val Cys Phe Ile Pro Arg Asp Asn Ile
        195                 200                 205

Leu Glu Val Leu Ala Glu Cys Glu Lys Lys Ala Lys Ala Glu Asp Leu
    210                 215                 220

Arg Cys Lys Ala Ile Asp Gly Val Pro Val Pro Asp Ile Ser Lys
225                 230                 235                 240

Ser Thr Tyr Gly Glu Thr
                245

<210> SEQ ID NO 27
<211> LENGTH: 693
<212> TYPE: DNA
<213> ORGANISM: Unknown
<220> FEATURE:
<223> OTHER INFORMATION: DNA obtained from environmental sample

<400> SEQUENCE: 27
atgatttatc agccggggac aacaggcatc gtcgtgcagg atattgcacg cgctgatcaa      60
gccattatcg atggcctagc agaatgtggt gtggcgacgg tgcatgaggc acaggggcgc     120
aagggcctgt tggcggatta tatgacgccg atttactcgg gcgcgcgcat cgctggatct     180
gcggtgacca ttctggcacc gccgtgtgac aattggatga tccatgtggc ggtagaacag     240
ttgcaaaagg gcgatgtgtt gctgctgggc acgatcacac cgtccaatgc tggctatttc     300
ggtgacttgc tggccacgtc agccatggcg cacggttgtc gcggattgat cattgatggc     360
ggtgtgcgcg atgtgcaaga gctgacggat atgggctttc cggtttggtc caaggccgta     420
catgcccaag gcacaatcaa agaaacgctg gatcggtca acgtgccagt tgtctgcggc     480
caagagttgg taaaccccgg tgatattgtg gtggccgacg atgacggggt gtgcgttgtg     540
cgccgcgaag aagctgctga tgtgctggct aaggcgcggg cgcgcgagag caatgaagcg     600
gccaagcgcg cgcgttttga ggccggtgag ctggggctgg atatctatga catgcgcgcg     660
cggctggccg aaaaaggact gaaatacgtc tga                                   693

<210> SEQ ID NO 28
<211> LENGTH: 230
<212> TYPE: PRT

```
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (27)...(179)
<223> OTHER INFORMATION: Demethylmenaquinone methyltransferase

<400> SEQUENCE: 28

Met Ile Tyr Gln Pro Gly Thr Thr Gly Ile Val Val Gln Asp Ile Ala
1               5                   10                  15

Arg Ala Asp Gln Ala Ile Ile Asp Gly Leu Ala Glu Cys Gly Val Ala
            20                  25                  30

Thr Val His Glu Ala Gln Gly Arg Lys Gly Leu Leu Ala Asp Tyr Met
        35                  40                  45

Thr Pro Ile Tyr Ser Gly Ala Arg Ile Ala Gly Ser Ala Val Thr Ile
    50                  55                  60

Leu Ala Pro Pro Cys Asp Asn Trp Met Ile His Val Ala Val Glu Gln
65                  70                  75                  80

Leu Gln Lys Gly Asp Val Leu Leu Gly Thr Ile Thr Pro Ser Asn
                85                  90                  95

Ala Gly Tyr Phe Gly Asp Leu Leu Ala Thr Ser Ala Met Ala His Gly
            100                 105                 110

Cys Arg Gly Leu Ile Ile Asp Gly Gly Val Arg Asp Val Gln Glu Leu
        115                 120                 125

Thr Asp Met Gly Phe Pro Val Trp Ser Lys Ala Val His Ala Gln Gly
    130                 135                 140

Thr Ile Lys Glu Thr Leu Gly Ser Val Asn Val Pro Val Val Cys Gly
145                 150                 155                 160

Gln Glu Leu Val Asn Pro Gly Asp Ile Val Val Ala Asp Asp Gly
                165                 170                 175

Val Cys Val Val Arg Arg Glu Glu Ala Ala Asp Val Leu Ala Lys Ala
            180                 185                 190

Arg Ala Arg Glu Ser Asn Glu Ala Lys Arg Ala Arg Phe Glu Ala
        195                 200                 205

Gly Glu Leu Gly Leu Asp Ile Tyr Asp Met Arg Ala Arg Leu Ala Glu
    210                 215                 220

Lys Gly Leu Lys Tyr Val
225                 230

<210> SEQ ID NO 29
<211> LENGTH: 756
<212> TYPE: DNA
<213> ORGANISM: Unknown
<220> FEATURE:
<223> OTHER INFORMATION: DNA obtained from environmental sample

<400> SEQUENCE: 29
ttgcagcgac agctttccac actgcagcgg cgatggaagg cttatacgtc gggcatggaa      60
cagaagattg cggaacggct gtcggccttg tcggtggcgc atctggccga tggctgcctg     120
cgtgccggaa cggcgatgcg ggtggtggcc aatctacccc cgatcgtagc tggtcagcga     180
acgtccggcc ggacacggcc ggtgcggcat tacggcagcg tcgacgtctt ccttgaagcg     240
ctggccgacc ccagggcggg cgatgtgctg gtcgtcgaca tggcgaccg ggacgatgaa      300 ggctgcatcg gcgacctgac ggcgctggaa gtcgctcagg ccgggctggc cgggatcatc     360
atctcggggc cggcaccgcga cacggcgatc ctccgctcca ttccaatcgc cttgttcagc    420
cgcggtgcct gcgcgcgtgg gccggtccgg ctcgacgtcc gcgcgccgga gacattcgtc     480
```

```
agcgcccgca ttggcgacga ggtcgtaacc gcagcagatt gggtagcggc cgatgacgac    540
ggcgccatct tcatcggcga caaccatatt gcggcggtgg tcgcggcggc ggagtcgatc    600
cgcgacaccg agctccggca gaccgggctg atgaaggccg ggacaagctt gcgcgagcag    660
cttgaggtcg cggcttatct ggacgcgcgg gcggcggatc cggcgctgga cttccgcgcc    720
catttgcgcg cgctcaacgc ggcgatcgag gaatga                              756
```

```
<210> SEQ ID NO 30
<211> LENGTH: 251
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (28)...(184)
<223> OTHER INFORMATION: Demethylmenaquinone methyltransferase

<400> SEQUENCE: 30
```

```
Met Gln Arg Gln Leu Ser Thr Leu Gln Arg Arg Trp Lys Ala Tyr Thr
1               5                   10                  15

Ser Gly Met Glu Gln Lys Ile Ala Glu Arg Leu Ser Ala Leu Ser Val
            20                  25                  30

Ala His Leu Ala Asp Gly Cys Leu Arg Ala Gly Thr Ala Met Arg Val
        35                  40                  45

Val Ala Asn Leu Pro Pro Ile Val Ala Gly Gln Arg Thr Ser Gly Arg
    50                  55                  60

Thr Arg Pro Val Arg His Tyr Gly Ser Val Asp Val Phe Leu Glu Ala
65                  70                  75                  80

Leu Ala Asp Pro Arg Ala Gly Asp Val Leu Val Val Asp Asn Gly Asp
                85                  90                  95

Arg Asp Asp Glu Gly Cys Ile Gly Asp Leu Thr Ala Leu Glu Val Ala
            100                 105                 110

Gln Ala Gly Leu Ala Gly Ile Ile Ile Ser Gly Arg His Arg Asp Thr
        115                 120                 125

Ala Ile Leu Arg Ser Ile Pro Ile Ala Leu Phe Ser Arg Gly Ala Cys
130                 135                 140

Ala Arg Gly Pro Val Arg Leu Asp Val Arg Ala Pro Glu Thr Phe Val
145                 150                 155                 160

Ser Ala Arg Ile Gly Asp Glu Val Val Thr Ala Ala Asp Trp Val Ala
                165                 170                 175

Ala Asp Asp Asp Gly Ala Ile Phe Ile Gly Asp Asn His Ile Ala Ala
            180                 185                 190

Val Val Ala Ala Ala Glu Ser Ile Arg Asp Thr Glu Leu Arg Gln Thr
        195                 200                 205

Gly Leu Met Lys Ala Gly Thr Ser Leu Arg Glu Gln Leu Glu Val Ala
    210                 215                 220

Ala Tyr Leu Asp Ala Arg Ala Ala Asp Pro Ala Leu Asp Phe Arg Ala
225                 230                 235                 240

His Leu Arg Ala Leu Asn Ala Ala Ile Glu Glu
                245                 250
```

```
<210> SEQ ID NO 31
<211> LENGTH: 327
<212> TYPE: DNA
<213> ORGANISM: Unknown
<220> FEATURE:
<223> OTHER INFORMATION: DNA obtained from environmental sample
```

<400> SEQUENCE: 31

```
gtgagacagg gaatgcgact tgctcacacg cgtgtggcgc ccgaacttgt atcggccttc    60
tcggctgttc agaccgccac gattcacgag gcacaaggtg gtatcggtgc ggtcgcggcg   120
gatattcgcc ctctcgaccg ggcaatgtcc atctgcggcc ctgccctgac gatcaaaact   180
ccgcccgcgg acaacctggc gcttcaccag gcgctttatc tcgcggaacc gggtgacgtg   240
ctggtggtcg attgcgcaag ccacaccgag gccgggcaat ggggcggcat tctcatggaa   300
gcagccaagg tgcgcggcat agccggg                                       327
```

<210> SEQ ID NO 32
<211> LENGTH: 109
<212> TYPE: PRT
<213> ORGANISM: Unknown
<220> FEATURE:
<223> OTHER INFORMATION: Protein obtained from environmental sample

<400> SEQUENCE: 32

```
Met Arg Gln Gly Met Arg Leu Ala His Thr Arg Val Ala Pro Glu Leu
1               5                   10                  15
Val Ser Ala Phe Ser Ala Val Gln Thr Ala Thr Ile His Glu Ala Gln
            20                  25                  30
Gly Gly Ile Gly Ala Val Ala Asp Ile Arg Pro Leu Asp Arg Ala
        35                  40                  45
Met Ser Ile Cys Gly Pro Ala Leu Thr Ile Lys Thr Pro Pro Ala Asp
    50                  55                  60
Asn Leu Ala Leu His Gln Ala Leu Tyr Leu Ala Glu Pro Gly Asp Val
65                  70                  75                  80
Leu Val Val Asp Cys Ala Ser His Thr Glu Ala Gly Gln Trp Gly Gly
                85                  90                  95
Ile Leu Met Glu Ala Ala Lys Val Arg Gly Ile Ala Gly
            100                 105
```

<210> SEQ ID NO 33
<211> LENGTH: 681
<212> TYPE: DNA
<213> ORGANISM: Unknown
<220> FEATURE:
<223> OTHER INFORMATION: DNA obtained from environmental sample

<400> SEQUENCE: 33

```
gcgctcgaga gcgtcacgac cgcgacgctg accaccgtgc tgctgaagca gggcctgcgc    60
aacgtctgga tgcgcggcac ccggccgctg gcgagcggtc agccgcgcaa ggtcgggcgc   120
gcgttcacgc tccgcttcgt gccggcgcgc gaggacctcg cgaccccggc ttcatggggc   180
gcgccgatct cgacccgcgc cgcgatcgag gcgatgccgg aaggcgtgat cgcggtcgcc   240
gatgcgatgg gcgtgactga cgccggcatc ttcggcgaca tcctgtgcgc ccggatgcgc   300
cggcgcaacg tggccgcgct cgtgaccgac ggcgtgatcc gcgacctggc cggcgtgctg   360
agcaccggcc tgccggtctg gtgccagggt accgcagcgc cttcgtcggt caccggcctg   420
accttcgtcg cctggcagca gccggtcggc tgcggtgggg tggcggtgtt cccgaacgac   480
gtggtcgtca tcgacgccga cggcgcggtc gtcatcccgg ctgcgctgct cgatggcgtc   540
atcgcggagg cgatcgagca ggagacccag gagggctgga tcatgcggga ggtggagggc   600
ggtgcggcgc tgccgggcct ctatccgatg aacgaggcga cgaaggcgcg ctacgaagcc   660
tggaagaagg cgagcgactg a                                             681
```

<210> SEQ ID NO 34
<211> LENGTH: 226
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (3)...(171)
<223> OTHER INFORMATION: Demethylmenaquinone methyltransferase

<400> SEQUENCE: 34

```
Ala Leu Glu Ser Val Thr Thr Ala Thr Leu Thr Thr Val Leu Leu Lys
1               5                   10                  15

Gln Gly Leu Arg Asn Val Trp Met Arg Gly Thr Arg Pro Leu Ala Ser
            20                  25                  30

Gly Gln Pro Arg Lys Val Gly Arg Ala Phe Thr Leu Arg Phe Val Pro
        35                  40                  45

Ala Arg Glu Asp Leu Ala Thr Pro Ala Ser Trp Gly Ala Pro Ile Ser
    50                  55                  60

Thr Arg Ala Ala Ile Glu Ala Met Pro Glu Gly Val Ile Ala Val Ala
65                  70                  75                  80

Asp Ala Met Gly Val Thr Asp Ala Gly Ile Phe Gly Asp Ile Leu Cys
                85                  90                  95

Ala Arg Met Arg Arg Asn Val Ala Ala Leu Val Thr Asp Gly Val
            100                 105                 110

Ile Arg Asp Leu Ala Gly Val Leu Ser Thr Gly Leu Pro Val Trp Cys
        115                 120                 125

Gln Gly Thr Ala Ala Pro Ser Ser Val Thr Gly Leu Thr Phe Val Ala
    130                 135                 140

Trp Gln Gln Pro Val Gly Cys Gly Gly Val Ala Val Phe Pro Asn Asp
145                 150                 155                 160

Val Val Val Ile Asp Ala Asp Gly Ala Val Val Ile Pro Ala Ala Leu
                165                 170                 175

Leu Asp Gly Val Ile Ala Glu Ala Ile Glu Gln Glu Thr Gln Glu Gly
            180                 185                 190

Trp Ile Met Arg Glu Val Glu Gly Gly Ala Ala Leu Pro Gly Leu Tyr
        195                 200                 205

Pro Met Asn Glu Ala Thr Lys Ala Arg Tyr Glu Ala Trp Lys Lys Ala
    210                 215                 220

Ser Asp
225
```

<210> SEQ ID NO 35
<211> LENGTH: 681
<212> TYPE: DNA
<213> ORGANISM: Unknown
<220> FEATURE:
<223> OTHER INFORMATION: DNA obtained from environmental sample

<400> SEQUENCE: 35

```
gtgaccgatc cggttgtcgt tcgacagatc gacaggccgt ccgcgaatct ggtcgctgat      60
ctgcagcgct acggcgtctc caccgtgcac gaggcgcaag ggcgtcgcgg cctgctcgcg     120
tcgtacatgc ggccgatcta tgccggcgcg ctcatcgccg gtcccgcgat acgtgtcctg     180
gtgccgcctg cgacaacttt gatgatccac gtcgccgtgg aagtgtgcca gcccggcgac     240
gttctcatcg tcgccaccac ctcgccgtgc accgacggct atttcggcga gctgctggcg     300
acgtcgctgc gggcccgcgg cgtggcgggg ctcgtgatcg atgcgggctg ccgggatgtt     360
```

```
cgcgcgctga cagaaatgcg atttcccgtc tggagccgcg cgatcagcgc gcagggaacc        420
gtcaaagcga cgctgggctc ggtgaacgcg gcggtggtgt gcgccggggc gtcggtgaga        480
gccggggatc tcatcgtggc cgacgatgac ggggtggtgg cggtgcggcg ggaggaagtc        540
gtcgccgtga cgcaggcagc cgaacagcgc gttcgcaagg aagagggcac gcgcgcacgg        600
ctcgcgcagg gcgagctcgg cctggacatt tacggcttgc gccagaagct gtcggatctc        660
ggcttgaagt catcgtcgtg a                                                  681
```

<210> SEQ ID NO 36
<211> LENGTH: 226
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 36

```
Met Thr Asp Pro Val Val Arg Gln Ile Asp Arg Pro Ser Ala Asn
 1               5                  10                  15

Leu Val Ala Asp Leu Gln Arg Tyr Gly Val Ser Thr Val His Glu Ala
                20                  25                  30

Gln Gly Arg Arg Gly Leu Leu Ala Ser Tyr Met Arg Pro Ile Tyr Ala
            35                  40                  45

Gly Ala Leu Ile Ala Gly Pro Ala Ile Thr Val Leu Val Pro Pro Gly
        50                  55                  60

Asp Asn Leu Met Ile His Val Ala Val Glu Val Cys Gln Pro Gly Asp
65                  70                  75                  80

Val Leu Ile Val Ala Thr Thr Ser Pro Cys Thr Asp Gly Tyr Phe Gly
                85                  90                  95

Glu Leu Leu Ala Thr Ser Leu Arg Ala Arg Gly Val Ala Gly Leu Val
            100                 105                 110

Ile Asp Ala Gly Cys Arg Asp Val Arg Ala Leu Thr Glu Met Arg Phe
        115                 120                 125

Pro Val Trp Ser Arg Ala Ile Ser Ala Gln Gly Thr Val Lys Ala Thr
    130                 135                 140

Leu Gly Ser Val Asn Ala Ala Val Val Cys Ala Gly Ala Ser Val Arg
145                 150                 155                 160

Ala Gly Asp Leu Ile Val Ala Asp Asp Gly Val Val Ala Val Arg
                165                 170                 175

Arg Glu Glu Val Val Ala Val Thr Gln Ala Ala Glu Gln Arg Val Arg
            180                 185                 190

Lys Glu Glu Gly Thr Arg Ala Arg Leu Ala Gln Gly Glu Leu Gly Leu
        195                 200                 205

Asp Ile Tyr Gly Leu Arg Gln Lys Leu Ser Asp Leu Gly Leu Lys Ser
    210                 215                 220

Ser Ser
225
```

<210> SEQ ID NO 37
<211> LENGTH: 675
<212> TYPE: DNA
<213> ORGANISM: Unknown
<220> FEATURE:
<223> OTHER INFORMATION: DNA obtained from environmental sample -continued

```
<400> SEQUENCE: 37
atggccggcg tcgtggttca acagatcgag cgcgccggtc tcgacactgc cgctgccctc      60
ggggaatgcg gcgtcgccac agtgcacgag gcgcagggcc ggacagggct gatgcgctcc     120
tacatgcggc cgatttattc aggcgcccgc gttgcgggcc ccgcggtaac ggtgtctatc     180
ccgccgggcg acaactggat gattcacgtc gctgtggaac agtgccggga aggcgacgtc     240
ctcgtcgtgg cgccgacgag tccttgcgag acggctatt tcggcgagct gctcgcctgc     300
tcgctgcaga cccgccgagt gagcggtctc atcatagagg ccggggtgcg cgacgtccgc     360
gagctgaccg agatgcggtt cccggtttgg tccaaggcga ttctcgcaca agggactgtg     420
aaggaaacca tcggctcggt gaacgtcgca atcgtctgcg ccggtgcggc ggtcagtccc     480
ggcgacgtga tcgtcgccga tgacgacggc gtctgcattg tgccgcgcgg acaggcggag     540
acggtgcttc aggcgagccg cgcccgcgag gcgaaggagg ccgaaacgcg gcggcggctc     600
cggtcgggcg aactcggcct cgatatctac agcatgcgcg aaaagctggc ggccaggggc     660
ctgaaatatg tctga                                                      675

<210> SEQ ID NO 38
<211> LENGTH: 224
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (21)...(173)
<223> OTHER INFORMATION: Demethylmenaquinone methyltransferase

<400> SEQUENCE: 38

Met Ala Gly Val Val Gln Gln Ile Glu Arg Ala Gly Leu Asp Thr
1               5                   10                  15

Ala Ala Ala Leu Gly Glu Cys Gly Val Ala Thr Val His Glu Ala Gln
            20                  25                  30

Gly Arg Thr Gly Leu Met Arg Ser Tyr Met Arg Pro Ile Tyr Ser Gly
        35                  40                  45

Ala Arg Val Ala Gly Pro Ala Val Thr Val Ser Ile Pro Pro Gly Asp
    50                  55                  60

Asn Trp Met Ile His Val Ala Val Glu Gln Cys Arg Glu Gly Asp Val
65                  70                  75                  80

Leu Val Val Ala Pro Thr Ser Pro Cys Glu Asp Gly Tyr Phe Gly Glu
                85                  90                  95

Leu Leu Ala Cys Ser Leu Gln Thr Arg Arg Val Ser Gly Leu Ile Ile
            100                 105                 110

Glu Ala Gly Val Arg Asp Val Arg Glu Leu Thr Glu Met Arg Phe Pro
        115                 120                 125

Val Trp Ser Lys Ala Ile Leu Ala Gln Gly Thr Val Lys Glu Thr Ile
130                 135                 140

Gly Ser Val Asn Val Ala Ile Val Cys Ala Gly Ala Ala Val Ser Pro
145                 150                 155                 160

Gly Asp Val Ile Val Ala Asp Asp Asp Gly Val Cys Ile Val Pro Arg
                165                 170                 175

Gly Gln Ala Glu Thr Val Leu Gln Ala Ser Arg Ala Arg Glu Ala Lys
            180                 185                 190

Glu Ala Glu Thr Arg Arg Arg Leu Arg Ser Gly Glu Leu Gly Leu Asp
        195                 200                 205

Ile Tyr Ser Met Arg Glu Lys Leu Ala Ala Arg Gly Leu Lys Tyr Val
```

<210> SEQ ID NO 39
<211> LENGTH: 672
<212> TYPE: DNA
<213> ORGANISM: Unknown
<220> FEATURE:
<223> OTHER INFORMATION: DNA obtained from environmental sample

<400> SEQUENCE: 39

| | |
|---|---|
| atggccaaag ttgttcaaaa tatcgaacgc gcagcccaaa aggtgattga tgcgcttggg | 60 |
| gcctgcggtg ttgccacggt gcatgaggcg caggggcgca aaggcctgct cgcttcctat | 120 |
| atgcggccga tttattccgg tgcgcggctt gcggcatcgg cggtgaccat atcggctgca | 180 |
| cccggtgata actggatggt gcatgtggcg attgagcaag tgaaagaggg cgacattttg | 240 |
| gtgcttgccc cgacctcgcc ttgtgaagac ggctattttg gcgatctgct ggcgacatcg | 300 |
| atgcaggcgc gtggcgggcg tgggctgatt atcgatgccg gggttcgcga tattcgcgat | 360 |
| ctgacggaaa tgggttttcc ggtgtggtca aaggcgattt atgcccaagg cacggtcaag | 420 |
| aaaacgctgg ggtcggttaa tattcctatc gtctgcgccg gtgcgcttat caatgctggc | 480 |
| gacattattg ttgccgatga tgacggtgtg tgtgttgtgg cccgagaaga ggccgaagcg | 540 |
| gtgctggcca aggcgcaggc gcgcgaggcc aatgaggaag acaagcgcaa gcggttggct | 600 |
| gccggtgagt tggggcttga tatgtataac atgcgcgcac ggctggcgga aaagggcctg | 660 |
| aaatatgttt ag | 672 |

<210> SEQ ID NO 40
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 40

Met Ala Lys Val Val Gln Asn Ile Glu Arg Ala Ala Gln Lys Val Ile
1               5                   10                  15

Asp Ala Leu Gly Ala Cys Gly Val Ala Thr Val His Glu Ala Gln Gly
            20                  25                  30

Arg Lys Gly Leu Leu Ala Ser Tyr Met Arg Pro Ile Tyr Ser Gly Ala
        35                  40                  45

Arg Leu Ala Ala Ser Ala Val Thr Ile Ser Ala Pro Gly Asp Asn
    50                  55                  60

Trp Met Val His Val Ala Ile Glu Gln Val Lys Glu Gly Asp Ile Leu
65                  70                  75                  80

Val Leu Ala Pro Thr Ser Pro Cys Glu Asp Gly Tyr Phe Gly Asp Leu
                85                  90                  95

Leu Ala Thr Ser Met Gln Ala Arg Gly Gly Arg Gly Leu Ile Ile Asp
            100                 105                 110

Ala Gly Val Arg Asp Ile Arg Asp Leu Thr Glu Met Gly Phe Pro Val
        115                 120                 125

Trp Ser Lys Ala Ile Tyr Ala Gln Gly Thr Val Lys Lys Thr Leu Gly
    130                 135                 140

Ser Val Asn Ile Pro Ile Val Cys Ala Gly Ala Leu Ile Asn Ala Gly
145                 150                 155                 160

```
Asp Ile Ile Val Ala Asp Asp Gly Val Cys Val Val Ala Arg Glu
                165                 170                 175

Glu Ala Glu Ala Val Leu Ala Lys Ala Gln Ala Arg Glu Ala Asn Glu
        180                 185                 190

Glu Asp Lys Arg Lys Arg Leu Ala Ala Gly Glu Leu Gly Leu Asp Met
    195                 200                 205

Tyr Asn Met Arg Ala Arg Leu Ala Glu Lys Gly Leu Lys Tyr Val
210                 215                 220

<210> SEQ ID NO 41
<211> LENGTH: 672
<212> TYPE: DNA
<213> ORGANISM: Unknown
<220> FEATURE:
<223> OTHER INFORMATION: DNA obtained from environmental sample

<400> SEQUENCE: 41
atgggtgtcg tggtccagaa cattgcccgc gcagcctccg atgtcatcga tcggctcgca      60
gcctgcggtg tcgcaacggt acatgaggcg cagggtcgca cggggctgct tgccagccat     120
atgcggccga tctatccggg cgcgcggctc gcggcaagcg cggtgaccat ctctgcgccg     180
ccaggtgaca actggatgat ccatgtggcg atcgagcagt tgaaggatgg cgacgtgctg     240
ctgctcgcgc cgacgagccc tgcgaggat ggctatttcg cgacctcct ggcgacgtcg      300 gccagggcga ggggctgccg gggcctgatc atcgatgccg gcgtgcgcga cgttgccgat     360
ctgaccgaga tgaagtttcc cgtctggtcg aaggcgatct ttgcgcaggg aaccgtcaag     420
gagactgtcg gatcggtgaa tgtaccggtc gtttgcgccg gtgctttcgt caatccgggc     480
gatgtgatcg tcgccgacga tgacggcgcc tgcgtcgtgc cccggcaaga cgcggccgat     540
gtggccgaca aggcggaggc acgtgtcgct gccgaggagg ccaagcgcaa gcggctggca     600
tcgggcgagc ttgggctcga catctacgac atgcgcgggc ggctggcgca gagggggcctg     660 aaatatgtct ga                                                         672

<210> SEQ ID NO 42
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 42

Met Gly Val Val Val Gln Asn Ile Ala Arg Ala Ala Ser Asp Val Ile
1               5                   10                  15

Asp Arg Leu Ala Ala Cys Gly Val Ala Thr Val His Glu Ala Gln Gly
            20                  25                  30

Arg Thr Gly Leu Leu Ala Ser His Met Arg Pro Ile Tyr Pro Gly Ala
        35                  40                  45

Arg Leu Ala Ala Ser Ala Val Thr Ile Ser Ala Pro Pro Gly Asp Asn
    50                  55                  60

Trp Met Ile His Val Ala Ile Glu Gln Leu Lys Asp Gly Asp Val Leu
65                  70                  75                  80

Leu Leu Ala Pro Thr Ser Pro Cys Glu Asp Gly Tyr Phe Gly Asp Leu
                85                  90                  95

Leu Ala Thr Ser Ala Arg Ala Arg Gly Cys Arg Gly Leu Ile Ile Asp
            100                 105                 110
```

```
Ala Gly Val Arg Asp Val Ala Asp Leu Thr Glu Met Lys Phe Pro Val
        115                 120                 125

Trp Ser Lys Ala Ile Phe Ala Gln Gly Thr Val Lys Glu Thr Val Gly
    130                 135                 140

Ser Val Asn Val Pro Val Cys Ala Gly Ala Phe Val Asn Pro Gly
145                 150                 155                 160

Asp Val Ile Val Ala Asp Asp Gly Ala Cys Val Val Pro Arg Gln
                165                 170                 175

Asp Ala Ala Asp Val Ala Asp Lys Ala Glu Ala Arg Val Ala Ala Glu
                180                 185                 190

Glu Ala Lys Arg Lys Arg Leu Ala Ser Gly Glu Leu Gly Leu Asp Ile
        195                 200                 205

Tyr Asp Met Arg Gly Arg Leu Ala Gln Arg Gly Leu Lys Tyr Val
    210                 215                 220
```

<210> SEQ ID NO 43
<211> LENGTH: 672
<212> TYPE: DNA
<213> ORGANISM: Unknown
<220> FEATURE:
<223> OTHER INFORMATION: DNA obtained from environmental sample

<400> SEQUENCE: 43

```
atgagcgtcg tcgttcagaa catcgcgcgc gccgatcaat ccatcgtcga taggctcggg    60
gcctgcggcg tcgccaccgt gcacgaagcg cagggccgca aaggattgct cgcgagccac   120
atgcggccga tctattccgg cgcgcggctc gcggcgagcg ccgtgaccat ctcggcgccg   180
ccgggtgaca attggatggt ccatgtcgcg atcgagcaat gcgagccgg cgacattatg   240
gtgctcgcgc cgaccagccc gtgcgaggat ggctatttcg gtgatctgct cgcgacctcg   300
gcgaaagcgc ggggctgccg cggtctcatc atcgatgccg gcgtgcgcga tgtcgccgat   360
ctcaccgcga tgcagtttcc cgtctggtcc aaggccgtct tcgcccaggg aaccgtgaag   420
gaaacgctcg gctcggtaaa catccccgtg gtctgcgccg gtgcgctggt caatccgggc   480
gatgtcatcg tcgccgatga cgatggtgtc tgcgtcgtgc cgcgaaga ggcggaggcg   540
gtggcgcaga aggccgaggc ccgcgtcgcc gccgaggagg ataagcgcaa gcgcctcgcc   600
gccggcgaac tcggcctcga catctacaag atgcgcgagc ggctcgccga aggggctc   660
aaatatgtct ga                                                      672
```

<210> SEQ ID NO 44
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 44

```
Met Ser Val Val Val Gln Asn Ile Ala Arg Ala Asp Gln Ser Ile Val
1               5                  10                  15

Asp Arg Leu Gly Ala Cys Gly Val Ala Thr Val His Glu Ala Gln Gly
            20                  25                  30

Arg Lys Gly Leu Leu Ala Ser His Met Arg Pro Ile Tyr Ser Gly Ala
        35                  40                  45

Arg Leu Ala Ala Ser Ala Val Thr Ile Ser Ala Pro Pro Gly Asp Asn
```

```
                50                    55                    60
Trp Met Val His Val Ala Ile Glu Gln Leu Arg Ala Gly Asp Ile Met
 65                  70                  75                  80

Val Leu Ala Pro Thr Ser Pro Cys Glu Asp Gly Tyr Phe Gly Asp Leu
                 85                  90                  95

Leu Ala Thr Ser Ala Lys Ala Arg Gly Cys Arg Gly Leu Ile Ile Asp
                100                 105                 110

Ala Gly Val Arg Asp Val Ala Asp Leu Thr Ala Met Gln Phe Pro Val
            115                 120                 125

Trp Ser Lys Ala Val Phe Ala Gln Gly Thr Val Lys Glu Thr Leu Gly
130                 135                 140

Ser Val Asn Ile Pro Val Val Cys Ala Gly Ala Leu Val Asn Pro Gly
145                 150                 155                 160

Asp Val Ile Val Ala Asp Asp Gly Val Cys Val Val Arg Arg Glu
                165                 170                 175

Glu Ala Glu Ala Val Ala Gln Lys Ala Glu Ala Arg Val Ala Ala Glu
            180                 185                 190

Glu Asp Lys Arg Lys Arg Leu Ala Ala Gly Glu Leu Gly Leu Asp Ile
            195                 200                 205

Tyr Lys Met Arg Glu Arg Leu Ala Glu Lys Gly Leu Lys Tyr Val
            210                 215                 220
```

<210> SEQ ID NO 45
<211> LENGTH: 672
<212> TYPE: DNA
<213> ORGANISM: Unknown
<220> FEATURE:
<223> OTHER INFORMATION: DNA obtained from environmental sample

<400> SEQUENCE: 45

```
atgaacgttg tcgtccagaa ctttgaacgg gctgatcctg cggttgttaa ggccttgggc    60
gaatgtggtg tggccacggt gcatgaagca cagggccgca aggggctttt agcctcttat   120
atacgcccga tttatagcgg aacttctatc ggggcttcgg ctgttaccat acttgcggct   180
ccatgcgaca actggatgct gcatgtggcg atcgaacaag tgcaagcggg cgatgtattg   240
gtactggcgg ttacgtcacc atcagacgca ggttactttg gcgatttgtt agcaacatct   300
gcgcaagcgc ggggttgcgc aggtttgatc actgatgcgg cgtacgcga tgtgcgcgat   360
ttgcaggcga tgaattttcc ggtttggtcg aaagcgatct gtgcgcaagg cacggtgaaa   420
gaaaccctgg gttcggtcaa cgttcccgtt gtctgtgcag gagcgaagat taatcccggt   480
gatgtgattg tggcggatga tgatggggtt tgcgctgtga agtgcgaaga ggcggcagag   540
gttttgaaaa aagcgcaagc gcgtttggcc aatgaagagc agaaacgtac gcgattggct   600
gatggtgagt tagggctgga catgtatgat atgcgcgggc gcctagctga aaaaggtctg   660
aaatatgtct aa                                                       672
```

<210> SEQ ID NO 46
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 46

```
Met Asn Val Val Gln Asn Phe Glu Arg Ala Asp Pro Ala Val Val
1               5                   10                  15

Lys Ala Leu Gly Glu Cys Gly Val Ala Thr Val His Glu Ala Gln Gly
            20                  25                  30

Arg Lys Gly Leu Leu Ala Ser Tyr Ile Arg Pro Ile Tyr Ser Gly Thr
        35                  40                  45

Ser Ile Gly Ala Ser Ala Val Thr Ile Leu Ala Pro Cys Asp Asn
    50                  55                  60

Trp Met Leu His Val Ala Ile Glu Gln Val Gln Ala Gly Asp Val Leu
65              70                  75                  80

Val Leu Ala Val Thr Ser Pro Ser Asp Ala Gly Tyr Phe Gly Asp Leu
                85                  90                  95

Leu Ala Thr Ser Ala Gln Ala Arg Gly Cys Ala Gly Leu Ile Thr Asp
            100                 105                 110

Ala Gly Val Arg Asp Val Arg Asp Leu Gln Ala Met Asn Phe Pro Val
        115                 120                 125

Trp Ser Lys Ala Ile Cys Ala Gln Gly Thr Val Lys Glu Thr Leu Gly
    130                 135                 140

Ser Val Asn Val Pro Val Val Cys Ala Gly Ala Lys Ile Asn Pro Gly
145                 150                 155                 160

Asp Val Ile Val Ala Asp Asp Gly Val Cys Ala Val Lys Cys Glu
                165                 170                 175

Glu Ala Ala Glu Val Leu Lys Lys Ala Gln Ala Arg Leu Ala Asn Glu
            180                 185                 190

Glu Gln Lys Arg Thr Arg Leu Ala Asp Gly Leu Gly Leu Asp Met
            195                 200                 205

Tyr Asp Met Arg Gly Arg Leu Ala Glu Lys Gly Leu Lys Tyr Val
210                 215                 220

<210> SEQ ID NO 47
<211> LENGTH: 672
<212> TYPE: DNA
<213> ORGANISM: Unknown
<220> FEATURE:
<223> OTHER INFORMATION: DNA obtained from environmental sample

<400> SEQUENCE: 47
atgggtattg ttgttcagaa catcaagcgg gcggaccccg ggatcatagc aggtcttggc      60
aaatgcggcg ttgccactgt gcatgaagcg caggggtgca aggggctcct ggcggcctat    120
atgcggccca tttattctgg cgcgcgcctt gccgcctccg ctgtcaccat ttccgcgccg    180
ccgggagaca actggatggt gcatgtcgcc attgagcagg tgaggcaagg tgatattctg    240
gttcttgccc aacatcgcc ctgtgaagac ggctatttcg gtgatttgct cgccacctcc    300
atgctgcagc gcggcggcag ggggctgatt attgacgccg gtgtccgcga tatccgtgat    360
ctgactcaaa tgaaatttcc ggtgtggtcg aaaaccgttt ttgcgcaggg caccgttaag    420
gaaacccttg gctctgtgaa cgtcccgata gtttgcgccg gtgaagtggt caatcctggc    480
gacatcatga ttgccgatga tgatggtgtg tgcgtggtcc ggcgcgacga cgctgaaagc    540
gtgcttgaaa aagcattggc gcgtgaggca aggaagaag atacacgcaa acgccttgcg    600
gcaggcgagc tgggtcttga tatttacggc atgcgcgcac gtctggccga aagggccta    660 aaatatgtct ga                                                         672

<210> SEQ ID NO 48
<211> LENGTH: 223
<212> TYPE: PRT
```

```
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 48
```

Met Gly Ile Val Val Gln Asn Ile Lys Arg Ala Asp Pro Gly Ile Ile
1               5                   10                  15

Ala Gly Leu Gly Lys Cys Gly Val Ala Thr Val His Glu Ala Gln Gly
            20                  25                  30

Cys Lys Gly Leu Leu Ala Ala Tyr Met Arg Pro Ile Tyr Ser Gly Ala
        35                  40                  45

Arg Leu Ala Ala Ser Ala Val Thr Ile Ser Ala Pro Pro Gly Asp Asn
    50                  55                  60

Trp Met Val His Val Ala Ile Glu Gln Val Arg Gln Gly Asp Ile Leu
65                  70                  75                  80

Val Leu Ala Pro Thr Ser Pro Cys Glu Asp Gly Tyr Phe Gly Asp Leu
                85                  90                  95

Leu Ala Thr Ser Met Leu Gln Arg Gly Arg Gly Leu Ile Ile Asp
            100                 105                 110

Ala Gly Val Arg Asp Ile Arg Asp Leu Thr Gln Met Lys Phe Pro Val
        115                 120                 125

Trp Ser Lys Thr Val Phe Ala Gln Gly Thr Val Lys Glu Thr Leu Gly
    130                 135                 140

Ser Val Asn Val Pro Ile Val Cys Ala Gly Glu Val Val Asn Pro Gly
145                 150                 155                 160

Asp Ile Met Ile Ala Asp Asp Asp Gly Val Cys Val Val Arg Arg Asp
                165                 170                 175

Asp Ala Glu Ser Val Leu Glu Lys Ala Leu Ala Arg Glu Ala Lys Glu
            180                 185                 190

Glu Asp Thr Arg Lys Arg Leu Ala Ala Gly Glu Leu Gly Leu Asp Ile
        195                 200                 205

Tyr Gly Met Arg Ala Arg Leu Ala Glu Lys Gly Leu Lys Tyr Val
    210                 215                 220

```
<210> SEQ ID NO 49
<211> LENGTH: 672
<212> TYPE: DNA
<213> ORGANISM: Unknown
<220> FEATURE:
<223> OTHER INFORMATION: DNA obtained from environmental sample

<400> SEQUENCE: 49
atgagcatcg tcgtccagaa catcgagcgc gccgacaagg atgcggttgt ggcactcggc      60
gaatgcggcg ttgcgacggt gcatgaggcg caggcccgca aagggctcat gcggccttac     120
atgcggccaa tctatgccgg cgcccgcatc gccggcccag ccgtgacggt ctcgatcgcg     180
ccgggcgaca actggatgat ccatgtggca gtggagcagt gccgcgacgg cgatatcctc     240
gtggtggcac cgaccagccc gagtgaagac ggctatttcg gcgaactgct ggcgcgctcg     300
ctcatggcgc gcggtgtgaa ggggctgatc atcgaagccg ggtgcgcgga cgtgcgcgac     360
ctcaccgaga tcaatttccc ggtctggtcg aaagcgatct ccgcgcaagg gacggtgaag     420
gaaacgctcg gctcggtgaa tgtgccggtc gtctgcgccg gcgcgctggt caatccgggc     480
gacgtcatca ttgccgatga cgacggcgtc tgtgtcgtgg cgcgcgctgc ggcaagtgac     540
```

```
gttgcgaagg cgtcccgaac ccgcgaagcc aaggaagccg aaacccgcaa gcgcctgatg      600
gcgggtgaac tcggactcga catctacggg atgcgcgaca agcttgcggc caagggcctg      660
aaatatgtct ga                                                           672
```

```
<210> SEQ ID NO 50
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 50
```

```
Met Ser Ile Val Val Gln Asn Ile Glu Arg Ala Asp Lys Asp Ala Val
1               5                   10                  15

Val Ala Leu Gly Glu Cys Gly Val Ala Thr Val His Glu Ala Gln Ala
            20                  25                  30

Arg Lys Gly Leu Met Arg Pro Tyr Met Arg Pro Ile Tyr Ala Gly Ala
        35                  40                  45

Arg Ile Ala Gly Pro Ala Val Thr Val Ser Ile Ala Pro Gly Asp Asn
    50                  55                  60

Trp Met Ile His Val Ala Val Glu Gln Cys Arg Asp Gly Asp Ile Leu
65                  70                  75                  80

Val Val Ala Pro Thr Ser Pro Ser Glu Asp Gly Tyr Phe Gly Glu Leu
                85                  90                  95

Leu Ala Arg Ser Leu Met Ala Arg Gly Val Lys Gly Leu Ile Ile Glu
            100                 105                 110

Ala Gly Val Arg Asp Val Arg Asp Leu Thr Glu Ile Asn Phe Pro Val
        115                 120                 125

Trp Ser Lys Ala Ile Ser Ala Gln Gly Thr Val Lys Glu Thr Leu Gly
    130                 135                 140

Ser Val Asn Val Pro Val Val Cys Ala Gly Ala Leu Val Asn Pro Gly
145                 150                 155                 160

Asp Val Ile Ile Ala Asp Asp Gly Val Cys Val Ala Arg Ala
                165                 170                 175

Ala Ala Ser Asp Val Ala Lys Ala Ser Arg Thr Arg Glu Ala Lys Glu
            180                 185                 190

Ala Glu Thr Arg Lys Arg Leu Met Ala Gly Glu Leu Gly Leu Asp Ile
        195                 200                 205

Tyr Gly Met Arg Asp Lys Leu Ala Ala Lys Gly Leu Lys Tyr Val
    210                 215                 220
```

```
<210> SEQ ID NO 51
<211> LENGTH: 672
<212> TYPE: DNA
<213> ORGANISM: Unknown
<220> FEATURE:
<223> OTHER INFORMATION: DNA obtained from environmental sample

<400> SEQUENCE: 51
atgggcgtcg tggtccagaa tatcgcccgg gccgagcagt ccgtcgtcga caggctggct      60
gcgtgcggtg ttgccacggt gcacgaggcg cagggccgca aggggctgct cgcgagttct     120
gtgcggccga tctatccggg cgcgcgggtg gcggccagcg cggtcacgat ctcagcgccg     180
ccgggtgaca actggatggt ccatgtagcg atcgaacagt gaaggagggg cgacatcctg     240
```

```
ctgttggcgc cgaccagtcc ctgcgaggat ggctatttcg gtgatctgct cgccacttcg    300
gccatggcgc ggggctgccg cggactgatc atagatgcgg gggtgcgcga cgtcgcggac    360
ctgacggcga tgcagtttcc agtctggtcc aaggcgatct tcgcccaagg caccgtcaag    420
gaaacgctgg gttcggtgaa tattcctgtg gtctgcgccg gcgcgctggt caatcccggt    480
gacgtgatcg tggccgatga cgacggcgtc tgcgtcgtcc gccgcgaaga ggcggccgcc    540
gtcgccgaaa aggcggaggc acgggtggcg atcgaggaag caaacgcaa gcggctcgcg    600 gcgggcgaac tcgggctcga tatttacgac atgcgcagtc gccttgccga aaggggctg    660 aaatatgtct ga                                                        672
```

<210> SEQ ID NO 52
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 52

```
Met Gly Val Val Gln Asn Ile Ala Arg Ala Glu Gln Ser Val Val
1               5                   10                  15

Asp Arg Leu Ala Ala Cys Gly Val Ala Thr Val His Glu Ala Gln Gly
            20                  25                  30

Arg Lys Gly Leu Leu Ala Ser Ser Val Arg Pro Ile Tyr Pro Gly Ala
        35                  40                  45

Arg Val Ala Ala Ser Ala Val Thr Ile Ser Ala Pro Pro Gly Asp Asn
    50                  55                  60

Trp Met Val His Val Ala Ile Glu Gln Leu Lys Glu Gly Asp Ile Leu
65                  70                  75                  80

Leu Leu Ala Pro Thr Ser Pro Cys Glu Asp Gly Tyr Phe Gly Asp Leu
                85                  90                  95

Leu Ala Thr Ser Ala Met Ala Arg Gly Cys Arg Gly Leu Ile Ile Asp
            100                 105                 110

Ala Gly Val Arg Asp Val Ala Asp Leu Thr Ala Met Gln Phe Pro Val
        115                 120                 125

Trp Ser Lys Ala Ile Phe Ala Gln Gly Thr Val Lys Glu Thr Leu Gly
    130                 135                 140

Ser Val Asn Ile Pro Val Cys Ala Gly Ala Leu Val Asn Pro Gly
145                 150                 155                 160

Asp Val Ile Val Ala Asp Asp Asp Gly Val Cys Val Val Arg Arg Glu
                165                 170                 175

Glu Ala Ala Ala Val Ala Glu Lys Ala Glu Ala Arg Val Ala Ile Glu
            180                 185                 190

Glu Gly Lys Arg Lys Arg Leu Ala Ala Gly Glu Leu Gly Leu Asp Ile
        195                 200                 205

Tyr Asp Met Arg Ser Arg Leu Ala Glu Lys Gly Leu Lys Tyr Val
    210                 215                 220
```

<210> SEQ ID NO 53
<211> LENGTH: 675
<212> TYPE: DNA
<213> ORGANISM: Unknown
<220> FEATURE:
<223> OTHER INFORMATION: DNA obtained from environmental sample -continued

<400> SEQUENCE: 53

```
atgaagccgg tggtggtgca gactatcgag cgggccgacc gagcgatcat cgagggtctg    60
gccgcgtgtg gcgttgccac cgtccatgag gcgcaggggc gccgggggct gcttgcgtcc   120
tacatgcgcc cgatctattc gggcgctgcg gttgcggcct cggccgtcac catcctctct   180
ccaccctgcg acaactggat gctgcacgtc gccatcgagc agatccagcc gggcgacatt   240
ctcgttctcg gcacgacctc tccgtccgat gccggctatt tcggtgatct gctggcgact   300
tcggccaagg cgcgcggttg cgtcgggttg gtcatcgatg ccggcgtacg cgatatccgc   360
gacctgacag cgatgcagtt ccggtctgg tccaaggccg tttcggccca gggcacgatc   420
aaggagacgc tgggttcggt caacgtcccc gtcgtctgcg ccggtgctct ggtcaatccc   480
ggcgacgtcg tcgtggccga tgacgacggt gtctgcgtgg tgcgccgcga ggaagccgcg   540
gaaacgctgg aaaaggcccg ggcgcggatc gccaatgagg aggaaaagcg ccagcgcttt   600
gccgctggcg aactcgggct cgacatctac aagatgcgcg aacgcctcgc tgccctgggg   660
ctcacctatg tctga                                                    675
```

<210> SEQ ID NO 54
<211> LENGTH: 224
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (21)...(173)
<223> OTHER INFORMATION: Demethylmenaquinone methyltransferase

<400> SEQUENCE: 54

```
Met Lys Pro Val Val Gln Thr Ile Glu Arg Ala Asp Arg Ala Ile
1               5                   10                  15

Ile Glu Gly Leu Ala Ala Cys Gly Val Ala Thr Val His Glu Ala Gln
            20                  25                  30

Gly Arg Arg Gly Leu Leu Ala Ser Tyr Met Arg Pro Ile Tyr Ser Gly
        35                  40                  45

Ala Ala Val Ala Ala Ser Ala Val Thr Ile Leu Ser Pro Pro Cys Asp
    50                  55                  60

Asn Trp Met Leu His Val Ala Ile Glu Gln Ile Gln Pro Gly Asp Ile
65                  70                  75                  80

Leu Val Leu Gly Thr Thr Ser Pro Ser Asp Ala Gly Tyr Phe Gly Asp
                85                  90                  95

Leu Leu Ala Thr Ser Ala Lys Ala Arg Gly Cys Val Gly Leu Val Ile
            100                 105                 110

Asp Ala Gly Val Arg Asp Ile Arg Asp Leu Thr Ala Met Gln Phe Pro
        115                 120                 125

Val Trp Ser Lys Ala Val Ser Ala Gln Gly Thr Ile Lys Glu Thr Leu
    130                 135                 140

Gly Ser Val Asn Val Pro Val Val Cys Ala Gly Ala Leu Val Asn Pro
145                 150                 155                 160

Gly Asp Val Val Val Ala Asp Asp Asp Gly Val Cys Val Val Arg Arg
                165                 170                 175

Glu Glu Ala Ala Glu Thr Leu Glu Lys Ala Arg Ala Arg Ile Ala Asn
            180                 185                 190

Glu Glu Glu Lys Arg Gln Arg Phe Ala Ala Gly Glu Leu Gly Leu Asp
        195                 200                 205

Ile Tyr Lys Met Arg Glu Arg Leu Ala Ala Leu Gly Leu Thr Tyr Val
```

<210> SEQ ID NO 55
<211> LENGTH: 678
<212> TYPE: DNA
<213> ORGANISM: Unknown
<220> FEATURE:
<223> OTHER INFORMATION: DNA obtained from environmental sample

<400> SEQUENCE: 55

```
atgaatgatc cggtggtggt ccggcaagtg gagcagccgc cagccgacgc cgttgtcgca      60
ttggagaagt gtggtgtgac gaccgtgcat gaagctcagg gacgttgtgg tctccttgcc     120
tcctacatgc gtccgattta ctcgggagca agcatcgccg gttccgctgt gactgtctct     180
ctgcctcctg gcgacaacct catgatccac gtcgccgtcg aggtttgcgg tccgggaaac     240
atcctggtcg tttcaccaac gtcgccttgc accgatggct acttcggaga gctgttggcg     300
acatctctcc gtgcccacgg tgtaagaggg ctggtgatcg acgccggctg ccgcgacgtc     360
cggtcgttaa ccgagatgaa atttcctgtc tggagccgcg gcatcagctc gcaagggaca     420
gtcaaagcca cgctcggatc tgtgaacgtg gcggtcactt gcgcgggtgc actggtcgaa     480
gctggcgatg taatcgtcgc cgatgacgat ggagttgtgg ttgtgaagcg cgcgcaggcg     540
caagaggtcg ccgccgcggc gcaacaacgg gttcgcaaag aagacgtaac tcgagagcga     600
cttgctcgtg gagaactcgg actggatatt tacgacatgc gccaaaagat cgcgcaactg     660
ggcctaaagt atctgtga                                                   678
```

<210> SEQ ID NO 56
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 56

```
Met Asn Asp Pro Val Val Arg Gln Val Glu Gln Pro Ala Asp
1               5                  10                  15

Ala Val Val Ala Leu Glu Lys Cys Gly Val Thr Thr Val His Glu Ala
            20                  25                  30

Gln Gly Arg Cys Gly Leu Leu Ala Ser Tyr Met Arg Pro Ile Tyr Ser
        35                  40                  45

Gly Ala Ser Ile Ala Gly Ser Ala Val Thr Val Ser Leu Pro Pro Gly
    50                  55                  60

Asp Asn Leu Met Ile His Val Ala Val Glu Val Cys Gly Pro Gly Asn
65                  70                  75                  80

Ile Leu Val Val Ser Pro Thr Ser Pro Cys Thr Asp Gly Tyr Phe Gly
                85                  90                  95

Glu Leu Leu Ala Thr Ser Leu Arg Ala His Gly Val Arg Gly Leu Val
            100                 105                 110

Ile Asp Ala Gly Cys Arg Asp Val Arg Ser Leu Thr Glu Met Lys Phe
        115                 120                 125

Pro Val Trp Ser Arg Gly Ile Ser Ser Gln Gly Thr Val Lys Ala Thr
    130                 135                 140

Leu Gly Ser Val Asn Val Ala Val Thr Cys Ala Gly Ala Leu Val Glu
145                 150                 155                 160
```

```
Ala Gly Asp Val Ile Val Ala Asp Asp Gly Val Val Val Lys
            165                 170                 175

Arg Ala Gln Ala Gln Glu Val Ala Ala Ala Gln Arg Val Arg
        180                 185                 190

Lys Glu Asp Val Thr Arg Glu Arg Leu Ala Arg Gly Glu Leu Gly Leu
        195                 200                 205

Asp Ile Tyr Asp Met Arg Gln Lys Ile Ala Gln Leu Gly Leu Lys Tyr
    210                 215                 220

Leu
225

<210> SEQ ID NO 57
<211> LENGTH: 678
<212> TYPE: DNA
<213> ORGANISM: Unknown
<220> FEATURE:
<223> OTHER INFORMATION: DNA obtained from environmental sample

<400> SEQUENCE: 57
atgaatgatc cggtggtagt ccgagaggtg gagcagccac cagcggatgc ggttgtcaca      60
ttggagaagt gcggagtgac aactgtgcat gaggcgcagg acgttgtgg ccttctcgcc     120 cactacatgc gtccgattta tcctggagcc accatcgccg gttccgctgt cactgtctct    180
ttgccgcctg gcgacaacct catgatccac gttgcggtcg aggtttgtcg tccgggaaac    240
atcctggtcg tttcaccgac gtcgccttgc accgatggct acttcggaga gctgttggcg    300
acatctctcc gtgcccacgg tgtaagaggg ctggtgatcg acgccggctg ccgcgacgtc    360
cggtcgttga ccgagatgaa atttcctgtc tggagccgcg gcatcagctc gcaagggacg    420
gtcaaagcca cgctcggatc tgtgaacgtg cggtcactt gcgcgggtgc actggtcgaa    480
gctggcgatg taatcgtcgc cgatgacgat ggagttgtgg ttgtgaagcg cgcgcaggcg    540
caagaggtcg ccgccgcggc gcaacaacgg gttcgcaaag aagacgtaac tcgagagcga    600
cttgctcgtg gagaactcgg actcgatatt tacgacatgc gccaaaagat cgcgcaactg    660
ggcctaaagt atctgtga                                                  678

<210> SEQ ID NO 58
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 58

Met Asn Asp Pro Val Val Arg Glu Val Glu Gln Pro Pro Ala Asp
1               5                   10                  15

Ala Val Val Thr Leu Glu Lys Cys Gly Val Thr Thr Val His Glu Ala
                20                  25                  30

Gln Gly Arg Cys Gly Leu Leu Ala His Tyr Met Arg Pro Ile Tyr Pro
            35                  40                  45

Gly Ala Thr Ile Ala Gly Ser Ala Val Thr Val Ser Leu Pro Pro Gly
        50                  55                  60

Asp Asn Leu Met Ile His Val Ala Val Glu Val Cys Arg Pro Gly Asn
65                  70                  75                  80

Ile Leu Val Val Ser Pro Thr Ser Pro Cys Thr Asp Gly Tyr Phe Gly
                85                  90                  95
```

```
Glu Leu Leu Ala Thr Ser Leu Arg Ala His Gly Val Arg Gly Leu Val
            100                 105                 110

Ile Asp Ala Gly Cys Arg Asp Val Arg Ser Leu Thr Glu Met Lys Phe
            115                 120                 125

Pro Val Trp Ser Arg Gly Ile Ser Ser Gln Gly Thr Val Lys Ala Thr
    130                 135                 140

Leu Gly Ser Val Asn Val Ala Val Thr Cys Ala Gly Ala Leu Val Glu
145                 150                 155                 160

Ala Gly Asp Val Ile Val Ala Asp Asp Gly Val Val Val Lys
                165                 170                 175

Arg Ala Gln Ala Gln Glu Val Ala Ala Ala Gln Arg Val Arg
            180                 185                 190

Lys Glu Asp Val Thr Arg Glu Arg Leu Ala Arg Gly Glu Leu Gly Leu
            195                 200                 205

Asp Ile Tyr Asp Met Arg Gln Lys Ile Ala Gln Leu Gly Leu Lys Tyr
    210                 215                 220

Leu
225

<210> SEQ ID NO 59
<211> LENGTH: 678
<212> TYPE: DNA
<213> ORGANISM: Unknown
<220> FEATURE:
<223> OTHER INFORMATION: DNA obtained from environmental sample

<400> SEQUENCE: 59
atgaatgatc cggtggtagt ccgagaggtg gagcagccac cagcggatgc ggttgtcaca    60
ttggagaagt gtggagtgac aaccgtgcat gaggcacagg gacgttgtgg ccttctcgcg   120
cactacatgc gtccgattta cccgggggca accatcgccg gttccgctgt cactgtctct   180
ttgccgcctg gcgacaacct catgatccac gtcgccgtcg aggtttgcgg tccgggaaac   240
atcctggtcg tttcaccgac gtcgccttgc accgatggct acttcggaga gctgttggcg   300
acatctctcc gtgcccacgg tgtaagaggg ctggtgatcg acgccggatg ccgtgatgtc   360
cggtcgttga ccgagatgaa atttcctgtc tggagccgcg cgatcagctc gcaagggaca   420
gtcaaagcca cgctcgggtc ggtgaacgtg gcggtcactt gcgcgggtgc actggtcgaa   480
gctggcgatg taatcgtcgc cgatgacgat ggagttgtgg ttgtgaagcg cgcgcgggcg   540
caagaggtcg cggccgcggc gcaacaacgg gttcgcaaag aagacgtaac tcgagagcga   600
cttgctcgtg gagaactcgg actcgatatt tacgacatgc gccaaaagat cgcgcaactg   660
ggcctaaagt atctgtga                                                 678

<210> SEQ ID NO 60
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 60

Met Asn Asp Pro Val Val Val Arg Glu Val Glu Gln Pro Pro Ala Asp
1               5                   10                  15

Ala Val Val Thr Leu Glu Lys Cys Gly Val Thr Thr Val His Glu Ala
```

20                  25                  30
Gln Gly Arg Cys Gly Leu Leu Ala His Tyr Met Arg Pro Ile Tyr Pro
            35                  40                  45

Gly Ala Thr Ile Ala Gly Ser Ala Val Thr Val Ser Leu Pro Pro Gly
        50                  55                  60

Asp Asn Leu Met Ile His Val Ala Val Glu Val Cys Gly Pro Gly Asn
65                  70                  75                  80

Ile Leu Val Val Ser Pro Thr Ser Pro Cys Thr Asp Gly Tyr Phe Gly
                85                  90                  95

Glu Leu Leu Ala Thr Ser Leu Arg Ala His Gly Val Arg Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Ile Ser Ser Gln Gly Thr Val Lys Ala Thr
130                 135                 140

Leu Gly Ser Val Asn Val Ala Val Thr Cys Ala Gly Ala Leu Val Glu
145                 150                 155                 160

Ala Gly Asp Val Ile Val Ala Asp Asp Gly Val Val Val Lys
                165                 170                 175

Arg Ala Arg Ala Gln Glu Val Ala Ala Ala Gln Gln Arg Val Arg
            180                 185                 190

Lys Glu Asp Val Thr Arg Glu Arg Leu Ala Arg Gly Glu Leu Gly Leu
        195                 200                 205

Asp Ile Tyr Asp Met Arg Gln Lys Ile Ala Gln Leu Gly Leu Lys Tyr
210                 215                 220

Leu
225

<210> SEQ ID NO 61
<211> LENGTH: 675
<212> TYPE: DNA
<213> ORGANISM: Unknown
<220> FEATURE:
<223> OTHER INFORMATION: DNA obtained from environmental sample

<400> SEQUENCE: 61
atgagcggcg tggttgtgcg ggaggtcgcc cgcccggcgc ccgatctcgt ggcctcgctc     60
gaagaggcgg gtgtctcaac cgtccacgaa gcacagggac gccggggact gctcgccacc    120
tacatgcgtc cgatctacgc cggagccacg ctcgcgggac cggcagtcac cgtcctcgtc    180 cccccggcg acaacctgat gattcacgta gccgtggagg tgtgccgccc gggtgacgtg    240
ctggtcgtcg ccgtcacgtc gccgtgcacc gacggttact tcggcgagct gctggcgacg    300
tcggttcgcg cgcgcggcgt caaggggctc gtcatcgatg caggctgccg ggacgtgcgg    360
gcgctcaccg agatgcggtt tccggtgtgg agccgggcgg tcagcgcgca gggcaccgtc    420
aaggccacgc tgggctccgt gagcgttccg gtcgtttgcg ccggcgcgct gatcgaggcc    480
ggcgacgtcg tcgtgggcga cgacgacgga gtggttgtcg tgaaacggag cgaggccgat    540
gcggtcgtga gtgcttcgcg ccagcggctc tcaaggaag aggggacgcg tcagcgcctg    600
gcaagcggtg aactcggtct ggacatctac tcgctgcgca aaacgctttc cgacctgggg    660
ctgaagtacc ggtaa                                                    675

<210> SEQ ID NO 62
<211> LENGTH: 224
<212> TYPE: PRT
<213> ORGANISM: Unknown

<220> FEATURE:
<223> OTHER INFORMATION: Protein obtained from environmental sample
<220> FEATURE:
<221> NAME/KEY: DOMAIN
<222> LOCATION: (21)...(173)
<223> OTHER INFORMATION: Demethylmenaquinone methyltransferase

<400> SEQUENCE: 62

```
Met Ser Gly Val Val Arg Glu Val Ala Arg Pro Ala Pro Asp Leu
1               5                   10                  15

Val Ala Ser Leu Glu Glu Ala Gly Val Ser Thr Val His Glu Ala Gln
            20                  25                  30

Gly Arg Arg Gly Leu Leu Ala Thr Tyr Met Arg Pro Ile Tyr Ala Gly
                35                  40                  45

Ala Thr Leu Ala Gly Pro Ala Val Thr Val Leu Val Pro Pro Gly Asp
    50                  55                  60

Asn Leu Met Ile His Val Ala Glu Val Cys Arg Pro Gly Asp Val
65                  70                  75                  80

Leu Val Val Ala Val Thr Ser Pro Cys Thr Asp Gly Tyr Phe Gly Glu
                85                  90                  95

Leu Leu Ala Thr Ser Val Arg Ala Arg Gly Val Lys Gly Leu Val Ile
                100                 105                 110

Asp Ala Gly Cys Arg Asp Val Arg Ala Leu Thr Glu Met Arg Phe Pro
            115                 120                 125

Val Trp Ser Arg Ala Val Ser Ala Gln Gly Thr Val Lys Ala Thr Leu
        130                 135                 140

Gly Ser Val Ser Val Pro Val Val Cys Ala Gly Ala Leu Ile Glu Ala
145                 150                 155                 160

Gly Asp Val Val Val Gly Asp Asp Gly Val Val Val Val Lys Arg
                165                 170                 175

Ser Glu Ala Asp Ala Val Val Ser Ala Ser Arg Gln Arg Leu Leu Lys
            180                 185                 190

Glu Glu Gly Thr Arg Gln Arg Leu Ala Ser Gly Glu Leu Gly Leu Asp
        195                 200                 205

Ile Tyr Ser Leu Arg Lys Thr Leu Ser Asp Leu Gly Leu Lys Tyr Arg
    210                 215                 220
```

<210> SEQ ID NO 63
<211> LENGTH: 693
<212> TYPE: DNA
<213> ORGANISM: Unknown
<220> FEATURE:
<223> OTHER INFORMATION: DNA obtained from environmental sample

<400> SEQUENCE: 63

```
atgaccggca tcgtcgtcca gtggttcgag cgcacgccgc ttgccgatgt cgcggcgctt      60
gccgagttcg gcgtggctac catccacgag gcgcaaggcc gcaaggggct gctcgcgtcc     120
tacatgcggc cgatctatgc gggtgctgcc gcggcgggca atgccgtcac agtatcggtg     180
cctcccggtg acaactggat gatccatgtg gcggtcgagg tgtgccgcga gggcgacgtg     240
ctggtggtcg ccccgacctc gccctgcgac aacggctatt tcggtgagct gctggcctgc     300
tcgctcaagg cgcgcggcgt gcgcgggctc gtcatcgagg ccggctgccg cgacgtgaag     360
ccactctccg acatgaagtt ccccgtgtgg tcgcgcgccg tttccgccca gggcaccgtc     420
aaggagagcc tgggcgacgt caacctgccg ctcgtgatcg ccagccagac cgtgcatcct     480
ggcgacgtgg tggtcgccga tgacgacggt gtcgtcatcg tcgctcgcgg cgaggtgcgc     540
gccgtcaccg ccaagtcgcg cgagcgcgag gacaaggagg ccgcaagccg cgagaagctg     600
```

```
agcaagggg aggtgggcct cgacatctac ggcatgcggg ccaagctgaa ggagaagggc    660
attcgctacg tcgcgaatcc cgacaaactc tga                                693
```

<210> SEQ ID NO 64
<211> LENGTH: 230
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (21)...(173)
<223> OTHER INFORMATION: Demethylmenaquinone methyltransferase

<400> SEQUENCE: 64

```
Met Thr Gly Ile Val Val Gln Trp Phe Glu Arg Thr Pro Leu Ala Asp
1               5                   10                  15

Val Ala Ala Leu Ala Glu Phe Gly Val Ala Thr Ile His Glu Ala Gln
            20                  25                  30

Gly Arg Lys Gly Leu Leu Ala Ser Tyr Met Arg Pro Ile Tyr Ala Gly
        35                  40                  45

Ala Ala Ala Gly Asn Ala Val Thr Val Ser Val Pro Pro Gly Asp
    50                  55                  60

Asn Trp Met Ile His Val Ala Val Glu Val Cys Arg Glu Gly Asp Val
65                  70                  75                  80

Leu Val Val Ala Pro Thr Ser Pro Cys Asp Asn Gly Tyr Phe Gly Glu
                85                  90                  95

Leu Leu Ala Cys Ser Leu Lys Ala Arg Gly Val Arg Gly Leu Val Ile
            100                 105                 110

Glu Ala Gly Cys Arg Asp Val Lys Pro Leu Ser Asp Met Lys Phe Pro
        115                 120                 125

Val Trp Ser Arg Ala Val Ser Ala Gln Gly Thr Val Lys Glu Ser Leu
    130                 135                 140

Gly Asp Val Asn Leu Pro Leu Val Ile Ala Ser Gln Thr Val His Pro
145                 150                 155                 160

Gly Asp Val Val Ala Asp Asp Gly Val Val Ile Val Ala Arg
                165                 170                 175

Gly Glu Val Arg Ala Val Thr Ala Lys Ser Arg Glu Arg Glu Asp Lys
            180                 185                 190

Glu Ala Ala Ser Arg Glu Lys Leu Ser Lys Gly Glu Val Gly Leu Asp
        195                 200                 205

Ile Tyr Gly Met Arg Ala Lys Leu Lys Glu Lys Gly Ile Arg Tyr Val
    210                 215                 220

Ala Asn Pro Asp Lys Leu
225                 230
```

<210> SEQ ID NO 65
<211> LENGTH: 672
<212> TYPE: DNA
<213> ORGANISM: Unknown
<220> FEATURE:
<223> OTHER INFORMATION: DNA obtained from environmental sample

<400> SEQUENCE: 65

```
atgagcatcg tcgtcacgaa gatcgagcgc gccggcgcgg cggccgtcgc cgcgctgcgc    60
acaagtggcg ttgccacagt gcacgaggcg caagggcgca cgggcttgat gcgtccctac    120
atgcggccga tctacccggg cgcgcgcatc gccggcacgg cgatcaccgt ctccctgcct    180
```

-continued

```
ccgggcgaca actggatgat ccacgtcgcg gtcgagcagt gccgcgaggg cgatatcctc      240
gtggtggcgc cgaccagccc gagcgacgac ggctatttcg gcgacctgct tggcaattcg      300
ctcgtcgcac gcggcgtcag gggcctggtg atcgaggccg gtgtgcgtga cgtgcgcgac      360
ctcacggaga tgcgctttcc ggtctggtcg aagacgattt cggcgcaagg cacggtcaag      420
gagacgttgg gctcggtcaa cgtgccgatc gtctgcgcgg gtgctgccgt gaaccccgga      480
gacgtgatcg tggccgacga cgacggcgtc tgcgtcgtgc cgcgccagac ggtcacagag      540
gtcgtcgagg cggcccacgc ccgcgaggcc aaggaggccg aggtccggca gcggctcatc      600
gcgggcgagc ttggcctcga cgtctacggc atgcgcgaga gctggcggc caagggcctc       660 aaatatgtct ga                                                          672
```

<210> SEQ ID NO 66
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: SIGNAL
<222> LOCATION: (1)...(27)
<220> FEATURE:
<221> NAME/KEY: DOMAIN
<222> LOCATION: (20)...(172)
<223> OTHER INFORMATION: Demethylmenaquinone methyltransferase

<400> SEQUENCE: 66

```
Met Ser Ile Val Val Thr Lys Ile Glu Arg Ala Gly Ala Ala Val
1               5                  10                  15

Ala Ala Leu Arg Thr Ser Gly Val Ala Thr Val His Glu Ala Gln Gly
            20                  25                  30

Arg Thr Gly Leu Met Arg Pro Tyr Met Arg Pro Ile Tyr Pro Gly Ala
        35                  40                  45

Arg Ile Ala Gly Thr Ala Ile Thr Val Ser Leu Pro Pro Gly Asp Asn
    50                  55                  60

Trp Met Ile His Val Ala Val Glu Gln Cys Arg Glu Gly Asp Ile Leu
65                  70                  75                  80

Val Val Ala Pro Thr Ser Pro Ser Asp Asp Gly Tyr Phe Gly Asp Leu
                85                  90                  95

Leu Gly Asn Ser Leu Val Ala Arg Gly Val Arg Gly Leu Val Ile Glu
            100                 105                 110

Ala Gly Val Arg Asp Val Arg Asp Leu Thr Glu Met Arg Phe Pro Val
        115                 120                 125

Trp Ser Lys Thr Ile Ser Ala Gln Gly Thr Val Lys Glu Thr Leu Gly
    130                 135                 140

Ser Val Asn Val Pro Ile Val Cys Ala Gly Ala Ala Val Asn Pro Gly
145                 150                 155                 160

Asp Val Ile Val Ala Asp Asp Asp Gly Val Cys Val Val Pro Arg Gln
                165                 170                 175

Thr Val Thr Glu Val Val Glu Ala Ala His Ala Arg Glu Ala Lys Glu
            180                 185                 190

Ala Glu Val Arg Gln Arg Leu Ile Ala Gly Glu Leu Gly Leu Asp Val
        195                 200                 205

Tyr Gly Met Arg Glu Lys Leu Ala Ala Lys Gly Leu Lys Tyr Val
    210                 215                 220
```

<210> SEQ ID NO 67
<211> LENGTH: 672

```
<212> TYPE: DNA
<213> ORGANISM: Unknown
<220> FEATURE:
<223> OTHER INFORMATION: DNA obtained from environmental sample

<400> SEQUENCE: 67
atgagcgttg tcgtcacgaa gatcgagcgc gccggcgccg aagctgttgt agcgctggcc    60
gaaagtggtg tgtcgaccgt gcacgaggcg cagggccgga ccgggctgat gcggccttat   120
atgcggccga tctacgcggg cgcgcggatc gccgggacgg cgatcaccgt gtcgctgcag   180
ccgggcgaca actggatgat ccatgtggcg gtcgagcaat gccggcaggg cgacatcctc   240
gtcgtggcgc cgaccagccc gagcgacgac gggtatttcg gcgacctgct cggcaattcg   300
cttgtcgcgc ggggcgtcag ggggctggtg atcgaggccg gcgtgcgcga cgtgcgcgat   360
ctgaccgcga tgggttttcc ggtatggtcg aagacagtct cggcgcaagg caccgtgaag   420
gagacgctcg gctcggtgaa cgtgcccgtc gtctgcgcgg gggcgaccgc aaaccccggt   480
gacgtgatcg tggccgatga cgacggcgtc tgcgtggtgc cgcgcgagac ggccgcggca   540
gtggtcgagg cggcccatgc gcgggaggtg aaggaggcag aggtacggcg gcggctgatc   600
tccggcgagc tcggcctaga catctacggc atgcgcgaca agctcgctgc caagggcctc   660
aaatatgtct ga                                                       672
```

```
<210> SEQ ID NO 68
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 68
```

Met Ser Val Val Val Thr Lys Ile Glu Arg Ala Gly Ala Glu Ala Val
1               5                   10                  15

Val Ala Leu Ala Glu Ser Gly Val Ser Thr Val His Glu Ala Gln Gly
            20                  25                  30

Arg Thr Gly Leu Met Arg Pro Tyr Met Arg Pro Ile Tyr Ala Gly Ala
        35                  40                  45

Arg Ile Ala Gly Thr Ala Ile Thr Val Ser Leu Gln Pro Gly Asp Asn
    50                  55                  60

Trp Met Ile His Val Ala Val Glu Gln Cys Arg Gln Gly Asp Ile Leu
65                  70                  75                  80

Val Val Ala Pro Thr Ser Pro Ser Asp Asp Gly Tyr Phe Gly Asp Leu
                85                  90                  95

Leu Gly Asn Ser Leu Val Ala Arg Gly Val Arg Gly Leu Val Ile Glu
            100                 105                 110

Ala Gly Val Arg Asp Val Arg Asp Leu Thr Ala Met Gly Phe Pro Val
        115                 120                 125

Trp Ser Lys Thr Val Ser Ala Gln Gly Thr Val Lys Glu Thr Leu Gly
    130                 135                 140

Ser Val Asn Val Pro Val Val Cys Ala Gly Ala Thr Ala Asn Pro Gly
145                 150                 155                 160

Asp Val Ile Val Ala Asp Asp Gly Val Cys Val Val Pro Arg Glu
                165                 170                 175

Thr Ala Ala Ala Val Val Glu Ala Ala His Ala Arg Glu Val Lys Glu
            180                 185                 190

```
Ala Glu Val Arg Arg Arg Leu Ile Ser Gly Glu Leu Gly Leu Asp Ile
            195                 200                 205

Tyr Gly Met Arg Asp Lys Leu Ala Ala Lys Gly Leu Lys Tyr Val
        210                 215                 220

<210> SEQ ID NO 69
<211> LENGTH: 672
<212> TYPE: DNA
<213> ORGANISM: Unknown
<220> FEATURE:
<223> OTHER INFORMATION: DNA obtained from environmental sample

<400> SEQUENCE: 69
atgggcaccg tggttcaaaa cattgcgcgc gctgaccact ccgtcatcga ccgccttgct      60
gcctgcggtg tcgccaccgt tcacgaggcc cagggccgca ccggattgct cgccagttac    120
atgcggccga tctatgcggg cgcgcggctg gccgctagcg ccgtcaccat ctccgcccca    180
ccgggcgaca actggatgat ccacgtcgcc atcgagcaac tcaaggcagg cgacatcatg    240
gtgctggccc cgaccagccc ctgcgaggac ggttatttcg gcgacctgct cgccacttcc    300
gcccaagcgc gagggtgcaa ggcctaatc atcgacgccg cgtgcgcga cgttgcagac     360 ctgaccgcga tgggatttcc cgtgtggtcc aaggccatct tcgcgcaggg tacggtcaag    420
gcgagtttgg gttcagtcaa tgtgtcggtg gtctgtgcta gtgccttgat caatccgggc    480
gacattgtcg tggccgacga tgatggtgtg tgtgtcgtac ggcgcgagga cgcggtctcc    540
gtggcggcga aggccgaagc gcgggtggca gccgaagagg acaagcgccg cgcctcgca    600 gggggcgaac tgggacttga tatttatggg atgcgcgaca cgctcgcggc caaggggcta    660
aaatatgtct ga                                                      672

<210> SEQ ID NO 70
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase
<220> FEATURE:
<221> NAME/KEY: SITE
<222> LOCATION: (149)...(152)
<223> OTHER INFORMATION: N-glycosylation site. Prosite id = PS00001

<400> SEQUENCE: 70

Met Gly Thr Val Val Gln Asn Ile Ala Arg Ala Asp His Ser Val Ile
1               5                   10                  15

Asp Arg Leu Ala Ala Cys Gly Val Ala Thr Val His Glu Ala Gln Gly
            20                  25                  30

Arg Thr Gly Leu Leu Ala Ser Tyr Met Arg Pro Ile Tyr Ala Gly Ala
        35                  40                  45

Arg Leu Ala Ala Ser Ala Val Thr Ile Ser Ala Pro Pro Gly Asp Asn
    50                  55                  60

Trp Met Ile His Val Ala Ile Glu Gln Leu Lys Ala Gly Asp Ile Met
65                  70                  75                  80

Val Leu Ala Pro Thr Ser Pro Cys Glu Asp Gly Tyr Phe Gly Asp Leu
                85                  90                  95

Leu Ala Thr Ser Ala Gln Ala Arg Gly Cys Lys Gly Leu Ile Ile Asp
            100                 105                 110
```

```
Ala Gly Val Arg Asp Val Ala Asp Leu Thr Ala Met Gly Phe Pro Val
        115                 120                 125

Trp Ser Lys Ala Ile Phe Ala Gln Gly Thr Val Lys Ala Ser Leu Gly
    130                 135                 140

Ser Val Asn Val Ser Val Cys Ala Ser Ala Leu Ile Asn Pro Gly
145                 150                 155                 160

Asp Ile Val Val Ala Asp Asp Gly Val Cys Val Arg Arg Glu
                165                 170                 175

Asp Ala Val Ser Val Ala Ala Lys Ala Glu Ala Arg Val Ala Ala Glu
        180                 185                 190

Glu Asp Lys Arg Arg Leu Ala Gly Gly Leu Gly Leu Asp Ile
        195                 200                 205

Tyr Gly Met Arg Asp Thr Leu Ala Ala Lys Gly Leu Lys Tyr Val
    210                 215                 220

<210> SEQ ID NO 71
<211> LENGTH: 672
<212> TYPE: DNA
<213> ORGANISM: Unknown
<220> FEATURE:
<223> OTHER INFORMATION: DNA obtained from environmental sample

<400> SEQUENCE: 71
atgagcgtcg tcgtccagac catcgcgcgc gccgatcaga cggtcatcga ccgcctcggc      60
gcctgcggcg tcgccaccgt acatgaggcg cagggccgca aggggctact cgcgagctac     120
atgcggccca tctattccgg cgcgcggctg gctgcgagcg cggtgacaat ttcggcgccg     180
cccggcgaca actggatgat ccacgtcgcc atcgagcagc tcaaggccgg cgacatcatg     240
gtgctcgctc ccaccagccc ctgcgaagac ggctatttcg cgacctgct cgcgacgtcg      300 gctgtggcgc gcggctgccg cgggctcgtc atcgaggccg gcgtgcgcga tgtggccgat     360
ctcaccgcga tgaaattccc ggtatggtcg aaagccatct ccgctcaggg caccgtcaag     420
gagacgctgg gctcggtgaa cgtgccgatc gtatgcgccg gcacgctggt cgagccgggc     480
gacgtcatcg tcgccgacga tgacggcgtc tgcgtcgtgc gccgcgaaga ggcggaggcc     540
gtggcgcaga aggccgaggc ccgcatcgcc accgaagagg acaagcgcaa cgcctggcg      600 ggcggcgagc tcggtctcga catctacaag atgcgcgagc ggctggccga aaaggactc      660 aaatatgtct ag                                                         672

<210> SEQ ID NO 72
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 72

Met Ser Val Val Val Gln Thr Ile Ala Arg Ala Asp Gln Thr Val Ile
1               5                   10                  15

Asp Arg Leu Gly Ala Cys Gly Val Ala Thr Val His Glu Ala Gln Gly
            20                  25                  30

Arg Lys Gly Leu Leu Ala Ser Tyr Met Arg Pro Ile Tyr Ser Gly Ala
        35                  40                  45

Arg Leu Ala Ala Ser Ala Val Thr Ile Ser Ala Pro Pro Gly Asp Asn
    50                  55                  60
```

```
Trp Met Ile His Val Ala Ile Glu Gln Leu Lys Ala Gly Asp Ile Met
 65                  70                  75                  80

Val Leu Ala Pro Thr Ser Pro Cys Glu Asp Gly Tyr Phe Gly Asp Leu
                 85                  90                  95

Leu Ala Thr Ser Ala Val Ala Arg Gly Cys Arg Gly Leu Val Ile Glu
            100                 105                 110

Ala Gly Val Arg Asp Val Ala Asp Leu Thr Ala Met Lys Phe Pro Val
        115                 120                 125

Trp Ser Lys Ala Ile Ser Ala Gln Gly Thr Val Lys Glu Thr Leu Gly
    130                 135                 140

Ser Val Asn Val Pro Ile Val Cys Ala Gly Thr Leu Val Glu Pro Gly
145                 150                 155                 160

Asp Val Ile Val Ala Asp Asp Gly Val Cys Val Val Arg Arg Glu
                165                 170                 175

Glu Ala Glu Ala Val Ala Gln Lys Ala Glu Ala Arg Ile Ala Thr Glu
            180                 185                 190

Glu Asp Lys Arg Lys Arg Leu Ala Gly Gly Glu Leu Gly Leu Asp Ile
        195                 200                 205

Tyr Lys Met Arg Glu Arg Leu Ala Glu Lys Gly Leu Lys Tyr Val
    210                 215                 220
```

<210> SEQ ID NO 73
<211> LENGTH: 690
<212> TYPE: DNA
<213> ORGANISM: Unknown
<220> FEATURE:
<223> OTHER INFORMATION: DNA obtained from environmental sample

<400> SEQUENCE: 73

```
atgagcgtgg tcatcaccaa tatccagcgc cccgatcccg agcacaccaa agcgctcgcc    60
gccttcggcg ttgcgactat tcacgaggcg cagggccgca ccggactgat gcagtccttc   120
atgcgaccga tctatgccgg cgcgcgcgcc gccggcaccg ccgtcaccgt gtcgctgccc   180
cccgccgaca actggatgat ccacgtcgcg gtggagcaat gccaggcagg cgacattctc   240
gtcgtcgcgc cgacctcgcc ctccgatgtc ggatatttcg gcgagctcct cgccacctcg   300
ctcgccgcac ggggcgtggt cggcctcatc atcgaaggcg gctgccgcga cgtcgcggca   360
ttgaccgaga tgggtttccc ggtctggtcg cgcgccgtat cggcgcaggg caccgtgaag   420
gagacgctcg gctccgtgaa cataccgatc gtctgcgccg gcgcgcatat tcatcccggc   480
gacttcgtcg ccgccgacga tgacggcgtg gtcgtcgtgc cccgcgccca cgtggcggaa   540
atcgccgccg cctccctcgc gcgcgaggac aaggaggccg ccgttcgcga gcgcctgaaa   600
tccggtgagc tcggcctcga tatttacggc atgcgcccgc gcctcaagga gaaaggcctc   660
gtctggcgcg aaacgccgga gaagaaatag                                   690
```

<210> SEQ ID NO 74
<211> LENGTH: 229
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 74

Met Ser Val Val Ile Thr Asn Ile Gln Arg Pro Asp Pro Glu His Thr

```
              1               5                   10                  15
Lys Ala Leu Ala Ala Phe Gly Val Ala Thr Ile His Glu Ala Gln Gly
                    20                  25                  30

Arg Thr Gly Leu Met Gln Ser Phe Met Arg Pro Ile Tyr Ala Gly Ala
            35                  40                  45

Arg Ala Ala Gly Thr Ala Val Thr Val Ser Leu Pro Pro Ala Asp Asn
    50                  55                  60

Trp Met Ile His Val Ala Val Glu Gln Cys Gln Ala Gly Asp Ile Leu
65                  70                  75                  80

Val Val Ala Pro Thr Ser Pro Ser Asp Val Gly Tyr Phe Gly Glu Leu
                85                  90                  95

Leu Ala Thr Ser Leu Ala Ala Arg Gly Val Val Gly Leu Ile Ile Glu
            100                 105                 110

Gly Gly Cys Arg Asp Val Ala Ala Leu Thr Glu Met Gly Phe Pro Val
        115                 120                 125

Trp Ser Arg Ala Val Ser Ala Gln Gly Thr Val Lys Glu Thr Leu Gly
    130                 135                 140

Ser Val Asn Ile Pro Ile Val Cys Ala Gly Ala His Ile His Pro Gly
145                 150                 155                 160

Asp Phe Val Ala Ala Asp Asp Gly Val Val Val Pro Arg Ala
                165                 170                 175

His Val Ala Glu Ile Ala Ala Ser Leu Ala Arg Glu Asp Lys Glu
            180                 185                 190

Ala Ala Val Arg Glu Arg Leu Lys Ser Gly Glu Leu Gly Leu Asp Ile
                195                 200                 205

Tyr Gly Met Arg Pro Arg Leu Lys Glu Lys Gly Leu Val Trp Arg Glu
            210                 215                 220

Thr Pro Glu Lys Lys
225

<210> SEQ ID NO 75
<211> LENGTH: 672
<212> TYPE: DNA
<213> ORGANISM: Unknown
<220> FEATURE:
<223> OTHER INFORMATION: DNA obtained from environmental sample

<400> SEQUENCE: 75
atgggagtcg tcgttcagaa tatcgcgcgg gccgagcagg agatcatcga ccggctggcc      60
gcctgcggcg ttgccaccgt tcacgaagcg caagggcgca aagggctgct ggcaagctat     120
atgcggccga tctatcaggg tgcgcggctc gccgcgagcg ccgtcacaat ctcggcgccg     180
ccgggcgaca actggatggt tcatgtcgcc atcgaacaga taagggccgg cgacatcctg     240
ctgcttgcgc ccacaagccc gtgcgaggac ggctattttg gcgatctcct cgcaacgtcc     300
gcgcaggcaa gggggtgccg cgggctggtc atcgacgctg gtgtgcgcga catcgccgat     360
ctgaaggcga tgaattttcc ggtctggtcg aaggccgtgt tcgcgcaggg aacgatcaag     420
gagacactcg gatcggtcaa tgtgcccgtg gtctgtgccg gagcgctggt caatccggga     480
gacgtgattg tggcggacga cgacggcgtc tgcgtcgtgc gccgggagga ggccgaaaac     540
gtagtccaga aagccgaggc gcgggtcagc gcggaagtgg ccaagcgcgc caggctcgca     600
gccggcgaac tcggcctcga catctacagg atgcgcgaaa ggctggcgga agggggctg     660 aaatatgtct ga                                                          672

<210> SEQ ID NO 76
```

<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 76

```
Met Gly Val Val Gln Asn Ile Ala Arg Ala Glu Gln Glu Ile Ile
1               5                   10                  15
Asp Arg Leu Ala Ala Cys Gly Val Ala Thr Val His Glu Ala Gln Gly
                20                  25                  30
Arg Lys Gly Leu Leu Ala Ser Tyr Met Arg Pro Ile Tyr Gln Gly Ala
            35                  40                  45
Arg Leu Ala Ala Ser Ala Val Thr Ile Ser Ala Pro Pro Gly Asp Asn
        50                  55                  60
Trp Met Val His Val Ala Ile Glu Gln Ile Arg Ala Gly Asp Ile Leu
65                  70                  75                  80
Leu Leu Ala Pro Thr Ser Pro Cys Glu Asp Gly Tyr Phe Gly Asp Leu
                85                  90                  95
Leu Ala Thr Ser Ala Gln Ala Arg Gly Cys Arg Gly Leu Val Ile Asp
            100                 105                 110
Ala Gly Val Arg Asp Ile Ala Asp Leu Lys Ala Met Asn Phe Pro Val
        115                 120                 125
Trp Ser Lys Ala Val Phe Ala Gln Gly Thr Ile Lys Glu Thr Leu Gly
    130                 135                 140
Ser Val Asn Val Pro Val Val Cys Ala Gly Ala Leu Val Asn Pro Gly
145                 150                 155                 160
Asp Val Ile Val Ala Asp Asp Gly Val Cys Val Val Arg Arg Glu
                165                 170                 175
Glu Ala Glu Asn Val Val Gln Lys Ala Glu Ala Arg Val Ser Ala Glu
            180                 185                 190
Val Ala Lys Arg Ala Arg Leu Ala Ala Gly Glu Leu Gly Leu Asp Ile
        195                 200                 205
Tyr Arg Met Arg Glu Arg Leu Ala Glu Lys Gly Leu Lys Tyr Val
    210                 215                 220
```

<210> SEQ ID NO 77
<211> LENGTH: 681
<212> TYPE: DNA
<213> ORGANISM: Unknown
<220> FEATURE:
<223> OTHER INFORMATION: DNA obtained from environmental sample

<400> SEQUENCE: 77

```
gtgaccgatc cggttgtcgc tcgacagatc gacaggccgc ccgcgaatct ggtcgccgat      60
ctgcagcgct acggcgtctc caccgtccac gaggcgcaag gcgtcgcgg  cctgctcgcg     120
tcgtacatgc ggccgatcta tccggcgcg  ctcattgccg gtcccgcgat cacggtcctg     180
gtaccgcctg gcgacaactt gatgatccac gtcgccgtgg aagtgtgcca gcctggcgac     240
gttctcgtcg tcgccacgac gtcgccgtgc accgacggct atttcggcga gctgctggcg     300
acgtcgctgc gggccgcgg  cgtggcgggg ctcgtgatca tgcgggctg  ccgggatgtt     360
cgcgcgctga cggaaatgcg atttcccgtc tggagccgcg cgatcagcgc gcagggaacc     420
gtcaaagcca cgctgggctc ggtgaacgcg gcggtggtgt gcgccgggac gtcggtgaga     480
```

```
gccggggatc tcatcgtggc cgacgatgac ggggtggtgg cggtgcggcg ggaggaagtc    540
gtcgccgtga cgcaggcggc cgaacagcgc gttcgcaagg aagagggcac gcgcgcacgg    600
ctcgcgcagg gcgagctcgg cctggacatt tacggcttgc gccagaagct gtcggatcta    660
ggcttgaagt catcgtcgtg a                                              681
```

```
<210> SEQ ID NO 78
<211> LENGTH: 226
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 78
```

```
Met Thr Asp Pro Val Val Ala Arg Gln Ile Asp Arg Pro Ala Asn
1               5                   10                  15

Leu Val Ala Asp Leu Gln Arg Tyr Gly Val Ser Thr Val His Glu Ala
            20                  25                  30

Gln Gly Arg Gly Leu Leu Ala Ser Tyr Met Arg Pro Ile Tyr Ala
        35                  40                  45

Gly Ala Leu Ile Ala Gly Pro Ala Ile Thr Val Leu Val Pro Pro Gly
50                  55                  60

Asp Asn Leu Met Ile His Val Ala Val Glu Val Cys Gln Pro Gly Asp
65                  70                  75                  80

Val Leu Val Val Ala Thr Thr Ser Pro Cys Thr Asp Gly Tyr Phe Gly
                85                  90                  95

Glu Leu Leu Ala Thr Ser Leu Arg Ala Arg Gly Val Ala Gly Leu Val
            100                 105                 110

Ile Asp Ala Gly Cys Arg Asp Val Arg Ala Leu Thr Glu Met Arg Phe
        115                 120                 125

Pro Val Trp Ser Arg Ala Ile Ser Ala Gln Gly Thr Val Lys Ala Thr
130                 135                 140

Leu Gly Ser Val Asn Ala Ala Val Val Cys Ala Gly Thr Ser Val Arg
145                 150                 155                 160

Ala Gly Asp Leu Ile Val Ala Asp Asp Gly Val Val Ala Val Arg
                165                 170                 175

Arg Glu Glu Val Val Ala Val Thr Gln Ala Ala Glu Gln Arg Val Arg
            180                 185                 190

Lys Glu Glu Gly Thr Arg Ala Arg Leu Ala Gln Gly Glu Leu Gly Leu
        195                 200                 205

Asp Ile Tyr Gly Leu Arg Gln Lys Leu Ser Asp Leu Gly Leu Lys Ser
    210                 215                 220

Ser Ser
225
```

```
<210> SEQ ID NO 79
<211> LENGTH: 678
<212> TYPE: DNA
<213> ORGANISM: Unknown
<220> FEATURE:
<223> OTHER INFORMATION: DNA obtained from environmental sample

<400> SEQUENCE: 79
atgagcgagc cggtcgtcgt tcggcagatc gagaggccct cttcggccgc gatcgccgat    60
ctccggcggt acggcgtctc gacggttcac gaagcgcagg gccgccgcgg actgctcgcg    120
```

```
tccggcctgc ggccgatcta tgcgaccgcg ctcatggcgg ccctgcgat cacggtgctg      180 gtcgcaccgg gcgacaacct gatgatccac gtcgccgtcg aggtctgcca gcccggggat      240
gtgctcgtgg tcacgccgac gtcaccgtgc acggacggct atttcggcga gctgctggcc      300
acgtcgctgc gggcgcgagg cgttgcgggc ctcgtcatcg acgccggctg ccgcgacatt      360
cgcgcgctga cggagatgcg gtttcccgta tggagtcgcg cgatcagcgc gcagggcacg      420
gtcaaagcca cgctcggctc cgtgaatgtc cccgtcgtct gcgccggcgc gcttgtcgaa      480
gcgggcgacg tcatcgtcgc cgacgatgac ggggtcgtgg tggtgaagcg gggcgaagtc      540
gacgtcgtca tccaggcggc ggagcagcgc gtgcgcaagg aagaagtcac gcgggcccgg      600
ctggcgcagg gcgagctcgg tctggacatc tacggcctgc gcaagaagat tgcggacctg      660
ggcttgaagt cgtcgtga                                                    678
```

<210> SEQ ID NO 80
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 80

```
Met Ser Glu Pro Val Val Arg Gln Ile Glu Arg Pro Ser Ser Ala
1               5                   10                  15

Ala Ile Ala Asp Leu Arg Arg Tyr Gly Val Ser Thr Val His Glu Ala
                20                  25                  30

Gln Gly Arg Arg Gly Leu Leu Ala Ser Gly Leu Arg Pro Ile Tyr Ala
            35                  40                  45

Thr Ala Leu Met Ala Gly Pro Ala Ile Thr Val Leu Val Ala Pro Gly
        50                  55                  60

Asp Asn Leu Met Ile His Val Ala Val Glu Val Cys Gln Pro Gly Asp
65                  70                  75                  80

Val Leu Val Val Thr Pro Thr Ser Pro Cys Thr Asp Gly Tyr Phe Gly
                85                  90                  95

Glu Leu Leu Ala Thr Ser Leu Arg Ala Arg Gly Val Ala Gly Leu Val
                100                 105                 110

Ile Asp Ala Gly Cys Arg Asp Ile Arg Ala Leu Thr Glu Met Arg Phe
            115                 120                 125

Pro Val Trp Ser Arg Ala Ile Ser Ala Gln Gly Thr Val Lys Ala Thr
        130                 135                 140

Leu Gly Ser Val Asn Val Pro Val Val Cys Ala Gly Ala Leu Val Glu
145                 150                 155                 160

Ala Gly Asp Val Ile Val Ala Asp Asp Gly Val Val Val Val Lys
                165                 170                 175

Arg Gly Glu Val Asp Val Ile Gln Ala Ala Glu Gln Arg Val Arg
            180                 185                 190

Lys Glu Glu Val Thr Arg Ala Arg Leu Ala Gln Gly Glu Leu Gly Leu
        195                 200                 205

Asp Ile Tyr Gly Leu Arg Lys Lys Ile Ala Asp Leu Gly Leu Lys Ser
    210                 215                 220

Ser
225
```

<210> SEQ ID NO 81
<211> LENGTH: 678
<212> TYPE: DNA
<213> ORGANISM: Unknown
<220> FEATURE:
<223> OTHER INFORMATION: DNA obtained from environmental sample

<400> SEQUENCE: 81

```
atgaacgagc cgaccgttgt tcgagcgatc gacaggccgc cggcggatgt ggtcgcggcg      60
ctccagcgct acggcgtgtc gaccgtgcat gaagcacaag ggagacgcgg cctcgtagcg     120
tcctgcatgc ggccgatcta caccggcgct ttggtcgccg gtcctgccgt aaccgtctcg     180
ctcccgccgg gcgacaacct catgattcac gtcgctgtcg aagcctgcca ggcgggcgac     240
gtgcttgtcg tggtgccgac ctccccgtgc acggacgggt atttcggtga gttactggcg     300
acgtcgctgc acgcacgcgg agtcgtggct ctcgtcatcg atgccggctg ccgcgacgtg     360
cgcgctctgt cggagatgcg atttcctgtc tggagccgcg cgatcagcgc tcagggcacg     420
gtcaaagcca cgttgggatc ggtgaacgtt cccgtggtgt gcgcgggagc gcccgtggag     480
cccggcgatg tgatcgtcgc cgacgacgat ggggtggtgg ttgtgaagcg cagcgaggtg     540
gagggggtgg cgcaggcgtc ggagcagcga gtcctgaagg aggaggcgac gcgcgagcgg     600
ttggcgcgcg cgagctgggc cctcgacatc tacgggctgc ggaaaaaggt gtcggacctc     660
ggcctgaaat attcgtga                                                   678
```

<210> SEQ ID NO 82
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 82

Met Asn Glu Pro Thr Val Val Arg Ala Ile Asp Arg Pro Pro Ala Asp
1               5                   10                  15

Val Val Ala Ala Leu Gln Arg Tyr Gly Val Ser Thr Val His Glu Ala
            20                  25                  30

Gln Gly Arg Arg Gly Leu Val Ala Ser Cys Met Arg Pro Ile Tyr Thr
        35                  40                  45

Gly Ala Leu Val Ala Gly Pro Ala Val Thr Val Ser Leu Pro Pro Gly
    50                  55                  60

Asp Asn Leu Met Ile His Val Ala Val Glu Ala Cys Gln Ala Gly Asp
65                  70                  75                  80

Val Leu Val Val Pro Thr Ser Pro Cys Thr Asp Gly Tyr Phe Gly
                85                  90                  95

Glu Leu Leu Ala Thr Ser Leu His Ala Arg Gly Val Val Ala Leu Val
            100                 105                 110

Ile Asp Ala Gly Cys Arg Asp Val Arg Ala Leu Ser Glu Met Arg Phe
        115                 120                 125

Pro Val Trp Ser Arg Ala Ile Ser Ala Gln Gly Thr Val Lys Ala Thr
    130                 135                 140

Leu Gly Ser Val Asn Val Pro Val Val Cys Ala Gly Ala Pro Val Glu
145                 150                 155                 160

Pro Gly Asp Val Ile Val Ala Asp Asp Asp Gly Val Val Val Val Lys
                165                 170                 175

```
Arg Ser Glu Val Glu Gly Val Ala Gln Ala Ser Glu Gln Arg Val Leu
            180                 185                 190

Lys Glu Glu Ala Thr Arg Glu Arg Leu Ala Arg Gly Glu Leu Gly Leu
        195                 200                 205

Asp Ile Tyr Gly Leu Arg Lys Lys Val Ser Asp Leu Gly Leu Lys Tyr
    210                 215                 220

Ser
225

<210> SEQ ID NO 83
<211> LENGTH: 678
<212> TYPE: DNA
<213> ORGANISM: Unknown
<220> FEATURE:
<223> OTHER INFORMATION: DNA obtained from environmental sample

<400> SEQUENCE: 83
atgagcgagc cggtcgtcgt tcggcagatc gagaggccct cttcggccgc gatcgccgat      60
ctccggcggt acggcgtctc gacggttcac gaagcgcagg gccgccgcgg actgctcgcg     120
tccggcctgc ggccgatcta tgcgagcgcg ctcatggtgg ccctgcgat cacggtgctg     180 gtcgcaccgg gcgacaacct gatgatccac gtcgccgtcg aggtctgcca gcccggggat     240
gtgctcgtgg tcacgccgac gtcaccgtgc acggacggca tttcggcga gctgctggcc     300 acgtcgctgc gggcgcgagg cgttgcgggc ctcgtcatcg acgccggctg ccgcgacatt     360
cgcgcgctga cggagatgcg gtttcccgta tggagtcgcg cgatcagcgc gcagggcacg     420
gtcaaagcca cgctcggctc cgtgaatgtc cccgtcgtct gcgccggcgc gctcgtcgaa     480
gcgggcgacg tcatcgtcgc cgacgatgac ggggtcgtgg tggtgaagcg gggcgaagtc     540
gacgtcgtca tccaggcggc ggagcagcgc gtgcgcaagg aagaagtcac gcgggcgcgg     600
ctggcgcagg gcgagctcgg tctggacatc tacggcctgc gcaagaagat tgcggacctg     660
ggcttgaagt cgttgtga                                                   678

<210> SEQ ID NO 84
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 84

Met Ser Glu Pro Val Val Arg Gln Ile Glu Arg Pro Ser Ser Ala
1               5                   10                  15

Ala Ile Ala Asp Leu Arg Arg Tyr Gly Val Ser Thr Val His Glu Ala
            20                  25                  30

Gln Gly Arg Arg Gly Leu Leu Ala Ser Gly Leu Arg Pro Ile Tyr Ala
        35                  40                  45

Ser Ala Leu Met Val Gly Pro Ala Ile Thr Val Leu Val Ala Pro Gly
    50                  55                  60

Asp Asn Leu Met Ile His Val Ala Val Glu Val Cys Gln Pro Gly Asp
65                  70                  75                  80

Val Leu Val Val Thr Pro Thr Ser Pro Cys Thr Asp Gly Tyr Phe Gly
                85                  90                  95

Glu Leu Leu Ala Thr Ser Leu Arg Ala Arg Gly Val Ala Gly Leu Val
```

```
                    100                 105                 110
Ile Asp Ala Gly Cys Arg Asp Ile Arg Ala Leu Thr Glu Met Arg Phe
        115                 120                 125

Pro Val Trp Ser Arg Ala Ile Ser Ala Gln Gly Thr Val Lys Ala Thr
    130                 135                 140

Leu Gly Ser Val Asn Val Pro Val Val Cys Ala Gly Ala Leu Val Glu
145                 150                 155                 160

Ala Gly Asp Val Ile Val Asp Asp Gly Val Val Val Lys
                165                 170                 175

Arg Gly Glu Val Asp Val Ile Gln Ala Ala Glu Gln Val Arg
            180                 185                 190

Lys Glu Glu Val Thr Arg Ala Arg Leu Ala Gln Gly Glu Leu Gly Leu
        195                 200                 205

Asp Ile Tyr Gly Leu Arg Lys Lys Ile Ala Asp Leu Gly Leu Lys Ser
    210                 215                 220

Leu
225

<210> SEQ ID NO 85
<211> LENGTH: 699
<212> TYPE: DNA
<213> ORGANISM: Unknown
<220> FEATURE:
<223> OTHER INFORMATION: DNA obtained from environmental sample

<400> SEQUENCE: 85
atgaccggca ttgtcgtcga gaccatcgag cgcgcgtcgc tcgccgacat cgccgcgttg     60
gccgaattcg gcgtcgccac catccacgag gcgcagggcc gcatcggcct gcttgcctcc    120
accatgcgcc cgatctacgc aggcgcggcg gccgccggca atgccgtcac cgtgtcggtg    180
ccgcccggcg acaactggat gatccacgtc gccgtcgagc agtgccgcga aggcgatatt    240
ctcgtcgtcg cccccaccag cccgaacgac aacggctact tggcgaaact gctggcctgc    300
tcgctcaagt cgcgcggcgt gcgcggcctc atcatcgagg ccggctgccg cgacgtgaaa    360
ccgctcaccg agatgaagtt ccccgtctgg tcccgcgccg tctcctccca gggcacggtg    420
aaggaaagcc tcggcgacgt gaacctgccg ctctcgatcg ccggccagct cgtcaacccc    480
ggcgatgtca tcgtcgccga tgacgacggc gtggtcgtgg tctcccgcaa tgaagtcagg    540
agcgtcaccg ccaagtcccg cgagcgcgaa gacaaggagg ccaagaaccg cgtgcagctc    600
caagccggcc agctcggcat cgacatctac ggcatgcgcg acaagctcaa ggccaagggc    660
ctccgctacg tcaaatccgc ggcggagttg aagaagtag                          699

<210> SEQ ID NO 86
<211> LENGTH: 232
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (21)...(173)
<223> OTHER INFORMATION: Demethylmenaquinone methyltransferase

<400> SEQUENCE: 86

Met Thr Gly Ile Val Val Glu Thr Ile Glu Arg Ala Ser Leu Ala Asp
1               5                   10                  15

Ile Ala Ala Leu Ala Glu Phe Gly Val Ala Thr Ile His Glu Ala Gln
            20                  25                  30
```

Gly Arg Ile Gly Leu Leu Ala Ser Thr Met Arg Pro Ile Tyr Ala Gly
            35                  40                  45

Ala Ala Ala Ala Gly Asn Ala Val Thr Val Ser Val Pro Pro Gly Asp
 50                  55                  60

Asn Trp Met Ile His Val Ala Val Glu Gln Cys Arg Glu Gly Asp Ile
 65                  70                  75                  80

Leu Val Val Ala Pro Thr Ser Pro Asn Asp Asn Gly Tyr Phe Gly Glu
                 85                  90                  95

Leu Leu Ala Cys Ser Leu Lys Ser Arg Gly Val Arg Gly Leu Ile Ile
                100                 105                 110

Glu Ala Gly Cys Arg Asp Val Lys Pro Leu Thr Glu Met Lys Phe Pro
                115                 120                 125

Val Trp Ser Arg Ala Val Ser Ser Gln Gly Thr Val Lys Glu Ser Leu
130                 135                 140

Gly Asp Val Asn Leu Pro Leu Ser Ile Ala Gly Gln Leu Val Asn Pro
145                 150                 155                 160

Gly Asp Val Ile Val Ala Asp Asp Gly Val Val Val Ser Arg
                165                 170                 175

Asn Glu Val Arg Ser Val Thr Ala Lys Ser Arg Glu Arg Glu Asp Lys
                180                 185                 190

Glu Ala Lys Asn Arg Val Gln Leu Gln Ala Gly Gln Leu Gly Ile Asp
                195                 200                 205

Ile Tyr Gly Met Arg Asp Lys Leu Lys Ala Lys Gly Leu Arg Tyr Val
210                 215                 220

Lys Ser Ala Ala Glu Leu Lys Lys
225                 230

<210> SEQ ID NO 87
<211> LENGTH: 672
<212> TYPE: DNA
<213> ORGANISM: Unknown
<220> FEATURE:
<223> OTHER INFORMATION: DNA obtained from environmental sample

<400> SEQUENCE: 87
atgggcattg tcgttcagaa cattcagcgg gcggagcagt ccgtcatcga tcgtctcgct      60
gcttgcggag ttgcgaccgt acatgaagcg cagggccgca aggggctgct cgccagctac     120
atgcggccga tttatccggg cgcgcggatc gcggcgagtg ccgtgacaat tccgcgcct     180 ccgggcgata actggatgct gcatgtggcg atcgagcaga tcaaggcggg cgatatccta     240
ctgcttgcgc cgaccagtcc ctgcgaggac ggttatttcg gcgatctctt ggcgacgtct     300
gccatggcac gcggctgccg cgggttggtg atcgatgccg cgtgcgcga tgtcgccgat      360 ctcaaggcga tgaattttcc cgtttggtcg aagacgatct ctgcacaggg gacggtcaag     420
gagacggtgg gctcggtcaa tattcccgtc gtctgcgcca gtgcgctcgt caatcctggc     480
gatgtgatcg ttgccgatga tgatggcgtc tgcgtcgtac ggcgggagga agctgccgag     540
gtcgcggata aggccgagca gcgggtcgcg gcagaagagg acaagcgccg gcgactggcc     600
gcgggtgaac tcgggctcga tatctacaag atgcgcgagc ggctggcgga agggggctg     660 aaatatgtct ag                                                         672

<210> SEQ ID NO 88
<211> LENGTH: 223
<212> TYPE: PRT
<213> ORGANISM: Unknown
<220> FEATURE:
<223> OTHER INFORMATION: Protein obtained from environmental sample

```
<220> FEATURE:
<221> NAME/KEY: DOMAIN
<222> LOCATION: (20)...(172)
<223> OTHER INFORMATION: Demethylmenaquinone methyltransferase

<400> SEQUENCE: 88

Met Gly Ile Val Val Gln Asn Ile Gln Arg Ala Glu Gln Ser Val Ile
1               5                   10                  15

Asp Arg Leu Ala Ala Cys Gly Val Ala Thr Val His Glu Ala Gln Gly
            20                  25                  30

Arg Lys Gly Leu Leu Ala Ser Tyr Met Arg Pro Ile Tyr Pro Gly Ala
        35                  40                  45

Arg Ile Ala Ala Ser Ala Val Thr Ile Ser Ala Pro Pro Gly Asp Asn
    50                  55                  60

Trp Met Leu His Val Ala Ile Glu Gln Ile Lys Ala Gly Asp Ile Leu
65                  70                  75                  80

Leu Leu Ala Pro Thr Ser Pro Cys Glu Asp Gly Tyr Phe Gly Asp Leu
                85                  90                  95

Leu Ala Thr Ser Ala Met Ala Arg Gly Cys Arg Gly Leu Val Ile Asp
            100                 105                 110

Ala Gly Val Arg Asp Val Ala Asp Leu Lys Ala Met Asn Phe Pro Val
        115                 120                 125

Trp Ser Lys Thr Ile Ser Ala Gln Gly Thr Val Lys Glu Thr Val Gly
    130                 135                 140

Ser Val Asn Ile Pro Val Val Cys Ala Ser Ala Leu Val Asn Pro Gly
145                 150                 155                 160

Asp Val Ile Val Ala Asp Asp Gly Val Cys Val Val Arg Arg Glu
                165                 170                 175

Glu Ala Ala Glu Val Ala Asp Lys Ala Glu Gln Arg Val Ala Ala Glu
            180                 185                 190

Glu Asp Lys Arg Arg Arg Leu Ala Ala Gly Glu Leu Gly Leu Asp Ile
        195                 200                 205

Tyr Lys Met Arg Glu Arg Leu Ala Glu Lys Gly Leu Lys Tyr Val
    210                 215                 220

<210> SEQ ID NO 89
<211> LENGTH: 696
<212> TYPE: DNA
<213> ORGANISM: Unknown
<220> FEATURE:
<223> OTHER INFORMATION: DNA obtained from environmental sample

<400> SEQUENCE: 89
atgaagcgcg gcgtggtggt gacccatatc gcgcgggcgg atgcggcgaa cgtggccgtg      60
ctgcgggagg caggcgttgc gaccgtccac gaggcgcaga gccggcttgg tcttctagcg     120
tgctacatgc ggccgatcta tccgggcgcg gccattgccg accggccgt cacggtgctc      180 gtgccgccgt cggacaactg gatgctgcat gtggcggtcg aacagtgccg cgcaggcgac     240
gtgctggtgg tggcgcccac gtctgcctgc gaggacgggt atttcgggga actgcttgcc     300
acgtcgctcg cgaagcgcgg cgtacagggc ctgatcatcg atgcgggctg ccgggatgtg     360
tgcgcgctca aggcaatgga ttttcccgtg tggtcgaagg ccgtctccgc gcagggcacg     420
gtcaaggaga cgctcggctc ggtcaatgtg ccggtcgtat gcgcgcagca gatcgtgcat     480
ccgggagacg tgatcgtggc cgatgacgac ggcatcgtcg tggcgccgct cgccaccgtc     540
gaggcggtag cgaaggccgc gcaggcgcgc ctggagaagg aagagaagac gcgtgcggtg     600
ctcgcaagcg gcacgctcgg cctcgactac tacgcgatgc gtgacaggct cgcggaaaga     660
```

```
ggcttgcgct acgtcgattc ggcctctgaa ctttga                                696
```

<210> SEQ ID NO 90
<211> LENGTH: 231
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 90

```
Met Lys Arg Gly Val Val Thr His Ile Ala Arg Ala Asp Ala Ala
1               5                   10                  15

Asn Val Ala Val Leu Arg Glu Ala Gly Val Ala Thr Val His Glu Ala
                20                  25                  30

Gln Ser Arg Leu Gly Leu Leu Ala Cys Tyr Met Arg Pro Ile Tyr Pro
            35                  40                  45

Gly Ala Ala Ile Ala Gly Pro Ala Val Thr Val Leu Val Pro Pro Ser
        50                  55                  60

Asp Asn Trp Met Leu His Val Ala Val Glu Gln Cys Arg Ala Gly Asp
65                  70                  75                  80

Val Leu Val Val Ala Pro Thr Ser Ala Cys Glu Asp Gly Tyr Phe Gly
                85                  90                  95

Glu Leu Leu Ala Thr Ser Leu Ala Lys Arg Gly Val Gln Gly Leu Ile
            100                 105                 110

Ile Asp Ala Gly Cys Arg Asp Val Cys Ala Leu Lys Ala Met Asp Phe
        115                 120                 125

Pro Val Trp Ser Lys Ala Val Ser Ala Gln Gly Thr Val Lys Glu Thr
130                 135                 140

Leu Gly Ser Val Asn Val Pro Val Cys Ala Gln Gln Ile Val His
145                 150                 155                 160

Pro Gly Asp Val Ile Val Ala Asp Asp Gly Ile Val Val Ala Pro
                165                 170                 175

Leu Ala Thr Val Glu Ala Val Ala Lys Ala Ala Gln Ala Arg Leu Glu
            180                 185                 190

Lys Glu Glu Lys Thr Arg Ala Val Leu Ala Ser Gly Thr Leu Gly Leu
        195                 200                 205

Asp Tyr Tyr Ala Met Arg Asp Arg Leu Ala Glu Arg Gly Leu Arg Tyr
210                 215                 220

Val Asp Ser Ala Ser Glu Leu
225                 230
```

<210> SEQ ID NO 91
<211> LENGTH: 678
<212> TYPE: DNA
<213> ORGANISM: Unknown
<220> FEATURE:
<223> OTHER INFORMATION: DNA obtained from environmental sample

<400> SEQUENCE: 91

```
atgaacaaac cggtggtggt ccggaaggtc gaacagccgc cacaagatgc ggtggcggct      60
ctggagaaat atggcgtgtc cacggtgcac gaagcgcaag ccgttgcgg gctgctcgcc     120
ccttacatgc gcccgatcta tgccggcgct tccatggccg ggcccgccgt caccgtctcc    180
cttccgcccg gtgacaacct catgatccat gtcgcggtcg aagtgtgcca gcccggaaac    240
```

```
attctggtcg tcgcccccac ttcaccttgt accgacgggt atttcggcga gttgctggct    300
acttccttgc gcgcccacgg cgtgaaggca ctcataatcg atgccggatg ccgtgacgtg    360
cgctccctca ccgaaatgaa gtttcccgtg tggagccgcg ccgtcagttc gcagggaaca    420
gtgaagtcca cgctcggatc agtgaacgtg gcgtagtgt gtgcgggcgc tttcatcgaa    480
gcgggcgaca tcgtcgtcgc tgatgatgac ggagttgtcg tcgtgaagcg actttcgcg    540 cgcgacgtgt tgaagcctg tgaacagagg gttcgcaagg aagaggcgac gcgggcacgg    600
ctggcgcggg gcgaacttgg gctggacatc tacggattgc gctccaaggt ggcggaactc    660
ggtctcaagt acatataa                                                  678
```

```
<210> SEQ ID NO 92
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 92
```

```
Met Asn Lys Pro Val Val Arg Lys Val Glu Gln Pro Gln Asp
1               5                   10                  15

Ala Val Ala Ala Leu Glu Lys Tyr Gly Val Ser Thr Val His Glu Ala
            20                  25                  30

Gln Gly Arg Cys Gly Leu Leu Ala Pro Tyr Met Arg Pro Ile Tyr Ala
        35                  40                  45

Gly Ala Ser Met Ala Gly Pro Ala Val Thr Val Ser Leu Pro Pro Gly
    50                  55                  60

Asp Asn Leu Met Ile His Val Ala Val Glu Val Cys Gln Pro Gly Asn
65                  70                  75                  80

Ile Leu Val Val Ala Pro Thr Ser Pro Cys Thr Asp Gly Tyr Phe Gly
                85                  90                  95

Glu Leu Leu Ala Thr Ser Leu Arg Ala His Gly Val Lys Ala Leu Ile
            100                 105                 110

Ile Asp Ala Gly Cys Arg Asp Val Arg Ser Leu Thr Glu Met Lys Phe
        115                 120                 125

Pro Val Trp Ser Arg Ala Val Ser Ser Gln Gly Thr Val Lys Ser Thr
    130                 135                 140

Leu Gly Ser Val Asn Val Gly Val Val Cys Ala Gly Ala Phe Ile Glu
145                 150                 155                 160

Ala Gly Asp Ile Val Ala Asp Asp Gly Val Val Val Lys
                165                 170                 175

Arg Thr Phe Ala Arg Asp Val Val Glu Ala Cys Glu Gln Arg Val Arg
            180                 185                 190

Lys Glu Glu Ala Thr Arg Ala Arg Leu Ala Arg Gly Glu Leu Gly Leu
        195                 200                 205

Asp Ile Tyr Gly Leu Arg Ser Lys Val Ala Glu Leu Gly Leu Lys Tyr
    210                 215                 220

Ile
225
```

```
<210> SEQ ID NO 93
<211> LENGTH: 678
<212> TYPE: DNA
<213> ORGANISM: Unknown
```

<220> FEATURE:
<223> OTHER INFORMATION: DNA obtained from environmental sample

<400> SEQUENCE: 93

```
atgaataaac cggtggtagt ccggcaagtg gagcagccac cagcggacgc ggttgcggcg      60
ctggagaagt atggcgtcac caccgtgcat gaggctcagg gacgttgtgg cctgctcgcg     120
cactacatgc gtccgatttt tccgggagcg gccatctcgg ttctgctgt caccgtagcc     180
ttgccgccgg gcgataacct catgatccac gtcgcggtcg aggtctgcgg cccgggaaac     240
atcctggtgg ttgcgccgac ctcgccttcg acggatggct acttcggtga gctgttggcg     300
acctctctgc gtgctcgcgg tgtgaaagga cttgtgattg atgccggatg ccgtgacgtt     360
cgctccctga ccgagatgaa attccccgtc tggagccgtg ccatcagctc gcagggaaca     420
gtcaaggcca ccctcggatc ggtgaatgtg ccggtcatgt gcgcgggcgc gctcgtcgaa     480
gctggggatg tcatcgtcgc cgatgatgat ggaattgtgg ttgtcaagcg cgcgcatgcg     540
cacgaggtgg ccgcggcggc agaacaaagg gtgcgcaaag agaatataac ccgcgaacgg     600
cttcgacgcg gagagctcgg actcgatatt tacgacatgc gccaaaaat cgcgcaactg     660
ggcctcaaat acctgtga                                                  678
```

<210> SEQ ID NO 94
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 94

```
Met Asn Lys Pro Val Val Arg Gln Val Glu Gln Pro Ala Asp
1               5                   10                  15

Ala Val Ala Ala Leu Glu Lys Tyr Gly Val Thr Thr Val His Glu Ala
                20                  25                  30

Gln Gly Arg Cys Gly Leu Leu Ala His Tyr Met Arg Pro Ile Phe Pro
            35                  40                  45

Gly Ala Ala Ile Ser Gly Ser Ala Val Thr Val Ala Leu Pro Pro Gly
        50                  55                  60

Asp Asn Leu Met Ile His Val Ala Val Glu Val Cys Gly Pro Gly Asn
65                  70                  75                  80

Ile Leu Val Val Ala Pro Thr Ser Pro Ser Thr Asp Gly Tyr Phe Gly
                85                  90                  95

Glu Leu Leu Ala Thr Ser Leu Arg Ala Arg Gly Val Lys Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Ile Ser Ser Gln Gly Thr Val Lys Ala Thr
    130                 135                 140

Leu Gly Ser Val Asn Val Pro Val Met Cys Ala Gly Ala Leu Val Glu
145                 150                 155                 160

Ala Gly Asp Val Ile Val Ala Asp Asp Gly Ile Val Val Lys
                165                 170                 175

Arg Ala His Ala His Glu Val Ala Ala Ala Glu Gln Arg Val Arg
            180                 185                 190

Lys Glu Asn Ile Thr Arg Glu Arg Leu Arg Arg Gly Glu Leu Gly Leu
```

```
                   195                 200                 205
Asp Ile Tyr Asp Met Arg Gln Lys Ile Ala Gln Leu Gly Leu Lys Tyr
        210                 215                 220

Leu
225
```

<210> SEQ ID NO 95
<211> LENGTH: 639
<212> TYPE: DNA
<213> ORGANISM: Unknown
<220> FEATURE:
<223> OTHER INFORMATION: DNA obtained from environmental sample

<400> SEQUENCE: 95

```
gtgagcgatc cgatcgccga cctgcgcggg tatggagtct cgacggttca cgaggcccag     60
ggccggcgcg gtctgctggc gccttacatg cgtccgatct atgccggcgc ccttgtcgcc    120
ggaccagccg tgacggttct ggtcccgccc ggcgacaacc tgatgatcca cgtcgccgtc    180
gagcggtgct cgccgggcga catcctcgtc gtcgcgccga cgtcgccgtg cacggacggc    240
tatttcggcg agctgctggc gacgtcgctg cgggcacgcg gtgtcgccgc actgatcatc    300
gacgccggct gcagggacgt gcgagcgctc accgagatgc gcttcccggt gtggagccgc    360
gccatcagcg cccaaggaac ggtgaaggcg acgctcggct cggtgaatgt gccagtggtc    420
tgcgccggag ccatcgtcgg tcctggcgac gtcatggttg cggacgatga cggcgtggtc    480
gtggtgagga aggacgaagt cgccgcggtg acgcaggcgg cggcgcagcg ggtccgcaaa    540
gaagagggca cgcgggcgcg gctggccgcg ggcgagctcg gcctggacat ctacggcctc    600
cggcagaagc tgtcggatct cggcctgaag tcgtcgtga                          639
```

<210> SEQ ID NO 96
<211> LENGTH: 212
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (9)...(161)
<223> OTHER INFORMATION: Demethylmenaquinone methyltransferase

<400> SEQUENCE: 96

```
Met Ser Asp Pro Ile Ala Asp Leu Arg Gly Tyr Gly Val Ser Thr Val
1               5                   10                  15

His Glu Ala Gln Gly Arg Arg Gly Leu Leu Ala Pro Tyr Met Arg Pro
            20                  25                  30

Ile Tyr Ala Gly Ala Leu Val Ala Gly Pro Ala Val Thr Val Leu Val
        35                  40                  45

Pro Pro Gly Asp Asn Leu Met Ile His Val Ala Val Glu Arg Cys Ser
    50                  55                  60

Pro Gly Asp Ile Leu Val Val Ala Pro Thr Ser Pro Cys Thr Asp Gly
65                  70                  75                  80

Tyr Phe Gly Glu Leu Leu Ala Thr Ser Leu Arg Ala Arg Gly Val Ala
                85                  90                  95

Ala Leu Ile Ile Asp Ala Gly Cys Arg Asp Val Arg Ala Leu Thr Glu
            100                 105                 110

Met Arg Phe Pro Val Trp Ser Arg Ala Ile Ser Ala Gln Gly Thr Val
        115                 120                 125

Lys Ala Thr Leu Gly Ser Val Asn Val Pro Val Val Cys Ala Gly Ala
    130                 135                 140
```

```
Ile Val Gly Pro Gly Asp Val Met Val Ala Asp Asp Gly Val Val
145                 150                 155                 160

Val Val Arg Lys Asp Glu Val Ala Ala Val Thr Gln Ala Ala Gln
                165                 170                 175

Arg Val Arg Lys Glu Glu Gly Thr Arg Ala Arg Leu Ala Ala Gly Glu
            180                 185                 190

Leu Gly Leu Asp Ile Tyr Gly Leu Arg Gln Lys Leu Ser Asp Leu Gly
        195                 200                 205

Leu Lys Ser Ser
    210

<210> SEQ ID NO 97
<211> LENGTH: 678
<212> TYPE: DNA
<213> ORGANISM: Unknown
<220> FEATURE:
<223> OTHER INFORMATION: DNA obtained from environmental sample

<400> SEQUENCE: 97
atgagcggcc ccacggtcgt tcgcgagatc gaccggccgg aaggcgacct cgtgaccgca       60
cttgagcacg cgggcgtgtc gacggtccac gaagcacagg gacggcgggg actgctcgcc      120
acctacatgc ggccgattta cgccggagcc gtgatcgccg gaccggcggt caccgtcctc      180
gtgccgcccg gcgacaacct gatgattcac gtggcggtcg aagtgtgccg cccgggtgac      240
gtgctggtcg tcgccgtcac gtcgccgtgt accgacggct acttcggtga gctgctggcg      300
acgtcggttc gcgcgcgcgg cgtcaaaggg ctcgtcatcg atgcagggtg ccgggacgtg      360
cgggcgctca ccgagatgcg gtttccggtg tggagccggg cggtcagtgc gcagggcacc      420
gtcaaggcca cgctcggctc cgtgaacgtt ccagtcgtgt gtgccggcgc gctcatcaca      480
ggtggagacg tcgtcatcgc cgacgacgat ggggtggtcg tggtgaagcg cgaggaagtg      540
gacgcggtcg ttcaggactc gcgccagcgg ctgctcaagg aagacgggac gcgagagcgt      600
ctcgcgacag gcgagctggg gctggacatc tactcgctgc gcaagatgct gtccgatctg      660
ggactgaagt accgatag                                                    678

<210> SEQ ID NO 98
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 98

Met Ser Gly Pro Thr Val Val Arg Glu Ile Asp Arg Pro Glu Gly Asp
1               5                   10                  15

Leu Val Thr Ala Leu Glu His Ala Gly Val Ser Thr Val His Glu Ala
            20                  25                  30

Gln Gly Arg Arg Gly Leu Leu Ala Thr Tyr Met Arg Pro Ile Tyr Ala
        35                  40                  45

Gly Ala Val Ile Ala Gly Pro Ala Val Thr Val Leu Val Pro Pro Gly
    50                  55                  60

Asp Asn Leu Met Ile His Val Ala Val Glu Val Cys Arg Pro Gly Asp
65                  70                  75                  80

Val Leu Val Val Ala Val Thr Ser Pro Cys Thr Asp Gly Tyr Phe Gly
```

```
                    85                  90                  95
Glu Leu Ala Thr Ser Val Arg Ala Arg Gly Val Lys Gly Leu Val
            100                 105                 110

Ile Asp Ala Gly Cys Arg Asp Val Arg Ala Leu Thr Glu Met Arg Phe
            115                 120                 125

Pro Val Trp Ser Arg Ala Val Ser Ala Gln Gly Thr Val Lys Ala Thr
            130                 135                 140

Leu Gly Ser Val Asn Val Pro Val Val Cys Ala Gly Ala Leu Ile Thr
145                 150                 155                 160

Gly Gly Asp Val Val Ile Ala Asp Asp Gly Val Val Val Lys
                165                 170                 175

Arg Glu Glu Val Asp Ala Val Val Gln Asp Ser Arg Gln Arg Leu Leu
            180                 185                 190

Lys Glu Asp Gly Thr Arg Glu Arg Leu Ala Thr Gly Glu Leu Gly Leu
            195                 200                 205

Asp Ile Tyr Ser Leu Arg Lys Met Leu Ser Asp Leu Gly Leu Lys Tyr
            210                 215                 220

Arg
225

<210> SEQ ID NO 99
<211> LENGTH: 639
<212> TYPE: DNA
<213> ORGANISM: Unknown
<220> FEATURE:
<223> OTHER INFORMATION: DNA obtained from environmental sample

<400> SEQUENCE: 99
gtgagcgatc cgatcgccga cctgcgaggg tatggtgtct ccacggttca cgaggcgcag      60
ggccggcgcg gcctgctggc gccttacatg cgtccgatct atgccggcgc gctcgtcgcc     120
ggaccagccg tgacggtcct ggtcccgccc ggcgacaacc tgatgatcca cgtcgctgtc     180
gagcggtgct cgccaggcga catcctcgtc gtcgcgccga cgtcgccgtg cacggacggc     240
tatttcggcg agctgctggc gacgtcgctg cgggcacgcg tgtcgccgc actgatcatc      300 gacgctggct gcagggacgt gcgagcgctc accgagatgc gcttcccggt gtggagccgc     360
gccatcagcg cccaaggaac ggtgaaagcg acgctcggct cggtgaatgt gccactggtc     420
tgcgccggag ccatcgtcgg tcctggcgac gtcatggttg cggacgatga cggcgtggtc     480
gtggtgagga aggacgaagt cgccgcggtg acgcaggcgg cggcgcagcg ggtccgcaaa     540
gaagaaggca cgcgggcgcg gctggccgcg ggcgagctcg gcctggacat ctacggcctc     600
cggcagaagc tgtcggatct cggcctgaag tcgtcgtga                           639

<210> SEQ ID NO 100
<211> LENGTH: 212
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (9)...(161)
<223> OTHER INFORMATION: Demethylmenaquinone methyltransferase

<400> SEQUENCE: 100

Met Ser Asp Pro Ile Ala Asp Leu Arg Gly Tyr Gly Val Ser Thr Val
1               5                   10                  15

His Glu Ala Gln Gly Arg Arg Gly Leu Leu Ala Pro Tyr Met Arg Pro
            20                  25                  30
```

Ile Tyr Ala Gly Ala Leu Val Ala Gly Pro Val Thr Val Leu Val
            35                  40                  45

Pro Pro Gly Asp Asn Leu Met Ile His Val Ala Val Glu Arg Cys Ser
 50                  55                  60

Pro Gly Asp Ile Leu Val Val Ala Pro Thr Ser Pro Cys Thr Asp Gly
 65                  70                  75                  80

Tyr Phe Gly Glu Leu Leu Ala Thr Ser Leu Arg Ala Arg Gly Val Ala
                 85                  90                  95

Ala Leu Ile Ile Asp Ala Gly Cys Arg Asp Val Arg Ala Leu Thr Glu
                100                 105                 110

Met Arg Phe Pro Val Trp Ser Arg Ala Ile Ser Ala Gln Gly Thr Val
                115                 120                 125

Lys Ala Thr Leu Gly Ser Val Asn Val Pro Leu Val Cys Ala Gly Ala
130                 135                 140

Ile Val Gly Pro Gly Asp Val Met Val Ala Asp Asp Gly Val Val
145                 150                 155                 160

Val Val Arg Lys Asp Glu Val Ala Ala Val Thr Gln Ala Ala Gln
                165                 170                 175

Arg Val Arg Lys Glu Glu Gly Thr Arg Ala Arg Leu Ala Ala Gly Glu
                180                 185                 190

Leu Gly Leu Asp Ile Tyr Gly Leu Arg Gln Lys Leu Ser Asp Leu Gly
                195                 200                 205

Leu Lys Ser Ser
    210

<210> SEQ ID NO 101
<211> LENGTH: 678
<212> TYPE: DNA
<213> ORGANISM: Unknown
<220> FEATURE:
<223> OTHER INFORMATION: DNA obtained from environmental sample

<400> SEQUENCE: 101
atgaacacac cggtggtagc aagacaagtg gagcagccac cagcggatgc aattgccgca    60
ttggagaagt gtggagtgac aaccgtccat gaggctcagg acgttgtgg cctccttgcg    120 tcctacattc gcccgattta cccgggagca gccatcgcag atccgctat cactgtgtct    180 ttgcctcctg gcgacaacct catgatccac gttgcggtgg aggtctgcgg tccgggaaac    240
atcctggtag tttccaccgac gtcgccttgt acggacggct acttcggtga gttgttggca    300
acatctctcc gtgcccacgg agtgattggg cttgtgatcg atgccggatg ccgtgatgtg    360
cgctctctga cagaaatgaa attcccggtc tggagccgcg ccatctgttc gcagggaca    420 gtcaaggcca cacttggatc ggtgaatgtg cccatcgtat gcgcgggtgc aatggtcgag    480
gctggtgatg catcgtcgc cgacgatgat ggcgttgtcg ttgtgaagcg agcgctggcg    540
caggagatcg ctgcggcggc ggaacaaagg gttcgcaaag agaatgtaac ccgcgaacga    600
ctcgcacgtg gagagctcgg acttgatatt tacgacatgc gccaaaagat cgcgcaactg    660
ggcctcaaat atctctga                                                678

<210> SEQ ID NO 102
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (28)...(174)
<223> OTHER INFORMATION: Demethylmenaquinone methyltransferase

<400> SEQUENCE: 102

```
Met Asn Thr Pro Val Val Ala Arg Gln Val Glu Gln Pro Ala Asp
1               5                   10                  15

Ala Ile Ala Ala Leu Glu Lys Cys Gly Val Thr Thr Val His Glu Ala
                20                  25                  30

Gln Gly Arg Cys Gly Leu Leu Ala Ser Tyr Ile Arg Pro Ile Tyr Pro
            35                  40                  45

Gly Ala Ala Ile Ala Gly Ser Ala Ile Thr Val Ser Leu Pro Pro Gly
        50                  55                  60

Asp Asn Leu Met Ile His Val Ala Val Glu Val Cys Gly Pro Gly Asn
65                  70                  75                  80

Ile Leu Val Val Ser Pro Thr Ser Pro Cys Thr Asp Gly Tyr Phe Gly
                85                  90                  95

Glu Leu Leu Ala Thr Ser Leu Arg Ala His Gly Val Ile Gly Leu Val
                100                 105                 110

Ile Asp Ala Gly Cys Arg Asp Val Arg Ser Leu Thr Glu Met Lys Phe
            115                 120                 125

Pro Val Trp Ser Arg Ala Ile Cys Ser Arg Gly Thr Val Lys Ala Thr
        130                 135                 140

Leu Gly Ser Val Asn Val Pro Ile Val Cys Ala Gly Ala Met Val Glu
145                 150                 155                 160

Ala Gly Asp Gly Ile Val Ala Asp Asp Gly Val Val Val Lys
                165                 170                 175

Arg Ala Leu Ala Gln Glu Ile Ala Ala Ala Glu Gln Arg Val Arg
                180                 185                 190

Lys Glu Asn Val Thr Arg Glu Arg Leu Ala Arg Gly Glu Leu Gly Leu
            195                 200                 205

Asp Ile Tyr Asp Met Arg Gln Lys Ile Ala Gln Leu Gly Leu Lys Tyr
        210                 215                 220

Leu
225
```

<210> SEQ ID NO 103
<211> LENGTH: 678
<212> TYPE: DNA
<213> ORGANISM: Unknown
<220> FEATURE:
<223> OTHER INFORMATION: DNA obtained from environmental sample

<400> SEQUENCE: 103

```
atgaatcgac cggtggtagt ccggcaagtg gagcaggcac cagcggatgc ggtcgccgca      60
ctggagaagt gcggagtgac caccgtgcat gaggctcagg gacggggtgg cctgcttgcc     120
tcctacatgc gcccgattta cccgggagca gccatcgccg gttccgcgat caccgtgtct     180
ttgcccctg gcgataacct catgatccac gtcgcagtgg aggtctgcgg tccgggaaac     240
attctggtgg tttcaccgat ctcgccttgt acgatggtt acttcggcga gctgttggca     300
acatccctcc gtgcccgcgg tgggagaggg cttgtgatcg atgccggatg ccgggacgtg     360
cgctctttaa cagaaatgaa atttccagtc tggagccgcg ccgtcagttc gcagggacga    420
gtcaaggcca cactgggatc ggtgaatgtg cccgtcgtgt gtgcgggcgc actggtcgag     480
gcgggtgatg tcatcgtcgc cgatgacgat ggagttgtgg tggtgaagcg cgcgctggcc     540
caggaggtcg ccgccgcagc ggaacaaagg gttcgcaaag agaacctgac ccgcgaacga     600
```

```
cttgcgcgtg gagaactcgg actcgatatt tacgacatgc gccaaaagat cgcgcaaatg    660
ggccttaaat atctctaa                                                  678
```

```
<210> SEQ ID NO 104
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase
```

<400> SEQUENCE: 104

| Met | Asn | Arg | Pro | Val | Val | Arg | Gln | Val | Glu | Gln | Ala | Pro | Ala | Asp |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Ala | Val | Ala | Ala | Leu | Glu | Lys | Cys | Gly | Val | Thr | Thr | Val | His | Glu | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gln | Gly | Arg | Gly | Gly | Leu | Leu | Ala | Ser | Tyr | Met | Arg | Pro | Ile | Tyr | Pro |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Gly | Ala | Ala | Ile | Ala | Gly | Ser | Ala | Ile | Thr | Val | Ser | Leu | Pro | Pro | Gly |
|-----|-----|-----|-----|-----|-----|-----|-----|-----|-----|-----|-----|-----|-----|-----|-----|
| 50  |     |     |     |     | 55  |     |     |     |     | 60  |     |     |     |     |     |

| Asp | Asn | Leu | Met | Ile | His | Val | Ala | Val | Glu | Val | Cys | Gly | Pro | Gly | Asn |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ile | Leu | Val | Val | Ser | Pro | Ile | Ser | Pro | Cys | Thr | Asp | Gly | Tyr | Phe | Gly |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Glu | Leu | Leu | Ala | Thr | Ser | Leu | Arg | Ala | Arg | Gly | Gly | Arg | Gly | Leu | Val |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Ile | Asp | Ala | Gly | Cys | Arg | Asp | Val | Arg | Ser | Leu | Thr | Glu | Met | Lys | Phe |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Pro | Val | Trp | Ser | Arg | Ala | Val | Ser | Ser | Gln | Gly | Thr | Val | Lys | Ala | Thr |
|-----|-----|-----|-----|-----|-----|-----|-----|-----|-----|-----|-----|-----|-----|-----|-----|
| 130 |     |     |     |     | 135 |     |     |     |     | 140 |     |     |     |     |     |

| Leu | Gly | Ser | Val | Asn | Val | Pro | Val | Val | Cys | Ala | Gly | Ala | Leu | Val | Glu |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Ala | Gly | Asp | Val | Ile | Val | Ala | Asp | Asp | Gly | Val | Val | Val | Val | Lys |
|-----|-----|-----|-----|-----|-----|-----|-----|-----|-----|-----|-----|-----|-----|-----|
|     |     |     |     | 165 |     |     |     |     | 170 |     |     |     |     | 175 |

| Arg | Ala | Leu | Ala | Gln | Glu | Val | Ala | Ala | Ala | Glu | Gln | Arg | Val | Arg |
|-----|-----|-----|-----|-----|-----|-----|-----|-----|-----|-----|-----|-----|-----|-----|
|     |     |     | 180 |     |     |     |     | 185 |     |     |     |     | 190 |     |

| Lys | Glu | Asn | Leu | Thr | Arg | Glu | Arg | Leu | Ala | Arg | Gly | Glu | Leu | Gly | Leu |
|-----|-----|-----|-----|-----|-----|-----|-----|-----|-----|-----|-----|-----|-----|-----|-----|
|     |     |     |     | 195 |     |     |     |     | 200 |     |     |     |     | 205 |     |

| Asp | Ile | Tyr | Asp | Met | Arg | Gln | Lys | Ile | Ala | Gln | Met | Gly | Leu | Lys | Tyr |
|-----|-----|-----|-----|-----|-----|-----|-----|-----|-----|-----|-----|-----|-----|-----|-----|
|     |     | 210 |     |     |     |     | 215 |     |     |     |     | 220 |     |     |     |

| Leu |
|-----|
| 225 |

```
<210> SEQ ID NO 105
<211> LENGTH: 678
<212> TYPE: DNA
<213> ORGANISM: Unknown
<220> FEATURE:
<223> OTHER INFORMATION: DNA obtained from environmental sample
```

<400> SEQUENCE: 105

```
atgaatacac cggtggtagt ccggcaagtg gagcagccac ctgcggaggc ggttgccgca    60
ctggaaaagc gtggggtgac aaccgtgcat gaggctcagg gacgttgtgg cctccttgcc    120
tcctacatgc gcccgattta cacgggagca gcgatcgcag gatccgctat cacagtgtcc    180
ttgccgcccg gcgacaacct catgatccac gttgccgtgg aggtatgtgg ttcaggaaac    240
```

-continued

```
atcctggtag tttcaccaac ctcgccttgt gcggatggct acttcggtga gctgttggca    300
acatctctcc gtgcccatgg tgtcagaggg ctggtgatcg atgcgggatg ccgtgatgtg    360
cgctccctaa cagagatgaa atttccggtc tggagccgcg ccgtcagctc acagggaca    420 gtcaaggcca cacttggatc ggtgaacgtg cccatcgttt gcgcgggtgc actggtcgac    480
gctggtgatg tcatcgtcgc agatgacgat ggcgttgtgg tggtgaagcg cgcgatggcg    540
caagaggtcg ccgcggcggc ggaacaaagg gttcgcaaag agaatctgac ccgcgaacga    600
cttgcgcgtg gtgaacttgg tctcgatatt tacgacatgc gccaaaagat cgcgcaactg    660
ggacttaagt atctgtaa                                                  678
```

<210> SEQ ID NO 106  
<211> LENGTH: 225  
<212> TYPE: PRT  
<213> ORGANISM: Unknown  
<220> FEATURE:  
<223> OTHER INFORMATION: Protein obtained from environmental sample  
<220> FEATURE:  
<221> NAME/KEY: DOMAIN  
<222> LOCATION: (22)...(174)  
<223> OTHER INFORMATION: Demethylmenaquinone methyltransferase

<400> SEQUENCE: 106

```
Met Asn Thr Pro Val Val Arg Gln Val Glu Gln Pro Pro Ala Glu
1               5                   10                  15

Ala Val Ala Ala Leu Glu Lys Arg Gly Val Thr Thr Val His Glu Ala
            20                  25                  30

Gln Gly Arg Cys Gly Leu Leu Ala Ser Tyr Met Arg Pro Ile Tyr Thr
        35                  40                  45

Gly Ala Ala Ile Ala Gly Ser Ala Ile Thr Val Ser Leu Pro Pro Gly
    50                  55                  60

Asp Asn Leu Met Ile His Val Ala Val Glu Val Cys Gly Ser Gly Asn
65                  70                  75                  80

Ile Leu Val Val Ser Pro Thr Ser Pro Cys Ala Asp Gly Tyr Phe Gly
                85                  90                  95

Glu Leu Leu Ala Thr Ser Leu Arg Ala His Gly Val Arg Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Val Ser Ser Gln Gly Thr Val Lys Ala Thr
    130                 135                 140

Leu Gly Ser Val Asn Val Pro Ile Val Cys Ala Gly Ala Leu Val Asp
145                 150                 155                 160

Ala Gly Asp Val Ile Val Ala Asp Asp Gly Val Val Val Val Lys
                165                 170                 175

Arg Ala Met Ala Gln Glu Val Ala Ala Ala Glu Gln Arg Val Arg
            180                 185                 190

Lys Glu Asn Leu Thr Arg Glu Arg Leu Ala Arg Gly Glu Leu Gly Leu
        195                 200                 205

Asp Ile Tyr Asp Met Arg Gln Lys Ile Ala Gln Leu Gly Leu Lys Tyr
    210                 215                 220

Leu
225
```

<210> SEQ ID NO 107  
<211> LENGTH: 636  
<212> TYPE: DNA

```
<213> ORGANISM: Unknown
<220> FEATURE:
<223> OTHER INFORMATION: DNA obtained from environmental sample

<400> SEQUENCE: 107
gtgagcgatc cgatcgccgc cctgcgcgga tatggcgttt cgacggtgca cgaggcgcag       60
gggcggcgcg gcctgctggc ccttacatg cgcccgatct atgccggtgc gctcctcgcc      120
gggcccgcgg tgacggtcct ggttcctcct ggcgacaacc tgatgatcca cgtggcggtc      180
gagaaatgct cgcctggaga cgtcctcgtc gtcgccccgg cgtctccgtg cacggacggc      240
tacttcggag aattgcttgc gacgtcgttg cgggcccgcg cgttgccgg cttgatcatc       300 gatgccggct gccgggatgt gcgcgcgctc acggagatgc ggtttccggt gtggagccgc      360
ttcgtctgcg ctcagggcac ggtgaaggcc acgctcggct cgctgaatgt gccgctggtc      420
tgcgccggcg ccctcatcgc tcccgctgat gtcatcgttg cagacgatga cggggtggtg      480
gtggtgaaga gggacgagat cgccatggtg acgcaggcgg cggagcagcg ggttcgcaaa      540
gaggaaggca cgcgcgcgcg gctcgccgcg ggcgagctcg gcctggacat ctacggcttg      600
cggcagaagc tgtcggacct cggcctcaag tcgtga                               636

<210> SEQ ID NO 108
<211> LENGTH: 211
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (9)...(161)
<223> OTHER INFORMATION: Demethylmenaquinone methyltransferase

<400> SEQUENCE: 108

Met Ser Asp Pro Ile Ala Ala Leu Arg Gly Tyr Gly Val Ser Thr Val
1               5                   10                  15

His Glu Ala Gln Gly Arg Arg Gly Leu Leu Ala Pro Tyr Met Arg Pro
            20                  25                  30

Ile Tyr Ala Gly Ala Leu Leu Ala Gly Pro Ala Val Thr Val Leu Val
        35                  40                  45

Pro Pro Gly Asp Asn Leu Met Ile His Val Ala Val Glu Lys Cys Ser
    50                  55                  60

Pro Gly Asp Val Leu Val Val Ala Pro Ala Ser Pro Cys Thr Asp Gly
65                  70                  75                  80

Tyr Phe Gly Glu Leu Leu Ala Thr Ser Leu Arg Ala Arg Gly Val Ala
                85                  90                  95

Gly Leu Ile Ile Asp Ala Gly Cys Arg Asp Val Arg Ala Leu Thr Glu
            100                 105                 110

Met Arg Phe Pro Val Trp Ser Arg Phe Val Cys Ala Gln Gly Thr Val
        115                 120                 125

Lys Ala Thr Leu Gly Ser Leu Asn Val Pro Leu Val Cys Ala Gly Ala
    130                 135                 140

Leu Ile Ala Pro Ala Asp Val Ile Val Ala Asp Asp Gly Val Val
145                 150                 155                 160

Val Val Lys Arg Asp Glu Ile Ala Met Val Thr Gln Ala Ala Glu Gln
                165                 170                 175

Arg Val Arg Lys Glu Glu Gly Thr Arg Ala Arg Leu Ala Ala Gly Glu
            180                 185                 190

Leu Gly Leu Asp Ile Tyr Gly Leu Arg Gln Lys Leu Ser Asp Leu Gly
        195                 200                 205
```

Leu Lys Ser
    210

<210> SEQ ID NO 109
<211> LENGTH: 678
<212> TYPE: DNA
<213> ORGANISM: Unknown
<220> FEATURE:
<223> OTHER INFORMATION: DNA obtained from environmental sample

<400> SEQUENCE: 109

```
atgaatacac cggtggtagt aagacaagtg gagcagccac cagcggatgc aattgccgca      60
ttaaagaagt gtggagtgac aaccgtccat gaggctcagg acgtggtgg cctccttgcg     120
tcctacatgc gcccgattta cccgggagca gccatcgcag atccgctat cactgtgtct     180
ttgcctcctg gcgacaacct catgatccac gttgcggtgg aggtctgcgg tccgggaaac     240
atcctggtag tttcaccgac gtcgccttgt acggacggct acttcggtga gttgttggca     300
acatctctcc gtgcccacgg agtgattggg cttgtgatcg atgccggatg ccgtgatgtg     360
cgctccctga cagaaatgaa gttcccggtc tggagccgcg ccatctgttc gcaagggaca     420
gtcaaggcca cacttggatc ggtgaatgtg cccatcgtat gcgcgggtgc attggtcgag     480
gctggtgatg tcatcgtcgc cgacgatgat ggcgttgtcg ttgtgaagcg agcgctggcg     540
caagagatcg ccgcggcggc ggaacaaagg gttcgcaaag agaatgtaac ccgcgaacga     600
ctcgcacgtg gagagctcgg acttgatatt tacgacatgc gccaaaagat cgcgcaactg     660
ggcctgaaat atctctga                                                   678
```

<210> SEQ ID NO 110
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 110

Met Asn Thr Pro Val Val Arg Gln Val Glu Gln Pro Pro Ala Asp
1               5                   10                  15

Ala Ile Ala Ala Leu Lys Lys Cys Gly Val Thr Thr Val His Glu Ala
            20                  25                  30

Gln Gly Arg Gly Gly Leu Leu Ala Ser Tyr Met Arg Pro Ile Tyr Pro
        35                  40                  45

Gly Ala Ala Ile Ala Gly Ser Ala Ile Thr Val Ser Leu Pro Pro Gly
    50                  55                  60

Asp Asn Leu Met Ile His Val Ala Val Glu Val Cys Gly Pro Gly Asn
65                  70                  75                  80

Ile Leu Val Val Ser Pro Thr Ser Pro Cys Thr Asp Gly Tyr Phe Gly
                85                  90                  95

Glu Leu Leu Ala Thr Ser Leu Arg Ala His Gly Val Ile Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Ile Cys Ser Gln Gly Thr Val Lys Ala Thr
    130                 135                 140

Leu Gly Ser Val Asn Val Pro Ile Val Cys Ala Gly Ala Leu Val Glu

```
              145                 150                 155                 160
Ala Gly Asp Val Ile Val Ala Asp Asp Gly Val Val Val Lys
                165                 170                 175

Arg Ala Leu Ala Gln Glu Ile Ala Ala Ala Glu Gln Arg Val Arg
            180                 185                 190

Lys Glu Asn Val Thr Arg Glu Arg Leu Ala Arg Gly Glu Leu Gly Leu
        195                 200                 205

Asp Ile Tyr Asp Met Arg Gln Lys Ile Ala Gln Leu Gly Leu Lys Tyr
    210                 215                 220

Leu
225

<210> SEQ ID NO 111
<211> LENGTH: 678
<212> TYPE: DNA
<213> ORGANISM: Unknown
<220> FEATURE:
<223> OTHER INFORMATION: DNA obtained from environmental sample

<400> SEQUENCE: 111
atgaaagagg cggtggtggt caggaatatt gagcgcccgc cggccgatgt gatcgcggcg      60
ctggaaaagt ttggtgtttc aacggtacac gaagcgcaag ccgccgcgg  acttctggcc    120 gcttatatga ggccgattta tggggcgcg  gccattgccg gcctgcggt  gactgtctcg    180 ttggctccgg gtgacaatct aatgattcac gtggccgtgg aagtttgccg gtcaggtgac    240
attctcgtgg tcgctccgac gtcgccgtgc acgatgggt  attttggcga ttgctggcg    300 acttccttgc gcgcgcacgg ggtaaaagga ctcgtgatcg aggcaggatg ccgcgatgtc    360
cgggcgctta cggagatgaa atttcccgtg tggagccgcg cggtgagttc gcagggaacg    420
gtgaaggcta gtttgggctc ggtgaacgtg ggaattgtgt gcgctgccgc ggcgatcgaa    480
gccggcgacg cgatcgttgc cgatgatgac ggcgttgtgg tggtgaaacg cggcgacgcc    540
gccagtgttg tcgccgcgtc gcagcaacgc gtccgcaagg aagaggctgc gcgaggacgc    600
ctggcgcgcg cgaactggg  cctggacatt tacggcctgc gcgccaaggt cgcggagctt    660
ggcttgaaat atttgtga                                                    678

<210> SEQ ID NO 112
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 112

Met Lys Glu Ala Val Val Arg Asn Ile Glu Arg Pro Pro Ala Asp
1                5                  10                  15

Val Ile Ala Ala Leu Glu Lys Phe Gly Val Ser Thr Val His Glu Ala
            20                  25                  30

Gln Gly Arg Arg Gly Leu Leu Ala Ala Tyr Met Arg Pro Ile Tyr Gly
        35                  40                  45

Gly Ala Ala Ile Ala Gly Pro Ala Val Thr Val Ser Leu Ala Pro Gly
    50                  55                  60

Asp Asn Leu Met Ile His Val Ala Val Glu Val Cys Arg Ser Gly Asp
65                  70                  75                  80
```

```
Ile Leu Val Val Ala Pro Thr Ser Pro Cys Thr Asp Gly Tyr Phe Gly
            85                  90                  95

Glu Leu Leu Ala Thr Ser Leu Arg Ala His Gly Val Lys Gly Leu Val
            100                 105                 110

Ile Glu Ala Gly Cys Arg Asp Val Arg Ala Leu Thr Glu Met Lys Phe
            115                 120                 125

Pro Val Trp Ser Arg Ala Val Ser Ser Gln Gly Thr Val Lys Ala Ser
            130                 135                 140

Leu Gly Ser Val Asn Val Gly Ile Val Cys Ala Ala Ala Ile Glu
145                 150                 155                 160

Ala Gly Asp Ala Ile Val Ala Asp Asp Gly Val Val Val Lys
            165                 170                 175

Arg Gly Asp Ala Ala Ser Val Val Ala Ala Ser Gln Gln Arg Val Arg
            180                 185                 190

Lys Glu Glu Ala Ala Arg Gly Arg Leu Ala Arg Gly Glu Leu Gly Leu
            195                 200                 205

Asp Ile Tyr Gly Leu Arg Ala Lys Val Ala Glu Leu Gly Leu Lys Tyr
            210                 215                 220

Leu
225

<210> SEQ ID NO 113
<211> LENGTH: 678
<212> TYPE: DNA
<213> ORGANISM: Unknown
<220> FEATURE:
<223> OTHER INFORMATION: DNA obtained from environmental sample

<400> SEQUENCE: 113
atgaaagggg cggtggtggt caggaatatc gagcgcccgc cggccgaggt ggtcgcggcg    60
ctggaaaagt ttggtgtttc gacggtgcac gaagcgcaag acgccgcgg acttctggcc   120 gcttatatga ggccgattta tgggggcgcg gccattgccg gcctgcggt gactgtctcg   180 ttggctccgg cgacaatttt aatgattcac gtggcggtgg aagtttgccg gtcaggcgac   240
attctcgtgg tcgctccgac gtcgccgtgc acggatgggt attttggcga gttgctggcg   300
acttccttgc gcgcgcacgg ggtaaaagga ctggtgatcg aggcaggatg ccgcgatgtc   360
cgggcgctta cggagatgaa atttcccgtg tggagccgcg cggtgagttc gcagggaacg   420
gtgaaggcta ctttgggctc ggtgaacgtg gaaattgtgt gcgctgccgc ggcgatcgaa   480
gccggtgacg tgatcgttgc cgatgatgac ggcgttgtgg tggtgaaacg gggcgacgcc   540
gccgctgtgg tcgccgcgtc gcagcaacgc gtccgcaaag aagaagctac gcgagaacgc   600
ctggcgcgcg gcgaactggg cctggacatt tacggcctgc gcgccaaggt cgcggagctt   660
ggcttgaaat atttgtga                                                 678

<210> SEQ ID NO 114
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 114

Met Lys Gly Ala Val Val Val Arg Asn Ile Glu Arg Pro Pro Ala Glu
1               5                   10                  15
```

Val Val Ala Ala Leu Glu Lys Phe Gly Val Ser Thr Val His Glu Ala
            20                  25                  30

Gln Gly Arg Arg Gly Leu Leu Ala Ala Tyr Met Arg Pro Ile Tyr Gly
        35                  40                  45

Gly Ala Ala Ile Ala Gly Pro Ala Val Thr Val Ser Leu Ala Pro Gly
    50                  55                  60

Asp Asn Leu Met Ile His Val Ala Val Glu Val Cys Arg Ser Gly Asp
65                  70                  75                  80

Ile Leu Val Val Ala Pro Thr Ser Pro Cys Thr Asp Gly Tyr Phe Gly
                85                  90                  95

Glu Leu Leu Ala Thr Ser Leu Arg Ala His Gly Val Lys Gly Leu Val
            100                 105                 110

Ile Glu Ala Gly Cys Arg Asp Val Arg Ala Leu Thr Glu Met Lys Phe
        115                 120                 125

Pro Val Trp Ser Arg Ala Val Ser Ser Gln Gly Thr Val Lys Ala Thr
130                 135                 140

Leu Gly Ser Val Asn Val Glu Ile Val Cys Ala Ala Ala Ile Glu
145                 150                 155                 160

Ala Gly Asp Val Ile Val Ala Asp Asp Gly Val Val Val Val Lys
                165                 170                 175

Arg Gly Asp Ala Ala Val Val Ala Ala Ser Gln Gln Arg Val Arg
            180                 185                 190

Lys Glu Glu Ala Thr Arg Glu Arg Leu Ala Arg Gly Glu Leu Gly Leu
        195                 200                 205

Asp Ile Tyr Gly Leu Arg Ala Lys Val Ala Glu Leu Gly Leu Lys Tyr
    210                 215                 220

Leu
225

<210> SEQ ID NO 115
<211> LENGTH: 672
<212> TYPE: DNA
<213> ORGANISM: Unknown
<220> FEATURE:
<223> OTHER INFORMATION: DNA obtained from environmental sample

<400> SEQUENCE: 115
atgtcggttg tcgttcagaa catcgagcgt gctgatcagt cggtcatcga ccggctggcc      60
gcctgcggcg ttgccacggt gcatgaagcg cagggccgca agggcctgct cgccagctat     120
atgcggccga tctttccggg tgcacgcctc gcggcgagtg ccgtcactat ctccgcacct     180
ccgggcgaca actggatgct gcatgtggcg atcgaacagt tgaaggccgg cgacattctg     240
ctgctcgccc cgaccagccc ctgcgaggac ggctatttcg gtgatctcct cgccacgtct     300
gcgcaggcgc gcggttgcga gggattgatc atcgatgcgg gtgttcggga tgtggctgat     360
ctgacggaga tgaaatttcc tgtctggtcg aaggcgatct tcgcccaggg cacagtcaag     420
gagaccctcg gttctgtgaa cgtaccggtc gtatgcgctg cgcctatgt tcgcccgggt      480 gatgtgatcg ttgccgatga tgatggcgtt tgtgttgtgc tgcgcgagga agctgaagtg     540
gtcgcaaaga aggcggaagc ccgtgttgcg gccgaagatg gtaaacgcaa gcggctcgcg     600
gccggcgaac tcggctcgga tatctacgac atgcgcggcc ggctggctga aaagggcctg     660
aagtatatct ga                                                         672

<210> SEQ ID NO 116
<211> LENGTH: 223

```
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 116
```

Met Ser Val Val Val Gln Asn Ile Glu Arg Ala Asp Gln Ser Val Ile
1               5                   10                  15

Asp Arg Leu Ala Ala Cys Gly Val Ala Thr Val His Glu Ala Gln Gly
            20                  25                  30

Arg Lys Gly Leu Leu Ala Ser Tyr Met Arg Pro Ile Phe Pro Gly Ala
        35                  40                  45

Arg Leu Ala Ala Ser Ala Val Thr Ile Ser Ala Pro Pro Gly Asp Asn
    50                  55                  60

Trp Met Leu His Val Ala Ile Glu Gln Leu Lys Ala Gly Asp Ile Leu
65                  70                  75                  80

Leu Leu Ala Pro Thr Ser Pro Cys Glu Asp Gly Tyr Phe Gly Asp Leu
                85                  90                  95

Leu Ala Thr Ser Ala Gln Ala Arg Gly Cys Glu Gly Leu Ile Ile Asp
            100                 105                 110

Ala Gly Val Arg Asp Val Ala Asp Leu Thr Glu Met Lys Phe Pro Val
        115                 120                 125

Trp Ser Lys Ala Ile Phe Ala Gln Gly Thr Val Lys Glu Thr Leu Gly
    130                 135                 140

Ser Val Asn Val Pro Val Val Cys Ala Gly Ala Tyr Val Arg Pro Gly
145                 150                 155                 160

Asp Val Ile Val Ala Asp Asp Gly Val Cys Val Val Leu Arg Glu
                165                 170                 175

Glu Ala Glu Val Val Ala Lys Lys Ala Glu Ala Arg Val Ala Ala Glu
            180                 185                 190

Asp Gly Lys Arg Lys Arg Leu Ala Ala Gly Glu Leu Gly Leu Asp Ile
        195                 200                 205

Tyr Asp Met Arg Gly Arg Leu Ala Glu Lys Gly Leu Lys Tyr Ile
    210                 215                 220

```
<210> SEQ ID NO 117
<211> LENGTH: 672
<212> TYPE: DNA
<213> ORGANISM: Unknown
<220> FEATURE:
<223> OTHER INFORMATION: DNA obtained from environmental sample

<400> SEQUENCE: 117
atgggtgtcg tcgtccagaa cattgaccgc gccgagcaag ccgtcatcga ccggctcgcc      60
gcctgcggcg tcgcgaccgt gcatgaggcg caggggcgca aggggctgct ggcgagctat     120
atgcggccga tctatcccgg cgcgcggatc gcggcgagtg cggtgacgat ctcggcgccg     180
cctggtgaca actggatggt gcatgtgcg atcgagcagg tgaaggatgg cgacatcctg      240
ctgctggcac cgaccagccc ctgcgaggac ggctatttcg gcgatctttt ggcgacctcg     300
gccttggcgc ggggctgccg cgggctggtc atcgatgccg gcgtgcgcga cgtcgctgac     360
cttgcggcga tgaagtttcc ggtctggtcg aaagcgatct cgcccaggg cacggtcaag      420
gaaacgctgg gttcggtgaa tgtgccggtc gtctgcgccg gcgcgctggt caaccccggc     480
gacgtgatcg tcgccgacga tgacggcgtt tgtgtcgttc gccgcgaaga ggcggcggag     540
```

```
gttgcagaca aggctgaggc ccacgtcgcg gcagaggagg gcaagcgcaa gcggctggcg    600
gccggcgagc ttggtctcga catctacgac atgcgcaagc ggctcgccga gaaagggctg    660
aaatatgtct ga                                                         672
```

<210> SEQ ID NO 118
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 118

```
Met Gly Val Val Gln Asn Ile Asp Arg Ala Glu Gln Ala Val Ile
1               5                   10                  15

Asp Arg Leu Ala Ala Cys Gly Val Ala Thr Val His Glu Ala Gln Gly
            20                  25                  30

Arg Lys Gly Leu Leu Ala Ser Tyr Met Arg Pro Ile Tyr Pro Gly Ala
        35                  40                  45

Arg Ile Ala Ala Ser Ala Val Thr Ile Ser Ala Pro Pro Gly Asp Asn
    50                  55                  60

Trp Met Val His Val Ala Ile Glu Gln Val Lys Asp Gly Asp Ile Leu
65                  70                  75                  80

Leu Leu Ala Pro Thr Ser Pro Cys Glu Asp Gly Tyr Phe Gly Asp Leu
                85                  90                  95

Leu Ala Thr Ser Ala Leu Ala Arg Gly Cys Arg Gly Leu Val Ile Asp
            100                 105                 110

Ala Gly Val Arg Asp Val Ala Asp Leu Ala Ala Met Lys Phe Pro Val
        115                 120                 125

Trp Ser Lys Ala Ile Phe Ala Gln Gly Thr Val Lys Glu Thr Leu Gly
    130                 135                 140

Ser Val Asn Val Pro Val Val Cys Ala Gly Ala Leu Val Asn Pro Gly
145                 150                 155                 160

Asp Val Ile Val Ala Asp Asp Gly Val Cys Val Val Arg Arg Glu
                165                 170                 175

Glu Ala Ala Glu Val Ala Asp Lys Ala Glu Ala His Val Ala Ala Glu
            180                 185                 190

Glu Gly Lys Arg Lys Arg Leu Ala Ala Gly Glu Leu Gly Leu Asp Ile
        195                 200                 205

Tyr Asp Met Arg Lys Arg Leu Ala Glu Lys Gly Leu Lys Tyr Val
    210                 215                 220
```

<210> SEQ ID NO 119
<211> LENGTH: 672
<212> TYPE: DNA
<213> ORGANISM: Unknown
<220> FEATURE:
<223> OTHER INFORMATION: DNA obtained from environmental sample

<400> SEQUENCE: 119

```
atgggtattg ttgttcagaa catcaagcgg gcggaccccg ggatcatagc aggtcttggc    60
aaatgcggcg ttgccactgt gcatgaagcg caggggtgca aggggctcct ggcggcctat    120
atgcggccca tttattctgg cgcgcgcctt gccgcctccg ctgtcaccat ttccgcgccg    180
ccgggagaca actggatggt gcatgtcgcc attgagcagg tgaggcaagg tgatattctg    240
```

```
gttcttgccc caacatcgcc ctgtgaagac ggctatttcg gtgatttgct cgccacctcc    300
atgctgcagc gcggcggcag ggggctgatt attgacgccg gtgtccgcga tatccgtgat    360
ctgactcaaa tgaaatttcc ggtgtggtcg aaaaccgttt ttgcgcaggg caccgttaag    420
gaaacccttg gctctgtgaa cgtcccgata gtttgcgccg gtgaagtggt caatcctggc    480
gacatcatga ttgccgatga tgatggtgtg tgcgtggtcc ggcgcgacga cgctgaaagc    540
gtgcttgaaa aagcattggc gcgtgaggca aggaagaag atacacgcaa acgccttgcg     600
gcaggcgagc tgggtcttga tatttacggc atgcgcgcac gtctggccga aaagggccta    660
aaatatgtct ga                                                        672
```

<210> SEQ ID NO 120
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 120

```
Met Gly Ile Val Val Gln Asn Ile Lys Arg Ala Asp Pro Gly Ile Ile
1               5                   10                  15

Ala Gly Leu Gly Lys Cys Gly Val Ala Thr Val His Glu Ala Gln Gly
            20                  25                  30

Cys Lys Gly Leu Leu Ala Ala Tyr Met Arg Pro Ile Tyr Ser Gly Ala
        35                  40                  45

Arg Leu Ala Ala Ser Ala Val Thr Ile Ser Ala Pro Pro Gly Asp Asn
    50                  55                  60

Trp Met Val His Val Ala Ile Glu Gln Val Arg Gln Gly Asp Ile Leu
65                  70                  75                  80

Val Leu Ala Pro Thr Ser Pro Cys Glu Asp Gly Tyr Phe Gly Asp Leu
                85                  90                  95

Leu Ala Thr Ser Met Leu Gln Arg Gly Gly Arg Gly Leu Ile Ile Asp
            100                 105                 110

Ala Gly Val Arg Asp Ile Arg Asp Leu Thr Gln Met Lys Phe Pro Val
        115                 120                 125

Trp Ser Lys Thr Val Phe Ala Gln Gly Thr Val Lys Glu Thr Leu Gly
    130                 135                 140

Ser Val Asn Val Pro Ile Val Cys Ala Gly Glu Val Val Asn Pro Gly
145                 150                 155                 160

Asp Ile Met Ile Ala Asp Asp Asp Gly Val Cys Val Val Arg Arg Asp
                165                 170                 175

Asp Ala Glu Ser Val Leu Glu Lys Ala Leu Ala Arg Glu Ala Lys Glu
            180                 185                 190

Glu Asp Thr Arg Lys Arg Leu Ala Ala Gly Glu Leu Gly Leu Asp Ile
        195                 200                 205

Tyr Gly Met Arg Ala Arg Leu Ala Glu Lys Gly Leu Lys Tyr Val
    210                 215                 220
```

<210> SEQ ID NO 121
<211> LENGTH: 696
<212> TYPE: DNA
<213> ORGANISM: Unknown
<220> FEATURE:
<223> OTHER INFORMATION: DNA obtained from environmental sample

<400> SEQUENCE: 121

```
atgaagcgcg gtgtcgtcgt cacccatatc gagcgcgcca acccgcgtga cgtggccgtg      60
cttcagcagg cgggcgctgc gaccgttcat gaagcgcaga gccgtctggg cctgctcgcg     120
tcgtacatgc ggcccatcta tgcgggcgcg tcaatcgcgg gatcggcggt gacggtgctc     180
gtgccgccgt cggacaactg gatgttgcac gttgccgccg aacagtgccg cgaaggcgac     240
gtgctcgtgg tcgcgccgac ttcgccgtgc gaagacggct acttcggcga actgctcgcg     300
acgtcgcttg ccgcgcgcgg tgtgcgcggg ctcatcatcg atgcgggctg tcgcgatgtg     360
cgcgcgctca aggacatgaa cttcccggtc tggtcgaaag cggtctctgc gcaaggcacg     420
gtgaaggaga cgctgggctc ggtcaatgtg cctgttgtgt gcgcacagca gatcgtgcat     480
gcgggcgacg tgatcgtcgc cgacgatgac ggcgtcgtgg tcgtgccgtt cgccacggtg     540
tcgcgcgtgg ccgaagcagc gcaggcgcgt ctcgcgaagg aagagaagac gcgttccgtg     600
ctcgcgacgg gcgtgctggg cctcgactac tacagcatgc gtgacaagct cgcggaaaag     660
ggcctgcgtt acgtcgggtc gatcgaggaa gcgtga                              696
```

<210> SEQ ID NO 122
<211> LENGTH: 231
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 122

```
Met Lys Arg Gly Val Val Thr His Ile Glu Arg Ala Asn Pro Arg
1               5                   10                  15

Asp Val Ala Val Leu Gln Gln Ala Gly Ala Ala Thr Val His Glu Ala
            20                  25                  30

Gln Ser Arg Leu Gly Leu Leu Ala Ser Tyr Met Arg Pro Ile Tyr Ala
        35                  40                  45

Gly Ala Ser Ile Ala Gly Ser Ala Val Thr Val Leu Val Pro Pro Ser
    50                  55                  60

Asp Asn Trp Met Leu His Val Ala Ala Glu Gln Cys Arg Glu Gly Asp
65                  70                  75                  80

Val Leu Val Val Ala Pro Thr Ser Pro Cys Glu Asp Gly Tyr Phe Gly
                85                  90                  95

Glu Leu Leu Ala Thr Ser Leu Ala Ala Arg Gly Val Arg Gly Leu Ile
            100                 105                 110

Ile Asp Ala Gly Cys Arg Asp Val Arg Ala Leu Lys Asp Met Asn Phe
        115                 120                 125

Pro Val Trp Ser Lys Ala Val Ser Ala Gln Gly Thr Val Lys Glu Thr
    130                 135                 140

Leu Gly Ser Val Asn Val Pro Val Val Cys Ala Gln Gln Ile Val His
145                 150                 155                 160

Ala Gly Asp Val Ile Val Ala Asp Asp Gly Val Val Val Pro
                165                 170                 175

Phe Ala Thr Val Ser Arg Val Ala Glu Ala Ala Gln Ala Arg Leu Ala
            180                 185                 190

Lys Glu Glu Lys Thr Arg Ser Val Leu Ala Thr Gly Val Leu Gly Leu
        195                 200                 205
```

```
Asp Tyr Tyr Ser Met Arg Asp Lys Leu Ala Glu Lys Gly Leu Arg Tyr
    210                 215                 220

Val Gly Ser Ile Glu Glu Ala
225                 230
```

<210> SEQ ID NO 123
<211> LENGTH: 678
<212> TYPE: DNA
<213> ORGANISM: Unknown
<220> FEATURE:
<223> OTHER INFORMATION: DNA obtained from environmental sample

<400> SEQUENCE: 123

```
atgaacaaac ccgtggtagt gcggcaactg gagcagccac ccgccgatgc ggttgcggcc      60
ctggagaagt atggcgtgac taccgtccac gaggctcagg gacgttgtgg cctgctggct     120
ccttatatgc gaccgatttt tgcgggagcc tgcatcgccg gttccgccgt caccgtgtct     180
ttgccgcccg gcgataactt catgatccac gttgccgtcg aggtctgcag tccgggcagc     240
attctcgtag tcgcccccac ctcaccttgc acggacggtt atttcggcga actcttggca     300
acttccctcc gcgctcacgg tgtcaaagga ctggtcattg atgccggctg ccggatgtt      360
cgctcgttaa cggaaatgaa attccccgtt tggagccgtg cggtgagttc gcaaggaacg     420
gtgaaggcta cgctcggatc tgtgaatgtg ccggtcattt gcgcgggcgc cgaggtggaa     480
gccggtgacg tcatcatcgc cgatgacgat ggtgtggtag tggtgaagcg tgcgactgcc     540
cacgaggtag cagcggcggc ggaacaacga gttcgcaagg agaatgccac tcgcgaacga     600
ctggcacgag gagaactcgg cctcgacatc tacgacatgc ggcaaaaaat cgcgcaactt     660
ggtctcaaat atctgtga                                                   678
```

<210> SEQ ID NO 124
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 124

```
Met Asn Lys Pro Val Val Arg Gln Leu Glu Gln Pro Ala Asp
1               5                   10                  15

Ala Val Ala Ala Leu Glu Lys Tyr Gly Val Thr Thr Val His Glu Ala
                20                  25                  30

Gln Gly Arg Cys Gly Leu Leu Ala Pro Tyr Met Arg Pro Ile Phe Ala
            35                  40                  45

Gly Ala Cys Ile Ala Gly Ser Ala Val Thr Val Ser Leu Pro Pro Gly
        50                  55                  60

Asp Asn Phe Met Ile His Val Ala Val Glu Val Cys Ser Pro Gly Ser
65                  70                  75                  80

Ile Leu Val Val Ala Pro Thr Ser Pro Cys Thr Asp Gly Tyr Phe Gly
                85                  90                  95

Glu Leu Leu Ala Thr Ser Leu Arg Ala His Gly Val Lys Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Val Ser Gln Gly Thr Val Lys Ala Thr
    130                 135                 140
```

```
Leu Gly Ser Val Asn Val Pro Val Ile Cys Ala Gly Ala Glu Val Glu
145                 150                 155                 160

Ala Gly Asp Val Ile Ile Ala Asp Asp Gly Val Val Val Lys
            165                 170                 175

Arg Ala Thr Ala His Glu Val Ala Ala Ala Glu Gln Arg Val Arg
            180                 185                 190

Lys Glu Asn Ala Thr Arg Glu Arg Leu Ala Arg Gly Glu Leu Gly Leu
        195                 200                 205

Asp Ile Tyr Asp Met Arg Gln Lys Ile Ala Gln Leu Gly Leu Lys Tyr
    210                 215                 220

Leu
225

<210> SEQ ID NO 125
<211> LENGTH: 678
<212> TYPE: DNA
<213> ORGANISM: Unknown
<220> FEATURE:
<223> OTHER INFORMATION: DNA obtained from environmental sample

<400> SEQUENCE: 125
atgaacgatc ccgtcgtcgt ccgagagatc gagaggccgt cggcgacgtc gatcgacgat       60
ctgcggcgtt tcggcgtctc gacggtgcac gaagcgcagg ggcgccgcgg gctgctcgca      120
tcgtacatgc ggccgatcta tgccggcgcg ctggtcgccg gcctgcgat taccgtcctg       180
gtgacgccgg gcgacaacct gatgatccat gtcgcggtcg agatctgcca gccaggcgat      240
gtcctcgtcg tcgccccgac gtcgccgtgc accgacggat acttcggcga gctgctggcg      300
acgtcgttgc gagcgcatgg cgtcgcgggt ctgatcatcg atgccggctg ccgggatgtt      360
cgctcgttga gcgagatgcg atttcccgtg tggagccgcg cgatcagcgc ccaggggacc      420
gtcaaggcga cgctgggttc ggtgaacgtg ccgctggtgt cgccggagc gctggtcgag       480
ccgggcgatg cgatcgtcgc cgacgacgac ggtgtcgtcg tcgtcaggcg ggaacaggtc      540
gacactgtgt gccaggcggc gggacagcgc gtgcgcaagg aagaggacac gcgcgcgcgg      600
ctggcgcaag gcgagcttgg cctcgacatc tacggcttgc gcaaaaagct gtcggacctc      660
gggttgaagt cgtcgtga                                                    678

<210> SEQ ID NO 126
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 126

Met Asn Asp Pro Val Val Arg Glu Ile Glu Arg Pro Ser Ala Thr
1               5                   10                  15

Ser Ile Asp Asp Leu Arg Arg Phe Gly Val Ser Thr Val His Glu Ala
            20                  25                  30

Gln Gly Arg Arg Gly Leu Leu Ala Ser Tyr Met Arg Pro Ile Tyr Ala
        35                  40                  45

Gly Ala Leu Val Ala Gly Pro Ala Ile Thr Val Leu Val Thr Pro Gly
    50                  55                  60

Asp Asn Leu Met Ile His Val Ala Val Glu Ile Cys Gln Pro Gly Asp
```

```
                65                  70                  75                  80
Val Leu Val Val Ala Pro Thr Ser Pro Cys Thr Asp Gly Tyr Phe Gly
                    85                  90                  95

Glu Leu Ala Thr Ser Leu Arg Ala His Gly Val Ala Gly Leu Ile
            100                 105                 110

Ile Asp Ala Gly Cys Arg Asp Val Arg Ser Leu Ser Glu Met Arg Phe
            115                 120                 125

Pro Val Trp Ser Arg Ala Ile Ser Ala Gln Gly Thr Val Lys Ala Thr
        130                 135                 140

Leu Gly Ser Val Asn Val Pro Leu Val Cys Ala Gly Ala Leu Val Glu
145                 150                 155                 160

Pro Gly Asp Ala Ile Val Ala Asp Asp Gly Val Val Val Arg
                165                 170                 175

Arg Glu Gln Val Asp Thr Val Cys Gln Ala Ala Gly Gln Arg Val Arg
            180                 185                 190

Lys Glu Glu Asp Thr Arg Ala Arg Leu Ala Gln Gly Glu Leu Gly Leu
        195                 200                 205

Asp Ile Tyr Gly Leu Arg Lys Lys Leu Ser Asp Leu Gly Leu Lys Ser
    210                 215                 220

Ser
225
```

<210> SEQ ID NO 127
<211> LENGTH: 678
<212> TYPE: DNA
<213> ORGANISM: Unknown
<220> FEATURE:
<223> OTHER INFORMATION: DNA obtained from environmental sample

<400> SEQUENCE: 127

```
atgaacgatc cggtcgtcgt tcgcgagatc gacaggccgg cgggtaccgc catcgacgat      60
ctccggcgct tcggcgtgtc gaccgtccac gaagcgcagg ggcgttgcgg cttgctcgct     120
tcgtacatac ggccgattta ttcaggcgcc ctgctcgccg gcccggcgat caccgtccag     180
gttacgcctg cgacaacct gatgatccac gtcgctgtcg aagtgtgccg gccaggagac     240
gtgctcgtcg tcgccccgac gtcgccgtgc acggatggct atttcggcga gctgctcgcg     300
acatcgctgc gtgcccacgg cgtcgtcggg ctgatcatcg acgccggttg ccgggacgtt     360
cgcgccttga gcgagatgcg atttcctgtg tggagtcgcg cgatcagcgc gcagggcacc     420
gtcaaagcca cgctgggctc ggtgaacgtg ccgctgttgt gtgccgggat gctggtcgag     480
gccggcgacg cgatcgtggc cgacgacgac ggagtggtgg tggtcaggcg gagccaggtc     540
gatgctgtcc gcgaggcggc cgaacgacgc gtgcgcaagg aagaggacac gcgggcccgg     600
ctcgcccgag gcgagcttgg cctcgacatc tacggcctgc gcaggaaact gtcagacccc     660
ggtttgaagt cgtcgtga                                                    678
```

<210> SEQ ID NO 128
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 128

```
Met Asn Asp Pro Val Val Arg Glu Ile Asp Arg Pro Ala Gly Thr
1               5                   10                  15

Ala Ile Asp Asp Leu Arg Arg Phe Gly Val Ser Thr Val His Glu Ala
            20                  25                  30

Gln Gly Arg Cys Gly Leu Leu Ala Ser Tyr Ile Arg Pro Ile Tyr Ser
        35                  40                  45

Gly Ala Leu Leu Ala Gly Pro Ala Ile Thr Val Gln Val Thr Pro Gly
50                  55                  60

Asp Asn Leu Met Ile His Val Ala Val Glu Val Cys Arg Pro Gly Asp
65              70                  75                  80

Val Leu Val Val Ala Pro Thr Ser Pro Cys Thr Asp Gly Tyr Phe Gly
                85                  90                  95

Glu Leu Leu Ala Thr Ser Leu Arg Ala His Gly Val Val Gly Leu Ile
            100                 105                 110

Ile Asp Ala Gly Cys Arg Asp Val Arg Ala Leu Ser Glu Met Arg Phe
            115                 120                 125

Pro Val Trp Ser Arg Ala Ile Ser Ala Gln Gly Thr Val Lys Ala Thr
        130                 135                 140

Leu Gly Ser Val Asn Val Pro Leu Leu Cys Ala Gly Met Leu Val Glu
145                 150                 155                 160

Ala Gly Asp Ala Ile Val Ala Asp Asp Gly Val Val Val Arg
                165                 170                 175

Arg Ser Gln Val Asp Ala Val Arg Glu Ala Ala Glu Arg Val Arg
            180                 185                 190

Lys Glu Glu Asp Thr Arg Ala Arg Leu Ala Arg Gly Leu Gly Leu
        195                 200                 205

Asp Ile Tyr Gly Leu Arg Arg Lys Leu Ser Asp Pro Gly Leu Lys Ser
    210                 215                 220

Ser
225

<210> SEQ ID NO 129
<211> LENGTH: 678
<212> TYPE: DNA
<213> ORGANISM: Unknown
<220> FEATURE:
<223> OTHER INFORMATION: DNA obtained from environmental sample

<400> SEQUENCE: 129
atgaacaaac cggtggtggt ccggaaggtc gaacagccgc cacaagatgc ggtggcggct      60
ctggagaaat atggcgtctc cacggtgcac gaagcgcaag gccgttgcgg gctgctcgcc     120
gcttacatgc gcccgatcta tgccggagct ccatggccg acccgccgt gaccgtttcc       180 cttccgcccg gtgacaacct catgatccac gtcgcggtcg aagtgtgcca ccccggaaac     240
attctggtcg tcgcccccac ttcaccttgt accgacgggt atttcggcga gttgctggct     300
acttccttgc gcgcccacgg cgtgaaggca ctcataatcg atgccggatg ccgtgacgtg     360 cgctcccctca ccgaaatgaa gtttcccgtg tggagccgcg ccgtcagttc gcagggaaca   420
gtgaagtcca cgctcggatc agtgaacgtg gcgtagtgt gtgcgggcgc tttcatcgaa      480
gcgggcgaca tcgtcgtcgc tgatgatgac ggagtcgtcg tcgtgaagag ggctttcgcg     540
cgcgacgtgt ttgaagcctg tgaacagagg gtccgcaagg aagaagcgac gcgggcacgc    600
ctggcgcagg gcgagcttgg tctggacatc tacggattgc gcgccaaagt ggcggagctc    660
ggtctcaagt acatataa                                                    678
```

<210> SEQ ID NO 130
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 130

```
Met Asn Lys Pro Val Val Arg Lys Val Glu Gln Pro Gln Asp
1               5                   10                  15

Ala Val Ala Ala Leu Glu Lys Tyr Gly Val Ser Thr Val His Glu Ala
                20                  25                  30

Gln Gly Arg Cys Gly Leu Leu Ala Ala Tyr Met Arg Pro Ile Tyr Ala
            35                  40                  45

Gly Ala Ser Met Ala Gly Pro Ala Val Thr Val Ser Leu Pro Pro Gly
50                  55                  60

Asp Asn Leu Met Ile His Val Ala Val Glu Val Cys His Pro Gly Asn
65                  70                  75                  80

Ile Leu Val Val Ala Pro Thr Ser Pro Cys Thr Asp Gly Tyr Phe Gly
                85                  90                  95

Glu Leu Leu Ala Thr Ser Leu Arg Ala His Gly Val Lys Ala Leu Ile
            100                 105                 110

Ile Asp Ala Gly Cys Arg Asp Val Arg Ser Leu Thr Glu Met Lys Phe
        115                 120                 125

Pro Val Trp Ser Arg Ala Val Ser Ser Gln Gly Thr Val Lys Ser Thr
130                 135                 140

Leu Gly Ser Val Asn Val Gly Val Val Cys Ala Gly Ala Phe Ile Glu
145                 150                 155                 160

Ala Gly Asp Ile Val Ala Asp Asp Gly Val Val Val Lys
                165                 170                 175

Arg Ala Phe Ala Arg Asp Val Val Glu Ala Cys Glu Gln Arg Val Arg
            180                 185                 190

Lys Glu Glu Ala Thr Arg Ala Arg Leu Ala Gln Gly Glu Leu Gly Leu
        195                 200                 205

Asp Ile Tyr Gly Leu Arg Ala Lys Val Ala Glu Leu Gly Leu Lys Tyr
210                 215                 220

Ile
225
```

<210> SEQ ID NO 131
<211> LENGTH: 672
<212> TYPE: DNA
<213> ORGANISM: Unknown
<220> FEATURE:
<223> OTHER INFORMATION: DNA obtained from environmental sample

<400> SEQUENCE: 131

```
atgagcatcg tcgtgcagaa catcgagcga gcggacctgg aggcggttac gacgcttggc      60
gaatgcggtg tggcgaccgt gcacgaggca caaggccgca cgggcctcat gctcccctat     120
atgcggccga tctggccggg cgcacggatc gcaggcccgg ctgtgaccgt ctccctgccg     180
ccgggcgaca actggatgat ccatgtcgcg gtggagcaat gccgggaggg cgacatcctg     240
atcgtggcgc cgaccagccc cagcgaggac ggctatttcg gcgagcttct ggcgcgctcg     300
ctcgtggcgc gcagcgtcaa gggcttcgtg atcgaggctg gggtgcgcga tgtgcgcgac     360
```

```
cttaccgaga tacgtttccc ggtctggtcg cgggcagtct ccgcccaggg cacggtcaag    420
gaaacgatcg gctcggtgaa cgtgccgatc gtctgcgcag gtgctgcggt gaatccgggc    480
gacgtggtcg tggctgacga tgacggcata tgtgtcgtgg ctcgcgacaa agctggtgag    540
gtggccaagg ctgcgcgagc gcgcgaggcg aaggaagctg aaacgcgccg ccggctgatc    600
aatggcgagc tcgggctcga catctatgga atgcgggaga agcttgcggc gaagggcctg    660
aaatatgtct ga                                                        672
```

```
<210> SEQ ID NO 132
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 132
```

```
Met Ser Ile Val Val Gln Asn Ile Glu Arg Ala Asp Leu Glu Ala Val
1               5                   10                  15

Thr Thr Leu Gly Glu Cys Gly Val Ala Thr Val His Glu Ala Gln Gly
            20                  25                  30

Arg Thr Gly Leu Met Leu Pro Tyr Met Arg Pro Ile Trp Pro Gly Ala
        35                  40                  45

Arg Ile Ala Gly Pro Ala Val Thr Val Ser Leu Pro Pro Gly Asp Asn
    50                  55                  60

Trp Met Ile His Val Ala Val Glu Gln Cys Arg Glu Gly Asp Ile Leu
65                  70                  75                  80

Ile Val Ala Pro Thr Ser Pro Ser Glu Asp Gly Tyr Phe Gly Glu Leu
                85                  90                  95

Leu Ala Arg Ser Leu Val Ala Arg Ser Val Lys Gly Phe Val Ile Glu
            100                 105                 110

Ala Gly Val Arg Asp Val Arg Asp Leu Thr Glu Ile Arg Phe Pro Val
        115                 120                 125

Trp Ser Arg Ala Val Ser Ala Gln Gly Thr Val Lys Glu Thr Ile Gly
    130                 135                 140

Ser Val Asn Val Pro Ile Val Cys Ala Gly Ala Ala Val Asn Pro Gly
145                 150                 155                 160

Asp Val Val Val Ala Asp Asp Asp Gly Ile Cys Val Val Ala Arg Asp
                165                 170                 175

Lys Ala Gly Glu Val Ala Lys Ala Ala Arg Ala Arg Glu Ala Lys Glu
            180                 185                 190

Ala Glu Thr Arg Arg Arg Leu Ile Asn Gly Glu Leu Gly Leu Asp Ile
        195                 200                 205

Tyr Gly Met Arg Glu Lys Leu Ala Ala Lys Gly Leu Lys Tyr Val
    210                 215                 220
```

```
<210> SEQ ID NO 133
<211> LENGTH: 672
<212> TYPE: DNA
<213> ORGANISM: Unknown
<220> FEATURE:
<223> OTHER INFORMATION: DNA obtained from environmental sample

<400> SEQUENCE: 133
atgaacatcg tcgtccagaa catcgagcgc gccgatccgg cggtgatcgc cggcctcgcc    60
```

```
gagtgcggcg tcgccacagt ccacgaagcg caggggcgca tcgggctgat gtcatcgaag    120
atgcggccga tctacgccgg cgcccgcatc gcggcctcgg cggtgaccgt gtcgctgccg    180
ccggccgaca actggatgat ccatgtcgcc gtggagcaga tcaaagcggg cgacgtcatg    240
gtcgtggcgc cgacctcgcc ctcggacgcg ggctattttg cgacctgct cgccaattcg     300 ctgcaggccc ggggctgcgc cggcctcgtg atcgatgccg gggtgcgcga cgtgcgtgac    360
cttaccgaaa tgcggttccc cgtctggtcg acggcgatct cggcgcaggg aaccgtcaag    420
gaaacgcttg gttcggtgaa cgtcccgatc gtctgcgccg gtgcacatgt cgaacccggc    480
gacgtgatcg tcgccgacga cgacggcgtc tgcatcgtca agcgcaccga cgcggctgcg    540
gtgctcgaaa aggcgcgggc ccggctcgcg aacgaaaccg acaagcgcga gaaactcgcg    600
aacggcacgc tgggcctcga tctctacaag atgcgcgagg cgctggagaa gaagggcctc    660
aggtatgcct ga                                                        672
```

<210> SEQ ID NO 134
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase
<220> FEATURE:
<221> NAME/KEY: SITE
<222> LOCATION: (193)...(196)
<223> OTHER INFORMATION: N-glycosylation site. Prosite id = PS00001
<220> FEATURE:
<221> NAME/KEY: SITE
<222> LOCATION: (204)...(207)
<223> OTHER INFORMATION: N-glycosylation site. Prosite id = PS00001

<400> SEQUENCE: 134

```
Met Asn Ile Val Val Gln Asn Ile Glu Arg Ala Asp Pro Ala Val Ile
1               5                   10                  15

Ala Gly Leu Ala Glu Cys Gly Val Ala Thr Val His Glu Ala Gln Gly
            20                  25                  30

Arg Ile Gly Leu Met Ser Ser Lys Met Arg Pro Ile Tyr Ala Gly Ala
        35                  40                  45

Arg Ile Ala Ala Ser Ala Val Thr Val Ser Leu Pro Pro Ala Asp Asn
    50                  55                  60

Trp Met Ile His Val Ala Val Glu Gln Ile Lys Ala Gly Asp Val Met
65                  70                  75                  80

Val Val Ala Pro Thr Ser Pro Ser Asp Ala Gly Tyr Phe Gly Asp Leu
                85                  90                  95

Leu Ala Asn Ser Leu Gln Ala Arg Gly Cys Ala Gly Leu Val Ile Asp
            100                 105                 110

Ala Gly Val Arg Asp Val Arg Asp Leu Thr Glu Met Arg Phe Pro Val
        115                 120                 125

Trp Ser Thr Ala Ile Ser Ala Gln Gly Thr Val Lys Glu Thr Leu Gly
    130                 135                 140

Ser Val Asn Val Pro Ile Val Cys Ala Gly Ala His Val Glu Pro Gly
145                 150                 155                 160

Asp Val Ile Val Ala Asp Asp Gly Val Cys Ile Val Lys Arg Thr
                165                 170                 175

Asp Ala Ala Ala Val Leu Glu Lys Ala Arg Ala Arg Leu Ala Asn Glu
            180                 185                 190
```

Thr Asp Lys Arg Glu Lys Leu Ala Asn Gly Thr Leu Gly Leu Asp Leu
        195                 200                 205

Tyr Lys Met Arg Glu Ala Leu Glu Lys Lys Gly Leu Arg Tyr Ala
    210                 215                 220

<210> SEQ ID NO 135
<211> LENGTH: 672
<212> TYPE: DNA
<213> ORGANISM: Unknown
<220> FEATURE:
<223> OTHER INFORMATION: DNA obtained from environmental sample

<400> SEQUENCE: 135

```
atgagcgtcg tcgtccagaa catcgcgcgc gccgatcaag cgatcgtcga tcggctcgcg    60
gcctgcggtg ttgccactgt gcatgaagcg cagggccgca agggactgct cgcgagccat   120
atgcggccga tctatcccgg taccgggctc gcggcgagcg ctgtgaccat ctcggcgccg   180
ccgggcgaca actggatggt ccacgtcgcg atcgagcaat gcgagcgggg cgacatcatg   240
gtgctcgccc cgaccagccc ctgcgaggat ggttatttcg gcgatctgct tgccacatcg   300
gcgaaagcac ggggctgccg cggtctcatc atcgatgccg gcgtccgcga tgtcgccgat   360
ctcacggcga tgcagtttcc tgtctggtcc aaggccatct tcgcgcaagg caccgtcaag   420
gaaacgctcg gctcggtgaa catcccggtg gtgtgcgcgg gtgcgctggt caatcccggc   480
gatgtcatcg tcgccgatga cgatggcgtc tgcgttgtgc gccgcgaaga ggcggaggcg   540
gtggcgcaga aggccgaagc ccgcgtcgcc gccgaggacg acaagcgcaa gcgcctcgcc   600
gccggcgaac tcggtctcga catctacaag atgcgcgagc ggctggccga aaggggctc   660
aaatatgtct ga                                                      672
```

<210> SEQ ID NO 136
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 136

Met Ser Val Val Val Gln Asn Ile Ala Arg Ala Asp Gln Ala Ile Val
1               5                   10                  15

Asp Arg Leu Ala Ala Cys Gly Val Ala Thr Val His Glu Ala Gln Gly
            20                  25                  30

Arg Lys Gly Leu Leu Ala Ser His Met Arg Pro Ile Tyr Pro Gly Thr
        35                  40                  45

Arg Leu Ala Ala Ser Ala Val Thr Ile Ser Ala Pro Pro Gly Asp Asn
    50                  55                  60

Trp Met Val His Val Ala Ile Glu Gln Leu Arg Ala Gly Asp Ile Met
65                  70                  75                  80

Val Leu Ala Pro Thr Ser Pro Cys Glu Asp Gly Tyr Phe Gly Asp Leu
                85                  90                  95

Leu Ala Thr Ser Ala Lys Ala Arg Gly Cys Arg Gly Leu Ile Ile Asp
            100                 105                 110

Ala Gly Val Arg Asp Val Ala Asp Leu Thr Ala Met Gln Phe Pro Val
        115                 120                 125

Trp Ser Lys Ala Ile Phe Ala Gln Gly Thr Val Lys Glu Thr Leu Gly
    130                 135                 140

Ser Val Asn Ile Pro Val Val Cys Ala Gly Ala Leu Val Asn Pro Gly
145                 150                 155                 160

Asp Val Ile Val Ala Asp Asp Gly Val Cys Val Arg Arg Glu
            165                 170                 175

Glu Ala Glu Ala Val Ala Gln Lys Glu Ala Arg Val Ala Ala Glu
                180                 185                 190

Asp Asp Lys Arg Lys Arg Leu Ala Ala Gly Glu Leu Gly Leu Asp Ile
        195                 200                 205

Tyr Lys Met Arg Glu Arg Leu Ala Glu Lys Gly Leu Lys Tyr Val
    210                 215                 220

<210> SEQ ID NO 137
<211> LENGTH: 672
<212> TYPE: DNA
<213> ORGANISM: Unknown
<220> FEATURE:
<223> OTHER INFORMATION: DNA obtained from environmental sample

<400> SEQUENCE: 137
atggctgtcg tggtccagaa tattgcccgt gccgaccagg cggtcattga ccggctggcc      60
gcctgtgatg tcgccacggt tcatgaggcg cagggccgca agggcctgct cgccggctac    120
atgcggccga tttatcccgg tgcccggatt gctgccagtg ccgtaacgat ctctgcgccg    180
cccggcgaca actggatggt ccatgtggcg atcaacagc tcaaggcggg cgatatcctg     240
ttgcttgcgc cgacaagccc ctgcgaggac ggctatttcg cgatcttct cgcgacgtcg     300 gccgttgcgc gcggctgccg cgggcttatc atcgatgccg cgtgcgtga cgttgccgat    360 ctcacggaaa tgaagtttcc ggtctggtcc aaggcggtct cgcccaggg cacggtcaag    420 gagacgctcg gctcggtcaa tgtgaccgtg gtctgtgccg gtgccctggt caatgccggc    480
gacgtgatcg tggccgacga cgatggcgtc tgcgtggtcc ggcgcgagga agcggctgac    540
gtggctgcca aagccgaggc gcgtgtcgct gccgaggagg caagcgcaa gcggctcgcg    600 gccggcgaac tcgggctcga catttacgac atgcgcgggc gattggcgga agggactg     660 agatatgtct ga                                                         672

<210> SEQ ID NO 138
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase
<220> FEATURE:
<221> NAME/KEY: SITE
<222> LOCATION: (149)...(152)
<223> OTHER INFORMATION: N-glycosylation site. Prosite id = PS00001

<400> SEQUENCE: 138

Met Ala Val Val Gln Asn Ile Ala Arg Ala Asp Gln Ala Val Ile
1               5                   10                  15

Asp Arg Leu Ala Ala Cys Asp Val Ala Thr Val His Glu Ala Gln Gly
            20                  25                  30

Arg Lys Gly Leu Leu Ala Gly Tyr Met Arg Pro Ile Tyr Pro Gly Ala
        35                  40                  45

Arg Ile Ala Ala Ser Ala Val Thr Ile Ser Ala Pro Pro Gly Asp Asn
    50                  55                  60

```
Trp Met Val His Val Ala Ile Glu Gln Leu Lys Ala Gly Asp Ile Leu
 65                  70                  75                  80

Leu Leu Ala Pro Thr Ser Pro Cys Glu Asp Gly Tyr Phe Gly Asp Leu
                 85                  90                  95

Leu Ala Thr Ser Ala Val Ala Arg Gly Cys Arg Gly Leu Ile Ile Asp
            100                 105                 110

Ala Gly Val Arg Asp Val Ala Asp Leu Thr Glu Met Lys Phe Pro Val
        115                 120                 125

Trp Ser Lys Ala Val Phe Ala Gln Gly Thr Val Lys Glu Thr Leu Gly
    130                 135                 140

Ser Val Asn Val Thr Val Val Cys Ala Gly Ala Leu Val Asn Ala Gly
145                 150                 155                 160

Asp Val Ile Val Ala Asp Asp Gly Val Cys Val Arg Arg Glu
                165                 170                 175

Glu Ala Ala Asp Val Ala Ala Lys Ala Glu Arg Val Ala Glu
                180                 185                 190

Glu Gly Lys Arg Lys Arg Leu Ala Ala Gly Glu Leu Gly Leu Asp Ile
        195                 200                 205

Tyr Asp Met Arg Gly Arg Leu Ala Glu Lys Gly Leu Arg Tyr Val
    210                 215                 220

<210> SEQ ID NO 139
<211> LENGTH: 693
<212> TYPE: DNA
<213> ORGANISM: Unknown
<220> FEATURE:
<223> OTHER INFORMATION: DNA obtained from environmental sample

<400> SEQUENCE: 139
atgaattatc agccggggac aacaggcatc gtcgtgcagg atattgcgcg cgctgatcaa      60
gccattatcg atggcctagc agaatgtggt gtggcgacgg tgcatgaggc acaagggcgc     120
aaggggctgt tggcggacta tatgacgccg atttttttcag gcgcgggcat cgctggatct    180
gcggtgacca ttctggcgcc accttgtgac aattggatga ttcatgtggc ggtagaacag    240
ttgcaaaagg gcgatgtgtt gctgctgggc acgatcacac cgtccaatgc tggctatttc    300
ggtgacttgc tggccacgtc agccatggcg cacggttgtc gcggattgat cattgatggc    360
ggtgtgcgcg atgtgcaaga gctgacggat atgggctttc cggtttggtc caaggccgta    420
catgcccaag gcacaatcaa agaaacgctg ggatcggtca acgtgccagt tgtctgcggc    480
caagagttgg taaatcccgg tgatattgtg gtggccgatg atgacggggt gtgcgttgtg    540
cgccgcgaag aagctgctga tgtgctggct aaggcgcggg cgcgcgagag taatgaagcc    600
gccaagcgcg cgcgttttga ggacggtgag ctggggctgg atatctatga catgcgcgcg    660
cggctggccg aaaagggact gaaatacgtc tga                                 693

<210> SEQ ID NO 140
<211> LENGTH: 230
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (27)...(179)
<223> OTHER INFORMATION: Demethylmenaquinone methyltransferase

<400> SEQUENCE: 140

Met Asn Tyr Gln Pro Gly Thr Thr Gly Ile Val Val Gln Asp Ile Ala
 1               5                  10                  15
```

```
Arg Ala Asp Gln Ala Ile Ile Asp Gly Leu Ala Glu Cys Gly Val Ala
             20                  25                  30

Thr Val His Glu Ala Gln Gly Arg Lys Gly Leu Leu Ala Asp Tyr Met
         35                  40                  45

Thr Pro Ile Phe Ser Gly Ala Gly Ile Ala Gly Ser Ala Val Thr Ile
     50                  55                  60

Leu Ala Pro Pro Cys Asp Asn Trp Met Ile His Val Ala Val Glu Gln
 65                  70                  75                  80

Leu Gln Lys Gly Asp Val Leu Leu Gly Thr Ile Thr Pro Ser Asn
                 85                  90                  95

Ala Gly Tyr Phe Gly Asp Leu Leu Ala Thr Ser Ala Met Ala His Gly
            100                 105                 110

Cys Arg Gly Leu Ile Ile Asp Gly Gly Val Arg Asp Val Gln Glu Leu
        115                 120                 125

Thr Asp Met Gly Phe Pro Val Trp Ser Lys Ala Val His Ala Gln Gly
130                 135                 140

Thr Ile Lys Glu Thr Leu Gly Ser Val Asn Val Pro Val Val Cys Gly
145                 150                 155                 160

Gln Glu Leu Val Asn Pro Gly Asp Ile Val Val Ala Asp Asp Gly
                165                 170                 175

Val Cys Val Val Arg Arg Glu Glu Ala Ala Asp Val Leu Ala Lys Ala
            180                 185                 190

Arg Ala Arg Glu Ser Asn Glu Ala Ala Lys Arg Ala Arg Phe Glu Asp
        195                 200                 205

Gly Glu Leu Gly Leu Asp Ile Tyr Asp Met Arg Ala Arg Leu Ala Glu
    210                 215                 220

Lys Gly Leu Lys Tyr Val
225                 230

<210> SEQ ID NO 141
<211> LENGTH: 672
<212> TYPE: DNA
<213> ORGANISM: Unknown
<220> FEATURE:
<223> OTHER INFORMATION: DNA obtained from environmental sample

<400> SEQUENCE: 141
atgagcgtcg tcgtccagaa catcgaacgc gccgacccgg actccgtcgc cgtgctcggc        60
gcgagcggcg tcgccaccgt gcacgaagcg caaggccgga cgggactcat gcggccctat       120
atgcggccga tctattcggg cgtgcgcatt gccggaccga ccgtcacggt ctccatcccg       180
ccgggcgaca actggatgat tcatgtcgcg gtcgagcagt gccgcgaagg cgacattctc       240
gttgtggctc cgaccagccc gagcgatgac ggctatttcg gcgacctgct tgccgggtcg       300
cttatggcac gaggcgtcaa ggctctcatc atcgaggccg gtgtgcgcga cgttcgcgat       360
ctgaccgaaa tgcgctttcc ggtctggtcg aagaccattt ccgcgcaggg aaccgtcaag       420
gaaacgcttg gctccgtgaa tgtgccgatc gtctgcgccg gtgcggcggt caatcccggc       480
gacgcggtcg tggccgatga cgacggcgta tgcgtcgtgc cgcgagagcg agcggccgag       540
gtggccaagg cgtcgcaggc ccgcgaggca aggaagccg gacgcgccg gcggctgatg        600 gccggtgaac tggggctcga catctacggc atgcgcgaga aactcgctgc caagggtttg       660
aaatatgtct ga                                                          672

<210> SEQ ID NO 142
<211> LENGTH: 223
```

```
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 142
```

| | | | | | | | | | | | | | | | |
|---|---|---|---|---|---|---|---|---|---|---|---|---|---|---|---|
| Met | Ser | Val | Val | Val | Gln | Asn | Ile | Glu | Arg | Ala | Asp | Pro | Asp | Ser | Val |
| 1 | | | | 5 | | | | | 10 | | | | | 15 | |
| Ala | Val | Leu | Gly | Ala | Ser | Gly | Val | Ala | Thr | Val | His | Glu | Ala | Gln | Gly |
| | | | 20 | | | | | 25 | | | | | 30 | | |
| Arg | Thr | Gly | Leu | Met | Arg | Pro | Tyr | Met | Arg | Pro | Ile | Tyr | Ser | Gly | Val |
| | | | 35 | | | | | 40 | | | | | 45 | | |
| Arg | Ile | Ala | Gly | Pro | Thr | Val | Thr | Val | Ser | Ile | Pro | Pro | Gly | Asp | Asn |
| | 50 | | | | | 55 | | | | | 60 | | | | |
| Trp | Met | Ile | His | Val | Ala | Val | Glu | Gln | Cys | Arg | Glu | Gly | Asp | Ile | Leu |
| 65 | | | | | 70 | | | | | 75 | | | | | 80 |
| Val | Val | Ala | Pro | Thr | Ser | Pro | Ser | Asp | Asp | Gly | Tyr | Phe | Gly | Asp | Leu |
| | | | | 85 | | | | | 90 | | | | | 95 | |
| Leu | Ala | Gly | Ser | Leu | Met | Ala | Arg | Gly | Val | Lys | Ala | Leu | Ile | Ile | Glu |
| | | | 100 | | | | | 105 | | | | | 110 | | |
| Ala | Gly | Val | Arg | Asp | Val | Arg | Asp | Leu | Thr | Glu | Met | Arg | Phe | Pro | Val |
| | | | 115 | | | | | 120 | | | | | 125 | | |
| Trp | Ser | Lys | Thr | Ile | Ser | Ala | Gln | Gly | Thr | Val | Lys | Glu | Thr | Leu | Gly |
| | 130 | | | | | 135 | | | | | 140 | | | | |
| Ser | Val | Asn | Val | Pro | Ile | Val | Cys | Ala | Gly | Ala | Ala | Val | Asn | Pro | Gly |
| 145 | | | | | 150 | | | | | 155 | | | | | 160 |
| Asp | Ala | Val | Val | Ala | Asp | Asp | Gly | Val | Cys | Val | Val | Pro | Arg | Glu |
| | | | | 165 | | | | | 170 | | | | | 175 |
| Arg | Ala | Ala | Glu | Val | Ala | Lys | Ala | Ser | Gln | Ala | Arg | Glu | Ala | Lys | Glu |
| | | | 180 | | | | | 185 | | | | | 190 | | |
| Ala | Gly | Thr | Arg | Arg | Arg | Leu | Met | Ala | Gly | Glu | Leu | Gly | Leu | Asp | Ile |
| | | | 195 | | | | | 200 | | | | | 205 | | |
| Tyr | Gly | Met | Arg | Glu | Lys | Leu | Ala | Ala | Lys | Gly | Leu | Lys | Tyr | Val | |
| | 210 | | | | | 215 | | | | | 220 | | | | |

```
<210> SEQ ID NO 143
<211> LENGTH: 672
<212> TYPE: DNA
<213> ORGANISM: Unknown
<220> FEATURE:
<223> OTHER INFORMATION: DNA obtained from environmental sample

<400> SEQUENCE: 143
atgagcgtcg tcgtccagaa catcgaacgc gccgacccgg actccgtcac cgtgctcggc      60
gcgagcggcg tcgccaccgt gcacgaagcg caaggccgga cgggactcat gcggccctac     120
atgcggccga tctattcggg cgtgcgcatt gccggaccgg ccgtcacggt ctccatcccg     180
ccgggcgaca actggatgat tcatgtcgcg gtcgagcagt gccgcgaagg cgacattctc     240
gttgtggctc cgaccagccc gagcgatgat ggctatttcg gcgacctgct tgccgggtcg     300
cttgtggcac gaggcgtcaa ggctctcatc atcgaggccg gtgtgcgcga cgttcgcgat     360
ctgaccgaaa tgcgctttcc ggtctggtcg aagaccattt ccgcgcaggg aaccgtcaag     420
gaaacgcttg gctccgtgaa tgtgccgatc gtctgcgccg gtgcggcggt caatcccggc     480
gacgcggtcg tggccgatga cgacggcgta tgcgtcgtgc cgcgagagcg agcggctgag     540
```

```
gtggccaagg cgtcgcaggc cgcgaggca aaggaggccg ggacgcgccg gcggctgatg    600
gccggtgaac tggggctcga catctacggc atgcgcgaga aactcgctgc caagggtttg    660
aaatatgtct ga                                                        672
```

<210> SEQ ID NO 144
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase
<220> FEATURE:
<221> NAME/KEY: SITE
<222> LOCATION: (1)...(21)
<223> OTHER INFORMATION: TonB-dependent receptor proteins signature 1.
      Prosite id = PS00430

<400> SEQUENCE: 144

```
Met Ser Val Val Gln Asn Ile Glu Arg Ala Asp Pro Asp Ser Val
1               5                   10                  15

Thr Val Leu Gly Ala Ser Gly Val Ala Thr Val His Glu Ala Gln Gly
            20                  25                  30

Arg Thr Gly Leu Met Arg Pro Tyr Met Arg Pro Ile Tyr Ser Gly Val
        35                  40                  45

Arg Ile Ala Gly Pro Ala Val Thr Val Ser Ile Pro Pro Gly Asp Asn
    50                  55                  60

Trp Met Ile His Val Ala Val Glu Gln Cys Arg Glu Gly Asp Ile Leu
65                  70                  75                  80

Val Val Ala Pro Thr Ser Pro Ser Asp Asp Gly Tyr Phe Gly Asp Leu
                85                  90                  95

Leu Ala Gly Ser Leu Val Ala Arg Gly Val Lys Ala Leu Ile Ile Glu
            100                 105                 110

Ala Gly Val Arg Asp Val Arg Asp Leu Thr Glu Met Arg Phe Pro Val
        115                 120                 125

Trp Ser Lys Thr Ile Ser Ala Gln Gly Thr Val Lys Glu Thr Leu Gly
    130                 135                 140

Ser Val Asn Val Pro Ile Val Cys Ala Gly Ala Ala Val Asn Pro Gly
145                 150                 155                 160

Asp Ala Val Val Ala Asp Asp Asp Gly Val Cys Val Val Pro Arg Glu
                165                 170                 175

Arg Ala Ala Glu Val Ala Lys Ala Ser Gln Ala Arg Glu Ala Lys Glu
            180                 185                 190

Ala Gly Thr Arg Arg Arg Leu Met Ala Gly Glu Leu Gly Leu Asp Ile
        195                 200                 205

Tyr Gly Met Arg Glu Lys Leu Ala Ala Lys Gly Leu Lys Tyr Val
    210                 215                 220
```

<210> SEQ ID NO 145
<211> LENGTH: 672
<212> TYPE: DNA
<213> ORGANISM: Unknown
<220> FEATURE:
<223> OTHER INFORMATION: DNA obtained from environmental sample

<400> SEQUENCE: 145

```
atgaccatcg tcgtcaccgg catcgagcgc gcgggagcgg acactgtcgc cgcgctgggc    60
```

-continued

```
acaagcggcg tcgcgaccgt acacgaggcg cagggccgca ccggcctgat gcgtccctac    120
atgcggccga tctatacggg agcgcgcatc gccgggacgg cgattaccgt gtcgctgccg    180
cccggcgaca actggatgat ccacgtcgcc gtcgagcagt gccggcaagg cgatatcctc    240
gtggtggcgc cgaccagccc gagcgacgac ggctatttcg cgacctgct cgccaattct    300 ctcgtcgccc gcggcgtgag gggcatggtc atcgaggccg cgtgcgtga cgttcgcgat    360 ctcaccgaga tgcgcttccc ggtctggtcg aagacgatct cggcgcaggg aacggtcaag    420
gagacgctcg gctcggtcaa cgtgccggtc gtctgcgctg gcttggccgt gaacccgggc    480
gacatcatcg tggccgacga cgacggcatc tgcgtggtgc cgcgccagac cgccgcgcag    540
gtcgtcgagg cggctcatgc gcgcgaggcg aaggaggcgg aggtccgtcg gcggctcatc    600
gccggcgaac tcggcctcga tatctacggc atgcgtgaga gctggcggc caagggcctg    660 aaatatgtct ga                                                        672
```

<210> SEQ ID NO 146
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 146

```
Met Thr Ile Val Val Thr Gly Ile Glu Arg Ala Gly Ala Asp Thr Val
1               5                   10                  15

Ala Ala Leu Gly Thr Ser Gly Val Ala Thr Val His Glu Ala Gln Gly
            20                  25                  30

Arg Thr Gly Leu Met Arg Pro Tyr Met Arg Pro Ile Tyr Thr Gly Ala
        35                  40                  45

Arg Ile Ala Gly Thr Ala Ile Thr Val Ser Leu Pro Pro Gly Asp Asn
    50                  55                  60

Trp Met Ile His Val Ala Val Glu Gln Cys Arg Gln Gly Asp Ile Leu
65                  70                  75                  80

Val Val Ala Pro Thr Ser Pro Ser Asp Asp Gly Tyr Phe Gly Asp Leu
                85                  90                  95

Leu Ala Asn Ser Leu Val Ala Arg Gly Val Arg Gly Met Val Ile Glu
            100                 105                 110

Ala Gly Val Arg Asp Val Arg Asp Leu Thr Glu Met Arg Phe Pro Val
        115                 120                 125

Trp Ser Lys Thr Ile Ser Ala Gln Gly Thr Val Lys Glu Thr Leu Gly
    130                 135                 140

Ser Val Asn Val Pro Val Val Cys Ala Gly Leu Ala Val Asn Pro Gly
145                 150                 155                 160

Asp Ile Ile Val Ala Asp Asp Gly Ile Cys Val Val Pro Arg Gln
                165                 170                 175

Thr Ala Ala Gln Val Val Glu Ala Ala His Ala Arg Glu Ala Lys Glu
            180                 185                 190

Ala Glu Val Arg Arg Arg Leu Ile Ala Gly Glu Leu Gly Leu Asp Ile
        195                 200                 205

Tyr Gly Met Arg Glu Lys Leu Ala Ala Lys Gly Leu Lys Tyr Val
    210                 215                 220
```

<210> SEQ ID NO 147

<211> LENGTH: 675
<212> TYPE: DNA
<213> ORGANISM: Unknown
<220> FEATURE:
<223> OTHER INFORMATION: DNA obtained from environmental sample

<400> SEQUENCE: 147

```
gtgagcggca tcgtcgtcca gaacatcgag cgcgccgacc ccgcgatcat cacgggcctc      60
gccgaatgcg gcgtcgccac ggtgcatgag gcgcagggcc gcaagggtct gctcgcgtcc     120
tacatgcggc cgatctatgc cggcgccgct gtcggcgcat cggcggtcac catcctcgcc     180
ccgccctgcg acaactggat ggtgcatgtg gcgatcgagc aggtgcgggc aggggacatc     240
ctcgtcctcg cgaccacctc gccctccgac gccggctatt cggcgatct g ctcgccacc     300
tcgatgaagg cccgcggcgg tgtcggcctc atcatcgatg ccggcgttcg tgacattcgc     360
gacctcacgg cggtgcagtt cccggtgtgg tccaaggccg tctgcgccca gggcaccatc     420
aaggaaacgc tgggctcggt gaacgtgccg gtggtctgtg ccggcgagct ggtcaacccg     480
ggcgatgtca tcgtcgccga tgacgacggc gtctgcgtcg tgcggcgcga ggaagctgcc     540
gatgtgctga agaaggcgca ggcccgcgtg gcgaacgaag cgacaagcg tcagcgcctc      600
gcggccggcg aactcggcct cgacatgtac aagatgcgcg acaagctgaa ggaaatgggc     660
ctcaaatatg tctga                                                     675
```

<210> SEQ ID NO 148
<211> LENGTH: 224
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (21)...(173)
<223> OTHER INFORMATION: Demethylmenaquinone methyltransferase

<400> SEQUENCE: 148

```
Met Ser Gly Ile Val Val Gln Asn Ile Glu Arg Ala Asp Pro Ala Ile
1               5                   10                  15

Ile Thr Gly Leu Ala Glu Cys Gly Val Ala Thr Val His Glu Ala Gln
            20                  25                  30

Gly Arg Lys Gly Leu Leu Ala Ser Tyr Met Arg Pro Ile Tyr Ala Gly
        35                  40                  45

Ala Ala Val Gly Ala Ser Ala Val Thr Ile Leu Ala Pro Pro Cys Asp
    50                  55                  60

Asn Trp Met Val His Val Ala Ile Glu Gln Val Arg Ala Gly Asp Ile
65                  70                  75                  80

Leu Val Leu Ala Thr Thr Ser Pro Ser Asp Ala Gly Tyr Phe Gly Asp
                85                  90                  95

Leu Leu Ala Thr Ser Met Lys Ala Arg Gly Gly Val Gly Leu Ile Ile
            100                 105                 110

Asp Ala Gly Val Arg Asp Ile Arg Asp Leu Thr Ala Val Gln Phe Pro
        115                 120                 125

Val Trp Ser Lys Ala Val Cys Ala Gln Gly Thr Ile Lys Glu Thr Leu
    130                 135                 140

Gly Ser Val Asn Val Pro Val Val Cys Ala Gly Glu Leu Val Asn Pro
145                 150                 155                 160

Gly Asp Val Ile Val Ala Asp Asp Gly Val Cys Val Val Arg Arg
                165                 170                 175

Glu Glu Ala Ala Asp Val Leu Lys Lys Ala Gln Ala Arg Val Ala Asn
```

-continued

```
                    180                 185                 190
Glu Gly Asp Lys Arg Gln Arg Leu Ala Ala Gly Glu Leu Gly Leu Asp
            195                 200                 205

Met Tyr Lys Met Arg Asp Lys Leu Lys Glu Met Gly Leu Lys Tyr Val
        210                 215                 220

<210> SEQ ID NO 149
<211> LENGTH: 678
<212> TYPE: DNA
<213> ORGANISM: Unknown
<220> FEATURE:
<223> OTHER INFORMATION: DNA obtained from environmental sample

<400> SEQUENCE: 149
atgaataaac cggtggtagt tcgacaggtc gagcagccat cagccgatgc ggttgcggca      60
ctagaaaagt gtggcgtaac gacggtgcat aaggctcagg gacgctgcgg cttgcttgca     120
gcctacatgc gaccgatttt cccaggagct agcatcgccg ttctgcggt cactgtgtcc      180 ctgccgccgg gcgacaacct gatgattcac gtcgcggtcg aggtctgcag cacaggaaac     240
attctggtgg tcgctccgac ctcgccatgc acggatggtt acttcggtga actcctcgca     300
acgtcgttgc gcgcgcacgg tgtaagaggc cttgtgatcg atgctggatg ccgtgacgtt     360
cgctctttga cggaaatgaa attcccggtc tggagccgcg ccatcagctc tcaggggaca     420
gtgaaagcca cactcggatc agtcaatgtg ccgatcacat gcgcggggac actcgttgaa     480
tccggtgacg tcatcgtcgc cgacgatgat ggtgtcgtag tcgtgaagcg tacggccgca     540
caagaagtcg ccgcagccgc tgaacaaagg gtgcgcaaag agaatgcgac ccgtgaacga     600
ctcgcacggg gcgaactcgg tctcgatatc tacgagatgc gccagaaaat cgcgcagctc     660
ggcctcaagt atctgtga                                                   678

<210> SEQ ID NO 150
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 150

Met Asn Lys Pro Val Val Arg Gln Val Glu Gln Pro Ser Ala Asp
1               5                  10                  15

Ala Val Ala Ala Leu Glu Lys Cys Gly Val Thr Thr Val His Lys Ala
            20                  25                  30

Gln Gly Arg Cys Gly Leu Leu Ala Ala Tyr Met Arg Pro Ile Phe Pro
        35                  40                  45

Gly Ala Ser Ile Ala Gly Ser Ala Val Thr Val Ser Leu Pro Pro Gly
    50                  55                  60

Asp Asn Leu Met Ile His Val Ala Val Glu Val Cys Ser Thr Gly Asn
65                  70                  75                  80

Ile Leu Val Val Ala Pro Thr Ser Pro Cys Thr Asp Gly Tyr Phe Gly
                85                  90                  95

Glu Leu Leu Ala Thr Ser Leu Arg Ala His Gly Val Arg Gly Leu Val
            100                 105                 110

Ile Asp Ala Gly Cys Arg Asp Val Arg Ser Leu Thr Glu Met Lys Phe
        115                 120                 125
```

```
Pro Val Trp Ser Arg Ala Ile Ser Ser Gln Gly Thr Val Lys Ala Thr
    130                 135                 140
Leu Gly Ser Val Asn Val Pro Ile Thr Cys Ala Gly Thr Leu Val Glu
145                 150                 155                 160
Ser Gly Asp Val Ile Val Ala Asp Asp Gly Val Val Val Lys
                165                 170                 175
Arg Thr Ala Ala Gln Glu Val Ala Ala Ala Glu Gln Arg Val Arg
            180                 185                 190
Lys Glu Asn Ala Thr Arg Glu Arg Leu Ala Arg Gly Glu Leu Gly Leu
        195                 200                 205
Asp Ile Tyr Glu Met Arg Gln Lys Ile Ala Gln Leu Gly Leu Lys Tyr
    210                 215                 220
Leu
225

<210> SEQ ID NO 151
<211> LENGTH: 675
<212> TYPE: DNA
<213> ORGANISM: Unknown
<220> FEATURE:
<223> OTHER INFORMATION: DNA obtained from environmental sample

<400> SEQUENCE: 151
atgagcggaa ttgttgtcca gaatatcgag cgcgccgacg cggcggtcat cgcagccttg      60
gaaagctgcg gcgtctcaac tgtgcacgag gctcaaggcc gtactggact gctggcttct     120
tatatgcgtc caatctacac aggtgcacgg atagcaggaa gtgcagtgac tatctccgca     180
cctcctggcg ataactggat ggtgcatgtg gctatcgagc aattgcacgc aggcgacata     240
ttgataatcg caccaacctc gccgtgcgaa gacggctatt tcggcgactt gctagccacg     300
tctgcgcagg cccgtgggtg caagggtctg attatcaacg ccggcgttcg cgatgtgcgc     360
gatttgactg aaatgggctt tcccgtctgg tcgaaggcca ttttgcccca aggcactatc     420
aaagcatcgc tgggttcggt caacataccc gtcgtgtgcg caggcgcgcc catcaatccc     480
ggcgatgtga ttgtggccga tgatgacggc gtttgtgtcg tgccgcgcca gaatgcggca     540
gaggtcgcaa aggcggcgaa ggcacgtgag gcgaacgagg ccgcaaagcg cgaccagctt     600
gcaaccggca tcttgggggct tgatatgtat gacatgcgcg gaaatctcgc cgagatgggg     660
ctgaaatata tatga                                                     675

<210> SEQ ID NO 152
<211> LENGTH: 224
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (21)...(173)
<223> OTHER INFORMATION: Demethylmenaquinone methyltransferase

<400> SEQUENCE: 152

Met Ser Gly Ile Val Val Gln Asn Ile Glu Arg Ala Asp Ala Ala Val
1               5                   10                  15
Ile Ala Ala Leu Glu Ser Cys Gly Val Ser Thr Val His Glu Ala Gln
            20                  25                  30
Gly Arg Thr Gly Leu Leu Ala Ser Tyr Met Arg Pro Ile Tyr Thr Gly
        35                  40                  45
Ala Arg Ile Ala Gly Ser Ala Val Thr Ile Ser Ala Pro Pro Gly Asp
    50                  55                  60
```

```
Asn Trp Met Val His Val Ala Ile Glu Gln Leu His Ala Gly Asp Ile
 65                  70                  75                  80

Leu Ile Ile Ala Pro Thr Ser Pro Cys Glu Asp Gly Tyr Phe Gly Asp
                 85                  90                  95

Leu Leu Ala Thr Ser Ala Gln Ala Arg Gly Cys Lys Gly Leu Ile Ile
            100                 105                 110

Asn Ala Gly Val Arg Asp Val Arg Asp Leu Thr Glu Met Gly Phe Pro
        115                 120                 125

Val Trp Ser Lys Ala Ile Phe Ala Gln Gly Thr Ile Lys Ala Ser Leu
    130                 135                 140

Gly Ser Val Asn Ile Pro Val Val Cys Ala Gly Ala Pro Ile Asn Pro
145                 150                 155                 160

Gly Asp Val Ile Val Ala Asp Asp Gly Val Cys Val Val Pro Arg
                165                 170                 175

Gln Asn Ala Ala Glu Val Ala Lys Ala Ala Lys Ala Arg Glu Ala Asn
            180                 185                 190

Glu Ala Ala Lys Arg Asp Gln Leu Ala Thr Gly Ile Leu Gly Leu Asp
        195                 200                 205

Met Tyr Asp Met Arg Gly Asn Leu Ala Glu Met Gly Leu Lys Tyr Ile
    210                 215                 220
```

<210> SEQ ID NO 153
<211> LENGTH: 672
<212> TYPE: DNA
<213> ORGANISM: Unknown
<220> FEATURE:
<223> OTHER INFORMATION: DNA obtained from environmental sample

<400> SEQUENCE: 153

```
atgtccgtcg tcgtccagaa catcgcgcgc gccgaccagt ccgtcatcga tcggctcggc      60
gcctgcggcg tcgccactgt gcatgaagcg cagggccgca cgggactgct agccagctac     120
atgcgcccca tctatcgggg tgcgcgtctg gccgcgagcg cggtgaccat ctcggccccg     180
cccggcgaca attggatgct ccatgtcgcc atcgagcagc tgaggcccgg cgacatcatg     240
gtgcttgccc ccaccagccc ctgcgaggat ggctatttcg gcgacctgct tgcgacatcg     300
gccctggcgc gcggctgccg tggtctcgtc atcgaggcgg gcgttcgcga tgtcgccgac     360
ctcaccgcga tgaagtttcc cgtctggtcc aaagccatct tcgcccaggg caccgtcaag     420
ggaacgctgg gttcggtgaa cgtgcccgtc gtctgtgccg gcgcgctgat caatcccggt     480
gacgtcattg tggccgatga cgatggcgtc tgcgtggtgc gccgcgagga agccgaagcg     540
gtggcgcaaa aggccgaggc gcgcgtcgcc gccgaagagg ataagcgcaa agcgcctcgcc    600
gccggcgaac tcgggctcga tatctacaag atgcgcgagc ggctcgccga aaagggactc     660
aaatatgtct ag                                                         672
```

<210> SEQ ID NO 154
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 154

Met Ser Val Val Val Gln Asn Ile Ala Arg Ala Asp Gln Ser Val Ile

```
                1               5                  10                 15
Asp Arg Leu Gly Ala Cys Gly Val Ala Thr Val His Glu Ala Gln Gly
                20                 25                 30

Arg Thr Gly Leu Leu Ala Ser Tyr Met Arg Pro Ile Tyr Arg Gly Ala
            35                 40                 45

Arg Leu Ala Ala Ser Ala Val Thr Ile Ser Ala Pro Pro Gly Asp Asn
        50                 55                 60

Trp Met Leu His Val Ala Ile Glu Gln Leu Arg Pro Gly Asp Ile Met
65                  70                 75                  80

Val Leu Ala Pro Thr Ser Pro Cys Glu Asp Gly Tyr Phe Gly Asp Leu
                85                 90                 95

Leu Ala Thr Ser Ala Leu Ala Arg Gly Cys Arg Gly Leu Val Ile Glu
            100                105                110

Ala Gly Val Arg Asp Val Ala Asp Leu Thr Ala Met Lys Phe Pro Val
            115                120                125

Trp Ser Lys Ala Ile Phe Ala Gln Gly Thr Val Lys Gly Thr Leu Gly
            130                135                140

Ser Val Asn Val Pro Val Val Cys Ala Gly Ala Leu Ile Asn Pro Gly
145                150                155                 160

Asp Val Ile Val Ala Asp Asp Gly Val Cys Val Arg Arg Glu
            165                170                175

Glu Ala Glu Ala Val Ala Gln Lys Glu Ala Arg Val Ala Ala Glu
            180                185                190

Glu Asp Lys Arg Lys Arg Leu Ala Ala Gly Glu Leu Gly Leu Asp Ile
            195                200                205

Tyr Lys Met Arg Glu Arg Leu Ala Glu Lys Gly Leu Lys Tyr Val
            210                215                220

<210> SEQ ID NO 155
<211> LENGTH: 672
<212> TYPE: DNA
<213> ORGANISM: Unknown
<220> FEATURE:
<223> OTHER INFORMATION: DNA obtained from environmental sample

<400> SEQUENCE: 155
atgaacatcg tggtgcagaa catcgagcgc gccgatccgg ccgtgatcgc cggactcgcg    60
gattgcggcg tcgccaccgt gcacgaggcg caggggcgca tcggactgat gtcgtccaag   120
atgcgaccga tctatccggg cgcgcgtgtc gcggcgtcgg cggtgacggt gtcgctgccg   180
ccggccgaca actggatgat tcatgtggcg gtggagcaga tcaaggccgg cgacatcatg   240
gtggtcgctc cgacctcgcc gtctgatgcc ggctacttcg cgacctact ggcgacctcg    300 ctcaaggcgc ggggctgcgt gggactggtg atcgacgcgg gggtgcgcga tgtgcgcgac   360
ctgaccgaaa tgcagttccc ggtgtggtcg acggcgatct cggcgcaggg gaccgtgaaa   420
gaaacgctgg gctcggtgaa cgtccctgtc atctgcgccg gcgcgcatgt ggagccgggc   480
gacgtgattg ttgccgacga cgacgggtc tgcatcgtca agcgtgccaa tgcggcggcg   540
gtgcttgaga aggcgcgagc gcgggtcgcc ggcgaagccg acaagcgcga gagattagcg   600
aacggcacgc tcgggctcga cctctacaag atgcgcgaag ggctggagaa gaagggtcta   660
aaatatgtct ga                                                       672

<210> SEQ ID NO 156
<211> LENGTH: 223
<212> TYPE: PRT
<213> ORGANISM: Unknown
```

```
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase
<220> FEATURE:
<221> NAME/KEY: SITE
<222> LOCATION: (204)...(207)
<223> OTHER INFORMATION: N-glycosylation site. Prosite id = PS00001

<400> SEQUENCE: 156
```

Met Asn Ile Val Val Gln Asn Ile Glu Arg Ala Asp Pro Ala Val Ile
1               5                   10                  15

Ala Gly Leu Ala Asp Cys Gly Val Ala Thr Val His Glu Ala Gln Gly
            20                  25                  30

Arg Ile Gly Leu Met Ser Ser Lys Met Arg Pro Ile Tyr Pro Gly Ala
        35                  40                  45

Arg Val Ala Ala Ser Ala Val Thr Val Ser Leu Pro Pro Ala Asp Asn
    50                  55                  60

Trp Met Ile His Val Ala Val Glu Gln Ile Lys Ala Gly Asp Ile Met
65                  70                  75                  80

Val Val Ala Pro Thr Ser Pro Ser Asp Ala Gly Tyr Phe Gly Asp Leu
                85                  90                  95

Leu Ala Thr Ser Leu Lys Ala Arg Gly Cys Val Gly Leu Val Ile Asp
            100                 105                 110

Ala Gly Val Arg Asp Val Arg Asp Leu Thr Glu Met Gln Phe Pro Val
        115                 120                 125

Trp Ser Thr Ala Ile Ser Ala Gln Gly Thr Val Lys Glu Thr Leu Gly
    130                 135                 140

Ser Val Asn Val Pro Val Ile Cys Ala Gly Ala His Val Glu Pro Gly
145                 150                 155                 160

Asp Val Ile Val Ala Asp Asp Asp Gly Val Cys Ile Val Lys Arg Ala
                165                 170                 175

Asn Ala Ala Ala Val Leu Glu Lys Ala Arg Ala Arg Val Ala Gly Glu
            180                 185                 190

Ala Asp Lys Arg Glu Arg Leu Ala Asn Gly Thr Leu Gly Leu Asp Leu
        195                 200                 205

Tyr Lys Met Arg Glu Gly Leu Glu Lys Lys Gly Leu Lys Tyr Val
    210                 215                 220

```
<210> SEQ ID NO 157
<211> LENGTH: 690
<212> TYPE: DNA
<213> ORGANISM: Unknown
<220> FEATURE:
<223> OTHER INFORMATION: DNA obtained from environmental sample

<400> SEQUENCE: 157
atgagcgtgg tcgtcaccgg cgtgcagcgg cccgctcccg cggacgtcgc ggcattgggc      60
cgcttcggcg tagcgacaat ccacgaggcg cagggacgca ctggactaat gcacgcttac     120
atgcggccga tctattccgg cgcgcatgtc tgcggtccag cggtaaccgt gtctctcccg     180
ccagcggaca actggatgat ccacgttgcc atcgagcaat gtgttgcagg cgacatcctc     240
gtggtggcac caacctcgcc ttccgacgcc ggctatttcg gcgagctact ggcaacctcg     300
cttcaggcgc gcggcgtgaa ggggcttatc atcgaggctg gctgccgcga tgtcgcggca     360
ctgactgcca tgcgcttccc ggtgtggtcg cgctcgatct ctgcgcaggg gacagtgaag     420
gagacgctcg gctcggtaaa tgtgcccgtc gtctgtaccg gcgcgctggt ggcgccgggc     480
```

```
gatgttatcg tcgctgacga cgatggagtt gtcgtggtcc caaaggacaa tgtggccgcc      540
atcgcctccg cctccgcggc gcgtgaggcg aaggaggaag aggtgcgggc gaagctcaag      600
gccggcgtgc tgggcctcga catctacggc gtgcgcgagc ggctgaagga gaagggcctt      660
cgctatcgtg ccgccgacga aggccactag                                       690
```

<210> SEQ ID NO 158
<211> LENGTH: 229
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase
<220> FEATURE:
<221> NAME/KEY: SITE
<222> LOCATION: (20)...(40)
<223> OTHER INFORMATION: Multicopper oxidases signature 1. Prosite
      id = PS00079

<400> SEQUENCE: 158

Met Ser Val Val Val Thr Gly Val Gln Arg Pro Ala Pro Ala Asp Val
1               5                   10                  15

Ala Ala Leu Gly Arg Phe Gly Val Ala Thr Ile His Glu Ala Gln Gly
            20                  25                  30

Arg Thr Gly Leu Met His Ala Tyr Met Arg Pro Ile Tyr Ser Gly Ala
        35                  40                  45

His Val Cys Gly Pro Ala Val Thr Val Ser Leu Pro Pro Ala Asp Asn
    50                  55                  60

Trp Met Ile His Val Ala Ile Glu Gln Cys Val Ala Gly Asp Ile Leu
65                  70                  75                  80

Val Val Ala Pro Thr Ser Pro Ser Asp Ala Gly Tyr Phe Gly Glu Leu
                85                  90                  95

Leu Ala Thr Ser Leu Gln Ala Arg Gly Val Lys Gly Leu Ile Ile Glu
            100                 105                 110

Ala Gly Cys Arg Asp Val Ala Ala Leu Thr Ala Met Arg Phe Pro Val
        115                 120                 125

Trp Ser Arg Ser Ile Ser Ala Gln Gly Thr Val Lys Glu Thr Leu Gly
    130                 135                 140

Ser Val Asn Val Pro Val Val Cys Thr Gly Ala Leu Val Ala Pro Gly
145                 150                 155                 160

Asp Val Ile Val Ala Asp Asp Gly Val Val Val Pro Lys Asp
                165                 170                 175

Asn Val Ala Ala Ile Ala Ser Ala Ser Ala Arg Glu Ala Lys Glu
            180                 185                 190

Glu Glu Val Arg Ala Lys Leu Lys Ala Gly Val Leu Gly Leu Asp Ile
        195                 200                 205

Tyr Gly Val Arg Glu Arg Leu Lys Glu Lys Gly Leu Arg Tyr Arg Ala
    210                 215                 220

Ala Asp Glu Gly His
225

<210> SEQ ID NO 159
<211> LENGTH: 672
<212> TYPE: DNA
<213> ORGANISM: Unknown
<220> FEATURE:
<223> OTHER INFORMATION: DNA obtained from environmental sample

<400> SEQUENCE: 159

```
atggcggtag tcgtccagaa tatcgagcgg gcggacggcg cggccatcga caagctggca      60
acatgcggcg tggcgaccgt gcacgaggcg caggggcgca ccggtctgct ggcatcggcc     120
atgcggccga tctacgccgg cgcccagatt gccggatcgg cgatcaccat ttcggcccca     180
cccggcgaca actggatggt gtacgtcgca atcgaacagc tcaagcaggg cgacgtgctg     240
gtgattgccc cgacgagtcc ctgtgaagac ggatacttcg gcgacctgct tgccacttcg     300
gcgatggcgc gcggctgccg cggcctgatc atcgatgcgg gcgtgcgcga cgtgcgcgat     360
ctgaccgcaa tgcgcttccc ggtctggtcc aaggcgatct cgcgcaggg aaccgtcaag      420
gagacgctcg gtcggtcaa cgtggcggtc gtgtgcgcca acgcgctggt caaccccggc     480
gacgtgatta tagccgacga cgacggcgtc gtcgtggtgc cacgcgcgca ggccggcgag     540
gtcctgaaga aggcggaagc gcgcatcgca tcggaagaag ccaagcgcaa gcggctggcg     600
gccggcgaac tcggcctcga tctctacgac atgcgcggca gactggccga caagggcctg     660
aagtatgttt ga                                                        672
```

<210> SEQ ID NO 160
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 160

```
Met Ala Val Val Gln Asn Ile Glu Arg Ala Asp Gly Ala Ala Ile
1               5                   10                  15
Asp Lys Leu Ala Thr Cys Gly Val Ala Thr Val His Glu Ala Gln Gly
            20                  25                  30
Arg Thr Gly Leu Leu Ala Ser Ala Met Arg Pro Ile Tyr Ala Gly Ala
        35                  40                  45
Gln Ile Ala Gly Ser Ala Ile Thr Ile Ser Ala Pro Pro Gly Asp Asn
    50                  55                  60
Trp Met Val Tyr Val Ala Ile Glu Gln Leu Lys Gln Gly Asp Val Leu
65                  70                  75                  80
Val Ile Ala Pro Thr Ser Pro Cys Glu Asp Gly Tyr Phe Gly Asp Leu
                85                  90                  95
Leu Ala Thr Ser Ala Met Ala Arg Gly Cys Arg Gly Leu Ile Ile Asp
            100                 105                 110
Ala Gly Val Arg Asp Val Arg Asp Leu Thr Ala Met Arg Phe Pro Val
        115                 120                 125
Trp Ser Lys Ala Ile Phe Ala Gln Gly Thr Val Lys Glu Thr Leu Gly
    130                 135                 140
Ser Val Asn Val Ala Val Val Cys Ala Asn Ala Leu Val Asn Pro Gly
145                 150                 155                 160
Asp Val Ile Ile Ala Asp Asp Asp Gly Val Val Val Pro Arg Ala
                165                 170                 175
Gln Ala Gly Glu Val Leu Lys Lys Ala Glu Ala Arg Ile Ala Ser Glu
            180                 185                 190
Glu Ala Lys Arg Lys Arg Leu Ala Ala Gly Glu Leu Gly Leu Asp Leu
        195                 200                 205
```

```
Tyr Asp Met Arg Gly Arg Leu Ala Asp Lys Gly Leu Lys Tyr Val
    210                 215                 220
```

<210> SEQ ID NO 161
<211> LENGTH: 699
<212> TYPE: DNA
<213> ORGANISM: Unknown
<220> FEATURE:
<223> OTHER INFORMATION: DNA obtained from environmental sample

<400> SEQUENCE: 161

```
atgagcgtgg tcgtcaccgg catcgcgcgg cctgaccgcg ccgaggtgga aggcttcgct      60
gccatcggcg tggcgaccat ccacgaggcg cagggccgca ccggcctgat gcagtccttc    120
atgcagccga tctataccgg cgcgcacatt ggcgggcccg cggtgacggt ctcgctgccg    180
cccggcgaca actggatgat tcacgtcgcg gtagagcagt gccaggccgg cgacgttctg    240
gtcgtcgccc ccacctcacc ctcggacgtc ggctatttcg gcgagctgct ggcgacctcg    300
ctcgtcgcac gcggcatccg cggcctcgtc atcgaggccg gctgccgcga taaaacggcg    360
ctgactgcga tgcgctttcc cgtttggtcc cgcgcggtct cggcgcaggg aacggtcaag    420
gagacgctcg gctcggtgaa tgtcccactc gtctgcgccg gtgcgctggt aaatcccggt    480
gatctcgtgg tcgccgatga cgacggtgtc gtcgttgtgc cgcgcgacaa ggtcgcggcg    540
gtgcgggcg catcgcttgc acgcgaggcg aaggaggatg ggtgcgcgc gcggctgcag    600
gccggcgagc tcggactcga cgtctacggc atgcgcgagc gcctgaagga aaaggggctg    660
gtctatcgcg cggcgaacac cgacgggaaa aacggctga                            699
```

<210> SEQ ID NO 162
<211> LENGTH: 232
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 162

```
Met Ser Val Val Thr Gly Ile Ala Arg Pro Asp Arg Ala Glu Val
1               5                   10                  15

Glu Gly Phe Ala Ala Ile Gly Val Ala Thr Ile His Glu Ala Gln Gly
            20                  25                  30

Arg Thr Gly Leu Met Gln Ser Phe Met Gln Pro Ile Tyr Thr Gly Ala
                35                  40                  45

His Ile Gly Gly Pro Ala Val Thr Val Ser Leu Pro Pro Gly Asp Asn
    50                  55                  60

Trp Met Ile His Val Ala Val Glu Gln Cys Gln Ala Gly Asp Val Leu
65                  70                  75                  80

Val Val Ala Pro Thr Ser Pro Ser Asp Val Gly Tyr Phe Gly Glu Leu
                85                  90                  95

Leu Ala Thr Ser Leu Val Ala Arg Gly Ile Arg Gly Leu Val Ile Glu
            100                 105                 110

Ala Gly Cys Arg Asp Lys Thr Ala Leu Thr Ala Met Arg Phe Pro Val
        115                 120                 125

Trp Ser Arg Ala Val Ser Ala Gln Gly Thr Val Lys Glu Thr Leu Gly
    130                 135                 140

Ser Val Asn Val Pro Leu Val Cys Ala Gly Ala Leu Val Asn Pro Gly
145                 150                 155                 160
```

```
Asp Leu Val Val Ala Asp Asp Gly Val Val Val Pro Arg Asp
            165                 170                 175

Lys Val Ala Ala Val Arg Ala Ala Ser Leu Ala Arg Glu Ala Lys Glu
        180                 185                 190

Asp Gly Val Arg Ala Arg Leu Gln Ala Gly Glu Leu Gly Leu Asp Val
    195                 200                 205

Tyr Gly Met Arg Glu Arg Leu Lys Glu Lys Gly Leu Val Tyr Arg Ala
    210                 215                 220

Ala Asn Thr Asp Gly Lys Asn Gly
225             230

<210> SEQ ID NO 163
<211> LENGTH: 699
<212> TYPE: DNA
<213> ORGANISM: Unknown
<220> FEATURE:
<223> OTHER INFORMATION: DNA obtained from environmental sample

<400> SEQUENCE: 163
atgagtgtcg tcgtcacagg aattccgcgg gcctcggcat ctgagatcga cgcgcttcgc    60
cgctgcgggg tggcgacgat ccacgaggcg caagggcgta ccggccttct gcgcgcgaac   120
atgcggccga tctacgctgg tgcccatgcc gtcggatcgg cggtgaccgt gtcgttgccc   180
ccggccgata actggatgat ccatgtggcg gtcgagcagt gtcaggcagg agacgtcctc   240
gtcgtggccc cgacttcgcc ttcggatgcc ggctactttg gcgagctgct ggcgacctct   300
ctcgccgcgc ggggtgtgcg cggcctcgtt atcgaggctg gtgccgcga cgtggcggcg   360 ttgacggcaa tgcgttttcc ggtctggtca cgcgccgtct ccgcacaagg acggtgaag   420 gagacgcttg gttcggtgaa tgtgccgatc atctgcgccg gtgctctcgt gaatccggga   480
gacgttgtcg ttgccgacga tgacggcgtg gtcgttgtgc cacgcatcgg agtggcggat   540
gtcgctgccg cctcggccgc gcgtgaagcg aaggaggatc aggtcagggc gcgcttcaag   600
gcgggcgagc tcgggctcga tatctatagg atgcgcgagc ggctgaagga aaaagggctc   660
gtctaccgta ccgcgggtga tggcccaggc gggggctag                          699

<210> SEQ ID NO 164
<211> LENGTH: 232
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 164

Met Ser Val Val Val Thr Gly Ile Pro Arg Ala Ser Ala Ser Glu Ile
1               5                   10                  15

Asp Ala Leu Arg Arg Cys Gly Val Ala Thr Ile His Glu Ala Gln Gly
            20                  25                  30

Arg Thr Gly Leu Leu Arg Ala Asn Met Arg Pro Ile Tyr Ala Gly Ala
        35                  40                  45

His Ala Val Gly Ser Ala Val Thr Val Ser Leu Pro Pro Ala Asp Asn
    50                  55                  60

Trp Met Ile His Val Ala Val Glu Gln Cys Gln Ala Gly Asp Val Leu
65                  70                  75                  80

Val Val Ala Pro Thr Ser Pro Ser Asp Ala Gly Tyr Phe Gly Glu Leu
```

```
                        85                  90                  95
Leu Ala Thr Ser Leu Ala Ala Arg Gly Val Arg Gly Leu Val Ile Glu
                100                 105                 110
Ala Gly Cys Arg Asp Val Ala Ala Leu Thr Ala Met Arg Phe Pro Val
            115                 120                 125
Trp Ser Arg Ala Val Ser Ala Gln Gly Thr Val Lys Glu Thr Leu Gly
        130                 135                 140
Ser Val Asn Val Pro Ile Ile Cys Ala Gly Ala Leu Val Asn Pro Gly
145                 150                 155                 160
Asp Val Val Ala Asp Asp Gly Val Val Val Pro Arg Ile
                165                 170                 175
Gly Val Ala Asp Val Ala Ala Ala Ser Ala Ala Arg Glu Ala Lys Glu
            180                 185                 190
Asp Gln Val Arg Ala Arg Phe Lys Ala Gly Glu Leu Gly Leu Asp Ile
        195                 200                 205
Tyr Arg Met Arg Glu Arg Leu Lys Glu Lys Gly Leu Val Tyr Arg Thr
210                 215                 220
Ala Gly Asp Gly Pro Gly Gly Gly
225                 230
```

<210> SEQ ID NO 165
<211> LENGTH: 672
<212> TYPE: DNA
<213> ORGANISM: Unknown
<220> FEATURE:
<223> OTHER INFORMATION: DNA obtained from environmental sample

<400> SEQUENCE: 165

```
atgggtgtgg tggtccagaa tatcgcccgc gccgcgcaat ccgtcatcga ccggctcgcg      60
gcttgcggcg tcgcgacggt tcatgaagca caggggcgca aaggcctgct cgccagccgt     120
atgcggccga tctatcccgg cgcccggatc gccgcgagcg cggtgacgat ctcagcgccg     180
cccggtgaca actggatgat tcatgtggcg atcgagcagc tcaagacggg tgacatcctg     240
cttctggcgc cgaccagtcc ttgcgaggac ggctatttcg cgatctgct tgcgacgtcc      300
gcgatggcgc ggggctgtcg gggattgatc atcgatgctg gcgtgcgcga tgtcgccgac     360
ctggccgcga tgaaattccc tgtctggtcg aaggccatct tcgcgcaggg cacggtcaag     420
gagacagtcg gttccgtgaa tgtgccggtc gtctgcgccg gcgcgctggt caatcccggc     480
gatgtgatcg tcgccgacga tgacggcgtc tgtgtcgtca ggcgcgagga tgcggctgat     540
gtggctgaca aggccgaggc gcgcgtcgcg gccgaagaga gcaagcgcaa gcggctagca     600
tcaggcgagc tcggtctcga catttacgat atgcgccaac ggctcacgga gaaaggcctt     660
agatatgtct ga                                                         672
```

<210> SEQ ID NO 166
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 166

```
Met Gly Val Val Val Gln Asn Ile Ala Arg Ala Ala Gln Ser Val Ile
1               5                   10                  15
```

```
Asp Arg Leu Ala Ala Cys Gly Val Ala Thr Val His Glu Ala Gln Gly
         20                  25                  30

Arg Lys Gly Leu Leu Ala Ser Arg Met Arg Pro Ile Tyr Pro Gly Ala
     35                  40                  45

Arg Ile Ala Ala Ser Ala Val Thr Ile Ser Ala Pro Pro Gly Asp Asn
 50                  55                  60

Trp Met Ile His Val Ala Ile Glu Gln Leu Lys Thr Gly Asp Ile Leu
 65                  70                  75                  80

Leu Leu Ala Pro Thr Ser Pro Cys Glu Asp Gly Tyr Phe Gly Asp Leu
                 85                  90                  95

Leu Ala Thr Ser Ala Met Ala Arg Gly Cys Arg Gly Leu Ile Ile Asp
            100                 105                 110

Ala Gly Val Arg Asp Val Ala Asp Leu Ala Ala Met Lys Phe Pro Val
        115                 120                 125

Trp Ser Lys Ala Ile Phe Ala Gln Gly Thr Val Lys Glu Thr Val Gly
    130                 135                 140

Ser Val Asn Val Pro Val Cys Ala Gly Ala Leu Val Asn Pro Gly
145                 150                 155                 160

Asp Val Ile Val Ala Asp Asp Gly Val Cys Val Val Arg Arg Glu
                165                 170                 175

Asp Ala Ala Asp Val Ala Asp Lys Ala Glu Ala Arg Val Ala Ala Glu
            180                 185                 190

Glu Ser Lys Arg Lys Arg Leu Ala Ser Gly Glu Leu Gly Leu Asp Ile
        195                 200                 205

Tyr Asp Met Arg Gln Arg Leu Thr Glu Lys Gly Leu Arg Tyr Val
    210                 215                 220
```

<210> SEQ ID NO 167
<211> LENGTH: 672
<212> TYPE: DNA
<213> ORGANISM: Unknown
<220> FEATURE:
<223> OTHER INFORMATION: DNA obtained from environmental sample

<400> SEQUENCE: 167

```
atgggcgtcg tggtccagaa catcgcccgc gccgagcgag atgtcatcga ccggcttgcg    60
atctgcggcg tcgcgaccgt gcatgaggcg caagggcgca aggggctgct ggcgagctat   120
atgcggccga tctatcccgg cgcgcggatt gcggcgagcg ccgtcaccat ttcggctccc   180
cccggtgaca actggatggt ccatgtggcg atcgagcagg tgagggaggg cgacatcctg   240
ctgctcgctc cgacgagccc ttgcgaggac gggtattttg cgacctgct ggcgacctcg   300
gccatggcgc gcggatgccg cgggctggtc atcgatgccg gcgtgcgtga tgtcgccgat   360
ctcacggcga tgcagttccc cgtctggtcg aaggcgatct tcgcacaggg cacggtcaag   420
gagacgctgg gctctgtgaa tgtgccggtc gtctgcgccg gcgcgcttat caatccgggc   480
gatgtcatcg tggcggatga tggcgtctc gcgtcgtca ggcgcgagga ggcggccgat   540
gtcgccgcca aggccgaggc gcgcgttggc ccgaggagg ccaagcgcaa gcgtctcgct   600
gccggcgaac tcggactcga catctacgat atgcgcaggc gtctcgccga aaggggattg   660
aaatatgtct ga                                                        672
```

<210> SEQ ID NO 168
<211> LENGTH: 223
<212> TYPE: PRT
<213> ORGANISM: Unknown
<220> FEATURE:
<223> OTHER INFORMATION: Protein obtained from environmental sample

```
<220> FEATURE:
<221> NAME/KEY: DOMAIN
<222> LOCATION: (20)...(172)
<223> OTHER INFORMATION: Demethylmenaquinone methyltransferase

<400> SEQUENCE: 168

Met Gly Val Val Val Gln Asn Ile Ala Arg Ala Glu Arg Asp Val Ile
1               5                   10                  15

Asp Arg Leu Ala Ile Cys Gly Val Ala Thr Val His Glu Ala Gln Gly
            20                  25                  30

Arg Lys Gly Leu Leu Ala Ser Tyr Met Arg Pro Ile Tyr Pro Gly Ala
        35                  40                  45

Arg Ile Ala Ala Ser Ala Val Thr Ile Ser Ala Pro Pro Gly Asp Asn
    50                  55                  60

Trp Met Val His Val Ala Ile Glu Gln Val Arg Glu Gly Asp Ile Leu
65                  70                  75                  80

Leu Leu Ala Pro Thr Ser Pro Cys Glu Asp Gly Tyr Phe Gly Asp Leu
                85                  90                  95

Leu Ala Thr Ser Ala Met Ala Arg Gly Cys Arg Gly Leu Val Ile Asp
            100                 105                 110

Ala Gly Val Arg Asp Val Ala Asp Leu Thr Ala Met Gln Phe Pro Val
        115                 120                 125

Trp Ser Lys Ala Ile Phe Ala Gln Gly Thr Val Lys Glu Thr Leu Gly
    130                 135                 140

Ser Val Asn Val Pro Val Val Cys Ala Gly Ala Leu Ile Asn Pro Gly
145                 150                 155                 160

Asp Val Ile Val Ala Asp Asp Gly Val Cys Val Arg Arg Glu
                165                 170                 175

Glu Ala Ala Asp Val Ala Ala Lys Ala Glu Ala Arg Val Gly Ala Glu
            180                 185                 190

Glu Ala Lys Arg Lys Arg Leu Ala Ala Gly Glu Leu Gly Leu Asp Ile
        195                 200                 205

Tyr Asp Met Arg Arg Arg Leu Ala Glu Lys Gly Leu Lys Tyr Val
    210                 215                 220

<210> SEQ ID NO 169
<211> LENGTH: 672
<212> TYPE: DNA
<213> ORGANISM: Unknown
<220> FEATURE:
<223> OTHER INFORMATION: DNA obtained from environmental sample

<400> SEQUENCE: 169
atgagtgtgg tcgttcagaa tatcgagcgg gccgatcccg ccatcatcgc cggccttgcc      60
gaatgcggtg tggcgaccgt ccacgaagcg cagggccgca agggcctgct ggcgtcctat     120
atgcgtccca tctactcggg cgcgcgcctg gcagcaagtg ccgtgaccat ttcggcgccg     180
ccctgcgaca actggatgtt gcatgtcgcc attgagaaat gcgggagggc gacattctc     240
gtcctcgccc caacgtcgcc gtctgacgct gggtactttg gcgacctgct ggccacttcg     300
gcgcaggccc gcggctgcaa gggcctgatc attgatgccg gcgtacgcga cgtggccgac     360
ctcacgcgga tgaaattccc cgtctggtcc aaggcgatat tgcccagggc cacgatcaag     420
gagacgctgg gctcggtcaa tgtgccgatt gtctgcgcgg cgagctggt caatgccggc     480
gacatcatcg tggccgatga cgatggggtt tgcgttgtgc gccgcgagga ggctgctgcg     540
gtgctcgaag cctcgcagaa gcgcgtggcc aatgaagaga gcacgcgcaa cgcctcgct     600
gccggggaac tgggactcga catctatgga atgcgccagc ggctgaccga aaggggttg     660
```
aagtatgtct ga                                                              672

<210> SEQ ID NO 170
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 170

Met Ser Val Val Val Gln Asn Ile Glu Arg Ala Asp Pro Ala Ile Ile
1               5                   10                  15

Ala Gly Leu Ala Glu Cys Gly Val Ala Thr Val His Glu Ala Gln Gly
            20                  25                  30

Arg Lys Gly Leu Leu Ala Ser Tyr Met Arg Pro Ile Tyr Ser Gly Ala
        35                  40                  45

Arg Leu Ala Ala Ser Ala Val Thr Ile Ser Ala Pro Pro Cys Asp Asn
    50                  55                  60

Trp Met Leu His Val Ala Ile Glu Lys Leu Arg Glu Gly Asp Ile Leu
65                  70                  75                  80

Val Leu Ala Pro Thr Ser Pro Ser Asp Ala Gly Tyr Phe Gly Asp Leu
                85                  90                  95

Leu Ala Thr Ser Ala Gln Ala Arg Gly Cys Lys Gly Leu Ile Ile Asp
            100                 105                 110

Ala Gly Val Arg Asp Val Ala Asp Leu Thr Arg Met Lys Phe Pro Val
        115                 120                 125

Trp Ser Lys Ala Ile Phe Ala Gln Gly Thr Ile Lys Glu Thr Leu Gly
    130                 135                 140

Ser Val Asn Val Pro Ile Val Cys Ala Gly Glu Leu Val Asn Ala Gly
145                 150                 155                 160

Asp Ile Ile Val Ala Asp Asp Asp Gly Val Cys Val Val Arg Arg Glu
                165                 170                 175

Glu Ala Ala Ala Val Leu Glu Ala Ser Gln Lys Arg Val Ala Asn Glu
            180                 185                 190

Glu Ser Thr Arg Lys Arg Leu Ala Ala Gly Glu Leu Gly Leu Asp Ile
        195                 200                 205

Tyr Gly Met Arg Gln Arg Leu Thr Glu Lys Gly Leu Lys Tyr Val
    210                 215                 220

<210> SEQ ID NO 171
<211> LENGTH: 672
<212> TYPE: DNA
<213> ORGANISM: Unknown
<220> FEATURE:
<223> OTHER INFORMATION: DNA obtained from environmental sample

<400> SEQUENCE: 171
atgaccgtcg tcgtccgcaa cttcgagcgc gcgtcgcccg aagtcgtagc cgtgctgggc      60
gaatgcggcg tggcgacggt gcatgaagcg caaggccgca gcggcctcat gctcgccttc     120
atgcggccga tcttcgcggg cgcccgcatc gccgggccgg cggtgacagt ttccgtcccg     180
ccgggcgaca actggatgat ccatgtggcg atcgagcagt gccgcgaagg cgacgtgctc     240
gtcgtggcgc cgaccagccc ctccgaggac ggctatttcg cgacctgct cgcgcactcg      300 ctgatggcgc ggggcgtcaa gggctcgtc attgaggccg cgttcgcga tctacgcgat       360

```
ctcaccgaga tgcgctttcc ggtctggtcc cggacgatct ccgcgcaggg aacggtcaag    420
gagacgctcg gctcggtgaa cgtgccgatc gtctgcgccg gcgcggcggt cgatccgggc    480
gacgtagtcg tggccgacga cgacggcgtc tgcatcgtga cgcgccccg gcggaagag    540 gtcgcgaaag cggcgcgcga acgcgaggcg aaggagaggg agacgcggcg gcggctggcc    600
gccggcgagc tcggtctcga catctatggc atgcgcgaga agcttgcggc caaagggctg    660
aaatatgtct ga                                                        672
```

<210> SEQ ID NO 172
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 172

```
Met Thr Val Val Val Arg Asn Phe Glu Arg Ala Ser Pro Glu Val Val
1               5                   10                  15

Ala Val Leu Gly Glu Cys Gly Val Ala Thr Val His Glu Ala Gln Gly
            20                  25                  30

Arg Ser Gly Leu Met Leu Ala Phe Met Arg Pro Ile Phe Ala Gly Ala
        35                  40                  45

Arg Ile Ala Gly Pro Ala Val Thr Val Ser Val Pro Pro Gly Asp Asn
    50                  55                  60

Trp Met Ile His Val Ala Ile Glu Gln Cys Arg Glu Gly Asp Val Leu
65                  70                  75                  80

Val Val Ala Pro Thr Ser Pro Ser Glu Asp Gly Tyr Phe Gly Asp Leu
                85                  90                  95

Leu Ala His Ser Leu Met Ala Arg Gly Val Lys Gly Leu Val Ile Glu
            100                 105                 110

Ala Gly Val Arg Asp Leu Arg Asp Leu Thr Glu Met Arg Phe Pro Val
        115                 120                 125

Trp Ser Arg Thr Ile Ser Ala Gln Gly Thr Val Lys Glu Thr Leu Gly
    130                 135                 140

Ser Val Asn Val Pro Ile Val Cys Ala Gly Ala Ala Val Asp Pro Gly
145                 150                 155                 160

Asp Val Val Val Ala Asp Asp Asp Gly Val Cys Ile Val Arg Arg Ala
                165                 170                 175

Arg Ala Glu Glu Val Ala Lys Ala Ala Arg Glu Arg Glu Ala Lys Glu
            180                 185                 190

Arg Glu Thr Arg Arg Arg Leu Ala Ala Gly Glu Leu Gly Leu Asp Ile
        195                 200                 205

Tyr Gly Met Arg Glu Lys Leu Ala Ala Lys Gly Leu Lys Tyr Val
    210                 215                 220
```

<210> SEQ ID NO 173
<211> LENGTH: 672
<212> TYPE: DNA
<213> ORGANISM: Unknown
<220> FEATURE:
<223> OTHER INFORMATION: DNA obtained from environmental sample

<400> SEQUENCE: 173

```
atgggcgttg tggtccagaa tgtcggccgc gccgaacaat ccgtcatcga ccggctcgca    60
```

```
gcctgtggcg tggcgactgt gcatgaggcg cagggccgcc ggggcctcct cgcgagctac    120
atgcggccga tctattccgg tgcacggatc gccgcgagtg cagtgacgat ctcggcgccg    180
cccagtgaca actggatgct gcatgtggcg atcgagcaat tgaagcaggg cgatctgctt    240
ctgctcgcgc ccaccagccc gtgcgaagac ggctatttcg gtgacctgct cgcgacctct    300
gccgtggcgc gaggttgccg cggcctgatc atcgacgcgg cgtacgcga tgtcgccgac    360 ctgacggcca tgtcgtttcc ggtctggtcc aaggcgatat ctgcgcaagg caccgtcaag    420
gagacattgg gctcggtgaa tgtgccggtc gtctgcgccg gtgcgctggt caacccaggc    480
gacgtgatcg tggccgacga cgatggcgtc tgcgtcgtgc ccgcgagga ggcggcggag    540 atcgccgaca aggccgaagc gcgcgtcgcg gccgaggaaa gcaagcgggc gcggctggca    600
gccggcgaac ttgggttgga tatctacgac atgcgcaagc ggctcgccga aaagggctg    660 aagtatgtct ga                                                       672
```

<210> SEQ ID NO 174
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 174

```
Met Gly Val Val Gln Asn Val Gly Arg Ala Glu Gln Ser Val Ile
1               5                   10                  15

Asp Arg Leu Ala Ala Cys Gly Val Ala Thr Val His Glu Ala Gln Gly
            20                  25                  30

Arg Arg Gly Leu Leu Ala Ser Tyr Met Arg Pro Ile Tyr Ser Gly Ala
        35                  40                  45

Arg Ile Ala Ala Ser Ala Val Thr Ile Ser Ala Pro Pro Ser Asp Asn
    50                  55                  60

Trp Met Leu His Val Ala Ile Glu Gln Leu Lys Gln Gly Asp Leu Leu
65                  70                  75                  80

Leu Leu Ala Pro Thr Ser Pro Cys Glu Asp Gly Tyr Phe Gly Asp Leu
                85                  90                  95

Leu Ala Thr Ser Ala Val Ala Arg Gly Cys Arg Gly Leu Ile Ile Asp
            100                 105                 110

Ala Gly Val Arg Asp Val Ala Asp Leu Thr Ala Met Ser Phe Pro Val
        115                 120                 125

Trp Ser Lys Ala Ile Ser Ala Gln Gly Thr Val Lys Glu Thr Leu Gly
    130                 135                 140

Ser Val Asn Val Pro Val Val Cys Ala Gly Ala Leu Val Asn Pro Gly
145                 150                 155                 160

Asp Val Ile Val Ala Asp Asp Gly Val Cys Val Val Arg Arg Glu
                165                 170                 175

Glu Ala Ala Glu Ile Ala Asp Lys Ala Glu Ala Arg Val Ala Ala Glu
            180                 185                 190

Glu Ser Lys Arg Ala Arg Leu Ala Ala Gly Leu Gly Leu Asp Ile
        195                 200                 205

Tyr Asp Met Arg Lys Arg Leu Ala Glu Lys Gly Leu Lys Tyr Val
    210                 215                 220
```

-continued

```
<210> SEQ ID NO 175
<211> LENGTH: 672
<212> TYPE: DNA
<213> ORGANISM: Unknown
<220> FEATURE:
<223> OTHER INFORMATION: DNA obtained from environmental sample

<400> SEQUENCE: 175
atgggtgtcg tcgtccagaa tatcgagcgc gccgatcctt cggtcatcga acggctggcg      60
gcatgcgggg ttgctactgt gcacgaagcg cagggacgca agggtctgct ggcgagccat     120
atgcggccga tctatgccgg tgcgcgcctt gcagccagtg ccgtgaccat atcggcgccg     180
ccgggcgata actggatgat ccatgtcgcc atcgaacagc tcagggcggg tgacataatg     240
gtgcttgccc cgacaagtcc ctgcgaggat ggctatttcg gcgacttgct ggcgacgtct     300
gctgcggcgc gaggctgccg ggggctgatc atcgatgcgg gcgtgcgtga cgtggcggac     360
ctgacggcga tgaagtttcc ggtgtggtcg aaggccattt ttgcgcaggg cacggtcaag     420
gaaacgctgg gctcggtcaa tgtgccggtg gtctgcgcgg agcgctggt  caacccgggc     480 gacgtgatcg tggccgatga cgacggcgtc tgcgtcgtgc gacgcgagga agcggccgcg     540
gtggccgaca aggccgaggc gcgcgtggct gcggaagagg acaagcgcag cgcctggcg      600 gccggggaac tgggcctcga catctacaag atgcgcgagc gcctggccga aagggcctc     660 aggtatgtct ga                                                        672

<210> SEQ ID NO 176
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 176

Met Gly Val Val Val Gln Asn Ile Glu Arg Ala Asp Pro Ser Val Ile
1               5                   10                  15

Glu Arg Leu Ala Ala Cys Gly Val Ala Thr Val His Glu Ala Gln Gly
            20                  25                  30

Arg Lys Gly Leu Leu Ala Ser His Met Arg Pro Ile Tyr Ala Gly Ala
        35                  40                  45

Arg Leu Ala Ala Ser Ala Val Thr Ile Ser Ala Pro Pro Gly Asp Asn
    50                  55                  60

Trp Met Ile His Val Ala Ile Glu Gln Leu Arg Ala Gly Asp Ile Met
65                  70                  75                  80

Val Leu Ala Pro Thr Ser Pro Cys Glu Asp Gly Tyr Phe Gly Asp Leu
                85                  90                  95

Leu Ala Thr Ser Ala Ala Ala Arg Gly Cys Arg Gly Leu Ile Ile Asp
            100                 105                 110

Ala Gly Val Arg Asp Val Ala Asp Leu Thr Ala Met Lys Phe Pro Val
        115                 120                 125

Trp Ser Lys Ala Ile Phe Ala Gln Gly Thr Val Lys Glu Thr Leu Gly
    130                 135                 140

Ser Val Asn Val Pro Val Val Cys Ala Gly Ala Leu Val Asn Pro Gly
145                 150                 155                 160

Asp Val Ile Val Ala Asp Asp Asp Gly Val Cys Val Val Arg Arg Glu
                165                 170                 175
```

```
Glu Ala Ala Ala Val Ala Asp Lys Ala Glu Arg Val Ala Ala Glu
            180                 185                 190

Glu Asp Lys Arg Arg Leu Ala Ala Gly Glu Leu Gly Leu Asp Ile
        195                 200                 205

Tyr Lys Met Arg Glu Arg Leu Ala Glu Lys Gly Leu Arg Tyr Val
    210                 215                 220

<210> SEQ ID NO 177
<211> LENGTH: 675
<212> TYPE: DNA
<213> ORGANISM: Unknown
<220> FEATURE:
<223> OTHER INFORMATION: DNA obtained from environmental sample

<400> SEQUENCE: 177 atgggggcg tagtcgtgca gaacatcgag cgggccgacg cggaaaccat ccgccggctc      60
ggcgaatgcg gtgtggcgac ggtgcacgag gcgcaggggc gcagcgggct gatggcgccc    120
catatgacgc cggtctggcg cggcgcatcg gttgccggtt cggcggtgac gatctccgcc    180
ccgcccggcg acaactggat gctgcacgtg gcgatcgagc aggtgcatga gggcgatatc    240
ctcgtgctgg cgccgaccag tccttccacg gacggctatt tcggcgattt gcttgccacc    300
tcggcgatgg cgcggggtg tcgcgggctg gtcatcgaag caggcgtgcg cgacgtggcc    360
gacctgacga agatgcggtt ccccgtctgg tcgaaggcgg tccacgcgca gggtacggtc    420
aaagagacgc cgggctcagt caacgtgccg gtcgtctgcg ccggtgccca tgtgcggccg    480
ggcgacgtca tcgtggccga cgatgacggc gtgtgcgtgg tcaggcgcga ggaggcggcg    540
gaaatattga ggaaggccga ggcccgcatc gccaacgaag ccgacaagcg cgagcgtttc    600
gccgccggcg aactcggcct cgacatctac ggcatgcgcg agaagctggc cgccaaggga    660
ttgaaatata tctga                                                    675

<210> SEQ ID NO 178
<211> LENGTH: 224
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (21)...(173)
<223> OTHER INFORMATION: Demethylmenaquinone methyltransferase

<400> SEQUENCE: 178

Met Gly Gly Val Val Gln Asn Ile Glu Arg Ala Asp Ala Glu Thr
1               5                   10                  15

Ile Arg Arg Leu Gly Glu Cys Gly Val Ala Thr Val His Glu Ala Gln
            20                  25                  30

Gly Arg Ser Gly Leu Met Ala Pro His Met Thr Pro Val Trp Arg Gly
        35                  40                  45

Ala Ser Val Ala Gly Ser Ala Val Thr Ile Ser Ala Pro Pro Gly Asp
    50                  55                  60

Asn Trp Met Leu His Val Ala Ile Glu Gln Val His Glu Gly Asp Ile
65                  70                  75                  80

Leu Val Leu Ala Pro Thr Ser Pro Ser Thr Asp Gly Tyr Phe Gly Asp
                85                  90                  95

Leu Leu Ala Thr Ser Ala Met Ala Arg Gly Cys Arg Gly Leu Val Ile
            100                 105                 110

Glu Ala Gly Val Arg Asp Val Ala Asp Leu Thr Lys Met Arg Phe Pro
        115                 120                 125
```

```
Val Trp Ser Lys Ala Val His Ala Gln Gly Thr Val Lys Glu Thr Pro
    130                 135                 140

Gly Ser Val Asn Val Pro Val Cys Ala Gly Ala His Val Arg Pro
145                 150                 155                 160

Gly Asp Val Ile Val Ala Asp Asp Gly Val Cys Val Val Arg Arg
                165                 170                 175

Glu Glu Ala Ala Glu Ile Leu Arg Lys Ala Glu Ala Arg Ile Ala Asn
            180                 185                 190

Glu Ala Asp Lys Arg Glu Arg Phe Ala Ala Gly Glu Leu Gly Leu Asp
        195                 200                 205

Ile Tyr Gly Met Arg Glu Lys Leu Ala Ala Lys Gly Leu Lys Tyr Ile
    210                 215                 220

<210> SEQ ID NO 179
<211> LENGTH: 672
<212> TYPE: DNA
<213> ORGANISM: Unknown
<220> FEATURE:
<223> OTHER INFORMATION: DNA obtained from environmental sample

<400> SEQUENCE: 179
atgggggtcg tggtccagaa catcgaacgc gccgatcagg ccgtcatcaa ccgccttgcc     60
gcctgcggcg tggccaccgt gcacgaggcg cagggccgca agggcctgct cgccgccaat    120
atgcgtccga tctacagcgg agaacgtctg gcggcctcgg ccgtgacgat tccgcgcccc    180
cccggtgaca actggatggt ccatgtcgcg atcgagcaat tgcaggccgg tgacatcatg    240
gttttggccc ccacctcgcc ctgcgaggac ggctatttcg gtgatcttct ggccacgtcg    300
gctatcgcac gtggctgcaa gggcctgatc atcgatgcgg cgtgcgcga tgtgtcggat    360 ctgacggcga tgaaattccc cgtctggtcc aaggcgatct tcgcccaagg cacggtcaag    420
gaaacccttg gtcggtgaa tattcccgtg gtctgcgccg gcgcgctgat caatcccggt    480
gatgtaattg tggccgatga cgacggcgtt tgcgtggtcc gccgcgagga agccgaagcc    540
gttgcagcca agccgaagc ccgtgtcgca gccgaagaag gcaagcgcgt gcgtctggcc    600
gcgggtgaac tgggccttga tatctataac atgcgcgaac gtctggccga agggcctg     660 aaatatgtct ga                                                       672

<210> SEQ ID NO 180
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 180

Met Gly Val Val Val Gln Asn Ile Glu Arg Ala Asp Gln Ala Val Ile
1               5                   10                  15

Asn Arg Leu Ala Ala Cys Gly Val Ala Thr Val His Glu Ala Gln Gly
            20                  25                  30

Arg Lys Gly Leu Leu Ala Ala Asn Met Arg Pro Ile Tyr Ser Gly Glu
        35                  40                  45

Arg Leu Ala Ala Ser Ala Val Thr Ile Ser Ala Pro Pro Gly Asp Asn
    50                  55                  60

Trp Met Val His Val Ala Ile Glu Gln Leu Gln Ala Gly Asp Ile Met
```

```
                65                  70                  75                  80
Val Leu Ala Pro Thr Ser Pro Cys Glu Asp Gly Tyr Phe Gly Asp Leu
                    85                  90                  95

Leu Ala Thr Ser Ala Ile Ala Arg Gly Cys Lys Gly Leu Ile Ile Asp
                100                 105                 110

Ala Gly Val Arg Asp Val Ser Asp Leu Thr Ala Met Lys Phe Pro Val
                115                 120                 125

Trp Ser Lys Ala Ile Phe Ala Gln Gly Thr Val Lys Glu Thr Leu Gly
            130                 135                 140

Ser Val Asn Ile Pro Val Val Cys Ala Gly Ala Leu Ile Asn Pro Gly
145                 150                 155                 160

Asp Val Ile Val Ala Asp Asp Gly Val Cys Val Val Arg Arg Glu
                165                 170                 175

Glu Ala Glu Ala Val Ala Ala Lys Ala Glu Ala Arg Val Ala Ala Glu
                180                 185                 190

Glu Gly Lys Arg Val Arg Leu Ala Ala Gly Leu Gly Leu Asp Ile
            195                 200                 205

Tyr Asn Met Arg Glu Arg Leu Ala Glu Lys Gly Leu Lys Tyr Val
        210                 215                 220

<210> SEQ ID NO 181
<211> LENGTH: 687
<212> TYPE: DNA
<213> ORGANISM: Unknown
<220> FEATURE:
<223> OTHER INFORMATION: DNA obtained from environmental sample

<400> SEQUENCE: 181
atgagcggtc atcgcatcgt ccgcaactat ccaaaagcag actcgggcgt cgcctccgct       60
ctgggcgctc tgggcagcgc gaccgtgcac gaggccatgg gccgcgtggg atacgccggc      120
caccgtatcc ggccgatcca gcagggcgtg tcgatcggcg gcaccgccgt aaccgtctcg      180
gtcgcaccgg gtgacaacct gatggttcac gccgcgattg ccgaggccaa cgaaggcgac      240
gtgctggtcg tcgttcccgt gagcgacagc gcgttcggct ttatcggcga cctgatggcg      300
actcagatgc gctctcgccg gctgcgcggt tacgtgacct ccggcggcgt gcgtgatacc      360
gccgagttgg cccgcttggg tttccggta tggacgaaat acgtctcgtc gcaagggacg       420
gtgaaagata ccccggctc ggtcaatgtg cccgtcgtgc tcgaaggcgt cgtggtccat       480
cctggagacg tcgtggtagc ggacgacgac ggcgtcacca tcgtgccgcg cgagatcgcc      540
gccgacacgc tccaggccgc tcgggcccgc gtggagaagg aagccgcgac ccgatcgcgg      600
tatgcggcgg cgagcttttc actcgacgtc aacaacctgc gcccgaccct cgcagcgctg      660
ggagtggagt atgtcgattt cgggtga                                         687

<210> SEQ ID NO 182
<211> LENGTH: 228
<212> TYPE: PRT
<213> ORGANISM: Unknown
<220> FEATURE:
<223> OTHER INFORMATION: Protein obtained from environmental sample
<220> FEATURE:
<221> NAME/KEY: SIGNAL
<222> LOCATION: (1)...(31)
<220> FEATURE:
<221> NAME/KEY: DOMAIN
<222> LOCATION: (22)...(174)
<223> OTHER INFORMATION: Demethylmenaquinone methyltransferase

<400> SEQUENCE: 182
```

```
Met Ser Gly His Arg Ile Val Arg Asn Tyr Pro Lys Ala Asp Ser Gly
1               5                   10                  15

Val Ala Ser Ala Leu Gly Ala Leu Gly Ser Ala Thr Val His Glu Ala
            20                  25                  30

Met Gly Arg Val Gly Tyr Ala Gly His Arg Ile Arg Pro Ile Gln Gln
                35                  40                  45

Gly Val Ser Ile Gly Gly Thr Ala Val Thr Val Ser Val Ala Pro Gly
    50                  55                  60

Asp Asn Leu Met Val His Ala Ala Ile Ala Glu Ala Asn Glu Gly Asp
65                  70                  75                  80

Val Leu Val Val Val Pro Val Ser Asp Ser Ala Phe Gly Phe Ile Gly
                85                  90                  95

Asp Leu Met Ala Thr Gln Met Arg Ser Arg Arg Leu Arg Gly Tyr Val
            100                 105                 110

Thr Ser Gly Gly Val Arg Asp Thr Ala Glu Leu Ala Arg Leu Gly Phe
                115                 120                 125

Pro Val Trp Thr Lys Tyr Val Ser Ser Gln Gly Thr Val Lys Asp Thr
    130                 135                 140

Pro Gly Ser Val Asn Val Pro Val Val Leu Glu Gly Val Val His
145                 150                 155                 160

Pro Gly Asp Val Val Ala Asp Asp Gly Val Thr Ile Val Pro
                165                 170                 175

Arg Glu Ile Ala Ala Asp Thr Leu Gln Ala Ala Arg Ala Arg Val Glu
            180                 185                 190

Lys Glu Ala Ala Thr Arg Ser Arg Tyr Ala Ala Gly Glu Leu Ser Leu
                195                 200                 205

Asp Val Asn Asn Leu Arg Pro Thr Leu Ala Ala Leu Gly Val Glu Tyr
210                 215                 220

Val Asp Phe Gly
225
```

<210> SEQ ID NO 183
<211> LENGTH: 693
<212> TYPE: DNA
<213> ORGANISM: Unknown
<220> FEATURE:
<223> OTHER INFORMATION: DNA obtained from environmental sample

<400> SEQUENCE: 183

```
atgcgcggcg tcgtggtccg gaacattcca cgcgccgacg cgcgcgagat cgcggttctg      60
catgaagcgg gcgtcgccac cgtgcacgag gcgcagagcc gcctcggtct gctcgcttcg     120
tacatgcggc ccatttacga gggcgcatcg attgccggtc cggccgtgac cgtgctcgtg     180
ccgccatcgg acaactggat gctgcacgtc gccgctgaac agtgccagcc cggcgatgtc     240
ctcgtggtcg cgccgacgtc gccgtgcgaa gacggctact cggcgaact gttggcgacg      300
tcgctggcac agctcggcgt gcgcggactg atcatcgatg cgggctgccg cgacatccgt     360
gcgctcaagg cgatgaattt ccccgtgtgg tcgaaaggga tctcggcgca agggaccgtc     420
aaggaaacgc tcgggtcggt gaacatcccc gtggtgtgcg cgcagcaact ggtgcgaccg     480
ggcgacgtga tcgtggccga tgacgatggc gtcgtggtcg tcgcgttcga cggtggcg       540
gccgtggcga gcgccgcacg cgcgcgcctc gagaaggaag agaagacgcg cagcgtgctt     600
gcgacaggcc agctcggtct cgactactac gcgatgcgcg agaagcttgc ggcaaagggt     660
ttgcgttacg tcgattccgc tgcgggtctt tga                                  693
```

```
<210> SEQ ID NO 184
<211> LENGTH: 230
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (21)...(173)
<223> OTHER INFORMATION: Demethylmenaquinone methyltransferase

<400> SEQUENCE: 184

Met Arg Gly Val Val Arg Asn Ile Pro Arg Ala Asp Ala Arg Glu
1               5                   10                  15

Ile Ala Val Leu His Glu Ala Gly Val Ala Thr Val His Glu Ala Gln
                20                  25                  30

Ser Arg Leu Gly Leu Leu Ala Ser Tyr Met Arg Pro Ile Tyr Glu Gly
            35                  40                  45

Ala Ser Ile Ala Gly Pro Ala Val Thr Val Leu Val Pro Pro Ser Asp
        50                  55                  60

Asn Trp Met Leu His Val Ala Ala Glu Gln Cys Gln Pro Gly Asp Val
65                  70                  75                  80

Leu Val Val Ala Pro Thr Ser Pro Cys Glu Asp Gly Tyr Phe Gly Glu
                85                  90                  95

Leu Leu Ala Thr Ser Leu Ala Gln Leu Gly Val Arg Gly Leu Ile Ile
            100                 105                 110

Asp Ala Gly Cys Arg Asp Ile Arg Ala Leu Lys Ala Met Asn Phe Pro
        115                 120                 125

Val Trp Ser Lys Gly Ile Ser Ala Gln Gly Thr Val Lys Glu Thr Leu
130                 135                 140

Gly Ser Val Asn Ile Pro Val Val Cys Ala Gln Gln Leu Val Arg Pro
145                 150                 155                 160

Gly Asp Val Ile Val Ala Asp Asp Gly Val Val Val Ala Phe
                165                 170                 175

Glu Thr Val Ala Ala Val Ala Ser Ala Ala Arg Ala Arg Leu Glu Lys
                180                 185                 190

Glu Glu Lys Thr Arg Ser Val Leu Ala Thr Gly Gln Leu Gly Leu Asp
            195                 200                 205

Tyr Tyr Ala Met Arg Glu Lys Leu Ala Ala Lys Gly Leu Arg Tyr Val
        210                 215                 220

Asp Ser Ala Ala Gly Leu
225                 230

<210> SEQ ID NO 185
<211> LENGTH: 678
<212> TYPE: DNA
<213> ORGANISM: Unknown
<220> FEATURE:
<223> OTHER INFORMATION: DNA obtained from environmental sample

<400> SEQUENCE: 185
atgaatcgac cggtggtagt ccggcaagtt gaacagccac cagcggatgc ggttgccgca      60
ctggagaggt atggcgtgac aaccgtccat gaggctcagg acccggtgg cctcctagcc     120 tcctacatgc gcccgattta cccgggagca gtcatcgccg gttccgcggt cactgtgtct     180
ttacctcctg gcgacaacct catgatccac gtggccgtgg aggtctgtgg tccgggaaac    240
attctggttg ttgcaccgat ctcgccgtgt acgatggct acttcggaga gctgttggca     300
acctctctcc gcgcccacgg tgtgcgaggg cttgtgatcg atgccggatg ccgggacgtg    360
```

-continued

```
cgctctctca cagaaatgaa atttccggcc tggagccgcg ccgtcagttc acaggggaca      420
gtcaaggcca ccctgggatc ggtgaatgtg ccgattgtgt gcgcgggcgc gcgggtcgag      480
gctggggatg tcatcgtcgc cgatgacgat ggagttgtgg tggtgaagcg cgcgctggcc      540
gaagaggtcg ccgccgcggc ggaacaaagg gttcgcaaag agaatgtgac ccgggaacga      600
cttgcgcgtg gagagctggg actcgatatt tacgacatgc gccaaaagat cgcacaactg      660
ggccttaaat atctctga                                                   678
```

<210> SEQ ID NO 186
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 186

Met Asn Arg Pro Val Val Arg Gln Val Glu Gln Pro Ala Asp
1               5                   10                  15

Ala Val Ala Ala Leu Glu Arg Tyr Gly Val Thr Thr Val His Glu Ala
            20                  25                  30

Gln Gly Pro Gly Gly Leu Leu Ala Ser Tyr Met Arg Pro Ile Tyr Pro
        35                  40                  45

Gly Ala Val Ile Ala Gly Ser Ala Val Thr Val Ser Leu Pro Pro Gly
    50                  55                  60

Asp Asn Leu Met Ile His Val Ala Val Glu Val Cys Gly Pro Gly Asn
65                  70                  75                  80

Ile Leu Val Val Ala Pro Ile Ser Pro Cys Thr Asp Gly Tyr Phe Gly
                85                  90                  95

Glu Leu Leu Ala Thr Ser Leu Arg Ala His Gly Val Arg Gly Leu Val
            100                 105                 110

Ile Asp Ala Gly Cys Arg Asp Val Arg Ser Leu Thr Glu Met Lys Phe
        115                 120                 125

Pro Ala Trp Ser Arg Ala Val Ser Ser Gln Gly Thr Val Lys Ala Thr
    130                 135                 140

Leu Gly Ser Val Asn Val Pro Ile Val Cys Ala Gly Ala Arg Val Glu
145                 150                 155                 160

Ala Gly Asp Val Ile Val Ala Asp Asp Gly Val Val Val Val Lys
                165                 170                 175

Arg Ala Leu Ala Glu Glu Val Ala Ala Ala Glu Gln Arg Val Arg
            180                 185                 190

Lys Glu Asn Val Thr Arg Glu Arg Leu Ala Arg Gly Glu Leu Gly Leu
        195                 200                 205

Asp Ile Tyr Asp Met Arg Gln Lys Ile Ala Gln Leu Gly Leu Lys Tyr
    210                 215                 220

Leu
225

<210> SEQ ID NO 187
<211> LENGTH: 678
<212> TYPE: DNA
<213> ORGANISM: Unknown
<220> FEATURE:
<223> OTHER INFORMATION: DNA obtained from environmental sample

<400> SEQUENCE: 187

-continued

```
atgaatcgac cggtggtagt ccggcaagtt gaacagccac cagcggatgc ggttgccgca    60
ctggagaagt atggcgtgac aaccgtccat gaggctcagg acccggtgg cctcctagcc    120 tcctacatgc gcccgattta cccgggagca gtcatcgccg gttccgcggt cactgtgtct    180
ttacctcctg gcgacaacct catgatccac gtggccgtgg aggtctgtgg tccgggaaac    240
attctggttg ttgcaccgat ctcgccgtgt acggatggct acttcggaga gctgttggca    300
acctctctcc gcgcccacgg tgtgcagggg cttgtgatcg atgccggatg ccgggacgtg    360
cgctctctca cagaaatgaa atttccggtc tggagccgcg ccgtcagtcc acagggaca    420 gtcaaggcca ccctgggatc ggtgaatgtg ccgattgtgt gcgcgggcgc gcgggtcgag    480
gctggggatg tcatcgtcgc cgatgacgat ggagttgtgg tggtgaagcg cgcgctggcc    540
gaagaggtcg ccgccgcggc ggaacaaagg gttcgcaaag agaatgtgac ccgggaacga    600
cttgcgcgtg gagagctggg actcgatatt tacgacatgc gccaaagat cgcacaactg    660 ggccttaaat atctctga                                                 678
```

<210> SEQ ID NO 188
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 188

```
Met Asn Arg Pro Val Val Arg Gln Val Glu Gln Pro Pro Ala Asp
1               5                   10                  15

Ala Val Ala Ala Leu Glu Lys Tyr Gly Val Thr Thr Val His Glu Ala
            20                  25                  30

Gln Gly Pro Gly Gly Leu Leu Ala Ser Tyr Met Arg Pro Ile Tyr Pro
        35                  40                  45

Gly Ala Val Ile Ala Gly Ser Ala Val Thr Val Ser Leu Pro Pro Gly
    50                  55                  60

Asp Asn Leu Met Ile His Val Ala Val Glu Val Cys Gly Pro Gly Asn
65                  70                  75                  80

Ile Leu Val Val Ala Pro Ile Ser Pro Cys Thr Asp Gly Tyr Phe Gly
                85                  90                  95

Glu Leu Leu Ala Thr Ser Leu Arg Ala His Gly Val Arg Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Val Ser Pro Gln Gly Thr Val Lys Ala Thr
    130                 135                 140

Leu Gly Ser Val Asn Val Pro Ile Val Cys Ala Gly Ala Arg Val Glu
145                 150                 155                 160

Ala Gly Asp Val Ile Val Ala Asp Asp Gly Val Val Val Lys
                165                 170                 175

Arg Ala Leu Ala Glu Glu Val Ala Ala Ala Glu Gln Arg Val Arg
            180                 185                 190

Lys Glu Asn Val Thr Arg Glu Arg Leu Ala Arg Gly Glu Leu Gly Leu
        195                 200                 205

Asp Ile Tyr Asp Met Arg Gln Lys Ile Ala Gln Leu Gly Leu Lys Tyr
    210                 215                 220
```

```
<210> SEQ ID NO 189
<211> LENGTH: 678
<212> TYPE: DNA
<213> ORGANISM: Unknown
<220> FEATURE:
<223> OTHER INFORMATION: DNA obtained from environmental sample

<400> SEQUENCE: 189
atgaacaaac cggtggtgat ccggcaactg gagcgggcgc cggctgatgc ggtggcggcg      60
ctcgaaaaat atggtgtgtc caccgtgcat gaagctcagg gacgttgcgg actactcgct     120
tcctacatgc gaccgattta tccgggtgcc gctattgccg gtcggcggt cacggtgtca      180 cttccgcccg gcgataacct gatgattcac gttgccgtcg aggtttgcca gtccggcgac     240
atactcgtgg ttgcccccac ctcgcctttgc tcggacggat acttcgggga ttgttggca    300 acatctttgc gcgcccacgg cgtgaagggg cttgtcattg aggcaggatg ccgtgatgtt     360
cgctcgctca ccgaaatgaa gttcccggtc tggagccgcg ccgtcagttc gcaaggcacc     420
gtgaagtcta acctcggatc ggtgaatgtg gcatagtct gtgcgggtgc acacattgac      480
gctggcgatg tggtcgtggc agatgacgac ggtgtcgtgg cggtgaagcg cgcatccgcc     540
caagaagtag ttggggcgtg cgaacaacgg gttcgcaagg aagaggcagc ccgtgagcgg     600
ctggcgcggg gagagcttgg cctcgacatc tacggcttgc gcacacgaat cgcggaaatg     660
ggtctcaagt atcaatga                                                   678

<210> SEQ ID NO 190
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 190
```

Met Asn Lys Pro Val Val Ile Arg Gln Leu Glu Arg Ala Pro Ala Asp
1               5                   10                  15

Ala Val Ala Ala Leu Glu Lys Tyr Gly Val Ser Thr Val His Glu Ala
            20                  25                  30

Gln Gly Arg Cys Gly Leu Leu Ala Ser Tyr Met Arg Pro Ile Tyr Pro
        35                  40                  45

Gly Ala Ala Ile Ala Gly Ser Ala Val Thr Val Ser Leu Pro Pro Gly
    50                  55                  60

Asp Asn Leu Met Ile His Val Ala Val Glu Val Cys Gln Ser Gly Asp
65                  70                  75                  80

Ile Leu Val Val Ala Pro Thr Ser Pro Cys Ser Asp Gly Tyr Phe Gly
                85                  90                  95

Glu Leu Leu Ala Thr Ser Leu Arg Ala His Gly Val Lys Gly Leu Val
            100                 105                 110

Ile Glu Ala Gly Cys Arg Asp Val Arg Ser Leu Thr Glu Met Lys Phe
        115                 120                 125

Pro Val Trp Ser Arg Ala Val Ser Ser Gln Gly Thr Val Lys Ser Asn
    130                 135                 140

Leu Gly Ser Val Asn Val Gly Ile Val Cys Ala Gly Ala His Ile Asp

```
                145                 150                 155                 160
Ala Gly Asp Val Val Ala Asp Asp Gly Val Val Ala Val Lys
                    165                 170                 175

Arg Ala Ser Ala Gln Glu Val Val Gly Ala Cys Glu Gln Arg Val Arg
                180                 185                 190

Lys Glu Glu Ala Ala Arg Glu Arg Leu Ala Arg Gly Glu Leu Gly Leu
            195                 200                 205

Asp Ile Tyr Gly Leu Arg Thr Arg Ile Ala Glu Met Gly Leu Lys Tyr
        210                 215                 220

Gln
225

<210> SEQ ID NO 191
<211> LENGTH: 678
<212> TYPE: DNA
<213> ORGANISM: Unknown
<220> FEATURE:
<223> OTHER INFORMATION: DNA obtained from environmental sample

<400> SEQUENCE: 191
atgaacaaac cggtggtgat ccggcaactg gagcgggcgc cggctgatgc ggtggcggcg      60
ctcgaaaaat atggtgtgtc caccgtgcat gaagctcagg gacgttgcgg actactcgct     120
tcctacatgc gaccgattta tccgggtgcc gctattgccg gtcggcggt cacggtgtca     180 cttccgcccg gcgataacct gatgattcac gttgccgtcg aggtttgcca gtccggcgac     240
atactcgtgg ttgccccccac ctcgcctttgc tcggacggat acttcgggga gttgttggca     300
acatctttgc gcgcccacgg cgtgaagggg cttgtcattg aggcaggatg ccgtgatgtt     360
cgctcgctca ccgaaatgaa gttcccggtc tggagccgcg ccgtcagttc gcaaggcacc     420
gtgaagtcta acctcggatc ggtgaatgtg gcatagtctt gtgcgggtgc acacattgac     480
gctggcgatg tggtcgtggc agatgacgac ggtgtcgtgg cggtgaagcg cgcatccgcc     540
caagaagtag ttggggcgtg cgaacaacgg gttcgcaagg aagaggcaac ccgtgagcgg     600
ctggcgcggg gagagcttgg cctcgacatc tacggcttgc gcacacgaat cgcggaaatg     660
ggtctcaagt atcaatga                                                  678

<210> SEQ ID NO 192
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 192

Met Asn Lys Pro Val Val Ile Arg Gln Leu Glu Arg Ala Pro Ala Asp
1               5                   10                  15

Ala Val Ala Ala Leu Glu Lys Tyr Gly Val Ser Thr Val His Glu Ala
            20                  25                  30

Gln Gly Arg Cys Gly Leu Leu Ala Ser Tyr Met Arg Pro Ile Tyr Pro
        35                  40                  45

Gly Ala Ala Ile Ala Gly Ser Ala Val Thr Val Ser Leu Pro Pro Gly
    50                  55                  60

Asp Asn Leu Met Ile His Val Ala Val Glu Val Cys Gln Ser Gly Asp
65                  70                  75                  80
```

```
Ile Leu Val Val Ala Pro Thr Ser Pro Cys Ser Asp Gly Tyr Phe Gly
                85                  90                  95

Glu Leu Leu Ala Thr Ser Leu Arg Ala His Gly Val Lys Gly Leu Val
            100                 105                 110

Ile Glu Ala Gly Cys Arg Asp Val Arg Ser Leu Thr Glu Met Lys Phe
        115                 120                 125

Pro Val Trp Ser Arg Ala Val Ser Ser Gln Gly Thr Val Lys Ser Asn
    130                 135                 140

Leu Gly Ser Val Asn Val Gly Ile Val Cys Ala Gly Ala His Ile Asp
145                 150                 155                 160

Ala Gly Asp Val Val Ala Asp Asp Gly Val Val Ala Val Lys
                165                 170                 175

Arg Ala Ser Ala Gln Glu Val Val Gly Ala Cys Glu Gln Arg Val Arg
            180                 185                 190

Lys Glu Glu Ala Thr Arg Glu Arg Leu Ala Arg Gly Glu Leu Gly Leu
        195                 200                 205

Asp Ile Tyr Gly Leu Arg Thr Arg Ile Ala Glu Met Gly Leu Lys Tyr
    210                 215                 220

Gln
225
```

<210> SEQ ID NO 193
<211> LENGTH: 678
<212> TYPE: DNA
<213> ORGANISM: Unknown
<220> FEATURE:
<223> OTHER INFORMATION: DNA obtained from environmental sample

<400> SEQUENCE: 193

```
atgaatacac cggtggtagt ccggcaggtg gagcagccgc cagcaggtgc ggttgccaca      60
ctggagaagt gtggggtgac aaccgtgcat gaggctcaag gacgttgtgg cctgcttgcg     120
ccctacctgc gcccgattta cccgggagca gccatcgccg gttccgcgat caccgtgact     180
ttgcctccgg gcgacaacct catgatccac gttgcggtgg aggtctgcgg tccgggaaac     240
attctcgtag tttcaccgac ctcggcttgc accgatggct acttcggtga gctgttggcc     300
acatctctcc gtgcccacgg tgtgagaggg ctggtgatcg atgccggatg ccgtgatgtg     360
cgctctctaa cagaaatgaa attcccggtc tggagccgcg ccgtcagtcc gcagggcacc     420
gtcaaggcca cgctgggatc ggtgaatgtg cccatcgtgt gcgcgggcgc actggtcgaa     480
gctggtgatg ttatcgtcgc cgatgacgat ggcgtggtgg tggtgaggcg cgcgctggcc     540
gaagaggtcg ccgcggcggc ggaacaaagg gttcagaaag agaatgtgac ccgcgagcgg     600
cttgcacgcg gagagctcgg cctcgatatt tacgacattc gccaacggat cgcgcaactg     660
ggccttaaat atctgtaa                                                    678
```

<210> SEQ ID NO 194
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 194

```
Met Asn Thr Pro Val Val Arg Gln Val Glu Gln Pro Pro Ala Gly
1               5                  10                  15
```

Ala Val Ala Thr Leu Glu Lys Cys Gly Val Thr Thr Val His Glu Ala
            20                  25                  30

Gln Gly Arg Cys Gly Leu Leu Ala Pro Tyr Leu Arg Pro Ile Tyr Pro
        35                  40                  45

Gly Ala Ala Ile Ala Gly Ser Ala Ile Thr Val Thr Leu Pro Pro Gly
    50                  55                  60

Asp Asn Leu Met Ile His Val Ala Val Glu Val Cys Gly Pro Gly Asn
65                  70                  75                  80

Ile Leu Val Val Ser Pro Thr Ser Ala Cys Thr Asp Gly Tyr Phe Gly
                85                  90                  95

Glu Leu Leu Ala Thr Ser Leu Arg Ala His Gly Val Arg Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Val Ser Pro Gln Gly Thr Val Lys Ala Thr
    130                 135                 140

Leu Gly Ser Val Asn Val Pro Ile Val Cys Ala Gly Ala Leu Val Glu
145                 150                 155                 160

Ala Gly Asp Val Ile Val Ala Asp Asp Gly Val Val Val Val Val Arg
                165                 170                 175

Arg Ala Leu Ala Glu Glu Val Ala Ala Ala Glu Gln Arg Val Gln
            180                 185                 190

Lys Glu Asn Val Thr Arg Glu Arg Leu Ala Arg Gly Glu Leu Gly Leu
        195                 200                 205

Asp Ile Tyr Asp Ile Arg Gln Arg Ile Ala Gln Leu Gly Leu Lys Tyr
    210                 215                 220

Leu
225

<210> SEQ ID NO 195
<211> LENGTH: 678
<212> TYPE: DNA
<213> ORGANISM: Unknown
<220> FEATURE:
<223> OTHER INFORMATION: DNA obtained from environmental sample

<400> SEQUENCE: 195
atgaatacac cggtggtagt ccggcaggtg gagcagccgc cagcaggtgc ggttgccaca      60
ctggagaagt gtggggtgac aaccgtgcat gaggctcaag acgttgtgg cctgcttgcg     120 ccctacatgc gcccgattta cccgggagca gccatcgccg gttccgcgat caccgtgact     180
ttgcctccgg cgacaacct catgatccac gttgcggtgg aggtctgcgg tccgggaaac     240
attttggtgg tttcaccgac ctcggcttgc accgatggct acttcggtga gctgttggcc     300
acctctctcc gtgctcacgg tgtgagaggg ctggtgatcg atgccggatg ccgtgatgtg     360
cgctctctaa cagaaatgaa attcccggtc tggagccgcg ccgtcagttc gcagggcacc     420
gtcaaggcca cactgggatc ggtgaatgtg cccatcgtgt gcgcgggcgc actggtcgaa     480
gctggtgatg tcatcgtcgc cgatgacgat ggagtggtgg tggtgaggcg cgcgctggcc     540
gaagaggtcg ccgccgcggc ggaacaaagg gctcagaaag agaatgtgac ccgcgagcga     600
ctggcgcgcg gagagctcgg cctcgatatt tacgacatgc gccaaaagat cgcgcaactg     660
ggccttaaat atccgtaa                                                   678

<210> SEQ ID NO 196
<211> LENGTH: 225

```
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 196

Met Asn Thr Pro Val Val Arg Gln Val Glu Gln Pro Pro Ala Gly
1               5                   10                  15

Ala Val Ala Thr Leu Glu Lys Cys Gly Val Thr Thr Val His Glu Ala
                20                  25                  30

Gln Gly Arg Cys Gly Leu Leu Ala Pro Tyr Met Arg Pro Ile Tyr Pro
            35                  40                  45

Gly Ala Ala Ile Ala Gly Ser Ala Ile Thr Val Thr Leu Pro Pro Gly
        50                  55                  60

Asp Asn Leu Met Ile His Val Ala Val Glu Val Cys Gly Pro Gly Asn
65                  70                  75                  80

Ile Leu Val Val Ser Pro Thr Ser Ala Cys Thr Asp Gly Tyr Phe Gly
                85                  90                  95

Glu Leu Leu Ala Thr Ser Leu Arg Ala His Gly Val Arg Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Val Ser Ser Gln Gly Thr Val Lys Ala Thr
130                 135                 140

Leu Gly Ser Val Asn Val Pro Ile Val Cys Ala Gly Ala Leu Val Glu
145                 150                 155                 160

Ala Gly Asp Val Ile Val Ala Asp Asp Gly Val Val Val Arg
                165                 170                 175

Arg Ala Leu Ala Glu Glu Val Ala Ala Ala Glu Arg Ala Gln
            180                 185                 190

Lys Glu Asn Val Thr Arg Glu Arg Leu Ala Arg Gly Glu Leu Gly Leu
                195                 200                 205

Asp Ile Tyr Asp Met Arg Gln Lys Ile Ala Gln Leu Gly Leu Lys Tyr
        210                 215                 220

Pro
225

<210> SEQ ID NO 197
<211> LENGTH: 678
<212> TYPE: DNA
<213> ORGANISM: Unknown
<220> FEATURE:
<223> OTHER INFORMATION: DNA obtained from environmental sample

<400> SEQUENCE: 197
atgaataaac cggtggtaat ccggcaagtg gagcagccac cagcggacgc cgttgcagca        60
ttggagaagt atgcgtcac aaccgtgcat gaggtgcagg acgctgtgg cctcctcgcg        120 cactacgtgc gtccgattta cgcaggagct gcaatcgcag gttccgctgt tactgtgtcg        180
ttgcctcccg gcgacaacct catgattcat gttgctgtcg aggtctgcgg tcctggaaat        240
attctggttg tttcacccac ctcccctgt acagacggct atttcggtga actgttggca        300
acgtctttgc gcgctcacgg agtgaagggg cttgtgatcg atgccggatg ccgcgacgtt        360
cgctcactga cggagatgaa attcccggtg tggagccggg ccatctgctc acaggggaca        420
```

```
gtcaaggcta cactcggatc ggtcaatgtg cccatcatgt gcgcgggcgc actcgtcgaa    480
gccggcgacg tcatcgtggc cgacgatgat ggagtggtgg ttgtgaagcg agcgatggcg    540
attgacgtcg ccgcggccgc cgagcaaagg gttcacaaag agaatacgac ccgcgaacgg    600
cttgcacgtg gagagcttgg gctcgatatt tacgagatgc gtcagaaaat cgtacaactg    660
ggccttaagt attcctga                                                  678
```

```
<210> SEQ ID NO 198
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase
<220> FEATURE:
<221> NAME/KEY: SITE
<222> LOCATION: (197)...(200)
<223> OTHER INFORMATION: N-glycosylation site. Prosite id = PS00001

<400> SEQUENCE: 198
```

Met Asn Lys Pro Val Val Ile Arg Gln Val Glu Gln Pro Ala Asp
1               5                   10                  15

Ala Val Ala Ala Leu Glu Lys Tyr Gly Val Thr Thr Val His Glu Val
            20                  25                  30

Gln Gly Arg Cys Gly Leu Leu Ala His Tyr Val Arg Pro Ile Tyr Ala
        35                  40                  45

Gly Ala Ala Ile Ala Gly Ser Ala Val Thr Val Ser Leu Pro Pro Gly
    50                  55                  60

Asp Asn Leu Met Ile His Val Ala Val Glu Val Cys Gly Pro Gly Asn
65                  70                  75                  80

Ile Leu Val Val Ser Pro Thr Ser Pro Cys Thr Asp Gly Tyr Phe Gly
                85                  90                  95

Glu Leu Leu Ala Thr Ser Leu Arg Ala His Gly Val Lys Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Ile Cys Ser Gln Gly Thr Val Lys Ala Thr
    130                 135                 140

Leu Gly Ser Val Asn Val Pro Ile Met Cys Ala Gly Ala Leu Val Glu
145                 150                 155                 160

Ala Gly Asp Val Ile Val Ala Asp Asp Gly Val Val Val Lys
                165                 170                 175

Arg Ala Met Ala Ile Asp Val Ala Ala Ala Glu Gln Arg Val His
            180                 185                 190

Lys Glu Asn Thr Thr Arg Glu Arg Leu Ala Arg Gly Glu Leu Gly Leu
        195                 200                 205

Asp Ile Tyr Glu Met Arg Gln Lys Ile Val Gln Leu Gly Leu Lys Tyr
    210                 215                 220

Ser
225

```
<210> SEQ ID NO 199
<211> LENGTH: 678
<212> TYPE: DNA
<213> ORGANISM: Unknown
<220> FEATURE:
<223> OTHER INFORMATION: DNA obtained from environmental sample
```

<400> SEQUENCE: 199

```
atgaacaagc ccgtggtggt gcgggacatc gagcggccgc cggcggatgc catcgcggcg        60
ctcgaacggt acggtgtgtc cacggtgcac gaggcgcagg gccgttgcgg gctgctggcc       120
ccttacatgc gtccgatcta tgcgggcgca gcgatcgctg gtcccgccgt acagtttca        180
cttccgccgg agacaacct gatgatccac gtcgccgtcg aagtgtgccg tcccggagac        240
atcctggttg tcacgccgac ctcgccgtgc accgacggct attttggaga gttgctcgcg       300
acttcgctgg ctgcgcacgg ggtgaaagga ctggtcattg atgcgggatg ccgcgatgtt       360
cgagcgttga ccgagatgaa atttcccgtc tggagccgcg ccgtgagttc gcagggaacg       420
gtgaaggcta cacttgggtc ggtgaatgtg acgattgcat gcgcggggc tacggttgag        480
cccggtgacg taatcgtagc ggacgatgat ggcgtcgttg tggtgaaacg ggctgaggcg       540
caagacgttg tcgccgcatc tgagcagaga gtgcgaaagg aagagggaac ccgtaaacgg       600
ctcgcgcagg gcgaactcgg cttggatatt tacggcttgc gcgcgaagat cgcggacctc       660
ggcctcaagt acttgtag                                                    678
```

<210> SEQ ID NO 200
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase
<220> FEATURE:
<221> NAME/KEY: SITE
<222> LOCATION: (151)...(154)
<223> OTHER INFORMATION: N-glycosylation site. Prosite id = PS00001

<400> SEQUENCE: 200

```
Met Asn Lys Pro Val Val Val Arg Asp Ile Glu Arg Pro Pro Ala Asp
1               5                  10                  15

Ala Ile Ala Ala Leu Glu Arg Tyr Gly Val Ser Thr Val His Glu Ala
            20                  25                  30

Gln Gly Arg Cys Gly Leu Leu Ala Pro Tyr Met Arg Pro Ile Tyr Ala
        35                  40                  45

Gly Ala Ala Ile Ala Gly Pro Ala Val Thr Val Ser Leu Pro Pro Gly
    50                  55                  60

Asp Asn Leu Met Ile His Val Ala Val Glu Val Cys Arg Pro Gly Asp
65                  70                  75                  80

Ile Leu Val Val Thr Pro Thr Ser Pro Cys Thr Asp Gly Tyr Phe Gly
                85                  90                  95

Glu Leu Leu Ala Thr Ser Leu Ala Ala His Gly Val Lys Gly Leu Val
            100                 105                 110

Ile Asp Ala Gly Cys Arg Asp Val Arg Ala Leu Thr Glu Met Lys Phe
        115                 120                 125

Pro Val Trp Ser Arg Ala Val Ser Ser Gln Gly Thr Val Lys Ala Thr
    130                 135                 140

Leu Gly Ser Val Asn Val Thr Ile Ala Cys Ala Gly Ala Thr Val Glu
145                 150                 155                 160

Pro Gly Asp Val Ile Val Ala Asp Asp Gly Val Val Val Lys
                165                 170                 175

Arg Ala Glu Ala Gln Asp Val Val Ala Ser Glu Gln Arg Val Arg
            180                 185                 190
```

```
Lys Glu Glu Gly Thr Arg Lys Arg Leu Ala Gln Gly Glu Leu Gly Leu
            195                 200                 205

Asp Ile Tyr Gly Leu Arg Ala Lys Ile Ala Asp Leu Gly Leu Lys Tyr
    210                 215                 220

Leu
225

<210> SEQ ID NO 201
<211> LENGTH: 633
<212> TYPE: DNA
<213> ORGANISM: Unknown
<220> FEATURE:
<223> OTHER INFORMATION: DNA obtained from environmental sample

<400> SEQUENCE: 201
atgagcaacg atttgcggcg cttcggcgtc tcgacgctgc acgaggcgca aggacggcgc        60
gggttgctcg cgtcatacat gcggccgatc tatccgggcg cgctggtcgc cggtccggcg       120
gtaaccgtcc tcgtgccgcc aggcgacaac ctggtgatcc acgtcgcggt ggaagcgtgc       180
gcgccgggcg acgtcctcgt cgtcgcgccg acgtcgccct gcacggacgg ctattttggc       240
gagctgctgg cgacgtcttt acgcgctcgg aacgtggcgg gcctggtgat cgacgccggc       300
tgccgggatg tccgtgcgct caccgagatg cggttcccgg tctggcgccg cgccatcagc       360
gcgcagggga cggtcaaggc gacgctcggc tctctgaaca cgccgatcgt ctgtgccgga       420
gcgctcgttg cccccggcga tgtcatcgtg gccgacgatg acggagtcgt cgtggtgaag       480
cgggaggaaa tcgcggcggt gacgcaggcg gcggagcagc gcgtccgcaa ggaagagggt       540
acgcgagcga ggctcgcaaa cggtgaactg ggtttggaca tctacggctt gcggcagaag       600
ctggcggacc tgggcctgaa gtcgtcatcg tga                                   633

<210> SEQ ID NO 202
<211> LENGTH: 210
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (6)...(158)
<223> OTHER INFORMATION: Demethylmenaquinone methyltransferase

<400> SEQUENCE: 202

Met Ser Asn Asp Leu Arg Arg Phe Gly Val Ser Thr Leu His Glu Ala
1               5                   10                  15

Gln Gly Arg Arg Gly Leu Leu Ala Ser Tyr Met Arg Pro Ile Tyr Pro
            20                  25                  30

Gly Ala Leu Val Ala Gly Pro Ala Val Thr Val Leu Val Pro Pro Gly
        35                  40                  45

Asp Asn Leu Val Ile His Val Ala Val Glu Ala Cys Ala Pro Gly Asp
    50                  55                  60

Val Leu Val Val Ala Pro Thr Ser Pro Cys Thr Asp Gly Tyr Phe Gly
65                  70                  75                  80

Glu Leu Leu Ala Thr Ser Leu Arg Ala Arg Asn Val Ala Gly Leu Val
                85                  90                  95

Ile Asp Ala Gly Cys Arg Asp Val Arg Ala Leu Thr Glu Met Arg Phe
            100                 105                 110

Pro Val Trp Arg Arg Ala Ile Ser Ala Gln Gly Thr Val Lys Ala Thr
        115                 120                 125
```

```
Leu Gly Ser Leu Asn Thr Pro Ile Val Cys Ala Gly Ala Leu Val Ala
        130                 135                 140

Pro Gly Asp Val Ile Val Ala Asp Asp Gly Val Val Val Val Lys
145                 150                 155                 160

Arg Glu Glu Ile Ala Ala Val Thr Gln Ala Ala Glu Gln Arg Val
            165                 170                 175

Lys Glu Glu Gly Thr Arg Ala Arg Leu Ala Asn Gly Glu Leu Gly Leu
            180                 185                 190

Asp Ile Tyr Gly Leu Arg Gln Lys Leu Ala Asp Leu Gly Leu Lys Ser
            195                 200                 205

Ser Ser
    210
```

<210> SEQ ID NO 203
<211> LENGTH: 699
<212> TYPE: DNA
<213> ORGANISM: Unknown
<220> FEATURE:
<223> OTHER INFORMATION: DNA obtained from environmental sample

<400> SEQUENCE: 203

```
atgaccggca ttgtcgtcga gaccatcgag cgcgcgtccc tcgccgacat cgccgcgctg      60
gccgagttcg gcgtcgccac catccacgag gcgcagggcc gcatcggtct cctcgcctcc     120
accatgcgcc cgatctacgc gggtgccgca gccgccggca tgccgtcac cgtgtcggtt      180 ccgcccggcg acaactggat gatccacgtg gccgtcgagc agtgccgcga gggcgacatc     240
ctggtggtgg cccccaccag cccgaacgac aacggctact cggcgaact gctggcctgc     300 tcgctcaagt cgcgcggcgt gcgcggcctc atcatcgaag ccggctgccg cgacgtgaaa     360
ccgctcaccg agatgaagtt ccccgtctgg tcccgcgccg tctcctccca aggcaccgtc     420
aaggaaagcc tcggcgacgt gaatctgccg ctctcgatcg cgggccagct cgtcaacccc     480
ggcgatgtca tcgtcgccga tgacgacggc gtggtcgtgg tcgcccgcag cgatgtgcgc     540
tcagtcaccg ccaagtcgcg cgaacgcgaa gacaaggaag ccaaaaaccg ggtgcaactc     600
caggccggcc agctcggcat tgacatctat ggcatgcgcg acaagctcaa ggccaaaggc     660
ctgcgctacg tgaaaagcgc ggcggacctg aagggctaa                            699
```

<210> SEQ ID NO 204
<211> LENGTH: 232
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (21)...(173)
<223> OTHER INFORMATION: Demethylmenaquinone methyltransferase

<400> SEQUENCE: 204

```
Met Thr Gly Ile Val Val Glu Thr Ile Glu Arg Ala Ser Leu Ala Asp
1               5                   10                  15

Ile Ala Ala Leu Ala Glu Phe Gly Val Ala Thr Ile His Glu Ala Gln
            20                  25                  30

Gly Arg Ile Gly Leu Leu Ala Ser Thr Met Arg Pro Ile Tyr Ala Gly
        35                  40                  45

Ala Ala Ala Ala Gly Asn Ala Val Thr Val Ser Val Pro Pro Gly Asp
    50                  55                  60

Asn Trp Met Ile His Val Ala Val Glu Gln Cys Arg Glu Gly Asp Ile
65                  70                  75                  80
```

```
Leu Val Val Ala Pro Thr Ser Pro Asn Asp Asn Gly Tyr Phe Gly Glu
                85                  90                  95

Leu Leu Ala Cys Ser Leu Lys Ser Arg Gly Val Arg Gly Leu Ile Ile
            100                 105                 110

Glu Ala Gly Cys Arg Asp Val Lys Pro Leu Thr Glu Met Lys Phe Pro
        115                 120                 125

Val Trp Ser Arg Ala Val Ser Ser Gln Gly Thr Val Lys Glu Ser Leu
    130                 135                 140

Gly Asp Val Asn Leu Pro Leu Ser Ile Ala Gly Gln Leu Val Asn Pro
145                 150                 155                 160

Gly Asp Val Ile Val Ala Asp Asp Gly Val Val Val Ala Arg
                165                 170                 175

Ser Asp Val Arg Ser Val Thr Ala Lys Ser Arg Glu Arg Glu Asp Lys
                180                 185                 190

Glu Ala Lys Asn Arg Val Gln Leu Gln Ala Gly Gln Leu Gly Ile Asp
            195                 200                 205

Ile Tyr Gly Met Arg Asp Lys Leu Lys Ala Lys Gly Leu Arg Tyr Val
210                 215                 220

Lys Ser Ala Ala Asp Leu Lys Gly
225                 230

<210> SEQ ID NO 205
<211> LENGTH: 678
<212> TYPE: DNA
<213> ORGANISM: Unknown
<220> FEATURE:
<223> OTHER INFORMATION: DNA obtained from environmental sample

<400> SEQUENCE: 205
atgaacacac cggtggtagc aagacaagtg gagcagccac cagcggatgc aattgccgca    60
ttggagaagt gtggagtgac aaccgtccat gaggctcagg acgttgtgg cctccttgcg    120 tcctacattc gcccgattta cccgggagca gccatcgcag atccgctat cactgtgtct    180 ttgcctcctg cgacaaacct catgatccac gttgcggtgg aggtctgcgg tccgggaaac    240
atcctggtag tttcaccgac gtcgccttgt acggacggct acttcggtga gttgttggca    300
acatctctcc gtgcccacgg agtgattggg cttgtgatcg atgccggatg ccgtgatgtg    360
cgctctctga cagaaatgaa attcccggtc tggagccgcg ccatctgttc gcaagggaca    420
gtcaaggcca cacttggatc ggtgaatgtg cccatcgtat gcgcgggtgc aatggtcgag    480
gctggtgatg tcatcgtcgc cgacgatgat ggcgttgtcg ttgtgaagcg agcgctggcg    540
caggagatcg ctgcggcggc ggaacaaagg gttcgcaaag agaatgtaac ccgcgaacga    600
ctcgcacgtg gagatctcgg acttgatatt tacgacatgc gccaaaagat cgcgcaactg    660
ggcctcaaat atctctga                                                 678

<210> SEQ ID NO 206
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (28)...(174)
<223> OTHER INFORMATION: Demethylmenaquinone methyltransferase

<400> SEQUENCE: 206

Met Asn Thr Pro Val Val Ala Arg Gln Val Glu Gln Pro Pro Ala Asp
```

```
                  1               5                  10                 15
              Ala Ile Ala Ala Leu Glu Lys Cys Gly Val Thr Thr Val His Glu Ala
                              20                  25                  30

Gln Gly Arg Cys Gly Leu Leu Ala Ser Tyr Ile Arg Pro Ile Tyr Pro
                              35                  40                  45

Gly Ala Ala Ile Ala Gly Ser Ala Ile Thr Val Ser Leu Pro Pro Gly
                              50                  55                  60

Asp Asn Leu Met Ile His Val Ala Val Glu Val Cys Gly Pro Gly Asn
               65                  70                  75                  80

Ile Leu Val Val Ser Pro Thr Ser Pro Cys Thr Asp Gly Tyr Phe Gly
                              85                  90                  95

Glu Leu Leu Ala Thr Ser Leu Arg Ala His Gly Val Ile Gly Leu Val
                              100                 105                 110

Ile Asp Ala Gly Cys Arg Asp Val Arg Ser Leu Thr Glu Met Lys Phe
                              115                 120                 125

Pro Val Trp Ser Arg Ala Ile Cys Ser Gln Gly Thr Val Lys Ala Thr
                              130                 135                 140

Leu Gly Ser Val Asn Val Pro Ile Val Cys Ala Gly Ala Met Val Glu
              145                 150                 155                 160

Ala Gly Asp Val Ile Val Ala Asp Asp Gly Val Val Val Lys
                              165                 170                 175

Arg Ala Leu Ala Gln Glu Ile Ala Ala Ala Glu Gln Arg Val Arg
                              180                 185                 190

Lys Glu Asn Val Thr Arg Glu Arg Leu Ala Arg Gly Asp Leu Gly Leu
                              195                 200                 205

Asp Ile Tyr Asp Met Arg Gln Lys Ile Ala Gln Leu Gly Leu Lys Tyr
                              210                 215                 220

Leu
              225

<210> SEQ ID NO 207
              <211> LENGTH: 678
              <212> TYPE: DNA
              <213> ORGANISM: Unknown
              <220> FEATURE:
              <223> OTHER INFORMATION: DNA obtained from environmental sample

<400> SEQUENCE: 207
atgaacaaac cggtggtgat ccggcaagtg gagcggccgc cggctgacgc ggtggcggcg        60
ctcgaaaccc atggcgtgtc caccgtgcat gaggcccagg ggcgttgcgg actgctcgct       120
tcctacatgc ggccgattta tcccggcgcc gcgattgccg gtcggcggt cacggtgtcg        180 cttccgcccg gcgataatct catgattcat gttgccgtgg aggtctgcca atccggcgac       240
attctcgtgg ttgctcccac gtcgccttgt tcggacggtt acttcggtga actcctggca       300
acctccctgc gggcgcacgg cgtcagggg ctcgttatcg atgcaggttg ccgcgacgtt        360
cgctcgctta ccgagatgaa gttccccgtc tggagccgcg ctgtcagttc gcaaggcacc       420
gtgaaatcca ctctcggatc ggtgaatgtg agcctcgttt cgccggagc acgcatcgaa        480 gccggcgatg tggtcgtcgc cgatgacgat ggcgtcgttg tggtggagcg agcacgcgcc       540
cacgaagtag tcgctgcgtg cgaacaacgc attcgcaagg aagaggcaac tcgcgagcgg       600
ctggcgcggg gagaactcgg actcgatatc tacggcttgc gcacaaaaat cgcggagatg       660
ggtctcaagt atcagtga                                                    678

<210> SEQ ID NO 208
```

```
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase
<220> FEATURE:
<221> NAME/KEY: SITE
<222> LOCATION: (151)...(154)
<223> OTHER INFORMATION: N-glycosylation site. Prosite id = PS00001

<400> SEQUENCE: 208

Met Asn Lys Pro Val Ile Arg Gln Val Glu Arg Pro Pro Ala Asp
 1               5                  10                  15

Ala Val Ala Ala Leu Glu Thr His Gly Val Ser Thr Val His Glu Ala
                 20                  25                  30

Gln Gly Arg Cys Gly Leu Leu Ala Ser Tyr Met Arg Pro Ile Tyr Pro
             35                  40                  45

Gly Ala Ala Ile Ala Gly Ser Ala Val Thr Val Ser Leu Pro Pro Gly
         50                  55                  60

Asp Asn Leu Met Ile His Val Ala Val Glu Val Cys Gln Ser Gly Asp
65                  70                  75                  80

Ile Leu Val Val Ala Pro Thr Ser Pro Cys Ser Asp Gly Tyr Phe Gly
                 85                  90                  95

Glu Leu Leu Ala Thr Ser Leu Arg Ala His Gly Val Arg Gly Leu Val
                100                 105                 110

Ile Asp Ala Gly Cys Arg Asp Val Arg Ser Leu Thr Glu Met Lys Phe
            115                 120                 125

Pro Val Trp Ser Arg Ala Val Ser Ser Gln Gly Thr Val Lys Ser Thr
        130                 135                 140

Leu Gly Ser Val Asn Val Ser Val Val Cys Ala Gly Ala Arg Ile Glu
145                 150                 155                 160

Ala Gly Asp Val Val Ala Asp Asp Gly Val Val Val Glu
                165                 170                 175

Arg Ala Arg Ala His Glu Val Val Ala Ala Cys Glu Gln Arg Ile Arg
                180                 185                 190

Lys Glu Glu Ala Thr Arg Glu Arg Leu Ala Arg Gly Leu Gly Leu
            195                 200                 205

Asp Ile Tyr Gly Leu Arg Thr Lys Ile Ala Glu Met Gly Leu Lys Tyr
        210                 215                 220

Gln
225

<210> SEQ ID NO 209
<211> LENGTH: 678
<212> TYPE: DNA
<213> ORGANISM: Unknown
<220> FEATURE:
<223> OTHER INFORMATION: DNA obtained from environmental sample

<400> SEQUENCE: 209
atgaatacac cagtggtagt ccgacaggtg cagcagccac cagccgaaac ggtggccgcg      60
ctggagaagt gtgggtgac aacggtgcat gaggctcagg acgtgctgg cctgcttgcg      120 tcctacatgc gcccgatcta cccgggagca gcgatcgctg gttccgctat cacggtgtct     180
ttgcctcccg gcgacaacct catgatccac gttgcggtgg aggtctgcgg cccgggaaac     240
atcctggtag tttcaccaac ctcgccttct acggatggct acttcggtga gctgttggca     300
```

```
acatctctcc gtgcccacgg tgtgagaggg cttgtgatcg atgctggatg ccgtgatgtg    360
cgctctttaa cagaaatgaa attccccgtc tggagccgcg ccatcaattc gcagggaca     420 gtcaagacca cacttggatc ggtgaatgtg cccatcgttt gcgcgggcgc actggtcgac    480
gctggagatg tcatcgtcgc ggatgacgat ggagttgtag ttgttaagca ggcgatggcg    540
cgagaggttg ccgcggcagc ggaacaaagg gttcgcaaag agaacctgac ccgcgaacga    600
cttgcgcgcg gagaacttgg tctcgacatt tacgagatac gacaaaagat cgcgcaacta    660
ggacttaagt atttgtaa                                                  678
```

```
<210> SEQ ID NO 210
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 210

Met Asn Thr Pro Val Val Arg Gln Val Gln Pro Pro Ala Glu
1               5                   10                  15

Thr Val Ala Ala Leu Glu Lys Cys Gly Val Thr Val His Glu Ala
            20                  25                  30

Gln Gly Arg Ala Gly Leu Leu Ala Ser Tyr Met Arg Pro Ile Tyr Pro
        35                  40                  45

Gly Ala Ala Ile Ala Gly Ser Ala Ile Thr Val Ser Leu Pro Pro Gly
    50                  55                  60

Asp Asn Leu Met Ile His Val Ala Val Glu Val Cys Gly Pro Gly Asn
65                  70                  75                  80

Ile Leu Val Val Ser Pro Thr Ser Pro Ser Thr Asp Gly Tyr Phe Gly
                85                  90                  95

Glu Leu Leu Ala Thr Ser Leu Arg Ala His Gly Val Arg Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Ile Asn Ser Gln Gly Thr Val Lys Thr Thr
    130                 135                 140

Leu Gly Ser Val Asn Val Pro Ile Val Cys Ala Gly Ala Leu Val Asp
145                 150                 155                 160

Ala Gly Asp Val Ile Val Ala Asp Asp Gly Val Val Val Lys
                165                 170                 175

Gln Ala Met Ala Arg Glu Val Ala Ala Ala Glu Gln Arg Val Arg
            180                 185                 190

Lys Glu Asn Leu Thr Arg Glu Arg Leu Ala Arg Gly Glu Leu Gly Leu
        195                 200                 205

Asp Ile Tyr Glu Ile Arg Gln Lys Ile Ala Gln Leu Gly Leu Lys Tyr
    210                 215                 220

Leu
225

<210> SEQ ID NO 211
<211> LENGTH: 702
<212> TYPE: DNA
<213> ORGANISM: Unknown
<220> FEATURE:
```

<223> OTHER INFORMATION: DNA obtained from environmental sample

<400> SEQUENCE: 211

```
gtgagcgccg tcatcaggaa cattccacgc tcgccgcccg agctcctcga tcgcttcaag    60
ggcctcggcg ttgcgaccgt ctcggaagcg cagggccgca agggcctttt ggccccgtat   120
atgcgcccga tctatccggg ggccgcgctg atcggcaatg cggtgacggc ctcggtcgcg   180
cccggcgaca attggacgat ccatgtcgcc gtcgaagtct gccaggaagg cgacgcgctc   240
gtcgtcgcgc ccacctcctt ctgcgaggac ggctatttcg gcgagctact cgccacgtct   300
ctgcagcagc gcggtgtgcg cgggctcatt ctcgaagcag gctgccgcga cgtgcgcgag   360
cttcaaagga tgaattttcc ggtttggtcg cgcgcaatct atgcgcaagg aactgtgaaa   420
gagacggtgg cgacgtgaaa cctgccgctc cgctgcgcag gccagatcgt caatgccggc   480
gatctcattg tcgccgacga cgacggcgtt tgcgtcgtgc cctatgccga tgtcgagaag   540
gtcttgaacg cggcccgcga acgtgcggcg aaggaagaga ggaaccgtgc cgagttcgcc   600
aagggcgtgc tcggcctcga cctctacaaa taccgcgagc gcctcgccgc caagggcctc   660
aaatatttcg acgacatcga ggcgtataag aaggcgaagt ga                     702
```

<210> SEQ ID NO 212
<211> LENGTH: 233
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 212

```
Met Ser Ala Val Ile Arg Asn Ile Pro Arg Ser Pro Glu Leu Leu
1               5                   10                  15
Asp Arg Phe Lys Gly Leu Gly Val Ala Thr Val Ser Glu Ala Gln Gly
            20                  25                  30
Arg Lys Gly Leu Leu Ala Pro Tyr Met Arg Pro Ile Tyr Pro Gly Ala
        35                  40                  45
Ala Leu Ile Gly Asn Ala Val Thr Ala Ser Val Ala Pro Gly Asp Asn
    50                  55                  60
Trp Thr Ile His Val Ala Val Glu Val Cys Gln Gly Asp Ala Leu
65                  70                  75                  80
Val Val Ala Pro Thr Ser Phe Cys Glu Asp Gly Tyr Phe Gly Glu Leu
                85                  90                  95
Leu Ala Thr Ser Leu Gln Gln Arg Gly Val Arg Gly Leu Ile Leu Glu
            100                 105                 110
Ala Gly Cys Arg Asp Val Arg Glu Leu Gln Arg Met Asn Phe Pro Val
        115                 120                 125
Trp Ser Arg Ala Ile Tyr Ala Gln Gly Thr Val Lys Glu Thr Val Gly
    130                 135                 140
Asp Val Asn Leu Pro Leu Arg Cys Ala Gly Gln Ile Val Asn Ala Gly
145                 150                 155                 160
Asp Leu Ile Val Ala Asp Asp Gly Val Cys Val Val Pro Tyr Ala
                165                 170                 175
Asp Val Glu Lys Val Leu Asn Ala Ala Arg Glu Arg Ala Ala Lys Glu
            180                 185                 190
Glu Arg Asn Arg Ala Glu Phe Ala Lys Gly Val Leu Gly Leu Asp Leu
        195                 200                 205
```

```
Tyr Lys Tyr Arg Glu Arg Leu Ala Ala Lys Gly Leu Lys Tyr Phe Asp
    210                 215                 220

Asp Ile Glu Ala Tyr Lys Lys Ala Lys
225                 230

<210> SEQ ID NO 213
<211> LENGTH: 690
<212> TYPE: DNA
<213> ORGANISM: Unknown
<220> FEATURE:
<223> OTHER INFORMATION: DNA obtained from environmental sample

<400> SEQUENCE: 213
atgagcgttg tcatcacgaa gattacgcgg ccggacccca acatgtgga gatgctggct      60 gctttcggtg tcgccaccat tcatgaggcg cagggccgca ccggcctgat gcagtcctac    120
atgcgccccg tctatgccgg cgcccgtgcc gccggcacag ccgtcacggt ctcgctgccc    180
cccgccgaca actggatgat ccatgtcgcc gtggagcagt gccgggaagg cgacattctc    240
gtcgtcgcgc ccacttcgcc ctccgatgtc gggtatttcg gcgagctgct ggcgacctcg    300
ctcgtcgccc gcggcgtccg cggcctcgtc attgaaggcg gctgccgcga tgtcagggcg    360
ctgaccgaga tgcgcttccc ggtctggtcg cgcgccattt ccgcgcaggg caccgtcaag    420
gaaacgctcg gctcggtgaa cgtgccgatc gtttgcgccg gcgcgcatat ccatcccggc    480
gatttcattg ccgccgacga cgatggcgtt gtcgtggtgc gccgcagccg cgtcgccgag    540
atcgccgccg ccgcgatggc gcgcgaagac aaggaaacaa ccgtccgcga cgcctgaaa     600 gccggagagc ttggcctcga catttacgga atgcgcccgc gtctcaagga aaagggcctc    660
gtctggcgcg agacgccgga gaaggagtag                                     690

<210> SEQ ID NO 214
<211> LENGTH: 229
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 214

Met Ser Val Val Ile Thr Lys Ile Thr Arg Pro Asp Pro Lys His Val
1               5                   10                  15

Glu Met Leu Ala Ala Phe Gly Val Ala Thr Ile His Glu Ala Gln Gly
                20                  25                  30

Arg Thr Gly Leu Met Gln Ser Tyr Met Arg Pro Val Tyr Ala Gly Ala
            35                  40                  45

Arg Ala Ala Gly Thr Ala Val Thr Val Ser Leu Pro Pro Ala Asp Asn
        50                  55                  60

Trp Met Ile His Val Ala Val Glu Gln Cys Arg Glu Gly Asp Ile Leu
65                  70                  75                  80

Val Val Ala Pro Thr Ser Pro Ser Asp Val Gly Tyr Phe Gly Glu Leu
                85                  90                  95

Leu Ala Thr Ser Leu Val Ala Arg Gly Val Arg Gly Leu Val Ile Glu
            100                 105                 110

Gly Gly Cys Arg Asp Val Arg Ala Leu Thr Glu Met Arg Phe Pro Val
        115                 120                 125

Trp Ser Arg Ala Ile Ser Ala Gln Gly Thr Val Lys Glu Thr Leu Gly
```

```
                130             135             140
Ser Val Asn Val Pro Ile Val Cys Ala Gly Ala His Ile His Pro Gly
145                 150                 155                 160

Asp Phe Ile Ala Ala Asp Asp Gly Val Val Val Arg Arg Ser
                165                 170                 175

Arg Val Ala Glu Ile Ala Ala Ala Met Ala Arg Glu Asp Lys Glu
            180                 185                 190

Thr Thr Val Arg Glu Arg Leu Lys Ala Gly Leu Gly Leu Asp Ile
                195                 200                 205

Tyr Gly Met Arg Pro Arg Leu Lys Glu Lys Gly Leu Val Trp Arg Glu
    210                 215                 220

Thr Pro Glu Lys Glu
225

<210> SEQ ID NO 215
<211> LENGTH: 702
<212> TYPE: DNA
<213> ORGANISM: Unknown
<220> FEATURE:
<223> OTHER INFORMATION: DNA obtained from environmental sample

<400> SEQUENCE: 215
gtgagcgccg tcatcaggaa cattccacgc tcgccgctcg agctcctcga tcgcttcaag    60
ggcctcggcg ttgcgaccgt ctcggaagcg cagggccgca agggcctttt ggcctcgtat   120
atgcgcccga tctatccggg ggccgcgctg atcggcaatg cggtgacggc ctcggtcgcg   180
cccggcgaca attggacgat ccatgtcgcc gtcgaagtct gccaggaagg cgacgcgctc   240
gtcgtcgcgc ccacctcctt ctgcgaggac ggctatttcg cgagctact cgccacgtct   300 ctgcagcagc gcggtgtgcg cgggctcatt ctcgaagcag gctgccgcga cgtgcgcgag   360
cttcaaagga tgaattttcc ggtttggtcg cgcgcaatct atgcgcaagg aactgtgaaa   420
gagacggtgg gcgacgtgaa cctgccgctc cgctgcgcag gccagatcgt caatgccggc   480
gatctcattg tcgccgacga cgacggcgtt tgcgtcgtgc cctatgccga tgtcgagaag   540
gtcttgaacg cggcccgcga acgtgcgcg aaggaagaga ggaaccgtgc cgagttcgcc   600
aagggcgtgc tcggcctcga cctctacaaa taccgcgagc gcctcgccgc caagggcctc   660
aaatatttcg acgacatcga ggcgtataag aaggcgaagt ga                      702

<210> SEQ ID NO 216
<211> LENGTH: 233
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 216

Met Ser Ala Val Ile Arg Asn Ile Pro Arg Ser Pro Leu Glu Leu Leu
1               5                   10                  15

Asp Arg Phe Lys Gly Leu Gly Val Ala Thr Val Ser Glu Ala Gln Gly
            20                  25                  30

Arg Lys Gly Leu Leu Ala Ser Tyr Met Arg Pro Ile Tyr Pro Gly Ala
        35                  40                  45

Ala Leu Ile Gly Asn Ala Val Thr Ala Ser Val Ala Pro Gly Asp Asn
    50                  55                  60
```

Trp Thr Ile His Val Ala Val Glu Val Cys Gln Glu Gly Asp Ala Leu
 65                  70                  75                  80

Val Val Ala Pro Thr Ser Phe Cys Glu Asp Gly Tyr Phe Gly Glu Leu
                 85                  90                  95

Leu Ala Thr Ser Leu Gln Gln Arg Gly Val Arg Gly Leu Ile Leu Glu
            100                 105                 110

Ala Gly Cys Arg Asp Val Arg Glu Leu Gln Arg Met Asn Phe Pro Val
        115                 120                 125

Trp Ser Arg Ala Ile Tyr Ala Gln Gly Thr Val Lys Glu Thr Val Gly
    130                 135                 140

Asp Val Asn Leu Pro Leu Arg Cys Ala Gly Gln Ile Val Asn Ala Gly
145                 150                 155                 160

Asp Leu Ile Val Ala Asp Asp Gly Val Cys Val Val Pro Tyr Ala
                165                 170                 175

Asp Val Glu Lys Val Leu Asn Ala Ala Arg Glu Arg Ala Ala Lys Glu
            180                 185                 190

Glu Arg Asn Arg Ala Glu Phe Ala Lys Gly Val Leu Gly Leu Asp Leu
            195                 200                 205

Tyr Lys Tyr Arg Glu Arg Leu Ala Ala Lys Gly Leu Lys Tyr Phe Asp
    210                 215                 220

Asp Ile Glu Ala Tyr Lys Lys Ala Lys
225                 230

<210> SEQ ID NO 217
<211> LENGTH: 702
<212> TYPE: DNA
<213> ORGANISM: Unknown
<220> FEATURE:
<223> OTHER INFORMATION: DNA obtained from environmental sample

<400> SEQUENCE: 217
gtgagcgtgg tcatccgaaa cattccgcgc acgccgctcg cgctgctgga cagtttcaaa      60
gggttcggcg ttgcgacgat ctcggaggcg cagggccgca agggcctcat ggcttcttat     120
atgcgtccga tttatccggg agctgagctt gtcggcaatg cggtgacggc ctcggtcgcg     180
cccggcgaca attggacgat ccatgtcgcg atcgaagtct gccaggaagg tgatgtgctc     240
gtggtcgcgc ctgcctcgtt ttgcgaggat ggctatttcg gcgagcttct cgcgacttcg     300
cttcagcagc gcggcgtgcg cgggctcatt ctcgaagccg gctgccgcga cgtacgcgcg     360
cttcagaaga tgaattttcc ggtttggtcg cgcgcgattt cgcacaagg aaccgtgaaa     420 gagacggtcg gcgacgtcaa cctgccgctc cactgcgcgg gccagatcgt gcatggcggc     480
gatctcatcg tcgccgatga tgacggcgtc tgcgtcgtgc cgcataccga tgtcgagaag     540
gtcttgagcg cggcgcgcga acgcgcggcg aaggaggagc gaaaccgcgc cgagtttgcc     600
aagggcgtgc tcggcctcga cctctacaaa taccgcgagc gcctcgctca aagggcctc     660 aagtattacg acgacatcga agcctataac aaagcgaagt ga                       702

<210> SEQ ID NO 218
<211> LENGTH: 233
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 218

```
Met Ser Val Val Ile Arg Asn Ile Pro Arg Thr Pro Leu Ala Leu Leu
1               5                   10                  15

Asp Ser Phe Lys Gly Phe Gly Val Ala Thr Ile Ser Glu Ala Gln Gly
            20                  25                  30

Arg Lys Gly Leu Met Ala Ser Tyr Met Arg Pro Ile Tyr Pro Gly Ala
        35                  40                  45

Glu Leu Val Gly Asn Ala Val Thr Ala Ser Val Ala Pro Gly Asp Asn
    50                  55                  60

Trp Thr Ile His Val Ala Ile Glu Val Cys Gln Gly Asp Val Leu
65                  70                  75                  80

Val Val Ala Pro Ala Ser Phe Cys Glu Asp Gly Tyr Phe Gly Glu Leu
                85                  90                  95

Leu Ala Thr Ser Leu Gln Gln Arg Gly Val Arg Gly Leu Ile Leu Glu
            100                 105                 110

Ala Gly Cys Arg Asp Val Arg Ala Leu Gln Lys Met Asn Phe Pro Val
        115                 120                 125

Trp Ser Arg Ala Ile Phe Ala Gln Gly Thr Val Lys Glu Thr Val Gly
    130                 135                 140

Asp Val Asn Leu Pro Leu His Cys Ala Gly Gln Ile Val His Gly Gly
145                 150                 155                 160

Asp Leu Ile Val Ala Asp Asp Gly Val Cys Val Pro His Thr
            165                 170                 175

Asp Val Glu Lys Val Leu Ser Ala Ala Arg Glu Arg Ala Ala Lys Glu
            180                 185                 190

Glu Arg Asn Arg Ala Glu Phe Ala Lys Gly Val Leu Gly Leu Asp Leu
        195                 200                 205

Tyr Lys Tyr Arg Glu Arg Leu Ala Gln Lys Gly Leu Tyr Tyr Asp
    210                 215                 220

Asp Ile Glu Ala Tyr Asn Lys Ala Lys
225                 230
```

<210> SEQ ID NO 219
<211> LENGTH: 672
<212> TYPE: DNA
<213> ORGANISM: Unknown
<220> FEATURE:
<223> OTHER INFORMATION: DNA obtained from environmental sample

<400> SEQUENCE: 219

```
atgagcgtgg tcgtgcagaa catcgaacgc gccgacgcgt catttgtggc aacgctcggc    60
gagtgcggcg tggcgaccgt gcacgaggcg caaggtcgaa ctggcttgat gcgcccttac   120
atgcgaccga tctacgccgg cgcccgcatc gccggaccgg cggtgacggt gtcgatcccg   180
cccggcgaca actggatgat ccacgtcgcg gtcgagcagt gccgcgaggg cgatatcctc   240
gtcgtggccc cgaccagccc gagcgaggac ggctatttcg gcgagttgct ggcgcgctcg   300
ctgctcgcgc gcggcgtgag gggtcttgtc atcgaggccg gcgtccgcga cgtacgcgat   360
ctcaccgaga tcaagttccc cgtatggtcc aaagcgatat cggcgcaagg cacggtgaag   420
gagacgatcg gctcggtgaa tgtgccggtc gtatgtgccg gcgccgccat caatcccggc   480
gatgtcatag tcgctgacga cgacggtgtc tgcgtcgtgt cacgcgaacg ggcggaagac   540
gtcgccaagg ccgcgcgcgc ccgcgaagcc aaggaagcgg aaacgcgcaa gcggctgata   600
tcaggcgagc tcggcctcga tatctacggc atgcgcgaga agctcgcggc gaaaggcctc   660
aaatatgcct ga                                                      672
```

<210> SEQ ID NO 220
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 220

```
Met Ser Val Val Gln Asn Ile Glu Arg Ala Asp Ala Ser Phe Val
1               5                   10                  15

Ala Thr Leu Gly Glu Cys Gly Val Ala Thr Val His Glu Ala Gln Gly
                20                  25                  30

Arg Thr Gly Leu Met Arg Pro Tyr Met Arg Pro Ile Tyr Ala Gly Ala
            35                  40                  45

Arg Ile Ala Gly Pro Ala Val Thr Val Ser Ile Pro Pro Gly Asp Asn
        50                  55                  60

Trp Met Ile His Val Ala Val Glu Gln Cys Arg Glu Gly Asp Ile Leu
65                  70                  75                  80

Val Val Ala Pro Thr Ser Pro Ser Glu Asp Gly Tyr Phe Gly Glu Leu
                85                  90                  95

Leu Ala Arg Ser Leu Leu Ala Arg Gly Val Arg Gly Leu Val Ile Glu
            100                 105                 110

Ala Gly Val Arg Asp Val Arg Asp Leu Thr Glu Ile Lys Phe Pro Val
        115                 120                 125

Trp Ser Lys Ala Ile Ser Ala Gln Gly Thr Val Lys Glu Thr Ile Gly
    130                 135                 140

Ser Val Asn Val Pro Val Val Cys Ala Gly Ala Ala Ile Asn Pro Gly
145                 150                 155                 160

Asp Val Ile Val Ala Asp Asp Gly Val Cys Val Val Ser Arg Glu
                165                 170                 175

Arg Ala Glu Asp Val Ala Lys Ala Ala Arg Ala Arg Glu Ala Lys Glu
            180                 185                 190

Ala Glu Thr Arg Lys Arg Leu Ile Ser Gly Glu Leu Gly Leu Asp Ile
        195                 200                 205

Tyr Gly Met Arg Glu Lys Leu Ala Ala Lys Gly Leu Lys Tyr Ala
    210                 215                 220
```

<210> SEQ ID NO 221
<211> LENGTH: 672
<212> TYPE: DNA
<213> ORGANISM: Unknown
<220> FEATURE:
<223> OTHER INFORMATION: DNA obtained from environmental sample

<400> SEQUENCE: 221

```
atgagcgtgg tcgtgcagaa catcgaacgc gccgacgcgt cttttgtggc aacgctcggc    60
gagtgcggcg tggcgaccgt gcacgaggcg caaggtcgaa ccggcttgat gcgcccctac   120
atgcgaccga tctacgccgg cgcccgcatc gccgggccgg cggtgacggt gtcgatccca   180 ccggcgaca  actggatgat ccacgtcgcg gtcgagcaat gccgcgacgg tgacatcctg   240
gtcgtcgcgc cgaccagccc gagcgaggac ggctatttcg gcgagttgct ggcgcgctcg   300
cttctcgcgc gtggcgtgag aggcctcgtc atcgaggccg gcgtccgcga cgtgcgcgac   360
cttaccgaaa tcggatttcc cgtctggtcg aaggcgatct ccgcacaagg caccgtcaag   420
```

-continued

```
gagacgctcg gcttggtgaa cgtgccggtt gtctgcgccg gcgctacggt caacccgggc    480
gatgtcatcg tcgcggacga cgacggtgtg tgcgtggtgc cacgcggcaa tgccgaagag    540
gtcgcgaagg ccgcccgcgc ccgcgaggca aaggaggcgg agacgagcaa gcggttgata    600
gcaggtgagc tcggcctcga catctacggc atgcgcgaga agctggcggc caagggcctc    660
aaatatgtct ga                                                        672
```

<210> SEQ ID NO 222
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 222

```
Met Ser Val Val Val Gln Asn Ile Glu Arg Ala Asp Ala Ser Phe Val
1               5                   10                  15

Ala Thr Leu Gly Glu Cys Gly Val Ala Thr Val His Glu Ala Gln Gly
            20                  25                  30

Arg Thr Gly Leu Met Arg Pro Tyr Met Arg Pro Ile Tyr Ala Gly Ala
        35                  40                  45

Arg Ile Ala Gly Pro Ala Val Thr Val Ser Ile Pro Pro Gly Asp Asn
    50                  55                  60

Trp Met Ile His Val Ala Val Glu Gln Cys Arg Asp Gly Asp Ile Leu
65                  70                  75                  80

Val Val Ala Pro Thr Ser Pro Ser Glu Asp Gly Tyr Phe Gly Glu Leu
                85                  90                  95

Leu Ala Arg Ser Leu Leu Ala Arg Gly Val Arg Gly Leu Val Ile Glu
            100                 105                 110

Ala Gly Val Arg Asp Val Arg Asp Leu Thr Glu Ile Gly Phe Pro Val
        115                 120                 125

Trp Ser Lys Ala Ile Ser Ala Gln Gly Thr Val Lys Glu Thr Leu Gly
    130                 135                 140

Leu Val Asn Val Pro Val Val Cys Ala Gly Ala Thr Val Asn Pro Gly
145                 150                 155                 160

Asp Val Ile Val Ala Asp Asp Gly Val Cys Val Val Pro Arg Gly
                165                 170                 175

Asn Ala Glu Glu Val Ala Lys Ala Arg Ala Arg Glu Ala Lys Glu
            180                 185                 190

Ala Glu Thr Ser Lys Arg Leu Ile Ala Gly Glu Leu Gly Leu Asp Ile
        195                 200                 205

Tyr Gly Met Arg Glu Lys Leu Ala Ala Lys Gly Leu Lys Tyr Val
    210                 215                 220
```

<210> SEQ ID NO 223
<211> LENGTH: 678
<212> TYPE: DNA
<213> ORGANISM: Unknown
<220> FEATURE:
<223> OTHER INFORMATION: DNA obtained from environmental sample

<400> SEQUENCE: 223

```
atgaacgagc cgatcgtcgt tcggacgatc gcgcggccgt cggccgaggc gatcgcggcg     60
ctgcagcggt acggcgtgtc gactgtgcat gaagcgcaag acgacgcggg actgctcggg    120
```

-continued

```
tctcgcttgc gaccgatcta cagcggcgcg gcgatcgccg gtccagcggt caccgtttcg    180
ctgccgcctg gtgacaacct catgattcac gtcgccgtcg aggtgtgcca gcctggcgac    240
gtgctcgtcg tggccccgac ctcccccctgc acggacggct atttcggtga actgttggcc   300
acgtcgtttc gcgcacgcgg cgtcgtcggc ctgatcatcg atgccggctg ccgcgacgtg    360
cgcgcgttgt cggagatgcg ctttcccgtc tggagccgcg cgatcagcgc gcagggtacg    420
gtgaaggcct cgttgggttc ggtgaacgtt gccgtcgtgt gtgggggagc gtccgtcaat    480
ccaggcgatg cgatcgtggc cgacgatgat ggggtggtgg tcgtggcgcg caacgaggtg    540
gaagcggtgg tgcaggcgtc ggagcagcgc atccggaagg aacaggcgac gcgcgagcgg    600
ctggcgagcg gtgaactggg cctcgatatc tacggcctca ggaaaaaggt gtcggacctc    660
gggctgaaat attcgtga                                                  678
```

<210> SEQ ID NO 224
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 224

```
Met Asn Glu Pro Ile Val Val Arg Thr Ile Ala Arg Pro Ser Ala Glu
1               5                   10                  15

Ala Ile Ala Ala Leu Gln Arg Tyr Gly Val Ser Thr Val His Glu Ala
                20                  25                  30

Gln Gly Arg Arg Gly Leu Leu Gly Ser Arg Leu Arg Pro Ile Tyr Ser
            35                  40                  45

Gly Ala Ala Ile Ala Gly Pro Ala Val Thr Val Ser Leu Pro Pro Gly
        50                  55                  60

Asp Asn Leu Met Ile His Val Ala Val Glu Val Cys Gln Pro Gly Asp
65                  70                  75                  80

Val Leu Val Val Ala Pro Thr Ser Pro Cys Thr Asp Gly Tyr Phe Gly
                85                  90                  95

Glu Leu Leu Ala Thr Ser Phe Arg Ala Arg Gly Val Val Gly Leu Ile
                100                 105                 110

Ile Asp Ala Gly Cys Arg Asp Val Arg Ala Leu Ser Glu Met Arg Phe
            115                 120                 125

Pro Val Trp Ser Arg Ala Ile Ser Ala Gln Gly Thr Val Lys Ala Ser
        130                 135                 140

Leu Gly Ser Val Asn Val Ala Val Val Cys Gly Gly Ala Ser Val Asn
145                 150                 155                 160

Pro Gly Asp Ala Ile Val Ala Asp Asp Gly Val Val Val Ala
                165                 170                 175

Arg Asn Glu Val Glu Ala Val Val Gln Ala Ser Glu Gln Arg Ile Arg
                180                 185                 190

Lys Glu Gln Ala Thr Arg Glu Arg Leu Ala Ser Gly Glu Leu Gly Leu
            195                 200                 205

Asp Ile Tyr Gly Leu Arg Lys Lys Val Ser Asp Leu Gly Leu Lys Tyr
        210                 215                 220

Ser
225
```

```
<210> SEQ ID NO 225
<211> LENGTH: 672
<212> TYPE: DNA
<213> ORGANISM: Unknown
<220> FEATURE:
<223> OTHER INFORMATION: DNA obtained from environmental sample

<400> SEQUENCE: 225
atgaacgttg tcgtccggaa tatcgagcgg gccgctgcgg atacgatcgc cgtgcttggc    60
gaatgcggcg tcgcgacggt gcacgaggca cagggccgca gcggcctcat gcgtccctat   120
atgcgaccga tctatacggg cgcgcgcatc gccggctcgg cggtcactgt gtcggtcccg   180
ccgggcgaca actggatgat ccatgtcgcg gtcgaacaat gccacgacgg cgacgtcctc   240
gtcgtggcgc cgaccagccc atgcgatgac ggctatttcg gcgagcttct ggcgcgctcg   300
ctgcgggcgc acggcgtgag aggcctcgtg atcgaggcag gcgtgcgcga cgtgcgcgat   360
ctcaccgaga tgcagttccc ggtctggtcg aaatcgatct ccgcgcaagg gacggtgaag   420
gagacgatcg gctcggtgaa cgtgccggtc gtctgcgcgg gtgccgccgt caatccgggc   480
gacgtcatcg tggccgacga cgatggcgtc tgcgttgtac cgcgaggcca ggcggcagtc   540
gttgccgagc gcacgcgc gcgcgaggcg aaggaggccg aggtccgcaa cgcctggtt   600 gccggggagc tcggtctcga catctacggc atgcgcgaac ggctggcggc gaagggcctg   660
aagtatgtct ga                                                        672

<210> SEQ ID NO 226
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 226
```

Met Asn Val Val Arg Asn Ile Glu Arg Ala Ala Ala Asp Thr Ile
1               5                   10                  15

Ala Val Leu Gly Glu Cys Gly Val Ala Thr Val His Glu Ala Gln Gly
            20                  25                  30

Arg Ser Gly Leu Met Arg Pro Tyr Met Arg Pro Ile Tyr Thr Gly Ala
        35                  40                  45

Arg Ile Ala Gly Ser Ala Val Thr Val Ser Val Pro Pro Gly Asp Asn
    50                  55                  60

Trp Met Ile His Val Ala Val Glu Gln Cys His Asp Gly Asp Val Leu
65                  70                  75                  80

Val Val Ala Pro Thr Ser Pro Cys Asp Asp Gly Tyr Phe Gly Glu Leu
                85                  90                  95

Leu Ala Arg Ser Leu Arg Ala His Gly Val Arg Gly Leu Val Ile Glu
            100                 105                 110

Ala Gly Val Arg Asp Val Arg Asp Leu Thr Glu Met Gln Phe Pro Val
        115                 120                 125

Trp Ser Lys Ser Ile Ser Ala Gln Gly Thr Val Lys Glu Thr Ile Gly
    130                 135                 140

Ser Val Asn Val Pro Val Val Cys Ala Gly Ala Ala Val Asn Pro Gly
145                 150                 155                 160

Asp Val Ile Val Ala Asp Asp Asp Gly Val Cys Val Val Pro Arg Gly
                165                 170                 175

```
Gln Ala Ala Val Val Ala Glu Ala Arg Ala Arg Glu Ala Lys Glu
            180                 185                 190

Ala Glu Val Arg Lys Arg Leu Val Ala Gly Glu Leu Gly Leu Asp Ile
            195                 200                 205

Tyr Gly Met Arg Glu Arg Leu Ala Ala Lys Gly Leu Lys Tyr Val
            210                 215                 220

<210> SEQ ID NO 227
<211> LENGTH: 678
<212> TYPE: DNA
<213> ORGANISM: Unknown
<220> FEATURE:
<223> OTHER INFORMATION: DNA obtained from environmental sample

<400> SEQUENCE: 227
atgaacaagc ccgtggttgt gcggaacatc gagcgtccgc cggcggatgc tgtggccgcg    60
cttgagaaat acggcgtgtc gacggtgcac gaggcccagg gccggaacgg cctactggcc   120
tcctatatgc gcccgatcta tgcaggagcc gcgatcgctg gaccagccgt cacagtttcc   180
ctcccgccgg gagacaacct gatgattcac gtcgccgtcg aggtctgtcg gcctggggat   240
gtcctcgttg ttgcgccgac atcgccatgc accgacggct attttggaga gttgcttgca   300
acttcgctcg cggcgcatgg ggtgaaaggc ttagtcattg aggcgggatg tcgcgacgtc   360
cgagctctga cggaaatgaa gtttccagtc tggagccgcg ccgtcagctc gcaaggaacg   420
gtgaaggcaa cacttgggtc ggtaaatgta acgattgttt gtgcgggtgc tgcggttgca   480
cccggtgatg tgatcgtggc ggacgatgat ggcgtcgttg tcgtgaaacg gacagaggcg   540
caagaggtcg ttaccgcatc tgagcagaga ttgcgaaagg aagagggaac ccgcaagcgg   600
cttgcttcgg gggaactcgg cctggatatt tacggcctgc gaccgaagat tgcagacctc   660
ggtctcaagt acttgtag                                                 678

<210> SEQ ID NO 228
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase
<220> FEATURE:
<221> NAME/KEY: SITE
<222> LOCATION: (151)...(154)
<223> OTHER INFORMATION: N-glycosylation site. Prosite id = PS00001

<400> SEQUENCE: 228

Met Asn Lys Pro Val Val Arg Asn Ile Glu Arg Pro Pro Ala Asp
1               5                   10                  15

Ala Val Ala Ala Leu Glu Lys Tyr Gly Val Ser Thr Val His Glu Ala
            20                  25                  30

Gln Gly Arg Asn Gly Leu Leu Ala Ser Tyr Met Arg Pro Ile Tyr Ala
        35                  40                  45

Gly Ala Ala Ile Ala Gly Pro Ala Val Thr Val Ser Leu Pro Pro Gly
    50                  55                  60

Asp Asn Leu Met Ile His Val Ala Val Glu Val Cys Arg Pro Gly Asp
65                  70                  75                  80

Val Leu Val Val Ala Pro Thr Ser Pro Cys Thr Asp Gly Tyr Phe Gly
                85                  90                  95

Glu Leu Leu Ala Thr Ser Leu Ala Ala His Gly Val Lys Gly Leu Val
```

```
                          100                 105                 110
Ile Glu Ala Gly Cys Arg Asp Val Arg Ala Leu Thr Glu Met Lys Phe
            115                 120                 125

Pro Val Trp Ser Arg Ala Val Ser Ser Gln Gly Thr Val Lys Ala Thr
        130                 135                 140

Leu Gly Ser Val Asn Val Thr Ile Val Cys Ala Gly Ala Val Ala
145                 150                 155                 160

Pro Gly Asp Val Ile Val Ala Asp Asp Gly Val Val Val Lys
                165                 170                 175

Arg Thr Glu Ala Gln Glu Val Val Thr Ala Ser Glu Gln Arg Leu Arg
            180                 185                 190

Lys Glu Glu Gly Thr Arg Lys Arg Leu Ala Ser Gly Glu Leu Gly Leu
        195                 200                 205

Asp Ile Tyr Gly Leu Arg Pro Lys Ile Ala Asp Leu Gly Leu Lys Tyr
    210                 215                 220

Leu
225

<210> SEQ ID NO 229
<211> LENGTH: 678
<212> TYPE: DNA
<213> ORGANISM: Unknown
<220> FEATURE:
<223> OTHER INFORMATION: DNA obtained from environmental sample

<400> SEQUENCE: 229
atgaacaagc ccgtggttgt gcggaacatc gagcgtccgc cggcggatgc tgtggccgcg    60
cttgagaaat acggcgtgtc gacggtgcac gaggcccagg gccggaacgg cctactggcc   120
tcctatatgc gcccgatcta tgcaggagcc gcgatcgctg accagccgt cacagtttcc    180 ctcccgccgg gagacaacct gatgattcac gtcgccgtcg aggtctgtcg gcctggggat   240
gtcctcgttg ttgcgccgac atcgccatgc accgacggct attttggaga gttgcttgca   300
acttcgctcg cggcgcatgg ggtgaaaggc ttagtcattg aggcgggatg tcgcgacgtc   360
cgagctctga cggaaatgaa gtttccagtc tggagccgcg ccgtcagctc gcaaggaacg   420
gtgaaggcaa cacttgggtc ggtaaatgta acgattgttt gtgcgggtgc tgcggttgca   480
cccggtgatg tgatcgtggc cgacgatgat ggcgtcgttg tcgtgaaacg gacagaggcg   540
caagaggccg ttaccgcatc tgagcagaga ttgcgaaagg aagagggaac ccgcaagcgg   600
cttgcttcgg gggaactcgg cctggatatt tacggcctgc gaccgaagat tgcagacctc   660
ggtctcaagt acttgtag                                                 678

<210> SEQ ID NO 230
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase
<220> FEATURE:
<221> NAME/KEY: SITE
<222> LOCATION: (151)...(154)
<223> OTHER INFORMATION: N-glycosylation site. Prosite id = PS00001

<400> SEQUENCE: 230

Met Asn Lys Pro Val Val Val Arg Asn Ile Glu Arg Pro Pro Ala Asp
1               5                   10                  15
```

```
Ala Val Ala Ala Leu Glu Lys Tyr Gly Val Ser Thr Val His Glu Ala
        20                  25                  30

Gln Gly Arg Asn Gly Leu Leu Ala Ser Tyr Met Arg Pro Ile Tyr Ala
            35                  40                  45

Gly Ala Ala Ile Ala Gly Pro Ala Val Thr Val Ser Leu Pro Pro Gly
 50                  55                  60

Asp Asn Leu Met Ile His Val Ala Val Glu Val Cys Arg Pro Gly Asp
 65                  70                  75                  80

Val Leu Val Val Ala Pro Thr Ser Pro Cys Thr Asp Gly Tyr Phe Gly
                85                  90                  95

Glu Leu Leu Ala Thr Ser Leu Ala Ala His Gly Val Lys Gly Leu Val
               100                 105                 110

Ile Glu Ala Gly Cys Arg Asp Val Arg Ala Leu Thr Glu Met Lys Phe
               115                 120                 125

Pro Val Trp Ser Arg Ala Val Ser Ser Gln Gly Thr Val Lys Ala Thr
130                 135                 140

Leu Gly Ser Val Asn Val Thr Ile Val Cys Ala Gly Ala Val Ala
145                 150                 155                 160

Pro Gly Asp Val Ile Ala Asp Asp Gly Val Val Val Lys
                165                 170                 175

Arg Thr Glu Ala Gln Glu Ala Val Thr Ala Ser Glu Gln Arg Leu Arg
               180                 185                 190

Lys Glu Glu Gly Thr Arg Lys Arg Leu Ala Ser Gly Glu Leu Gly Leu
           195                 200                 205

Asp Ile Tyr Gly Leu Arg Pro Lys Ile Ala Asp Leu Gly Leu Lys Tyr
210                 215                 220

Leu
225

<210> SEQ ID NO 231
<211> LENGTH: 678
<212> TYPE: DNA
<213> ORGANISM: Unknown
<220> FEATURE:
<223> OTHER INFORMATION: DNA obtained from environmental sample

<400> SEQUENCE: 231
atgaatgaac cggtggtaat ccggcaggtg gagcagccac cagcagacgc agttgccgca      60
ttggagaaat gtggcgtgac aaccgtccat gaagctcaag acgttgtgg cctgcttgcg     120
cactacatgc gtcccatttt cccgggagca accatcgcgg gttccgccgt caccgtgtct     180
ctgcctcccg gtgacaacct catgatccac gttgcggtcg aagtctgcag gccgggaaac     240
atcctggtcg tttcaccgac atcgccgtgc tcggatggct acttcggcga gctattggca     300
acttctctgc gtgctcacgg tgtaagaggg cttgtgatcg acgccggatg cagggacgtc     360
cgctcgctga ctgagatgaa atttcccgtc tggagccgcg ccatcagttc gcagggtacc     420
gtcaaagcca cgctcggatc ggtgaatgtg ccgatcacgt gcgcgggcgc gttagtcgac     480
gcaggtgatg tcattgtcgc tgacgatgat ggagttgtg ttgtgaagcg cgcgcaggcg     540
caagaggtcg ctgccgcggc ggagcaaagg gttcgcaaag agaacgcgac ccgcgaacga     600
cttgcacgtg gagagctagg actcgatatt tacgacatgc gccagaagat cgcgcaactg     660
ggccttaagt atcggtga                                                   678

<210> SEQ ID NO 232
<211> LENGTH: 225
```

```
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 232
```

| | | | | | | | | | | | | | | |
|---|---|---|---|---|---|---|---|---|---|---|---|---|---|---|
| Met | Asn | Glu | Pro | Val | Val | Ile | Arg | Gln | Val | Glu | Gln | Pro | Ala | Asp |
| 1 | | | | 5 | | | | | 10 | | | | | 15 |
| Ala | Val | Ala | Ala | Leu | Glu | Lys | Cys | Gly | Val | Thr | Thr | Val | His | Glu | Ala |
| | | | 20 | | | | | 25 | | | | | 30 | | |
| Gln | Gly | Arg | Cys | Gly | Leu | Leu | Ala | His | Tyr | Met | Arg | Pro | Ile | Phe | Pro |
| | | | 35 | | | | | 40 | | | | | 45 | | |
| Gly | Ala | Thr | Ile | Ala | Gly | Ser | Ala | Val | Thr | Val | Ser | Leu | Pro | Pro | Gly |
| | | 50 | | | | | 55 | | | | | 60 | | | |
| Asp | Asn | Leu | Met | Ile | His | Val | Ala | Val | Glu | Val | Cys | Arg | Pro | Gly | Asn |
| 65 | | | | | 70 | | | | | 75 | | | | | 80 |
| Ile | Leu | Val | Val | Ser | Pro | Thr | Ser | Pro | Cys | Ser | Asp | Gly | Tyr | Phe | Gly |
| | | | | 85 | | | | | 90 | | | | | 95 | |
| Glu | Leu | Leu | Ala | Thr | Ser | Leu | Arg | Ala | His | Gly | Val | Arg | Gly | Leu | Val |
| | | | | 100 | | | | | 105 | | | | | 110 | |
| Ile | Asp | Ala | Gly | Cys | Arg | Asp | Val | Arg | Ser | Leu | Thr | Glu | Met | Lys | Phe |
| | | | 115 | | | | | 120 | | | | | 125 | | |
| Pro | Val | Trp | Ser | Arg | Ala | Ile | Ser | Ser | Gln | Gly | Thr | Val | Lys | Ala | Thr |
| | | | 130 | | | | | 135 | | | | | 140 | | |
| Leu | Gly | Ser | Val | Asn | Val | Pro | Ile | Thr | Cys | Ala | Gly | Ala | Leu | Val | Asp |
| 145 | | | | | 150 | | | | | 155 | | | | | 160 |
| Ala | Gly | Asp | Val | Ile | Val | Ala | Asp | Asp | Gly | Val | Val | Val | Lys |
| | | | | 165 | | | | | 170 | | | | | 175 |
| Arg | Ala | Gln | Ala | Gln | Glu | Val | Ala | Ala | Ala | Glu | Gly | Arg | Val | Arg |
| | | | | 180 | | | | | 185 | | | | | 190 |
| Lys | Glu | Asn | Ala | Thr | Arg | Glu | Arg | Leu | Ala | Arg | Gly | Glu | Leu | Gly | Leu |
| | | | | 195 | | | | | 200 | | | | | 205 | |
| Asp | Ile | Tyr | Asp | Met | Arg | Gln | Lys | Ile | Ala | Gln | Leu | Gly | Leu | Lys | Tyr |
| | | 210 | | | | | 215 | | | | | 220 | | | |
| Arg |
| 225 |

```
<210> SEQ ID NO 233
<211> LENGTH: 678
<212> TYPE: DNA
<213> ORGANISM: Unknown
<220> FEATURE:
<223> OTHER INFORMATION: DNA obtained from environmental sample

<400> SEQUENCE: 233
atgaacaaac cggtggtgat ccggcaagtg gagcggccgc cggctgacgc ggtggcggcg      60
ctcgaaacct atggcgtgtc caccgtgcac gaggcccagg ggcgttgcgg gctgctcgct     120
tcctacatgc ggccgattta tggcggcgcc ctgattgccg gtcggcggt  cacggtgtca     180 cttccgcccg gcgataatct gatgattcac gttgccgtgg aggtctgcca atccggcgac     240
attctcgtgg ttgctcccac gtcgccttgt tcggacggtt acttcggtga acttctggca     300
acctccctgc gggcacacgg cgtcaagggg ctcgtgattg atgcgggttg ccgcgacgtt     360
cggtcgctta ccgaaatgaa gttccccgtc tggagccgcg ctgtcagttc gcaaggaacc     420
```

```
gtgaaatcga ctctcggatc ggtgaatgta agcgtcgttt gcgccggagc acgcatcgaa    480
gccggcgatg tggtcgtcgc ggatgacgat ggcgtcgtgg tggtggcgcg ggcacgcgcc    540
cacgaagtag tcgcggcgtg cgaacaacgc attcgcaagg aagaggcaac ccgcgaacgg    600
ctggcgcggg gagaactcgg actcgatatc tacggcttgc gcacaaaaat cgcggagatg    660
ggtctcgagt atcaatga                                                  678
```

<210> SEQ ID NO 234
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase
<220> FEATURE:
<221> NAME/KEY: SITE
<222> LOCATION: (151)...(154)
<223> OTHER INFORMATION: N-glycosylation site. Prosite id = PS00001

<400> SEQUENCE: 234

```
Met Asn Lys Pro Val Val Ile Arg Gln Val Glu Arg Pro Ala Asp
1               5                   10                  15

Ala Val Ala Ala Leu Glu Thr Tyr Gly Val Ser Thr Val His Glu Ala
            20                  25                  30

Gln Gly Arg Cys Gly Leu Leu Ala Ser Tyr Met Arg Pro Ile Tyr Gly
        35                  40                  45

Gly Ala Leu Ile Ala Gly Ser Ala Val Thr Val Ser Leu Pro Pro Gly
    50                  55                  60

Asp Asn Leu Met Ile His Val Ala Val Glu Val Cys Gln Ser Gly Asp
65                  70                  75                  80

Ile Leu Val Val Ala Pro Thr Ser Pro Cys Ser Asp Gly Tyr Phe Gly
                85                  90                  95

Glu Leu Leu Ala Thr Ser Leu Arg Ala His Gly Val Lys Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Val Ser Ser Gln Gly Thr Val Lys Ser Thr
    130                 135                 140

Leu Gly Ser Val Asn Val Ser Val Val Cys Ala Gly Ala Arg Ile Glu
145                 150                 155                 160

Ala Gly Asp Val Val Ala Asp Asp Gly Val Val Val Ala
                165                 170                 175

Arg Ala Arg Ala His Glu Val Val Ala Ala Cys Glu Gln Arg Ile Arg
            180                 185                 190

Lys Glu Glu Ala Thr Arg Glu Arg Leu Ala Arg Gly Glu Leu Gly Leu
        195                 200                 205

Asp Ile Tyr Gly Leu Arg Thr Lys Ile Ala Glu Met Gly Leu Glu Tyr
    210                 215                 220

Gln
225
```

<210> SEQ ID NO 235
<211> LENGTH: 678
<212> TYPE: DNA
<213> ORGANISM: Unknown
<220> FEATURE:
<223> OTHER INFORMATION: DNA obtained from environmental sample

<400> SEQUENCE: 235

```
atgaatgaac cggtggtaat ccggcaggtg gagcagccac cagcagacgc agttgccgca      60
ttggagaaat gtggcgtgac aaccgtccat gaagctcaag gacgttgtgg cctgcttgcg     120
cactacatgc gtcccatttt cccgggagca accatcgcgg gttccgccgt caccgtgtct     180
ctgcctcccg gtgacaacct catgatccac gttgcggtcg aagtctgcag gccgggaaac     240
atcctggtcg tttcaccgac atcgccgtgc tcggatggct acttcggcga gctattggca     300
acttctctgc atgctcacgg tgtaagaggg cttgtgatcg acgccggatg cagggacgtc     360
cgctcgctga ctgagatgaa atttcccgtc tggagccgcg ccatcagttc gcagggtacc     420
gtcaaagcca cgctcggatc ggtgaatgtg ccgatcacgt gcgcgggcgc gttagtcgac     480
gcaggtgata tcattgtcgc tgacgatgat ggagttgtgg ttgtgaagcg cgcgcaggcg     540
caagaggtcg ctgccgcggc ggagcaaagg gttcgcaaag agaacgcgac ccgcgaacga     600
cttgcacgtg gagagctagg actcgatatt tacgacatgc cagaagat cgcacaactg       660
ggccttaagt atcggtga                                                  678
```

```
<210> SEQ ID NO 236
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase
```

<400> SEQUENCE: 236

```
Met Asn Glu Pro Val Ile Arg Gln Val Glu Gln Pro Pro Ala Asp
1               5                   10                  15

Ala Val Ala Ala Leu Glu Lys Cys Gly Val Thr Thr Val His Glu Ala
            20                  25                  30

Gln Gly Arg Cys Gly Leu Leu Ala His Tyr Met Arg Pro Ile Phe Pro
        35                  40                  45

Gly Ala Thr Ile Ala Gly Ser Ala Val Thr Val Ser Leu Pro Pro Gly
    50                  55                  60

Asp Asn Leu Met Ile His Val Ala Val Glu Val Cys Arg Pro Gly Asn
65                  70                  75                  80

Ile Leu Val Val Ser Pro Thr Ser Pro Cys Ser Asp Gly Tyr Phe Gly
                85                  90                  95

Glu Leu Leu Ala Thr Ser Leu His Ala His Gly Val Arg Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Ile Ser Ser Gln Gly Thr Val Lys Ala Thr
    130                 135                 140

Leu Gly Ser Val Asn Val Pro Ile Thr Cys Ala Gly Ala Leu Val Asp
145                 150                 155                 160

Ala Gly Asp Ile Ile Val Ala Asp Asp Gly Val Val Val Lys
                165                 170                 175

Arg Ala Gln Ala Gln Glu Val Ala Ala Ala Glu Gln Arg Val Arg
            180                 185                 190

Lys Glu Asn Ala Thr Arg Glu Arg Leu Ala Arg Gly Glu Leu Gly Leu
        195                 200                 205
```

```
Asp Ile Tyr Asp Met Arg Gln Lys Ile Ala Gln Leu Gly Leu Lys Tyr
    210                 215                 220

Arg
225
```

<210> SEQ ID NO 237
<211> LENGTH: 678
<212> TYPE: DNA
<213> ORGANISM: Unknown
<220> FEATURE:
<223> OTHER INFORMATION: DNA obtained from environmental sample

<400> SEQUENCE: 237

```
atgaacaagc ccgtggtggt ccggcacgtg gagcagccac ctgctgatgc ggtagccgct      60
ttggaaaagt atggcgtgtc aaccgttcat gaggcccagg gacggtcggg tcttctcgcc     120
agttacctgc ggccgatctt tgccggcgcc tcaatcgcag gccggcggt tacggtctcg      180
ctgccacctg gggacaattt gatgatccac gtcgccgtcg aggtgtgcac gcctggaagc     240
atccttgtcg tcgccccaac ctccccttgt acggacggct atttcggaga gctgctggcg     300
acctcgcttc gcgcacacgg cgtaaagggg ttggtcatcg atgccgggtg tcgcgacgtt     360
aggtctttaa cggaaatgaa ctttcccgtt tggagccgct cggtcagttc gcaaggaacc     420
gtcaaagcga cgttgggatc ggtgaatgta ggcgtcgtct cgccggtgc atacgtcgag      480
ccaggcgacg tgatcgtcgc ggacgatgac ggagttgtag tcgtgaagcg ggcggctgcg     540
cccgaggctg tcgtcgcctc cgaagcgaga gttcgtaaag aagccgcgac gcgcgagcgt     600
ctctcccgcg gagagcttgg ccttgacatc tacggcctac gttcaaagat tgcggacctt     660
ggcctcgagt atctgtga                                                    678
```

<210> SEQ ID NO 238
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 238

```
Met Asn Lys Pro Val Val Arg His Val Glu Gln Pro Ala Asp
1               5                   10                  15

Ala Val Ala Ala Leu Glu Lys Tyr Gly Val Ser Thr Val His Glu Ala
                20                  25                  30

Gln Gly Arg Ser Gly Leu Leu Ala Ser Tyr Leu Arg Pro Ile Phe Ala
            35                  40                  45

Gly Ala Ser Ile Ala Gly Pro Ala Val Thr Val Ser Leu Pro Pro Gly
        50                  55                  60

Asp Asn Leu Met Ile His Val Ala Val Glu Val Cys Thr Pro Gly Ser
65                  70                  75                  80

Ile Leu Val Val Ala Pro Thr Ser Pro Cys Thr Asp Gly Tyr Phe Gly
                85                  90                  95

Glu Leu Leu Ala Thr Ser Leu Arg Ala His Gly Val Lys Gly Leu Val
            100                 105                 110

Ile Asp Ala Gly Cys Arg Asp Val Arg Ser Leu Thr Glu Met Asn Phe
        115                 120                 125

Pro Val Trp Ser Arg Ser Val Ser Gln Gly Thr Val Lys Ala Thr
    130                 135                 140
```

```
Leu Gly Ser Val Asn Val Gly Val Val Cys Ala Gly Ala Tyr Val Glu
145                 150                 155                 160

Pro Gly Asp Val Ile Val Ala Asp Asp Gly Val Val Val Lys
                165                 170                 175

Arg Ala Ala Ala Pro Glu Ala Val Val Ala Ser Glu Ala Arg Val Arg
            180                 185                 190

Lys Glu Ala Ala Thr Arg Glu Arg Leu Ser Arg Gly Glu Leu Gly Leu
        195                 200                 205

Asp Ile Tyr Gly Leu Arg Ser Lys Ile Ala Asp Leu Gly Leu Glu Tyr
    210                 215                 220

Leu
225

<210> SEQ ID NO 239
<211> LENGTH: 678
<212> TYPE: DNA
<213> ORGANISM: Unknown
<220> FEATURE:
<223> OTHER INFORMATION: DNA obtained from environmental sample

<400> SEQUENCE: 239
atgaacaaac cggtggtgat ccggcaagcg gagcggccgc cggctgacgc ggtggcggcg      60
ctcgcaacct atggcgtgtc caccgtgcat gaggcccagg ggcgttgcgg actgctcgct     120
tcctacatgc ggccgattta tcacggcacc gcgattgccg ggtcggcggt cacggtgtcc     180
cttccgcccg cgacaatctg atgattcac gttgccgtgg aggtctgcca atccggcgac      240
attctcgtgg tcgctcccac gtcgccctgt ccgacggtt acttcggcga actcctggcc     300
acctctctgc gggcgcacgg cgtcaagggg ctcgttattg atgcgggttg ccgcgacgtt     360
cgctcgctca gcgcaatgaa gttccccgtc tggagccgcg ctgtcagttc gcaaggcacc     420
gtgaaatcta ctctcggatc ggtgaatgtg agcgtcgttt gcgccggagc acgcatcgaa     480
gccggcgacg tggtcgtcgc ggatgacgat ggcgtcgtgg tggtggagcg agcatccgcc     540
cacgaagtag tcgtggcgtg cgaacaacgc cttcgcaagg aagaggcaac tcgcgagcgc     600
ctggcgcggg gagaactcgg actcgacatc tacggcttgc gcacaaaagt cgcggagatg     660
ggtctcaagt atcaatga                                                   678

<210> SEQ ID NO 240
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase
<220> FEATURE:
<221> NAME/KEY: SITE
<222> LOCATION: (151)...(154)
<223> OTHER INFORMATION: N-glycosylation site. Prosite id = PS00001

<400> SEQUENCE: 240

Met Asn Lys Pro Val Val Ile Arg Gln Ala Glu Arg Pro Ala Asp
1               5                   10                  15

Ala Val Ala Ala Leu Ala Thr Tyr Gly Val Ser Thr Val His Glu Ala
            20                  25                  30

Gln Gly Arg Cys Gly Leu Leu Ala Ser Tyr Met Arg Pro Ile Tyr His
        35                  40                  45
```

```
Gly Thr Ala Ile Ala Gly Ser Ala Val Thr Val Ser Leu Pro Pro Gly
 50                  55                  60

Asp Asn Leu Met Ile His Val Ala Val Glu Val Cys Gln Ser Gly Asp
 65                  70                  75                  80

Ile Leu Val Val Ala Pro Thr Ser Pro Cys Ser Asp Gly Tyr Phe Gly
                 85                  90                  95

Glu Leu Leu Ala Thr Ser Leu Arg Ala His Gly Val Lys Gly Leu Val
                100                 105                 110

Ile Asp Ala Gly Cys Arg Asp Val Arg Ser Leu Ser Ala Met Lys Phe
                115                 120                 125

Pro Val Trp Ser Arg Ala Val Ser Ser Gln Gly Thr Val Lys Ser Thr
            130                 135                 140

Leu Gly Ser Val Asn Val Ser Val Val Cys Ala Gly Ala Arg Ile Glu
145                 150                 155                 160

Ala Gly Asp Val Val Ala Asp Asp Gly Val Val Val Glu
                165                 170                 175

Arg Ala Ser Ala His Glu Val Val Ala Cys Glu Gln Arg Leu Arg
                180                 185                 190

Lys Glu Glu Ala Thr Arg Glu Arg Leu Ala Arg Gly Glu Leu Gly Leu
            195                 200                 205

Asp Ile Tyr Gly Leu Arg Thr Lys Val Ala Glu Met Gly Leu Lys Tyr
    210                 215                 220

Gln
225
```

<210> SEQ ID NO 241
<211> LENGTH: 678
<212> TYPE: DNA
<213> ORGANISM: Unknown
<220> FEATURE:
<223> OTHER INFORMATION: DNA obtained from environmental sample
<400> SEQUENCE: 241

```
atgaacaaac cggtggtgat ccggcaagtg gagcggccgc cggctgacgc ggtggcggcg     60
ctcgcaacct atggcgtgtc caccgtgcat gaggcccagg ggcgttgcgg actgctcgct    120
tcctacatgc ggccgattta tcccggcacc gcgattgccg gtcggcggt cacggtgtcc    180
cttccgcccg cgacaatct gatgattcac gttgccgtgg aggtctgcca atccggcgac    240
attctcgtgg tcgctcccac gtcgccttgt tcggacggtt acttcggcga actcctggcc    300
acctctctgc gggcgcacga cgtcaagggg ctcgttattg atgcgggttg ccgcgacgtt    360
cgctcgctca gcgcaatgaa gttccccgtc tggagccgcg ctgtcagttc gcaaagcacc    420
gtgaaatcta ctctcggatc ggtgaatgtg agcgtcgttt gcgccggagc acgcatcgaa    480
gccggcgacg tggtcgtcgc ggatgacgat ggcgtcgtgg tggtggagcg agcatccgcc    540
cacgaagtag tcgcggcgtg cgaacaacgc cttcgcaagg aagaggcaac tcgcgagcgc    600
ctggcgcggg gagaactcgg actcgacatc tacggcttgc gcacaaaagt cgcggagatg    660
ggtctcaagt atcaatga                                                  678
```

<210> SEQ ID NO 242
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)

<223> OTHER INFORMATION: Demethylmenaquinone methyltransferase
<220> FEATURE:
<221> NAME/KEY: SITE
<222> LOCATION: (151)...(154)
<223> OTHER INFORMATION: N-glycosylation site. Prosite id = PS00001

<400> SEQUENCE: 242

```
Met Asn Lys Pro Val Ile Arg Gln Val Glu Arg Pro Pro Ala Asp
1               5                   10                  15
Ala Val Ala Ala Leu Ala Thr Tyr Gly Val Ser Thr Val His Glu Ala
                20                  25                  30
Gln Gly Arg Cys Gly Leu Leu Ala Ser Tyr Met Arg Pro Ile Tyr Pro
            35                  40                  45
Gly Thr Ala Ile Ala Gly Ser Ala Val Thr Val Ser Leu Pro Pro Gly
        50                  55                  60
Asp Asn Leu Met Ile His Val Ala Val Glu Val Cys Gln Ser Gly Asp
65                  70                  75                  80
Ile Leu Val Val Ala Pro Thr Ser Pro Cys Ser Asp Gly Tyr Phe Gly
                85                  90                  95
Glu Leu Leu Ala Thr Ser Leu Arg Ala His Asp Val Lys Gly Leu Val
                100                 105                 110
Ile Asp Ala Gly Cys Arg Asp Val Arg Ser Leu Ser Ala Met Lys Phe
            115                 120                 125
Pro Val Trp Ser Arg Ala Val Ser Ser Gln Ser Thr Val Lys Ser Thr
        130                 135                 140
Leu Gly Ser Val Asn Val Ser Val Val Cys Ala Gly Ala Arg Ile Glu
145                 150                 155                 160
Ala Gly Asp Val Val Ala Asp Asp Gly Val Val Val Glu
                165                 170                 175
Arg Ala Ser Ala His Glu Val Val Ala Ala Cys Glu Gln Arg Leu Arg
                180                 185                 190
Lys Glu Glu Ala Thr Arg Glu Arg Leu Ala Arg Gly Glu Leu Gly Leu
            195                 200                 205
Asp Ile Tyr Gly Leu Arg Thr Lys Val Ala Glu Met Gly Leu Lys Tyr
        210                 215                 220
Gln
225
```

<210> SEQ ID NO 243
<211> LENGTH: 678
<212> TYPE: DNA
<213> ORGANISM: Unknown
<220> FEATURE:
<223> OTHER INFORMATION: DNA obtained from environmental sample

<400> SEQUENCE: 243

```
atgaacagac ctgtggttgt ccgggaggtg gagcggccgc cggcagatgc tgtgacagcg      60
ctcgagcagt acggggtatc gacggtgcat gaagctcaag ggcgttgcgg gttactcgca     120
tcgtatatgc ggccgattta tgccggagcg ccatcgctg gtcccgccgt gactgtttct      180
ctacctccgg gagacaactt gatgattcac gtggcggtcg aggtctgccg tccgggagac     240
atcctcgttg tggcgccgac gtcgccgtgt acggatggct attttggaga gctgcttgca     300
acttcactcc gagcacatgg cgtgaaagga cttgtgatcg atgcgggatg tcgcgatgtt     360
cgctcgctga ctgagatgaa gtttcccgtg tggagtcgcg cggtgagttc gcagggaacg     420
gtgaaggcga cgctcggatc agtaaatgtg agtatcgtgt cgccggcgc actcgtcgaa     480
gccggcgatg tcatcatcgc ggatgacgat ggagccgtag ttgtgaggag gacagccgcg     540
```

```
aaagacgtgg tcgcggcgtc tgaacagaga gtgcgaaaag aagaggcgac gcgaaggcgg    600
cttgcgcaag gcgaactcgg tctggacatc tacgggttgc gcgcgaaaat cgcggacctc    660
ggtctcaagt acctgtaa                                                  678
```

<210> SEQ ID NO 244
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase
<220> FEATURE:
<221> NAME/KEY: SITE
<222> LOCATION: (151)...(154)
<223> OTHER INFORMATION: N-glycosylation site. Prosite id = PS00001

<400> SEQUENCE: 244

```
Met Asn Arg Pro Val Val Arg Glu Val Arg Pro Ala Asp
1               5                   10              15

Ala Val Thr Ala Leu Glu Gln Tyr Gly Val Ser Thr Val His Glu Ala
            20                  25                  30

Gln Gly Arg Cys Gly Leu Leu Ala Ser Tyr Met Arg Pro Ile Tyr Ala
        35                  40                  45

Gly Ala Ala Ile Ala Gly Pro Ala Val Thr Val Ser Leu Pro Pro Gly
    50                  55                  60

Asp Asn Leu Met Ile His Val Ala Val Glu Val Cys Arg Pro Gly Asp
65                  70                  75                  80

Ile Leu Val Val Ala Pro Thr Ser Pro Cys Thr Asp Gly Tyr Phe Gly
                85                  90                  95

Glu Leu Leu Ala Thr Ser Leu Arg Ala His Gly Val Lys Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Val Ser Ser Gln Gly Thr Val Lys Ala Thr
    130                 135                 140

Leu Gly Ser Val Asn Val Ser Ile Val Cys Ala Gly Ala Leu Val Glu
145                 150                 155                 160

Ala Gly Asp Val Ile Ile Ala Asp Asp Gly Ala Val Val Arg
                165                 170                 175

Arg Thr Ala Ala Lys Asp Val Ala Ala Ser Glu Gln Arg Val Arg
            180                 185                 190

Lys Glu Glu Ala Thr Arg Arg Leu Ala Gln Gly Leu Gly Leu
        195                 200                 205

Asp Ile Tyr Gly Leu Arg Ala Lys Ile Ala Asp Leu Gly Leu Lys Tyr
    210                 215                 220

Leu
225
```

<210> SEQ ID NO 245
<211> LENGTH: 678
<212> TYPE: DNA
<213> ORGANISM: Unknown
<220> FEATURE:
<223> OTHER INFORMATION: DNA obtained from environmental sample

<400> SEQUENCE: 245

-continued

```
atgaacaagt ccgtggtggt tcgcaacgtc gagcagcctc ctgccgatgc catggccgcg    60
ctcgaaaaat atggcgtttc caccgttcac gaagcgcaag gccgctgcgg cttgctcgcc   120
tcttacatgc gcccaatttt cggggggtgcc tccgtcgccg gccccgcggt caccgtctcc   180
gtgccgccg cgacaacct catgattcac gtcgctgtag aagtctgccg cccgggagac    240
attctcgtcg tagcccccac atcgcgctgc accgacggct acttcggcga actactagcc   300
acttcgttgc gcgcccacgg cgtcaaaggc ctcgtcatcg atgccggttg ccgcgacgtc   360
cgctccttga ccgaaatgaa atttcccgtc tggagccgcg ccatcagttc gcaaggcacc   420
gtcaaatcca ctgtgggctc ggtaaacgtc ccgtcgtgt gtgcgggcgc actcatcgca   480
cccggcgacg tcatggtcgc ggatgacgat ggcgttgtcg tcgtgcagcg cgccgccgcc   540
cgcgacgtcg tcgccgcctc ggaacaaagg attcgcaagg aagaagccac acgtgagcgt   600
ctggtgcgcg gtgaactcag cctcgatatc tacggcctgc gcgcaaaact caccgaattg   660
ggtctcacgt acttgtag                                                  678
```

```
<210> SEQ ID NO 246
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase
<220> FEATURE:
<221> NAME/KEY: SITE
<222> LOCATION: (2)...(5)
<223> OTHER INFORMATION: N-glycosylation site. Prosite id = PS00001

<400> SEQUENCE: 246

Met Asn Lys Ser Val Val Arg Asn Val Glu Gln Pro Pro Ala Asp
 1               5                  10                  15

Ala Met Ala Ala Leu Glu Lys Tyr Gly Val Ser Thr Val His Glu Ala
                20                  25                  30

Gln Gly Arg Cys Gly Leu Leu Ala Ser Tyr Met Arg Pro Ile Phe Gly
             35                  40                  45

Gly Ala Ser Val Ala Gly Pro Ala Val Thr Val Ser Val Pro Pro Gly
         50                  55                  60

Asp Asn Leu Met Ile His Val Ala Val Glu Val Cys Arg Pro Gly Asp
65                  70                  75                  80

Ile Leu Val Val Ala Pro Thr Ser Arg Cys Thr Asp Gly Tyr Phe Gly
                 85                  90                  95

Glu Leu Leu Ala Thr Ser Leu Arg Ala His Gly Val Lys Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Ile Ser Ser Gln Gly Thr Val Lys Ser Thr
    130                 135                 140

Val Gly Ser Val Asn Val Pro Val Cys Ala Gly Ala Leu Ile Ala
145                 150                 155                 160

Pro Gly Asp Val Met Val Ala Asp Asp Gly Val Val Val Gln
                165                 170                 175

Arg Ala Ala Ala Arg Asp Val Val Ala Ala Ser Glu Gln Arg Ile Arg
            180                 185                 190

Lys Glu Glu Ala Thr Arg Glu Arg Leu Val Arg Gly Glu Leu Ser Leu
        195                 200                 205
```

```
Asp Ile Tyr Gly Leu Arg Ala Lys Leu Thr Glu Leu Gly Leu Thr Tyr
    210                 215                 220

Leu
225
```

```
<210> SEQ ID NO 247
<211> LENGTH: 678
<212> TYPE: DNA
<213> ORGANISM: Unknown
<220> FEATURE:
<223> OTHER INFORMATION: DNA obtained from environmental sample

<400> SEQUENCE: 247
```

| | | |
|---|---|---|
| gtgacgggtc cgatcgtcgt tcgcaccatc gacagaccga tggccgatgt cgtcgccgcg | 60 |
| ctgcagcgcc atggcgtctc gacggttcac gaagcacaag ggcgacgggg actgctcgcg | 120 |
| tcctgcgtgc ggccgatcta tgtgggcgcc gtgattgcgg gtcctgccgt caccgtctcg | 180 |
| ctgccacctg gcgacaacct gatgattcac gtcgcggtgg agatgtgtca gcccggcgat | 240 |
| gtcctcgtcg tcgccccgac ctctccgtgc accgacggct atttcggcga actgctggcg | 300 |
| acctcattgc acgcccgcgg cgtcacggga ctcatcatcg atgccggctg ccgggacgtt | 360 |
| cgcgccttga cggacatgcg atttccggtt tggagccgcg cgatcagcgc gcagggcacc | 420 |
| gtcaagtcaa cgctcggatc agtgaacgtg ccggtggtgt cgcgccggagc gttggtccac | 480 |
| gcgggcgacg ccatcgtggc ggatgacgat ggcgtggtgg tggtgagacg ggaagaggcg | 540 |
| gggaccgtgt cggaggcgtg cgcggagcgg gcgcgcaagg aagaggccac gagggaacgg | 600 |
| ctcgcgcgag gcgagcttgg tctcgatatc tacggcctgc gaaaaaaact caccgacctc | 660 |
| ggcctgaagt attcgtag | 678 |

```
<210> SEQ ID NO 248
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 248

Met Thr Gly Pro Ile Val Val Arg Thr Ile Asp Arg Pro Met Ala Asp
1               5                   10                  15

Val Val Ala Ala Leu Gln Arg His Gly Val Ser Thr Val His Glu Ala
                20                  25                  30

Gln Gly Arg Arg Gly Leu Leu Ala Ser Cys Val Arg Pro Ile Tyr Val
            35                  40                  45

Gly Ala Val Ile Ala Gly Pro Ala Val Thr Val Ser Leu Pro Pro Gly
        50                  55                  60

Asp Asn Leu Met Ile His Val Ala Val Glu Met Cys Gln Pro Gly Asp
65                  70                  75                  80

Val Leu Val Val Ala Pro Thr Ser Pro Cys Thr Asp Gly Tyr Phe Gly
                85                  90                  95

Glu Leu Leu Ala Thr Ser Leu His Ala Arg Gly Val Thr Gly Leu Ile
                100                 105                 110

Ile Asp Ala Gly Cys Arg Asp Val Arg Ala Leu Thr Asp Met Arg Phe
            115                 120                 125

Pro Val Trp Ser Arg Ala Ile Ser Ala Gln Gly Thr Val Lys Ser Thr
```

```
              130                 135                 140
Leu Gly Ser Val Asn Val Pro Val Val Cys Ala Gly Ala Leu Val His
145                 150                 155                 160

Ala Gly Asp Ala Ile Val Ala Asp Asp Gly Val Val Val Arg
                165                 170                 175

Arg Glu Glu Ala Gly Thr Val Ser Glu Ala Cys Ala Glu Arg Ala Arg
                180                 185                 190

Lys Glu Ala Thr Arg Glu Arg Leu Ala Arg Gly Leu Gly Leu
                195                 200                 205

Asp Ile Tyr Gly Leu Arg Lys Lys Leu Thr Asp Leu Gly Leu Lys Tyr
    210                 215                 220

Ser
225

<210> SEQ ID NO 249
<211> LENGTH: 678
<212> TYPE: DNA
<213> ORGANISM: Unknown
<220> FEATURE:
<223> OTHER INFORMATION: DNA obtained from environmental sample

<400> SEQUENCE: 249
atgaacaagt ccgtggtggt tcgcaacgtc gagcagcctc ctgccgatgc catggccgcg    60
ctcgaaaaat atggcgtttc caccgttcac gaagcgcaag gccgctgcgg cttgctcgcc   120
tcttacatgc gcccaatttt cggggggtgcc tccgtcgccg ccccgcggt caccgtctcc   180 gtgccgcccg cgacaacct catgattcac gtcgctgtag aagtctgccg cccgggagac   240
attctcgtcg tagcccccac atcgccctgc accgacggct acttcggcga actactagcc   300
acttcgttgc gcgcccacgg cgtcaaaggc ctcgtcatcg atgccggttg ccgcgacgtc   360
cgctccttga ccgaaatgaa atttcccgtc tggagccgcg ccatcagttc gcaaggcacc   420
gtcaaatcca ctgtgggctc ggtaaacgtc ccgtcgtgt gtgcgggcgc actcatcgca   480
cccggcgacg tcatggtcgc ggatgacgat ggcgttgtcg tcgtgcagcg cgccgccgcc   540
cgcgacgtcg tcgccgcctc ggaacaaagg attcgcaagg aagaagccac acgtgagcgt   600
ctggtgcgcg gtgaactcgg cctcgatatc tacggcctgc gcgcaaaact caccgaattg   660
ggtgtcacgt acttgtag                                                678

<210> SEQ ID NO 250
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase
<220> FEATURE:
<221> NAME/KEY: SITE
<222> LOCATION: (2)...(5)
<223> OTHER INFORMATION: N-glycosylation site. Prosite id = PS00001

<400> SEQUENCE: 250

Met Asn Lys Ser Val Val Arg Asn Val Glu Gln Pro Pro Ala Asp
1                5                  10                  15

Ala Met Ala Ala Leu Glu Lys Tyr Gly Val Ser Thr Val His Glu Ala
                20                  25                  30

Gln Gly Arg Cys Gly Leu Leu Ala Ser Tyr Met Arg Pro Ile Phe Gly
            35                  40                  45
```

Gly Ala Ser Val Ala Gly Pro Ala Val Thr Val Ser Val Pro Pro Gly
 50                  55                  60

Asp Asn Leu Met Ile His Val Ala Val Glu Val Cys Arg Pro Gly Asp
 65                  70                  75                  80

Ile Leu Val Val Ala Pro Thr Ser Pro Cys Thr Asp Gly Tyr Phe Gly
                 85                  90                  95

Glu Leu Leu Ala Thr Ser Leu Arg Ala His Gly Val Lys Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Ile Ser Ser Gln Gly Thr Val Lys Ser Thr
130                 135                 140

Val Gly Ser Val Asn Val Pro Val Val Cys Ala Gly Ala Leu Ile Ala
145                 150                 155                 160

Pro Gly Asp Val Met Val Ala Asp Asp Gly Val Val Val Gln
                165                 170                 175

Arg Ala Ala Arg Asp Val Val Ala Ala Ser Glu Gln Arg Ile Arg
            180                 185                 190

Lys Glu Glu Ala Thr Arg Glu Arg Leu Val Arg Gly Glu Leu Gly Leu
        195                 200                 205

Asp Ile Tyr Gly Leu Arg Ala Lys Leu Thr Glu Leu Gly Val Thr Tyr
210                 215                 220

Leu
225

<210> SEQ ID NO 251
<211> LENGTH: 693
<212> TYPE: DNA
<213> ORGANISM: Unknown
<220> FEATURE:
<223> OTHER INFORMATION: DNA obtained from environmental sample

<400> SEQUENCE: 251
atgaacaagc cggcattcgt tcgccccgta gttgttcgca atgtcgagca accttctgcc      60
gacgcggtag ccgcgctcga aaatatggc gtctcgaccg ttcatgaagc gcagggccgc     120
tgtggcttgc tcgcttcctg tatccgcccg attttcgcgg gcgccgccgt cgccggtccc     180
gtggtcaccg tttccgtgcc gccagggac aacctgatga ttcacgtcgc agtggaagtc     240
tgccgcccgg gagatatcct cgtcgtagcc ccaacgtctc cttgcaccga cggctacttc     300
ggcgaactat tggccacttc gcttcgcgcg cacggcgtca agggcttgat tattgacgcc     360
ggctgccgtg acgtccgcgc cctcaccgaa atgaaatttc ccgtctggag ccgcgccgtc     420
agttcgcaag cactgtcaa atccacgtta ggctcggtga atgtttcagt cgtctgtgcc     480
ggcgcactgg tcgcacccgg cgacgtcatc gtcgccgatg acgacggagt ggtcgtcgtc     540
cagcgcgctg ccgcccgcga ggtagtcgcc gccgcagaac aaaggattcg caaggaagaa     600
gccactcgcg aacgcctcgc gcgcggtgaa ctcggtctcg atatctacag cctgcgcgca     660
aaactcaccg aactcggcct cacctacttg tga                                  693

<210> SEQ ID NO 252
<211> LENGTH: 230
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN

```
<222> LOCATION: (27)...(179)
<223> OTHER INFORMATION: Demethylmenaquinone methyltransferase
<220> FEATURE:
<221> NAME/KEY: SITE
<222> LOCATION: (156)...(159)
<223> OTHER INFORMATION: N-glycosylation site. Prosite id = PS00001

<400> SEQUENCE: 252
```

| | | | | | | | | | | | | | | | |
|---|---|---|---|---|---|---|---|---|---|---|---|---|---|---|---|
| Met | Asn | Lys | Pro | Ala | Phe | Val | Arg | Pro | Val | Val | Arg | Asn | Val | Glu | |
| 1 | | | | 5 | | | | | 10 | | | | | 15 | |
| Gln | Pro | Ser | Ala | Asp | Ala | Val | Ala | Ala | Leu | Glu | Lys | Tyr | Gly | Val | Ser |
| | | | 20 | | | | | 25 | | | | | 30 | | |
| Thr | Val | His | Glu | Ala | Gln | Gly | Arg | Cys | Gly | Leu | Leu | Ala | Ser | Cys | Ile |
| | | 35 | | | | | 40 | | | | | 45 | | | |
| Arg | Pro | Ile | Phe | Ala | Gly | Ala | Ala | Val | Ala | Gly | Pro | Val | Val | Thr | Val |
| | 50 | | | | | 55 | | | | | 60 | | | | |
| Ser | Val | Pro | Pro | Gly | Asp | Asn | Leu | Met | Ile | His | Val | Ala | Val | Glu | Val |
| 65 | | | | | 70 | | | | 75 | | | | | 80 | |
| Cys | Arg | Pro | Gly | Asp | Ile | Leu | Val | Val | Ala | Pro | Thr | Ser | Pro | Cys | Thr |
| | | | | 85 | | | | | 90 | | | | | 95 | |
| Asp | Gly | Tyr | Phe | Gly | Glu | Leu | Leu | Ala | Thr | Ser | Leu | Arg | Ala | His | Gly |
| | | | 100 | | | | | 105 | | | | | 110 | | |
| Val | Lys | Gly | Leu | Ile | Ile | Asp | Ala | Gly | Cys | Arg | Asp | Val | Arg | Ala | Leu |
| | | 115 | | | | | 120 | | | | | 125 | | | |
| Thr | Glu | Met | Lys | Phe | Pro | Val | Trp | Ser | Arg | Ala | Val | Ser | Ser | Gln | Gly |
| 130 | | | | | 135 | | | | | 140 | | | | | |
| Thr | Val | Lys | Ser | Thr | Leu | Gly | Ser | Val | Asn | Val | Ser | Val | Cys | Ala | |
| 145 | | | | | 150 | | | | | 155 | | | | 160 | |
| Gly | Ala | Leu | Val | Ala | Pro | Gly | Asp | Val | Ile | Val | Ala | Asp | Asp | Gly | |
| | | | | 165 | | | | | 170 | | | | | 175 | |
| Val | Val | Val | Val | Gln | Arg | Ala | Ala | Arg | Glu | Val | Val | Ala | Ala | Ala | |
| | | | 180 | | | | | 185 | | | | | 190 | | |
| Glu | Gln | Arg | Ile | Arg | Lys | Glu | Glu | Ala | Thr | Arg | Glu | Arg | Leu | Ala | Arg |
| | | 195 | | | | | 200 | | | | | 205 | | | |
| Gly | Glu | Leu | Gly | Leu | Asp | Ile | Tyr | Ser | Leu | Arg | Ala | Lys | Leu | Thr | Glu |
| | 210 | | | | | 215 | | | | | 220 | | | | |
| Leu | Gly | Leu | Thr | Tyr | Leu | | | | | | | | | | |
| 225 | | | | | 230 | | | | | | | | | | |

```
<210> SEQ ID NO 253
<211> LENGTH: 702
<212> TYPE: DNA
<213> ORGANISM: Unknown
<220> FEATURE:
<223> OTHER INFORMATION: DNA obtained from environmental sample
<400> SEQUENCE: 253
atgagcggta tcgtcgtcca ggacttcgag cgcgcatcgc tcgccgacat caaggcgctc      60
gccgagttcg gcgtcgccac gatccacgag gcgcagggcc gcgttggcct gctcgcgtcg     120
tacatgcgcc cgatttatgc gggagctgca gccgccggca atgccgtcac cgtgtccggtg    180
ccgccgggcg acaactggat gatccacgtg gcggtggagg tgtgccgcga gggcgacatc     240
ctcgtggtgg cgccgacctc gccaaacgac aacggctact cggcgagct gctggcgtct     300
tcactgaaga gccgcggtgt gcgtgggctc gtcatcgagg ccggatgccg cgacgtgaag     360
ccctcaccg acatgaaatt cccggtgtgg tcgcgcgccg tgtccgcgca agggacagtc     420
aaggagagcc tcggcgatgt gaacctcccg cttgtcattg ccgggcagac ggtgaacccc     480
```

```
ggcgacgtga tcgtggctga cgacgacggc gttgtcatcg ttggccgcag cgaggtgcgc    540
gccgtgacga ccaaatcgcg cgagcgcgag gagaaggagg ccaagaaccg cttgcagctc    600
accagcggcc agctcggcat cgacatctat ggtatgcgcg gcaagctcaa ggaaaagggg    660
ctgcgctacg tgaagaacgc gagcgagttg aaggccaaat aa                      702
```

<210> SEQ ID NO 254
<211> LENGTH: 233
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (21)...(173)
<223> OTHER INFORMATION: Demethylmenaquinone methyltransferase
<220> FEATURE:
<221> NAME/KEY: SITE
<222> LOCATION: (229)...(232)
<223> OTHER INFORMATION: N-glycosylation site. Prosite id = PS00001

<400> SEQUENCE: 254

```
Met Ser Gly Ile Val Val Gln Asp Phe Glu Arg Ala Ser Leu Ala Asp
1               5                   10                  15

Ile Lys Ala Leu Ala Glu Phe Gly Val Ala Thr Ile His Glu Ala Gln
            20                  25                  30

Gly Arg Val Gly Leu Leu Ala Ser Tyr Met Arg Pro Ile Tyr Ala Gly
        35                  40                  45

Ala Ala Ala Ala Gly Asn Ala Val Thr Val Ser Val Pro Pro Gly Asp
    50                  55                  60

Asn Trp Met Ile His Val Ala Glu Val Cys Arg Glu Gly Asp Ile
65                  70                  75                  80

Leu Val Val Ala Pro Thr Ser Pro Asn Asp Asn Gly Tyr Phe Gly Glu
                85                  90                  95

Leu Leu Ala Ser Ser Leu Lys Ser Arg Gly Val Arg Gly Leu Val Ile
            100                 105                 110

Glu Ala Gly Cys Arg Asp Val Lys Pro Leu Thr Asp Met Lys Phe Pro
        115                 120                 125

Val Trp Ser Arg Ala Val Ser Ala Gln Gly Thr Val Lys Glu Ser Leu
    130                 135                 140

Gly Asp Val Asn Leu Pro Leu Val Ile Ala Gly Gln Thr Val Asn Pro
145                 150                 155                 160

Gly Asp Val Ile Val Ala Asp Asp Gly Val Val Ile Val Gly Arg
                165                 170                 175

Ser Glu Val Arg Ala Val Thr Thr Lys Ser Arg Glu Arg Glu Lys
            180                 185                 190

Glu Ala Lys Asn Arg Leu Gln Leu Thr Ser Gly Gln Leu Gly Ile Asp
        195                 200                 205

Ile Tyr Gly Met Arg Gly Lys Lys Glu Lys Gly Leu Arg Tyr Val
    210                 215                 220

Lys Asn Ala Ser Glu Leu Lys Ala Lys
225                 230
```

<210> SEQ ID NO 255
<211> LENGTH: 681
<212> TYPE: DNA
<213> ORGANISM: Unknown
<220> FEATURE:
<223> OTHER INFORMATION: DNA obtained from environmental sample

<400> SEQUENCE: 255

-continued

```
atgaacgatc cgatcgtcgt tcgacagatc gacagaccat caggcccttc ggtcgatagt      60
ctgcgtcgct ttggcgtctc gaccgtgcac gaggcacagg ggcgccgcgg gctgctcgcg     120
tcgcacatgc ggccgattta cgccggtgcg ctcgtcgctg tccagcgat cactgtcctg      180 gtgccgccgg gcgacaacct gatgattcac gtcgcggtgg aggtgtgcca gccgggtgac     240
gttctcgttg ttgctccgac gtcgccgtgc accgacggct atttcggcga gctgctggcg     300
acctcgctgc gggctcgtgg cgtggcggga ctcatcatcg acgccggttg ccgggatgtt     360
cgggcgctga gcgagatgcg atttcccgtc tggagtcgcg cgatcagcgc gcagggtacc     420
gtcaaggcga cgctgggttc ggtgaacgtg cccctggtgt gcgccggggc gctggtcgag     480
gcgggagaca ttgtcgtcgc cgacgatgac ggcgtcgtga tcgtcaagaa ggatcaggtc     540
gatgcggtca ctcaggcagc cgaacagcgc gtgcgcaaag aagaggacac acgggcgcgg     600
ttggcgcgag cgagctcgg cctggacatc tacgccttgc gcaagaagct gtcggacctc      660
gggctgaagt cgtcgtcgtg a                                              681
```

<210> SEQ ID NO 256
<211> LENGTH: 226
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 256

```
Met Asn Asp Pro Ile Val Val Arg Gln Ile Asp Arg Pro Ser Gly Pro
1               5                   10                  15

Ser Val Asp Ser Leu Arg Arg Phe Gly Val Ser Thr Val His Glu Ala
            20                  25                  30

Gln Gly Arg Arg Gly Leu Leu Ala Ser His Met Arg Pro Ile Tyr Ala
        35                  40                  45

Gly Ala Leu Val Ala Gly Pro Ala Ile Thr Val Leu Val Pro Pro Gly
    50                  55                  60

Asp Asn Leu Met Ile His Val Ala Val Glu Val Cys Gln Pro Gly Asp
65                  70                  75                  80

Val Leu Val Val Ala Pro Thr Ser Pro Cys Thr Asp Gly Tyr Phe Gly
                85                  90                  95

Glu Leu Leu Ala Thr Ser Leu Arg Ala Arg Gly Val Ala Gly Leu Ile
            100                 105                 110

Ile Asp Ala Gly Cys Arg Asp Val Arg Ala Leu Ser Glu Met Arg Phe
        115                 120                 125

Pro Val Trp Ser Arg Ala Ile Ser Ala Gln Gly Thr Val Lys Ala Thr
    130                 135                 140

Leu Gly Ser Val Asn Val Pro Leu Val Cys Ala Gly Ala Leu Val Glu
145                 150                 155                 160

Ala Gly Asp Ile Val Val Ala Asp Asp Gly Val Val Ile Val Lys
                165                 170                 175

Lys Asp Gln Val Asp Ala Val Thr Gln Ala Ala Glu Gln Arg Val Arg
            180                 185                 190

Lys Glu Glu Asp Thr Arg Ala Arg Leu Ala Arg Gly Glu Leu Gly Leu
        195                 200                 205

Asp Ile Tyr Ala Leu Arg Lys Lys Leu Ser Asp Leu Gly Leu Lys Ser
    210                 215                 220
```

Ser Ser
225

<210> SEQ ID NO 257
<211> LENGTH: 678
<212> TYPE: DNA
<213> ORGANISM: Unknown
<220> FEATURE:
<223> OTHER INFORMATION: DNA obtained from environmental sample

<400> SEQUENCE: 257

```
atgaacgatc ccttcgtcgt tcgacaggtg gaccgaccgt cagctgcgtc gatcgacgat      60
ctgcggcgat tcggcgtctc gaccgtgcac gaggcccagg ggcgccgcgg gttgctcgca     120
tcgtacatgc ggccgatcta caccggtgcg ctcgtcgccg tcctgccat cacggtcctg      180
gtggcgccgg gcgacaacct gatgatccac gtcgcggtgg aggtgtgcca gcctggtgat     240
gtcctcgtcg tcgccccgac gtcgccatgc acggacgggt atttcggcga actgctggcg     300
acctcgttgc gggctcgcgg cgtcgcaggg ctcatcatcg acgccggctg ccgcgatgtt     360
cgagcgttga gcgagatgcg gtttcccgtc tggagtcgcg cgatcagcgc gcagggcacc     420
gtcaaggcga cgctgggttc ggtgaatgtg ccgctgatgt gcgccggaac gctggtcgag     480
gccggagacg tgatcgtggc cgatgatgac ggcgtcgtgg tcgtcaagcg ggagcaggtc     540
gatgccgtaa cgcaggccgc cgaacagcgc gtgcgaaagg aagaggacac acgggcacgg     600
ctcgcgcgag gcgagctggg cctcgacatc tacggcttgc gcaagaaact gtcggacctc     660
ggtttgaagt cgtcgtga                                                   678
```

<210> SEQ ID NO 258
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 258

Met Asn Asp Pro Phe Val Val Arg Gln Val Asp Arg Pro Ser Ala Ala
1               5                   10                  15

Ser Ile Asp Asp Leu Arg Arg Phe Gly Val Ser Thr Val His Glu Ala
                20                  25                  30

Gln Gly Arg Arg Gly Leu Leu Ala Ser Tyr Met Arg Pro Ile Tyr Thr
            35                  40                  45

Gly Ala Leu Val Ala Gly Pro Ala Ile Thr Val Leu Val Ala Pro Gly
        50                  55                  60

Asp Asn Leu Met Ile His Val Ala Val Glu Val Cys Gln Pro Gly Asp
65                  70                  75                  80

Val Leu Val Val Ala Pro Thr Ser Pro Cys Thr Asp Gly Tyr Phe Gly
                85                  90                  95

Glu Leu Leu Ala Thr Ser Leu Arg Ala Arg Gly Val Ala Gly Leu Ile
            100                 105                 110

Ile Asp Ala Gly Cys Arg Asp Val Arg Ala Leu Ser Glu Met Arg Phe
        115                 120                 125

Pro Val Trp Ser Arg Ala Ile Ser Ala Gln Gly Thr Val Lys Ala Thr
    130                 135                 140

Leu Gly Ser Val Asn Val Pro Leu Met Cys Ala Gly Thr Leu Val Glu

```
145                 150                 155                 160
Ala Gly Asp Val Ile Val Ala Asp Asp Gly Val Val Val Lys
                165                 170                 175

Arg Glu Gln Val Asp Ala Val Thr Gln Ala Ala Glu Gln Arg Val Arg
            180                 185                 190

Lys Glu Glu Asp Thr Arg Ala Arg Leu Ala Arg Gly Glu Leu Gly Leu
        195                 200                 205

Asp Ile Tyr Gly Leu Arg Lys Lys Leu Ser Asp Leu Gly Leu Lys Ser
    210                 215                 220

Ser
225

<210> SEQ ID NO 259
<211> LENGTH: 579
<212> TYPE: DNA
<213> ORGANISM: Unknown
<220> FEATURE:
<223> OTHER INFORMATION: DNA obtained from environmental sample

<400> SEQUENCE: 259
atgcggccca tctatgccgg tgcggcggcc gccggcagcg ccgtcaccgt atccgtacct      60
ccgggcgaca actggatgat ccacgtggcc gtcgaagtct gccgcgaagg cgacgtgctg     120
gtcgtcgccc caacctcgcc atgcgataac ggctacttcg gcgagctgct cgccagctcg     180
ctcaagtccc gtggcgtgcg cgggcttgtc atcgaggcag gctgtcgcga cgtgagagca     240
ctctcggata tgaaattccc ggtctggtcg cgggccgtct ccgcgcaagg cactgtgaag     300
gaaagcctgg gcgacgtgaa cctgccgctc gtgatcgccg acagctcgt caatccgggc      360 gatgtcgtgg ttgccgacga cgacggcgtc gtcgtcgtgg cgcggttaga agcgcgcgcc     420
gtgaccgcca agtcgcacga acgggagcag aaagaagcag ccaaccgcga gcagctgagc     480
aagggtgagc tcggcatcga tacctacggc atgcgcaaga agctcgccga caaggggctg     540
cgctacgtcg ccaccgccga agaactcaag gcgaagtga                             579

<210> SEQ ID NO 260
<211> LENGTH: 192
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (1)...(132)
<223> OTHER INFORMATION: Demethylmenaquinone methyltransferase

<400> SEQUENCE: 260

Met Arg Pro Ile Tyr Ala Gly Ala Ala Ala Gly Ser Ala Val Thr
1               5                   10                  15

Val Ser Val Pro Pro Gly Asp Asn Trp Met Ile His Val Ala Val Glu
            20                  25                  30

Val Cys Arg Glu Gly Asp Val Leu Val Ala Pro Thr Ser Pro Cys
        35                  40                  45

Asp Asn Gly Tyr Phe Gly Glu Leu Leu Ala Ser Ser Leu Lys Ser Arg
    50                  55                  60

Gly Val Arg Gly Leu Val Ile Glu Ala Gly Cys Arg Asp Val Arg Ala
65                  70                  75                  80

Leu Ser Asp Met Lys Phe Pro Val Trp Ser Arg Ala Val Ser Ala Gln
                85                  90                  95

Gly Thr Val Lys Glu Ser Leu Gly Asp Val Asn Leu Pro Leu Val Ile
```

```
                100             105             110
Ala Gly Gln Leu Val Asn Pro Gly Asp Val Val Ala Asp Asp
            115             120             125

Gly Val Val Val Ala Arg Leu Glu Ala Arg Ala Val Thr Ala Lys
    130             135             140

Ser His Glu Arg Glu Gln Lys Glu Ala Ala Asn Arg Glu Gln Leu Ser
145             150             155             160

Lys Gly Glu Leu Gly Ile Asp Thr Tyr Gly Met Arg Lys Lys Leu Ala
                165             170             175

Asp Lys Gly Leu Arg Tyr Val Ala Thr Ala Glu Glu Leu Lys Ala Lys
            180             185             190

<210> SEQ ID NO 261
<211> LENGTH: 678
<212> TYPE: DNA
<213> ORGANISM: Unknown
<220> FEATURE:
<223> OTHER INFORMATION: DNA obtained from environmental sample

<400> SEQUENCE: 261
atgaatcaac cggcggtagt ccgccacgtg gagcagccac ccgccgacgc ggttgcggcg    60
ctggagaagt atggtgtgac gaccgtgcat gaagctcagg gacgttgtgg cctccttgcc   120
gcgtacatgc gtccgatttt cccgggagcg gccatcgccg gctccgctgt caccgtgtcg   180
ttgcctcccg gcgacaacct catgatccat gtcgcggtcg aggtctgcag gccgggaaac   240
atcctggtcg tttcacccac ctcgcccttgt accgacggat acttcggtga actgttggca   300
acttctctgc gagctcacgg cgtgcaaggt cttgtgattg atgccggatg ccgcgacgtt   360
cgaccgctga ctgagatgaa attcccggtc tggagccgga ccatcagctc gcaggggacg   420
gtcaaggcca cactcggatc ggtcaatgtc ccgatcatgt gcgcgggcgc actcgtcgaa   480
gctggcgacg tcatcatcgc cgatgacgat ggggtcgtgg ttgtcaagcg tgcagacgcg   540
caccaggtcg ctgctgctgc ggaacaaagg gttcggaaag agaatgtgac ccgtgagcga   600
cttgcgcgtg gagagctagg actcgatatc tacgacatgc gccagaaaat cgcgcaactg   660
ggcctcaaat acctgtaa                                                 678

<210> SEQ ID NO 262
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 262

Met Asn Gln Pro Ala Val Val Arg His Val Glu Gln Pro Pro Ala Asp
1               5                   10                  15

Ala Val Ala Ala Leu Glu Lys Tyr Gly Val Thr Thr Val His Glu Ala
            20                  25                  30

Gln Gly Arg Cys Gly Leu Leu Ala Ala Tyr Met Arg Pro Ile Phe Pro
        35                  40                  45

Gly Ala Ala Ile Ala Gly Ser Ala Val Thr Val Ser Leu Pro Pro Gly
    50                  55                  60

Asp Asn Leu Met Ile His Val Ala Val Glu Val Cys Arg Pro Gly Asn
65                  70                  75                  80
```

```
Ile Leu Val Val Ser Pro Thr Ser Pro Cys Thr Asp Gly Tyr Phe Gly
            85                  90                  95
Glu Leu Leu Ala Thr Ser Leu Arg Ala His Gly Val Gln Gly Leu Val
            100                 105                 110
Ile Asp Ala Gly Cys Arg Asp Val Arg Pro Leu Thr Glu Met Lys Phe
            115                 120                 125
Pro Val Trp Ser Arg Thr Ile Ser Ser Gln Gly Thr Val Lys Ala Thr
            130                 135                 140
Leu Gly Ser Val Asn Val Pro Ile Met Cys Ala Gly Ala Leu Val Glu
145                 150                 155                 160
Ala Gly Asp Val Ile Ile Ala Asp Asp Gly Val Val Val Val Lys
                    165                 170                 175
Arg Ala Asp Ala His Gln Val Ala Ala Ala Glu Gln Arg Val Arg
                    180                 185                 190
Lys Glu Asn Val Thr Arg Glu Arg Leu Ala Arg Gly Glu Leu Gly Leu
            195                 200                 205
Asp Ile Tyr Asp Met Arg Gln Lys Ile Ala Gln Leu Gly Leu Lys Tyr
210                 215                 220
Leu
225

<210> SEQ ID NO 263
<211> LENGTH: 678
<212> TYPE: DNA
<213> ORGANISM: Unknown
<220> FEATURE:
<223> OTHER INFORMATION: DNA obtained from environmental sample

<400> SEQUENCE: 263
atgaataaac cggtggtagt tcgtcaagtg gagcagccac caacggatgc ggttacggca      60
ctagaaaagt atggcgtgac gaccgtgcat gaagcccagg acgttgtgg  cctccttgcc     120 tcctacatgc gtccgatttt tccgggagcg agcatcgcgg ttctgccgt  cactgtgtct     180 ttgcctcctg cgacaacct  gatgatccac gtggcggtcg aggtctgtgg tccgggaaat     240
atcctcgtcg tttcgccgac ttcgccttgt accgatggct acttcggtga attgttggcc     300
acttccctgc gtcccgagg  tgtccaagga ttagtcatcg atgccggatg ccgtgacgtc     360
cgctcgctga cggagatgaa attcccggtc tggagtcgtg ccatcagctc gcagggcaca     420
gtcaaagcca cccttggatc ggtgaacgtg ccgatcatgt gtgcgggtgc gtccgtggaa     480
gcgggcgatg taattgtggc cgatgatgat ggagttgttg tcgtgaagcg tgcggccgca     540
caagacgtcg ctgcggccgc ggaacaaagg gttcgcaagg aaaacgcgac ccgcgaacgt     600
cttgcacgcg gcgaactcgg actcgatatc tacgacatgc gccagaagat cgcgcagctg     660
ggcctcaaat atctgtga                                                  678

<210> SEQ ID NO 264
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 264

Met Asn Lys Pro Val Val Val Arg Gln Val Glu Gln Pro Pro Thr Asp
1               5                   10                  15
```

Ala Val Thr Ala Leu Glu Lys Tyr Gly Val Thr Thr Val His Glu Ala
        20                  25                  30

Gln Gly Arg Cys Gly Leu Leu Ala Ser Tyr Met Arg Pro Ile Phe Pro
            35                  40                  45

Gly Ala Ser Ile Ala Gly Ser Ala Val Thr Val Ser Leu Pro Pro Gly
    50                  55                  60

Asp Asn Leu Met Ile His Val Ala Val Glu Val Cys Gly Pro Gly Asn
65                  70                  75                  80

Ile Leu Val Val Ser Pro Thr Ser Pro Cys Thr Asp Gly Tyr Phe Gly
                85                  90                  95

Glu Leu Leu Ala Thr Ser Leu Arg Ala Arg Gly Val Gln Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Ile Ser Ser Gln Gly Thr Val Lys Ala Thr
130                 135                 140

Leu Gly Ser Val Asn Val Pro Ile Met Cys Ala Gly Ala Ser Val Glu
145                 150                 155                 160

Ala Gly Asp Val Ile Val Ala Asp Asp Gly Val Val Val Val Lys
                165                 170                 175

Arg Ala Ala Gln Asp Val Ala Ala Ala Glu Gln Arg Val Arg
            180                 185                 190

Lys Glu Asn Ala Thr Arg Glu Arg Leu Ala Arg Gly Glu Leu Gly Leu
                195                 200                 205

Asp Ile Tyr Asp Met Arg Gln Lys Ile Ala Gln Leu Gly Leu Lys Tyr
    210                 215                 220

Leu
225

<210> SEQ ID NO 265
<211> LENGTH: 678
<212> TYPE: DNA
<213> ORGANISM: Unknown
<220> FEATURE:
<223> OTHER INFORMATION: DNA obtained from environmental sample

<400> SEQUENCE: 265
atgacgggtc ctatcgtcgt gcgtcacatc gaacggccac cggcagctgc cgtggcacgg      60
ctgcaggagt acggcgtggc gacggtccac gaagcgcaag acgccgcgg gttgctggcc     120 gcctatatgc gaccgatcta tgcgggcgca gccattgcgg gccctgcggt cacggtgtcc     180
gttccgccgg cgacaaacct gatgatccac gtcgcggtgg aggtctgcca gccgggagac     240
gtgctcgtcg tcgctcccac gtcaccgtgc acggacggct acttcggcga gctgctcgcg     300
acctcgctgc aggctcatgg cgtcgtcgcg ctcgtcatcg acgccggatg ccagagatgtg    360 cgtgccatga cagagatgcg cttccccgtc tggagccgcg cagtcagttc gcagggcacc     420
gtgaaagcga cgctggggtc ggtgaacgtg ccggtggcat gtgcgggcac gctcgtgaat     480
cccggcgatg tcgtcatagc ggatgatgac ggcgttgtgg tggtgaggcg agacgaggtg     540
gaagagaccg tgagctcgtc ggaaaagcgg atccagaaag aggcgattac gcgagagcgg     600
ctcgccagcg cgagctcggg gctggatatc tacgggctgc ggaagaaact cgccgacctc     660
ggactgaagt actcataa                                                   678

<210> SEQ ID NO 266
<211> LENGTH: 225

```
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 266
```

Met Thr Gly Pro Ile Val Val Arg His Ile Glu Arg Pro Ala Ala
1               5                   10                  15

Ala Val Ala Arg Leu Gln Glu Tyr Gly Val Ala Thr Val His Glu Ala
            20                  25                  30

Gln Gly Arg Arg Gly Leu Leu Ala Ala Tyr Met Arg Pro Ile Tyr Ala
            35                  40                  45

Gly Ala Ala Ile Ala Gly Pro Ala Val Thr Val Ser Val Pro Pro Gly
        50                  55                  60

Asp Asn Leu Met Ile His Val Ala Val Glu Val Cys Gln Pro Gly Asp
65                  70                  75                  80

Val Leu Val Val Ala Pro Thr Ser Pro Cys Thr Asp Gly Tyr Phe Gly
                85                  90                  95

Glu Leu Leu Ala Thr Ser Leu Gln Ala His Gly Val Val Ala Leu Val
            100                 105                 110

Ile Asp Ala Gly Cys Arg Asp Val Arg Ala Met Thr Glu Met Arg Phe
        115                 120                 125

Pro Val Trp Ser Arg Ala Val Ser Ser Gln Gly Thr Val Lys Ala Thr
130                 135                 140

Leu Gly Ser Val Asn Val Pro Val Ala Cys Ala Gly Thr Leu Val Asn
145                 150                 155                 160

Pro Gly Asp Val Val Ile Ala Asp Asp Gly Val Val Val Arg
                165                 170                 175

Arg Asp Glu Val Glu Glu Thr Val Ser Ser Ser Glu Lys Arg Ile Gln
            180                 185                 190

Lys Glu Ala Ile Thr Arg Glu Arg Leu Ala Ser Gly Glu Leu Gly Leu
            195                 200                 205

Asp Ile Tyr Gly Leu Arg Lys Lys Leu Ala Asp Leu Gly Leu Lys Tyr
        210                 215                 220

Ser
225

```
<210> SEQ ID NO 267
<211> LENGTH: 678
<212> TYPE: DNA
<213> ORGANISM: Unknown
<220> FEATURE:
<223> OTHER INFORMATION: DNA obtained from environmental sample

<400> SEQUENCE: 267
atgaatacac cgttggtagt ccgacaagtc gagcagccac cagcggacgc ggttgcggca      60
ttggaaaagt gcggagtcac aaccgtgcat gaggctcagg acgtggtgg cctcttttgcc    120 tcctacatgc gcccgattta cccgggagca accatcgcag atccgccat cacagtgtct     180 gtgcctccgg cgacaaacct tatgatccat gtggctgtgg aagtctgcgg tgcgggaaac   240
atcctggtgg tttcaccaac ctccccttgt acggatggat acttcggtga gctgttggca    300
acatctcttc gcgcccacgg tgtgaggggg cttgtgatcg atgccggatg tcgtgatgtg    360
cgctctctga cggatatgaa atttccggtt tggagtcgca ccgtcagttc gcaagggaca    420
```

```
gtcaaggcca cactcggatc ggtgaatgta cccatcgttt gtgcgggcgc gatggttgag        480
gccggtgatg tgatcgtcgc cgacgacgat ggagttgtgg tggtgaagcg cgcgctggcg        540
ccagaggtcg ccgcggcggc gcaacaaagg gttcgcaaag agaatttggc ccgcgaacga        600
cttggacgcg gagaactcgg actcgacatt tatgacatgc gcgaaaagat cgcgaaactg        660
ggccttaagt atttgtaa                                                      678
```

```
<210> SEQ ID NO 268
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 268
```

```
Met Asn Thr Pro Leu Val Val Arg Gln Val Glu Gln Pro Pro Ala Asp
1               5                   10                  15

Ala Val Ala Ala Leu Glu Lys Cys Gly Val Thr Thr Val His Glu Ala
            20                  25                  30

Gln Gly Arg Gly Gly Leu Phe Ala Ser Tyr Met Arg Pro Ile Tyr Pro
        35                  40                  45

Gly Ala Thr Ile Ala Gly Ser Ala Ile Thr Val Ser Val Pro Pro Gly
    50                  55                  60

Asp Asn Leu Met Ile His Val Ala Val Glu Val Cys Gly Ala Gly Asn
65                  70                  75                  80

Ile Leu Val Val Ser Pro Thr Ser Pro Cys Thr Asp Gly Tyr Phe Gly
                85                  90                  95

Glu Leu Leu Ala Thr Ser Leu Arg Ala His Gly Val Arg Gly Leu Val
            100                 105                 110

Ile Asp Ala Gly Cys Arg Asp Val Arg Ser Leu Thr Asp Met Lys Phe
        115                 120                 125

Pro Val Trp Ser Arg Thr Val Ser Ser Gln Gly Thr Val Lys Ala Thr
    130                 135                 140

Leu Gly Ser Val Asn Val Pro Ile Val Cys Ala Gly Ala Met Val Glu
145                 150                 155                 160

Ala Gly Asp Val Ile Val Ala Asp Asp Gly Val Val Val Lys
                165                 170                 175

Arg Ala Leu Ala Pro Glu Val Ala Ala Ala Gln Gln Arg Val Arg
            180                 185                 190

Lys Glu Asn Leu Ala Arg Glu Arg Leu Gly Arg Gly Glu Leu Gly Leu
        195                 200                 205

Asp Ile Tyr Asp Met Arg Glu Lys Ile Ala Lys Leu Gly Leu Lys Tyr
    210                 215                 220

Leu
225
```

```
<210> SEQ ID NO 269
<211> LENGTH: 678
<212> TYPE: DNA
<213> ORGANISM: Unknown
<220> FEATURE:
<223> OTHER INFORMATION: DNA obtained from environmental sample

<400> SEQUENCE: 269
atgaacacac cggtcgtagt ccggcaagtg gagcaaccat caatggatgt gattgcagcc        60
```

```
ctggagaaac atggtgtgac gaccgtacat gaggcccagg gacgttgtgg cctgctggcg    120
tgttacatgc gtccgatttt ccccggagcg agcatcgctg gttccgcggt cactgtttct    180 ttgcccccg gcgataatct tatgatccac gttgcggtcg aggtctgcag tccagggaac     240
atccttgtag ttgccccgac ctcgccttgc acggatggct atttcggaga attgttggca    300
acttccctgc gcgctcgcgg tgtgaaaggt ctcgtgattg atgccggatg ccgtgatgtt    360
cgctctttga cggaaatgaa gttcccggtc tggagccgag cgatcagctc gcagggaacg    420
gtcaaatcta cactcggctc cgtgaacgtg cctatcctgt gcgcgggcgc actcgtcgag    480
gccggcgata tcatcgccgc cgatgacgac ggcgttgtcg ttgtcaagcg cgcaatggcg    540
caggaggtcg ccacggcggc agaacaaagg gtgcgcaaag agaatgtgac ccgagagcgt    600
cttgcgcggg gagatctcgg gctcgatatc tacgacatgc ggcagaaact cgcccaactg    660
ggcctcaaat atctgtga                                                  678
```

<210> SEQ ID NO 270
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 270

```
Met Asn Thr Pro Val Val Arg Gln Val Glu Gln Pro Ser Met Asp
1               5                   10                  15

Val Ile Ala Ala Leu Glu Lys His Gly Val Thr Thr Val His Glu Ala
            20                  25                  30

Gln Gly Arg Cys Gly Leu Leu Ala Cys Tyr Met Arg Pro Ile Phe Pro
        35                  40                  45

Gly Ala Ser Ile Ala Gly Ser Ala Val Thr Val Ser Leu Pro Pro Gly
    50                  55                  60

Asp Asn Leu Met Ile His Val Ala Val Glu Val Cys Ser Pro Gly Asn
65                  70                  75                  80

Ile Leu Val Val Ala Pro Thr Ser Pro Cys Thr Asp Gly Tyr Phe Gly
                85                  90                  95

Glu Leu Leu Ala Thr Ser Leu Arg Ala Arg Gly Val Lys Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Ile Ser Ser Gln Gly Thr Val Lys Ser Thr
    130                 135                 140

Leu Gly Ser Val Asn Val Pro Ile Leu Cys Ala Gly Ala Leu Val Glu
145                 150                 155                 160

Ala Gly Asp Ile Ile Ala Ala Asp Asp Gly Val Val Val Lys
                165                 170                 175

Arg Ala Met Ala Gln Glu Val Ala Thr Ala Ala Glu Gln Arg Val Arg
            180                 185                 190

Lys Glu Asn Val Thr Arg Glu Arg Leu Ala Arg Gly Asp Leu Gly Leu
        195                 200                 205

Asp Ile Tyr Asp Met Arg Gln Lys Leu Ala Gln Leu Gly Leu Lys Tyr
    210                 215                 220

Leu
```

```
<210> SEQ ID NO 271
<211> LENGTH: 678
<212> TYPE: DNA
<213> ORGANISM: Unknown
<220> FEATURE:
<223> OTHER INFORMATION: DNA obtained from environmental sample

<400> SEQUENCE: 271
atgaaccaag ccgtggtggt ccggaatatc gagcgcccgc cgcggatgt agttgctgcg     60 ttggagaaac ttggtgtttc cacggtgcac gaggcgcagg acgttgcgg tctgttcgct    120 acgtatatga ggccgattta tgcgggtgcg gcgattgccg gccggcggt taccgtatcg    180 ttgccgccgg gtgacaattt gatgattcac gtggccgtgg aagtgtgccg cgcggggga c   240 attttggtgg tcgcgccgac ttcgccttgc acggacgggt atttcggcga attgctggcg    300
acttcgttgc gcgcacatgg cgtcaagggc ctggtgatcg atgcggggtg ccgcgacgtc    360
cgagcgctcg cggagatgaa atttcccgtg tggagccgcg cagtaagttc gcagggaacg    420
gtgaagtcga cccttggttc ggtaaacgtc ggaattgtgt gcgcaggagc acgcgtggaa    480
gccggagacg tgatcgttgc cgacgatgac ggcgtagtgg gggtgaagtg cggcgcagcg    540
caggaagtgg ttgccgcggc gcagctgcgc gttcgcaagg aagaggccac gcgcgaacgc    600
ttggggcgtg gcgagctcgg cctggatatc cacgggctgc gggccaaggt cgcggagctt    660
ggcctgaaat atttgtga                                                   678

<210> SEQ ID NO 272
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 272
```

Met Asn Gln Ala Val Val Val Arg Asn Ile Glu Arg Pro Pro Ala Asp
1               5                  10                  15

Val Val Ala Ala Leu Glu Lys Leu Gly Val Ser Thr Val His Glu Ala
                20                  25                  30

Gln Gly Arg Cys Gly Leu Phe Ala Thr Tyr Met Arg Pro Ile Tyr Ala
            35                  40                  45

Gly Ala Ala Ile Ala Gly Pro Ala Val Thr Val Ser Leu Pro Pro Gly
        50                  55                  60

Asp Asn Leu Met Ile His Val Ala Val Glu Val Cys Arg Ala Gly Asp
65                  70                  75                  80

Ile Leu Val Val Ala Pro Thr Ser Pro Cys Thr Asp Gly Tyr Phe Gly
                85                  90                  95

Glu Leu Leu Ala Thr Ser Leu Arg Ala His Gly Val Lys Gly Leu Val
            100                 105                 110

Ile Asp Ala Gly Cys Arg Asp Val Arg Ala Leu Ala Glu Met Lys Phe
        115                 120                 125

Pro Val Trp Ser Arg Ala Val Ser Ser Gln Gly Thr Val Lys Ser Thr
    130                 135                 140

Leu Gly Ser Val Asn Val Gly Ile Val Cys Ala Gly Ala Arg Val Glu
145                 150                 155                 160

```
Ala Gly Asp Val Ile Val Ala Asp Asp Gly Val Val Gly Val Lys
            165                 170                 175

Cys Gly Ala Ala Gln Glu Val Val Ala Ala Gln Leu Arg Val Arg
        180                 185                 190

Lys Glu Glu Ala Thr Arg Glu Arg Leu Gly Arg Gly Glu Leu Gly Leu
    195                 200                 205

Asp Ile His Gly Leu Arg Ala Lys Val Ala Glu Leu Gly Leu Lys Tyr
    210                 215                 220

Leu
225

<210> SEQ ID NO 273
<211> LENGTH: 678
<212> TYPE: DNA
<213> ORGANISM: Unknown
<220> FEATURE:
<223> OTHER INFORMATION: DNA obtained from environmental sample

<400> SEQUENCE: 273
atgaacaagc ccgtggttgt gcggaacatc gagcgtccgc cggcggatgc tgtggccgcg    60
cttgagaaat acggcgtgtc gacggtgcac gaggcccagg gccggaacgg cctactggcc   120
tcctatatgc gcccgatcta tgcaggagcc gcgatcgctg gaccagccgt cacagtttcc   180
ctcccgccgg gagacaacct gatgattcac gtcgccgtcg aggtctgtcg acctggggat   240
gtcctcgttg ttgcgccgac atcgccatgc accgacggct attttggcga gttgcttgca   300
acttcgctcg cggcgcatgg ggtgaaaggc ttgatcattg aggcgggatg tcgcgacgtc   360
cgagctctga cggaaatgaa gtttccagtc tggagccgcg ccgtcagctc gcaaggaacg   420
gtgaaggcaa cacttgggtc ggtaaatgta acgattgttt gtgcgggtgc tgcggttgcg   480
cccggtgatg tgatcgtggc ggacgatgat ggcgtcgttg tcgtgaaacg gacagaggcg   540
caagaggtcg ttaccgcatc tgagcagaga ttgcgaaagg aagagggaac ccgcaagcgg   600
cttgcttcgg gggaactcgg cctggatatt tacggcctgc gagcgaagat tgcagacctc   660
ggtctcaagt acttgtag                                                 678

<210> SEQ ID NO 274
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase
<220> FEATURE:
<221> NAME/KEY: SITE
<222> LOCATION: (151)...(154)
<223> OTHER INFORMATION: N-glycosylation site. Prosite id = PS00001

<400> SEQUENCE: 274

Met Asn Lys Pro Val Val Arg Asn Ile Glu Arg Pro Pro Ala Asp
1               5                   10                  15

Ala Val Ala Ala Leu Glu Lys Tyr Gly Val Ser Thr Val His Glu Ala
            20                  25                  30

Gln Gly Arg Asn Gly Leu Leu Ala Ser Tyr Met Arg Pro Ile Tyr Ala
        35                  40                  45

Gly Ala Ala Ile Ala Gly Pro Ala Val Thr Val Ser Leu Pro Pro Gly
    50                  55                  60

Asp Asn Leu Met Ile His Val Ala Val Glu Val Cys Arg Pro Gly Asp
```

```
                65                  70                  75                  80
Val Leu Val Val Ala Pro Thr Ser Pro Cys Thr Asp Gly Tyr Phe Gly
                    85                  90                  95

Glu Leu Leu Ala Thr Ser Leu Ala Ala His Gly Val Lys Gly Leu Ile
            100                 105                 110

Ile Glu Ala Gly Cys Arg Asp Val Arg Ala Leu Thr Glu Met Lys Phe
        115                 120                 125

Pro Val Trp Ser Arg Ala Val Ser Ser Gln Gly Thr Val Lys Ala Thr
    130                 135                 140

Leu Gly Ser Val Asn Val Thr Ile Val Cys Ala Gly Ala Ala Val Ala
145                 150                 155                 160

Pro Gly Asp Val Ile Val Ala Asp Asp Gly Val Val Val Lys
            165                 170                 175

Arg Thr Glu Ala Gln Glu Val Val Thr Ala Ser Glu Gln Arg Leu Arg
            180                 185                 190

Lys Glu Glu Gly Thr Arg Lys Arg Leu Ala Ser Gly Glu Leu Gly Leu
                195                 200                 205

Asp Ile Tyr Gly Leu Arg Ala Lys Ile Ala Asp Leu Gly Leu Lys Tyr
    210                 215                 220

Leu
225

<210> SEQ ID NO 275
<211> LENGTH: 690
<212> TYPE: DNA
<213> ORGANISM: Unknown
<220> FEATURE:
<223> OTHER INFORMATION: DNA obtained from environmental sample

<400> SEQUENCE: 275
atgcctatcg ttgttacgaa gatcgaccga cccagcgcgg cggacgtcga aaggatcgcc      60
gcctatggtg tcgcgacctt gcatgaagcg caaggacgaa ccgggttgat ggcgtccaat     120
atgcgcccaa tctatcgccc tgcgcacatt gccgggcccg cggtgacctg ccttgtggcg     180
cctggcgaca attggatgat ccatgtcgcc gtcgaacagt gccagccggg agatgtcctg     240
gtcgtggtac cgaccagccc ctgcgaagac ggctatttcg gcgatctgct ggcgacctcg     300
ctgcggtcgc gcggggtcaa aggtctgatc atcgaggccg cgtacgcga tatcgcgaca      360 ttgaccgaga tgaaattccc ggtctggtcc aaggcggtgt cgcgcaagg aacggtcaag     420 gagaccatcg ccagcgtcaa tgtgccccct cgtctgcgcg gcgcccgcat cgtgccgggc     480
gatctgatcg ttgccgacga cgacggggtc gtcgtgattc aagacgttc cgttccggcg     540 gtcctttcca gcgccgaggc ccgcgaagag aaggaagccc gcaaccgcgc cgcttcgaa      600 gctggcgagc tgggcctcga cgtctacaac atgcgccagc gcctggccga caagggcttg     660
cgctatgtcg agcggctgcc cgaggaatag                                      690

<210> SEQ ID NO 276
<211> LENGTH: 229
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 276
```

```
Met Pro Ile Val Val Thr Lys Ile Asp Arg Pro Ser Ala Ala Asp Val
1               5                   10                  15

Glu Arg Ile Ala Ala Tyr Gly Val Ala Thr Leu His Glu Ala Gln Gly
            20                  25                  30

Arg Thr Gly Leu Met Ala Ser Asn Met Arg Pro Ile Tyr Arg Pro Ala
        35                  40                  45

His Ile Ala Gly Pro Ala Val Thr Cys Leu Val Ala Pro Gly Asp Asn
    50                  55                  60

Trp Met Ile His Val Ala Val Glu Gln Cys Gln Pro Gly Asp Val Leu
65              70                  75                  80

Val Val Val Pro Thr Ser Pro Cys Glu Asp Gly Tyr Phe Gly Asp Leu
                85                  90                  95

Leu Ala Thr Ser Leu Arg Ser Arg Gly Val Lys Gly Leu Ile Ile Glu
            100                 105                 110

Ala Gly Val Arg Asp Ile Ala Thr Leu Thr Glu Met Lys Phe Pro Val
        115                 120                 125

Trp Ser Lys Ala Val Phe Ala Gln Gly Thr Val Lys Glu Thr Ile Ala
    130                 135                 140

Ser Val Asn Val Pro Leu Val Cys Ala Gly Ala Arg Ile Val Pro Gly
145                 150                 155                 160

Asp Leu Ile Val Ala Asp Asp Gly Val Val Ile Pro Arg Arg
                165                 170                 175

Ser Val Pro Ala Val Leu Ser Ser Ala Glu Ala Arg Glu Glu Lys Glu
                180                 185                 190

Ala Arg Asn Arg Ala Arg Phe Glu Ala Gly Glu Leu Gly Leu Asp Val
            195                 200                 205

Tyr Asn Met Arg Gln Arg Leu Ala Asp Lys Gly Leu Arg Tyr Val Glu
        210                 215                 220

Arg Leu Pro Glu Glu
225
```

<210> SEQ ID NO 277
<211> LENGTH: 678
<212> TYPE: DNA
<213> ORGANISM: Unknown
<220> FEATURE:
<223> OTHER INFORMATION: DNA obtained from environmental sample

<400> SEQUENCE: 277

```
atgaatacac cggtggtagt ccgacaagtg gagcagccac cagcggatgc ggttgccgca      60
ttggagaagt gtggagtgac caccgtgcat gaggcgcagg gacgctgcgg cctccttgcg     120
tcctacatgc gcccaattta cccgggagca gccatcgccg gttccgctat cactgtgtct     180
ttgcctcctg gcgacaacct catgatccat gttgcggtgg aggtctgcag tccgggaaat     240
atcctggtag tttcaccggc ctcgccttgt accgatggct acttcggtga gctgttggcg     300
acgtctctcc gtgcccacgg cgtgagaggg cttgtgatcg aggcgggatg ccgtgacgtg     360
cgctctctaa cagaaatgaa attcccggtc tggagccgcg ccatcagttc gcagggggaca     420
gtcaaggcta cacttggatc ggtaaacgtg cccatcgtgt gcgcgggcgc acgggtcgag     480
gctggtgatg tcatcgtcgc cgatgacgat ggagtggtgg ttgtgaagcg ggcgcttgcg     540
caagaggtcg ccgcggcggc ggaacaaagg gttcgcaaag agaatgcgac ccgcgaacga     600
cttgcgcgcg gagaactcgg actcgatatt tacgacctgc gccaaaagat cgctcaactg     660
ggccttaaat atctgtga                                                    678
```

```
<210> SEQ ID NO 278
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 278

Met Asn Thr Pro Val Val Arg Gln Val Glu Gln Pro Pro Ala Asp
1               5                   10                  15

Ala Val Ala Ala Leu Glu Lys Cys Gly Val Thr Val His Glu Ala
                20                  25                  30

Gln Gly Arg Cys Gly Leu Leu Ala Ser Tyr Met Arg Pro Ile Tyr Pro
            35                  40                  45

Gly Ala Ala Ile Ala Gly Ser Ala Ile Thr Val Ser Leu Pro Pro Gly
        50                  55                  60

Asp Asn Leu Met Ile His Val Ala Val Glu Val Cys Ser Pro Gly Asn
65                  70                  75                  80

Ile Leu Val Val Ser Pro Ala Ser Pro Cys Thr Asp Gly Tyr Phe Gly
                85                  90                  95

Glu Leu Leu Ala Thr Ser Leu Arg Ala His Gly Val Arg Gly Leu Val
            100                 105                 110

Ile Glu Ala Gly Cys Arg Asp Val Arg Ser Leu Thr Glu Met Lys Phe
        115                 120                 125

Pro Val Trp Ser Arg Ala Ile Ser Ser Gln Gly Thr Val Lys Ala Thr
    130                 135                 140

Leu Gly Ser Val Asn Val Pro Ile Val Cys Ala Gly Ala Arg Val Glu
145                 150                 155                 160

Ala Gly Asp Val Ile Val Ala Asp Asp Gly Val Val Val Val Lys
                165                 170                 175

Arg Ala Leu Ala Gln Glu Val Ala Ala Ala Glu Gln Arg Val Arg
            180                 185                 190

Lys Glu Asn Ala Thr Arg Glu Arg Leu Ala Arg Gly Glu Leu Gly Leu
        195                 200                 205

Asp Ile Tyr Asp Leu Arg Gln Lys Ile Ala Gln Leu Gly Leu Lys Tyr
    210                 215                 220

Leu
225

<210> SEQ ID NO 279
<211> LENGTH: 678
<212> TYPE: DNA
<213> ORGANISM: Unknown
<220> FEATURE:
<223> OTHER INFORMATION: DNA obtained from environmental sample

<400> SEQUENCE: 279
atgaataaac cggtggtagt gcggcaagtc gagcagccac ccgccgatgc ggttgcggcc      60
ctggagaagt atggcgtgac caccgtgcac gaagctcaag cgcgttgtgg cctgctggct     120
ccctatatgc gcccgatttt tgcgggagca tgcatcgccg gttccgccgt gaccgtgtct     180
ttgccgcctg gcgataatct catgatccac gttgccgtcg aggtctgcac tccgggcagc     240
attctggtag ttgcccccac ctcgcccttg cacgacggtt atttcgggga actcctggca     300
acttccctgc tcgctcacgg tgtcaaagga ttggtcatcg atgctggctg tcgggatgtt     360
```

```
cgctcgttaa cggaaatgaa attccccgtc tggagccgtg ctgtcagttc tcaaggaacg    420
gtgaaggcca cgctcggatc ggtgaatgtg ccggtcattt gcgcgggcgc ggaggtggag    480
gctggcgata tcatcatcgc cgatgatgat ggtgtggtgg tggtgaagcg cacgctggcg    540
cacgaggtgg cagcggcggc ggaactacgg gttcgcaagg agaatgccac cgcgaacga    600 ctcgcacgag gggatctcgg cctcgatatc tacgacatgc ggcaaaaaat cgcgcaactt    660
ggtctcaaat atctgtga                                                  678
```

```
<210> SEQ ID NO 280
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 280
```

```
Met Asn Lys Pro Val Val Arg Gln Val Glu Gln Pro Ala Asp
1               5                   10                  15

Ala Val Ala Ala Leu Glu Lys Tyr Gly Val Thr Thr Val His Glu Ala
            20                  25                  30

Gln Ala Arg Cys Gly Leu Leu Ala Pro Tyr Met Arg Pro Ile Phe Ala
        35                  40                  45

Gly Ala Cys Ile Ala Gly Ser Ala Val Thr Val Ser Leu Pro Pro Gly
    50                  55                  60

Asp Asn Leu Met Ile His Val Ala Val Glu Val Cys Thr Pro Gly Ser
65                  70                  75                  80

Ile Leu Val Val Ala Pro Thr Ser Pro Cys Thr Asp Gly Tyr Phe Gly
                85                  90                  95

Glu Leu Leu Ala Thr Ser Leu Leu Ala His Gly Val Lys Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Val Ser Ser Gln Gly Thr Val Lys Ala Thr
    130                 135                 140

Leu Gly Ser Val Asn Val Pro Val Ile Cys Ala Gly Ala Glu Val Glu
145                 150                 155                 160

Ala Gly Asp Ile Ile Ile Ala Asp Asp Gly Val Val Val Lys
                165                 170                 175

Arg Thr Leu Ala His Glu Val Ala Ala Ala Glu Leu Arg Val Arg
            180                 185                 190

Lys Glu Asn Ala Thr Arg Glu Arg Leu Ala Arg Gly Asp Leu Gly Leu
        195                 200                 205

Asp Ile Tyr Asp Met Arg Gln Lys Ile Ala Gln Leu Gly Leu Lys Tyr
    210                 215                 220

Leu
225
```

```
<210> SEQ ID NO 281
<211> LENGTH: 678
<212> TYPE: DNA
<213> ORGANISM: Unknown
<220> FEATURE:
<223> OTHER INFORMATION: DNA obtained from environmental sample

<400> SEQUENCE: 281
```

-continued

```
atgaacaagc cgtggtcgt ccggcacgtg gaccaaccgt cagccgacgt tgtggctgcg    60
ctggagaagt acggagtctc gaccgtgcac gaagcgcaag gccgttgcgg tctactggcc   120
tcgtacatgc acccgattta tcccggcgat ccatcgctg ggcctgcggt cacggtttcg    180
cttccgccag gtgacaattt gatgatccat gttgcggtcg aggtctgccc ggcgggaagc   240
gttctggtcg tggctcccac ctcaccgtgc acagacggtt atttcggcga attgctggca   300
acttctctgc gcgctcacca tgtgacgggg ttggttatcg atgccggttg ccgcgacgtt   360
cgctcactca cggaaatgaa gtttccggtg tggagtcgcg ccgtcagttc acaggggacc   420
gtaaagtcga cgcttggctc cgtgaacgtg ccagtagtgt gcgccggggc ccatgtcgaa   480
gcgggcgata tcatcgtcgc cgatgacgat ggagtggtag ttgtaaagcg attggacgca   540
cccgaggtag tcgctgcgtg cgaacaaagg gttcgcaagg aacaggtgac gcgcgaacgg   600
ctggcgcgcg cgaactggg tctggatatt tacggcctgc gaagcaaaat cgccgaactt    660
ggcctcaagt acgagtag                                                 678
```

<210> SEQ ID NO 282
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 282

```
Met Asn Lys Pro Val Val Arg His Val Asp Gln Pro Ser Ala Asp
  1               5                  10                  15

Val Val Ala Ala Leu Glu Lys Tyr Gly Val Ser Thr Val His Glu Ala
                 20                  25                  30

Gln Gly Arg Cys Gly Leu Leu Ala Ser Tyr Met His Pro Ile Tyr Pro
             35                  40                  45

Gly Asp Ser Ile Ala Gly Pro Ala Val Thr Val Ser Leu Pro Pro Gly
         50                  55                  60

Asp Asn Leu Met Ile His Val Ala Val Glu Val Cys Pro Ala Gly Ser
 65                  70                  75                  80

Val Leu Val Val Ala Pro Thr Ser Pro Cys Thr Asp Gly Tyr Phe Gly
                 85                  90                  95

Glu Leu Leu Ala Thr Ser Leu Arg Ala His His Val Thr Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Val Ser Ser Gln Gly Thr Val Lys Ser Thr
    130                 135                 140

Leu Gly Ser Val Asn Val Pro Val Val Cys Ala Gly Ala His Val Glu
145                 150                 155                 160

Ala Gly Asp Ile Ile Val Ala Asp Asp Gly Val Val Val Val Lys
                165                 170                 175

Arg Leu Asp Ala Pro Glu Val Val Ala Ala Cys Glu Gln Arg Val Arg
            180                 185                 190

Lys Glu Gln Val Thr Arg Glu Arg Leu Ala Arg Gly Glu Leu Gly Leu
        195                 200                 205

Asp Ile Tyr Gly Leu Arg Ser Lys Ile Ala Glu Leu Gly Leu Lys Tyr
    210                 215                 220
```

Glu
225

<210> SEQ ID NO 283
<211> LENGTH: 678
<212> TYPE: DNA
<213> ORGANISM: Unknown
<220> FEATURE:
<223> OTHER INFORMATION: DNA obtained from environmental sample

<400> SEQUENCE: 283

```
atgaatacac cggtggtagt ccggcaagtg gagcagccac cagcggacgc ggtggccgca    60
ttggagaact gtggcgtgac caccgtgcat gaggctcagg acgtagtgg cctgcttgcc   120
tcctacatgc gcccgattta ccagggagca gccatcgcag gttccgctct caccgtgtct   180
ttgcctccgg gcgacaacct catgatgcat gttgcggtag agttctgcgg cccgggaaat   240
atcctggtcg ttgcaccgac ctcgccctgt acggatggct acttcggtga gctgttggca   300
acatctctcc gtgcccacgg tgggagaggg cttgtgatcg atgccggatg ccgtgacctg   360
cgctctctaa cagaaatgaa attccctgtc tggagccgcg ccatcagttc gcaagggacg   420
gtcaaggcca cacttggatc cgtgaatgtg cccatcgtat gcgcgggcgc attggtcgag   480
gccggagatg tcatcgtcgc cgatgacgat ggagttgtgg ttgtgaagcg cgccctcgcg   540
caagaggtca gggcggcggc ggagcaaagg gttcgcaaag aaaatgcgac ccgcgaaaga   600
ctcgcacgtg gagaactcgg actcgacatt tacgacatgc gccaaagat cgcgcagctg   660
ggccttaaat atctgtga                                                 678
```

<210> SEQ ID NO 284
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 284

Met Asn Thr Pro Val Val Arg Gln Val Glu Gln Pro Ala Asp
1               5                   10                  15

Ala Val Ala Ala Leu Glu Asn Cys Gly Val Thr Thr Val His Glu Ala
                20                  25                  30

Gln Gly Arg Ser Gly Leu Leu Ala Ser Tyr Met Arg Pro Ile Tyr Gln
            35                  40                  45

Gly Ala Ala Ile Ala Gly Ser Ala Leu Thr Val Ser Leu Pro Pro Gly
        50                  55                  60

Asp Asn Leu Met Met His Val Ala Val Glu Phe Cys Gly Pro Gly Asn
65                  70                  75                  80

Ile Leu Val Val Ala Pro Thr Ser Pro Cys Thr Asp Gly Tyr Phe Gly
                85                  90                  95

Glu Leu Leu Ala Thr Ser Leu Arg Ala His Gly Gly Arg Gly Leu Val
            100                 105                 110

Ile Asp Ala Gly Cys Arg Asp Leu Arg Ser Leu Thr Glu Met Lys Phe
        115                 120                 125

Pro Val Trp Ser Arg Ala Ile Ser Ser Gln Gly Thr Val Lys Ala Thr
    130                 135                 140

Leu Gly Ser Val Asn Val Pro Ile Val Cys Ala Gly Ala Leu Val Glu

```
                145                 150                 155                 160
Ala Gly Asp Val Ile Val Ala Asp Asp Gly Val Val Val Lys
                    165                 170                 175
Arg Ala Leu Ala Gln Glu Val Arg Ala Ala Ala Glu Gln Arg Val Arg
                180                 185                 190
Lys Glu Asn Ala Thr Arg Glu Arg Leu Ala Arg Gly Glu Leu Gly Leu
            195                 200                 205
Asp Ile Tyr Asp Met Arg Gln Lys Ile Ala Gln Leu Gly Leu Lys Tyr
        210                 215                 220
Leu
225

<210> SEQ ID NO 285
<211> LENGTH: 678
<212> TYPE: DNA
<213> ORGANISM: Unknown
<220> FEATURE:
<223> OTHER INFORMATION: DNA obtained from environmental sample

<400> SEQUENCE: 285
atgaatacac cggtggtagt aagacaagtg gagcagccac cagcggatgc aattgccgca      60
ttgaagaagt gtggcgtgac aaccgtccac gaggctcagg acgtggtgg ccttcttgcg     120 tcctacatgc gcccgattta cccgggagca gccatcgcag atccgctat cactgtgtct     180 ttgcctcctg gcgacaacct catgatccac gttgcggtgg aggtctgcgg tccgggaaac     240
atcctggtag tttcaccgac ctcgccttgt acgatggct acttcggtga gttgttggca     300
acatctctcc gtgcccaggg cgtgattggg cttgtgatcg atgccggatg ccgtgacgtg     360
cgctctctaa cagaaatgaa attcccggtc tggagccgcg ccatctgttc gcaagggaca     420
gtcaaggcca cacttggatc ggtgaatgtg cccatcgtat gcgcgggtgc attggtcgag     480
gctggtgatg tcatcgtcgc cgacgacgat ggcgttgtgg ttgtaaagcg agcgctggcg     540
caagaggtcg ccgctgcggc ggaacaaaag gttcgcaaag agaatgtaac ccgcgaacga     600
ctcgcacgtg gagagctcgg acttgatatt tacgacatgc gccaaaagat cgcgcaactg     660
ggcctcaaat atctgtga                                                   678

<210> SEQ ID NO 286
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 286

Met Asn Thr Pro Val Val Arg Gln Val Glu Gln Pro Pro Ala Asp
1               5                   10                  15

Ala Ile Ala Ala Leu Lys Lys Cys Gly Val Thr Thr Val His Glu Ala
            20                  25                  30

Gln Gly Arg Gly Gly Leu Leu Ala Ser Tyr Met Arg Pro Ile Tyr Pro
        35                  40                  45

Gly Ala Ala Ile Ala Gly Ser Ala Ile Thr Val Ser Leu Pro Pro Gly
    50                  55                  60

Asp Asn Leu Met Ile His Val Ala Val Glu Val Cys Gly Pro Gly Asn
65                  70                  75                  80
```

```
Ile Leu Val Val Ser Pro Thr Ser Pro Cys Thr Asp Gly Tyr Phe Gly
                85                  90                  95
Glu Leu Leu Ala Thr Ser Leu Arg Ala Gln Gly Val Ile Gly Leu Val
            100                 105                 110
Ile Asp Ala Gly Cys Arg Asp Val Arg Ser Leu Thr Glu Met Lys Phe
        115                 120                 125
Pro Val Trp Ser Arg Ala Ile Cys Ser Gln Gly Thr Val Lys Ala Thr
    130                 135                 140
Leu Gly Ser Val Asn Val Pro Ile Val Cys Ala Gly Ala Leu Val Glu
145                 150                 155                 160
Ala Gly Asp Val Ile Val Ala Asp Asp Gly Val Val Val Val Val Lys
                165                 170                 175
Arg Ala Leu Ala Gln Glu Val Ala Ala Ala Glu Gln Lys Val Arg
            180                 185                 190
Lys Glu Asn Val Thr Arg Glu Arg Leu Ala Arg Gly Glu Leu Gly Leu
        195                 200                 205
Asp Ile Tyr Asp Met Arg Gln Lys Ile Ala Gln Leu Gly Leu Lys Tyr
    210                 215                 220
Leu
225

<210> SEQ ID NO 287
<211> LENGTH: 678
<212> TYPE: DNA
<213> ORGANISM: Unknown
<220> FEATURE:
<223> OTHER INFORMATION: DNA obtained from environmental sample

<400> SEQUENCE: 287
atgaacaaac cgttggtgat ccggcaagtg gagcggccgc cggctgacgc tgtggcggcg      60
ctcgaaaaat atggcgtgtc caccgtgcat gaagcccagg gacgttgcgg actgctcgct     120
tcctacatgc gaccgattta tcccggtgct gccgttgccg gttcggcggt caccgtatcc     180
cttccgcccg cgataatctg atgattcac gttgctgtcg aggtctgcca gtccggcgat      240
attctcgtgg ttgctccgac ctcgccttgc tcggacggat acttcggtga ttgctggcg      300 acgtccttgc gcgcgcacgg cgtgaagggc ctcgtcattg acgcggggtg ccgtgacgtt     360
cgctcactta ccgaaatgag gttccccgtc tggagccgca gcgtcagctc gcaaggtacc     420
gtgaagtcta ctctcggatc tgtgaatgtg agcattgttt gtgccggcgc gcacatcgaa     480
gctggtgatg tgatcgtcgc ggatgacgac ggtgtcgtgg tggtgaagcg cgcatccgcc     540
cacgaagtag tcgcggcgtg cgaacagcgg gttcgcaagg aagaggtcac tcgggagcgg     600
ttggcgcgcg gggagcttgg gcttgacatc tacgggttgc gcacaaaaat cgcggaaatg     660
ggtctcaagt atcaatga                                                    678

<210> SEQ ID NO 288
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase
<220> FEATURE:
<221> NAME/KEY: SITE
<222> LOCATION: (151)...(154)
<223> OTHER INFORMATION: N-glycosylation site. Prosite id = PS00001
```

<400> SEQUENCE: 288

```
Met Asn Lys Pro Leu Val Ile Arg Gln Val Glu Arg Pro Pro Ala Asp
1               5                   10                  15
Ala Val Ala Ala Leu Glu Lys Tyr Gly Val Ser Thr Val His Glu Ala
            20                  25                  30
Gln Gly Arg Cys Gly Leu Leu Ala Ser Tyr Met Arg Pro Ile Tyr Pro
        35                  40                  45
Gly Ala Ala Val Ala Gly Ser Ala Val Thr Val Ser Leu Pro Pro Gly
    50                  55                  60
Asp Asn Leu Met Ile His Val Ala Val Glu Val Cys Gln Ser Gly Asp
65                  70                  75                  80
Ile Leu Val Val Ala Pro Thr Ser Pro Cys Ser Asp Gly Tyr Phe Gly
                85                  90                  95
Glu Leu Leu Ala Thr Ser Leu Arg Ala His Gly Val Lys Gly Leu Val
            100                 105                 110
Ile Asp Ala Gly Cys Arg Asp Val Arg Ser Leu Thr Glu Met Arg Phe
        115                 120                 125
Pro Val Trp Ser Arg Ser Val Ser Ser Gln Gly Thr Val Lys Ser Thr
    130                 135                 140
Leu Gly Ser Val Asn Val Ser Ile Val Cys Ala Gly Ala His Ile Glu
145                 150                 155                 160
Ala Gly Asp Val Ile Val Asp Asp Asp Gly Val Val Val Val Lys
                165                 170                 175
Arg Ala Ser Ala His Glu Val Val Ala Ala Cys Glu Gln Arg Val Arg
            180                 185                 190
Lys Glu Glu Val Thr Arg Glu Arg Leu Ala Arg Gly Glu Leu Gly Leu
        195                 200                 205
Asp Ile Tyr Gly Leu Arg Thr Lys Ile Ala Glu Met Gly Leu Lys Tyr
    210                 215                 220
Gln
225
```

<210> SEQ ID NO 289
<211> LENGTH: 678
<212> TYPE: DNA
<213> ORGANISM: Unknown
<220> FEATURE:
<223> OTHER INFORMATION: DNA obtained from environmental sample

<400> SEQUENCE: 289

```
atgaacaagc ccgtggttgt gcggaacatc gagcgtccgc cggcggatgc tgtggccgcg      60
cttgagaaat acggcgtgtc gacggtgcac gaggcccagg gccggaacgg cctactggcc     120
tcctatatgc gcccgatcta tgcaggagcc gcgatcgctg accagccgt cacagtttcc      180
ctcccgccgg agacaacct gatgattcac gtcgccgtcg aggtctgtcg gcctggggat      240
gtcctcgttg ttgcgccgac atcgccatgc accgacggct atttggaga gttgcttgca      300
acttcgctcg cggcgcatgg ggtgaaaggc ttagtcattg aggcgggatg tcgcgacgtc     360
cgagctctga tggaaatgaa gtttccagtc tggagccgcg ccgtcaactc gcaaggaacg     420
gtgaaggcaa cacttgggtc ggtaaatgta acgattgttt gtgcgggtgc tgcggttgcg     480
cccggtgatg tgatcgtggc ggacgatgat ggcgtcgttg tcgtgaaacg gacagaggcg     540
caagaggtcg ttaccgcatc tgagcagaga ttgcgaaagg aagagggaac ccgcaagcgg     600
cttgcttcgg gggaactcgg cctggatatt tacggcctgc gagcgaagat tgcagacctc     660
ggtctcaagt acttgtag                                                    678
```

<210> SEQ ID NO 290
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase
<220> FEATURE:
<221> NAME/KEY: SITE
<222> LOCATION: (151)...(154)
<223> OTHER INFORMATION: N-glycosylation site. Prosite id = PS00001

<400> SEQUENCE: 290

```
Met Asn Lys Pro Val Val Arg Asn Ile Glu Arg Pro Pro Ala Asp
1               5                   10                  15

Ala Val Ala Ala Leu Glu Lys Tyr Gly Val Ser Thr Val His Glu Ala
            20                  25                  30

Gln Gly Arg Asn Gly Leu Leu Ala Ser Tyr Met Arg Pro Ile Tyr Ala
        35                  40                  45

Gly Ala Ala Ile Ala Gly Pro Ala Val Thr Val Ser Leu Pro Pro Gly
    50                  55                  60

Asp Asn Leu Met Ile His Val Ala Val Glu Val Cys Arg Pro Gly Asp
65                  70                  75                  80

Val Leu Val Val Ala Pro Thr Ser Pro Cys Thr Asp Gly Tyr Phe Gly
                85                  90                  95

Glu Leu Leu Ala Thr Ser Leu Ala Ala His Gly Val Lys Gly Leu Val
            100                 105                 110

Ile Glu Ala Gly Cys Arg Asp Val Arg Ala Leu Met Glu Met Lys Phe
        115                 120                 125

Pro Val Trp Ser Arg Ala Val Asn Ser Gln Gly Thr Val Lys Ala Thr
    130                 135                 140

Leu Gly Ser Val Asn Val Thr Ile Val Cys Ala Gly Ala Ala Val Ala
145                 150                 155                 160

Pro Gly Asp Val Ile Val Ala Asp Asp Gly Val Val Val Val Lys
                165                 170                 175

Arg Thr Glu Ala Gln Glu Val Val Thr Ala Ser Glu Gln Arg Leu Arg
            180                 185                 190

Lys Glu Glu Gly Thr Arg Lys Arg Leu Ala Ser Gly Glu Leu Gly Leu
        195                 200                 205

Asp Ile Tyr Gly Leu Arg Ala Lys Ile Ala Asp Leu Gly Leu Lys Tyr
    210                 215                 220

Leu
225
```

<210> SEQ ID NO 291
<211> LENGTH: 678
<212> TYPE: DNA
<213> ORGANISM: Unknown
<220> FEATURE:
<223> OTHER INFORMATION: DNA obtained from environmental sample

<400> SEQUENCE: 291

```
atgaataaac cggtggtagt ccggcaagtg gagcagccac ccgcggacgc ggttgcggcg    60
ctggagaagt atggcgttac caccgtgcat gaggctcagg gacgttgtgg cctgctcgcg   120
cactacatgc gtccgatttt tccgggagcg gccatctcgg gttctgctgt caccgtagct   180
```

```
ttgccgccgg gcgataacct catgatccac gtcgcggtcg aggtctgcgg cccgggaaac   240
atcctggttg tggcaccgac ctcgccttcg acgatggct acttcggtga gctgttggcg    300
acctctttgc gtgctcacgg tgtgaaaggg cttgtgattg atgccggatg ccgtgacgtt   360
cgctccctga ccgagatgaa attccccgtc tggagccgtg ccatcagctc gcagggaaca   420
gtcaaggcca ccctcggatc ggtgaatgtg ccggtcatgt gcgcgggcgc gctcgtcgaa   480
gctggggatg tcatcgtcgc cgatgatgat ggagttgtgg ttgtgaagcg cgcgaatgcg   540
cacgaggtgg ccgcggcggc agaacaaagg gtgcgcaagg agaatataac ccgcgaacgg   600
cttcgacgcg gagagctcgg actcgatatt tacgacatgc gccaaaaaat cgcgcaactg   660
ggcctcaaat acctgtga                                                 678
```

<210> SEQ ID NO 292
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 292

```
Met Asn Lys Pro Val Val Arg Gln Val Glu Gln Pro Ala Asp
1               5                   10                  15

Ala Val Ala Ala Leu Glu Lys Tyr Gly Val Thr Thr Val His Glu Ala
            20                  25                  30

Gln Gly Arg Cys Gly Leu Leu Ala His Tyr Met Arg Pro Ile Phe Pro
        35                  40                  45

Gly Ala Ala Ile Ser Gly Ser Ala Val Thr Val Ala Leu Pro Pro Gly
    50                  55                  60

Asp Asn Leu Met Ile His Val Ala Val Glu Val Cys Gly Pro Gly Asn
65                  70                  75                  80

Ile Leu Val Val Ala Pro Thr Ser Pro Ser Thr Asp Gly Tyr Phe Gly
                85                  90                  95

Glu Leu Leu Ala Thr Ser Leu Arg Ala His Gly Val Lys Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Ile Ser Ser Gln Gly Thr Val Lys Ala Thr
    130                 135                 140

Leu Gly Ser Val Asn Val Pro Val Met Cys Ala Gly Ala Leu Val Glu
145                 150                 155                 160

Ala Gly Asp Val Ile Val Ala Asp Asp Gly Val Val Val Lys
                165                 170                 175

Arg Ala Asn Ala His Glu Val Ala Ala Ala Glu Gln Arg Val Arg
            180                 185                 190

Lys Glu Asn Ile Thr Arg Glu Arg Leu Arg Arg Gly Glu Leu Gly Leu
        195                 200                 205

Asp Ile Tyr Asp Met Arg Gln Lys Ile Ala Gln Leu Gly Leu Lys Tyr
    210                 215                 220

Leu
225
```

<210> SEQ ID NO 293
<211> LENGTH: 678

```
<212> TYPE: DNA
<213> ORGANISM: Unknown
<220> FEATURE:
<223> OTHER INFORMATION: DNA obtained from environmental sample

<400> SEQUENCE: 293
atgaatcgac cggtggtagt ccggcaagtt gaacagccac cagcggatgc ggttgccgca      60
ctggagaagt atggcgtgac aaccgtccat gaggctcagg gacccggtgg cctcctagcc     120
tcctacatgc gcccgattta cccgggagca gtcatcgccg gttccgcggt cactgtgtct     180
ttacctcctg gcgacaacct catgatccac gtggccgtgg aggtctgtgg tccgggaaac     240
attctggttg ttgcaccgat ctcgccgtgt acgatggct acttcggaga gctgttggca      300
acctctctcc gcgcccacgg tgtgcgaggg cttgtgatcg atgccggatg ccgggacgtg     360
cgctctctca cagaaatgaa atttccggtc tggagccgcg ccgtcagttc acaggggaca     420
gtcaaggcca ccctgggatc ggtgaatgtg ccgattgtgt gcgcgggcgc gcgggtcggg     480
gctggggatg tcatcgtcgc cgatgacgat ggagttgtgg tggtgaagcg cgcgctggcc     540
gaagaggtcg ccgccgcggc ggaacaaagg gttcgcaaag agaatgtgac ccgggaacga     600
cttgcgcgtg agagctggg actcgatatt tacgacatgc gccaaaagat cgcacaactg      660
ggccttaaat atctctga                                                    678

<210> SEQ ID NO 294
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 294

Met Asn Arg Pro Val Val Arg Gln Val Glu Gln Pro Ala Asp
1               5                   10                  15

Ala Val Ala Ala Leu Glu Lys Tyr Gly Val Thr Thr Val His Glu Ala
                20                  25                  30

Gln Gly Pro Gly Gly Leu Leu Ala Ser Tyr Met Arg Pro Ile Tyr Pro
            35                  40                  45

Gly Ala Val Ile Ala Gly Ser Ala Val Thr Val Ser Leu Pro Pro Gly
        50                  55                  60

Asp Asn Leu Met Ile His Val Ala Val Glu Val Cys Gly Pro Gly Asn
65                  70                  75                  80

Ile Leu Val Val Ala Pro Ile Ser Pro Cys Thr Asp Gly Tyr Phe Gly
                85                  90                  95

Glu Leu Leu Ala Thr Ser Leu Arg Ala His Gly Val Arg Gly Leu Val
            100                 105                 110

Ile Asp Ala Gly Cys Arg Asp Val Arg Ser Leu Thr Glu Met Lys Phe
        115                 120                 125

Pro Val Trp Ser Arg Ala Val Ser Ser Gln Gly Thr Val Lys Ala Thr
130                 135                 140

Leu Gly Ser Val Asn Val Pro Ile Val Cys Ala Gly Ala Arg Val Gly
145                 150                 155                 160

Ala Gly Asp Val Ile Val Ala Asp Asp Gly Val Val Val Lys
                165                 170                 175

Arg Ala Leu Ala Glu Glu Val Ala Ala Ala Glu Gln Arg Val Arg
            180                 185                 190
```

Lys Glu Asn Val Thr Arg Glu Arg Leu Ala Arg Gly Glu Leu Gly Leu
            195                 200                 205

Asp Ile Tyr Asp Met Arg Gln Lys Ile Ala Gln Leu Gly Leu Lys Tyr
        210                 215                 220

Leu
225

<210> SEQ ID NO 295
<211> LENGTH: 678
<212> TYPE: DNA
<213> ORGANISM: Unknown
<220> FEATURE:
<223> OTHER INFORMATION: DNA obtained from environmental sample

<400> SEQUENCE: 295

```
atgaataaac cggtggtagt ccggcaagtg gagcagccgc cagcggacgc ggttgcggcg     60
ctggagaagt atggcgtcac caccgtgcat gaggctcagg gacgttgtgg cctgctcggg    120
cactacatgc gtccgatttt tccgggagcg gccatctcgg gttctgcagt caccgtagct    180
ttgccgccgg gcgataacct catgatccac gtcgcggtcg aggtctgcgg cccgggaaac    240
atcctggtgg ttgcaccgac ctcgccttcg acggatggct acttcggtga gctgttggcg    300
acctctctgc gtgctcgcga tgtgaaaggg cttgtgattg atgccggatg ccgtgacgtt    360
cgctccctga ccgagatgaa attccccgtc tggagccgtg ccatcagctc gcagggaacg    420
gtcaaggcca ccctcggatc ggtgaatgtg ccggtcacgt gcgcgggcgc gctcgtcgaa    480
gccggggatg tcatcgtcgc cgatgatgat ggagttgtgg ttgtgaagcg cgcgcatgcg    540
cacgaggtgg cggcggcggc agaacaaagg gtgcgcaaag agaatataac ccgcgaacgg    600
cttcgacgcg gagagctcgg actcgatatt tacgacatgc gccaaaagat cgcgcaactg    660
ggcctcaaat acctgtga                                                  678
```

<210> SEQ ID NO 296
<211> LENGTH: 225
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (22)...(174)
<223> OTHER INFORMATION: Demethylmenaquinone methyltransferase

<400> SEQUENCE: 296

Met Asn Lys Pro Val Val Arg Gln Val Glu Gln Pro Ala Asp
1               5                   10                  15

Ala Val Ala Ala Leu Glu Lys Tyr Gly Val Thr Thr Val His Glu Ala
            20                  25                  30

Gln Gly Arg Cys Gly Leu Leu Gly His Tyr Met Arg Pro Ile Phe Pro
        35                  40                  45

Gly Ala Ala Ile Ser Gly Ser Ala Val Thr Val Ala Leu Pro Pro Gly
    50                  55                  60

Asp Asn Leu Met Ile His Val Ala Val Glu Val Cys Gly Pro Gly Asn
65                  70                  75                  80

Ile Leu Val Val Ala Pro Thr Ser Pro Ser Thr Asp Gly Tyr Phe Gly
                85                  90                  95

Glu Leu Leu Ala Thr Ser Leu Arg Ala Arg Asp Val Lys Gly Leu Val
            100                 105                 110

Ile Asp Ala Gly Cys Arg Asp Val Arg Ser Leu Thr Glu Met Lys Phe

```
                    115                 120                 125
Pro Val Trp Ser Arg Ala Ile Ser Ser Gln Gly Thr Val Lys Ala Thr
    130                 135                 140

Leu Gly Ser Val Asn Val Pro Val Thr Cys Ala Gly Ala Leu Val Glu
145                 150                 155                 160

Ala Gly Asp Val Ile Val Ala Asp Asp Gly Val Val Val Lys
                165                 170                 175

Arg Ala His Ala His Glu Val Ala Ala Ala Glu Gln Arg Val Arg
                180                 185                 190

Lys Glu Asn Ile Thr Arg Glu Arg Leu Arg Gly Glu Leu Gly Leu
                195                 200                 205

Asp Ile Tyr Asp Met Arg Gln Lys Ile Ala Gln Leu Gly Leu Lys Tyr
    210                 215                 220

Leu
225

<210> SEQ ID NO 297
<211> LENGTH: 672
<212> TYPE: DNA
<213> ORGANISM: Unknown
<220> FEATURE:
<223> OTHER INFORMATION: DNA obtained from environmental sample

<400> SEQUENCE: 297
atgggtgtcg tcgtccaaaa catcgagcgg gctgcgcaag ggaccatcga ccgcctcgcc    60
gcctgcgggg tggctaccgt ccatgaagcg caggggcgca aggggctgct ggcgagccac   120
atgcggccgg tctacagggg cgcacggctc gccgcgagcg cggtgacgat tcggcgccg   180 cccggcgaca actggatgat ccatgtcgcc atcgagcagc tccaagccgg cgacatcatg   240
gtgctggcgc cgaccagccc gtgcgaggac ggatatttcg gcgacctcct ggcgacctcg   300
gcgcaggcgc gcgggtgcaa ggggctggtg atcgatgccg cgtgcgcga cgttgccgac   360 cttacggcaa tgcagttccc ggtgtggtcg aaggcgatct tcgcgcaggg cacgctgaaa   420
gagacgctgg gttcggtgaa cgtgccggtg gtctgcgccg gcgcgctggt caacccgggc   480
gacgtcatcg tcgccgatga cgacgggtc tgcgtggtac gccgcgagga ggtcgaggca   540
gtggcggaaa aggcggaagc ccgcgtcgct gccgaggagg acaagcgcaa gcgcctcgcc   600
gggggagaac tggggctcga catctacaag atgcgcgagc gcttggccga agggcctc   660 aaatatgtct ga                                                       672

<210> SEQ ID NO 298
<211> LENGTH: 223
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (20)...(172)
<223> OTHER INFORMATION: Demethylmenaquinone methyltransferase

<400> SEQUENCE: 298

Met Gly Val Val Val Gln Asn Ile Glu Arg Ala Ala Gln Gly Thr Ile
1               5                   10                  15

Asp Arg Leu Ala Ala Cys Gly Val Ala Thr Val His Glu Ala Gln Gly
                20                  25                  30

Arg Lys Gly Leu Leu Ala Ser His Met Arg Pro Val Tyr Arg Gly Ala
            35                  40                  45
```

```
Arg Leu Ala Ala Ser Ala Val Thr Ile Ser Ala Pro Pro Gly Asp Asn
 50                  55                  60

Trp Met Ile His Val Ala Ile Glu Gln Leu Gln Ala Gly Asp Ile Met
 65                  70                  75                  80

Val Leu Ala Pro Thr Ser Pro Cys Glu Asp Gly Tyr Phe Gly Asp Leu
                 85                  90                  95

Leu Ala Thr Ser Ala Gln Ala Arg Gly Cys Lys Gly Leu Val Ile Asp
            100                 105                 110

Ala Gly Val Arg Asp Val Ala Asp Leu Thr Ala Met Gln Phe Pro Val
        115                 120                 125

Trp Ser Lys Ala Ile Phe Ala Gln Gly Thr Leu Lys Glu Thr Leu Gly
    130                 135                 140

Ser Val Asn Val Pro Val Val Cys Ala Gly Ala Leu Val Asn Pro Gly
145                 150                 155                 160

Asp Val Ile Val Ala Asp Asp Gly Val Cys Val Val Arg Arg Glu
                165                 170                 175

Glu Val Glu Ala Val Ala Glu Lys Ala Glu Ala Arg Val Ala Ala Glu
                180                 185                 190

Glu Asp Lys Arg Lys Arg Leu Ala Gly Gly Glu Leu Gly Leu Asp Ile
            195                 200                 205

Tyr Lys Met Arg Glu Arg Leu Ala Glu Lys Gly Leu Lys Tyr Val
    210                 215                 220

<210> SEQ ID NO 299
<211> LENGTH: 501
<212> TYPE: DNA
<213> ORGANISM: Unknown
<220> FEATURE:
<223> OTHER INFORMATION: DNA obtained from environmental sample

<400> SEQUENCE: 299
atgggttcct tggcaactgc cgaagcttgt gacacgaatg cagcacacct gacaagcggt    60
gacatccggg tcctgccacc actcttcaag atttacgggc aaagtcgggc attctctggg   120
ccaatcgtga ctgtgaaggt atttgaagac aatgtgctgg tacgggaact tcttgaaacc   180
aaaggcgacg gtagagttct ggtgatagac ggcggaggga gcatgaggtg tgccttggtc   240
ggaggaaacc tggggcagtt agcgcagaac atggggtggg cggggattgt tgtaaacggg   300
tgcataagag acgtagatga gatcaacggg tgcgatgttg gggttagagc attggcatcc   360
catccacaga agtcgaataa aaaggggcat ggggagaaac acatgccgat taatatcgcg   420
ggcacgatga tccgagacgg agagtggttg tatgcagaca gtgatggcat tctcatctcc   480
agaactgagc tctctatcta g                                             501

<210> SEQ ID NO 300
<211> LENGTH: 166
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (2)...(159)
<223> OTHER INFORMATION: Demethylmenaquinone methyltransferase

<400> SEQUENCE: 300

Met Gly Ser Leu Ala Thr Ala Glu Ala Cys Asp Thr Asn Ala Ala His
 1               5                  10                  15

Leu Thr Ser Gly Asp Ile Arg Val Leu Pro Pro Leu Phe Lys Ile Tyr
                20                  25                  30
```

Gly Gln Ser Arg Ala Phe Ser Gly Pro Ile Val Thr Val Lys Val Phe
            35                  40                  45

Glu Asp Asn Val Leu Val Arg Glu Leu Leu Glu Thr Lys Gly Asp Gly
 50                  55                  60

Arg Val Leu Val Ile Asp Gly Gly Ser Met Arg Cys Ala Leu Val
 65                  70                  75                  80

Gly Gly Asn Leu Gly Gln Leu Ala Gln Asn Met Gly Trp Ala Gly Ile
                85                  90                  95

Val Val Asn Gly Cys Ile Arg Asp Val Asp Glu Ile Asn Gly Cys Asp
            100                 105                 110

Val Gly Val Arg Ala Leu Ala Ser His Pro Gln Lys Ser Asn Lys Lys
            115                 120                 125

Gly His Gly Glu Lys His Met Pro Ile Asn Ile Ala Gly Thr Met Ile
        130                 135                 140

Arg Asp Gly Glu Trp Leu Tyr Ala Asp Ser Asp Gly Ile Leu Ile Ser
145                 150                 155                 160

Arg Thr Glu Leu Ser Ile
                165

<210> SEQ ID NO 301
<211> LENGTH: 501
<212> TYPE: DNA
<213> ORGANISM: Unknown
<220> FEATURE:
<223> OTHER INFORMATION: DNA obtained from environmental sample

<400> SEQUENCE: 301
atgggttcct tggcaactgc cgaagcttgt gacacgaatg cagcacacct gacaagcggt      60
gacatccggg tcctgccacc actcttcaag atttacgggc aaagtcgggc attctctggg     120
ccaatcgtga ctgtgaaggt atttgaagac aatgtgctgg tacgggaact tcttgaaacc     180
aaaggcgacg gtagagttct ggtgatagac ggcggaggga gcatgaggtg tgccttggtc     240
ggaggaaacc tggggcagtt agctcagaac atggggtggg cagggattgt tgtaaacggg     300
tgcataagag acatagatga gatcaacggg tgcgatgttg ggttagagc attggcatcc      360 catccacaga agtcgaataa aaaggggcat ggggagaaac acatgccgat taatatcgcg     420
ggcacgatga tccgagacgg agagtggttg tatgcagaca gtgatggcat tctcatctcc     480
agaactgagc tctctatcta g                                               501

<210> SEQ ID NO 302
<211> LENGTH: 166
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (2)...(159)
<223> OTHER INFORMATION: Demethylmenaquinone methyltransferase

<400> SEQUENCE: 302

Met Gly Ser Leu Ala Thr Ala Glu Ala Cys Asp Thr Asn Ala Ala His
 1               5                  10                  15

Leu Thr Ser Gly Asp Ile Arg Val Leu Pro Pro Leu Phe Lys Ile Tyr
                20                  25                  30

Gly Gln Ser Arg Ala Phe Ser Gly Pro Ile Val Thr Val Lys Val Phe
            35                  40                  45

Glu Asp Asn Val Leu Val Arg Glu Leu Leu Glu Thr Lys Gly Asp Gly

```
                50                  55                  60
Arg Val Leu Val Ile Asp Gly Gly Ser Met Arg Cys Ala Leu Val
 65                  70                  75                  80

Gly Gly Asn Leu Gly Gln Leu Ala Gln Asn Met Gly Trp Ala Gly Ile
                 85                  90                  95

Val Val Asn Gly Cys Ile Arg Asp Ile Asp Glu Ile Asn Gly Cys Asp
                100                 105                 110

Val Gly Val Arg Ala Leu Ala Ser His Pro Gln Lys Ser Asn Lys Lys
                115                 120                 125

Gly His Gly Glu Lys His Met Pro Ile Asn Ile Ala Gly Thr Met Ile
                130                 135                 140

Arg Asp Gly Glu Trp Leu Tyr Ala Asp Ser Asp Gly Ile Leu Ile Ser
145                 150                 155                 160

Arg Thr Glu Leu Ser Ile
                165

<210> SEQ ID NO 303
<211> LENGTH: 501
<212> TYPE: DNA
<213> ORGANISM: Unknown
<220> FEATURE:
<223> OTHER INFORMATION: DNA obtained from environmental sample

<400> SEQUENCE: 303
atggccttag taaccactgc cgaagtttgt gatgcgaacc cacagctcat tgtgagcggc    60
gagcttcgcg cactccatcc aattttccaa atttacggta ggcggcaagt cttctccggg   120
cccgttgtta cgctgaaggt gtttgaagat aatgtgttgg tgcgcgaatt tcttgaggag   180
aggggcaatg gcagggttct tgttgtcgat ggtggtggca gcttgagatg cgcaatactc   240
ggtggcaacc ccgttgtaca agctcagaac aacgggtggg ctggcattgt ggttaacggg   300
tgtataaggg atgttgatga atcaacgggt gcgacattg gagtcagagc tctggccgcg   360
cacccggtga agccaataa gaaaggcatc ggtgagaagc atgttccggt gaacattggt   420
ggaacccgta tatgtgatgg agagtggctc tatgcagata ccgatggtat tttggtgtct   480
aaaaccgagt tgtctgtcta a                                            501

<210> SEQ ID NO 304
<211> LENGTH: 166
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (2)...(159)
<223> OTHER INFORMATION: Demethylmenaquinone methyltransferase

<400> SEQUENCE: 304

Met Ala Leu Val Thr Thr Ala Glu Val Cys Asp Ala Asn Pro Gln Leu
 1               5                  10                  15

Ile Val Ser Gly Glu Leu Arg Ala Leu His Pro Ile Phe Gln Ile Tyr
                20                  25                  30

Gly Arg Arg Gln Val Phe Ser Gly Pro Val Val Thr Leu Lys Val Phe
             35                  40                  45

Glu Asp Asn Val Leu Val Arg Glu Phe Leu Glu Glu Arg Gly Asn Gly
 50                  55                  60

Arg Val Leu Val Val Asp Gly Gly Gly Ser Leu Arg Cys Ala Ile Leu
 65                  70                  75                  80
```

```
Gly Gly Asn Pro Val Val Gln Ala Gln Asn Asn Gly Trp Ala Gly Ile
                85                  90                  95

Val Val Asn Gly Cys Ile Arg Asp Val Asp Glu Ile Asn Gly Cys Asp
            100                 105                 110

Ile Gly Val Arg Ala Leu Ala Ala His Pro Val Lys Ala Asn Lys Lys
        115                 120                 125

Gly Ile Gly Glu Lys His Val Pro Val Asn Ile Gly Gly Thr Arg Ile
    130                 135                 140

Cys Asp Gly Glu Trp Leu Tyr Ala Asp Thr Asp Gly Ile Leu Val Ser
145                 150                 155                 160

Lys Thr Glu Leu Ser Val
                165

<210> SEQ ID NO 305
<211> LENGTH: 639
<212> TYPE: DNA
<213> ORGANISM: Unknown
<220> FEATURE:
<223> OTHER INFORMATION: DNA obtained from environmental sample

<400> SEQUENCE: 305
ttggatcaaa tccacaaatc cggcattatc cccgtcgtcg aaatcgactc ggtagaacgc      60
gccgtcccgc tggctgaggc attgcttgca ggagggctga cggtcgtgga gatcaccctc     120
cgcaccgggg cggcgctcga gtcgattcga gcaattgctc agcaggtacc agaggtcagt     180
gtcggggcag gaacagtcat tacctgggaa caggcgcagg cggcacgtga tgcaggcgcg     240
cagttcctcg tctcaccggg gatggtggag caggttgtca tctgggcgca ggagcaccag     300
cttccgatca tacctggcgc agcaactccc accgagatga tccgcggcat caacctgggg     360
ctcaacctcc tgaaattctt tcccgccgaa acgatgggtg gggtaagcgc tgttaaggcg     420
ttatctgacc cgtttccgca gttgaaattc attcccacgg gcggcatcag gttggaaaat     480
gcagcttcgt atctcgcgca tcctaaaatc catgctgtgg gcggctcgtg gatagcgaaa     540
cgagagatga tcgcggatgg cagatttgat gagatccggc gtatggcaca ggaagccaga     600
gacctggtaa agcagatcag gaggaaaacg atcccatga                            639

<210> SEQ ID NO 306
<211> LENGTH: 212
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (1)...(195)
<223> OTHER INFORMATION: KDPG and KHG aldolase
<220> FEATURE:
<221> NAME/KEY: SITE
<222> LOCATION: (32)...(41)
<223> OTHER INFORMATION: KDPG and KHG aldolases active site. Prosite
      id = PS00159

<400> SEQUENCE: 306

Met Asp Gln Ile His Lys Ser Gly Ile Ile Pro Val Val Glu Ile Asp
1               5                   10                  15

Ser Val Glu Arg Ala Val Pro Leu Ala Glu Ala Leu Leu Ala Gly Gly
            20                  25                  30

Leu Thr Val Val Glu Ile Thr Leu Arg Thr Gly Ala Ala Leu Glu Ser
        35                  40                  45

Ile Arg Ala Ile Ala Gln Gln Val Pro Glu Val Ser Val Gly Ala Gly
    50                  55                  60
```

```
Thr Val Ile Thr Trp Glu Gln Ala Gln Ala Arg Asp Gly Ala
 65                  70                  75                  80

Gln Phe Leu Val Ser Pro Gly Met Val Glu Gln Val Val Ile Trp Ala
                 85                  90                  95

Gln Glu His Gln Leu Pro Ile Ile Pro Gly Ala Ala Thr Pro Thr Glu
            100                 105                 110

Met Ile Arg Gly Ile Asn Leu Gly Leu Asn Leu Leu Lys Phe Phe Pro
        115                 120                 125

Ala Glu Thr Met Gly Gly Val Ser Ala Val Lys Ala Leu Ser Asp Pro
    130                 135                 140

Phe Pro Gln Leu Lys Phe Ile Pro Thr Gly Gly Ile Arg Leu Glu Asn
145                 150                 155                 160

Ala Ala Ser Tyr Leu Ala His Pro Lys Ile His Ala Val Gly Gly Ser
                165                 170                 175

Trp Ile Ala Lys Arg Glu Met Ile Ala Asp Gly Arg Phe Asp Glu Ile
            180                 185                 190

Arg Arg Met Ala Gln Glu Ala Arg Asp Leu Val Lys Gln Ile Arg Arg
        195                 200                 205

Lys Thr Ile Pro
    210

<210> SEQ ID NO 307
<211> LENGTH: 639
<212> TYPE: DNA
<213> ORGANISM: Unknown
<220> FEATURE:
<223> OTHER INFORMATION: DNA obtained from environmental sample

<400> SEQUENCE: 307
ttgactttga acaaggcgt gttgcctttg tattttaata aggacgagga ggtgagtatc      60
gctgttttaa aagctttata tgaagcggga attcgtacag ttgaatatac gaatcgtggt    120
gaagccgcat tgaaaaactt taagtcgttg cgcaaggtat gtgataccga attgaatgga    180
atgtacctcg gtattgggac gattaaaaat ggccagcagg cacaagcttt tgtgatgca    240 ggtgcagatt atttaattag tccgggtgta gtggatgatg cagcaaaagt tgccgatcaa    300
aatggtttgt tatatgtgcc tggtgcaatg accccaacag aaattatcag ggcagagcaa    360
caatttggat caacgctggt gaaactttt ccgggtaata ttttaggccc tggctttgtt    420
agtgctatta agaattgtt cagcggattg aaatttatta ttaccggagg agttgaaccg    480
gaagaaaata atttgaaagg atggttcaac gcaggtgccg cagctgtggg catgggaagt    540
aaattaatta ccaaacaggt tttgaaaat aaagactatg caaaaattac agagttaact    600
aaggaatctt taagactgat taaattggtc agagggtaa                           639

<210> SEQ ID NO 308
<211> LENGTH: 212
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (2)...(199)
<223> OTHER INFORMATION: KDPG and KHG aldolase

<400> SEQUENCE: 308

Met Thr Leu Lys Gln Gly Val Leu Pro Leu Tyr Phe Asn Lys Asp Glu
1               5                  10                  15
```

```
Glu Val Ser Ile Ala Val Leu Lys Ala Leu Tyr Glu Ala Gly Ile Arg
            20                  25                  30

Thr Val Glu Tyr Thr Asn Arg Gly Glu Ala Ala Leu Lys Asn Phe Lys
        35                  40                  45

Ser Leu Arg Lys Val Cys Asp Thr Glu Leu Asn Gly Met Tyr Leu Gly
    50                  55                  60

Ile Gly Thr Ile Lys Asn Gly Gln Gln Ala Gln Ala Phe Val Asp Ala
65                  70                  75                  80

Gly Ala Asp Tyr Leu Ile Ser Pro Gly Val Val Asp Ala Ala Lys
                85                  90                  95

Val Ala Asp Gln Asn Gly Leu Leu Tyr Val Pro Gly Ala Met Thr Pro
            100                 105                 110

Thr Glu Ile Ile Arg Ala Glu Gln Gln Phe Gly Ser Thr Leu Val Lys
        115                 120                 125

Leu Phe Pro Gly Asn Ile Leu Gly Pro Gly Phe Val Ser Ala Ile Lys
    130                 135                 140

Glu Leu Phe Ser Gly Leu Lys Phe Ile Ile Thr Gly Val Glu Pro
145                 150                 155                 160

Glu Glu Asn Asn Leu Lys Gly Trp Phe Asn Ala Gly Ala Ala Ala Val
                165                 170                 175

Gly Met Gly Ser Lys Leu Ile Thr Lys Gln Val Leu Glu Asn Lys Asp
            180                 185                 190

Tyr Ala Lys Ile Thr Glu Leu Thr Lys Glu Ser Leu Arg Leu Ile Lys
        195                 200                 205

Leu Val Arg Gly
    210

<210> SEQ ID NO 309
<211> LENGTH: 687
<212> TYPE: DNA
<213> ORGANISM: Unknown
<220> FEATURE:
<223> OTHER INFORMATION: DNA obtained from environmental sample

<400> SEQUENCE: 309
atgagtattg ctgcaaatac aggtgtagac aaaaaaaatg agatcctaca attaacattg      60
caacaaggtg tgttgccttt gtattttaat aaagatgaag aagtgagtat tgctgttttg     120
aaagcgttat atgaggcagg cattcgcaca gttgagtata ccaatcgtgg agaagccgca     180
ttaaaaaatt ttaaagtact gagaaaaatt tgtgatacgg aattgagtgg attatacctg     240
ggtatcggca ccattaaaaa tggagaacag gcaaaagctt ttgttgatgc cggtgcagat     300
tatttaatta gtccgggtgt ggtagatgat gcagcaaaaa ttgctgatca aaatggattg     360
ttatatgtgc ctggtgccat gacgccaact gaaattatca gggcagaaca atttggtgca     420
acactggtaa acttttttcc cggtaatatt ttaggccctg gtttcgttag tgccgttaag     480
gaattattca gcggtttgaa atttatcatc actggtggag tagaacctga gaaaataat      540 ttgaaaggat ggtttaatgc aggtgctgcg gccgtaggaa tgggaagtaa attgatcaca     600
aaacaaactt tggaaaataa agactacgca aaaattacag agctcacgaa agagtcttta     660
agattgattg aactggtgcg gaaataa                                         687

<210> SEQ ID NO 310
<211> LENGTH: 228
<212> TYPE: PRT
<213> ORGANISM: Unknown
<220> FEATURE:
<223> OTHER INFORMATION: Protein obtained from environmental sample
```

```
<220> FEATURE:
<221> NAME/KEY: DOMAIN
<222> LOCATION: (16)...(215)
<223> OTHER INFORMATION: KDPG and KHG aldolase

<400> SEQUENCE: 310
```

| | | | | | | | | | | | | | | |
|---|---|---|---|---|---|---|---|---|---|---|---|---|---|---|
| Met | Ser | Ile | Ala | Ala | Asn | Thr | Gly | Val | Asp | Lys | Lys | Asn | Glu | Ile | Leu |
| 1 | | | | 5 | | | | | 10 | | | | | 15 | |
| Gln | Leu | Thr | Leu | Gln | Gln | Gly | Val | Leu | Pro | Leu | Tyr | Phe | Asn | Lys | Asp |
| | | 20 | | | | | 25 | | | | | 30 | | | |
| Glu | Glu | Val | Ser | Ile | Ala | Val | Leu | Lys | Ala | Leu | Tyr | Glu | Ala | Gly | Ile |
| | | 35 | | | | | 40 | | | | | 45 | | | |
| Arg | Thr | Val | Glu | Tyr | Thr | Asn | Arg | Gly | Glu | Ala | Ala | Leu | Lys | Asn | Phe |
| | 50 | | | | | 55 | | | | | 60 | | | | |
| Lys | Val | Leu | Arg | Lys | Ile | Cys | Asp | Thr | Glu | Leu | Ser | Gly | Leu | Tyr | Leu |
| 65 | | | | | 70 | | | | | 75 | | | | | 80 |
| Gly | Ile | Gly | Thr | Ile | Lys | Asn | Gly | Glu | Gln | Ala | Lys | Ala | Phe | Val | Asp |
| | | | | 85 | | | | | 90 | | | | | 95 | |
| Ala | Gly | Ala | Asp | Tyr | Leu | Ile | Ser | Pro | Gly | Val | Val | Asp | Asp | Ala | Ala |
| | | | 100 | | | | | 105 | | | | | 110 | | |
| Lys | Ile | Ala | Asp | Gln | Asn | Gly | Leu | Leu | Tyr | Val | Pro | Gly | Ala | Met | Thr |
| | | 115 | | | | | 120 | | | | | 125 | | | |
| Pro | Thr | Glu | Ile | Ile | Arg | Ala | Glu | Gln | Phe | Gly | Ala | Thr | Leu | Val | Lys |
| | 130 | | | | | 135 | | | | | 140 | | | | |
| Leu | Phe | Pro | Gly | Asn | Ile | Leu | Gly | Pro | Gly | Phe | Val | Ser | Ala | Val | Lys |
| 145 | | | | | 150 | | | | | 155 | | | | | 160 |
| Glu | Leu | Phe | Ser | Gly | Leu | Lys | Phe | Ile | Ile | Thr | Gly | Gly | Val | Glu | Pro |
| | | | | 165 | | | | | 170 | | | | | 175 | |
| Glu | Glu | Asn | Asn | Leu | Lys | Gly | Trp | Phe | Asn | Ala | Gly | Ala | Ala | Ala | Val |
| | | | 180 | | | | | 185 | | | | | 190 | | |
| Gly | Met | Gly | Ser | Lys | Leu | Ile | Thr | Lys | Gln | Thr | Leu | Glu | Asn | Lys | Asp |
| | | 195 | | | | | 200 | | | | | 205 | | | |
| Tyr | Ala | Lys | Ile | Thr | Glu | Leu | Thr | Lys | Glu | Ser | Leu | Arg | Leu | Ile | Glu |
| | 210 | | | | | 215 | | | | | 220 | | | | |
| Leu | Val | Arg | Lys | | | | | | | | | | | | |
| 225 | | | | | | | | | | | | | | | |

```
<210> SEQ ID NO 311
<211> LENGTH: 600
<212> TYPE: DNA
<213> ORGANISM: Unknown
<220> FEATURE:
<223> OTHER INFORMATION: DNA obtained from environmental sample

<400> SEQUENCE: 311
atgatattcg ccgatgccat agccgaatgc ggcctcatcg ccatcctgcg cggcattgca      60
acggctgaaa ttgaagccgt gggacaagcc ctcatcgaag ccggcattcg cgtcgctgaa     120
attccgctga actcgccgga tccatttgcc tccatcgaga aaatggccaa ggccttcaag     180
ggcgagctgg ttgtcggggc tggaaccgtt ctcagtgtgc aggatgtcaa tttactgaaa     240
gcccatggcg gccagatcag cgtttctccc gattgcaacg aggcggtggt cgcacgcacc     300
aaagaactgg tctggagcc cgttccggc gtcttcacgc ccactgaggc ttttgccgcg     360
atccgcgccg gggcaaccca tatcaagttg tttccggcgg aagccgcaag ccccgcaacc     420
atcagggcct ggcgcgctgt tcttccaaag catgtgaaaa tctatccggt gggcggcatc     480
acgccagcaa atatgcaggg ctgggttgat gccggcgccg caggctttgg aattggctca     540
```

```
aatatctata agcagggggc cacagccgcc aacgtggcaa aggcggccaa ggaattcttt      600
```

```
<210> SEQ ID NO 312
<211> LENGTH: 200
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (4)...(198)
<223> OTHER INFORMATION: KDPG and KHG aldolase

<400> SEQUENCE: 312

Met Ile Phe Ala Asp Ala Ile Ala Glu Cys Gly Leu Ile Ala Ile Leu
1               5                   10                  15

Arg Gly Ile Ala Thr Ala Glu Ile Glu Ala Val Gly Gln Ala Leu Ile
            20                  25                  30

Glu Ala Gly Ile Arg Val Ala Glu Ile Pro Leu Asn Ser Pro Asp Pro
        35                  40                  45

Phe Ala Ser Ile Glu Lys Met Ala Lys Ala Phe Lys Gly Glu Leu Val
    50                  55                  60

Val Gly Ala Gly Thr Val Leu Ser Val Gln Asp Val Asn Leu Leu Lys
65                  70                  75                  80

Ala His Gly Gly Gln Ile Ser Val Ser Pro Asp Cys Asn Glu Ala Val
                85                  90                  95

Val Ala Arg Thr Lys Glu Leu Gly Leu Glu Pro Val Pro Gly Val Phe
            100                 105                 110

Thr Pro Thr Glu Ala Phe Ala Ala Ile Arg Ala Gly Ala Thr His Ile
        115                 120                 125

Lys Leu Phe Pro Ala Glu Ala Ser Pro Ala Thr Ile Arg Ala Trp
    130                 135                 140

Arg Ala Val Leu Pro Lys His Val Lys Ile Tyr Pro Val Gly Gly Ile
145                 150                 155                 160

Thr Pro Ala Asn Met Gln Gly Trp Val Asp Ala Gly Ala Ala Gly Phe
                165                 170                 175

Gly Ile Gly Ser Asn Ile Tyr Lys Gln Gly Ala Thr Ala Ala Asn Val
            180                 185                 190

Ala Lys Ala Ala Lys Glu Phe Phe
        195                 200
```

```
<210> SEQ ID NO 313
<211> LENGTH: 681
<212> TYPE: DNA
<213> ORGANISM: Unknown
<220> FEATURE:
<223> OTHER INFORMATION: DNA obtained from environmental sample

<400> SEQUENCE: 313
atgagccagc ccgatagaaa cctgaaggag accgtgattg cgttaactaa ggaatgcggg      60
gttctgccct gcatcaagtt gcgcaaaaaa gatgatttta ttgcctatgc ccaggcgatg     120
tatgacggag gagctcgcgt catcgaagtg accatgacaa ctccaggcgc cctggaagcg     180
atcgaagcca tttcgtctgc ctttaaagac aaactctatg ttgcttcggg caccacattg     240
gacgcgtcca ctgcgcgcga ggtcatcact cacggcggaa gctgcattgt taatccttgt     300
gtcatccccg aagtgatcga tgtcgccaac cgctatggca ttccagttta ttccggagca     360
ttcactgcga ccgaggtgtt cacggcgatg gcgccggag cgtccatggt caaatatttt     420
cccgggggtc tgggcggcgc caagtacatg accaatctga aatggtatt cccagaagtg     480
```

```
aacctgattc cttcagggggg aattaacctt gataatgctc ccgaatttat tcgcgccggc    540
gcctgcgctg tcagtggtgc acgaactttc atggatcacg aaatgattgc caagcatggt    600
ttgaaatgga ttactcaaca gacgtcaaaa ttcattgaag tggttctgga agcgaagcgg    660
aacgctccag agttgccttg a                                               681
```

<210> SEQ ID NO 314
<211> LENGTH: 226
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (12)...(207)
<223> OTHER INFORMATION: KDPG and KHG aldolase

<400> SEQUENCE: 314

```
Met Ser Gln Pro Asp Arg Asn Leu Lys Glu Thr Val Ile Ala Leu Thr
1               5                   10                  15

Lys Glu Cys Gly Val Leu Pro Cys Ile Lys Leu Arg Lys Lys Asp Asp
            20                  25                  30

Phe Ile Ala Tyr Ala Gln Ala Met Tyr Asp Gly Gly Ala Arg Val Ile
        35                  40                  45

Glu Val Thr Met Thr Thr Pro Gly Ala Leu Glu Ile Glu Ala Ile
    50                  55                  60

Ser Ser Ala Phe Lys Asp Lys Leu Tyr Val Ala Ser Gly Thr Thr Leu
65                  70                  75                  80

Asp Ala Ser Thr Ala Arg Glu Val Ile Thr His Gly Gly Ser Cys Ile
                85                  90                  95

Val Asn Pro Cys Val Ile Pro Glu Val Ile Asp Val Ala Asn Arg Tyr
            100                 105                 110

Gly Ile Pro Val Tyr Ser Gly Ala Phe Thr Ala Thr Glu Val Phe Thr
        115                 120                 125

Ala Met Arg Ala Gly Ala Ser Met Val Lys Ile Phe Pro Gly Gly Leu
    130                 135                 140

Gly Gly Ala Lys Tyr Met Thr Asn Leu Lys Met Val Phe Pro Glu Val
145                 150                 155                 160

Asn Leu Ile Pro Ser Gly Gly Ile Asn Leu Asp Asn Ala Pro Glu Phe
                165                 170                 175

Ile Arg Ala Gly Ala Cys Ala Val Ser Gly Ala Arg Thr Phe Met Asp
            180                 185                 190

His Glu Met Ile Ala Lys His Gly Leu Lys Trp Ile Thr Gln Gln Thr
        195                 200                 205

Ser Lys Phe Ile Glu Val Val Leu Glu Ala Lys Arg Asn Ala Pro Glu
    210                 215                 220

Leu Pro
225
```

<210> SEQ ID NO 315
<211> LENGTH: 576
<212> TYPE: DNA
<213> ORGANISM: Unknown
<220> FEATURE:
<223> OTHER INFORMATION: DNA obtained from environmental sample

<400> SEQUENCE: 315

```
atggcacaat ttacaagaat agaagttgca acagcaatga agaaactgg gatgattcct    60
```

```
ttgttttta  acaacgattt  agaattaagt  aaaaaagtat  taaaagcttg  ttacgatggt      120
ggagcacgct  taatggaatt  tactgctcgt  ggagattttg  cacacgaagt  ttttggtgaa      180
ttaacaaaat  atgcaattgc  agaattacca  ggaatgatta  tgggtgtagg  ttctgtaacc      240
gatgcagctg  cagcatcttt  atacatggct  ttaggagcaa  actttattgt  aactccagta      300
ttaagagaag  atatagcaat  tgtttgtaac  agacgtaaag  ttttatggtc  tcctggttgt      360
ggaactttaa  ctgaaattac  taaggccgaa  gaattaggat  gtgaaattgt  aaaattattc      420
cctggtgata  tttatggacc  tcaatttgta  aaaggaatta  aaggaccaca  accttggact      480
agtgtaatgc  caactggagg  agtttctcca  acaaaagaaa  atttaacagg  ttggtttaat      540
gcaggtgtaa  cttgtgttgg  aatgggatct  caatta                                 576
```

<210> SEQ ID NO 316
<211> LENGTH: 192
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (9)...(192)
<223> OTHER INFORMATION: KDPG and KHG aldolase
<220> FEATURE:
<221> NAME/KEY: SITE
<222> LOCATION: (176)...(179)
<223> OTHER INFORMATION: N-glycosylation site. Prosite id = PS00001

<400> SEQUENCE: 316

```
Met Ala Gln Phe Thr Arg Ile Glu Val Ala Thr Ala Met Lys Glu Thr
 1               5                  10                  15

Gly Met Ile Pro Leu Phe Phe Asn Asn Asp Leu Glu Leu Ser Lys Lys
            20                  25                  30

Val Leu Lys Ala Cys Tyr Asp Gly Gly Ala Arg Leu Met Glu Phe Thr
        35                  40                  45

Ala Arg Gly Asp Phe Ala His Glu Val Phe Gly Glu Leu Thr Lys Tyr
    50                  55                  60

Ala Ile Ala Glu Leu Pro Gly Met Ile Met Gly Val Gly Ser Val Thr
65                  70                  75                  80

Asp Ala Ala Ala Ser Leu Tyr Met Ala Leu Gly Ala Asn Phe Ile
                85                  90                  95

Val Thr Pro Val Leu Arg Glu Asp Ile Ala Ile Val Cys Asn Arg Arg
            100                 105                 110

Lys Val Leu Trp Ser Pro Gly Cys Gly Thr Leu Thr Glu Ile Thr Lys
        115                 120                 125

Ala Glu Glu Leu Gly Cys Glu Ile Val Lys Leu Phe Pro Gly Asp Ile
    130                 135                 140

Tyr Gly Pro Gln Phe Val Lys Gly Ile Lys Gly Pro Gln Pro Trp Thr
145                 150                 155                 160

Ser Val Met Pro Thr Gly Gly Val Ser Pro Thr Lys Glu Asn Leu Thr
                165                 170                 175

Gly Trp Phe Asn Ala Gly Val Thr Cys Val Gly Met Gly Ser Gln Leu
            180                 185                 190
```

<210> SEQ ID NO 317
<211> LENGTH: 612
<212> TYPE: DNA
<213> ORGANISM: Unknown
<220> FEATURE:
<223> OTHER INFORMATION: DNA obtained from environmental sample -continued

<400> SEQUENCE: 317

```
atgagcgggc gagagatcat tgcgatcctg cggggcgtgc gcccgaatga ggtggtggcc      60
attgggcacg ttctgctgga tgcaggtatc gacaagatcg aagttccgct gaattccccc     120
gatgcctttg aaagcattgc cttttggcg gatgcgtttc acgatagtgc ggtgataggt      180
gctggcaccg ttctgacgcc acaagacgtg gtgaaggtgc atcaacaggg tggcgcgatg    240
gtggtatcgc ctgattgcaa tccggatgtg atcaaggcaa ccaaggcgct gggcatgttg    300
tcttaccccg tgttttcac cccgaccgaa gcttttaccg ccctgcgttc tggtgcggat     360
gggatcaaac tgtttcctgc ttcaggcatt ggccctgcag gctggccgc gatgttggcc     420
gttttgccca caggcatgcg cagctatgcg gtgggggcg tcgggccaga tagcttcgcg     480
ccttggatcg gagttggcgt gaccggattt ggcattggaa cgggcctgtt caaaccgggg    540
tttggcacgg ctgatgtggc taaacgggca gcggacattg tggcggccta tgatcggggt    600
attttgaaat ga                                                         612
```

<210> SEQ ID NO 318
<211> LENGTH: 203
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (1)...(192)
<223> OTHER INFORMATION: KDPG and KHG aldolase

<400> SEQUENCE: 318

```
Met Ser Gly Arg Glu Ile Ile Ala Ile Leu Arg Gly Val Arg Pro Asn
1               5                   10                  15

Glu Val Val Ala Ile Gly His Val Leu Leu Asp Ala Gly Ile Asp Lys
            20                  25                  30

Ile Glu Val Pro Leu Asn Ser Pro Asp Ala Phe Glu Ser Ile Ala Leu
        35                  40                  45

Leu Ala Asp Ala Phe His Asp Ser Ala Val Ile Gly Ala Gly Thr Val
    50                  55                  60

Leu Thr Pro Gln Asp Val Val Lys Val His Gln Gln Gly Gly Ala Met
65                  70                  75                  80

Val Val Ser Pro Asp Cys Asn Pro Asp Val Ile Lys Ala Thr Lys Ala
                85                  90                  95

Leu Gly Met Leu Ser Tyr Pro Val Phe Thr Pro Thr Glu Ala Phe
            100                 105                 110

Thr Ala Leu Arg Ser Gly Ala Asp Gly Ile Lys Leu Phe Pro Ala Ser
        115                 120                 125

Gly Ile Gly Pro Ala Gly Leu Ala Ala Met Leu Ala Val Leu Pro Thr
    130                 135                 140

Gly Met Arg Ser Tyr Ala Val Gly Gly Val Gly Pro Asp Ser Phe Ala
145                 150                 155                 160

Pro Trp Ile Gly Val Gly Val Thr Gly Phe Gly Ile Gly Thr Gly Leu
                165                 170                 175

Phe Lys Pro Gly Phe Gly Thr Ala Asp Val Ala Lys Arg Ala Ala Asp
            180                 185                 190

Ile Val Ala Ala Tyr Asp Arg Gly Ile Leu Lys
        195                 200
```

<210> SEQ ID NO 319
<211> LENGTH: 600

```
<212> TYPE: DNA
<213> ORGANISM: Unknown
<220> FEATURE:
<223> OTHER INFORMATION: DNA obtained from environmental sample

<400> SEQUENCE: 319
gtgccggttc tggtcatcga agacgtcaat gatgccgtgc cgcttgccaa ggccttggtg      60
gccggtggtt tgcgcgtgct tgaaatcacc ctgcgcagtg ccgccgccga ggaaagcatt     120
aaacgtatta tcgccgaagt tcccgatgca attaccggtg cgggcaccgt gatcaatgcc     180
aaacagatgg aacgtatggc cgaaatcggt tgtgcttttg cggtttcgcc gggccatacc     240
gatggtttgc ttaaggccgc caaagatacc ggcgtgccgt tgctgccggg tgccggaacg     300
ccgtctgaaa tcatgcatct gattgatcat ggctatgaca tcttgaaatt cttcccggcc     360
gaacaacagg gcggtgtttc gatgcttaaa gccctgtctg gcccgctgcc acaggtgaaa     420
ttctgcccga cggtggtgt gtcgctggca aatttggggg attatctcgc cctgccaaat     480
atcatcaccg ttggtgggtc gtgggtctcg ccaaaaagcg cggtcaaggc cggtgactgg     540
gcaacgatca cgcgcctggc acaggaagca accgacaagg ttgccgaact cgcggttaa      600

<210> SEQ ID NO 320
<211> LENGTH: 199
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (1)...(186)
<223> OTHER INFORMATION: KDPG and KHG aldolase
<220> FEATURE:
<221> NAME/KEY: SITE
<222> LOCATION: (23)...(32)
<223> OTHER INFORMATION: KDPG and KHG aldolases active site. Prosite
      id = PS00159
<220> FEATURE:
<221> NAME/KEY: SITE
<222> LOCATION: (112)...(125)
<223> OTHER INFORMATION: KDPG and KHG aldolases Schiff-base forming
      residue. Prosite id = PS00160

<400> SEQUENCE: 320

Met Pro Val Leu Val Ile Glu Asp Val Asn Asp Ala Val Pro Leu Ala
1               5                   10                  15

Lys Ala Leu Val Ala Gly Gly Leu Arg Val Leu Glu Ile Thr Leu Arg
            20                  25                  30

Ser Ala Ala Ala Glu Glu Ser Ile Lys Arg Ile Ile Ala Glu Val Pro
        35                  40                  45

Asp Ala Ile Thr Gly Ala Gly Thr Val Ile Asn Ala Lys Gln Met Glu
    50                  55                  60

Arg Met Ala Glu Ile Gly Cys Ala Phe Ala Val Ser Pro Gly His Thr
65                  70                  75                  80

Asp Gly Leu Leu Lys Ala Ala Lys Asp Thr Gly Val Pro Leu Leu Pro
                85                  90                  95

Gly Ala Gly Thr Pro Ser Glu Ile Met His Leu Ile Asp His Gly Tyr
            100                 105                 110

Asp Ile Leu Lys Phe Phe Pro Ala Glu Gln Gln Gly Gly Val Ser Met
        115                 120                 125

Leu Lys Ala Leu Ser Gly Pro Leu Pro Gln Val Lys Phe Cys Pro Thr
    130                 135                 140

Gly Gly Val Ser Leu Ala Asn Leu Gly Asp Tyr Leu Ala Leu Pro Asn
145                 150                 155                 160
```

```
Ile Ile Thr Val Gly Gly Ser Trp Val Ser Pro Lys Ser Ala Val Lys
            165                 170                 175

Ala Gly Asp Trp Ala Thr Ile Thr Arg Leu Ala Gln Glu Ala Thr Asp
        180                 185                 190

Lys Val Ala Glu Leu Arg Gly
        195

<210> SEQ ID NO 321
<211> LENGTH: 654
<212> TYPE: DNA
<213> ORGANISM: Unknown
<220> FEATURE:
<223> OTHER INFORMATION: DNA obtained from environmental sample

<400> SEQUENCE: 321
atgaccagcg aaacgaacca gatattagag gcgaaatttg ccgctgcgcc ggtggtgccc        60
ctgatcgaag ccagtgaccc tacggttgcg gtagcaatcg caaaagcgct gcaggcgggc       120
ggcctcgatg tgatcgaagt cgtcctccgg accgacgcgg cgctcgattg catggaagcc       180
attatcgcgg agacttcgga catcattgtt ggcgcgggaa caatcttgac cgctgacgat       240
gcgaaggcag ctgttacccg cggcgcgcag ttcattgtgt gcccgggact ggtcgacgcg       300
gtggtcaatt tctgcaaggc aaatgatctt ccggtcttcc cgggaacaat gaccccgggc       360
gaagtgcaac aggcccataa tctcggtctc ggaacggtga aattctttcc cgccaaactc       420
gctggcggtg tgccgatgct caaggcattg agctcggtct ttcgcaatat gcgtttcatg       480
ccgacgggtg gggtgtcagc agagaatctg ggcgaatttc tggccgtgcc ttccgtaatt       540
gcctgcggcg gtagctggct cacgccgaaa gcggctatcg acgcgggcga ttacgatgca       600
atcaccaagc tggcccgtga agctgtcgct ctcgcacgtg cctctagacc ataa             654

<210> SEQ ID NO 322
<211> LENGTH: 217
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (9)...(204)
<223> OTHER INFORMATION: KDPG and KHG aldolase

<400> SEQUENCE: 322

Met Thr Ser Glu Thr Asn Gln Ile Leu Glu Ala Lys Phe Ala Ala Ala
  1               5                  10                  15

Pro Val Val Pro Leu Ile Glu Ala Ser Asp Pro Thr Val Ala Val Ala
            20                  25                  30

Ile Ala Lys Ala Leu Gln Ala Gly Gly Leu Asp Val Ile Glu Val Val
        35                  40                  45

Leu Arg Thr Asp Ala Ala Leu Asp Cys Met Glu Ala Ile Ile Ala Glu
    50                  55                  60

Thr Ser Asp Ile Ile Val Gly Ala Gly Thr Ile Leu Thr Ala Asp Asp
 65                  70                  75                  80

Ala Lys Ala Ala Val Thr Arg Gly Ala Gln Phe Ile Val Cys Pro Gly
                85                  90                  95

Leu Val Asp Ala Val Val Asn Phe Cys Lys Ala Asn Asp Leu Pro Val
            100                 105                 110

Phe Pro Gly Thr Met Thr Pro Gly Glu Val Gln Gln Ala His Asn Leu
        115                 120                 125
```

```
Gly Leu Gly Thr Val Lys Phe Phe Pro Ala Lys Leu Ala Gly Gly Val
            130                 135                 140

Pro Met Leu Lys Ala Leu Ser Ser Val Phe Arg Asn Met Arg Phe Met
145                 150                 155                 160

Pro Thr Gly Gly Val Ser Ala Glu Asn Leu Gly Glu Phe Leu Ala Val
                165                 170                 175

Pro Ser Val Ile Ala Cys Gly Gly Ser Trp Leu Thr Pro Lys Ala Ala
                180                 185                 190

Ile Asp Ala Gly Asp Tyr Asp Ala Ile Thr Lys Leu Ala Arg Glu Ala
            195                 200                 205

Val Ala Leu Ala Arg Ala Ser Arg Pro
    210                 215

<210> SEQ ID NO 323
<211> LENGTH: 603
<212> TYPE: DNA
<213> ORGANISM: Unknown
<220> FEATURE:
<223> OTHER INFORMATION: DNA obtained from environmental sample

<400> SEQUENCE: 323
atgacgttcc ccctgagatc actcgtggaa gccgcgacca aggcaccgat tgtacccgtt      60
ctggtcgtcg accgcattga agttgcggcc ccccttgcgc gggcgcttgt tgatggcggc     120
ctgacaattg ccgaagtcac gctgcgaaca ccttcggggc tggcggtaat cgaagagatg     180
aaatccgccg agcccggcct gaaggtcggc gcgggcaccg tgttgaccga atccgatgtc     240
gagaacgcat tggcggccgg cgcggatttc ctcgtggcac cgggcatgtc gccaaaactg     300
ttggccggac tgggtggcca ccgccgcctg atgatccctg cgttgcgac agccagcgaa      360 gccatggcca ggcacgagga cgggttcgac ctgttgaaac tgtttccggc ctcgattgcc     420
ggcggagtca gcgctctcaa ggcgcttggc ggtccgctgc cgcacctgcg cttcatgccg     480
accggcggca tcaccgaggc ggatgtcggc aaataccctcg cccttcccaa tgttttcgcg     540
gccggaggct cgtggattgc gacgggcgcc gacattgctg ccgaagactc gagccgaatt     600
ctt                                                                   603

<210> SEQ ID NO 324
<211> LENGTH: 201
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (9)...(201)
<223> OTHER INFORMATION: KDPG and KHG aldolase
<220> FEATURE:
<221> NAME/KEY: SITE
<222> LOCATION: (40)...(49)
<223> OTHER INFORMATION: KDPG and KHG aldolases active site. Prosite
      id = PS00159

<400> SEQUENCE: 324

Met Thr Phe Pro Leu Arg Ser Leu Val Glu Ala Ala Thr Lys Ala Pro
1               5                   10                  15

Ile Val Pro Val Leu Val Val Asp Arg Ile Glu Val Ala Ala Pro Leu
            20                  25                  30

Ala Arg Ala Leu Val Asp Gly Gly Leu Thr Ile Ala Glu Val Thr Leu
        35                  40                  45

Arg Thr Pro Ser Gly Leu Ala Val Ile Glu Glu Met Lys Ser Ala Glu
    50                  55                  60
```

```
Pro Gly Leu Lys Val Gly Ala Gly Thr Val Leu Thr Glu Ser Asp Val
 65                  70                  75                  80

Glu Asn Ala Leu Ala Ala Gly Ala Asp Phe Leu Val Ala Pro Gly Met
                 85                  90                  95

Ser Pro Lys Leu Leu Ala Gly Leu Gly Gly His Arg Arg Leu Met Ile
            100                 105                 110

Pro Gly Val Ala Thr Ala Ser Glu Ala Met Ala Arg His Glu Asp Gly
        115                 120                 125

Phe Asp Leu Leu Lys Leu Phe Pro Ala Ser Ile Ala Gly Gly Val Ser
130                 135                 140

Ala Leu Lys Ala Leu Gly Gly Pro Leu Pro His Leu Arg Phe Met Pro
145                 150                 155                 160

Thr Gly Gly Ile Thr Glu Ala Asp Val Gly Lys Tyr Leu Ala Leu Pro
                165                 170                 175

Asn Val Phe Ala Ala Gly Gly Ser Trp Ile Ala Thr Gly Ala Asp Ile
            180                 185                 190

Ala Ala Glu Asp Ser Ser Arg Ile Leu
        195                 200
```

<210> SEQ ID NO 325
<211> LENGTH: 648
<212> TYPE: DNA
<213> ORGANISM: Unknown
<220> FEATURE:
<223> OTHER INFORMATION: DNA obtained from environmental sample

<400> SEQUENCE: 325

```
atacaagaag taaaggagat tggtttattg cctttatatt atcacgacga tgcagctatt      60
tgtctgaaag tagctaatac tttgtatgat gccgatgtaa aatgcataga atttacaaac     120
cgtggtgaat atgcacttac aaactttaaa cacttagtga agctgagaga tgaaaagatg     180
aaaggtctat tgcttgcagt gggcacaatt aaaaccggga cggatgctca gaaatttatt     240
gatgccggtg ccgattttt gatcagccca atatttgaca gcagcgtttg cgatacggcc     300
tatttgaata aaacgttgtg ataccaggt tgtacaacgc aacagaaat tcatgtagca      360
cagcaagcgg ttgtaagct tatcaaatta ttcccgggaa atgtactggg gccgggtttt     420
gtagaagcga tcatgccatt attcagtgga attgatttta cgatcactgg tggagtagaa     480
gcaacagaag caaatctggg tgcctggttt aaatcaggtg tgaaggtagt tggaatgggc     540
agcaagctta taacaaaaga cattttaaag aatggtgatt atgatggatt gaaagctaaa     600
acaaaagaag tgctttcaat aattcgacat attaaatcag ctaaatag              648
```

<210> SEQ ID NO 326
<211> LENGTH: 215
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (1)...(200)
<223> OTHER INFORMATION: KDPG and KHG aldolase
<220> FEATURE:
<221> NAME/KEY: SITE
<222> LOCATION: (104)...(107)
<223> OTHER INFORMATION: N-glycosylation site. Prosite id = PS00001

<400> SEQUENCE: 326

```
Ile Gln Glu Val Lys Glu Ile Gly Leu Leu Pro Leu Tyr Tyr His Asp
1               5                   10                  15
```

```
Asp Ala Ala Ile Cys Leu Lys Val Ala Asn Thr Leu Tyr Asp Ala Asp
            20                  25                  30

Val Lys Cys Ile Glu Phe Thr Asn Arg Gly Glu Tyr Ala Leu Thr Asn
         35                  40                  45

Phe Lys His Leu Val Lys Leu Arg Asp Glu Lys Met Lys Gly Leu Leu
 50                  55                  60

Leu Ala Val Gly Thr Ile Lys Thr Gly Thr Asp Ala Gln Lys Phe Ile
 65                  70                  75                  80

Asp Ala Gly Ala Asp Phe Leu Ile Ser Pro Ile Phe Asp Ser Ser Val
                85                  90                  95

Cys Asp Thr Ala Tyr Leu Asn Lys Thr Leu Trp Ile Pro Gly Cys Thr
            100                 105                 110

Thr Pro Thr Glu Ile His Val Ala Gln Gln Ala Gly Cys Lys Leu Ile
            115                 120                 125

Lys Leu Phe Pro Gly Asn Val Leu Gly Pro Gly Phe Val Glu Ala Ile
130                 135                 140

Met Pro Leu Phe Ser Gly Ile Asp Phe Thr Ile Thr Gly Gly Val Glu
145                 150                 155                 160

Ala Thr Glu Ala Asn Leu Gly Ala Trp Phe Lys Ser Gly Val Lys Val
                165                 170                 175

Val Gly Met Gly Ser Lys Leu Ile Thr Lys Asp Ile Leu Lys Asn Gly
            180                 185                 190

Asp Tyr Asp Gly Leu Lys Ala Lys Thr Lys Glu Val Leu Ser Ile Ile
            195                 200                 205

Arg His Ile Lys Ser Ala Lys
            210                 215

<210> SEQ ID NO 327
<211> LENGTH: 642
<212> TYPE: DNA
<213> ORGANISM: Unknown
<220> FEATURE:
<223> OTHER INFORMATION: DNA obtained from environmental sample

<400> SEQUENCE: 327
atggaacaat ctatctttga ttacttctac aaaatcggcg tcattcccgt actggaaatc      60
gactcggcgc ttcatgccaa accgttagcc gaggcgctgc tggcaggagg tctgcctatc     120
gccgagatca cactgcgcac cgaggcagcg ctcgaggcga ttcgcactat tgcgcgcgat     180
gtaccggatg tcatcgtcgg ggctggaacc gtgataacct gggaacaagc cgaagcggca     240
cgtgacgcgg gcgcgcaatt tctcgtctca cccgggatgg tggagcaggt tgtcatctgg     300
gcacaggaaa atcaaatccc tgttctgccc ggcgctgtga ccccaccga atgatccgc      360 gccatccatc tcggtttgaa gtttctgaaa ttttccat cggaagctgt aggcggactc     420
aaagccctca aggccctctc agacccctttc cgggattgc gatttatccc aaccggtgga     480
gtgaagtttg agaatctggc ggattatcta caaatggaaa agatccacgc tgtcggcggc     540
tcgtggatgg caaagcgcca gatgatcgcc gaccgaaaat tcgacgagat tacgcgattg     600
gcgaatgaag ccagcgacct tgtgacaaaa atcaggaagt ag                        642

<210> SEQ ID NO 328
<211> LENGTH: 213
<212> TYPE: PRT
<213> ORGANISM: Unknown
<220> FEATURE:
<223> OTHER INFORMATION: Protein obtained from environmental sample
<220> FEATURE:
```

```
<221> NAME/KEY: DOMAIN
<222> LOCATION: (5)...(200)
<223> OTHER INFORMATION: KDPG and KHG aldolase
<220> FEATURE:
<221> NAME/KEY: SITE
<222> LOCATION: (37)...(46)
<223> OTHER INFORMATION: KDPG and KHG aldolases active site. Prosite
      id = PS00159

<400> SEQUENCE: 328

Met Glu Gln Ser Ile Phe Asp Tyr Phe Tyr Lys Ile Gly Val Ile Pro
1               5                   10                  15

Val Leu Glu Ile Asp Ser Ala Leu His Ala Lys Pro Leu Ala Glu Ala
            20                  25                  30

Leu Leu Ala Gly Gly Leu Pro Ile Ala Glu Ile Thr Leu Arg Thr Glu
        35                  40                  45

Ala Ala Leu Glu Ala Ile Arg Thr Ile Ala Arg Asp Val Pro Asp Val
    50                  55                  60

Ile Val Gly Ala Gly Thr Val Ile Thr Trp Glu Gln Ala Glu Ala Ala
65                  70                  75                  80

Arg Asp Ala Gly Ala Gln Phe Leu Val Ser Pro Gly Met Val Glu Gln
                85                  90                  95

Val Val Ile Trp Ala Gln Glu Asn Gln Ile Pro Val Leu Pro Gly Ala
            100                 105                 110

Val Thr Pro Thr Glu Met Ile Arg Ala Ile His Leu Gly Leu Lys Phe
        115                 120                 125

Leu Lys Phe Phe Pro Ser Glu Ala Val Gly Gly Leu Lys Ala Leu Lys
    130                 135                 140

Ala Leu Ser Asp Pro Phe Pro Gly Leu Arg Phe Ile Pro Thr Gly Gly
145                 150                 155                 160

Val Lys Phe Glu Asn Leu Ala Asp Tyr Leu Gln Met Glu Lys Ile His
                165                 170                 175

Ala Val Gly Gly Ser Trp Met Ala Lys Arg Gln Met Ile Ala Asp Arg
            180                 185                 190

Lys Phe Asp Glu Ile Thr Arg Leu Ala Asn Glu Ala Ser Asp Leu Val
        195                 200                 205

Thr Lys Ile Arg Lys
    210

<210> SEQ ID NO 329
<211> LENGTH: 618
<212> TYPE: DNA
<213> ORGANISM: Unknown
<220> FEATURE:
<223> OTHER INFORMATION: DNA obtained from environmental sample

<400> SEQUENCE: 329
atgactcgct tttctgaact tatgtcaggg caaacattac tgcctataat tcaagccgac        60
acaccagagc aaggcgttaa aatagctcaa gctatggcta atgctggcct tactttggtt       120
gaagtagtac ttagaactga tgcatcgtta gatgcattaa aagctattaa agagcaggtg       180
ccagcgctta agtaggtgc aggcacagta ataaatactg acattttaga gcaagcactt       240
gcagcaggtg ccgactttat tgttacgcca gcagtgtctc cgcaattatt agccgcgcta       300
acaaaatgca atgtgccggt acttcctggt gtgtctaaca cgggtgacat tttaatggcg       360
cttgagtacg gttttgaaga acaaaaatta ttccctgcat cgctcgctgg tggtgcacca       420
ttcgtatcgg ctgtctcgtc agtatttaga gctgctagct tttgtcctac aggtggcgta       480
agcgagcaaa ataaaatgga ttacttatct ttaaataatg tatttgctgt gggtggtact       540
```

-continued

```
tggattgcaa ataaagagtg ggttgcacaa gaaaactggc aagcaattac tgactcgtgt    600
attcaagcat taaagtag                                                  618
```

<210> SEQ ID NO 330
<211> LENGTH: 205
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (4)...(199)
<223> OTHER INFORMATION: KDPG and KHG aldolase

<400> SEQUENCE: 330

```
Met Thr Arg Phe Ser Glu Leu Met Ser Gly Gln Thr Leu Leu Pro Ile
1               5                   10                  15

Ile Gln Ala Asp Thr Pro Glu Gln Gly Val Lys Ile Ala Gln Ala Met
            20                  25                  30

Ala Asn Ala Gly Leu Thr Leu Val Glu Val Val Leu Arg Thr Asp Ala
        35                  40                  45

Ser Leu Asp Ala Leu Lys Ala Ile Lys Glu Gln Val Pro Ala Leu Lys
    50                  55                  60

Val Gly Ala Gly Thr Val Ile Asn Thr Asp Ile Leu Glu Gln Ala Leu
65                  70                  75                  80

Ala Ala Gly Ala Asp Phe Ile Val Thr Pro Ala Val Ser Pro Gln Leu
                85                  90                  95

Leu Ala Ala Leu Thr Lys Cys Asn Val Pro Val Leu Pro Gly Val Ser
            100                 105                 110

Asn Thr Gly Asp Ile Leu Met Ala Leu Glu Tyr Gly Phe Glu Glu Gln
        115                 120                 125

Lys Leu Phe Pro Ala Ser Leu Ala Gly Gly Ala Pro Phe Val Ser Ala
    130                 135                 140

Val Ser Ser Val Phe Arg Ala Ala Ser Phe Cys Pro Thr Gly Gly Val
145                 150                 155                 160

Ser Glu Gln Asn Lys Met Asp Tyr Leu Ser Leu Asn Asn Val Phe Ala
                165                 170                 175

Val Gly Gly Thr Trp Ile Ala Asn Lys Glu Trp Val Ala Gln Glu Asn
            180                 185                 190

Trp Gln Ala Ile Thr Asp Ser Cys Ile Gln Ala Leu Lys
        195                 200                 205
```

<210> SEQ ID NO 331
<211> LENGTH: 663
<212> TYPE: DNA
<213> ORGANISM: Unknown
<220> FEATURE:
<223> OTHER INFORMATION: DNA obtained from environmental sample

<400> SEQUENCE: 331

```
atggcatatc cgaccgcggt caattcacag attaccgaca cagcaggcaa ggttttgcat    60
cgcaaactga ttgctatttt acgcggagtg aagcccgatg aagcggcatc catggcgcgt   120
gtgctggtcg atgccgggat cacgatgatc gaggtgccgc tgaattcccc ggaaccgctt   180
aaaagcattg cgatcatgaa ggcagaagtc ggtgacgcgg ccctgatcgg ggcaggtacg   240
gtcttaacgg tcgaggatgt tgtgaacgtt cgtgacgcgg cggtgagtt tgttgtgtcg   300 cccaattacg atgtcgatgt gattaaaaaa accaaggaag tcggtatggg aagttggccg   360
```

-continued

```
ggggtgctga ctccgaccga atgtttcgcc gcgatcaagg ccggggcgga tgggcttaaa      420
atattccctg ccagcatcat tggcgcatcg gggatttcgg cgatgcgggc ggttttgcca      480
aaagatatgc cggtttatgc ggttggtggt gttgggccgg atgattttgc gacctatgcc      540 aaggcgggt  gcgatggttt cggccttgga tcgggatt   ataaacccgg cctgacagcg      600
gacgaagtat cggggcgcgc tattgccttc gtaacggcgc atgacgcggt atttgcgggc      660
tag                                                                    663
```

```
<210> SEQ ID NO 332
<211> LENGTH: 220
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (15)...(211)
<223> OTHER INFORMATION: KDPG and KHG aldolase

<400> SEQUENCE: 332

Met Ala Tyr Pro Thr Ala Val Asn Ser Gln Ile Thr Asp Thr Ala Gly
1               5                   10                  15

Lys Val Leu His Arg Lys Leu Ile Ala Ile Leu Arg Gly Val Lys Pro
            20                  25                  30

Asp Glu Ala Ala Ser Met Ala Arg Val Leu Val Asp Ala Gly Ile Thr
        35                  40                  45

Met Ile Glu Val Pro Leu Asn Ser Pro Glu Pro Leu Lys Ser Ile Ala
    50                  55                  60

Ile Met Lys Ala Glu Val Gly Asp Ala Ala Leu Ile Gly Ala Gly Thr
65                  70                  75                  80

Val Leu Thr Val Glu Asp Val Val Asn Val Arg Asp Ala Gly Gly Glu
                85                  90                  95

Phe Val Val Ser Pro Asn Tyr Asp Val Asp Val Ile Lys Lys Thr Lys
            100                 105                 110

Glu Val Gly Met Gly Ser Trp Pro Gly Val Leu Thr Pro Thr Glu Cys
        115                 120                 125

Phe Ala Ala Ile Lys Ala Gly Ala Asp Gly Leu Lys Ile Phe Pro Ala
    130                 135                 140

Ser Ile Ile Gly Ala Ser Gly Ile Ser Ala Met Arg Ala Val Leu Pro
145                 150                 155                 160

Lys Asp Met Pro Val Tyr Ala Val Gly Val Gly Pro Asp Asp Phe
                165                 170                 175

Ala Thr Tyr Ala Lys Ala Gly Cys Asp Gly Phe Gly Leu Gly Ser Gly
            180                 185                 190

Ile Tyr Lys Pro Gly Leu Thr Ala Asp Glu Val Ser Gly Arg Ala Ile
        195                 200                 205

Ala Phe Val Thr Ala His Asp Ala Val Phe Ala Gly
    210                 215                 220

<210> SEQ ID NO 333
<211> LENGTH: 648
<212> TYPE: DNA
<213> ORGANISM: Unknown
<220> FEATURE:
<223> OTHER INFORMATION: DNA obtained from environmental sample

<400> SEQUENCE: 333
atggcgattg atcccgccgc tgccagtcgg cgcatgcgcg aattggcggc gctggccccg       60
```

-continued

```
gtgatcccgg tgctggtgat cgaggatgcc gcaagggcga ggcccctggc cgaggcgctg    120
gtggcgggtg tcctgccggt gctggaggtg acgctgcgca ccccggccgc gccagaggtc    180
attcgcgaga tgtcccgggt cccgggggcc attgtcggcg ccggcaccgt gatcacaccg    240
gccgacgtgc ggatcgcaca gcggcgggg gcccgattcg ccgtctcccc cggcgcgacc    300
gatgcgttgc tcgatgcctg cgaagcggcg gggctgccgc tcctgcccgg cgcggccacg    360
gcgagcgagg cgatggcgct tctggcgcgc ggctacgaca tgctgaagtt ctttcccgcc    420
gaggcagtgg gcggcgcggc ggcgcttgca gcgctgggcg cgccgctgcc gcagatttcc    480
ttctgcccga ccggagggt cagcccggca aacgcgcccg actacctcgc cttgcccacg    540
gttccctgcg tcggcggcag ctgggtggcc ccgaaaccac aggtcgccgc cggcgactgg    600
gacgcgatcc gtgccctcgc cgaacacgcc cgcaccctcg cgccctga                 648
```

```
<210> SEQ ID NO 334
<211> LENGTH: 215
<212> TYPE: PRT
<213> ORGANISM: Unknown
<220> FEATURE:
<223> OTHER INFORMATION: Protein obtained from environmental sample
<220> FEATURE:
<221> NAME/KEY: DOMAIN
<222> LOCATION: (12)...(206)
<223> OTHER INFORMATION: KDPG and KHG aldolase
<220> FEATURE:
<221> NAME/KEY: SITE
<222> LOCATION: (44)...(53)
<223> OTHER INFORMATION: KDPG and KHG aldolases active site. Prosite
      id = PS00159
<220> FEATURE:
<221> NAME/KEY: SITE
<222> LOCATION: (133)...(146)
<223> OTHER INFORMATION: KDPG and KHG aldolases Schiff-base forming
      residue. Prosite id = PS00160

<400> SEQUENCE: 334

Met Ala Ile Asp Pro Ala Ala Ser Arg Arg Met Arg Glu Leu Ala
1               5                   10                  15

Ala Leu Ala Pro Val Ile Pro Val Leu Val Ile Glu Asp Ala Ala Arg
                20                  25                  30

Ala Arg Pro Leu Ala Glu Ala Leu Val Ala Gly Gly Leu Pro Val Leu
            35                  40                  45

Glu Val Thr Leu Arg Thr Pro Ala Ala Pro Glu Val Ile Arg Glu Met
        50                  55                  60

Ser Arg Val Pro Gly Ala Ile Val Gly Ala Gly Thr Val Ile Thr Pro
65                  70                  75                  80

Ala Asp Val Arg Ile Ala Gln Ala Ala Gly Ala Arg Phe Ala Val Ser
                85                  90                  95

Pro Gly Ala Thr Asp Ala Leu Leu Asp Ala Cys Glu Ala Ala Gly Leu
            100                 105                 110

Pro Leu Leu Pro Gly Ala Ala Thr Ala Ser Glu Ala Met Ala Leu Leu
        115                 120                 125

Ala Arg Gly Tyr Asp Met Leu Lys Phe Phe Pro Ala Glu Ala Val Gly
    130                 135                 140

Gly Ala Ala Ala Leu Ala Ala Leu Gly Ala Pro Leu Pro Gln Ile Ser
145                 150                 155                 160

Phe Cys Pro Thr Gly Gly Val Ser Pro Ala Asn Ala Pro Asp Tyr Leu
                165                 170                 175

Ala Leu Pro Thr Val Pro Cys Val Gly Gly Ser Trp Val Ala Pro Lys
            180                 185                 190
```

```
Pro Gln Val Ala Ala Gly Asp Trp Asp Ala Ile Arg Ala Leu Ala Glu
        195                 200                 205

His Ala Arg Thr Leu Ala Pro
    210                 215

<210> SEQ ID NO 335
<211> LENGTH: 19
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(19)
<223> OTHER INFORMATION: b is c, g, or t
<220> FEATURE:
<221> NAME/KEY: misc_feature
<222> LOCATION: (1)..(19)
<223> OTHER INFORMATION: y is c or t
<220> FEATURE:
<221> NAME/KEY: misc_feature
<222> LOCATION: (1)..(19)
<223> OTHER INFORMATION: r is a or g
<220> FEATURE:
<221> NAME/KEY: misc_feature
<222> LOCATION: (1)..(19)
<223> OTHER INFORMATION: w is a or t

<400> SEQUENCE: 335
aargtbtwyg argacaatg                                              19

<210> SEQ ID NO 336
<211> LENGTH: 18
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(18)
<223> OTHER INFORMATION: d is a, g, or t
<220> FEATURE:
<221> NAME/KEY: misc_feature
<222> LOCATION: (1)..(18)
<223> OTHER INFORMATION: y is c or t
<220> FEATURE:
<221> NAME/KEY: misc_feature
<222> LOCATION: (1)..(18)
<223> OTHER INFORMATION: r is a or g
<220> FEATURE:
<221> NAME/KEY: misc_feature
<222> LOCATION: (1)..(18)
<223> OTHER INFORMATION: w is a or t

<400> SEQUENCE: 336
gcdcagawca ayggrtgg                                               18

<210> SEQ ID NO 337
<211> LENGTH: 23
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(23)
<223> OTHER INFORMATION: d is a, g, or t
<220> FEATURE:
<221> NAME/KEY: misc_feature
<222> LOCATION: (1)..(23)
<223> OTHER INFORMATION: y is c or t
<220> FEATURE:
<221> NAME/KEY: misc_feature
<222> LOCATION: (1)..(23)
```

```
<223> OTHER INFORMATION: r is a or g
<220> FEATURE:
<221> NAME/KEY: misc_feature
<222> LOCATION: (1)..(23)
<223> OTHER INFORMATION: s is c or g

<400> SEQUENCE: 337
ccatcrsyat cdgcrtadag cca                                              23

<210> SEQ ID NO 338
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(20)
<223> OTHER INFORMATION: d is a, g, or t
<220> FEATURE:
<221> NAME/KEY: misc_feature
<222> LOCATION: (1)..(20)
<223> OTHER INFORMATION: y is c or t
<220> FEATURE:
<221> NAME/KEY: misc_feature
<222> LOCATION: (1)..(20)
<223> OTHER INFORMATION: r is a or g
<220> FEATURE:
<221> NAME/KEY: misc_feature
<222> LOCATION: (1)..(20)
<223> OTHER INFORMATION: n is a, c, g, or t

<400> SEQUENCE: 338
gcrtadagcc aytcnccrtc                                                  20

<210> SEQ ID NO 339
<211> LENGTH: 30
<212> TYPE: DNA
<213> ORGANISM: Artificial sequence
<220> FEATURE:
<223> OTHER INFORMATION: Primer

<400> SEQUENCE: 339
ataagacata tgcctatcgt tgttacgaag                                       30

<210> SEQ ID NO 340
<211> LENGTH: 33
<212> TYPE: DNA
<213> ORGANISM: Artificial sequence
<220> FEATURE:
<223> OTHER INFORMATION: Primer

<400> SEQUENCE: 340
ataagaggat ccttattcct cgggcagccg ctc                                   33

<210> SEQ ID NO 341
<211> LENGTH: 30
<212> TYPE: DNA
<213> ORGANISM: Artificial sequence
<220> FEATURE:
<223> OTHER INFORMATION: Primer

<400> SEQUENCE: 341
ataagacata tgaacagacc tgtggttgtc                                       30

<210> SEQ ID NO 342
<211> LENGTH: 33
<212> TYPE: DNA
<213> ORGANISM: Artificial sequence
<220> FEATURE:
```

-continued

<223> OTHER INFORMATION: Primer

<400> SEQUENCE: 342
ataagaggat ccttacaggt acttgagacc gag    33

<210> SEQ ID NO 343
<211> LENGTH: 30
<212> TYPE: DNA
<213> ORGANISM: Artificial sequence
<220> FEATURE:
<223> OTHER INFORMATION: Primer

<400> SEQUENCE: 343
ataagacata tgagcgtggt catccgaaac    30

<210> SEQ ID NO 344
<211> LENGTH: 33
<212> TYPE: DNA
<213> ORGANISM: Artificial sequence
<220> FEATURE:
<223> OTHER INFORMATION: Primer

<400> SEQUENCE: 344
ataagaggat ccttacttcg ctttgttata ggc    33

<210> SEQ ID NO 345
<211> LENGTH: 30
<212> TYPE: DNA
<213> ORGANISM: Artificial sequence
<220> FEATURE:
<223> OTHER INFORMATION: Primer

<400> SEQUENCE: 345
ataagacata tgaacaagcc cgtggttgtg    30

<210> SEQ ID NO 346
<211> LENGTH: 34
<212> TYPE: DNA
<213> ORGANISM: Artificial sequence
<220> FEATURE:
<223> OTHER INFORMATION: Primer

<400> SEQUENCE: 346
ataagaggat ccttacaagt acttgagacc gagg    34

<210> SEQ ID NO 347
<211> LENGTH: 29
<212> TYPE: DNA
<213> ORGANISM: Artificial sequence
<220> FEATURE:
<223> OTHER INFORMATION: Primer

<400> SEQUENCE: 347
ataagacata tgagcgtggt cgtcaccgg    29

<210> SEQ ID NO 348
<211> LENGTH: 34
<212> TYPE: DNA
<213> ORGANISM: Artificial sequence
<220> FEATURE:
<223> OTHER INFORMATION: Primer

<400> SEQUENCE: 348
ataagaggat ccttagccgt ttttcccgtc ggtg    34

<210> SEQ ID NO 349

```
<211> LENGTH: 33
<212> TYPE: DNA
<213> ORGANISM: Artificial sequence
<220> FEATURE:
<223> OTHER INFORMATION: Primer

<400> SEQUENCE: 349
agaagacata tgatgagcat cgtcgtccag aac                                    33

<210> SEQ ID NO 350
<211> LENGTH: 34
<212> TYPE: DNA
<213> ORGANISM: Artificial sequence
<220> FEATURE:
<223> OTHER INFORMATION: Primer

<400> SEQUENCE: 350
agaagaggat cctcagacat atttcaggcc cttg                                   34

<210> SEQ ID NO 351
<211> LENGTH: 30
<212> TYPE: DNA
<213> ORGANISM: Artificial sequence
<220> FEATURE:
<223> OTHER INFORMATION: Primer

<400> SEQUENCE: 351
agaagacata tgatgagcgt ggtcatcacc                                        30

<210> SEQ ID NO 352
<211> LENGTH: 33
<212> TYPE: DNA
<213> ORGANISM: Artificial sequence
<220> FEATURE:
<223> OTHER INFORMATION: Primer

<400> SEQUENCE: 352
acaacaggat ccctatttct tctccggcgt ttc                                    33

<210> SEQ ID NO 353
<211> LENGTH: 30
<212> TYPE: DNA
<213> ORGANISM: Artificial sequence
<220> FEATURE:
<223> OTHER INFORMATION: Primer

<400> SEQUENCE: 353
ataatacata tgagcgtcgt cgttcagaac                                        30

<210> SEQ ID NO 354
<211> LENGTH: 34
<212> TYPE: DNA
<213> ORGANISM: Artificial sequence
<220> FEATURE:
<223> OTHER INFORMATION: Primer

<400> SEQUENCE: 354
ataataggat ccttagacat atttgagccc cttc                                   34

<210> SEQ ID NO 355
<211> LENGTH: 33
<212> TYPE: DNA
<213> ORGANISM: Artificial sequence
<220> FEATURE:
<223> OTHER INFORMATION: Primer

<400> SEQUENCE: 355
```

```
agaagacata tgatgtcggt tgtcgttcag aac                           33
```

<210> SEQ ID NO 356
<211> LENGTH: 31
<212> TYPE: DNA
<213> ORGANISM: Artificial sequence
<220> FEATURE:
<223> OTHER INFORMATION: Primer

<400> SEQUENCE: 356

```
agaagaggat cctcagatat acttcaggcc c                            31
```

<210> SEQ ID NO 357
<211> LENGTH: 852
<212> TYPE: DNA
<213> ORGANISM: Artificial sequence
<220> FEATURE:
<223> OTHER INFORMATION: ATCC 4978 DAAT

<400> SEQUENCE: 357

```
atgagttata gcttatggaa tgaccaaatt gtgaatgatg aagaagtagt agttgataag    60
gaggaccgtg gctatcaatt tggcgatggt gtttatgaag ttgtaaaagt atataacggt   120
gaattattta cagcggagga gcatgtcgat cgttttacg cgagtgctga aaaaattcgc    180
gttacgatcc cttatacaaa agacaaattg catcaattat tgcatcagtt agttgaaatg   240
aataaagttc aaacaggaca tatttatttc caaattacgc gtggtgcagg ccctcgtaat   300
catatttttcc ctggtgatga agtgaagcca gtattaacag gtaataccaa ggaaaatcca   360
cgtcccgtag caaactttga aaaaggtgtg aagcaacat ttgtagaaga cattcgttgg    420
ttacgctgtg acattaaatc attaaattta cttggtgcgg tacttgctaa caagaagca    480
catgaaaaag gatgctatga agcggtttta catcgtgatg aaatcgtaac agaaggctct   540
tcttcaaata tttatggaat taagatggc gtattataca cacatccagc gaataacttc    600
atcttaaatg tgattacacg tcaagtaatc attaaatgtg ctgctgaaat tggcttacca   660
gtgaaggaag aagcaatgac aaaaactcag cttcttgcaa tggatgaagt gattgtttca   720
tcaacgactt cagaagtaac gccaattatc gacatagatg aacagtaat tggtgcgggt    780
aaaccgggtg actggacacg taaattacaa gcacaatttg atacgaaaat cccaaaaggt   840
attcgcgcat aa                                                      852
```

<210> SEQ ID NO 358
<211> LENGTH: 283
<212> TYPE: PRT
<213> ORGANISM: Artificial sequence
<220> FEATURE:
<223> OTHER INFORMATION: ATCC 4978 DAAT

<400> SEQUENCE: 358

```
Met Ser Tyr Ser Leu Trp Asn Asp Gln Ile Val Asn Asp Glu Glu Val
1               5                   10                  15

Val Val Asp Lys Glu Asp Arg Gly Tyr Gln Phe Gly Asp Gly Val Tyr
                20                  25                  30

Glu Val Val Lys Val Tyr Asn Gly Glu Leu Phe Thr Ala Glu Glu His
            35                  40                  45

Val Asp Arg Phe Tyr Ala Ser Ala Glu Lys Ile Arg Val Thr Ile Pro
        50                  55                  60

Tyr Thr Lys Asp Lys Leu His Gln Leu Leu His Gln Leu Val Glu Met
65                  70                  75                  80

Asn Lys Val Gln Thr Gly His Ile Tyr Phe Gln Ile Thr Arg Gly Ala
```

```
                    85                  90                  95
Gly Pro Arg Asn His Ile Phe Pro Gly Asp Glu Val Lys Pro Val Leu
            100                 105                 110

Thr Gly Asn Thr Lys Glu Asn Pro Arg Pro Val Ala Asn Phe Glu Lys
        115                 120                 125

Gly Val Lys Ala Thr Phe Val Glu Asp Ile Arg Trp Leu Arg Cys Asp
    130                 135                 140

Ile Lys Ser Leu Asn Leu Leu Gly Ala Val Leu Ala Lys Gln Glu Ala
145                 150                 155                 160

His Glu Lys Gly Cys Tyr Glu Ala Val Leu His Arg Asp Glu Ile Val
                165                 170                 175

Thr Glu Gly Ser Ser Ser Asn Ile Tyr Gly Ile Lys Asp Gly Val Leu
            180                 185                 190

Tyr Thr His Pro Ala Asn Asn Phe Ile Leu Asn Gly Ile Thr Arg Gln
        195                 200                 205

Val Ile Ile Lys Cys Ala Ala Glu Ile Gly Leu Pro Val Lys Glu Glu
    210                 215                 220

Ala Met Thr Lys Thr Gln Leu Leu Ala Met Asp Glu Val Ile Val Ser
225                 230                 235                 240

Ser Thr Thr Ser Glu Val Thr Pro Ile Ile Asp Ile Asp Gly Thr Val
                245                 250                 255

Ile Gly Ala Gly Lys Pro Gly Asp Trp Thr Arg Lys Leu Gln Ala Gln
            260                 265                 270

Phe Asp Thr Lys Ile Pro Lys Gly Ile Arg Ala
        275                 280

<210> SEQ ID NO 359
<211> LENGTH: 35
<212> TYPE: DNA
<213> ORGANISM: Artificial sequence
<220> FEATURE:
<223> OTHER INFORMATION: Mutagenic primer

<400> SEQUENCE: 359
gtgattgttt catcaacgaa ttcagaagta acgcc                          35

<210> SEQ ID NO 360
<211> LENGTH: 35
<212> TYPE: DNA
<213> ORGANISM: Artificial sequence
<220> FEATURE:
<223> OTHER INFORMATION: Mutagenic primer

<400> SEQUENCE: 360
gtgattgttt catcaacgcg ttcagaagta acgcc                          35

<210> SEQ ID NO 361
<211> LENGTH: 35
<212> TYPE: DNA
<213> ORGANISM: Artificial sequence
<220> FEATURE:
<223> OTHER INFORMATION: Mutagenic primer

<400> SEQUENCE: 361
gtgattgttt catcaacgag ttcagaagta acgcc                          35

<210> SEQ ID NO 362
<211> LENGTH: 35
<212> TYPE: DNA
<213> ORGANISM: Artificial sequence
<220> FEATURE:
```

<223> OTHER INFORMATION: Mutagenic primer

<400> SEQUENCE: 362
gtgattgttt catcaacggc ttcagaagta acgcc         35

<210> SEQ ID NO 363
<211> LENGTH: 31
<212> TYPE: DNA
<213> ORGANISM: Artificial sequence
<220> FEATURE:
<223> OTHER INFORMATION: Mutagenic primer

<400> SEQUENCE: 363
gtgcaggccc tcgtgctcat attttccctg g         31

<210> SEQ ID NO 364
<211> LENGTH: 45
<212> TYPE: DNA
<213> ORGANISM: Artificial sequence
<220> FEATURE:
<223> OTHER INFORMATION: Mutagenic primer

<400> SEQUENCE: 364
gaagtgattg tttcatcaac gcagtcagaa gtaacgccaa ttatc         45

<210> SEQ ID NO 365
<211> LENGTH: 40
<212> TYPE: DNA
<213> ORGANISM: Artificial sequence
<220> FEATURE:
<223> OTHER INFORMATION: Mutagenic primer

<400> SEQUENCE: 365
catatgagtt atagcttatg gaatgaccaa attgtgaatg         40

<210> SEQ ID NO 366
<211> LENGTH: 34
<212> TYPE: DNA
<213> ORGANISM: Artificial sequence
<220> FEATURE:
<223> OTHER INFORMATION: Mutagenic primer

<400> SEQUENCE: 366
ctcgagtgcg gccgcaagct tgtcgacgga gctc         34

<210> SEQ ID NO 367
<211> LENGTH: 95
<212> TYPE: DNA
<213> ORGANISM: Artificial sequence
<220> FEATURE:
<223> OTHER INFORMATION: Mutagenic primer

<400> SEQUENCE: 367
aatatttatg gaattaaaga tggcgtatta tacacacatc cagcgaataa catgatctta         60
aatggtatta cacgtcaagt aatcattaaa tgtgc         95

<210> SEQ ID NO 368
<211> LENGTH: 34
<212> TYPE: DNA
<213> ORGANISM: Artificial sequence
<220> FEATURE:
<223> OTHER INFORMATION: Mutagenic primer

<400> SEQUENCE: 368
ggccagtgaa ttgtaatacg actcactata gggc         34

```
<210> SEQ ID NO 369
<211> LENGTH: 42
<212> TYPE: DNA
<213> ORGANISM: Artificial sequence
<220> FEATURE:
<223> OTHER INFORMATION: Mutagenic primer

<400> SEQUENCE: 369
cgccatcttt aattccataa atatttgaag aagagccttc tg                    42

<210> SEQ ID NO 370
<211> LENGTH: 66
<212> TYPE: DNA
<213> ORGANISM: Artificial sequence
<220> FEATURE:
<223> OTHER INFORMATION: Mutagenic primer

<400> SEQUENCE: 370
gcaacatttg tagaagacat tcgttgggaa tactgttaca ttaaatcatt aaatttactt    60
ggtgcg                                                             66

<210> SEQ ID NO 371
<211> LENGTH: 55
<212> TYPE: DNA
<213> ORGANISM: Artificial sequence
<220> FEATURE:
<223> OTHER INFORMATION: Mutagenic primer

<400> SEQUENCE: 371
gtattataca cacatccagc gaataactac atcttaaatg gtattacacg tcaag        55

<210> SEQ ID NO 372
<211> LENGTH: 64
<212> TYPE: DNA
<213> ORGANISM: Artificial sequence
<220> FEATURE:
<223> OTHER INFORMATION: Mutagenic primer

<400> SEQUENCE: 372
gcaatggatg aagtgattgt ttcatcaacg actaaagaag taacgccaat tatcgacata    60
gatg                                                               64

<210> SEQ ID NO 373
<211> LENGTH: 64
<212> TYPE: DNA
<213> ORGANISM: Artificial sequence
<220> FEATURE:
<223> OTHER INFORMATION: Mutagenic primer

<400> SEQUENCE: 373
gcaatggatg aagtgattgt ttcatcaacg aataaagaag taacgccaat tatcgacata    60
gatg                                                               64

<210> SEQ ID NO 374
<211> LENGTH: 64
<212> TYPE: DNA
<213> ORGANISM: Artificial sequence
<220> FEATURE:
<223> OTHER INFORMATION: Mutagenic primer

<400> SEQUENCE: 374
gcaatggatg aagtgattgt ttcatcaacg aatcgtgaag taacgccaat tatcgacata    60
gatg                                                               64
```

```
<210> SEQ ID NO 375
<211> LENGTH: 16
<212> TYPE: PRT
<213> ORGANISM: P. striata
<220> FEATURE:
<221> NAME/KEY: misc_feature
<222> LOCATION: (12)..(12)
<223> OTHER INFORMATION: Xaa can be any naturally occurring amino acid

<400> SEQUENCE: 375

Leu Thr Ala Val Leu Lys Ala Asp Ala Tyr Gly Xaa Gly Ile Gly Leu
1               5                   10                  15

<210> SEQ ID NO 376
<211> LENGTH: 28
<212> TYPE: DNA
<213> ORGANISM: Artificial sequence
<220> FEATURE:
<223> OTHER INFORMATION: Primer

<400> SEQUENCE: 376
agaagacata tgcccttcg ccgtaggg                                          28

<210> SEQ ID NO 377
<211> LENGTH: 32
<212> TYPE: DNA
<213> ORGANISM: Artificial sequence
<220> FEATURE:
<223> OTHER INFORMATION: Primer

<400> SEQUENCE: 377
agaagaggat cctcagtcga cgagtatctt cg                                    32

<210> SEQ ID NO 378
<211> LENGTH: 1230
<212> TYPE: DNA
<213> ORGANISM: Artificial sequence
<220> FEATURE:
<223> OTHER INFORMATION: KT2440 BAR

<400> SEQUENCE: 378
atgccctttc gccgtaccct tctggctgca tccctggcac ttctgatcac cggacaggcc      60
cccctgtatg cggcaccacc gttgtcgatg acaacggca ccaacaccct gaccgtgcaa     120
aacagcaatg cctgggtcga agtcagcgcc agcgccctgc agcacaacat ccgcacgctg     180
caggccgagc tggccggcaa gtccaagctg tgcgccgtgc tcaaggccga tgcctatggc     240
cacggtatcg gcctggtaat gccatcgatc atcgcccaag gcgtgccctg cgtggcggtg     300
gccagcaacg aggaggcccg cgtggtccgc gccagtggct tcaccgggca actggtgcgg     360
gtacgcctgg ccagcctcag cgagctggaa gatggcttgc agtacgacat ggaagagctg     420
gtgggcagcg cggaatttgc cgccaggcc gatgccatcg ccgcgcgcca tggcaagacc     480
ttgcgcattc acatggcgct caactccagc ggcatgagcc gcaacggggt ggagatggcc     540
acctggtccg gccgtggcga agcgctgcag atcaccgacc agaagcacct caagctggtc     600
gcgctgatga cccacttcgc cgtggaagac aaggacgatg tacgcaaggg cctggcggca     660
ttcaacgagc agaccgactg gttgatcaag cacgccaggc tggaccgcag caagctcacc     720
ctgcacgccg ccaactcgtt cgctacgctg gaagtgccgg aagcgcgcct ggacatggta     780
cgaacgggtg gcgcgctgtt cggcgacacc gtgccggcgc gcaccgagta caaacgtgcg     840
atgcagttca atcgcacgt ggcggcggtg cacagctatc cggccggcaa caccgtgggc     900
tatgaccgca ccttcacct ggcccgtgat tcgcggctgg ccaacattac ggtcgggtac     960
```

-continued

```
tccgatggct accgccgggt attcaccaac aagggccatg tgctgatcaa cggccaccgt    1020
gtgccggtcg tgggcaaggt gtcgatgaac acgctgatgg tcgatgtcac cgacttccct    1080
gatgtgaagg ggggtaacga agtggtgctg ttcggcaagc aggccggggg cgaaatcacc    1140
caggccgaga tggaagaaat caacggcgcg ttgctcgccg atttgtacac cgtatggggc    1200
aattccaacc cgaagatact cgtcgactga                                     1230
```

<210> SEQ ID NO 379
<211> LENGTH: 409
<212> TYPE: PRT
<213> ORGANISM: Artificial sequence
<220> FEATURE:
<223> OTHER INFORMATION: KT2440 BAR

<400> SEQUENCE: 379

Met Pro Phe Arg Arg Thr Leu Leu Ala Ala Ser Leu Ala Leu Leu Ile
1               5                   10                  15

Thr Gly Gln Ala Pro Leu Tyr Ala Ala Pro Pro Leu Ser Met Asp Asn
            20                  25                  30

Gly Thr Asn Thr Leu Thr Val Gln Asn Ser Asn Ala Trp Val Glu Val
        35                  40                  45

Ser Ala Ser Ala Leu Gln His Asn Ile Arg Thr Leu Gln Ala Glu Leu
    50                  55                  60

Ala Gly Lys Ser Lys Leu Cys Ala Val Leu Lys Ala Asp Ala Tyr Gly
65                  70                  75                  80

His Gly Ile Gly Leu Val Met Pro Ser Ile Ala Gln Gly Val Pro
                85                  90                  95

Cys Val Ala Val Ala Ser Asn Glu Glu Ala Arg Val Val Arg Ala Ser
            100                 105                 110

Gly Phe Thr Gly Gln Leu Val Arg Val Arg Leu Ala Ser Leu Ser Glu
        115                 120                 125

Leu Glu Asp Gly Leu Gln Tyr Asp Met Glu Glu Leu Val Gly Ser Ala
    130                 135                 140

Glu Phe Ala Arg Gln Ala Asp Ala Ile Ala Ala Arg His Gly Lys Thr
145                 150                 155                 160

Leu Arg Ile His Met Ala Leu Asn Ser Ser Gly Met Ser Arg Asn Gly
                165                 170                 175

Val Glu Met Ala Thr Trp Ser Gly Arg Gly Glu Ala Leu Gln Ile Thr
            180                 185                 190

Asp Gln Lys His Leu Lys Leu Val Ala Leu Met Thr His Phe Ala Val
        195                 200                 205

Glu Asp Lys Asp Val Arg Lys Gly Leu Ala Ala Phe Asn Glu Gln
    210                 215                 220

Thr Asp Trp Leu Ile Lys His Ala Arg Leu Asp Arg Ser Lys Leu Thr
225                 230                 235                 240

Leu His Ala Ala Asn Ser Phe Ala Thr Leu Glu Val Pro Glu Ala Arg
                245                 250                 255

Leu Asp Met Val Arg Thr Gly Gly Ala Leu Phe Gly Asp Thr Val Pro
            260                 265                 270

Ala Arg Thr Glu Tyr Lys Arg Ala Met Gln Phe Lys Ser His Val Ala
        275                 280                 285

Ala Val His Ser Tyr Pro Ala Gly Asn Thr Val Gly Tyr Asp Arg Thr
    290                 295                 300

Phe Thr Leu Ala Arg Asp Ser Arg Leu Ala Asn Ile Thr Val Gly Tyr
305                 310                 315                 320

```
Ser Asp Gly Tyr Arg Arg Val Phe Thr Asn Lys Gly His Val Leu Ile
                325                 330                 335

Asn Gly His Arg Val Pro Val Val Gly Lys Val Ser Met Asn Thr Leu
            340                 345                 350

Met Val Asp Val Thr Asp Phe Pro Asp Val Lys Gly Gly Asn Glu Val
        355                 360                 365

Val Leu Phe Gly Lys Gln Ala Gly Gly Glu Ile Thr Gln Ala Glu Met
    370                 375                 380

Glu Glu Ile Asn Gly Ala Leu Leu Ala Asp Leu Tyr Thr Val Trp Gly
385                 390                 395                 400

Asn Ser Asn Pro Lys Ile Leu Val Asp
                405

<210> SEQ ID NO 380
<211> LENGTH: 1152
<212> TYPE: DNA
<213> ORGANISM: Geobacillus stearothermophilus

<400> SEQUENCE: 380
atggacgagt tcaccgcga tacgtgggcg gaagtggatt tggacgccat ttacgacaat      60
gtggagaatt tgcgccgttt gctgccggac gacacgcaca ttatggcggt cgtgaaggcg     120
aacgcctatg acatggggga tgtgcaggtg gcaaggacag cgctcgaagc gggggcctcc     180
cgcctggcgg ttgcctttt ggatgaggcg ctcgctttaa gggaaaaagg aatcgaagcg     240
ccgattctag ttctcggggc ttcccgtcca gctgatgcgg cgctgccgc ccagcagcgc     300
attgccctga ccgtgttccg ctccgactgg ttggaagaag cgtccgccct tacagcggc     360
ccttttccta ttcatttcca tttgaaaatg gacaccggca tgggacggct tggagtgaaa     420
gacgaggaag agacgaaacg aatcgtagcg ctgattgagc gccatccgca ttttgtgctt     480
gaagggggtgt acacgcattt gcgactgcg atgaggtga acaccgatta ttttttcctat     540
cagtataccc gttttttgca catgctcgaa tggctgccgt cgcgcccgcc gctcgtccat     600
tgcgccaaca cgcagcgtc gctccgtttc cctgaccgga cgttcaatat ggtccgcttc     660
ggcattgcca tgtatgggct tgccccgtcg cccggcatca agccgctgct gccgtatcca     720
ttaaaagaag catttcgct ccatagccgc ctcgtacacg tcaaaaaact gcaaccaggc     780
gaaaaggtga gctatggtgc gacgtacact gcgcagacgg aggagtggat cgggacgatt     840
ccgatcggct atgcggacgg ctggctccgc cgcctgcagc actttcatgt ccttgttgac     900
ggacaaaagg cgccgattgt cggccgcatt tgcatggacc agtgcatgat ccgcctgcct     960
ggtccgctgc cggtcggcac gaaggtgaca ctgattggtc gccaagggga cgaggtaatt    1020
tccattgatg atgtcgctcg ccatttggaa acgatcaact acgaagtgcc ttgcacgatc    1080
agttatcgag tgccccgtat ttttttccgc cataagcgta atgatggaagt gagaaacgcc    1140
gttggccgcg ga                                                        1152

<210> SEQ ID NO 381
<211> LENGTH: 384
<212> TYPE: PRT
<213> ORGANISM: Geobacillus stearothermophilus

<400> SEQUENCE: 381

Met Asp Glu Phe His Arg Asp Thr Trp Ala Glu Val Asp Leu Asp Ala
1               5                   10                  15

Ile Tyr Asp Asn Val Glu Asn Leu Arg Arg Leu Leu Pro Asp Asp Thr
            20                  25                  30
```

His Ile Met Ala Val Lys Ala Asn Ala Tyr Gly His Gly Asp Val
             35                  40                  45

Gln Val Ala Arg Thr Ala Leu Glu Ala Gly Ala Ser Arg Leu Ala Val
 50                  55                  60

Ala Phe Leu Asp Glu Ala Leu Ala Leu Arg Glu Lys Gly Ile Glu Ala
 65                  70                  75                  80

Pro Ile Leu Val Leu Gly Ala Ser Arg Pro Asp Ala Ala Leu Ala
                 85                  90                  95

Ala Gln Gln Arg Ile Ala Leu Thr Val Phe Arg Ser Asp Trp Leu Glu
                100                 105                 110

Glu Ala Ser Ala Leu Tyr Ser Gly Pro Phe Pro Ile His Phe His Leu
                115                 120                 125

Lys Met Asp Thr Gly Met Gly Arg Leu Gly Val Lys Asp Glu Glu
                130                 135                 140

Thr Lys Arg Ile Val Ala Leu Ile Glu Arg His Pro His Phe Val Leu
145                 150                 155                 160

Glu Gly Val Tyr Thr His Phe Ala Thr Ala Asp Glu Val Asn Thr Asp
                    165                 170                 175

Tyr Phe Ser Tyr Gln Tyr Thr Arg Phe Leu His Met Leu Glu Trp Leu
                180                 185                 190

Pro Ser Arg Pro Pro Leu Val His Cys Ala Asn Ser Ala Ala Ser Leu
            195                 200                 205

Arg Phe Pro Asp Arg Thr Phe Asn Met Val Arg Phe Gly Ile Ala Met
        210                 215                 220

Tyr Gly Leu Ala Pro Ser Pro Gly Ile Lys Pro Leu Leu Pro Tyr Pro
225                 230                 235                 240

Leu Lys Glu Ala Phe Ser Leu His Ser Arg Leu Val His Val Lys Lys
                    245                 250                 255

Leu Gln Pro Gly Glu Lys Val Ser Tyr Gly Ala Thr Tyr Thr Ala Gln
                260                 265                 270

Thr Glu Glu Trp Ile Gly Thr Ile Pro Ile Gly Tyr Ala Asp Gly Trp
            275                 280                 285

Leu Arg Arg Leu Gln His Phe His Val Leu Val Asp Gly Gln Lys Ala
        290                 295                 300

Pro Ile Val Gly Arg Ile Cys Met Asp Gln Cys Met Ile Arg Leu Pro
305                 310                 315                 320

Gly Pro Leu Pro Val Gly Thr Lys Val Thr Leu Ile Gly Arg Gln Gly
                325                 330                 335

Asp Glu Val Ile Ser Ile Asp Asp Val Ala Arg His Leu Glu Thr Ile
                340                 345                 350

Asn Tyr Glu Val Pro Cys Thr Ile Ser Tyr Arg Val Pro Arg Ile Phe
            355                 360                 365

Phe Arg His Lys Arg Ile Met Glu Val Arg Asn Ala Val Gly Arg Gly
        370                 375                 380

<210> SEQ ID NO 382
<211> LENGTH: 43
<212> TYPE: DNA
<213> ORGANISM: Artificial sequence
<220> FEATURE:
<223> OTHER INFORMATION: Mutagenic primer

<400> SEQUENCE: 382
gccatttgga aacgatcaac gcggaagtgc cttgcacgat cag         43

```
<210> SEQ ID NO 383
<211> LENGTH: 30
<212> TYPE: DNA
<213> ORGANISM: Artificial sequence
<220> FEATURE:
<223> OTHER INFORMATION: Primer

<400> SEQUENCE: 383
gatataccat ggcatactca ttatggaatg                                    30

<210> SEQ ID NO 384
<211> LENGTH: 32
<212> TYPE: DNA
<213> ORGANISM: Artificial sequence
<220> FEATURE:
<223> OTHER INFORMATION: Primer

<400> SEQUENCE: 384
gttatcggat ccttaggcat taattgaaat tg                                 32

<210> SEQ ID NO 385
<211> LENGTH: 36
<212> TYPE: DNA
<213> ORGANISM: Artificial sequence
<220> FEATURE:
<223> OTHER INFORMATION: Primer

<400> SEQUENCE: 385
gaggagctcg agtcagacgt atttcagtcc tttttc                             36

<210> SEQ ID NO 386
<211> LENGTH: 29
<212> TYPE: DNA
<213> ORGANISM: Artificial sequence
<220> FEATURE:
<223> OTHER INFORMATION: Primer

<400> SEQUENCE: 386
agaagacata tgatttatca gccggggac                                     29

<210> SEQ ID NO 387
<211> LENGTH: 30
<212> TYPE: DNA
<213> ORGANISM: Artificial sequence
<220> FEATURE:
<223> OTHER INFORMATION: Primer

<400> SEQUENCE: 387
agaagacata tgggtgtcgt cgtccaaaac                                    30

<210> SEQ ID NO 388
<211> LENGTH: 31
<212> TYPE: DNA
<213> ORGANISM: Artificial sequence
<220> FEATURE:
<223> OTHER INFORMATION: Primer

<400> SEQUENCE: 388
ataataggat ccttagacat atttgaggcc c                                  31

<210> SEQ ID NO 389
<211> LENGTH: 28
<212> TYPE: DNA
<213> ORGANISM: Artificial sequence
<220> FEATURE:
<223> OTHER INFORMATION: Primer

<400> SEQUENCE: 389
```
ataatacata tgaagccggt ggtggtgc                                          28

<210> SEQ ID NO 390
<211> LENGTH: 31
<212> TYPE: DNA
<213> ORGANISM: Artificial sequence
<220> FEATURE:
<223> OTHER INFORMATION: Primer

<400> SEQUENCE: 390
agaagaggat ccttagacat aggtgagccc c                                      31

<210> SEQ ID NO 391
<211> LENGTH: 26
<212> TYPE: DNA
<213> ORGANISM: Artificial sequence
<220> FEATURE:
<223> OTHER INFORMATION: Primer

<400> SEQUENCE: 391
ataataccat gggtgtcgtg gtccag                                            26

<210> SEQ ID NO 392
<211> LENGTH: 32
<212> TYPE: DNA
<213> ORGANISM: Artificial sequence
<220> FEATURE:
<223> OTHER INFORMATION: Primer

<400> SEQUENCE: 392
agaagaggat ccttagacat atttcaggcc cc                                     32

<210> SEQ ID NO 393
<211> LENGTH: 30
<212> TYPE: DNA
<213> ORGANISM: Artificial sequence
<220> FEATURE:
<223> OTHER INFORMATION: Primer

<400> SEQUENCE: 393
gcggaacata tgtttgagaa cattaccgcc                                        30

<210> SEQ ID NO 394
<211> LENGTH: 32
<212> TYPE: DNA
<213> ORGANISM: Artificial sequence
<220> FEATURE:
<223> OTHER INFORMATION: Primer

<400> SEQUENCE: 394
ataaccggat ccttacagca ctgccacaat cg                                     32

<210> SEQ ID NO 395
<211> LENGTH: 36
<212> TYPE: DNA
<213> ORGANISM: Artificial sequence
<220> FEATURE:
<223> OTHER INFORMATION: Primer

<400> SEQUENCE: 395
cgctcttatg gttcggtttg cttgggttgc tcaccc                                 36

<210> SEQ ID NO 396
<211> LENGTH: 36
<212> TYPE: DNA
<213> ORGANISM: Artificial sequence

```
<220> FEATURE:
<223> OTHER INFORMATION: Primer

<400> SEQUENCE: 396
gggtgagcaa cccaagctttt ccgaaccata agagcg                               36

<210> SEQ ID NO 397
<211> LENGTH: 39
<212> TYPE: DNA
<213> ORGANISM: Artificial sequence
<220> FEATURE:
<223> OTHER INFORMATION: Primer

<400> SEQUENCE: 397
caaaaaatac cagcgttaag ggagtgtggg tgagcaacc                             39

<210> SEQ ID NO 398
<211> LENGTH: 29
<212> TYPE: DNA
<213> ORGANISM: Artificial sequence
<220> FEATURE:
<223> OTHER INFORMATION: Primer

<400> SEQUENCE: 398
cattaccgcc gctactgccg acccgattc                                        29

<210> SEQ ID NO 399
<211> LENGTH: 39
<212> TYPE: DNA
<213> ORGANISM: Artificial sequence
<220> FEATURE:
<223> OTHER INFORMATION: Primer

<400> SEQUENCE: 399
caccaaaaat tacctcggcg tagacggcat ccctgaatt                             39

<210> SEQ ID NO 400
<211> LENGTH: 35
<212> TYPE: DNA
<213> ORGANISM: Artificial sequence
<220> FEATURE:
<223> OTHER INFORMATION: Primer

<400> SEQUENCE: 400
tgatgcggaa aatcacgctc ttgacttcga tgcac                                 35

<210> SEQ ID NO 401
<211> LENGTH: 35
<212> TYPE: DNA
<213> ORGANISM: Artificial sequence
<220> FEATURE:
<223> OTHER INFORMATION: Primer

<400> SEQUENCE: 401
gcggcgccat ggaaaatgat ccgattggtc taatg                                 35

<210> SEQ ID NO 402
<211> LENGTH: 33
<212> TYPE: DNA
<213> ORGANISM: Artificial sequence
<220> FEATURE:
<223> OTHER INFORMATION: Primer

<400> SEQUENCE: 402
gcggcggtcg acgcaattac aattgtgttt gtc                                   33
```

```
<210> SEQ ID NO 403
<211> LENGTH: 34
<212> TYPE: DNA
<213> ORGANISM: Artificial sequence
<220> FEATURE:
<223> OTHER INFORMATION: Primer

<400> SEQUENCE: 403
gcggcgccat ggatgtatgt ataattttat ttag                            34

<210> SEQ ID NO 404
<211> LENGTH: 36
<212> TYPE: DNA
<213> ORGANISM: Artificial sequence
<220> FEATURE:
<223> OTHER INFORMATION: Primer

<400> SEQUENCE: 404
gcggcggtcg acaaatttca ttattcattc taattt                          36

<210> SEQ ID NO 405
<211> LENGTH: 36
<212> TYPE: DNA
<213> ORGANISM: Artificial sequence
<220> FEATURE:
<223> OTHER INFORMATION: Primer

<400> SEQUENCE: 405
ggccggcata tgtcgatcct taacgactac aaacgt                          36

<210> SEQ ID NO 406
<211> LENGTH: 36
<212> TYPE: DNA
<213> ORGANISM: Artificial sequence
<220> FEATURE:
<223> OTHER INFORMATION: Primer

<400> SEQUENCE: 406
ggaaggctcg agtcatgatt ggtttccaga caaatt                          36

<210> SEQ ID NO 407
<211> LENGTH: 27
<212> TYPE: PRT
<213> ORGANISM: Artificial Sequence
<220> FEATURE:
<223> OTHER INFORMATION: Synthetic Signal Sequence

<400> SEQUENCE: 407

Met Ser Ile Val Val Thr Lys Ile Glu Arg Ala Gly Ala Ala Ala Val
1               5                   10                  15

Ala Ala Leu Arg Thr Ser Gly Val Ala Thr Val
            20                  25

<210> SEQ ID NO 408
<211> LENGTH: 28
<212> TYPE: DNA
<213> ORGANISM: Artificial Sequence
<220> FEATURE:
<223> OTHER INFORMATION: Primer

<400> SEQUENCE: 408
ataatacata tgcccttctc ccgtaccc                                   28

<210> SEQ ID NO 409
<211> LENGTH: 31
<212> TYPE: DNA
<213> ORGANISM: Artificial Sequence
```

```
<220> FEATURE:
<223> OTHER INFORMATION: Primer

<400> SEQUENCE: 409
gcggcgggat ccttactgat ctttcaggat t                              31

<210> SEQ ID NO 410
<211> LENGTH: 1230
<212> TYPE: DNA
<213> ORGANISM: Artificial Sequence
<220> FEATURE:
<223> OTHER INFORMATION: Synthetic Pseudomonas taetrolens arginine
      racemase

<400> SEQUENCE: 410
atgcccttct cccgtaccct gctcgccctt tccttggca tggcattgct gcaaaacccg    60
gcctttgctg cgccacccct gtcgatgacc gacggcgtag ctcaagtgaa tacccaggac   120
agcaatgcct gggtcgaaat caataaagcc gcgttcgagc acaacatacg gactctgcaa   180
accgccctcg ccggcaagtc gcagatctgc gccgtactca aggcggatgc ctatggccac   240
ggtatcggct tgttgatgcc ctcggtgatc gccatgggtg ttccctgtgt cggtgtcgcc   300
agcaacgaag aagcccgcgt cgtgcgcgag agcggtttca agggtcaact gatacgcgtg   360
cgcaccgctg ccctgagcga actggaagct gcactgccgt acaacatgga agagctggtg   420
ggcaacctgg acttcgcggt caaggccagc ctgattgccg aggatcacgg tcgcccgctg   480
gtggtgcacc tgggtctgaa ttccagcggc atgagccgta acggagtgga catgaccacc   540
gctcagggcc gtcgtgatgc ggtagctatc accaaggtgc aaacctgga agtgcgggcg   600 atcatgaccc acttcgcggt cgaagatgct gccgacgtgc gtgccgggct caaggccttc   660
aatcagcaag cccaatggct gatgaacgtg gcccagcttg atcgcagcaa gatcaccctg   720
cacgcggcca actcgttcgc cacactggag gtgcccgaat cgcatctgga catggtccgc   780
cccggcggcg cgctgttcgg cgacaccgta ccgtcccaca ccgagtacaa gcgggtcatg   840
cagttcaagt cccacgtggc gtcggtcaac agctacccca agggcaacac cgtcggttat   900
gaccgcacgt acaccctggg ccgcgactcg cggctggcca acatcaccgt cggctactct   960
gacggctacc gccgcgcgtt taccaataaa gggattgtgc tgatcaacgg ccatcgcgtg  1020
ccagtggtgg gcaaagtctc gatgaacacc ctgatggtgg acgtcactga cgcgccggat  1080
gtgaaaagcg gcgatgaagt ggtgctgttc gggcaccagg gcaaggccga gattacccag  1140
gctgagatcg aagacatcaa cggtgcactg cttgcggatc tgtataccgt gtggggcaat  1200
tccaacccta aaatcctgaa agatcagtaa                                  1230

<210> SEQ ID NO 411
<211> LENGTH: 29
<212> TYPE: DNA
<213> ORGANISM: Artificial Sequence
<220> FEATURE:
<223> OTHER INFORMATION: Primer

<400> SEQUENCE: 411
tacccaggct gagatggaag acatcaacg                                   29

<210> SEQ ID NO 412
<211> LENGTH: 23
<212> TYPE: DNA
<213> ORGANISM: Artificial Sequence
<220> FEATURE:
<223> OTHER INFORMATION: Primer
```

-continued

```
<400> SEQUENCE: 412
gccagcaacg argargcmcg cgt                                             23

<210> SEQ ID NO 413
<211> LENGTH: 18
<212> TYPE: DNA
<213> ORGANISM: Artificial Sequence
<220> FEATURE:
<223> OTHER INFORMATION: Primer

<400> SEQUENCE: 413
tggccstkga tcagcaca                                                   18

<210> SEQ ID NO 414
<211> LENGTH: 716
<212> TYPE: DNA
<213> ORGANISM: Artificial Sequence
<220> FEATURE:
<223> OTHER INFORMATION: A.caviae PCR product

<400> SEQUENCE: 414
gccagcaacg argargcmcg cgttgcccgc gagaagggct tcgaaggtcg cctgatgcgg     60
gtacgtgccg ccaccccgga tgaagtggag caggccctgc cctacaagct ggaggagctc    120
atcggcagcc tggagagcgc caaggggatc gccgacatcg cccagcgcca tcacaccaac    180
atcccggtgc acatcggcct gaactccgcc ggcatgagcc gcaacggcat cgatctgcgc    240
caggacgatg ccaaggccga tgccctggcc atgctcaagc tcaaggggat caccccggtc    300
ggcatcatga cccacttccc ggtggaggag aaagaggacg tcaagctggg gctggcccag    360
ttcaagctgg actaccagtg gctcatcgac gccggcaagc tggatcgcag caagctcacc    420
atccacgccg ccaactcctt cgccaccctg gaagtaccgg aagcctactt tgacatggtg    480
cgcccgggcg gcatcatcta tggcgacacc attccctcct acaccgagta caagaaggtg    540
atggcgttca gacccaggt cgcctccgtc aaccactacc cggcgggcaa caccgtcggc    600
tatgaccgca ccttcaccct caagcgcgac tccctgctgg ccaacctgcc gatgggctac    660
tccgacggct accgccgcgc catgagcaac aaggcctatg tgctgatcma sggcca       716

<210> SEQ ID NO 415
<211> LENGTH: 238
<212> TYPE: PRT
<213> ORGANISM: Aeromonas caviae
<220> FEATURE:
<221> NAME/KEY: MISC_FEATURE
<222> LOCATION: (237)..(237)
<223> OTHER INFORMATION: Xaa can be Phe, Gln, Asn or Lys

<400> SEQUENCE: 415

Ala Ser Asn Glu Glu Ala Arg Val Ala Arg Glu Lys Gly Phe Glu Gly
1               5                   10                  15

Arg Leu Met Arg Val Arg Ala Ala Thr Pro Asp Glu Val Glu Gln Ala
            20                  25                  30

Leu Pro Tyr Lys Leu Glu Glu Leu Ile Gly Ser Leu Glu Ser Ala Lys
        35                  40                  45

Gly Ile Ala Asp Ile Ala Gln Arg His His Thr Asn Ile Pro Val His
    50                  55                  60

Ile Gly Leu Asn Ser Ala Gly Met Ser Arg Asn Gly Ile Asp Leu Arg
65                  70                  75                  80

Gln Asp Asp Ala Lys Ala Asp Ala Leu Ala Met Leu Lys Leu Lys Gly
                85                  90                  95
```

```
Ile Thr Pro Val Gly Ile Met Thr His Phe Pro Val Glu Glu Lys Glu
            100                 105                 110

Asp Val Lys Leu Gly Leu Ala Gln Phe Lys Leu Asp Tyr Gln Trp Leu
            115                 120                 125

Ile Asp Ala Gly Lys Leu Asp Arg Ser Lys Leu Thr Ile His Ala Ala
            130                 135                 140

Asn Ser Phe Ala Thr Leu Glu Val Pro Glu Ala Tyr Phe Asp Met Val
145                 150                 155                 160

Arg Pro Gly Gly Ile Tyr Gly Asp Thr Ile Pro Ser Tyr Thr Glu
                    165                 170                 175

Tyr Lys Lys Val Met Ala Phe Lys Thr Gln Val Ala Ser Val Asn His
            180                 185                 190

Tyr Pro Ala Gly Asn Thr Val Gly Tyr Asp Arg Thr Phe Thr Leu Lys
            195                 200                 205

Arg Asp Ser Leu Leu Ala Asn Leu Pro Met Gly Tyr Ser Asp Gly Tyr
            210                 215                 220

Arg Arg Ala Met Ser Asn Lys Ala Tyr Val Leu Ile Xaa Gly
225                 230                 235
```

<210> SEQ ID NO 416
<211> LENGTH: 1227
<212> TYPE: DNA
<213> ORGANISM: Aeromonas caviae

<400> SEQUENCE: 416

```
atgcacaaga aaacactgct cgcgaccctg atctttggcc tgctggccgg ccaggcagtc      60
gccgccccct atctgccgct cgccgacgac caccgcaacg gtcaggaaca gaccgccgcc    120
aacgcctggc tggaagtgga tctcggcgcc ttcgagcaca catccagac cctgaagaat     180
cgcctcggtg acaagggccc gcagatctgc gccatcatga aggcggacgc ctacggtcac    240
ggcatcgacc tgctggtccc ttccgtggtc aaggcaggca tccctgcat cggcatcgcc    300
agcaacgaag aagcacgtgt tgcccgcgag aagggcttcg aaggtcgcct gatgcgggta    360
cgtgccgcca ccccggatga agtggagcag gccctgccct acaagctgga ggagctcatc    420
ggcagcctgg agagcgccaa ggggatcgcc gacatcgccc agcgccatca caccaacatc    480
ccggtgcaca tcggcctgaa ctcgccggc atgagccgca acggcatcga tctgcgccag    540
gacgatgcca aggccgatgc cctggccatg ctcaagctca aggggatcac cccggtcggc    600
atcatgaccc acttcccggt ggaggagaaa gaggacgtca agctggggct ggcccagttc    660
aagctggact accagtggct catcgacgcc ggcaagctgg atcgcagcaa gctcaccatc    720
cacgccgcca actccttcgc caccctggaa gtaccggaag cctactttga catggtgcgc    780
ccgggcggca tcatctatgg cgacaccatt ccctcctaca ccgagtacaa gaaggtgatg    840
gcgttcaaga cccaggtcgc ctccgtcaac cactacccgg cgggcaacac cgtcggctat    900
gaccgcacct tcaccctcaa gcgcgactcc ctgctggcca acctgccgat gggctactcc    960
gacggctacc gccgcgccat gagcaacaag gcctatgtgc tgatccatgg ccagaaggcc   1020
cccgtcgtgg gcaagacttc catgaacacc accatggtgg acgtcaccga catcaagggg   1080
atcaaacccg gtgacgaggt ggtcctgttc ggacgccagg gtgatgccga ggtgaaacaa   1140
tctgatctgg aggagtacaa cggtgccctc ttggcggaca tgtacaccgt ctggggctat   1200
accaaccccca agaagatcaa gcgctaa                                      1227
```

<210> SEQ ID NO 417
<211> LENGTH: 408
<212> TYPE: PRT
<213> ORGANISM: Aeromonas caviae

<400> SEQUENCE: 417

```
Met His Lys Lys Thr Leu Leu Ala Thr Leu Ile Phe Gly Leu Leu Ala
1               5                   10                  15

Gly Gln Ala Val Ala Ala Pro Tyr Leu Pro Leu Ala Asp Asp His Arg
            20                  25                  30

Asn Gly Gln Glu Gln Thr Ala Ala Asn Ala Trp Leu Glu Val Asp Leu
        35                  40                  45

Gly Ala Phe Glu His Asn Ile Gln Thr Leu Lys Asn Arg Leu Gly Asp
    50                  55                  60

Lys Gly Pro Gln Ile Cys Ala Ile Met Lys Ala Asp Ala Tyr Gly His
65                  70                  75                  80

Gly Ile Asp Leu Leu Val Pro Ser Val Val Lys Ala Gly Ile Pro Cys
                85                  90                  95

Ile Gly Ile Ala Ser Asn Glu Glu Ala Arg Val Ala Arg Glu Lys Gly
            100                 105                 110

Phe Glu Gly Arg Leu Met Arg Val Arg Ala Ala Thr Pro Asp Glu Val
        115                 120                 125

Glu Gln Ala Leu Pro Tyr Lys Leu Glu Glu Leu Ile Gly Ser Leu Glu
    130                 135                 140

Ser Ala Lys Gly Ile Ala Asp Ile Ala Gln Arg His His Thr Asn Ile
145                 150                 155                 160

Pro Val His Ile Gly Leu Asn Ser Ala Gly Met Ser Arg Asn Gly Ile
                165                 170                 175

Asp Leu Arg Gln Asp Asp Ala Lys Ala Asp Ala Leu Ala Met Leu Lys
            180                 185                 190

Leu Lys Gly Ile Thr Pro Val Gly Ile Met Thr His Phe Pro Val Glu
        195                 200                 205

Glu Lys Glu Asp Val Lys Leu Gly Leu Ala Gln Phe Lys Leu Asp Tyr
    210                 215                 220

Gln Trp Leu Ile Asp Ala Gly Lys Leu Asp Arg Ser Lys Leu Thr Ile
225                 230                 235                 240

His Ala Ala Asn Ser Phe Ala Thr Leu Glu Val Pro Glu Ala Tyr Phe
                245                 250                 255

Asp Met Val Arg Pro Gly Gly Ile Ile Tyr Gly Asp Thr Ile Pro Ser
            260                 265                 270

Tyr Thr Glu Tyr Lys Lys Val Met Ala Phe Lys Thr Gln Val Ala Ser
        275                 280                 285

Val Asn His Tyr Pro Ala Gly Asn Thr Val Gly Tyr Asp Arg Thr Phe
    290                 295                 300

Thr Leu Lys Arg Asp Ser Leu Leu Ala Asn Leu Pro Met Gly Tyr Ser
305                 310                 315                 320

Asp Gly Tyr Arg Arg Ala Met Ser Asn Lys Ala Tyr Val Leu Ile His
                325                 330                 335

Gly Gln Lys Ala Pro Val Val Gly Lys Thr Ser Met Asn Thr Thr Met
            340                 345                 350

Val Asp Val Thr Asp Ile Lys Gly Ile Lys Pro Gly Asp Glu Val Val
        355                 360                 365

Leu Phe Gly Arg Gln Gly Asp Ala Glu Val Lys Gln Ser Asp Leu Glu
    370                 375                 380
```

```
Glu Tyr Asn Gly Ala Leu Leu Ala Asp Met Tyr Thr Val Trp Gly Tyr
385                 390                 395                 400

Thr Asn Pro Lys Lys Ile Lys Arg
                405
```